US011161915B2

(12) United States Patent
Urosev et al.

(10) Patent No.: US 11,161,915 B2
(45) Date of Patent: Nov. 2, 2021

(54) ANTIGEN-BINDING POLYPEPTIDE CONSTRUCTS COMPRISING KAPPA AND LAMBDA LIGHT CHAINS AND USES THEREOF

(71) Applicant: ZYMEWORKS INC., Vancouver (CA)

(72) Inventors: Dunja Urosev, Vancouver (CA); Stacey A. L. Tom-Yew, Coquitlam (CA); Leonard G. Presta, San Francisco, CA (US); Mario Sanches, Vancouver (CA)

(73) Assignee: ZYMEWORKS INC., Vancouver (CA)

( * ) Notice: Subject to any disclaimer, the term of this patent is extended or adjusted under 35 U.S.C. 154(b) by 0 days.

(21) Appl. No.: 15/765,574

(22) PCT Filed: Oct. 7, 2016

(86) PCT No.: PCT/CA2016/051183
§ 371 (c)(1),
(2) Date: Apr. 3, 2018

(87) PCT Pub. No.: WO2017/059551
PCT Pub. Date: Apr. 13, 2017

(65) Prior Publication Data

US 2019/0338048 A1 Nov. 7, 2019

Related U.S. Application Data

(60) Provisional application No. 62/239,206, filed on Oct. 8, 2015, provisional application No. 62/261,769, filed on Dec. 1, 2015.

(51) Int. Cl.
*C07K 16/46* (2006.01)
*A61K 47/68* (2017.01)
*C07K 16/24* (2006.01)
*C07K 16/32* (2006.01)

(52) U.S. Cl.
CPC ........ *C07K 16/468* (2013.01); *A61K 47/6803* (2017.08); *C07K 16/244* (2013.01); *C07K 16/32* (2013.01); *C07K 2317/21* (2013.01); *C07K 2317/24* (2013.01); *C07K 2317/31* (2013.01); *C07K 2317/522* (2013.01); *C07K 2317/55* (2013.01); *C07K 2317/56* (2013.01); *C07K 2317/92* (2013.01); *C07K 2317/94* (2013.01)

(58) Field of Classification Search
CPC .............. C07K 16/468; C07K 2317/55; C07K 2317/50
USPC .......................................... 424/133.1, 136.1
See application file for complete search history.

(56) References Cited

U.S. PATENT DOCUMENTS 5,731,168 A 3/1998 Carter et al.
5,807,706 A 9/1998 Carter et al.
5,821,333 A 10/1998 Carter et al.
6,809,185 B1 10/2004 Schoonjans et al.
7,183,076 B2 2/2007 Arathoon et al.
7,642,228 B2 1/2010 Carter et al.
7,695,936 B2 4/2010 Carter et al.
7,947,271 B2 5/2011 Browning et al.
7,951,917 B1 5/2011 Arathoon et al.
8,501,185 B2 8/2013 Heitner Hansen et al.
8,592,562 B2 11/2013 Kannan et al.
9,527,927 B2 12/2016 Chowdhury et al.
9,708,388 B2 7/2017 Beckmann
9,771,573 B2 9/2017 Ohru et al.
9,914,785 B2 * 3/2018 Corper ................... C07K 16/36
10,077,298 B2 * 9/2018 Corper ............... C07K 16/2863
2007/0196363 A1 8/2007 Arathoon et al.
2008/0050370 A1 2/2008 Glaser et al.
2009/0162360 A1 6/2009 Klein et al.
2009/0182127 A1 7/2009 Kjaergaard et al.
2009/0232811 A1 9/2009 Klein et al.
2009/0263392 A1 10/2009 Igawa et al.

(Continued)

FOREIGN PATENT DOCUMENTS

EP 2543680 A1 1/2013
WO 199627011 3/1994

(Continued)

OTHER PUBLICATIONS

Lewis, S.M. et al. (Nature Biotechnology. Jan. 26, 2014 (Jan. 26, 2014)).*
Spreter Von Kreudenstein et al. (Methods. Nov. 6, 2013 (Jun. 11, 2013).*
Chen, Lei, et al., "Preferential Germline Usage and VH/VL Pairing Observed in Human Antibodies selected by mRNA display.", *Protein Engineering, Design & Selection: Peds*, Oct. 2015, vol. 28, No. 10, pp. 427-435.
Lui, Zhi, et al., "A Novel Antibody Engineering Strategy for Making Monovalent Bispecific Heterodimeric IgG Antibodies by Electrostatis Steering Mechanism", *Journal of Biological Chemistry*, vol. 290, No. 12, Mar. 2015, pp. 7535-7562.

(Continued)

*Primary Examiner* — Lynn A Bristol
(74) *Attorney, Agent, or Firm* — Kilpatrick Townsend & Stockton LLP

(57) ABSTRACT

Provided herein are multispecific antigen-binding polypeptide constructs comprising at least two different heterodimers, each comprising a heavy chain and a light chain. At least one heterodimer comprises a Fab region comprising a lambda light chain and at least one heterodimer comprises a Fab region comprising a kappa light chain. One or more of the immunoglobulin heavy and light chains that form the antigen-binding polypeptide construct comprise amino acid modifications that promote correct pairing between the heavy and light chains to form the desired multispecific antigen-binding polypeptide construct. The amino acid modifications may be in the $C_{H1}$ and/or $C_L$ domains, in the $V_H$ and/or $V_L$ domains, or a combination thereof.

26 Claims, 32 Drawing Sheets

Specification includes a Sequence Listing.

(56) References Cited

U.S. PATENT DOCUMENTS

| | | | |
|---|---|---|---|
| 2010/0015133 A1 | 1/2010 | Igawa et al. |
| 2010/0105874 A1 | 4/2010 | Schuurman et al. |
| 2010/0256338 A1 | 10/2010 | Brinkmann et al. |
| 2010/0286374 A1 | 11/2010 | Kannan et al. |
| 2010/0322935 A1 | 12/2010 | Croasdale et al. |
| 2010/0331527 A1 | 12/2010 | Davis et al. |
| 2011/0008345 A1 | 1/2011 | Ashman et al. |
| 2011/0275787 A1 | 11/2011 | Kufer et al. |
| 2011/0287009 A1 | 11/2011 | Scheer et al. |
| 2011/0293613 A1 | 12/2011 | Brinkmann et al. |
| 2012/0143580 A1 | 6/2012 | Constantine et al. |
| 2012/0149876 A1 | 6/2012 | Spreter Von Kreudenstein et al. |
| 2012/0244578 A1 | 9/2012 | Kannan et al. |
| 2013/0078249 A1 | 3/2013 | Ast et al. |
| 2013/0195849 A1 | 8/2013 | Spreter Von Kreudenstein et al. |
| 2013/0336973 A1 | 12/2013 | Spreter Von Kreudenstein et al. |
| 2014/0066599 A2 | 3/2014 | Blein et al. |
| 2014/0154254 A1 | 6/2014 | Kannan et al. |
| 2014/0179547 A1 | 6/2014 | Fischer et al. |
| 2014/0187753 A1 | 7/2014 | Blein et al. |
| 2014/0200331 A1 | 7/2014 | Corper et al. |
| 2014/0370020 A1 | 12/2014 | Kuramochi et al. |
| 2015/0284470 A1 | 10/2015 | Spreter Von Kreudenstein et al. |
| 2015/0307594 A1 | 10/2015 | Corper et al. |
| 2016/0257763 A1 | 9/2016 | Spreter Von Kreudenstein et al. |
| 2017/0204199 A1* | 7/2017 | Sanches ............... C07K 16/468 |
| 2018/0179296 A1* | 6/2018 | Corper ................... C07K 16/36 |
| 2019/0002589 A1 | 1/2019 | Bardroff et al. |
| 2019/0085055 A1* | 3/2019 | Corper ............... C07K 16/2863 |
| 2019/0218311 A1 | 7/2019 | Loew et al. |

FOREIGN PATENT DOCUMENTS

| | | |
|---|---|---|
| WO | 2006108905 | 10/2006 |
| WO | 2007110205 | 10/2007 |
| WO | 2009089004 | 7/2009 |
| WO | 199404690 | 1/2010 |
| WO | 2010085682 | 7/2010 |
| WO | 2010115553 | 10/2010 |
| WO | 2011131746 | 10/2011 |
| WO | 2011133886 | 12/2011 |
| WO | 2011147982 | 12/2011 |
| WO | 2012008635 | 1/2012 |
| WO | 2012020096 | 2/2012 |
| WO | 2012023053 | 2/2012 |
| WO | 2012073985 | 6/2012 |
| WO | 2012131555 | 10/2012 |
| WO | 2012143523 | 10/2012 |
| WO | 2013002362 | 1/2013 |
| WO | 2013005194 | 1/2013 |
| WO | 2013065708 | 5/2013 |
| WO | 2013096291 | 6/2013 |
| WO | 2014081955 | 5/2014 |
| WO | 2014/082179 A1 | 6/2014 |
| WO | 2014124326 | 8/2014 |
| WO | 2014/150973 A1 | 9/2014 |
| WO | 2014150973 | 9/2014 |
| WO | 2015052230 | 4/2015 |
| WO | 2015/173756 A2 | 11/2015 |
| WO | 2015173756 | 11/2015 |
| WO | 2015/181805 A1 | 12/2015 |
| WO | 2016026943 | 2/2016 |
| WO | 2016172485 | 10/2016 |
| WO | 2017117179 | 7/2017 |
| WO | 2018141894 | 8/2018 |
| WO | 2018158719 | 9/2018 |
| WO | 2018057955 | 3/2019 |

OTHER PUBLICATIONS

International Search Report received in the corresponding PCT Application No. PCT/CA2016/051183, dated Dec. 16, 2016.

Fischer, N. et al., "Exploiting light chains for the scalable generation and platform purification of native human bispecific JgG". Nature Communications, Feb. 12, 2015 (Feb. 12, 2015), vol. 6:6113, pp. 1-12.

Klein, C. et al., "The use of CrossMAb technology for the generation of bi- and multispecific antibodies". mAbs, Aug./Sep. 2016 (Aug. 9, 2016), vol. 8( 6), pp. 1010-1020, ISSN 1942-0862.

U.S. Appl. No. 15/896,170 Office Action dated Sep. 18, 2019.

U.S. Appl. No. 15/896,170 Office Action dated May 18, 2020.

U.S. Appl. No. 15/314,496 Office Action dated Jan. 6, 2020.

U.S. Appl. No. 16/122,417 Restriction Requirement dated Mar. 6, 2020.

Fischer, et al., 'Exploiting light chaings for the scalable generation and platform purification of native human bispecific igG', Nature Communications, 2015.

Aaltintas, I., et al., Targeting epidermal growth factor receptor in tumors: From conventional monoclonal antibodies via heavy chain-only antibodies to nanobodies. Eur J Pharm Sci. Mar. 12, 2012; 45(4): 399-407.

Atwell et al., Stable Heterodimers from Remodeling the Domain Interface of a Homodimer Using a Phage Display Library, Journal of Molecular Biology, vol. 270, No. 1, Jul. 4, 1997, pp. 26-35.

Beck et al., Strategies and Challenges for the Next Generation of Therapeutic Antibodies, Nature Reviews Immunology, vol. 10, No. 5, May 2010, pp. 345-352.

Chames et al., Therapeutic Antibodies: Successes, Limitations and Hopes for the Future, British Journal of Pharmacology, vol. 157, No. 2, 2009, pp. 220-223.

Chen, L., et al., Preferential Germline Usage and VH/VL Pairing Observed in Human Antibodies selected by mRNA display. Protein Engineering, Design & Selection: Peds. Oct. 2015; 28(10) 427-435.

Colman, Effects of Amino Acid Sequence Changes on Antibody-antigen Interactions, Research in Immunology, vol. 145, No. 1, Jan. 1994, pp. 33-36.

Coloma et al., Design and Production of Novel Tetravalent Bispecific Antibodies, Nature Biotechnology, vol. 15, No. 2, Feb. 1997, pp. 159-163.

Dall'Acqua et al., Contribution of Domain Interface Residues to the Stability of Antibody CH3 Domain Homodimers, Biochemistry, American Chemical Society, vol. 37, No. 26, Jun. 30, 1998, pp. 9266-9273.

Davis et al., SEEDbodies: Fusion Proteins Based on Strand-exchange Engineered Domain (SEED) CH3 Heterodimers in an Fc Analogue Platform for Asymmetric Binders or Immunofusions and Bispecific Antibodies, Protein Engineering, Design & Selection, vol. 23, No. 4, Feb. 4, 2010, pp. 195-202.

Demarest et al., Antibody Therapeutics, Antibody Engineering, and the Merits of Protein Stability, Current Opinion in Drug Discovery and Development vol. 11, No. 5, Sep. 2008, pp. 675-687.

Demarest et al., Optimization of the Antibody CH3 Domain by Residue Frequency Analysis of IgG Sequences, Journal of Molecular Biology, vol. 335, No. 1, Jan. 2, 2004, pp. 41-48.

Edwards, B.M., et al. The remarkable flexibility of the human antibody repertoire; isolation of over one thousand different antibodies to a single protein, BLyS. J. Mol. Biol. 2003; 334(1):103-118.

Fischer, N., et al.. Exploiting light chains for the scalable generation and platform purification or native human bispecific IgG. Nature Communications, Feb. 12, 2015; 6(6113):1-12.

Gramer, M. J., et al., Production of stable bispecific IgG1 by controlled Fab-arm exchange Scalability from bench to large-scale manufacturing by application of standard approaches. mAbs. Nov. 1, 2013;5(6):962-973.

Gunasekaran et al., Enhancing Antibody Fc Heterodimer Formation Through Electrostatic Steering Effects: Applications to Bispecific Molecules and Monovalent IgG mailed on J. Biol. Chem., vol. 285, No. 25, Jun. 18, 2010, pp. 19637-19646.

Heads, J.T., Relative stabilities of IgG1 and IgG4 Fab Domains: Influence of the Light-Heavy interchain disulfide bond architecture. Protein Science. Jul. 2012; 21(9): 1315-1322.

Igawa, T., et al., VH/VL interface engineering to promote selective expression and inhibit conformational isomerization of thrombopoietin receptor agonist single-chain diabody. Protein Eng Des Sel. Aug. 2010; 23(8):667-677.

(56) References Cited

OTHER PUBLICATIONS

Jordan et al., Structural Understanding of Stabilization Patterns in Engineered Bispecific Ig-like Antibody Molecules, proteins: structure. Function. And bioinformatics, vol. 77, No. 4, Dec. 1, 2009, pp. 832-841.
Kabat, E.A., et al., Sequences of proteins of Immunological Interest. Diae publishing, 5th Ed., vol. 1, 1991, NIH Publication 91-3242 (pp. 647-657, 661-669).
Klein et al., Progress in Overcoming the Chain Association Issue in Bispecific Heterodimeric LgG Antibodies, mAbs. vol. 4, No. 6, Nov. 2012, pp. 653-663.
Labrijin, A. F., et al.. Efficient generation of stable bispecific IgG1 by controlled Fab-arm exchange. PNAS, Mar. 26, 2013; 110(13):5145-5150.
Lewis et al., Generation of Bispecific IgG Antibodies by Structure-Based Design of an Orthogonal Fab Interface, Nature Biotechnology, vol. 32, No. 2, Jan. 26, 2014, pp. 191-198.
Liu, Z., et al., A Novel Antibody Engineering Strategy for Making Monovalent Bispecific Heterodimeric IgG Antibodies by Electrostatic Steering Mechanism. Journal of Biological Chemistry. Mar. 2015; 290(12):7535-7562.
Lu, D. et al., Fab-scFv Fusion Protein: An Efficient Approach to Production of Bispecific Antibody Fragments mailed on Journal of Immunological Methods, vol. 267, No. 2, 2002, pp. 213-226.
Merchant et al., An Efficient Route to Human Bispecific IgG, Nature Biotechnology, vol. 16, No. 7, Jul. 16, 1998, pp. 677-681.
Merk et al., Cell-Free Expression of Two Single-Chain Monoclonal Antibodies against Lysozyme: Effect of Domain Arrangement on the Expression, J. Biochem., vol. 125, Dec. 31, 1999, pp. 328-333.
Miller et al., Stability Engineering of scFvs for the Development of Bispecific and Multivalent Antibodies, Protein Engineering. Design and selection, Oxford Journal, vol. 23, No. 7., Jul. 1, 2010, pp. 549-557.
Moore et al., A Novel Bispecific Antibody Format Enables Simultaneous Bivalent and Monovalent Co-engagement of Distinct Target Antigens, mAbs, vol. 3, No. 6, 2011, pp. 546-557.
Padlan, E. A., et al., Antibody Fab assembly: The interface residues between CH1 and CL. Molecular Immunology, Sep. 1986; 23(9):951-960.
Presta, et al., Engineering Therapeutic Antibodies for Improved Function, Biochem. Soc. Trans., vol. 30, No. 4, Aug. 2002, pp. 487-490.
Ridgway et al., Knobs-into-Holes' Engineering of Antibody CH3 Domains for Heavy Chain Heterodimerization, Protein Engineering, vol. 9, No. 7, Jul. 1996, pp. 617-621.
Schaefer, W., et a., Immunoglobulin domain crossover as a generic approach for the production of bispecific IgG antibodies. PNAS, Jul. 5, 2011; 108(27):11187-11192.
Schlatter et al., On the Optimal ratio of Heavy to Light Chain Genes for Efficient Recombinant Antibody Production by CHO Cells, Biotechnology Progress, vol. 21, No. 1, Jan.-Feb. 2005, pp. 122-133.
Segal et al., Introduction: Bispecific Antibodies, Journal of Immunological Methods, vol. 248, No. 1-2, Feb. 1, 2001, pp. 1-6.
Spreter Von Kreudenstein, T., et al., Improving biophysical properties of a bispecific antibody scaffold to aid developability. Sep./Oct. 2013, mAbs, vol. 5, No. 5, pp. 646-654.
Spreter Von Kreudenstein, T., et al., Protein engineering and the use of molecular modeling and simulation: the case of heterodimeric Fe engineering. Methods. Jan. 1, 2014;65(1):77-94.
Stanglmaier et al., Bi20 (fBTA05), a Novel Trifunctional Bispecific Antibody (Anti-CD20 X Anti-CD3), Mediates Efficient Killing of B-cell Lymphoma Cells Even with Very Low CD20 Expression Levels, International Journal of Cancer, vol. 123, 2008, pp. 1181-1189.
Strop, P., et al., Generating bispecific human IgG1 and IgG2 antibodies from any antibody pair. J Mol Biol. Jul. 13, 2012; 420(3):204-219.
Suresh et al., Bispecific Monoclonal Antibodies from Hybrid Hybridomas, Methods in Enzymology, vol. 121, 1986, pp. 210-228.
Zhu et al., Remodeling Domain Interfaces to Enhance Heterodimer Formation. Protein Science, vol. 6, No. 4, Apr. 1997, pp. 781-788.
U.S. Appl. No. 14/648,222, Restriction Requirement dated May 9, 2016.
U.S. Appl. No. 14/648,222, Restriction Requirement dated Dec. 2, 2016.
U.S. Appl. No. 14/648,222, Non-Final Office Action dated May 16, 2017.
U.S. Appl. No. 14/648,222, Final Office Action dated Dec. 29, 2017.
U.S. Appl. No. 14/648,222, Notice of Allowance dated May 8, 2018.
U.S. Appl. No. 16/122,417 Office Action dated Jun. 19, 2020.
U.S. Appl. No. 14/092,804, Restriction Requirement dated Jun. 18, 2015.
U.S. Appl. No. 14/092,804, Non-Final Office Action dated Sep. 10, 2015.
U.S. Appl. No. 14/092,804, Restriction Requirement dated May 12, 2016.
U.S. Appl. No. 14/092,804, Final Office Action dated Dec. 29, 2016.
U.S. Appl. No. 14/092,804, Notice of Allowance dated Nov. 1, 2017.
U.S. Appl. No. 15/896,170, Restriction Requirement dated Jun. 26, 2019.
U.S. Appl. No. 15/314,496, Restriction Requirement dated May 8, 2018.
U.S. Appl. No. 15/314,496, Non-Final Office Action dated Oct. 17, 2018.
U.S. Appl. No. 15/314,496, Final Office Action dated Apr. 24, 2019.
U.S. Appl. No. 15/314,496, Final Office Action dated Jul. 28, 2020.
Notice of Allowance dated Mar. 30, 2021 in U.S. Appl. No. 15/896,170.
Non Final Office Action dated Mar. 30, 2021 in U.S. Appl. No. 15/314,496.
Final Office Action dated Feb. 1, 2021 in U.S. Appl. No. 15/896,170.
Final Office Action dated Feb. 8, 2021 in U.S. Appl. No. 16/122,417.

* cited by examiner

FIGURE 1C

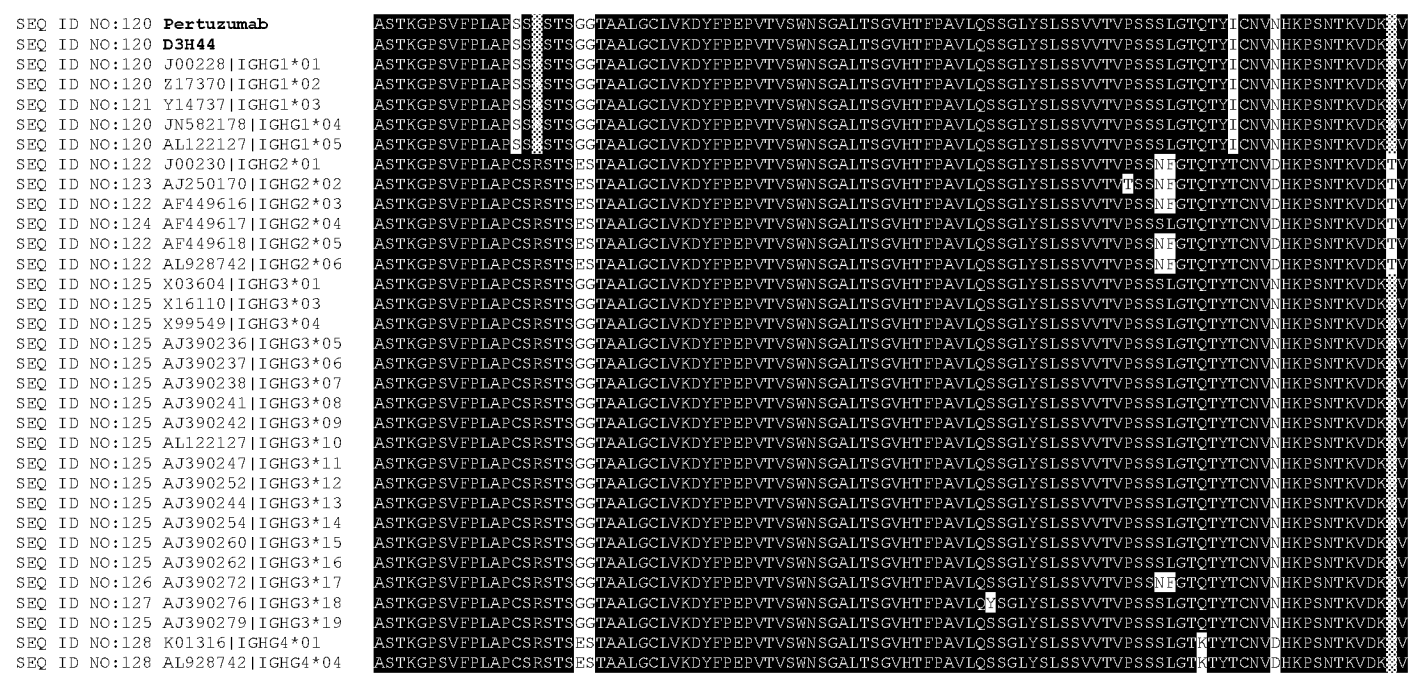

| | | |
|---|---|---|
| SEQ ID NO:120 | **Pertuzumab** | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| SEQ ID NO:120 | **D3H44** | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| SEQ ID NO:120 | J00228\|IGHG1*01 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| SEQ ID NO:120 | Z17370\|IGHG1*02 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| SEQ ID NO:121 | Y14737\|IGHG1*03 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRV |
| SEQ ID NO:120 | JN582178\|IGHG1*04 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| SEQ ID NO:120 | AL122127\|IGHG1*05 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| SEQ ID NO:122 | J00230\|IGHG2*01 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO:123 | AJ250170\|IGHG2*02 | ASTKGPSVFPLAPCSRSTSESTAALGCLVKDYFPEPVTVSWNSGALTSGVHTFPAVLQSSGLYSLSSVVTVTSSNFGTQTYTCNVDHKPSNTKVDKTV |
| SEQ ID NO:122 | AF449616\|IGHG2*03 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO:124 | AF449617\|IGHG2*04 | ASTKGPSVFPLAPCSRSTSESTAALGCLVKDYFPEPVTVSWNSGALTSGVHTFPAVLQSSGLYSLSSVVTVPSSSLGTQTYTCNVDHKPSNTKVDKTV |
| SEQ ID NO:122 | AF449618\|IGHG2*05 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO:122 | AL928742\|IGHG2*06 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO:125 | X03604\|IGHG3*01 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | X16110\|IGHG3*03 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | X99549\|IGHG3*04 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390236\|IGHG3*05 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390237\|IGHG3*06 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390238\|IGHG3*07 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390241\|IGHG3*08 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390242\|IGHG3*09 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AL122127\|IGHG3*10 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390247\|IGHG3*11 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390252\|IGHG3*12 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390244\|IGHG3*13 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390254\|IGHG3*14 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390260\|IGHG3*15 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:125 | AJ390262\|IGHG3*16 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:126 | AJ390272\|IGHG3*17 | ASTKGPSVFPLAPCSRSTSGGTAALGCLVKDYFPEPVTVSWNSGALTSGVHTFPAVLQSSGLYSLSSVVTVPSSNFGTQTYTCNVNHKPSNTKVDKRV |
| SEQ ID NO:127 | AJ390276\|IGHG3*18 | ASTKGPSVFPLAPCSRSTSGGTAALGCLVKDYFPEPVTVSWNSGALTSGVHTFPAVLQYSGLYSLSSVVTVPSSSLGTQTYTCNVNHKPSNTKVDKRV |
| SEQ ID NO:125 | AJ390279\|IGHG3*19 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO:128 | K01316\|IGHG4*01 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRV |
| SEQ ID NO:128 | AL928742\|IGHG4*04 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRV |

FIGURE 1D

| | |
|---|---|
| SEQ ID NO:129 **Pertuzumab** | RTVAAPSVFIFPPSDEQLKSGTASVVCLLNNFYPREAKVQWKVDNALQSGNSQESVTEQ SKDSTYSLSSTLTLSKADYEKHKVYACEVTHQGLSSPVTKSFNRGEC |
| SEQ ID NO:129 **D3H44** | RTVAAPSVFIFPPSDEQLKSGTASVVCLLNNFYPREAKVQWKVDNALQSGNSQESVTEQ SKDSTYSLSSTLTLSKADYEKHKVYACEVTHQGLSSPVTKSFNRGEC |
| SEQ ID NO:129 J00241\|IGKC*01 | RTVAAPSVFIFPPSDEQLKSGTASVVCLLNNFYPREAKVQWKVDNALQSGNSQESVTEQ SKDSTYSLSSTLTLSKADYEKHKVYACEVTHQGLSSPVTKSFNRGEC |
| SEQ ID NO:130 M11736\|IGKC*02 | RTVAAPSVFIFPPSDEQLKSGTASVVCLLNNFYPREAKVQWKVDNALQSGNSQESVTEQ SKDSTYSLSSTLTLSKADYEKHKVYAGEVTHQGLSSPVTKSFNRGEC |
| SEQ ID NO:131 M11737\|IGKC*03 | RTVAAPSVFIFPPSDEQLKSGTASVVCLLNNFYPREAKVQRKVDNALQSGNSQESVTEQ SKDSTYSLSSTLTLSKADYEKHKVYACEVTHQGLSSPVTKSFNRGEC |
| SEQ ID NO:132 AF017732\|IGKC*04 | RTVAAPSVFIFPPSDEQLKSGTASVVCLLNNFYPREAKVQWKVDNALQSGNSQESVTEQ SKDSTYSLSSTLTLSKADYEKHK YACEVTHQGLSSPVTKSFNRGEC |
| SEQ ID NO:133 AF113887\|IGKC*05 | RTVAAPSVFIFPPSDEQLKSGTASVVCLLNNFYPREAKVQWKVDNALQSGNSQESVTEQ SKDSTYSLSNTLTLSKADYEKHKVYACEVTHQGLSSPVTKSFNRGEC |

FIGURE 1F

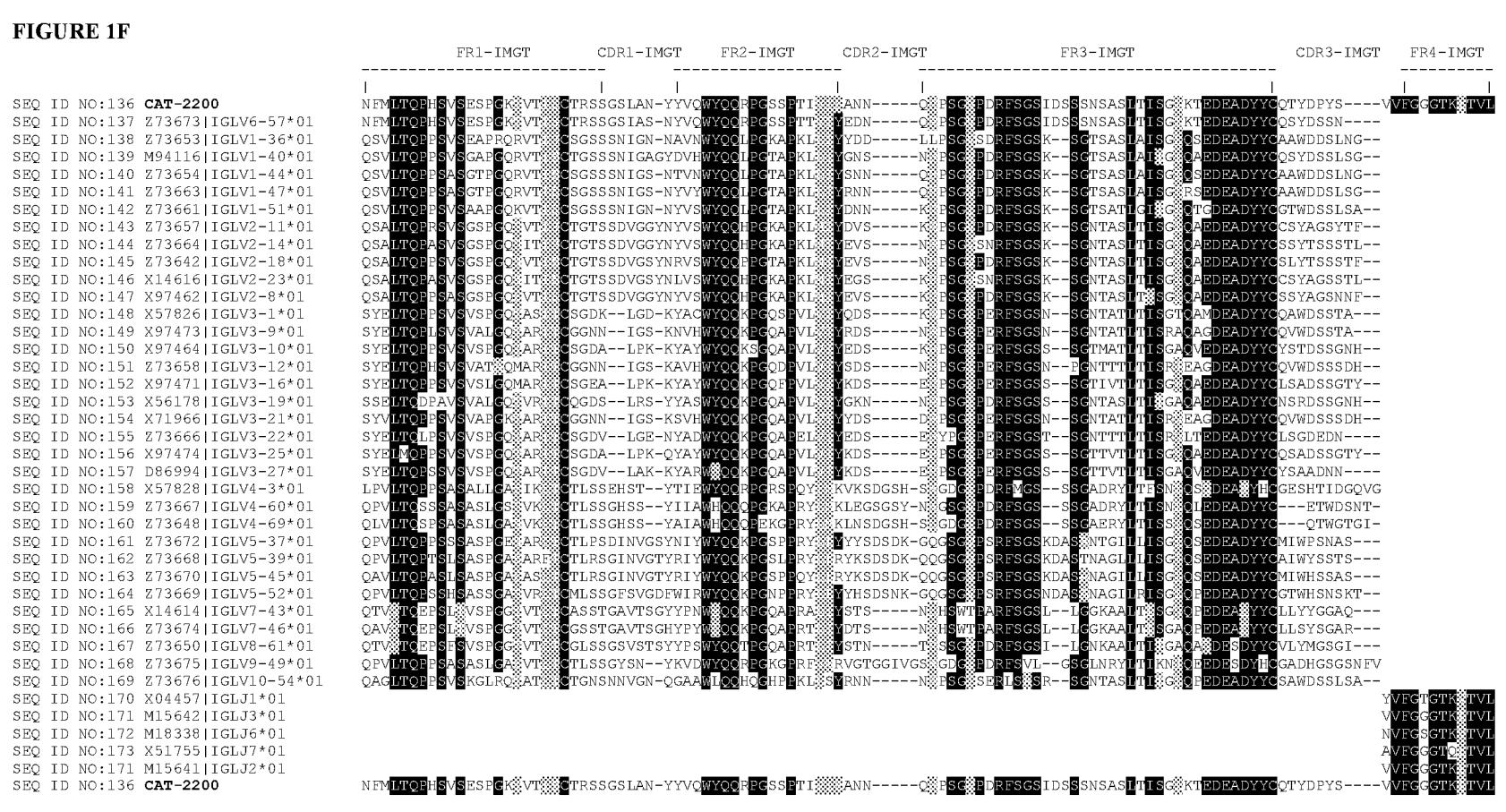

```
                              FR1-IMGT           CDR1-IMGT   FR2-IMGT   CDR2-IMGT        FR3-IMGT                 CDR3-IMGT   FR4-IMGT
SEQ ID NO:136 CAT-2200           NFMLTQPHSVSESPGK VT  CTRSSGSLAN-YYVQWYQQRPGSSPTI   ANN-----Q PSG PDRFSGSIDSSSNSASLTISG KTEDEADYYCQTYDPYS----VVFGGGTK TVL
SEQ ID NO:137 Z73673|IGLV6-57*01 NFMLTQPHSVSESPGK VT  CTRSSGSIAS-NYVQWYQQRPGSSPTT  YEDN-----Q PSG PDRFSGSIDSSSNSASLTISG KTEDEADYYCQSYDSSN----
SEQ ID NO:138 Z73653|IGLV1-36*01 QSVLTQPPSVSEAPRQRVT  CSGSSSNIGN-NAVNWYQQLPGKAPKL  YYDD-----LLPSG SDRFSGSK--SGTSASLAISG QSEDEADYYCAAWDDSLNG--
SEQ ID NO:139 M94116|IGLV1-40*01 QSVLTQPPSVSGAPGQRVT  CTGSSSNIGAGYDVHWYQQLPGTAPKL  YGNS-----N PSG PDRFSGSK--SGTSASLAI G QAEDEADYYCQSYDSSLSG--
SEQ ID NO:140 Z73654|IGLV1-44*01 QSVLTQPPSASGTPGQRVT  CSGSSSNIGS-NTVNWYQQLPGTAPKL  YSNN-----Q PSG PDRFSGSK--SGTSASLAISG QSEDEADYYCAAWDDSLNG--
SEQ ID NO:141 Z73663|IGLV1-47*01 QSVLTQPPSASGTPGQRVT  CSGSSSNIGS-NYVYWYQQLPGTAPKL  YRNN-----Q PSG PDRFSGSK--SGTSASLAISG RSEDEADYYCAAWDDSLSG--
SEQ ID NO:142 Z73661|IGLV1-51*01 QSVLTQPPSVSAAPGQKVT  CSGSSSNIGN-NYVSWYQQLPGTAPKL  YDNN-----K PSG PDRFSGSK--SGTSATLGI G QTGDEADYYCGTWDSSLSA--
SEQ ID NO:143 Z73657|IGLV2-11*01 QSALTQPRSVSGSPGQ VT  CTGTSSDVGGYNYVSWYQQHPGKAPKL  YDVS-----K PSG PDRFSGSK--SGNTASLTISG QAEDEADYYCCSYAGSYTF--
SEQ ID NO:144 Z73664|IGLV2-14*01 QSALTQPASVSGSPGQ IT  CTGTSSDVGGYNYVSWYQQHPGKAPKL  YEVS-----N PSG SNRFSGSK--SGNTASLTISG QAEDEADYYCSSYTSSSTL--
SEQ ID NO:145 Z73642|IGLV2-18*01 QSALTQPPSVSGSPGQ VT  CTGTSSDVGSYNRVSWYQQPPGTAPKL  YEVS-----N PSG PDRFSGSK--SGNTASLTISG QAEDEADYYCSLYTSSSTF--
SEQ ID NO:146 X14616|IGLV2-23*01 QSALTQPASVSGSPGQ IT  CTGTSSDVGSYNLVSWYQQHPGKAPKL  YEGS-----K PSG SNRFSGSK--SGNTASLTISG QAEDEADYYCCSYAGSSTL--
SEQ ID NO:147 X97462|IGLV2-8*01  QSALTQPPSASGSPGQ VT  CTGTSSDVGGYNYVSWYQQHPGKAPKL  YEVS-----K PSG PDRFSGSK--SGNTASLT SG QAEDEADYYCSSYAGSNNF--
SEQ ID NO:148 X57826|IGLV3-1*01  SYELTQPPSVSVSPGQ AS  CSGDK--LGD-KYACWYQQKPGQSPVL  YQDS-----K PSG PERFSGSN--SGNTATLTISGTQAMDEADYYCQAWDSSTA---
SEQ ID NO:149 X97473|IGLV3-9*01  SYELTQPLSVSVALGQ AR  CGGNN--IGS-KNVHWYQQKPGQAPVL  YRDS-----N PSG PERFSGSN--SGNTATLTISRAQAGDEADYYCQVWDSSTA---
SEQ ID NO:150 X97464|IGLV3-10*01 SYELTQPPSVSVSPGQ AR  CSGDA--LPK-KYAYWYQQKSGQAPVL  YEDS-----K PSG PERFSGSS--SGTMATLTISGAQVEDEADYYCYSTDSSGNH--
SEQ ID NO:151 Z73658|IGLV3-12*01 SYELTQPHSVSVAT QMAR  CGGNN--IGS-KAVHWYQQKPGQDPVL  YSDS-----N PSG PERFSGSN--PGNTTTLTISR EAGDEADYYCQVWDSSSDH--
SEQ ID NO:152 X97471|IGLV3-16*01 SYELTQPPSVSVSLGQMAR  CSGEA--LPK-KYAYWYQQKPGQFPVL  YKDS-----E PSG PERFSGSS--SGTIVTLTISG QAEDEADYYCLSADSSGTY--
SEQ ID NO:153 X56178|IGLV3-19*01 SSELTQDPAVSVALGQ VR  CQGDS--LRS-YYASWYQQKPGQAPVL  YGKN-----N PSG PDRFSGSS--SGNTASLTI GAQAEDEADYYCNSRDSSGNH--
SEQ ID NO:154 X71966|IGLV3-21*01 SYVLTQPPSVSVAPGK AR  CGGNN--IGS-KSVHWYQQKPGQAPVL  YYDS-----D PSG PERFSGSN--SGNTATLTISR EAGDEADYYCQVWDSSSDH--
SEQ ID NO:155 Z73666|IGLV3-22*01 SYELTQLPSVSVSPGQ AR  CSGDV--LGE-NYADWYQQKPGQAPEL  YEDS-----E YPG PERFSGST--SGNTTTLTISR LTEDEADYYCLSGDEDN----
SEQ ID NO:156 X97474|IGLV3-25*01 SYELMQPPSVSVSPGQ AR  CSGDA--LPK-QYAYWYQQKPGQAPVL  YKDS-----E PSG PERFSGSS--SGTTVTLTISG QAEDEADYYCQSADSSGTY--
SEQ ID NO:157 D86994|IGLV3-27*01 SYELTQPSSVSVSPGQ AR  CSGDV--LAK-KYARW QQKPGQAPVL  YKDS-----E PSG PERFSGSS--SGTTVTLTISGAQVEDEADYYCYSAADNN----
SEQ ID NO:158 X57828|IGLV4-3*01  LPVLTQPPSASALLGA IK  CTLSSEHST--YTIEWYQQRPGRSPQY  KVKSDGSH-S GDG PDRFMGS--SSGADRYLTFSN QS DEA YHCGESHTIDGQVG
SEQ ID NO:159 Z73667|IGLV4-60*01 QPVLTQSSSASASLGS VK  CTLSSGHSS--YIIAWHQQQPGKAPRY  KLEGSGSY-N GSG PDRFSGS--SSGADRYLTISN QLEDEADYYC---ETWDSNT-
SEQ ID NO:160 Z73648|IGLV4-69*01 QLVLTQSPSASASLGA VK  CTLSSGHSS--YAIAWHQQQPEKGPRY  KLNSDGSH-S GDG PDRFSGS--SSGAERYLTISS QSEDEADYYC---QTWGTGI-
SEQ ID NO:161 Z73672|IGLV5-37*01 QPVLTQPPSSSASPGE AR  CTLPSDINVGSYNIYWYQQKPGSPPRY  YYYSDSDK-GQGSG PSRFSGSKDAS NTGILLISG QSEDEADYYCMIWPSNAS---
SEQ ID NO:162 Z73668|IGLV5-39*01 QPVLTQPTSLSASPGA ARF CTLRSGINVGTYRIYWYQQKPGSLPRY  RYKSDSDK-QQGSG PSRFSGSKDASTNAGLLLISG QSEDEADYYCAIWYSSTS---
SEQ ID NO:163 Z73670|IGLV5-45*01 QAVLTQPASLSASPGA AS  CTLRSGINVGTYRIYWYQQKPGSPPQY  RYKSDSDK-QQGSG PSRFSGSKDAS NAGILLISG QSEDEADYYCMIWHSSAS---
SEQ ID NO:164 Z73669|IGLV5-52*01 QPVLTQPSSHSASSGA VR  CMLSSGFSVGDFWIRWYQQKPGNPPRY  YYHSDSNK-GQGSG PSRFSGSNDAS NAGILRISG QPEDEADYYCGTWHSNSKT--
SEQ ID NO:165 X14614|IGLV7-43*01 QTV TQEPSL VSPGG VT  CASSTGAVTSGYYPNW QQKPGQAPRA  YSTS-----N HSWTPARFSGSL--LGGKAALT SG QPEDEA YYCLLYYGGAQ---
SEQ ID NO:166 Z73674|IGLV7-46*01 QAV TQEPSL VSPGG VT  CGSSTGAVTSGHYPYW QQKPGQAPRT  YDTS-----N HSWTPARFSGSL--LGGKAALT SGAQPEDEA YYCLLSYSGAR---
SEQ ID NO:167 Z73650|IGLV8-61*01 QTV TQEPSFSVSPGG VT  CGLSSGSVSTSYYPSWYQQTPGQAPRT  YSTN-----T SSG PDRFSGSI--LGNKAALTI GAQA DESDYYCVLYMGSGI---
SEQ ID NO:168 Z73675|IGLV9-49*01 QPVLTQPPSASASLGA VT  CTLSSGYSN--YKVDWYQQRPGKGPRF  RVGTGGIVGS GDG PDRFSVL--GSGLNRYLTIKN QEEDESDYHCGADHGSGSNFV
SEQ ID NO:169 Z73676|IGLV10-54*01 QAGLTQPPSVSKGLRQ AT  CTGNSNNVGN-QGAAWLQQHQGHPPKL SYRNN-----N PSG SERLS SR--SGNTASLTI G QPEDEADYYCSAWDSSLSA--
SEQ ID NO:170 X04457|IGLJ1*01                                                                                                                  YVFGTGTK TVL
SEQ ID NO:171 M15642|IGLJ3*01                                                                                                                  VVFGGGTK TVL
SEQ ID NO:172 M18338|IGLJ6*01                                                                                                                  NVFGSGTK TVL
SEQ ID NO:173 X51755|IGLJ7*01                                                                                                                  AVFGGGTQ TVL
SEQ ID NO:171 M15641|IGLJ2*01                                                                                                                  VVFGGGTK TVL
SEQ ID NO:136 CAT-2200           NFMLTQPHSVSESPGK VT  CTRSSGSLAN-YYVQWYQQRPGSSPTI   ANN-----Q PSG PDRFSGSIDSSSNSASLTISG KTEDEADYYCQTYDPYS----VVFGGGTK TVL
```

FIGURE 1G

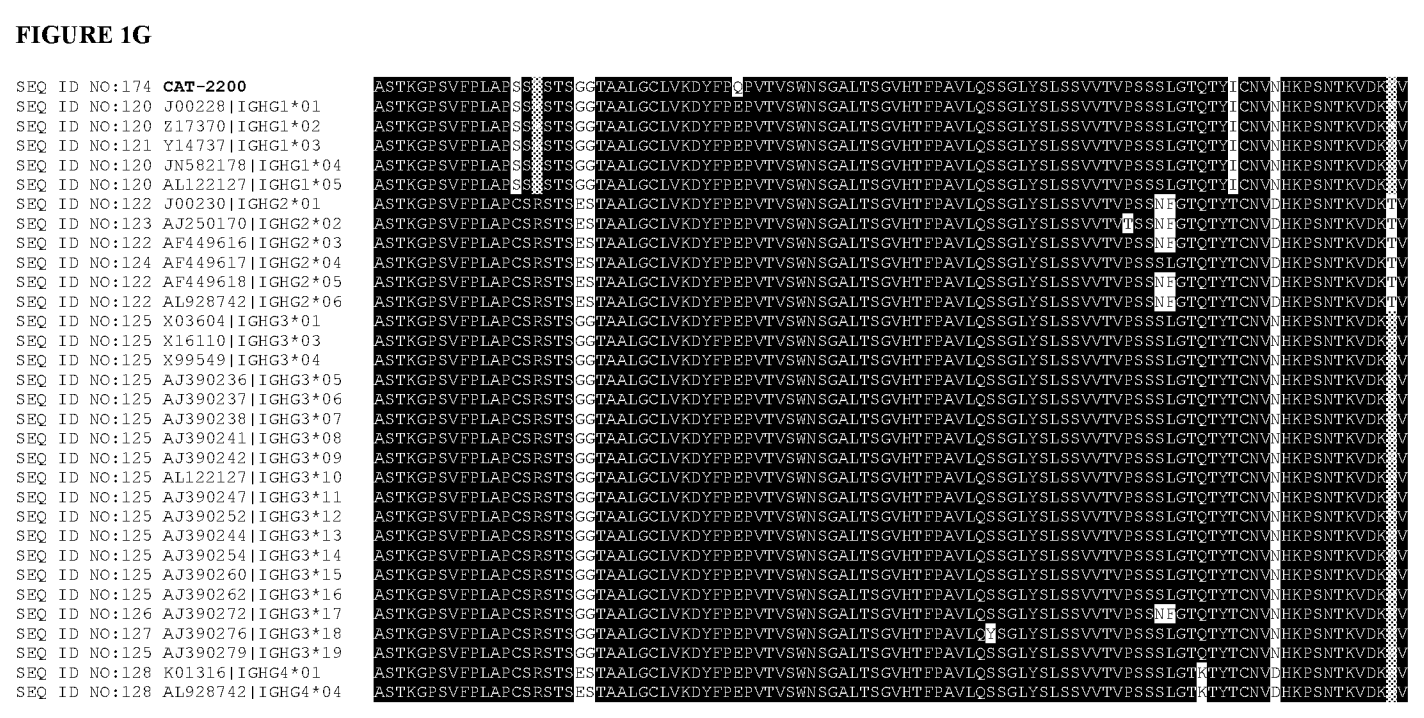

| | |
|---|---|
| SEQ ID NO:174 **CAT-2200** | ASTKGPSVFPLAPSS[illegible]STSGGTAALGCLVKDYFPQPVTVSWNSGALTSGVHTFPAVLQSSGLYSLSSVVTVPSSSLGTQTYICNVNHKPSNTKVDK[illegible]V |
| SEQ ID NO:120 J00228\|IGHG1*01 | ASTKGPSVFPLAPSS[illegible]STSGGTAALGCLVKDYFPEPVTVSWNSGALTSGVHTFPAVLQSSGLYSLSSVVTVPSSSLGTQTYICNVNHKPSNTKVDK[illegible]V |
| SEQ ID NO:120 Z17370\|IGHG1*02 | ASTKGPSVFPLAPSS[illegible]STSGGTAALGCLVKDYFPEPVTVSWNSGALTSGVHTFPAVLQSSGLYSLSSVVTVPSSSLGTQTYICNVNHKPSNTKVDK[illegible]V |
| SEQ ID NO:121 Y14737\|IGHG1*03 | ASTKGPSVFPLAPSS[illegible]STSGGTAALGCLVKDYFPEPVTVSWNSGALTSGVHTFPAVLQSSGLYSLSSVVTVPSSSLGTQTYICNVNHKPSNTKVDK[illegible]V |
| SEQ ID NO:120 JN582178\|IGHG1*04 | ASTKGPSVFPLAPSS[illegible]STSGGTAALGCLVKDYFPEPVTVSWNSGALTSGVHTFPAVLQSSGLYSLSSVVTVPSSSLGTQTYICNVNHKPSNTKVDK[illegible]V |
| SEQ ID NO:120 AL122127\|IGHG1*05 | ASTKGPSVFPLAPSS[illegible]STSGGTAALGCLVKDYFPEPVTVSWNSGALTSGVHTFPAVLQSSGLYSLSSVVTVPSSSLGTQTYICNVNHKPSNTKVDK[illegible]V |
| SEQ ID NO:122 J00230\|IGHG2*01 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO:123 AJ250170\|IGHG2*02 | ASTKGPSVFPLAPCSRSTSESTAALGCLVKDYFPEPVTVSWNSGALTSGVHTFPAVLQSSGLYSLSSVVTVTSSNFGTQTYTCNVDHKPSNTKVDKTV |
| SEQ ID NO:122 AF449616\|IGHG2*03 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO:124 AF449617\|IGHG2*04 | ASTKGPSVFPLAPCSRSTSESTAALGCLVKDYFPEPVTVSWNSGALTSGVHTFPAVLQSSGLYSLSSVVTVPSSSLGTQTYTCNVDHKPSNTKVDKTV |
| SEQ ID NO:122 AF449618\|IGHG2*05 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO:122 AL928742\|IGHG2*06 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO:125 X03604\|IGHG3*01 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 X16110\|IGHG3*03 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 X99549\|IGHG3*04 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390236\|IGHG3*05 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390237\|IGHG3*06 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390238\|IGHG3*07 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390241\|IGHG3*08 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390242\|IGHG3*09 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AL122127\|IGHG3*10 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390247\|IGHG3*11 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390252\|IGHG3*12 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390244\|IGHG3*13 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390254\|IGHG3*14 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390260\|IGHG3*15 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:125 AJ390262\|IGHG3*16 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:126 AJ390272\|IGHG3*17 | ASTKGPSVFPLAPCSRSTSGGTAALGCLVKDYFPEPVTVSWNSGALTSGVHTFPAVLQSSGLYSLSSVVTVPSSNFGTQTYTCNVNHKPSNTKVDK[illegible]V |
| SEQ ID NO:127 AJ390276\|IGHG3*18 | ASTKGPSVFPLAPCSRSTSGGTAALGCLVKDYFPEPVTVSWNSGALTSGVHTFPAVLQYSGLYSLSSVVTVPSSSLGTQTYTCNVNHKPSNTKVDK[illegible]V |
| SEQ ID NO:125 AJ390279\|IGHG3*19 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDK[illegible]V |
| SEQ ID NO:128 K01316\|IGHG4*01 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDK[illegible]V |
| SEQ ID NO:128 AL928742\|IGHG4*04 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDK[illegible]V |

FIGURE 1H

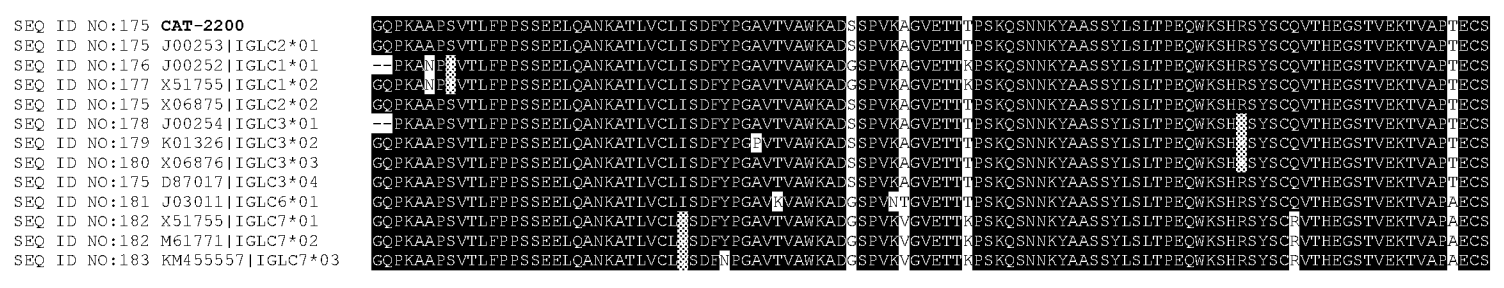

| | |
|---|---|
| SEQ ID NO:175 **CAT-2200** | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| SEQ ID NO:175 J00253\|IGLC2*01 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| SEQ ID NO:176 J00252\|IGLC1*01 | --PKANPSVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS |
| SEQ ID NO:177 X51755\|IGLC1*02 | GQPKANPSVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS |
| SEQ ID NO:175 X06875\|IGLC2*02 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| SEQ ID NO:178 J00254\|IGLC3*01 | --PKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPTECS |
| SEQ ID NO:179 K01326\|IGLC3*02 | GQPKAAPSVTLFPPSSEELQANKATLVCLISDFYPGPVTVAWKADSSPVKAGVETTTPSKQSNNKYAASSYLSLTPEQWKSHKSYSCQVTHEGSTVEKTVAPTECS |
| SEQ ID NO:180 X06876\|IGLC3*03 | GQPKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPTECS |
| SEQ ID NO:175 D87017\|IGLC3*04 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| SEQ ID NO:181 J03011\|IGLC6*01 | GQPKAAPSVTLFPPSSEELQANKATLVCLISDFYPGAVKVAWKADGSPVNTGVETTTPSKQSNNKYAASSYLSLTPEQWKSHRSYSCQVTHEGSTVEKTVAPAECS |
| SEQ ID NO:182 X51755\|IGLC7*01 | GQPKAAPSVTLFPPSSEELQANKATLVCLVSDFYPGAVTVAWKADGSPVKVGVETTKPSKQSNNKYAASSYLSLTPEQWKSHRSYSCRVTHEGSTVEKTVAPAECS |
| SEQ ID NO:182 M61771\|IGLC7*02 | GQPKAAPSVTLFPPSSEELQANKATLVCLVSDFYPGAVTVAWKADGSPVKVGVETTKPSKQSNNKYAASSYLSLTPEQWKSHRSYSCRVTHEGSTVEKTVAPAECS |
| SEQ ID NO:183 KM455557\|IGLC7*03 | GQPKAAPSVTLFPPSSEELQANKATLVCLVSDFNPGAVTVAWKADGSPVKVGVETTKPSKQSNNKYAASSYLSLTPEQWKSHRSYSCRVTHEGSTVEKTVAPAECS |

FIG. 3
B
A
D3H44 C-Kappa
CAT-2200 C-Lambda
D3H44 CH1
CAT-2200 CH1

Design 3972, CAT-2200/Pertuzumab system

A

Design 3972, CAT-2200/SGN-CD19a system

Design 3972, CR8071/SGN-CD19a system

C

G

*Constructs refer to specific presence of tags (FLAG or HA) on one of the light chains or absence of any tags.

*Constructs refer to specific presence of tags (FLAG or HA) on one of the light chains or absence of any tags.

ANTIGEN-BINDING POLYPEPTIDE CONSTRUCTS COMPRISING KAPPA AND LAMBDA LIGHT CHAINS AND USES THEREOF

SEQUENCE LISTING

The instant application contains a Sequence Listing which has been submitted electronically in ASCII format and is hereby incorporated by reference in its entirety. Said ASCII copy, created on Dec. 1, 2015, is named 0966216 and is 20.0 bytes in size.

BACKGROUND

Bispecific antibodies are capable of binding to two different epitopes, and are often prepared based on the immunoglobulin heavy and light chains of two different monospecific parent antibodies. The ability to bind to two different epitopes or antigens makes bispecific antibodies an attractive tool for therapeutic applications where there is a benefit to targeting more than one antigen or epitope in the treatment of disease. However, efficiently producing bispecific antibodies in a format that is similar to naturally occurring antibodies can be difficult, since antibody heavy chains have evolved to bind antibody light chains in a relatively promiscuous manner. As a result of this promiscuous pairing, concomitant expression of the two different heavy chains and two different light chains of a bispecific antibody naturally leads to the scrambling of heavy chain-light chain pairings. This scrambling remains a major challenge for the generation of bispecific therapeutics, where homogeneous pairing is an essential requirement for good manufacturability and biological efficacy.

Some approaches have been described to prepare bispecific antibodies in a format similar to naturally occurring antibodies. However, these approaches have been developed and exemplified for cases where both of the parent antibodies used to prepare the bispecific antibody have light chains of the kappa gene family.

Although the majority of known therapeutic antibodies (and thus potential parent antibodies) have kappa light chains, there are some that have lambda light chains. Kappa and lambda light chains differ from each other in both structure and sequence.

A review of various approaches to produce bispecific antibodies in a format similar to naturally occurring antibodies from two parent antibodies can be found in Klein et al., (2012) mAbs 4:6, 1-11. International Patent Application No. PCT/EP2011/056388 (WO 2011/131746) describes an in vitro method for generating a heterodimeric protein in which asymmetrical mutations are introduced into the CH3 regions of two monospecific starting proteins in order to drive directional "Fab-arm" or "half-molecule" exchange between two monospecific IgG4- or IgG4-like antibodies upon incubation under reducing conditions.

US Patent Publication No. 2009/0182127 (Novo Nordisk, Inc.) describes the generation of bi-specific antibodies by modifying amino acid residues at the Fc interface and at the CH1:CL interface of light-heavy chain pairs that reduce the ability of the light chain of one pair to interact with the heavy chain of the other pair. International Patent Publication Nos. WO2014/081955 (Amgen), and WO2014/150973 (Eli Lilly) describe amino acid residues in the lambda light chain that may potentially be modified to drive desired pairing specificity. Neither of these publications describe complementary amino acid modifications that can be used to prepare a bispecific antibody from one parent antibody with a kappa light chain and another parent antibody with a lambda light chain. International Patent Publication No. WO2012/131555 (Glenmark), describes replacing the interface between the heavy chain and lambda light chain of an antibody with that of a TCR (T-cell receptor) domain interface.

SUMMARY

The present disclosure provides multi specific antigen-binding polypeptides comprising an immunoglobulin lambda light chain and an immunoglobulin kappa light chain. In one aspect, the antigen-binding polypeptide is a construct comprising a first heterodimer and a second heterodimer. In one embodiment, the first heterodimer (H1L1) comprises a first immunoglobulin heavy chain polypeptide sequence (H1), and an immunoglobulin lambda light chain polypeptide sequence (L1) that form a first Fab region that specifically binds to a first antigen; and the second heterodimer (H2L2) comprises a second immunoglobulin heavy chain polypeptide sequence (H2), and an immunoglobulin kappa light chain polypeptide sequence (L2) that form a second Fab region that specifically binds to a second antigen. In some embodiments, H1 is distinct from H2. In some embodiments, H1 and H2 comprise a heavy chain variable domain (VH domain) and a heavy chain constant domain 1 (CH1 domain). In one embodiment, L1 comprises a lambda light chain variable (VL-lambda) domain and a lambda light chain constant (CL-lambda) domain. In one embodiment, L2 comprises a kappa light chain variable (VL-kappa) domain and a kappa light chain constant (CL-kappa) domain. In some embodiments, one or more of H1, H2, L1, and L2 comprise amino acid modifications as compared to corresponding wild type H1, H2, L1, and L2 polypeptide sequences, wherein the amino acid modifications promote preferential pairing of H1 with L1 as compared to L2, and/or promote preferential pairing of H2 with L2 as compared to L1. In some embodiments, the amino acid modifications do not introduce a new cysteine residue. In one embodiment, the amino acid modifications do not remove a naturally occurring cysteine residue.

In some embodiments, the construct comprises amino acid modifications that promote preferential pairing of H1 with L1 as compared to L2, and/or that promote preferential pairing of H2 with L2 as compared to L1, when H1, H2, L1 and L2 are co-expressed in a cell or a mammalian cell, or when H1, H2, L1 and L2 are co-expressed in a cell-free expression system, or when H1 and L1 are produced in a (first) cell and H2 and L2 are produced in a second (e.g., different) cell and the products of the two cells are mixed via a redox production method, or when H1 and L1 are produced in a first cell-free expression system and H2 and L2 are produced in a second (e.g., different) cell-free expression system and the products of the two cell-free expression systems are mixed.

In some embodiments of the construct, each heterodimer comprises a single Fab.

In some embodiments of the antigen-binding polypeptide constructs described herein:

a. H2 comprises amino acid substitution at position 143; L2 comprises an amino acid substitution at position 124; and
   i. H1 comprises amino acid substitution at position 186 or 179, and L1 comprises amino acid substitution at position 180;
   ii. H1 comprises amino acid substitution at position 186; and L1 comprises amino acid substitutions at position 133;

iii. H1 comprises amino acid substitution at position 143; and L1 comprises amino acid substitutions at position 133; or iv. H1 comprises amino acid substitution at position 188; and L1 comprises amino acid substitutions at position 178;

b. H1 comprises amino acid substitution at position 143; L1 comprises amino acid substitution at position 131; and i. H2 comprises amino acid substitution at positions 186, or 124 and 186, and L2 comprises amino acid substitution at positions 133, or 133 and 160, or 124 and 133, or 176 and 180; or ii. H2 comprises amino acid substitution at position 188; and L2 comprises amino acid substitutions at position 131;

iii. H2 comprises amino acid substitution at position 143; and L2 comprises amino acid substitutions at positions 124 and 133, or 124 and 133 and 180;

c. H1 comprises amino acid substitution at position 143; L1 comprises amino acid substitution at position 131; and i. H2 comprises amino acid substitution at positions 124 and 186, or 124 and 179, or 188, and L2 comprises amino acid substitution at positions 176 and 178, or 176 and 180, or 131; or ii. H2 comprises amino acid substitution at positions 143 and 188, or 143, or 124 and 143; and L2 comprises amino acid substitutions at positions 124 and 176 and 178, or 124 and 178, or 124 and 180, or 124 and 176 and 180, or 124, or 124 and 176;

d. H1 comprises amino acid substitution at position 179, 186, 143 and/or 188; L1 comprises amino acid substitution at position 180, 133 and/or 176 and 178; H2 comprises amino acid substitution at position 143, and L2 comprises amino acid substitution at position 131 and/or 124;

e. H1 comprises amino acid substitution at position 39 or comprises no amino acid substitutions that promote preferential pairing; L1 comprises amino acid substitution at position 38 or comprises no amino acid substitutions that promote preferential pairing; H2 comprises amino acid substitution at position 39, and L2 comprises amino acid substitution at position 38;

f. H1 comprises amino acid substitution at position 143; L1 comprises amino acid substitution at position 131; and i. H2 comprises amino acid substitution at positions 188 or 124 and 186, and L2 comprises amino acid substitution at positions 176 and 178, or 176 and 180, or 131; or ii. H2 comprises amino acid substitution at position 143 or 186; and L2 comprises amino acid substitutions at positions 124 and 133, or 124 and 133 and 180;

g. H1 comprises amino acid substitution at position 188; L1 comprises amino acid substitution at positions 176 and 178, or 178; and i. H2 comprises amino acid substitution at positions 177 and 188, and L2 comprises amino acid substitution at positions 176 and 178; or ii. H2 comprises amino acid substitution at position 186 or 124 or 124 and 179; and L2 comprises amino acid substitutions at positions 176, or 131 and 176;

h. H1 comprises amino acid substitution at position 186; L1 comprises amino acid substitution at position 133; and i. H2 comprises amino acid substitution at position 188, and L2 comprises amino acid substitution at position 131; or ii. H2 comprises amino acid substitution at positions 177 and 188; and L2 comprises amino acid substitutions at positions 176 and 178; or iii. H1 comprises amino acid substitution at positions 124 and 190; L1 comprises amino acid substitution at position 135; H2 comprises amino acid substitution at positions 124 or 188, and L2 comprises amino acid substitution at positions 176, or 176 and 178;

i. H1 comprises amino acid substitution at positions 177 and 188; L1 comprises amino acid substitution at position 176 and 178; and a. H2 comprises amino acid substitution at position 188, and L2 comprises amino acid substitution at positions 176 and 178, or 131;

b. H2 comprises amino acid substitution at position 186; and L2 comprises amino acid substitutions at positions 133, or 124 and 160 and 180;

c. H2 comprises amino acid substitution at position 124, or 124 and 179, or 124 and 186; and L2 comprises amino acid substitutions at positions 176, or 176 and 178, or 176 and 180; or d. H2 comprises amino acid substitution at position 143; and L2 comprises amino acid substitutions at positions 133, or 124 and 133;

j. H1 comprises amino acid substitution at position 188; L1 comprises amino acid substitution at position 178; H2 comprises amino acid substitution at position 124 or 188, and L2 comprises amino acid substitution at positions 176 and 178, or 176 and 180, or 176;

k. or H1 comprises amino acid substitution at positions 145 and 188; L1 comprises amino acid substitution at position 178; and H2 comprises amino acid substitution at position 124 and/or 188, and L2 comprises amino acid substitution at one or more of positions 124, 133, and 178;

l. H1 comprises amino acid substitution at position 174, 179 or 186; L1 comprises amino acid substitution at position 176 or 180; H2 comprises amino acid substitution at position 143 or 190, and L2 comprises amino acid substitution at position 131, 135 or 124; or m. H1 comprises amino acid substitution at position 174; L1 comprises amino acid substitution at position 176; H2 comprises amino acid substitution at position 190; and L2 comprises no amino acid substitutions that promote preferential pairing or comprises amino acid substitution at position 135;

n. H1 comprises amino acid substitution at positions 143 and 190; L1 comprises amino acid substitution at position 133; H2 comprises amino acid substitution at position 124, and L2 comprises amino acid substitution at positions 131 and 135;

o. H1 comprises amino acid substitution at position 143 and/or 186; L1 comprises amino acid substitution at position 133; H2 comprises amino acid substitution at position 124, and L2 comprises amino acid substitution at position 131;

p. H1 comprises amino acid substitution at positions 143 and 179; L1 comprises amino acid substitution at positions 124 and 178; H2 comprises amino acid substitution at position 186, and L2 comprises amino acid substitution at positions 178 and 180, or 160 and 180;

q. H1 comprises amino acid substitution at position 143; L1 comprises amino acid substitution at position 124; H2 comprises amino acid substitution at position 179 or 186, and L2 comprises amino acid substitution at position 124 and 160 and 180;

r. H1 comprises amino acid substitution at position 186; L1 comprises amino acid substitution at positions 180 or 178 and 180; H2 comprises amino acid substitution at position 143 and/or 179, and L2 comprises amino acid substitution at positions 124 and 178, or 131;

s. H1 comprises amino acid substitution at position 179; L1 comprises amino acid substitution at position 180; H2 comprises amino acid substitution at position 143, and L2 comprises amino acid substitution at position 124;

t. H1 comprises amino acid substitution at position 143 or 186; L1 comprises amino acid substitution at position 180 or comprises no amino acid substitutions that promote preferential pairing; H2 comprises amino acid substitution at positions 143 and 145, and L2 comprises amino acid substitution at position 124;

u. H1 comprises no amino acid substitutions that promote preferential pairing; L1 comprises amino acid substitution at position 135; H2 comprises amino acid substitution at position 139, and L2 comprises amino acid substitution at position 116;

v. H1 comprises no amino acid substitutions that promote preferential pairing or comprises amino acid substitution at position 45; L1 comprises no amino acid substitutions that promote preferential pairing; H2 comprises amino acid substitution at position 45, and L2 comprises amino acid substitution at position 44;

w. H1 comprises amino acid substitution at position 139; L1 comprises amino acid substitution at position 116; H2 comprises no amino acid substitutions that promote preferential pairing, and L2 comprises amino acid substitution at position 135; or x. H1 comprises amino acid substitution at position 124; L1 comprises amino acid substitution at position 176; H2 comprises amino acid substitution at position 124, and L2 comprises amino acid substitution at position 176.

In some embodiments, the affinity of the first Fab region for the first antigen is within about 1, 2, 3, 4, 5, 6, 7, 8, 9, 10, 20, 25, 30, 35, 40, 45, 50 or 100-fold of the affinity of a Fab region formed by the corresponding wild type H1 and L1 polypeptide sequences for the first antigen, and/or the affinity of the second Fab region for the second antigen is within about 1, 2, 3, 4, 5, 6, 7, 8, 9, 10, 20, 25, 30, 35, 40, 45, 50 or 100-fold of the affinity of a Fab region formed by the corresponding wild type H2 and L2 polypeptide sequences for the second antigen.

In some embodiments, the melting temperature (Tm) of the first Fab region is within about 0, 1, 2, 3, 4, 5, 6, 7, 8, 9, 10, or 20° C. of the Tm of a Fab region formed by the corresponding wild type H1 and L1 polypeptide sequences for the first antigen, and/or the melting temperature (Tm) of the second Fab region is within about 0, 1, 2, 3, 4, 5, 6, 7, 8, 9, 10, or 20° C. of the Tm of a Fab region formed by the corresponding wild type H2 and L2 polypeptide sequences for the second antigen.

In some embodiments of the antigen-binding polypeptide construct:

a. H1 and L1 are wild type polypeptide sequences and H2 and L2 each comprise at least one amino acid modification;
b. one or more of H1, L1, and H2 comprise at least one amino acid modification, and L2 is a wild type polypeptide sequence;
c. one or more of H1, L1, and L2 comprise at least one amino acid modification, and H2 is a wild type polypeptide sequence;
d. one or more of H1, H2, and L2 comprise at least one amino acid modification and L1 is a wild type polypeptide sequence;
e. one or more of L1, H2, and L2 comprise at least one amino acid modification and H1 is a wild type polypeptide sequence; or
f. H1, L1, H2, and L2 each comprise at least one amino acid modification.

In some embodiments, the amino acid modifications are in:

a. the CH1 domains of H1 and H2, the CL-lambda domain of L1 and the CL-kappa domain of L2; or
b. the CH1 and VH domains of H1 and H2, the CL-lambda domain and VL-lambda domain of L1, and the CL-kappa domain and VL-kappa domain of L2.

In some embodiments, the amino acid modifications are in:

a. at least two of the CH1 domain of H1, the CH1 domain of H2, the CL-lambda domain of L1 and the CL-kappa domain of L2;
b. at least two of the CH1 and VH domains of H1 and H2, the CL-lambda domain and VL-lambda domain of L1, and the CL-kappa domain and VL-kappa domain of L2, or
c. at least two of the VH domain of H1, the VH domain of H2, the VL-lambda domain of L1, and the VL-kappa domain of L2.

In some embodiments, H1, L1, H2, and/or L2 comprises at least 1, 2, 3, 4, 5, 6, 7, or 8, amino acid mutations in the Fab region. In some embodiments, at least one of H1, H2, L1 and L2 comprises at least 2, 3, 4, 5, 6, 7, 8, 9, or 10 amino acid modifications of at least one constant domain and/or at least one variable domain.

In one embodiment, one or more of H1, H2, L1 and L2 comprise amino acid modifications that promote preferential pairing of H1 with L1 as compared to L2 to form H1L1, or H2 with L2 as compared to L1 to form H2L2, such that the relative pairing of at least one of H1L1 or H2L2 is at least about 10% greater relative to wild-type, and the relative pairing of the other is within about 10% of wild-type or at least about 10% greater relative to wild-type.

In some embodiments, the amino acid modifications promote preferential pairing of H1 with L1 as compared to L2 to form H1L1, or H2 with L2 as compared to L1 to form H2L2, where the ratio of H1L1:H1L2 is at least 40:60 and the ratio of H2L2:H2L1 is at least 60:40; or the amino acid modifications promote preferential pairing of H1 with L1 as compared to L2 to form H1L1, or H2 with L2 as compared to L1 to form H2L2, where the ratio of H2L2:H2L1 is at least 40:60 and the ratio of H1L1:H1L2 is at least 60:40.

In some embodiments, the thermal stability of the first Fab region is within about 0, 1, 2, or 3° C. of the Tm of a Fab region formed by the corresponding wild type H1 and L1 polypeptide sequences. In some embodiments, the thermal stability of the second Fab region is within about 0, 1, 2, or 3° C. of the Tm of the Fab region formed by the corresponding wild type H2 and L2 polypeptide sequences.

In some embodiments, the amino acid modifications are selected from the group consisting of the unique identifier Mab design sets shown in Table 4A or 4B. In some embodiments, the amino acid modifications are selected from the group consisting of the unique identifier Mab design sets shown in one or more of Tables 10-A1 to 10-A12. In some embodiments, the amino acid modifications are selected from the group consisting of the unique identifier Mab design sets shown in any one of Tables 10-B1 to 10-B10.

In some embodiments, the construct further comprises a dimeric Fc having two Fc polypeptides each comprising a CH3 domain sequence and coupled with or without linkers to one of the first Fab region and second Fab region. In some embodiments, the Fc is a human Fc, a human IgG1 Fc, a human IgA Fc, a human IgG Fc, a human IgD Fc, a human IgE Fc, a human IgM Fc, a human IgG2 Fc, a human IgG3

Fc, or a human IgG4 Fc. In one embodiment, the Fc comprises one or more modifications as compared to wild type, in at least one of the CH3 domain sequences that promote the formation of a heterodimeric Fc.

In some embodiments, the Fc comprises:

i) a heterodimeric IgG1 Fc having the modifications L351Y_F405A_Y407V in the first Fc polypeptide, and the modifications T366L_K392M_T394W in the second Fc polypeptide;

ii) a heterodimeric IgG1 Fc having the modifications L351Y_F405A_Y407V in the first Fc polypeptide, and the modifications T366L_K392L_T394W in the second Fc polypeptide;

iii) a heterodimeric IgG1 Fc having the modifications T350V_L351Y_F405A_Y407V in the first Fc polypeptide, and the modifications T350V_T366L_K392L_T394W in the second Fc polypeptide;

iv) a heterodimeric IgG1 Fc having the modifications T350V_L351Y_F405A_Y407V in the first Fc polypeptide, and the modifications T350V_T366L_K392M_T394W in the second Fc polypeptide; or v) a heterodimeric IgG1 Fc having the modifications T350V_L351Y_S400E_F405A_Y407V in the first Fc polypeptide, and the modifications T350V_T366L_N390R_K392M_T394W in the second Fc polypeptide.

In some embodiments, the Fc further comprises at least one CH2 domain sequence. In one embodiment, the Fc comprises one or more modifications to promote selective binding of Fc-gamma receptors, to reduce or eliminate binding to Fc-gamma receptors, or to promote binding to FcRn.

In some embodiments, when H1, L1, H2 and L2 are co-expressed, the change in the amount of total correct pairing as measured by the sum of H1L1 and H2L2 pairing is greater than about 5%, 10%, 15%, 20%, 25%, 30%, 35%, 40%, or 45% compared to the pairing of corresponding H1, L1, H2 and L2 polypeptide chains without amino acid substitutions in the Fab region that promote preferential pairing; or the change in the amount of total correct pairing, as measured by the amount of bispecific antibody produced as a percentage of species other than half-antibodies produced, is greater than about 5%, 10%, 20%, 30%, 40%, 50%, 60%, 70%, or 80%, compared to the pairing of corresponding H1, L1, H2 and L2 polypeptide chains without amino acid substitutions in the Fab region that promote preferential pairing, or the change in the amount of total correct pairing, as measured by the amount of bispecific antibody produced as a percentage of all species produced, is greater than about 5%, 10%, 20%, 30%, 40%, 50%, 60%, 70%, or 80%, compared to the pairing of corresponding H1, L1, H2 and L2 polypeptide chains without amino acid substitutions in the Fab region that promote preferential pairing.

In some embodiments, the linkers comprise one or more polypeptide linkers, one or more antibody hinge regions, or one or more IgG1 hinge regions. In one embodiment, the one or more polypeptide linkers comprise one or more modifications as compared to a wild type polypeptide linker.

In some embodiments, the amino acid modifications comprise amino acid substitutions.

In some embodiments, the sequences of one or more of H1, H2, L1, and L2 are derived from human sequences or humanized sequences.

In some embodiments, the constructs described herein are conjugated to a therapeutic agent or drug.

In another aspect, the disclosure provides an isolated recombinant polynucleotide or set of isolated recombinant polynucleotides that encode(s) the constructs described herein. In some embodiments, provided are a vector or a set of vectors comprising one or more of the polynucleotides or sets of polynucleotides described herein. In some embodiments, the vector or at least one vector of the set of vectors is multi-cistronic.

In another aspect, the disclosure provides an isolated cell comprising the polynucleotide or set of polynucleotides, or the vector or set of vectors described herein. In some embodiments, the cell is a yeast cell, a bacterial cell, an insect cell, or a mammalian cell. In some embodiments, the isolated cell is stably transfected or transiently transfected with the vector or set of vectors described herein.

In another aspect, a pharmaceutical composition comprising the antigen-binding polypeptide constructs described herein is provided. In some embodiments, the pharmaceutical composition comprises a pharmaceutically acceptable carrier. In some embodiments, the pharmaceutical composition further comprises one or more substances selected from the group consisting of a buffer, an antioxidant, a low molecular weight molecule, a drug, a protein, an amino acid, a carbohydrate, a lipid, a chelating agent, a stabilizer, and an excipient.

In another aspect, a method of preparing the constructs described herein is described. In some embodiments, the method comprises the steps of:

(a) obtaining a host cell comprising a polynucleotide or set of polynucleotides encoding the antigen-binding polypeptide construct;

(b) culturing the host cell in a host cell culture under conditions that allow expression of the antigen-binding polypeptide construct, and (c) collecting the antigen-binding polypeptide construct from the host cell culture.

In some embodiments, the host cell is transiently transfected or stably transfected with the polynucleotide or set polynucleotides described herein.

In another aspect, a computer-readable storage medium is provided. In some embodiments, the computer-readable storage medium stores a dataset comprising data representing complementary amino acid modifications in a first heterodimer comprising a first immunoglobulin heavy chain polypeptide sequence (H1) and a first immunoglobulin lambda light chain polypeptide sequence (L1); and/or a second heterodimer comprising a second immunoglobulin heavy chain polypeptide sequence (H2) and a second immunoglobulin kappa light chain polypeptide sequence (L2). In some embodiments, the H1 and H2 polypeptide sequences stored in the dataset comprise at least a heavy chain variable domain (VH domain) and a heavy chain constant domain (CH1 domain) and are distinct from each other. In some embodiments, the L1 and L2 polypeptide sequences stored in the dataset comprise at least a light chain variable domain (VL domain) and a light chain constant domain (CL domain). In some embodiments, the complementary amino acid modifications stored in the dataset promote preferential pairing of H1 with L1 as compared to L2, and of H2 with L2 as compared to L1. In some embodiments, the dataset comprises data representing those modifications listed in Table 4A or Table 4B or a subset of those modifications. In some embodiments, the dataset comprises data representing those modifications listed in one or more of Tables 10-A1 to 10-A12 or Tables 10-B1 to 10-B10, or a subset of those modifications In another aspect, a method of producing a bispecific antigen-binding polypeptide construct is described. In some embodiments, the bispecific antigen-binding polypeptide construct produced by the method comprises:

a. a first heterodimer comprising a first immunoglobulin heavy chain polypeptide sequence (H1) and a first immunoglobulin lambda light chain polypeptide sequence (L1); and b. a second heterodimer comprising a second immunoglobulin heavy chain polypeptide sequence (H2) and a second immunoglobulin kappa light chain polypeptide sequence (L2).

In some embodiments, the H1 and H2 polypeptide sequences produced by the method comprise at least a heavy chain variable domain (VH domain) and a heavy chain constant domain (CH1 domain) and are distinct from each other. In some embodiments, the L1 and L2 polypeptide sequences produced by the method comprise a light chain variable domain (VL domain) and a light chain constant domain (CL domain). In some embodiments, one or more of H1, L1, H2, and L2 polypeptide sequences produced by the method comprise amino acid modifications that promote preferential pairing of H1 with L1 as compared to L2 and of H2 with L2 as compared to L1.

In some embodiments, the method of producing the bispecific antigen-binding polypeptide construct comprises:

a. introducing one or more complementary amino acid modifications from the dataset described herein into H1, L1, H2 and/or L2; and b. co-expressing H1, L1, H2 and L2 in a host cell to produce an expression product comprising the bi-specific antigen-binding polypeptide construct.

In some embodiments, the method further comprises determining the amount of the bispecific antigen-binding polypeptide construct in the expression product relative to other polypeptide products to select a preferred subset of complementary amino acid modifications that provide an increased amount of the bispecific antigen-binding polypeptide construct as compared to the amount of bispecific antigen-binding polypeptide construct in an expression product resulting from the co-expression of wild type H1, L1, H2 and L2. In some embodiments, the bispecific antigen-binding polypeptide construct is produced with a purity of greater than 70% compared to the other polypeptide products. In some embodiments, the construct produced by the method comprises an Fc comprising at least two CH3 domain sequences, and the Fc is coupled, with or without one or more linkers, to the first heterodimer and the second heterodimer. In some embodiments, the Fc is a heterodimeric Fc comprising one or more amino acid modifications that promote formation of a heterodimeric Fc over a homodimeric Fc.

In some embodiments of the method for producing the bispecific antigen-binding polypeptide construct, when H1, L1, H2 and L2 are co-expressed, the change in the amount of total correct pairing as measured by the sum of % H1L1 and % H2L2 produced is greater than about 5%, 10%, 15%, 20%, 25%, 30%, 35%, 40%, or 45% compared to the pairing of corresponding H1, L1, H2 and L2 polypeptide chains without amino acid substitutions in the Fab region that promote preferential pairing; or the change in the amount of total correct pairing as measured by the amount of bispecific antibody produced as a percentage of species other than half-antibodies produced is greater than about 5%, 10%, 20%, 30%, 40%, 50%, 60%, 70%, or 80%, compared to the pairing of corresponding H1, L1, H2 and L2 polypeptide chains without amino acid substitutions in the Fab region that promote preferential pairing; or the change in the amount of total correct pairing as measured by the amount of bispecific antibody produced as a percentage of all species produced is greater than about 5%, 10%, 20%, 30%, 40%, 50%, 60%, 70%, or 80%, compared to the pairing of corresponding H1, L1, H2 and L2 polypeptide chains without amino acid substitutions in the Fab region that promote preferential pairing.

BRIEF DESCRIPTION OF THE FIGURES

FIG. 1 depicts D3H44, Pertuzumab, and CAT-2200 heavy chain and light chain amino acid sequences aligned against human germline sequences for Variable and Constant domains. Translated protein sequences for each Domain, Germline, and Allele were obtained by directly querying the IMGT/GENE-DB (http://www.imgt.org/genedb/query). IMGT/DomainGapAlign (http://www.imgt.org/3Dstructure-DB/cgi/DomainGapAlign.cgi) was used to determine the closest gene/allele. Identification of consensus sequences was performed by BoxShade (http://www.ch.embnet.org/softwareBOX_form.html) with a 0.8 cut-off. Amino acid residues shaded in black represent amino acid sequence identity, while those shaded in gray represent amino acid sequence similarity. The assignment of amino acids to each domain in FIG. 1 was made according to IMGT definitions as described in Lefranc M.-P. et al. "IMGT unique numbering for immunoglobulin and T cell receptor constant domains and Ig superfamily C-like domains" Dev. Comp. Immunol., 2005, 29, 185-203, and Lefranc, M.-P., Pommié, C., Ruiz, M., Giudicelli, V., Foulquier, E., Truong, L., Thouvenin-Contet, V. and Lefranc, G. "IMGT unique numbering for immunoglobulin and T cell receptor variable domains and Ig superfamily V-like domains" Dev. Comp. Immunol., 27, 55-77 (2003). FIG. 1C depicts Pertuzumab and D3H44 constant heavy 1 (CH1) domains aligned against human CH1 IGHG germline subgroups. The closest gene and allele sequence to Pertuzumab and D3H44 IGHG is J00228|IGHG1*01. FIG. 1D depicts Pertuzumab and D3H44 constant light (CL) domains aligned against human kappa IGKC germline subgroups. The closest gene and allele sequence to Pertuzumab and D3H44 IGKC is J00241|IGKC*01. FIG. 1F depicts CAT-2200 VL domain aligned against human lambda IGLV and IGLJ germline subgroups (one representative sequence is displayed from each gene and allele). The closest gene and allele sequences to CAT-2200 IGLV and IGLJ are Z73673|IGLV6-57*01 and M15641|IGLJ2*01, respectively. FIG. 1G depicts CAT-2200 CH1 domain aligned against human CH1 IGHG germline subgroups. The closest gene and allele sequence to CAT-2200 IGHG is J00228|IGHG1*01. FIG. 1H depicts CAT-2200 CL domain aligned against human lambda IGLC germline subgroups. The closest gene and allele sequence to CAT-2200 IGLC is J00253|IGLC2*01.

FIG. 3A exemplifies the typical conformational differences seen between a kappa and lambda light chain when aligned on their respective heavy chain. FIG. 3B presents a view of the light chain interface (with heavy chain removed) of the model presented in FIG. 3A, to further exemplify the conformational differences. The dotted arrows point to the conformational rearrangement of the secondary structure elements at the interface between heavy and light chains.

FIG. 10 depicts min-max box plots summarizing the performance of all K-L designs tested in the SMCA in three bispecific systems, by design cluster.

FIG. 12 depicts DSC sensorgrams of the bispecific antibodies produced using Mab design set 3972 (SMCA design ID) (in each of three bispecific systems), and the wild-type parent antibodies for each system.

FIG. 15 depicts UPLC-SEC profiles of protein-A and prep-SEC purified bispecific antibodies and parent antibodies.

FIG. 16 depicts the process for selecting wild-type reference values for the calculation of 'change in total pairing with respect to WT' and 'change in total bispecific with respect to WT', for designs tested in SMCA, in cases where the corresponding WT bispecific construct had not been assessed by SMCA.

DETAILED DESCRIPTION

Figure 1A:
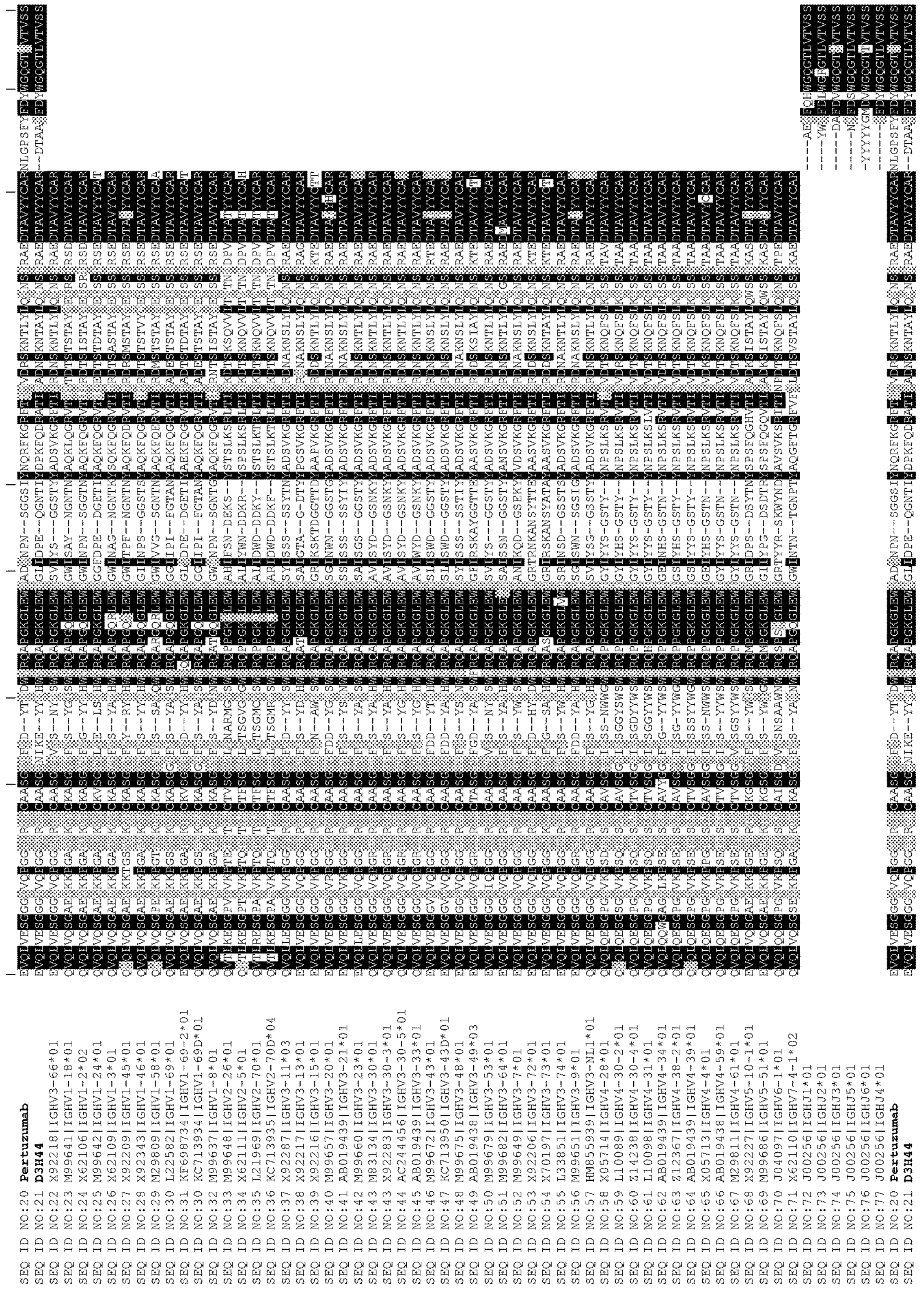
FIG. 1A depicts Pertuzumab and D3H44 variable heavy (VH) domains aligned against human IGHV and IGHJ germline subgroups (one representative sequence is displayed for each gene and allele). The closest gene and allele sequences to Pertuzumab IGHV and IGHJ are X92218|IGHV3-66*01 and J00256|IGHJ4*01, respectively. The closest gene and allele sequences to D3H44 IGHV and IGHJ are X92218|IGHV3-66*01 and J00256|IGHJ4*01, respectively.

Provided herein are engineered antibodies (also referred to herein as multispecific antigen-binding polypeptide constructs) which can comprise first heterodimer (H1L1) having a first immunoglobulin heavy chain (H1) and an immunoglobulin lambda light chain (L1) which pair to form a first Fab region, and a second heterodimer (H2L2) having an immunoglobulin heavy chain (H2) and an immunoglobulin kappa light chain (L2) which pair to form a second Fab region. The first Fab region typically binds to a first antigen and the second Fab region typically binds to a second antigen. In some embodiments, the first and second antigens are different from each other. H1 is distinct from H2. One or more of the immunoglobulin heavy chains and light chains are engineered to comprise amino acid modifications that promote preferential pairing of correctly paired heavy and light chains (H1L1 or H2L2) when co-expressed or co-produced. More specifically, the amino acid modifications promote preferential pairing between each heavy chain and the correct light chain such that the heavy chain of the first heterodimer (H1) can preferentially pair with L1 rather than L2, and the heavy chain of the second heterodimer (H2) can preferentially pair with L2 rather than L1. As a result, co-expression of H1, L1, H2 and L2 polypeptides can enable the production of correctly paired bispecific antibody with reduced or limited mispairing, thus decreasing the number and amount of mispaired species produced and potentially improving manufacturability. In one embodiment, the amino acid modifications in the Fab regions are paired with amino acid modifications in the Fc region that promote formation of a heterodimeric Fc region to further reduce the amount of mispaired heavy chains. The amino acid modifications do not significantly affect the thermal stability of the correctly paired heterodimers, or the binding affinity of each correctly paired heterodimer for antigen as compared to heterodimers that are formed from wild type H1 and L1, or H2 and L2 polypeptides.

Also provided herein are methods of making the multispecific antigen-binding polypeptide constructs described above.

Definitions

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means ±1%, 2%, 3%, 4%, 5%, 6%, 7%, 8%, 9% or 10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. In addition, it should be understood that the individual single chain polypeptides or immunoglobulin constructs derived from various combinations of the structures and substituents described herein are disclosed by the present application to the same extent as if each single chain polypeptide or heterodimer were set forth individually. Thus, selection of particular components to form individual single chain polypeptides or heterodimers is within the scope of the present disclosure.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

In the present application, amino acid names and atom names (e.g. N, O, C, etc.) are used as defined by the Protein DataBank (PDB) (www.pdb.org), which is based on the IUPAC nomenclature (IUPAC Nomenclature and Symbolism for Amino Acids and Peptides (residue names, atom names etc.), Eur. J. Biochem., 138, 9-37 (1984) together with their corrections in Eur. J. Biochem., 152, 1 (1985). The term "amino acid residue" is primarily intended to indicate an amino acid residue contained in the group consisting of the 20 naturally occurring amino acids, i.e. alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "nucleotide sequence" or "nucleic acid sequence" is intended to indicate a consecutive stretch of two or more nucleotide molecules. The nucleotide sequence can be of genomic, cDNA, RNA, semisynthetic or synthetic origin, or any combination thereof.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing a nucleic acid sequence into a cell.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refer to compounds that have the same basic chemical structure as a naturally occurring amino acid, i.e., a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as alanine, ornithine, etc.; and chemically synthesized compounds having properties known in the art to be characteristic of amino acids. Examples of non-naturally occurring amino acids include, but are not limited to, N-methyl amino acids (e.g. methyl alanine), D-amino acids, histidine-like amino acids (e.g., 2-amino-histidine, hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the antigen-binding polypeptide constructs described herein can be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids are referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that may be considered conservative substitutions for one another:

Alanine (A), Glycine (G);
Aspartic acid (D), Glutamic acid (E);
Asparagine (N), Glutamine (Q);
Arginine (R), Lysine (K);
Isoleucine (I), Leucine (L), Methionine (M), Valine (V);
Phenylalanine (F), Tyrosine (Y), Tryptophan (W); and
Serine (S), Threonine (T);
(see, e.g., Creighton, Proteins: Structures and Molecular Properties (W H Freeman & Co.; 2nd edition (December 1993).

The terms "identical" or percent "identity," in the context of two or more nucleic acids or polypeptide sequences, refer to two or more sequences or subsequences that are the same. Sequences are "substantially identical" or "substantially similar" if they have a percentage of amino acid residues or nucleotides that are the same (i.e., at least about 50%, 55%, 60%, 65%, 70%, 75%, 80%, 85%, 90%, 91%, 92%, 93%, 94%, 95%, 96%, 97%, 98%, or 99% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the antigen-binding polypeptide constructs described herein, including homologs from species other than human, can be obtained by a process comprising the steps of screening a library under stringent hybridization conditions with a labeled probe having a polynucleotide sequence of the antigen-binding polypeptide constructs described herein or a fragment thereof, and isolating full-length cDNA and genomic clones containing said polynucleotide sequence. Such hybridization techniques are well known to the skilled artisan.

Examples of an algorithm that is suitable for determining percent sequence identity and sequence similarity are the BLAST™ and BLAST™ 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST™ analyses is publicly available through the National Center for Biotechnology Information (see the internet at www.ncbi.nlm.nih.gov). Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. Examples of algorithm parameters for the BLASTN program (for nucleotide sequences) are wordlength (W) of 11, an expectation (E) of 10, M=5, N=−4 and a comparison of both strands. For amino acid sequences, examples of algorithm parameters for the BLASTP program are wordlength of 3, expectation (E) of 10, and the BLOSUM62 scoring matrix (see Henikoff and Henikoff, *Proc. Natl. Acad. Sci. USA* 89:10915, 1989).

A derivative, or a variant of a polypeptide is said to share "homology" or be "homologous" with the peptide if the amino acid sequences of the derivative or variant has at least 50% identity over a sequence that is 100 amino acids in length from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

As used herein, an "isolated" polypeptide or construct means a construct or polypeptide that has been identified and separated and/or recovered from a component of its natural cell culture environment. Contaminant components of its natural environment are materials that would typically interfere with diagnostic or therapeutic uses for the heteromultimer, and can include enzymes, hormones, and other proteinaceous or non-proteinaceous solutes.

In certain embodiments, as used herein, "isolated" antigen-binding polypeptide constructs describe antigen-binding polypeptide constructs that have been identified and separated and/or recovered from a component of its natural cell culture environment. For example, an isolated bispecific antigen-binding polypeptide construct described herein comprises heterodimer pairs or "isolated" heterodimer pairs that comprise a heterodimer or heterodimer pair that has been identified and separated and/or recovered from a component of its natural cell culture environment. Contaminant components of its natural environment are materials that would interfere with diagnostic or therapeutic uses for the heterodimer or antigen-binding polypeptide constructs, and can include enzymes, hormones, and other proteinaceous or non-proteinaceous solutes.

The heterodimers and antigen-binding polypeptide constructs can be purified to substantial homogeneity. The phrases "substantially homogeneous", "substantially homogeneous form" and "substantial homogeneity" are used to indicate that the correctly paired product is substantially devoid of by-products originating from undesired polypeptide combinations (e.g. homodimers or mispaired heterodimers). In the context of an LCCA design set (H1L1L2), the correctly paired product is the heterodimer comprising H1 and L1 (H1L1). In the context of an LCCA design set (H2L1L2), the correctly paired product is the heterodimer comprising H2 and L2 (H2L2). In one embodiment, in the context of a bispecific antigen-binding polypeptide construct, where H1, L1, H2, and L2 are expressed, the correctly paired product is a heterodimer pair comprising correctly paired H1L1 and H2L2 (H1L1H2L2). In some embodiments, in the context of a bispecific antigen-binding polypeptide construct, where H1, L1, H2, and L2 are expressed, the correctly paired product can comprise additional products that exhibit correct pairing in at least one Fab region such as, for example, H1L1H2L1 or H1L2H2L2, or where "half antibodies" are produced, H1L1 or H2L2. Expressed in terms of purity, in one embodiment, substantial homogeneity means that the amount of completely mispaired by-products does not exceed 20%, for example is below 10%, below 5%, below 1%, or below 0.5% of the total LC-MS intensity from all species present in the mixture, wherein the percentages reflect results from Mass Spectrometric analysis.

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

As used herein, the terms "antibody" and "immunoglobulin" or "antigen-binding polypeptide construct" are used interchangeably. An "antigen-binding polypeptide construct" refers to a polypeptide substantially encoded by an immunoglobulin gene or immunoglobulin genes, or one or more fragments thereof, which specifically bind an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin isotypes, IgG, IgM, IgA, IgD, and IgE, respectively. Further, the antibody can belong to one of a number of subtypes, for instance, the IgG can belong to the IgG1, IgG2, IgG3, or IgG4 subclasses.

An exemplary immunoglobulin (antibody) structural unit is composed of two pairs of polypeptide chains, each pair having one immunoglobulin "light" (about 25 kD) and one immunoglobulin "heavy" chain (about 50-70 kD). This type of immunoglobulin or antibody structural unit is considered to be "naturally occurring." The term "light chain" includes a full-length light chain and fragments thereof having sufficient variable domain sequence to confer binding specificity. A full-length light chain includes a variable domain, VL, and a constant domain, CL. The variable domain of the light chain is at the amino-terminus of the polypeptide. Light chains include kappa chains and lambda chains. The term "heavy chain" includes a full-length heavy chain and fragments thereof having sufficient variable region sequence to confer binding specificity. A full-length heavy chain includes a variable domain, VH, and three constant domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subclasses), IgA (including IgA1 and IgA2 subclasses), IgM, IgD and IgE. The term "variable region" or "variable domain" refers to a portion of the light and/or heavy chains of an antibody generally responsible for antigen recognition, typically including approximately the amino-terminal 120 to 130 amino acids in the heavy chain (VH) and about 100 to 110 amino terminal amino acids in the light chain (VL).

A "complementarity determining region" or "CDR" is an amino acid sequence that contributes to antigen-binding specificity and affinity. "Framework" regions (FR) can aid in maintaining the proper conformation of the CDRs to promote binding between the antigen-binding region and an antigen. Structurally, framework regions can be located in antibodies between CDRs. The variable regions typically exhibit the same general structure of relatively conserved framework regions (FR) joined by three hyper variable regions, CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat Sequences of Proteins of Immunological Interest (National Institutes of Health, Bethesda, Md. (1987 and 1991)), unless stated otherwise.

A "multispecific antigen-binding polypeptide construct" or "multispecific antibody" is one that targets or binds to more than one distinct antigen or epitope. A "bispecific," "dual-specific" or "bifunctional" antigen-binding polypeptide construct or antibody is a species of multispecific antigen-binding polypeptide construct that targets or binds to two different antigens or epitopes. In general, a bispecific antigen-binding polypeptide construct can have two different antigen-binding domains. The two antigen-binding domains of a bispecific antigen-binding polypeptide construct or antibody will bind to two different epitopes, which can reside on the same or different molecular targets. In one embodiment, the bispecific antigen-binding polypeptide construct is in a naturally occurring format. In other words, the bispecific antigen-binding polypeptide construct has the same format as a naturally occurring IgG, IgA, IgM, IgD, or IgE antibody.

Antibody heavy chains pair with antibody light chains and meet or contact one another at one or more "interfaces." An "interface" includes one or more "contact" amino acid residues in a first polypeptide that interact with one or more "contact" amino acid residues of a second polypeptide. For example, an interface exists between the two CH3 domains of a dimerized Fc region, between the CH1 domain of the heavy chain and CL domain of the light chain, and between the VH domain of the heavy chain and the VL domain of the light chain. The "interface" can be derived from an IgG antibody and for example, from a human IgG1 antibody.

The term "amino acid modifications" as used herein includes, but is not limited to, amino acid insertions, deletions, substitutions, chemical modifications, physical modifications, and rearrangements.

The amino acid residues for the immunoglobulin heavy and light chains may be numbered according to several conventions including Kabat (as described in Kabat and Wu, 1991; Kabat et al, Sequences of proteins of immunological interest. 5th Edition—US Department of Health and Human Services, NIH publication no. 91-3242, p 647 (1991)), IMGT (as set forth in Lefranc, M.-P., et al. IMGT®, the international ImMunoGeneTics information System® Nucl. Acids Res, 37, D1006-D1012 (2009), and Lefranc, M.-P., IMGT, the International ImMunoGeneTics Information System, Cold Spring Harb Protoc. 2011 Jun. 1; 2011(6)), 1JPT (as described in Katja Faelber, Daniel Kirchhofer, Leonard Presta, Robert F Kelley, Yves A Muller, The 1.85 Å resolution crystal structures of tissue factor in complex with humanized fab d3h44 and of free humanized fab d3h44: revisiting the solvation of antigen combining sites1, Journal of Molecular Biology, Volume 313, Issue 1, Pages 83-97,) and EU (according to the EU index as in Kabat referring to the numbering of the EU antibody (Edelman et al., 1969, Proc Natl Acad Sci USA 63:78-85)). Kabat numbering is used herein for the VH, CH1, CL, and VL domains unless otherwise indicated. EU numbering is used herein for the CH3 and CH2 domains, and the hinge region unless otherwise indicated. Table 22A provides a correspondence table showing the amino acid numbering for selected positions in the IgG1 heavy chain polypeptide using IMGT, Kabat, 1JPT, and EU numbering systems. Table 22B provides a correspondence table showing the amino acid numbering for selected positions in the lambda light chain polypeptide using IMGT and Kabat numbering systems. Table 22C provides a correspondence table showing the amino acid numbering for selected positions in the kappa light chain polypeptide using IMGT, 1JPT and Kabat numbering systems.

Antigen-Binding Polypeptide Constructs

The antigen-binding polypeptide constructs (i.e. antibodies) described herein can be multispecific or bispecific. A multispecific antigen-binding polypeptide construct can comprise at least a first heterodimer (H1L1) having a first immunoglobulin heavy chain polypeptide sequence (H1) and an immunoglobulin lambda light chain polypeptide sequence (L1) that form a first Fab region and at least a second heterodimer (H2L2) having an immunoglobulin heavy chain polypeptide sequence (H2) and an immunoglobulin kappa light chain polypeptide sequence (L2) that form a second Fab region, where H1 and H2 are distinct from each other. In one embodiment, the bispecific antigen-binding polypeptide construct comprises a first heterodimer (H1L1) having a first immunoglobulin heavy chain polypeptide sequence (H1) and an immunoglobulin lambda light chain polypeptide sequence (L1) that form a first Fab region and a second heterodimer (H2L2) having an immunoglobulin heavy chain polypeptide sequence (H2) and an immunoglobulin kappa light chain polypeptide sequence (L2) that form a second Fab region, where H1 and H2 are distinct from each other. In one embodiment, each heterodimer comprises a single Fab region. The term "Fab region" as used herein refers to the region resulting from the pairing of one immunoglobulin light chain polypeptide sequence with a one immunoglobulin heavy chain polypeptide sequence, and is composed of the VH and CH1 domains of the immunoglobulin heavy chain polypeptide sequence, and the VL and CL domains of the immunoglobulin light chain polypeptide sequence. In some embodiments, the first Fab region binds to a first antigen, and the second Fab region binds to a second antigen. The first and second antigens can be the same or different. One or more of the immunoglobulin heavy chains and light chains can comprise amino acid modifications that promote preferential pairing of correctly paired heavy and light chains when co-expressed or co-produced.

When the antigen-binding polypeptide construct is a bispecific antigen-binding polypeptide construct (i.e. bispecific antibody), it can also be referred to as a "heterodimer pair."

For the sake of illustration, the first heterodimer of the antigen-binding polypeptide construct is referred to as H1L1, and comprises a first immunoglobulin heavy chain polypeptide sequence (H1) paired with an immunoglobulin lambda light chain polypeptide sequence (L1), and the second heterodimer is referred to as H2L2 and comprises a second immunoglobulin heavy chain polypeptide sequence (H2) paired with an immunoglobulin kappa light chain polypeptide sequence (L2). It should be understood, however, that this designation is arbitrary and meant only to specify that one heterodimer comprises an immunoglobulin kappa light chain and the other comprises an immunoglobulin lambda light chain. The Fab region of the first heterodimer, H1L1, may also be referred to herein as the "lambda Fab"; while the Fab region of the second heterodimer, H2L2, may also be referred to herein as the "kappa Fab."

Parent Antibodies

The immunoglobulin heavy chain polypeptide sequences, also referred to as "heavy chains," and immunoglobulin light chain polypeptide sequences, also referred to as "light chains," of each heterodimer can be obtained from one or more parent antibodies, where at least one parent antibody comprises a kappa light chain, and at least one other parent antibody comprises a lambda light chain, and the amino acid modifications that promote preferential pairing are engineered into these heavy and light chains. The parent immunoglobulin heavy chain and immunoglobulin light chain sequences lacking the amino acid modifications that promote preferential pairing are referred to as wild type immunoglobulin heavy chain polypeptide sequences, wild type immunoglobulin kappa light chain polypeptide sequences, and wild type immunoglobulin lambda light chain polypeptides sequences. In one embodiment, the heavy and light chains of the heterodimers of the antigen-binding polypeptide construct are obtained from two parent antibodies. Generally, the two parent antibodies are different from each other; however, this is not necessarily always the case. In one embodiment, the antigen-binding polypeptide construct is a bispecific antigen-binding polypeptide construct where each heterodimer is obtained from a different parent antibody. In another embodiment, the antigen-binding polypeptide construct is a bispecific antigen-binding polypeptide construct where both parent antibodies bind to the same antigen, but target different epitopes on the same antigen. In one embodiment, at least one parent antibody is monospecific, i.e. can bind to only one epitope. In another embodiment, at least one parent antibody can bind to more than one epitope.

The heavy chain and light chain of each heterodimer of the antigen-binding polypeptide construct pair to form a Fab region that specifically binds to the same antigen as the parent antibody they were obtained from. For example, if a bispecific antigen-binding polypeptide construct was prepared based on parent antibodies CAT-2200 (containing a lambda light chain, and binding to IL-17A) and D3H44 (containing a kappa light chain, and binding to tissue factor), the heavy chain and light chain of one heterodimer would pair to form a Fab region that binds to IL-17A, and the heavy and light chain of the second heterodimer would pair to form a Fab region that binds to tissue factor.

The parent antibodies can be obtained from species including, but not limited to humans, mice, rats, rabbits, sheep, cows, goats or camels. In one embodiment, the parent antibodies can be obtained from humans or mice.

Parent antibodies can also include those that are prepared from hybridomas using standard monoclonal antibody production protocols, such as those described by Kohler and Milstein (Nature, 256:495-497, 1975).

Antibodies binding to a particular target may also be identified by a number of different strategies, including phage display, in vitro display, and other methods. These strategies result in antibodies that are in scFv format, Fab format or full-length IgG format. A review of these strategies are found in Chapter 4 of *Therapeutic Antibody Engineering*, by William R. Strohl and Lila M. Strohl, Woodhead Publishing series in Biomedicine No 11, ISBN 1 907568 37 9, October 2012. In one embodiment, parent antibodies include antibodies identified by phage display or in vitro display. Antibodies identified in formats other than Fab or full-length IgG formats can be converted into same as known in the art. Methods of converting scFvs to Fabs are well known in the art (see for example, Steinwand et al. Mabs 6: 204-218, or Zuberbuhler et al. Protein Engineering, Design & Selection 22:169-174). In one embodiment, antibodies originally identified as scFvs, but where the scFv has been converted to Fab format and engineered into the form of a conventional or naturally occurring antibody may also be used as parent antibodies.

In one embodiment, the heavy chains and light chains of each heterodimer of the antigen-binding polypeptide construct can be obtained from a parent antibody that is a humanized antibody. Humanized antibodies can be obtained by substituting the complementarity determining region (CDR) of a human antibody for the CDR of an antibody derived from a nonhuman mammal, for example, a mouse. Methods for identifying CDRs are known in the art (Kabat et al., Sequence of Proteins of Immunological Interest (1987), National Institute of Health, Bethesda, Md.; Chothia et al., Nature (1989) 342:877). General genetic recombination techniques suitable for this purpose are also known (see European Patent Application Publication No. EP 125023; and WO 96/02576). For example, the CDR of a mouse antibody can be determined by known methods, and a DNA can be prepared such that it encodes an antibody in which the CDR is ligated with the framework region (FR) of a human antibody. A humanized antibody can then be produced using a system that uses conventional expression vectors. Such DNAs can be synthesized by PCR, using as primers several oligonucleotides designed to include portions that overlap the ends of both the CDR and FR regions (see the method described in WO 98/13388). Human antibody FRs linked via CDRs are selected such that the CDRs form a suitable antigen-binding site. If required, amino acids in the FRs of an antibody variable region may be modified so that the CDRs of the reshaped human antibody can form a suitable antigen-binding domain (Sato, K. et al., Cancer Res. (1993) 53:851-856). Modifiable amino acid residues in the FRs include portions that directly bind to an antigen via non-covalent bonds (Amit et al., Science (1986) 233: 747-53), portions that have some impact or effect on the CDR structure (Chothia et al., J. Mol. Biol. (1987) 196: 901-17), and portions involved in the interaction between VH and VL (EP 239400).

In one embodiment, the heavy chains and light chains of each heterodimer of the antigen-binding polypeptide construct can be obtained from a parent antibody that is a chimeric antibody. Chimeric antibodies are antibodies prepared by combining sequences derived from different animals. For example, a chimeric antibody can be produced by combining the heavy chain and light chain variable domains from a mouse antibody with the heavy chain and light chain constant domains from a human antibody. Chimeric antibodies can be prepared by known methods. To obtain such chimeric antibodies, for example, a DNA encoding an antibody variable domain may be ligated with a nucleic acid encoding a human antibody constant domain; the resulting ligation product can be inserted into an expression vector; and the construct can be introduced into a host cell to produce the chimeric antibody.

The heavy and light chains of the heterodimers can be obtained from numerous parent antibodies known in the art. Most antibodies can serve as a parent antibody, provided that they comprise an immunoglobulin heavy chain polypeptide sequence that pairs with an immunoglobulin light chain polypeptide sequence to form Fab region that binds to an antigen. In one embodiment, at least one parent antibody is a therapeutic antibody i.e. an antibody that is used to treat a disease. Non-limiting examples of suitable therapeutic antibodies comprising a kappa light chain and the antigens they bind to are identified in Table A below:

TABLE A

Exemplary therapeutic antibodies comprising a kappa light chain

| Antibody | Antigens |
|---|---|
| ABI793 | CD40 Ligand |
| ABT-806 | Epidermal growth factor receptor |
| AV-203 | Receptor tyrosine-protein kinase erbB-3 |
| BTI-322 | CD2 |
| Bioanalytica patent anti-HSP90 | Heat shock protein 90 homolog |
| CTM01 | Mucin 1 |
| Centocor patent anti-GLP-1R | Glucagon-like peptide 1 Receptor |
| Chugai AHM | Bone marrow stromal antigen 2 |
| DX-2930 | Kallikrein |
| Genmab patent anti-CD20 | B-lymphocyte antigen CD20 |
| HuMax-CD32b | Fc-gamma-RIIB (CD32b) |
| HuMax-IL8 | Interleukin 8 |
| IMA-026 | Interleukin 13 |
| IMMU-114 | HLA-DR |
| Immunomedics hA19 | CD19 |
| Immunomedics patent anti-IGF-1R | Insulin-like Growth Factor 1 Receptor |
| MDX-1303 | Anthrax Protective antigen |
| MDX-1401 | CD30 |
| MEDI0639 | Delta like ligand 4 |
| MEDI4893 | *Staphylococcus aureus* alpha toxin |
| MGA271 | B7-H3 |
| MGAWN1 | West Nile Virus Envelope Protein |
| MH166 | Interleukin 6 |
| MT293 | Collagen |
| Macrogenics patent anti-KID3 | KID3 |
| OPR-003 | Interleukin 6 |
| Stem Centrx patent anti-Cadherin-1 | Cadherin-1 |
| abagovomab | Antibody against Cancer antigen 125 |
| abituzumab | Integrin alpha-V |
| abrilumab | Integrin alpha4 beta7 |
| actoxumab | *C. difficile* Toxin A |
| adalimumab | Tumor necrosis factor-alpha |
| adecatumumab | Epithelial cell adhesion molecule |
| aducanumab | Amyloid beta |
| afasevikumab | Interleukin 17A, Interleukin 17F |
| Alemtuzumab | CD52 |
| Alirocumab | Proprotein Convertase Subtilisin/Kexin Type 9 |
| Amatuximab | Mesothelin |
| Anifrolumab | Interferon alpha receptor 1 |
| Anrukinzumab | Interleukin 13 |
| Ascrinvacumab | Activin receptor like kinase 1 |
| Atezolizumab | Programmed Cell Death 1 Ligand 1 |
| Atinumab | Nogo-A |
| Basiliximab | Interleukin-2 receptor alpha chain |
| Bavituximab | Phosphatidylserine |
| Begelomab | CD26 |
| Benralizumab | Interleukin 5 receptor subunit alpha |
| Bertilimumab | Chemokine (C-C motif) ligand 11 |
| besilesomab | CEA (carcinoembryonic antigen)-related antigen |
| bezlotoxumab | *C. difficile* Toxin B |
| bimekizumab | Interleukin 17A, Interleukin 17F |
| bleselumab | CD40 |
| blosozumab | Sclerostin |
| bococizumab | Proprotein Convertase Subtilisin/Kexin Type 9 |
| brodalumab | Interleukin 17 Receptor Alpha |
| canakinumab | Interleukin 1, beta |
| carlumab | Monocyte chemoattractant protein-1 |
| cetuximab | Epidermal growth factor receptor |

TABLE A-continued

Exemplary therapeutic antibodies comprising a kappa light chain

| Antibody | Antigens |
|---|---|
| clazakizumab | Interleukin 6 |
| codrituzumab | Glypican 3 |
| conatumumab | Cytokine Death Receptor 5 |
| concizumab | Tissue factor pathway inhibitor |
| crenezumab | Amyloid beta |
| dacetuzumab | CD40 |
| daclizumab | Interleukin-2 receptor alpha chain |
| dalotuzumab | Insulin-like Growth Factor 1 Receptor |
| daratumumab | CD38 (ADP-ribosyl cyclase 1) |
| dectrekumab | Interleukin 13 |
| demcizumab | Delta like ligand 4 |
| dinutuximab | GD2 ganglioside |
| dupilumab | Interleukin 4 Receptor Alpha |
| durvalumab | Programmed Cell Death 1 Ligand 1 |
| ecromeximab | GD3 Ganglioside |
| efalizumab | Integrin Î ± L |
| eldelumab | Interferon Gamma-inducible Protein (IP-10) |
| elgemtumab | Receptor tyrosine-protein kinase erbB-3 |
| elotuzumab | SLAM family member 7 |
| elsilimomab | Interleukin 6 |
| emactuzumab | CSF-1 Receptor |
| emibetuzumab | cMet Receptor |
| enavatuzumab | TWEAK Receptor |
| enokizumab | Interluekin 9 |
| enoticumab | Delta like ligand 4 |
| ensituximab | Mucin 5AC |
| etaracizumab | Integrin alphaV beta3 |
| etrolizumab | Integrin alpha4 beta7 |
| evinacumab | Angiopoietin-like protein 3 |
| farletuzumab | Folate Receptor Alpha |
| fasinumab | Nerve growth factor |
| fibatuzumab | EphA3 receptor tyrosine kinase |
| ficlatuzumab | Hepatocyte growth/scatter factor |
| figitumumab | Insulin-like Growth Factor 1 Receptor |
| flanvotumab | Tyrosinase-related protein 1 |
| fletikumab | Interleukin 20 |
| foralumab | T-cell surface glycoprotein CD3 epsilon chain |
| foravirumab | Rabies virus glycoprotein |
| fresolimumab | Transforming growth factor beta |
| fulranumab | Nerve growth factor |
| ganitumab | Insulin-like Growth Factor 1 Receptor |
| gantenerumab | Amyloid beta |
| gevokizumab | Interleukin 1, beta |
| girentuximab | Carbonic anhydrase IX |
| golimumab | Tumor necrosis factor-alpha |
| ibalizumab | CD4 |
| icrucumab | FMS-like tyrosine kinase-1 |
| imalumab | Macrophage migration inhibitory factor |
| imgatuzumab | Epidermal growth factor receptor |
| inclacumab | P-selectin |
| indusatumab | Guanylyl cyclase C |
| inebilizumab | CD19 |
| infliximab | Tumor necrosis factor-alpha |
| intetumumab | Integrin alpha-V |
| ipilimumab | Cytotoxic T-Lymphocyte Antigen 4 |
| isatuximab | CD38 (ADP-ribosyl cyclase 1) |
| itolizumab | CD6 |
| ixekizumab | Interleukin 17A |
| keliximab | CD4 |
| labetuzumab | Carcinoembryonic antigen |
| landogrozumab | Myostatin |
| lebrikizumab | Interleukin 13 |
| lemalesomab | NCA-90 granulocyte cell antigen |
| lenzilumab | Granulocyte Macrophage Colony Stimulating Factor |
| libivirumab | Hepatitis B virus surface antigen |
| ligelizumab | Immunoglobulin E |
| lilotomab | Leukocyte antigen CD37 |
| lirilumab | KIR Inhibitory Receptor |
| lodelcizumab | Proprotein Convertase Subtilisin/Kexin Type 9 |
| lucatumumab | CD40 |
| lumiliximab | CD23 - low affinity IgE Fc receptor |
| lumretuzumab | Receptor tyrosine-protein kinase erbB-3 |
| margetuximab | Human Epidermal growth factor Receptor 2 |
| matuzumab | Epidermal growth factor receptor |
| mepolizumab | Interleukin 5 |
| metelimumab | Transforming growth factor beta 1 |
| milatuzumab | Major histocompatibility complex |
| mogamulizumab | C-C chemokine receptor type 4 |
| monalizumab | NKG2A |
| motavizumab | Respiratory Syncytial Virus F protein |
| namilumab | Granulocyte Macrophage Colony Stimulating Factor |
| natalizumab | Integrin Alpha 4 |
| necitumumab | Epidermal growth factor receptor |
| nemolizumab | Interleukin 31 receptor subunit alpha |
| nesvacumab | Angiopoietin 2 |
| nimotuzumab | Epidermal growth factor receptor |
| nivolumab | Programmed Cell Death 1 |
| obinutuzumab | B-lymphocyte antigen CD20 |
| ocaratuzumab | B-lymphocyte antigen CD20 |
| ocrelizumab | B-lymphocyte antigen CD20 |
| ofatumumab | B-lymphocyte antigen CD20 |
| olaratumab | Platelet-derived Growth Factor Receptor Alpha subunit |
| olokizumab | Interleukin 6 |
| omalizumab | Immunoglobulin E |
| ontuxizumab | Endosialin |
| opicinumab | LRR and Ig domain ‘containing, Nogo receptor’ interacting protein |
| oregovomab | Cancer antigen 125 |
| oxelumab | OX40 Ligand |
| ozanezumab | Nogo-A |
| pagibaximab | *Staphylococcus epidermidis* lipoteichoic acid |
| palivizumab | Respiratory Syncytial Virus F protein |
| pamrevlumab | Connective Tissue Growth Factor |
| panitumumab | Epidermal growth factor receptor |
| panobacumab | *Pseudomonas aeruginosa* serotype IATS O11 |
| parsatuzumab | Epidermal Growth Factor Domain-Like 7 |
| pascolizumab | Interleukin 4 |
| pateclizumab | Lymphotoxin alpha |
| patritumab | Receptor tyrosine-protein kinase erbB-3 |
| pembrolizumab | Programmed Cell Death 1 |
| perakizumab | Interleukin 17A |
| pertuzumab | Human Epidermal growth factor Receptor 2 |
| pidilizumab | Programmed Cell Death 1 |
| plozalizumab | C-C chemokine receptor type 2 |
| ponezumab | Amyloid beta |
| pritoxaximab | Shiga toxin (*E. coli*) |
| pritumumab | Vimentin |
| quilizumab | Immunoglobulin E M1 prime |
| racotumomab | Ganglioside GM3 |
| ralpancizumab | Proprotein Convertase Subtilisin/Kexin Type 9 |
| ramucirumab | VEGFR-2 Kinase insert domain receptor |
| rilotumumab | Hepatocyte growth/scatter factor |
| rinucumab | Platelet-derived growth factor receptor Beta |
| risankizumab | Interleukin 23 p19 |
| rituximab | B-lymphocyte antigen CD20 |
| robatumumab | Insulin-like Growth Factor 1 Receptor |
| roledumab | Rh blood group, D antigen |
| romosozumab | Sclerostin |
| rontalizumab | Interferon alpha |
| rovalpituzumab | DLL3 |
| ruplizumab | CD40 Ligand |
| samalizumab | CD200 |
| sarilumab | Interleukin-6 receptor |
| secukinumab | Interleukin 17A |
| setoxaximab | Shiga toxin (*E. coli*) |
| sifalimumab | Interferon alpha |
| siltuximab | Interleukin 6 |
| simtuzumab | Lysyl oxidase-like-2 |
| sirukumab | Interleukin 6 |
| sofituzumab | Cancer antigen 125 |
| solanezumab | Amyloid beta |
| sontuzumab | Mucin 1 |
| suvizumab | HIV-1 envelope glycoprotein gp120 third variable loop V3 |
| tabalumab | B-cell activating factor |
| talizumab | Immunoglobulin E |
| tanezumab | Nerve growth factor |
| tarextumab | Notch2, Notch3 |
| tefibazumab | *Staphylococcus aureus* Clumping factor A |

TABLE A-continued

| Antibody | Antigens |
|---|---|
| Exemplary therapeutic antibodies comprising a kappa light chain | |
| tenatumomab | Tenascin C |
| teplizumab | T-cell surface glycoprotein CD3 epsilon chain |
| teprotumumab | Insulin-like Growth Factor 1 Receptor |
| tigatuzumab | Cytokine Death Receptor 5 |
| tildrakizumab | Interleukin 23 p19 |
| tocilizumab | Interleukin-6 receptor |
| toralizumab | CD40 Ligand |
| tovetumab | Platelet-derived Growth Factor Receptor Alpha subunit |
| trastuzumab | Human Epidermal growth factor Receptor 2 |
| tregalizumab | CD4 |
| tremelimumab | Cytotoxic T-Lymphocyte Antigen 4 |
| trevogrumab | Myostatin |
| ublituximab | B-lymphocyte antigen CD20 |
| ulocuplumab | Chemokine receptor CXCR4 |
| urelumab | 4-1BB ligand receptor |
| urtoxazumab | *Escherichia coli* Shiga-like toxin II B subunit |
| vapaliximab | Vascular Adhesion Protein VAP-1 |
| varlilumab | CD27 |
| vatelizumab | Integrin Alpha 2 Beta 1 |
| vedolizumab | Integrin alpha4 beta7 |
| veltuzumab | B-lymphocyte antigen CD20 |
| vesencumab | Neuropilin-1 |
| visilizumab | CD3 T-Cell Co-Receptor |
| vorsetuzumab | CD70 |
| zalutumumab | Epidermal growth factor receptor |
| zanolimumab | CD4 |
| zatuximab | Epidermal growth factor receptor |

Non-limiting examples of suitable therapeutic antibodies comprising a lambda light chain and the antigens they bind to are identified in Table B below:

TABLE B

| Antibody | Antigens |
|---|---|
| Exemplary therapeutic antibodies comprising a lambda light chain | |
| avelumab | Programmed Cell Death 1 Ligand 1 |
| belimumab | B-cell activating factor |
| bimagrumab | activin receptor MB |
| briakinumab | Interleukin 12 |
| brontictuzumab | Notch1 |
| cixutumumab | Insulin-like Growth Factor 1 Receptor |
| drozitumab | Cytokine Death Receptor 5 |
| evolocumab | Proprotein Convertase Subtilisin/Kexin Type 9 |
| exbivirumab | Hepatitis B virus surface antigen |
| fezakinumab | Interleukin 22 |
| galiximab | CD80 |
| guselkumab | Interleukin 23 p19 |
| lexatumumab | Cytokine Death Receptor 5 |
| mapatumumab | TRAIL Receptor-1 |
| mavrilimumab | Granulocyte-macrophage colony-stimulating factor receptor subunit alpha |
| namatumab | Ron Receptor |
| orticumab | Oxidized LDL |
| otelixizumab | CD3 T-Cell Co-Receptor |
| rafivirumab | Rabies virus glycoprotein |
| raxibacumab | Anthrax Protective antigen |
| seribantumab | Receptor tyrosine-protein kinase erbB-3 |
| tesidolumab | Complement component 5 |
| tezepelumab | Thymic Stromal Lymphopoietin |
| tralokinumab | Interleukin 13 |
| vantictumab | Frizzled receptor |

Immunoglobulin Subclasses

Immunoglobulin heavy chains of the parent antibodies fall within the following classes: IgA1, IgA2, IgM, IgD, IgE, IgG1, IgG2, IgG3, and IgG4. In one embodiment, the first and second heterodimer of the antigen-binding polypeptide construct comprises an IgG heavy chain. In one embodiment, the first and second heterodimer of the antigen-binding polypeptide construct comprises an IgG1 heavy chain. The immunoglobulin light chains of the parent antibodies are either kappa light chains or lambda light chains.

The antigen-binding polypeptide constructs described herein comprise at least one heterodimer having an immunoglobulin heavy chain polypeptide sequence and an immunoglobulin kappa light chain polypeptide sequence, and at least another heterodimer having an immunoglobulin heavy chain polypeptide sequence and an immunoglobulin lambda light chain polypeptide sequence. In one embodiment, the antigen-binding polypeptide construct comprises one heterodimer having an IgG heavy chain polypeptide sequence and an immunoglobulin kappa light chain polypeptide sequence, and another heterodimer having an IgG heavy chain polypeptide sequence and an immunoglobulin lambda light chain polypeptide sequence.

In one embodiment, the antigen-binding polypeptide construct comprises a heterodimer having a heavy chain with a VH domain selected from the VH domain germline groups IGHV1, IGHV2, IGHV3, IGHV4, IGHV5, IGHV6 or IGHV7. In one embodiment, the antigen-binding polypeptide construct comprises a heterodimer having a heavy chain with a VH domain from germline subgroup IGHV3. In another embodiment, the antigen-binding polypeptide construct comprises a heterodimer having a heavy chain with a J segment selected from the J segment germline genes IGHJ1, IGHJ2, IGHJ3, IGHJ4, IGHJ5, or IGHJ6. In another embodiment, the antigen-binding polypeptide construct comprises a heterodimer having a heavy chain with a J segment from germline subgroup IGHJ4. In one embodiment, the antigen-binding polypeptide construct comprises a heterodimer having a heavy chain with a CH1 domain selected from the CH1 domain germline subgroups IGHG1, IGHG2, IGHG3, or IGHG4. In one embodiment, the antigen-binding polypeptide construct comprises a heterodimer having a heavy chain with a CH1 domain from germline subgroup IGHG1.

For heterodimers comprising a lambda light chain polypeptide sequence, the lambda light chains can comprise a CL-lambda domain selected from the germline genes IGLC1, IGLC2, IGLC3, IGLC6, or IGLC7. In one embodiment, the antigen-binding polypeptide construct comprises a heterodimer having a lambda light chain comprising a CL-lambda domain from germline subgroup IGLC2. The lambda light chains can comprise a VL-lambda domain selected from the germline subgroups IGLV1, IGLV2, IGLV3, IGLV4, IGLV5, IGLV6, IGLV7, IGLV8, IGLV9, IGLV10 or IGLV11. In one embodiment, the antigen-binding polypeptide construct comprises a heterodimer with a lambda light chain having a VL-lambda domain from the germline subgroup IGLV6. In another embodiment, the antigen-binding polypeptide construct comprises a heterodimer having lambda light chain with a lambda J segment selected from the J segment germline genes IGLJ1, IGLJ2, IGLJ3, IGLJ6 or IGLJ7. In another embodiment, the antigen-binding polypeptide construct comprises a heterodimer having a heavy chain with a lambda J segment from germline subgroup IGLJ2.

For heterodimers comprising a kappa light chain polypeptide sequence, the kappa light chains can comprise a CL-kappa domain selected from the CL germline alleles IGKC*01, IGKC*02, IGKC*03, IGKC*04, or IGKC*05. In one embodiment, the antigen-binding polypeptide construct comprises a heterodimer having a kappa light chain comprising a CL-kappa domain from germline subgroup IGKC*01. The kappa light chains can comprise a VL-kappa domain selected from the germline subgroups IGKV1, IGKV1D, IGKV2, IGKV3, IGKV4, IGKV5, or IGKV6. In one embodiment, the antigen-binding polypeptide construct comprises a heterodimer with a kappa light chain having a VL-kappa domain from the germline subgroup IGKV1. In another embodiment, the antigen-binding polypeptide construct comprises a heterodimer having kappa light chain with a J segment selected from the J segment germline genes IGKJ1, IGKJ2, IGKJ3, IGKJ4 or IGKJ5. In another embodiment, the antigen-binding polypeptide construct comprises a heterodimer having a kappa light chain with a J segment from germline subgroup IGKJ1 or IGKJ2.

Immunoglobulin heavy chains typically comprise at least one variable (VH) domain, and three constant domains, CH1, CH2, and CH3. In one embodiment, each heavy chain of the first heterodimer and second heterodimer of the antigen-binding polypeptide construct comprises a VH domain, a CH1 domain, a CH2 domain, and a CH3 domain. In another embodiment, each heavy chain of the first heterodimer and second heterodimer comprises a VH domain, a CH1 domain, and a CH3 domain. In still another embodiment, each heavy chain of the first heterodimer and second heterodimer comprises a VH domain and a CH1 domain. Immunoglobulin light chains typically comprise one variable (VL) domain and one constant (CL) domain. In one embodiment, the light chain of each heterodimer comprises a VL domain and a CL domain.

As indicated above, in some embodiments, the immunoglobulin heavy chain polypeptide sequence and the immunoglobulin light chain polypeptide sequence of each heterodimer can be obtained from a known therapeutic antibody, or from an antibody that binds various target molecules or cancer antigens. The amino acid and nucleotide sequences of numerous such molecules are readily available (see for example, GenBank Accession No: AJ308087.1 (Humanized anti-human tissue factor antibody D3H44 light chain variable region and CL domain); GenBank Accession No: AJ308086.1 (humanized anti-human tissue factor antibody D3H44 heavy chain variable region and CH1 domain); GenBank Accession No: HC359025.1 (Pertuzumab Fab light chain gene module); GenBank Accession No: HC359024.1 (Pertuzumab Fab heavy chain gene module); GenBank Accession No: GM685465.1 (Antibody Trastuzumab (=Herceptin)-wildtype; light chain); GenBank Accession No: GM685463.1 (Antibody Trastuzumab (=Herceptin)-wildtype; heavy chain); GenBank Accession No: GM685466.1 (Antibody Trastuzumab (=Herceptin)-GC-optimized light chain); and GenBank Accession No: GM685464.1 (Antibody Trastuzumab (=Herceptin)-GC-optimized heavy chain. The sequences of each of the polypeptides described above are available from the NCBI website as of Nov. 28, 2012 and are each incorporated by reference in its entirety for all purposes. Amino acid and nucleotide sequences for cetuximab are also known in the art, see for example the Drug Bank website supported by Canadian Institutes of Health Research, Alberta Innovates—Health Solutions, and by The Metabolomics Innovation Centre (TMIC), Accession No. DB00002.

Amino Acid Modifications that Promote Preferential Pairing

One or more of the heavy and light chains H1, L1, H2, and L2 comprise amino acid modifications that promote preferential pairing between heavy and light chains, that are engineered into the heavy and light chains of the parent antibodies. In one embodiment, two of the heavy and light chains H1, L1, H2, and L2 comprise amino acid modifications that promote preferential pairing between heavy and light chains. In one embodiment, three of the heavy and light chains H1, L1, H2, and L2 comprise amino acid modifications that promote preferential pairing between heavy and light chains.

In some embodiments, the amino acid modifications can be asymmetric, in that the amino acid positions that are modified are different between H1 and H2, and between L1 and L2.

In one embodiment, H2 and L2 comprise amino acid modifications that promote preferential pairing between heavy and light chains, while H1 and L1 do not. In one embodiment, H1, L1, and H2 comprise amino acid modifications that promote preferential pairing between heavy and light chains, while L2 does not. In one embodiment, H1, H2, and L2 comprise amino acid modifications that promote preferential pairing between heavy and light chains, while L1 does not. In one embodiment, L1, H2 and L2 comprise amino acid modifications that promote preferential pairing between heavy and light chains, while H1 does not.

In one embodiment, the one or more amino acid modifications comprise one or more amino acid substitutions. The amino acid modifications promote preferential pairing of H1 with L1 and H2 with L2 when H1 or H2 are co-expressed with L1 and L2, or when H1, L1, H2, and L2 are co-expressed. As indicated above, for the sake of illustration, the heterodimers of the antigen-binding polypeptide construct will be identified as follows: the H1L1 heterodimer comprises a lambda light chain L1, and the H2L2 heterodimer comprises a kappa light chain L2.

A "Mab design," or "Mab design set" as used herein refers to a specific set of amino acid modifications that promote preferential pairing that are present in one set of H1, L1, H2 and L2, and is also identified as H1L1H2L2. Amino acid modifications in one or more of H1, L1, H2, and L2 that promote preferential pairing are referred to and presented as Mab designs or Mab design sets (i.e. H1L1H2L2). The Mab design sets are initially tested as LCCA design sets (i.e. H1L1L2 or H2L1L2) to determine the strength of pairing specificity, where H1 and H2 are individually co-expressed with L1 and L2.

In one embodiment, the amino acid modifications can be made to one or more amino acids that are part of the interface between the light chain and heavy chain. In one embodiment, the amino acid modifications introduced in the immunoglobulin heavy chain polypeptide sequences and immunoglobulin light chain polypeptide sequences are complementary to each other. Complementarity at the heavy and light chain interface can be achieved on the basis of steric and hydrophobic contacts, electrostatic/charge interactions or a combination of these and a variety of other interactions. The complementarity between protein surfaces is broadly described in the literature in terms of lock and key fit, knob into hole, protrusion and cavity, donor and acceptor etc., all implying the nature of structural and chemical match between the two interacting surfaces. In one embodiment, at least one of the heterodimers comprises an amino acid modification introduced in the immunoglobulin heavy and immunoglobulin light chains that introduce a new hydrogen bond across the light and heavy chain at the interface. In one embodiment, at least one of the heterodimers comprises an amino acid modification introduced in the immunoglobulin heavy and immunoglobulin light chains that introduces a new salt bridge across the light and heavy chain at the interface.

In one embodiment, the amino acid modifications of the Mab design set promote preferential pairing predominately through electrostatic attraction and repulsion. In one embodiment, the amino acid modifications of the Mab design set promote preferential pairing through predominantly steric mechanisms. Such Mab designs are included in Tables 4A, 4B, 7A and 7B, with selected examples including those having unique identifiers 10771-11335, 10771-11360, 10780-11417. In one embodiment the amino acid modifications of the Mab design set promote preferential pairing using both steric and electrostatic mechanisms.

In one embodiment, one or more of H1, L1, H2, and L2 comprise amino acid modifications wherein H1 and L1 do not include amino acid modifications that promote preferential pairing and H2 and L2 each comprise at least one amino acid modification that promotes preferential pairing. In one embodiment, one or more of H1, L1, H2, and L2 comprise amino acid modifications wherein one or more of H1, L1, and H2 comprise at least one amino acid modification that promotes preferential pairing, and L2 does not include amino acid modifications that promote preferential pairing. In one embodiment, one or more of H1, L1, H2, and L2 comprise amino acid modifications wherein one or more of H1, L1, and L2 comprise at least one amino acid modification that promotes preferential pairing, and H2 does not include amino acid modifications that promote preferential pairing. In one embodiment, one or more of H1, L1, H2, and L2 comprise amino acid modifications wherein one or more of H1, H2, and L2 comprise at least one amino acid modification that promotes preferential pairing and L1 does not include amino acid modifications that promote preferential pairing. In one embodiment, one or more of H1, L1, H2, and L2 comprise amino acid modifications wherein one or more of L1, H2, and L2 comprise at least one amino acid modification that promotes preferential pairing and H1 does not include amino acid modifications that promote preferential pairing. In one embodiment, one or more of H1, L1, H2, and L2 comprise amino acid modifications wherein each of L1, H2, and L2 comprise at least one amino acid modification that promotes preferential pairing.

The amino acid modifications can be in the constant domains and/or the variable domains of one or more of H1, L1, H2, and L2. In one embodiment, the amino acid modifications can be in the CH1 domains of H1 and H2, the CL-lambda domain of L1 and the CL-kappa domain of L2. In another embodiment, the amino acid modifications can be in the CH1 and VH domains of H1 and H2, the CL-lambda and VL-lambda domains of L1 and the CL-kappa and VL-kappa domains of L2. In another embodiment, the amino acid modifications can be in the VH domains of H1 and H2, the VL-lambda domain of L1 and the VL-kappa domain of L2.

In one embodiment, the amino acid modifications can be in the framework regions of one or more of H1, L1, H2 and L2. In one embodiment the amino acid modifications are limited to the conserved framework residues of the variable (VH, VL) and constant (CH1, CL) domains as indicated by the Kabat numbering of residues. For example, Almagro [Frontiers In Bioscience (2008) 13: 1619-1633] provides a definition of the framework residues on the basis of Kabat, Chotia, and IMGT numbering schemes.

The number of amino acid modifications in each Mab design or Mab design set can vary. In one embodiment, H1 comprises 0 to 8 amino acid modifications, 0 to 7 amino acid modifications, 0 to 6 amino acid modifications, 0 to 5 amino acid modifications, 0 to 4 amino acid modifications, 0 to 3 amino acid modifications, 0 to 2 amino acid modifications, one amino acid modification, or no amino acid modifications. In one embodiment, L1 comprises 0 to 8 amino acid modifications, 0 to 7 amino acid modifications, 0 to 6 amino acid modifications, 0 to 5 amino acid modifications, 0 to 4 amino acid modifications, 0 to 3 amino acid modifications, 0 to 2 amino acid modifications, one amino acid modification, or no amino acid modifications. In one embodiment, H2 comprises 0 to 8 amino acid modifications, 0 to 7 amino acid modifications, 0 to 6 amino acid modifications, 0 to 5 amino acid modifications, 0 to 4 amino acid modifications, 0 to 3 amino acid modifications, 0 to 2 amino acid modifications, one amino acid modification, or no amino acid modifications. In one embodiment, L2 comprises 0 to 8 amino acid modifications, 0 to 7 amino acid modifications, 0 to 6 amino acid modifications, 0 to 5 amino acid modifications, 0 to 4 amino acid modifications, 0 to 3 amino acid modifications, 0 to 2 amino acid modifications, one amino acid modification, or no amino acid modifications.

In one embodiment, the total number of amino acid modifications in H1, L1, H2, and L2 is less than 20, less than 15, less than 12, less than 11, less than 10, less than 9, less than 8, less than 7, less than 6, less than 5, less than 4, or less than 3. In one embodiment, the total number of amino acid modifications in H1, L1, H2 and L2 is 2.

In one embodiment, the amino acid modifications can be designed specifically for a kappa-lambda system, where one parent antibody comprises a kappa light chain polypeptide sequence, and one parent antibody comprises a lambda light chain polypeptide sequence. Such amino acid modifications or designs are referred to herein as K-L designs. Examples of such amino acid modifications or K-L designs are shown in Table 4A, Table 7A, and Tables 10-A1 to 10-A12.

In another embodiment, the amino acid modifications can be initially identified with respect to a kappa-kappa system (K-K designs), where both parent antibodies comprise a kappa light chain polypeptide sequence, and subsequently ported to a kappa-lambda system. One of skill in the art would understand how these designs can be ported to a kappa-lambda system. For example, the heavy and light chains of the kappa and lambda parent antibodies can be aligned to determine the equivalent lambda light chain positions corresponding to the K-K designs. The equivalent lambda light chain positions can then be modified to conform to the K-K design. Such amino acid modifications or designs are referred to herein as K-K-derived K-L designs, and can fall into the following groups: a) those where no changes are required to the designs, and the amino acid residues modified in the kappa-kappa system are identical to those modified in the kappa-lambda system; b) those that contain silent modifications, where at least one modification made in the kappa-kappa system is unnecessary in the kappa-lambda system, because the modification naturally exists in the lambda light chain polypeptide sequence; c) those that contain amino acid modifications to at least one amino acid residue at the same relative position in the kappa light chain polypeptide sequence and the lambda light chain polypeptide sequence, but where the initial amino acid residue at that positions differs between the kappa and lambda light chain polypeptide sequences, resulting in the same amino acid modification at the position, and d) those that contain at least one additional amino acid modification in the kappa-lambda system compared to the kappa-kappa system. Examples of such K-K-derived K-L designs are provided in Table 4B, Table 7B, and Tables 10-B1 to 10-B10. Specific examples of group a) are marked by asterisk in Table 4B. A specific example of group b) is demonstrated by the Mab design set with the unique identifier 10689-10707. The silent modification is in L1 (Q160E is absent in the WT in lambda as the residue at position 160 is E and not Q). A specific example of group c) is demonstrated by the Mab design set with the unique identifier 10652-10734 where in L1, amino acid residue 124 is an E in WT lambda and a Q in the WT kappa. A specific example of group d) is demonstrated by the Mab design set with the unique identifier 10684-10706, which includes the amino acid modification K129T.

In one embodiment, one or more of H1, L1, H2, and L2 comprises amino acid modifications that promote preferential pairing of H1 with L1 as compared to L2 and of H2 with L2 as compared to L1, where the amino acid modifications comprise conservative amino acid substitutions of the Mab design sets provided in Table 4A, Table 4B, Table 7A, Table 7B, Tables 10-A1 to 10-A12, and Tables 10-B1 to 10-B10.

In one embodiment, the amino acid modifications do not introduce a new cysteine residue and do not remove a naturally occurring cysteine residue in the immunoglobulin heavy chains or the immunoglobulin light chains within the same design.

The combination of amino acid modifications in H1, L1, H2 and L2 that promote preferential pairing are referred to in general as designs. The designs may be more specifically referred to as "LCCA designs" (in the context of H1, L1, L2 or H2, L1, L2) or "Mab designs" (in the context of H1, L1, H2, L2). Typically, LCCA designs are engineered with one or more specific complementary LCCA designs based on each heavy chain of the desired bispecific antibody and accordingly are typically presented in a format where amino acid modifications in all four polypeptide chains of the bispecific antibody are identified (see for example, Tables 4A and 4B). Although specific amino acid substitutions may be identified throughout, it should be understood that conservative substitution at each amino acid position may also be contemplated. Furthermore, for the sake of illustration, the H1L1 heterodimer represents a heterodimer comprising a lambda light chain, and the H2L2 heterodimer represents a heterodimer comprising a kappa light chain, unless otherwise indicated. Finally, all amino acid residues or positions are numbered according to the Kabat numbering system, unless otherwise indicated.

The designs comprise driver sets of complementary amino acid substitutions that promote preferential pairing, and may also comprise secondary substitutions. The secondary substitutions may act to optimize the performance of the driver sets.

One or more driver sets may be employed to promote preferential pairing. These driver sets may be used individually, or in combination, to promote preferential pairing. In one embodiment, the driver set is an electrostatic driver set in which electrostatic attraction and repulsion are expected to be the predominant factors promoting preferential pairing. For example, a design in which H1 comprises the amino acid substitution 186K, L1 comprises the amino acid substitution 133D, H2 comprises the amino acid substitution 188D, and L2 comprises the amino acid substitution 131K, may promote preferential pairing by an electrostatic mechanism. Numerous other examples of electrostatic drivers are found throughout the examples. In one embodiment, one or more electrostatic driver sets may be selected from those identified in Table C:

TABLE C

| Exemplary electrostatic driver sets | | | | |
|---|---|---|---|---|
| Electrostastic Driver | H1 | L1 | H2 | L2 |
| 1 | L143D or L143D_Q179E | T131R/K | S188K OR L124R_S186R | S176D_T178E or S176D_T180E or S131D |
| 2 | L143D or L143D_Q179E | T131R/K | L143R OR S186K | Q124E_V133D or Q124E_V133D_T180D |
| 3 | L143D OR L143D_Q179E | T131K/R | S186K or L124R_S186K | V133D OR V133D_Q160E or Q124E_V133D or S176D_T180E |
| 4 | L143D OR L143D_Q179E | T131K/R | S188K | S131D/E |
| 5 | L143D OR L143D_Q179E | T131K/R | L143R/K | Q124E_V133D or Q124E_V133D_T180D |
| 6 | L143D OR L143D_Q179E | T131K/R | L124R_S186R/K OR L124R_Q179K OR S188K | S176D_T178E or S176D_T180E or S131D/E |
| 7 | L143D OR L143D_Q179E | T131K/R | L143R_S188K or L143K/R or L124R_L143K | Q124E_V133D_S176D_T178D/E or Q124E_V133D_T178E or Q124E_V133D_T180D or Q124E_S176D_T180E |
| 8 | S188K | S176E/DY178E or Y178E/D or S176D_Y178T | V177D_S188D | S176K_T178R/K |
| 9 | S188K | S176E/DY178E or Y178E/D or S176D_Y178T | S186E or L124E/L124E_Q179E | S176K/R or S131K/R_S176R/K |
| 10 | S186K | V133D | S188D | S131K |
| 11 | S186K | V133D | V177D_S188D | S176K_T178R/K |
| 12 | V177D_S188D | S176K_Y178K/R | S188K | S176E/D_T178E or S131D/E |
| 13 | V177D_S188D | S176K_Y178K/R | S186K/R | V133D or Q124E_Q160E_T180E |
| 14 | V177D_S188D | S176K_Y178K/R | L124R or L124R_Q179K or L124R_S186R | S176D or S176D_T178D S176D_T180E |
| 15 | V177D_S188D | S176K_Y178K/R | L143K/R | V133D or Q124E_V133D |
| 16 | S188E | Y178K | L124R or S188K (also in combination with L143K or S186R or Q179K) | S176D/E_T178D/E or S176D/ET180E or S176D or in combination with Q124E or Q124E_V133D or Q124E_Q160E |

TABLE C-continued

| Exemplary electrostatic driver sets | | | | |
|---|---|---|---|---|
| Electrostastic Driver | H1 | L1 | H2 | L2 |
| 17 | S186R or Q179K | S180E | L143E or L143E_Q179E | Q124R/K_T178R or Q124R_Q160R/K_T178R or Q124R_T129K_T178R or Q124R_T129K_Q160K_T178R |
| 18 | S186K | V133D | L143E or L143E_Q179E | Q124R/K_T178R or Q124R_Q160R/K_T178R or Q124R_T129K_T178R or Q124R_T129K_Q160K_T178R |
| 19 | L143K or L143K_V190K or L124K_L143K | V133D or T131E/D_V133D | L143E or L143E_Q179E | Q124R/K_T178R or Q124R_Q160R/K_T178R or Q124R_T129K_T178R or Q124R_T129K_Q160K_T178R |
| 20 | S188K | S176D/E_Y178E or Y178E/D | L143E or L143E_Q179E | Q124R/K_T178R or Q124R_Q160R/K_T178R or Q124R_T129K_T178R or Q124R_T129K_Q160K_T178R |
| 21 | Q179K or S186R or L143K or S188K | S180E or V133D or S176E_Y178E | L143E or L143E_Q179E | S131K or Q124R_T178R or Q124R_Q160K_T178R or T129K_S131K |
| 22 | Q179K or S186R | S180E | L143E or L143E_Q179E | S131K or Q124R_T178R or Q124R_Q160K_T178R |
| 23 | L143K_V190K | V133D | L124E | S131K_L135K |
| 24 | L143K or S186K or L124K_L143K | V133D or T131D/E_V133D | L124E_Q179E or L124E_S186E or L124E_K143E | S131K/R_S176R or S131R_L135K |
| 25 | L143E_Q179E | E124K_Y178R | S186R | T178E_T180E or Q160E_T180E |
| 26 | L143E | E124R | S186R or Q179K | Q124E_Q160E_T180E |
| 27 | S186R | S180E or Y178E_S180E | L143E and/or Q179E | Q124K_T178R or S131K |
| 28 | Q179K | S180E | L143E | Q124R or Q124R_Q160K_T178R |
| 29 | L124E | S176R | L124R | S176D |

In one embodiment, the driver set is a disulphide steering driver set, which may act to disfavor formation of the disulphide bond in mispaired heterodimers. An example of this type of driver set would include 125R in H1, 122D in L1, 228D in H2, and 121K in L2.

In one embodiment the driver set may be a steric driver set, which may act to promote sterically complementary interactions between correctly paired heterodimers and steric incompatibility between mispaired heterodimers. Non-limiting examples of steric driver sets are shown in Table D, where "-" indicates no amino acid substitutions are present that promote preferential pairing.

TABLE D

| Exemplary steric driver sets | | | | |
|---|---|---|---|---|
| | Driver | | | |
| | H1 | L1 | H2 | L2 |
| Steric 1 | 174G | 116F_176F | 190F | 135A |
| Steric 2 | 139W | — | — | 135W |
| Steric 3 | — or 188A | — or 176A_178W | 188W or 186I/L_188W | 176V or 176A_178A |
| Steric 4 | — or 143A | — or 133W | 124W | 133A |

In one embodiment, the driver set is a variable design driver set. Such variable design driver sets comprise one or more amino acid modifications in the variable domains of the kappa and/or lambda Fabs that promote preferential pairing. In one embodiment, the variable design driver set promotes preferential pairing based on steric mechanisms. In one embodiment, the variable design drive set promotes preferential pairing based on electrostatic mechanisms. Non-limiting examples of variable design driver sets are shown in Table E, where "-" indicates no amino acid modifications present in that polypeptide that promote preferential pairing.

TABLE E

| Exemplary variable domain driver sets | | | | |
|---|---|---|---|---|
| | Driver | | | |
| | H1 | L1 | H2 | L2 |
| Variable domain (steric) | 45F | — | 45A/P | 44F |
| Variable domain (steric) | — | — | 45A/P | 44F |
| Variable domain (electrostatic) | 39K/R | 38E/D | 39E/D | 38K/R |
| Variable domain (electrostatic) | 39E/D | 38K/R | 39K/R | 38E/D |
| Variable domain (electrostatic) | — | — | 39E/D | 38R/K |

In one embodiment, one or more non-naturally occurring disulphide bonds may be engineered into one or both heterodimers of the antigen-binding polypeptide construct. An example of this type of amino acid modification is one in which the heavy chain comprises a 122C substitution, paired with a 124C substitution in the kappa light chain.

Secondary substitutions may be included in a design in order to optimize the pairing performance of the design. For example, secondary substitutions may act to A) optimize the number of contacts between the heavy and the correctly paired light chain, B) provide a conducive environment for the drivers, C) optimize the hydrogen bonding network for the driver sets, or D) provide steric accommodation for the drivers. Non-limiting examples of these types of secondary substitutions are shown in Table F, where "Lk" designates a kappa light chain specific substitution, "L1" designates a lambda light chain specific substitution. "L" designates a light chain specific substitution in either kappa or lambda light chain, and "H" designates a heavy chain specific substitution.

TABLE F

| Exemplary secondary substitutions | | | |
|---|---|---|---|
| A) Optimizing contacts | B) Conducive environment | C) Hydrogen Bonding network optimization | D) Steric accommodation |
| | | | L1/178F/T |
| | | | L1/178L |
| Lk/178F | | | |
| Lk/178L | | | |
| | | | L/133A |
| | | | L/133G |
| | | | H/143I |
| | H/146G | | |
| | | | L/133I/L |
| | | | L/131S |
| | | H/143T/S | H/143T/S |
| | | Lk/178S | |
| | | H/177T | |
| H/188T | | | |
| H/177I | | | |
| | | | L/135S |
| H/188L | | | |
| H/139I | | | |
| H/190I | | | |
| | | L/133S/T | |
| | H/145T | | |
| | L1/129T | | |
| | L1/124Q | | |

Antigen-binding polypeptide constructs may be engineered with different combinations of amino acid modifications corresponding to the driver sets and secondary substitutions described above. Non-limiting specific examples of such combinations grouped into clusters based on common features are described below. As described herein, combinations of amino acid modifications at multiple positions within a single chain are identified using "_" between each position modified. For example, "124_186" indicates that both positions 124 and 186 are modified in the polypeptide chain referred to. Likewise, "124_133_180" indicates that all of positions 124, 133, and 180 are modified in the polypeptide chain referred to.

K-L Cluster 1:

In one embodiment, the antigen-binding polypeptide construct comprises a combination of amino acid substitutions according to K-L cluster 1 wherein:

H1 comprises amino acid substitution at position 143; L1 comprises amino acid substitution at position 131; and a) H2 comprises amino acid substitution at positions 188 or 124_186, and L2 comprises amino acid substitution at positions 176_178 or 176_180 or 131; or b) H2 comprises amino acid substitution at position 143 or 186; and L2 comprises amino acid substitutions at positions 124_133 or 124_133_180.

In some embodiments, H1 further comprises amino acid substitutions at one or more of positions 125, 145 and 179, L1 further comprises amino acid substitution at one or more of positions 122, 124, and 133, H2 further comprises amino acid substitution at position 228, and/or L2 further comprises amino acid substitutions at position 121.

In one embodiment, the antigen-binding polypeptide construct comprises a combination of amino acid substitutions according to K-L cluster 1 wherein: H1 comprises amino acid substitution at positions 125_143_145; L1 comprises amino acid substitution at positions 122_124_131; and H2 comprises amino acid substitution at position 228, and L2 comprises amino acid substitution at positions 121_133. In some embodiments, H1 further comprises amino acid substitutions at position 179, L1 further comprises amino acid substitution at position 133, H2 further comprises amino acid substitution at one or more of positions 124, 143, 186, and 188, and L2 further comprises amino acid substitutions at one or more of positions 124, 131, 176, 178, and 180.

In some embodiments, the antigen-binding polypeptide construct comprises a combination of amino acid substitutions according to K-L cluster 1 wherein H1 comprises amino acid substitutions at positions 125_143_145, or 125_143_145_179; L1 comprises amino acid substitutions at positions 122_124_131, or 122_124_131_133; H2 comprises amino acid substitutions at positions 124_186_228, 143_228, 143_186_228, 186_228, or 188_228, and L2 comprises amino acid substitutions at positions 121_124_133, 121_124_133_180, 121_131_133_178_121_133_176_178 or 121_133_176_180.

In some embodiments, the antigen-binding polypeptide construct comprises a combination of amino acid substitutions according to K-L cluster 1 wherein the amino acid substitutions in H1 are selected from 125R, 145T, 143D, 143E, 179E, and conservative substitutions thereof; the amino acid substitutions in L1 are selected from 124Q, 122D, 131K, 131R, 133S, and conservative substitutions thereof; the amino acid substitutions in H2 are selected from 228D, 124R, 143I, 143R, 186K, 186R, 188K, and conservative substitutions thereof; the amino acid substitutions in L2 are selected from 124E, 121K, 131D, 176D, 178E, 178F, 180D, 180E, 133D, 133G, 133I, and conservative substitutions thereof.

In some embodiments, the antigen-binding polypeptide construct has an H1L1 heterodimer comprising a combination of amino acid substitutions according to K-L cluster 1, wherein the H1L1 heterodimer comprises one of the following sets of amino acid substitutions:

| H1 | L1 |
|---|---|
| 125R_143D_145T | 122D_124Q_131K_133S |
| 125R_143E_145T_179E | 122D_124Q_131R |
| 125R_143E_145T_179E | 122D_124Q_131K |

In one embodiment, H1 comprises 125R_143E_145T_179E and L1 comprises 122D_124Q_131R. In another embodiment, H1 comprises 125R_143E_145T and L1 comprises 122D_124Q_131R. In further embodiments, the antigen-binding polypeptide construct has an H2L2 heterodimer comprising a combination of amino acid substitutions according to K-L cluster 1, wherein the H2L2 heterodimer comprises one of the following sets of amino acid substitutions:

| H2 | L2 |
|---|---|
| 188K_228D | 121K_133I_176D_178E |
| 188K_228D | 121K_131D_133G_178F |
| 124R_186R_228D | 121K_133G_176D_180E |
| 124R_186R_228D | 121K_133G_176D_180E |
| 143R_228D | 121K_124E_133D_180D |

-continued

| H2 | L2 |
|---|---|
| 143R_228D | 121K_124E_133D |
| 143I_186K_228D | 121K_124E_133D |
| 186K_228D | 121K_124E_133D |

In some embodiments, the antigen-binding polypeptide construct comprises a combination of one H1L1 heterodimer with one H2L2 heterodimer. In one embodiment, H1 comprises 125R_143E_145T_179E, L1 comprises 122D_124Q_131R, H2 comprises 188K_228D, and L2 comprises 121K_133I_176D_178E. In another embodiment, H1 comprises 125R_143D_145T, L1 comprises 122D_124Q_131R, H2 comprises 143R_228D, and L2 comprises 121K_124E_133D.

In some embodiments, the antigen-binding polypeptide construct comprises a combination of amino acid substitutions according to K-L cluster 1, comprising a disulfide steering driver set.

In one embodiment, the amino acid combinations of K-L cluster 1 comprises one or more secondary substitutions selected from Table F.

In one embodiment, the antigen-binding polypeptide construct comprises a combination of amino acid substitutions according to K-L cluster 1 as set forth in one or more of the designs in Table 10-A1.

K-L Cluster 2:

In one embodiment, the antigen-binding polypeptide construct comprises a combination of amino acid substitutions according to K-L cluster 2 wherein:

H1 comprises amino acid substitution at position 143; L1 comprises amino acid substitution at position 131; and c) H2 comprises amino acid substitution at positions 186 or 124_186, and L2 comprises amino acid substitution at positions 133 or 133_160 or 124_133 or 176_180; or d) H2 comprises amino acid substitution at position 188; and L2 comprises amino acid substitutions at position 131;

e) H2 comprises amino acid substitution at position 143; and L2 comprises amino acid substitutions at positions 124_133 or 124_133_180;

In some embodiments, H1 further comprises amino acid substitutions at one or more of positions 139, 145, 174, and 179, L1 further comprises amino acid substitutions at one or more of positions 116, 124, 133 and 176, H2 further comprises amino acid substitution at one or more of positions 190, 39, and 45, and/or L2 further comprises amino acid substitutions at one or more of positions 135, 178, 38, and 44.

In one embodiment, the antigen-binding polypeptide construct comprises a combination of amino acid substitutions according to K-L cluster 2 wherein H1 comprises amino acid substitution at positions 143_145; L1 comprises amino acid substitution at position 131; and H2 comprises amino acid substitutions at position 143 or 186 or 188, and L2 comprises amino acid substitution at position 133. In some embodiments, H1 further comprises amino acid substitutions at one or more of positions 139, 174, and 179, L1 further comprises amino acid substitution at one or more of positions 116, 124, 133, and 176, H2 further comprises amino acid substitution at one or more of positions, 124, 190, 39, and 45 and L2 further comprises amino acid substitutions at one or more of positions 124, 131, 135, 160, 176, 178, 180, 38, 44.

In some embodiments, the antigen-binding polypeptide construct comprises a combination of amino acid substitutions according to K-L cluster 2 wherein H1 comprises amino acid substitutions at positions 139_143_145, 143_145, 143_145_174, or 143_145_179; L1 comprises amino acid substitutions at positions 116_124_131_176, 124_131, 124_131_133, 124_131_133_176, 131, or 131_133; H2 comprises amino acid substitutions at positions 124_186_190, 143, 143_186, 143_186_190, 143_190, 186, 186_190, 188, 39_143, or 45_143, and L2 comprises amino acid substitutions at positions 124_133, 124_133_135, 124_133_135_180, 124_133_180, 131_133_135_178, 131_133_178, 133, 133_135_176_180, 133_160, 38_124_133, or 44_124_133.

In some embodiments, the antigen-binding polypeptide construct comprises a combination of amino acid substitutions according to K-L cluster 2 wherein the amino acid substitutions in H1 are selected from 139W, 143D, 145T, 174G, 179E, and conservative substitutions thereof; the amino acid substitutions in L1 are selected from 124Q, 176F, 116F, 131K, 131R, 133S, and conservative substitutions thereof; the amino acid substitutions in H2 are selected from 124R, 143I, 143K, 143R, 186K, 188K, 190F, 39E, 45P, and conservative substitutions thereof; the amino acid substitutions in L2 are selected from 124E, 131D, 131E, 133D, 133G, 135A, 135W, 160E, 176D, 178F, 180D, 180E, 38R, 44F, and conservative substitutions thereof.

In some embodiments, the antigen-binding polypeptide construct has an H1L1 heterodimer comprising a combination of amino acid substitutions according to K-L cluster 2, wherein the H1L1 heterodimer comprises one of the following sets of amino acid substitutions:

| H1 | L1 |
|---|---|
| 139W_143D_145T | 124Q_131K_133S |
| 139W_143D_145T | 124Q_131R |
| 143D_145T | 124Q_131K |
| 143D_145T | 124Q_131K_133S |
| 143D_145T | 124Q_131R |
| 143D_145T | 131K |
| 143D_145T | 131K_133S |
| 143D_145T_174G | 116F_124Q_131R_176F |
| 143D_145T_174G | 124Q_131K_133S_176F |
| 143D_145T_174G | 116F_124Q_131K_176F |
| 143D_145T_179E | 124Q_131K |
| 143D_145T_179E | 124Q_131K_133S |
| 143D_145T_179E | 131K |
| 143D_145T_179E | 131K_133S |

In further embodiments, the antigen-binding polypeptide construct has an H2L2 heterodimer comprising a combination of amino acid substitutions according to K-L cluster 2, wherein the H2L2 heterodimer comprises one of the following sets of amino acid substitutions:

| H2 | L2 |
|---|---|
| 143I_186K | 133D |
| 143I_186K | 133D_160E |
| 143I_186K | 124E_133D_135W |
| 143I_186K_190F | 124E_133D_135A |
| 186K | 124E_133D |
| 186K | 133D_160E |
| 186K | 133D |
| 186K | 124E_133D_135W |
| 186K_190F | 124E_133D_135A |
| 124R_186K_190F | 133G_135A_176D_180E |
| 188K | 131D_133G_135W_178F |

-continued

| H2 | L2 |
|---|---|
| 188K | 131D_133G_178F |
| 188K | 131E_133G_178F |
| 143K/R | 124E_133D |
| 143R | 124E_133D_135W_180D |
| 143R | 124E_133D_135W |
| 143R | 124E_133D_180D |
| 143R_190F | 124E_133D_135A |
| 45P_143R | 44F_124E_133D |
| 39E_143R | 38R_124E_133D |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 143D_145T | 124Q_131R | 188K | 131D_133G_178F |
| 143D_145T_174G | 116F_124Q_131R_176F | 143R_190F | 124E_133D_135A |
| 139W_143D_145T | 124Q_131R | 143R | 124E_133D_135W |
| 143D_145T | 124Q_131R | 143R | 124E_133D_180D |

In some embodiments, the antigen-binding polypeptide construct comprises a combination of amino acid substitutions according to K-L cluster 2, having one or more of steric 1, steric 2, variable domain steric, or variable domain electrostatic driver sets.

In one embodiment, the amino acid combinations of K-L cluster 2 comprises one or more secondary substitutions selected from Table F.

In one embodiment, the antigen-binding polypeptide construct comprises a combination of amino acid substitutions according to K-L cluster 2 as set forth in one or more of the designs in Table 10-A2.

K-L Cluster 3:

In one embodiment, the antigen-binding polypeptide construct comprises a combination of amino acid substitutions according to K-L cluster 3 wherein:

H1 comprises amino acid substitution at position 143; L1 comprises amino acid substitution at position 131; and a) H2 comprises amino acid substitution at positions 124_186 or 124_179 or 188, and L2 comprises amino acid substitution at positions 176_178 or 176_180 or 131; or b) H2 comprises amino acid substitution at positions 143_188 or 143 or 124_143; and L2 comprises amino acid substitutions at positions 124_176_178 or 124_178 or 124_180 or 124_176_180 or 124, or 124_176.

In some embodiments, H1 further comprises amino acid substitutions at one or more of positions 139, 145, 174, and 179, L1 further comprises amino acid substitution at one or more of positions 116, 124, and 176, H2 further comprises amino acid substitution at one or more of positions 177, 190, 39, and 45, and/or L2 further comprises amino acid substitutions at one or more of positions 133, 135, 178, 38, and 44.

In one embodiment, the antigen-binding polypeptide construct comprises a combination of amino acid substitutions according to K-L cluster 3 wherein: H1 comprises amino acid substitution at positions 143_145; L1 comprises amino acid substitution at positions 124_131; and H2 comprises amino acid substitution at one or more of positions 143, 124, and 188, and L2 comprises amino acid substitution at positions 133 or 176_178. In some embodiments, H1 further comprises amino acid substitutions at one or more of positions 139, 174, and 179, L1 further comprises amino acid substitution at position 116 or 176, H2 further comprises amino acid substitution at one or more of positions 177, 179, 186, 190, 39, and 45, and/or L2 further comprises amino acid substitutions at one or more of positions 124, 131, 135, 180, 38, and 44.

In some embodiments, the antigen-binding polypeptide construct comprises a combination of amino acid substitutions according to K-L cluster 3 wherein H1 comprises amino acid substitutions at positions 139_143_145, 139_143_145_179, 143_145, 143_145_174_179, or 143_145_179; L1 comprises amino acid substitutions at positions 116_124_131_176, or at 124_131; H2 comprises amino acid substitutions at positions 124_143, 124_179, 124_186, 143, 143_188, 177_188, 188, 188_190, 39_124_179, or 45_124_179, and L2 comprises amino acid substitutions at positions 124_133, 124_133_176, 124_133_176_178, 124_133_176_180, 124_133_178, 124_133_180, 131_133_178, 133_135_176_178, 133_135_176_180, 133_176_178, 133_176_180, 176_178, 38_133_176_180, or 44_133_176_180.

In some embodiments, the antigen-binding polypeptide construct comprises a combination of amino acid substitutions according to K-L cluster 3 wherein the amino acid substitutions in H1 are selected from 139W, 174G, 145T, 143D, 143E, 179E, and conservative substitutions thereof; the amino acid substitutions in L1 are selected from 116F, 124Q, 131K, 131R, 176F, and conservative substitutions thereof; the amino acid substitutions in H2 are selected from 124R, 143K, 143R, 177I, 179K, 186K, 186R, 188K, 190F, 39E, 45P, and conservative substitutions thereof; the amino acid substitutions in L2 are selected from 135A, 135W, 44F, 124E, 38R, 131D, 131E, 176D, 176E, 178D, 178E, 178F, 180D, 180E, 133D, 133G, 133I, 133L, and conservative substitutions thereof.

In some embodiments, the antigen-binding polypeptide construct has an H1L1 heterodimer comprising a combination of amino acid substitutions according to K-L cluster 3, wherein the H1L1 heterodimer comprises one of the following sets of amino acid substitutions:

| H1 | L1 |
|---|---|
| 139W_143D_145T | 124Q_131R |
| 139W_143E_145T_179E | 124Q_131K |
| 143D_145T | 124Q_131R |
| 143E_145T_179E | 124Q_131R |
| 143E_145T_174G_179E | 116F_124Q_131R_176F |

In further embodiments, the antigen-binding polypeptide construct has an H2L2 heterodimer comprising a combination of amino acid substitutions according to K-L cluster 3, wherein the H2L2 heterodimer comprises one of the following sets of amino acid substitutions:

| H2 | L2 |
|---|---|
| 124R_179K | 133G_176D_178E |
| 124R_186K/R | 133G_176D_180E |
| 124R_186K/R | 133G_135W_176D_180E |
| 188K | 131D_133G_178F |
| 188K | 131E_133G_178F |
| 188K | 176E_178E |
| 188K | 133I_135W_176D_178E |
| 188K | 133I_176D_178E |
| 143R_188K | 124E_133D_176D_178D |
| 143R_188K | 124E_133D_176D_178E |
| 143R_188K | 124E_133D_178E |
| 143K/R | 124E_133D |
| 143K/R | 124E_133D_180D |
| 124R_143K | 124E_133G_176D_180E |
| 124R_143K | 124E_133G_176D |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 143E_145T_179E | 124Q_131K | 124R_186K | 133G_176D_178E |
| 143E_145T_179E | 124Q_131K | 143K | 124E_133D |
| 143D_145T | 124Q_131R | 188K | 176E_178E |
| 143D_145T | 124Q_131K | 124R_186R | 133G_176D_180E |
| 139W_143D_145T | 124Q_131R | 124R_186K | 133G_135W_176D_180E |

In some embodiments, the antigen-binding polypeptide construct comprises a combination of amino acid substitutions according to K-L cluster 3, having one or more of steric 1, steric 2, variable domain steric or variable domain electrostatic driver sets.

In one embodiment, the amino acid combinations of K-L cluster 3 comprise one or more secondary substitutions selected from Table F.

In one embodiment, the antigen-binding polypeptide construct comprises a combination of amino acid substitutions according to K-L cluster 3, as set forth in one or more of the designs in Table 10-A3.

K-L Cluster 4:

In one embodiment, the antigen-binding polypeptide construct comprises a combination of amino acid substitutions according to K-L cluster 4 wherein: H1 comprises amino acid substitution at position 188; L1 comprises amino acid substitution at positions 176_178 or 178; and a) H2 comprises amino acid substitution at positions 177_188, and L2 comprises amino acid substitution at positions 176_178; or
b) H2 comprises amino acid substitution at position 186 or 124 or 124_179; and L2 comprises amino acid substitutions at positions 176 or 131_176.

In some embodiments, H1 further comprises amino acid substitutions at one or more of positions 125, 139, and 177, L1 further comprises amino acid substitution at one or more of positions 122, 129, and 133, H2 further comprises amino acid substitution at one or more of positions 145, 228, 45, and 39, and/or L2 further comprises amino acid substitutions at one or more of positions 135, 44, 38, 121, and 133.

In one embodiment, the antigen-binding polypeptide construct comprises a combination of amino acid substitutions according to K-L cluster 4 wherein: H1 comprises no amino acid substitutions that promote preferential pairing or comprises amino acid substitution at position 188; L1 comprises no amino acid substitutions that promote preferential pairing or comprises amino acid substitution at positions 176_178; H2 comprises amino acid substitution at positions 188 or 186_188, and L2 comprises amino acid substitution at positions 176_178.

In one embodiment, the antigen-binding polypeptide construct comprises a combination of amino acid substitutions according to K-L cluster 4 wherein: H1 comprises no amino acid substitutions that promote preferential pairing or comprises amino acid substitution at position 188; L1 comprises no amino acid substitutions that promote preferential pairing or comprises amino acid substitution at positions 178; H2 comprises amino acid substitution at one or more of positions 124, 186, and 188, and L2 comprises amino acid substitution at position 176. In some embodiments, H1 further comprises amino acid substitutions at one or more of positions 125, 139, and 177, L1 further comprises amino acid substitution at one or more of positions 122, 129, 133, and 176, H2 further comprises amino acid substitution at one or more of positions 145, 228, 45, 177, 179, and 39, and/or L2 further comprises amino acid substitutions at one or more of positions 135, 44, 38, 121, 131, 178, and 133.

In some embodiments, the antigen-binding polypeptide construct comprises a combination of amino acid substitutions according to K-L cluster 4 wherein H1 comprises no amino acid substitutions that promote preferential pairing or comprises amino acid substitutions at positions 125_188, 139_188, 188, or 177_188; L1 comprises no amino acid substitutions that promote preferential pairing or comprises amino acid substitutions at positions 129_176_178, 129_178, 122_129_176_178, 176_178, or 133_176_178; H2 comprises amino acid substitutions at positions 145_186, 145_186_228, 145_177_188, 124, 124_145_179, 124_145_179_186_188, 124_145_179_188, 124_186_188, 124_188, 45_124_145_179, 39_124_145_179, or 186_188, and L2 comprises amino acid substitutions at positions 44_131_133_176, 38_131_133_176, 121_131_176, 131_135_176, 131_176, 131_133_176, 131_133_176_178, 176, 176_178, 133_176, or 133_176_178.

In some embodiments, the antigen-binding polypeptide construct comprises a combination of amino acid substitutions according to K-L cluster 4 wherein the amino acid substitutions in H1 are selected from 125R, 139W, 188A, 188K, and 177I, and conservative substitutions thereof; the amino acid substitutions in L1 are selected from 129T, 122D, 176A, 176D, 176E, 133I, 133L, 178D, 178E, 178T, and 178W, and conservative substitutions thereof; the amino acid substitutions in H2 are selected from 124E, 145T, 177D, 179E, 186E, 186I, 186L, 188D, 188W, 228D, 39E, and 45P, and conservative substitutions thereof; the amino acid substitutions in L2 are selected from 121K, 131K, 131R, 133A, 133G, 135W, 176A, 176K, 176R, 176V, 178A, 178K, 178L, 178R, 38R, and 44F, and conservative substitutions thereof.

In some embodiments, the antigen-binding polypeptide construct has an H1L1 heterodimer comprising a combination of amino acid substitutions according to K-L cluster 4, wherein the H1L1 heterodimer comprises one of the following sets of amino acid substitutions:

In further embodiments, the antigen-binding polypeptide construct has an H2L2 heterodimer comprising a combination of amino acid substitutions according to K-L cluster 4, wherein the H2L2 heterodimer comprises one of the following sets of amino acid substitutions:

| H2 | L2 |
|---|---|
| 145T_186E | 131K_135W_176K |
| 145T_186E_228D | 131K_176K |
| 145T_186E_228D | 121K_131K_176K |
| 124E | 133G_176R |
| 124E | 133A_176K |
| 124E_186I_188W | 133G_176R_178A |
| 124E_188W | 133A_176K_178A |
| 124E_145T_179E | 131K_133G_176R |
| 124E_145T_179E | 131R_133G_176R |
| 124E_145T_179E_186I_188W | 131R_133G_176R_178A |
| 124E_145T_179E_188W | 131K_133G_176R_178A |
| 45P_L124E_145T_179E | 44F_131R_133G_176R |
| 39E_L124E_145T_179E | 38R_131R_133G_176R |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 188K | 176E_178E | 124E_145T_179E | 131R_133G_176R |
| 125R_188K | 122D_129T_176E_178E | 145T_186E_228D | 121K_131K_176K |
| 188K | 129T_178D | 145T_186E | 131K_176K |

In some embodiments, the antigen-binding polypeptide construct comprises a combination of amino acid substitutions according to K-L cluster 4, having one or more of electrostatic, disulfide steering, steric 3, variable domain steric and variable domain electrostatic driver sets.

In one embodiment, the amino acid combinations of K-L cluster 4 comprise one or more secondary substitutions selected from Table F.

In one embodiment, the antigen-binding polypeptide construct comprises a combination of amino acid substitutions according to K-L cluster 4 as set forth in one or more of the designs in Table 10-A4.

K-L Cluster 5:

In one embodiment, the antigen-binding polypeptide construct comprises a combination of amino acid substitutions according to K-L cluster 5 wherein:

H1 comprises amino acid substitution at position 186; L1 comprises amino acid substitution at position 133; and a) H2 comprises amino acid substitution at position 188, and L2 comprises amino acid substitution at position 131; or b) H2 comprises amino acid substitution at positions 177_188; and L2 comprises amino acid substitutions at positions 176_178; or wherein H1 comprises amino acid substitution at positions 124_190; L1 comprises amino acid substitution at position 135; H2 comprises amino acid substitution at positions 124 or 188, and L2 comprises amino acid substitution at positions 176 or 176_178.

In some embodiments, H1 further comprises amino acid substitutions at position, 143 and/or 188, L1 further comprises amino acid substitution at position 131 and/or 178, H2 further comprises amino acid substitution at positions 143 and/or 145, and/or L2 further comprises amino acid substitutions at position 133 and/or 178.

In one embodiment, the antigen-binding polypeptide construct comprises a combination of amino acid substitutions according to K-L cluster 5 wherein: H1 comprises amino acid substitution at position 186 or 124; L1 comprises amino acid substitution at position 133 and/or 135; and H2 comprises amino acid substitutions at one or more of positions 188, 177 and 124, and L2 comprises amino acid substitution at position 176 and/or 131.

In some embodiments, H1 further comprises amino acid substitutions at one or more of positions 143, 188, and 190, L1 further comprises amino acid substitution at positions 131 and/or 178, H2 further comprises amino acid substitution at positions 143 and/or 145, and/or L2 further comprises amino acid substitutions at positions 133 and/or 178.

In some embodiments, the antigen-binding polypeptide construct comprises a combination of amino acid substitutions according to K-L cluster 5 wherein H1 comprises amino acid substitutions at positions 124_190, 143_186_188, or 186_188; L1 comprises amino acid substitutions at positions 131_133_178, 133_135, 133_135_178, 133_178, or 135_178; H2 comprises amino acid substitutions at positions 124, 143_188, 145_177_188, or 177_188, and L2 comprises amino acid substitutions at positions 131_176_178, 131_178, 133_176, 133_176_178, or 176_178.

In some embodiments, the antigen-binding polypeptide construct comprises a combination of amino acid substitutions according to K-L cluster 5 wherein the amino acid substitutions in H1 are selected from 124E, 143S, 186K, 188T, 190D, 190E, and conservative substitutions thereof; the amino acid substitutions in L1 are selected from 131S, 133D, 133I, 135K, 135R, 178F, 178T, and conservative substitutions thereof; the amino acid substitutions in H2 are selected from 124R, 143T, 145T, 177D, 177I, 188D, 188K, and conservative substitutions thereof; the amino acid substitutions in L2 are selected from 131K, 133G, 133L, 176A, 176D, 176K, 178E, 178K, 178R, 178S, and conservative substitutions thereof.

In some embodiments, the antigen-binding polypeptide construct has an H1L1 heterodimer comprising a combination of amino acid substitutions according to K-L cluster 5, wherein the H1L1 heterodimer comprises one of the following sets of amino acid substitutions:

| H1 | L1 |
|---|---|
| 186K_188T | 133D_178T |
| 186K_188T | 131S_133D_178T |
| 143S_186K_188T | 133D_178T |

-continued

| H1 | L1 |
|---|---|
| 124E_190E/D | 133I_135R_178F |
| 124E_190E/D | 133I_135K_178F |
| 124E_190E/D | 133I_135K |
| 124E_190E/D | 135K_178F |

In further embodiments, the antigen-binding polypeptide construct has an H2L2 heterodimer comprising a combination of amino acid substitutions according to K-L cluster 5, wherein the H2L2 heterodimer comprises one of the following sets of amino acid substitutions:

| H2 | L2 |
|---|---|
| 145T_177D_188D | 176K_178K |
| 145T_177D_188D | 176K_178R |
| 124R | 133G_176D |
| 143T_188D | 131K_178S |
| 143T_188D | 131K_176A_178S |
| 177I_188K | 133L_176D_178E |

In some embodiments, the antigen-binding polypeptide construct comprises a combination of one H1L1 heterodimer with one H2L2 heterodimer. In one embodiment, the combination of H1L1 heterodimer and H2L2 heterodimer is one where H1 comprises 186K_188T, L1 comprises 133D_178T, H2 comprises 145T_177D_188D, and L2 comprises 176K_178K.

In one embodiment, the amino acid combinations of K-L cluster 5 comprise one or more secondary substitutions selected from Table F.

In one embodiment, the antigen-binding polypeptide construct comprises a combination of amino acid substitutions according to K-L cluster 5, as set forth in one or more of the designs in Table 10-A5.

K-L Cluster 6:

In one embodiment, the antigen-binding polypeptide construct comprises a combination of amino acid substitutions according to K-L cluster 6 wherein:

H1 comprises amino acid substitution at positions 177_188; L1 comprises amino acid substitution at position 176_178; and a) H2 comprises amino acid substitution at position 188, and L2 comprises amino acid substitution at positions 176_178 or 131;
b) H2 comprises amino acid substitution at position 186; and L2 comprises amino acid substitutions at positions 133 or 124_160_180;
c) H2 comprises amino acid substitution at position 124 or 124_179 or 124_186; and L2 comprises amino acid substitutions at positions 176 or 176_178 or 176_180; or
d) H2 comprises amino acid substitution at position 143; and L2 comprises amino acid substitutions at positions 133 or 124_133.

In some embodiments, H1 further comprises amino acid substitutions at 145 and/or 146, and/or H2 further comprises amino acid substitution at one or more of positions 143 and/or 177.

In one embodiment, the antigen-binding polypeptide construct comprises a combination of amino acid substitutions according to K-L cluster 6 wherein:

H1 comprises amino acid substitution at positions 177_188; L1 comprises amino acid substitution at positions 176_178; and H2 comprises amino acid substitution at one or more of positions 124, 143, 179, 186, and 188, and L2 comprises amino acid substitution at one or more of positions 133, 176, and 178.

In some embodiments, H1 further comprises amino acid substitutions at 145 and/or 146 positions, H2 further comprises amino acid substitution at position 177, and/or L2 further comprises amino acid substitutions at one or more of positions 124, 131, 160, and 180.

In some embodiments, the antigen-binding polypeptide construct comprises a combination of amino acid substitutions according to K-L cluster 6 wherein H1 comprises amino acid substitutions at positions 145_177_188, or 146_177_188; L1 comprises amino acid substitutions at positions 176_178; H2 comprises amino acid substitutions at positions 124, 124_179, 124_186, 143, 143_186_188, 177_188, 179, 186, 186_188, or 188, and L2 comprises amino acid substitutions at positions 124_133, 124_160_176_178_180, 124_160_180, 131_133_178, 133, 133_176, 133_176_178, 133_176_180, or 176_178.

In some embodiments, the antigen-binding polypeptide construct comprises a combination of amino acid substitutions according to K-L cluster 6 wherein the amino acid substitutions in H1 are selected from 145T, 146T, 177D, 188D, and conservative substitutions thereof; the amino acid substitutions in L1 are selected from 176K, 178K, 178L, 178R, and conservative substitutions thereof; the amino acid substitutions in H2 are selected from 124R, 143K, 143R, 143S, 177I, 179K, 186K, 186R, 188K, 188T, 188W, and conservative substitutions thereof; the amino acid substitutions in L2 are selected from 124E, 131D, 131E, 133D, 133G, 133I, 133L, 160E, 176A, 176D, 176E, 178A, 178D, 178E, 178F, 180E, and conservative substitutions thereof.

In some embodiments, the antigen-binding polypeptide construct has an H1L1 heterodimer comprising a combination of amino acid substitutions according to K-L cluster 6, wherein the H1L1 heterodimer comprises one of the following sets of amino acid substitutions:

| H1 | L1 |
|---|---|
| 146T_177D_188D | 176K_178K |
| 145T_177D_188D | 176K_178L |
| 145T_177D_188D | 176K_178R |

In further embodiments, the antigen-binding polypeptide construct has an H2L2 heterodimer comprising a combination of amino acid substitutions according to K-L cluster 6, wherein the H2L2 heterodimer comprises one of the following sets of amino acid substitutions:

| H2 | L2 |
|---|---|
| 124R | 133G_176D |
| 124R | 133G_176D_178D |
| 124R_179K | 133G_176D_180E |
| 124R_186R | 133G_176D_180E |
| 143K | 124E_133D |
| 143K | 133D |
| 179K or 186R | 124E_160E_180E |
| 186R_188W | 124E_160E_176A_178A_180E |
| 143S_186K_188T | 133D |
| 186K_188T | 133D |
| 188K | 131D_133G_178F |
| 188K | 131E_133G_178F |
| 188K | 176D_178E |

-continued

| H2 | L2 |
|---|---|
| 188K | 176E_178E |
| 177I_188K | 133I_176E_178E |
| 177I_188K | 133L_176D_178E |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 145T_177D_188D | 176K_178K | 124R | 133G_176D |
| 145T_177D_188D | 176K_178K | 143K | 124E_133D |

In some embodiments, the antigen-binding polypeptide construct comprises a combination of amino acid substitutions according to K-L cluster 6, having a steric driver set.

In one embodiment, the amino acid combinations of K-L cluster 6 comprise one or more secondary substitutions selected from Table F.

In one embodiment, the antigen-binding polypeptide construct comprises a combination of amino acid substitutions according to K-L cluster 6, as set forth one or more of the designs in Table 10-A6.

K-L Cluster 7:

In one embodiment, the antigen-binding polypeptide construct comprises a combination of amino acid substitutions according to K-L cluster 7 wherein:

H1 comprises amino acid substitution at position 188; L1 comprises amino acid substitution at position 178; H2 comprises amino acid substitution at position 124 or 188, and L2 comprises amino acid substitution at positions 176_178 or 176_180 or 176. In some embodiments, H1 further comprises amino acid substitutions at one or more of positions 125, 139, 145, and 177, L1 further comprises amino acid substitution at position 122, H2 further comprises amino acid substitution at one or more of positions 143, 177, 179, 186, 228, 39, and 45, and/or L2 further comprises amino acid substitutions at one or more of positions 121, 124, 133, 135, 160, 38, and 44.

In one embodiment, the antigen-binding polypeptide construct comprises a combination of amino acid substitutions according to K-L cluster 7 wherein: H1 comprises amino acid substitution at positions 145_188; L1 comprises amino acid substitution at position 178; and H2 comprises amino acid substitution at position 124 and/or 188, and L2 comprises amino acid substitution at one or more of positions 124, 133, and 178.

In some embodiments, H1 further comprises amino acid substitutions at one or more of positions 125, 139, and 177, L1 further comprises amino acid substitution at position 122, H2 further comprises amino acid substitution at one or more of positions 143, 177, 179, 186, 228, 39, and 45, and/or L2 further comprises amino acid substitutions at one or more of positions 121, 135, 160, 176, 180, 38, and 44.

In some embodiments, the antigen-binding polypeptide construct comprises a combination of amino acid substitutions according to K-L cluster 7 wherein H1 comprises amino acid substitutions at positions 125_145_188, 139_145_188, 145_177_188, or 145_188; L1 comprises amino acid substitutions at positions 122_178, or 178; H2 comprises amino acid substitutions at positions 124, 124_143, 124_179, 124_186, 124_186_228, 124_188, 124_228, 143_188, 177_188, 179_188, 186_188, 188, 188_228, 39_124_179, or 45_124_179, and L2 comprises amino acid substitutions at positions 121_133_176, 121_133_176_180, 121_176_178, 124_133_176, 124_133_176_178, 124_133_176_178_180, 124_133_176_180, 124_133_178, 124_160_176_178, 124_160_176_178_180, 124_176_178_180, 124_176_180, 133_135_176, 133_135_176_180, 133_176, 133_176_178, 133_176_180, 135_176_178, 176_178, 38_133_176_180, or 44_133_176_180.

In some embodiments, the antigen-binding polypeptide construct comprises a combination of amino acid substitutions according to K-L cluster 7 wherein the amino acid substitutions in H1 are selected from 125R, 139W, 145T, 177T, 188E, and conservative substitutions thereof; the amino acid substitutions in L1 are selected from 122D, 178K, and conservative substitutions thereof; the amino acid substitutions in H2 are selected from 124K, 124R, 143K, 143R, 177I, 179K, 186R, 188K, 228D, 39E, 45P, and conservative substitutions thereof; the amino acid substitutions in L2 are selected from 121K, 124E, 133D, 133G, 133L, 135W, 160E, 176D, 176E, 178D, 178E, 180E, 38R, 44F, and conservative substitutions thereof.

In some embodiments, the antigen-binding polypeptide construct has an H1L1 heterodimer comprising a combination of amino acid substitutions according to K-L cluster 7, wherein the H1L1 heterodimer comprises one of the following sets of amino acid substitutions:

| H1 | L1 |
|---|---|
| 125R_145T_188E | 122D_178K |
| 139W_145T_188E | 178K |
| 145T_188E | 178K |
| 145T_177T_188E | 178K |

In further embodiments, the antigen-binding polypeptide construct has an H2L2 heterodimer comprising a combination of amino acid substitutions according to K-L cluster 7, wherein the H2L2 heterodimer comprises one of the following sets of amino acid substitutions:

| H2 | L2 |
|---|---|
| 124R | 133G_176D |
| 124R | 133G_135W_176D |
| 124R | 133G_135W_176D_180E |
| 124R | 133G_176D_180E |
| 124R_228D | 121K_133G_176D |
| 124R_186R_228D | 121K_133G_176D_180E |
| 188K_228D | 121K_176E_178E |
| 124R_143K | 124E_133G_176D_180E |
| 124R_143K | 124E_133G_176D |
| 124R_143K | 124E_133G_176D_178E_180E |
| 124R_179K | 133G_176D_180E |
| 124R_186R | 133G_135W_176D_180E |
| 45P_124R_179K | 44F_133G_176D_180E |
| 39E_124R_179K | 38R_133G_176D_180E |
| 124K_188K | 124E_133G_176D_178D |
| 124R_188K | 124E_133D_176E_178E_180E |
| 143K_188K | 124E_133D_176E_180E |
| 143K_188K | 124E_133D_176D_178E |
| 143K_188K | 124E_133D_178E |
| 179K_188K | 124E_176E_180E |
| 179K_188K | 124E_176E_178D_180E |
| 179K_188K | 124E_176E_178E_180E |
| 186R_188K | 124E_160E_176D_178D_180E |
| 186R_188K | 124E_160E_176D_178D |

-continued

| H2 | L2 |
|---|---|
| 188K | 135W_176E_178E |
| 188K | 176D_178E |
| 188K | 176E_178E |
| 177I_188K | 133L_176D_T178E |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 145T_188E | 178K | 143R_188K | 124E_133D_178E |
| 125R_145T_188E | 122D_178K | 188K_228D | 121K_176E_178E |
| 145T_188E | 178K | 124R | 133G_176D |

In some embodiments, the antigen-binding polypeptide construct of K-L cluster 7 comprises a combination of amino acid substitutions having one or more driver sets selected from a disulfide steering driver set, a steric 2 driver set, and a variable domain driver set.

In one embodiment, the amino acid combinations of K-L cluster 7 comprise one or more secondary substitutions selected from Table F.

In one embodiment, the antigen-binding polypeptide construct comprises a combination of amino acid substitutions according to K-L cluster 7, as set forth in one or more of the designs set forth in Table 10-A7.

K-L Cluster 8:

In one embodiment, the antigen-binding polypeptide construct comprises a combination of amino acid substitutions according to K-L cluster 8 wherein:

H2 comprises amino acid substitution at position 143; L2 comprises amino acid substitution at position 124; and a) H1 comprises amino acid substitution at position 186 or 179, and L1 comprises amino acid substitution at position 180;
b) H1 comprises amino acid substitution at position 186; and L1 comprises amino acid substitutions at position 133;
c) H1 comprises amino acid substitution at position 143; and L1 comprises amino acid substitutions at position 133; or
d) H1 comprises amino acid substitution at position 188; and L1 comprises amino acid substitutions at position 178.

In some embodiments, H1 further comprises amino acid substitutions at one or more of positions 124, 139, 177, and 190, L1 further comprises amino acid substitution at one or more of positions 129, 131, 135, and 176, H2 further comprises amino acid substitution at one or more of positions 122, 124, 145, 179, 186, 188, 39, and 45, and/or L2 further comprises amino acid substitutions at one or more of positions 129, 133, 135, 160, 176, 178, 38, and 44.

In one embodiment, the antigen-binding polypeptide construct comprises a combination of amino acid substitutions according to K-L cluster 8 wherein: H1 comprises amino acid substitution at positions 143, 186, 179 and/or 188; L1 comprises amino acid substitution at positions 129 and/or 178; and H2 comprises amino acid substitution at position 143, and L2 comprises amino acid substitution at position 124. In some embodiments, H1 further comprises amino acid substitutions at one or more of positions 124, 139, 177, and 190, L1 further comprises amino acid substitution at one or more of positions 131, 133, 135, 176, and 180, H2 further comprises amino acid substitution at one or more of positions 122, 124, 145, 179, 186, 188, 39, and 45, and/or L2 further comprises amino acid substitutions at one or more of positions 129, 133, 135, 160, 176, 178, 38, and 44.

In some embodiments, the antigen-binding polypeptide construct comprises a combination of amino acid substitutions according to K-L cluster 8 wherein H1 comprises amino acid substitutions at positions 124_143, 139_143, 139_143_186, 139_186, 139_188, 143, 143_179, 143_186, 143_186_188, 143_190, 177_188, 179, 179_190, 186, or 186_188, 188; L1 comprises amino acid substitutions at positions 129_131_133, 129_133, 129_133_135, 129_133_135_180, 129_133_178, 129_133_180, 129_176_178, 129_176_178_180, 129_178, 129_178_180, 129_180, 133_176_178, 133_178, or 176_178; H2 comprises amino acid substitutions at positions 122_143_145, 122_143_145_179, 124_143_145, 124_143_145_179, 143_145, 143_145_179, 143_145_179_186_188, 143_145_179_188, 143_145_188, 39_143_145_179, or 45_143_145_179, and L2 comprises amino acid substitutions at positions 124_129_160_178, 124_129_178, 124_133_178, 124_135_160_178, 124_135_178, 124_160_176_178, 124_160_178, 124_176_178, 124_178, 38_124_178, or 44_124_178.

In some embodiments, the antigen-binding polypeptide construct comprises a combination of amino acid substitutions according to K-L cluster 8 wherein the amino acid substitutions in H1 are selected from 124K, 139W, 143A, 143I, 143K, 143S, 177I, 179K, 186K, 186R, 188K, 188T, 190K, and conservative substitutions thereof; the amino acid substitutions in L1 are selected from 129T, 131D, 131E, 133D, 133L, 133W, 135S, 176A, 176D, 176E, 178D, 178E, 178T, 178W, 180E, and conservative substitutions thereof; the amino acid substitutions in H2 are selected from 122C, 124W, 143E, 145T, 179E, 186I, 188L, 188W, 39E, 45P, and conservative substitutions thereof; the amino acid substitutions in L2 are selected from 124C, 124K, 124R, 129K, 133A, 135W, 160K, 160R, 176A, 178R, 38R, 44F, and conservative substitutions thereof.

In some embodiments, the antigen-binding polypeptide construct has an H1L1 heterodimer comprising a combination of amino acid substitutions according to K-L cluster 8, wherein the H1L1 heterodimer comprises one of the following sets of amino acid substitutions:

| H1 | L1 |
|---|---|
| 143A_179K | 129T_133W_180E |
| 179K | 129T_180E |
| 179K | 129T_178E_180E |
| 179K_190K | 129T_133D_135S_180E |
| 143K_190K | 129T_133D_135S |
| 124K_143K | 129T_131E_133D |
| 124K_143K | 129T_131D_133D |
| 139W_143K | 129T_133D |
| 143K | 129T_131E/D_133D |
| 143A_186R | 129T_133W_180E |
| 186R | 129T_176A_178W_180E |
| 186R | 129T_180E |
| 186K | 129T_133D_178T |
| 139W_186K | 129T_133D_178T |
| 139W_143I_186K | 129T_133D_178T |
| 186K_188T | 133D_178T |
| 143S_186K_188T | 133D_178T |
| 188K | 129T_176D_178T |
| 139W_188K | 129T_176E_178E |

-continued

| H1 | L1 |
|---|---|
| 188K | 129T_178D |
| 188K | 129T_178E |
| 188K | 176E_178E |
| 177I_188K | 133L_176D_178E |

In further embodiments, the antigen-binding polypeptide construct has an H2L2 heterodimer comprising a combination of amino acid substitutions according to K-L cluster 8, wherein the H2L2 heterodimer comprises one of the following sets of amino acid substitutions:

| H2 | L2 |
|---|---|
| 122C_143E_145T | 124C_160K_178R |
| 122C_143E_145T_179E | 124C_160K_178R |
| 124W_143E_145T | 124K_133A_178R |
| 124W_143E_145T_179E | 124K_133A_178R |
| 143E_145T | 124K_178R |
| 143E_145T | 124R_160K_178R |
| 143E_145T | 124R_129K_160K_178R |
| 143E_145T_179E | 124R_135W_160K_178R |
| 143E_145T_179E | 124R_135W_178R |
| 143E_145T_179E | 124R_160K_178R |
| 143E_145T_179E | 124R_160R_178R |
| 143E_145T_179E | 124R_129K_160K_178R |
| 143E_145T_179E | 124R_129K_178R |
| 143E_145T_179E | 124R_178R |
| 45P_143E_145T_179E | 44F_124K_178R |
| 45P_143E_145T_179E | 44F_124R_178R |
| 39E_143E_145T_179E | 38R_124K_178R |
| 39E_143E_145T_179E | 38R_124R_178R |
| 143E_145T_179E_186I_188W | 124R_176A_178R |
| 143E_145T_179E_186I_188W | 124R_160R_176A_178R |
| 143E_145T_179E_188L | 124K_178R |
| 143E_145T_179E_188L | 124R_160K_178R |
| 143E_145T_179E_188L | 124R_178R |
| 143E_145T_179E_188W | 124R_176A_178R |
| 143E_145T_188W | 124R_160R_176A_178R |
| 143E_145T_188L | 124R_178R |
| 143E_145T_188L | 124R_160K_178R |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 143K | 129T_133D | 124W_143E_145T_179E | 124K_133A_178R |
| 179K | 129T_180E | 143E_145T_188L | 124R_160K_178R |
| 186R | 129T_180E | 45P_143E_145T_179E | 44F_124K_178R |
| 139W_143K | 129T_133D | 143E_145T_179E | 124R_135W_178R |
| 179K | 129T_178E_180E | 143E_145T_179E | 124R_178R |

In some embodiments, the antigen-binding polypeptide construct comprises a combination of amino acid substitutions according to K-L cluster 8 having one or more of steric 2, steric 3, steric 4, and variable domain driver sets. In one embodiment, the antigen-binding polypeptide construct comprises a combination of amino acid substitutions according to K-L cluster 8 that introduce a non-naturally occurring disulphide bond.

In one embodiment, the amino acid combinations of K-L cluster 8 comprise one or more secondary substitutions selected from Table F.

In one embodiment, the antigen-binding polypeptide construct comprises a combination of amino acid substitutions according to K-L cluster 8, as set forth in one or more of the designs in Table 10-A8.

K-L Cluster 9:

In one embodiment, the antigen-binding polypeptide construct comprises a combination of amino acid substitutions according to K-L cluster 9 wherein:

H1 comprises amino acid substitution at position 179, 186, 143 and/or 188; L1 comprises amino acid substitution at position 180, 133 and/or 176_178; H2 comprises amino acid substitution at position 143, and L2 comprises amino acid substitution at position 131 and/or 124. In some embodiments, H1 further comprises amino acid substitutions at position 125, L1 further comprises amino acid substitution at position 122 or 129, H2 further comprises amino acid substitution at one or more of positions 145, 179 and 228, and/or L2 further comprises amino acid substitutions at one or more of positions 121, 129, 135, 160, and 178.

In one embodiment, the antigen-binding polypeptide construct comprises a combination of amino acid substitutions according to K-L cluster 9 wherein: H1 comprises amino acid substitution at position 125; L1 comprises amino acid substitution at positions 122_129; and H2 comprises amino acid substitution at position 145, and L2 comprises amino acid substitution at position 121 and/or 124. In some embodiments, H1 further comprises amino acid substitutions at one or more of positions 143, 179, 186, and 188, L1 further comprises amino acid substitution at one or more of positions, 133, 176, 178, and 180, H2 further comprises amino acid substitution at one or more of positions 143, 179, and 228, and/or L2 further comprises amino acid substitutions at one or more of positions 129, 131, 135, 160, and 178.

In some embodiments, the antigen-binding polypeptide construct comprises a combination of amino acid substitutions according to K-L cluster 9 wherein H1 comprises amino acid substitutions at positions 125_143, 125_179, 125_186, or 125_188; L1 comprises amino acid substitutions at positions 122_129_133, 122_129_176_178, or 122_129_180; H2 comprises amino acid substitutions at positions 143_145, 143_145_179, 143_145_179_228, 143_145_228, or 145_179_228, and L2 comprises amino acid substitutions at positions 121_124_160_178, 121_124_178, 121_129_131, 121_131, 124_135_160_178, or 124_135_178.

In some embodiments, the antigen-binding polypeptide construct comprises a combination of amino acid substitutions according to K-L cluster 9 wherein the amino acid substitutions in H1 are selected from 125R, 143K, 179K, 186R, 188K, and conservative substitutions thereof; the amino acid substitutions in L1 are selected from 122D, 129T, 133D, 176D, 176E, 178E, 178T, 180E, and conservative substitutions thereof; the amino acid substitutions in H2 are selected from 143E, 145T, 179E, 228D, and conservative substitutions thereof; the amino acid substitutions in L2 are selected from 135W, 124R, 160K, 121K, 131K, 129K, 178R, and conservative substitutions thereof.

In some embodiments, the antigen-binding polypeptide construct has an H1L1 heterodimer comprising a combination of amino acid substitutions according to K-L cluster 9, wherein the H1L1 heterodimer comprises one of the following sets of amino acid substitutions:

| H1 | L1 |
|---|---|
| 125R_143K | 122D_129T_133D |
| 125R_179K | 122D_129T_180E |
| 125R_186R | 122D_129T_180E |
| 125R_188K | 122D_129T_176D_178T |
| 125R_188K | 122D_129T_176E_178E |

In further embodiments, the antigen-binding polypeptide construct has an H2L2 heterodimer comprising a combination of amino acid substitutions according to K-L cluster 9, wherein the H2L2 heterodimer comprises one of the following sets of amino acid substitutions:

| H2 | L2 |
|---|---|
| 143E_145T | 124R_135W_160K_178R |
| 143E_145T | 124R_135W_178R |
| 143E_145T_228D | 121K_124R_160K_178R |
| 143E_145T_228D | 121K_124R_178R |
| 145T_179E_228D | 121K_129K_131K |
| 145T_179E_228D | 121K_131K |
| 143E_145T_179E | 124R_135W_160K_178R |
| 143E_145T_179E | 124R_135W_160K_178R |
| 143E_145T_179E_228D | 121K_124R_178R |
| 143E_145T_179E_228D | 121K_124R_160K_178R |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 125R_179K | 122D_129T_180E | 143E_145T_228D | 121K_124R_178R |
| 125R_188K | 122D_129T_176E_178E | 143E_145T_179E_228D | 121K_124R_178R |

In some embodiments, the antigen-binding polypeptide construct comprises a combination of amino acid substitutions according to K-L cluster 9, having a disulfide steering driver set.

In one embodiment, the amino acid combinations of K-L cluster 9 comprise one or more secondary substitutions selected from Table F.

In one embodiment, the antigen-binding polypeptide construct comprises a combination of amino acid substitutions according to K-L cluster 9, as set forth in one or more of the designs in Table 10-A9.

K-L Cluster 10:

In one embodiment, the antigen-binding polypeptide construct comprises a combination of amino acid substitutions according to K-L cluster 10 wherein: H1 comprises amino acid substitution at position 174, 179 or 186; L1 comprises amino acid substitution at position 176 or 180; H2 comprises amino acid substitution at position 143 or 190, and L2 comprises amino acid substitution at position 131, 135 or 124; or H1 comprises amino acid substitution at position 174; L1 comprises amino acid substitution at position 176; H2 comprises amino acid substitution at position 190; and L2 comprises no amino acid substitutions that promote preferential pairing or comprises amino acid substitution at position 135. In some embodiments, H1 further comprises amino acid substitutions at position 143, L1 further comprises amino acid substitution at one or more of positions 116, 129 and 133, H2 further comprises amino acid substitution at one or more of positions 145, 179, and 188, and/or L2 further comprises amino acid substitutions at one or more of positions 133, 160 and 178.

In one embodiment, the antigen-binding polypeptide construct comprises a combination of amino acid substitutions according to K-L cluster 10 wherein: H1 comprises amino acid substitution at positions 174 and/or 186; L1 comprises amino acid substitution at positions 176 and/or 180; and H2 comprises amino acid substitution at position 145, 190 and/or 188, and L2 comprises amino acid substitution at positions 135, 131, 178, or 133 or comprises no amino acid substitutions that promote preferential pairing. In some embodiments, H1 further comprises amino acid substitutions at one or more of positions 143 and/or 179, L1 further comprises amino acid substitution at one or more of positions 116, 129, and 133, H2 further comprises amino acid substitution at positions 143 and/or 179, and/or L2 further comprises amino acid substitutions at positions 124 and/or 160.

In some embodiments, the antigen-binding polypeptide construct comprises a combination of amino acid substitutions according to K-L cluster 10 wherein H1 comprises amino acid substitutions at positions 143_174, 174, 174_179, 174_186, or 186; L1 comprises amino acid substitutions at positions 116_129_133_176, 116_129_176_180, 116_176, 129_180, or 176; H2 comprises amino acid substitutions at positions 143_145_179_188_190, 143_145_179_190, 143_145_190, 143_190, 145_179, 145_179_188_190, 188, or 190, and L2 comprises amino acid substitutions at positions 124_135_160_178, 124_135_178, 131, 131_135, 133, 135, 135_178, 178, or comprises no amino acid substitutions that promote preferential pairing.

In some embodiments, the antigen-binding polypeptide construct comprises a combination of amino acid substitutions according to K-L cluster 10 wherein the amino acid substitutions in H1 are selected from 143K, 174G, 179K, 186R, and conservative substitutions thereof; the amino acid substitutions in L1 are selected from 116F, 129T, 133D, 176F, 180E, and conservative substitutions thereof; the amino acid substitutions in H2 are selected from 143E, 143I, 145T, 179E, 188F, 190F, and conservative substitutions thereof; the amino acid substitutions in L2 are selected from 124K, 124R, 131K, 133A, 135A, 160K, 178F, 178R, and conservative substitutions thereof.

In some embodiments, the antigen-binding polypeptide construct has an H1L1 heterodimer comprising a combination of amino acid substitutions according to K-L cluster 10, wherein the H1L1 heterodimer comprises one of the following sets of amino acid substitutions:

| H1 | L1 |
|---|---|
| 143K_174G | 116F_129T_133D_176F |
| 186R | 129T_180E |
| 174G_179K | 116F_129T_176F_180E |
| 174G_186R | 116F_129T_176F_180E |
| 174G | 176F |
| 174G | 116F_176F |

In further embodiments, the antigen-binding polypeptide construct has an H2L2 heterodimer comprising a combination of amino acid substitutions according to K-L cluster 10, wherein the H2L2 heterodimer comprises one of the following sets of amino acid substitutions:

| H2 | L2 |
|---|---|
| 145T_179E | 131K |
| 145T_179E_188F_190F | 131K_135A |
| 143I_190F | 135A |
| 143I_190F | — |
| 143I_190F | 178F |
| 188F | 133A |
| 190F | — |
| 190F | 135A |
| 190F | 135A_178F |
| 190F | 178F |
| 143E_145T_179E_188F_190F | 124K_135A_178R |
| 143E_145T_179E_190F | 124R_135A_178R |
| 143E_145T_179E_190F | 124K_135A_178R |
| 143E_145T_179E_190F | 124R_135A_160K_178R |
| 143E_145T_190F | 124R_135A_160K_178R |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 143K_174G | 116F_129T_133D_176F | 143E_145T_179E_190F | 124R_135A_178R |
| 174G_179K | 116F_129T_176F_180E | 143E_145T_179E_190F | 124K_135A_178R |

In some embodiments, the antigen-binding polypeptide construct comprises a combination of amino acid substitutions according to K-L cluster 10, having a steric 1 driver set.

In one embodiment, the amino acid combinations of K-L cluster 10 comprise one or more secondary substitutions selected from Table F.

In one embodiment, the antigen-binding polypeptide construct comprises a combination of amino acid substitutions according to K-L cluster 10, as set forth in one or more of the designs in Table 10-A10.

K-L Cluster 11:

In one embodiment, the antigen-binding polypeptide construct comprises a combination of amino acid substitutions according to K-L cluster 11 wherein: H1 comprises amino acid substitution at positions 143_190; L1 comprises amino acid substitution at position 133; H2 comprises amino acid substitution at position 124, and L2 comprises amino acid substitution at positions 131_135. In some embodiments, H1 further comprises amino acid substitutions at position 125, L1 further comprises amino acid substitution at one or more of positions 122, 129 and 135, H2 further comprises amino acid substitution at one or more of positions 139, 145, 190, and 228, and/or L2 further comprises amino acid substitutions at position 121.

In one embodiment, the antigen-binding polypeptide construct comprises a combination of amino acid substitutions according to K-L cluster 11 wherein:

H1 comprises amino acid substitution at positions 143_190; L1 comprises amino acid substitution at positions 129_133_135; and H2 comprises amino acid substitution at position 124_145, and L2 comprises amino acid substitution at positions 131_135. In some embodiments, H1 further comprises amino acid substitutions at position 125, L1 further comprises amino acid substitution at position 122, H2 further comprises amino acid substitution at one or more of positions 139, 190 and 228, and/or L2 further comprises amino acid substitutions at position 121.

In some embodiments, the antigen-binding polypeptide construct comprises a combination of amino acid substitutions according to K-L cluster 11 wherein H1 comprises amino acid substitutions at positions 125_143_190, or 143_190; L1 comprises amino acid substitutions at positions 122_129_133_135, or 129_133_135; H2 comprises amino acid substitutions at positions 124_139_145_190, 124_139_145_190_228, or 124_145, and L2 comprises amino acid substitutions at positions 121_131_135, or 131_135.

In some embodiments, the antigen-binding polypeptide construct comprises a combination of amino acid substitutions according to K-L cluster 11 wherein the amino acid substitutions in H1 are selected from 125R, 143K, 190K, and conservative substitutions thereof; the amino acid substitutions in L1 are selected from 122D, 129T, 133D, 135S, and conservative substitutions thereof; the amino acid substitutions in H2 are selected from 124E, 1391, 145T, 1901, 228D, and conservative substitutions thereof the amino acid substitutions in L2 are selected from 121K, 131K, 135K, and conservative substitutions thereof.

In some embodiments, the antigen-binding polypeptide construct has an H1L1 heterodimer comprising a combination of amino acid substitutions according to K-L cluster 11, wherein the H1L1 heterodimer comprises one of the following sets of amino acid substitutions:

| H1 | L1 |
|---|---|
| 143K_190K | 129T_133D_135S |
| 125R_143K_190K | 122D_129T_133D_135S |

In further embodiments, the antigen-binding polypeptide construct has an H2L2 heterodimer comprising a combination of amino acid substitutions according to K-L cluster 11, wherein the H2L2 heterodimer comprises one of the following sets of amino acid substitutions:

| H2 | L2 |
|---|---|
| 124E_139I_145T_190I | 131K_135K |
| 124E_139I_145T_190I | 131K_135K |
| 124E_139I_145T_190I_228D | 121K_131K_135K |

In some embodiments, the antigen-binding polypeptide construct comprises a combination of one H1L1 heterodimer with one H2L2 heterodimer. In one embodiment, the combination of H1L1 heterodimer and H2L2 heterodimer is one in which H1 comprises 143K_190K, L1 comprises 129T_133D_135S, H2 comprises 124E_145T, and L2 comprises 131K_135K.

In some embodiments, the antigen-binding polypeptide construct comprises a combination of amino acid substitutions according to K-L cluster 11, having a disulfide steering driver set.

In one embodiment, the amino acid combinations of K-L cluster 11 comprise one or more secondary substitutions selected from Table F.

In one embodiment, the antigen-binding polypeptide construct comprises a combination of amino acid substitutions according to K-L cluster 11, as set forth in one or more of the designs in Table 10-All.

K-L Cluster 12:

In one embodiment, the antigen-binding polypeptide construct comprises a combination of amino acid substitutions according to K-L cluster 12 wherein: H1 comprises amino acid substitution at position 143 and/or 186; L1 comprises amino acid substitution at position 133; H2 comprises amino acid substitution at position 124, and L2 comprises amino acid substitution at position 131. In some embodiments, H1 further comprises amino acid substitutions at one or more of positions 124, 125, 139, and 188, L1 further comprises amino acid substitution at one or more of positions 122, 129, 131, and 178, H2 further comprises amino acid substitution at one or more of positions 143, 145, 179, 186, 188, 228, 39, and 45, and/or L2 further comprises amino acid substitutions at one or more of positions 121, 133, 135, 176, 178, 38, and 44.

In some embodiments, the antigen-binding polypeptide construct comprises a combination of amino acid substitutions according to K-L cluster 12 wherein H1 comprises amino acid substitutions at positions 124_143, 125_143, 125_143_186, 125_186, 125_186_188, 139_143, 139_143_186, 139_186, 139_186_188, 143, or 186_188; L1 comprises amino acid substitutions at positions 122_129_133, 122_129_133_178, 122_133_178, 129_131_133, 129_133, 129_133_178, or 133_178; H2 comprises amino acid substitutions at positions 124_143_145, 124_145_179, 124_145_179_186_188, 124_145_179_188, 124_145_179_228, 124_145_186, 39_124_145_179, or 45_124_145_179, and L2 comprises amino acid substitutions at positions 121_131_133_176, 131_133_135, 131_133_135_176, 131_133_135_178, 131_133_176, 131_133_176_178, 38_131_133_176, or 44_131_133_176.

In some embodiments, the antigen-binding polypeptide construct comprises a combination of amino acid substitutions according to K-L cluster 12 wherein the amino acid substitutions in H1 are selected from 124K, 125R, 139W, 143I, 143K, 186K, 188T, and conservative substitutions thereof; the amino acid substitutions in L1 are selected from 122D, 129T, 131D, 131E, 133D, 178T, and conservative substitutions thereof; the amino acid substitutions in H2 are selected from 124E, 143E, 145T, 179E, 186E, 186I, 188W, 228D, 39E, 45P, and conservative substitutions thereof; the amino acid substitutions in L2 are selected from 121K, 131K, 131R, 133G, 133S, 133T, 135K, 135W, 176R, 178A, 178S, 38R, 44F, and conservative substitutions thereof.

In some embodiments, the antigen-binding polypeptide construct has an H1L1 heterodimer comprising a combination of amino acid substitutions according to K-L cluster 12, wherein the H1L1 heterodimer comprises one of the following sets of amino acid substitutions:

| H1 | L1 |
|---|---|
| 143K | 129T_133D |
| 143K | 129T_131D_133D |
| 143K | 129T_131E_133D |
| 124K_143K | 129T_131D_133D |
| 124K_143K | 129T_131E_133D |
| 139W_143K | 129T_133D |
| 125R_143K | 122D_129T_133D |
| 125R_143I_186K | 122D_129T_133D_178T |
| 125R_186K | 122D_129T_133D_178T |
| 125R_186K_188T | 122D_133D_178T |
| 139W_143I_186K | 129T_133D_178T |
| 139W_186K | 129T_133D_178T |
| 139W_186K_188T | 133D_178T |
| 186K_188T | 133D_178T |

In further embodiments, the antigen-binding polypeptide construct has an H2L2 heterodimer comprising a combination of amino acid substitutions according to K-L cluster 12, wherein the H2L2 heterodimer comprises one of the following sets of amino acid substitutions:

| H2 | L2 |
|---|---|
| 124E_145T_179E | 121K_131R_133G_176R |
| 124E_145T_179E | 131K_133G_176R |
| 124E_145T_179E | 131K_133G_176R_178A |
| 124E_145T_179E | 131R_133G_135W_176R |
| 124E_145T_179E | 131R_133G_176R |
| 124E_145T_179E | 131R_133G_176R_178A |
| 124E_145T_186E | 131R_133S_135K |
| 124E_143E_145T | 131R_133T_135K_178S |
| 45P_124E_145T_179E | 44F_131R_133G_176R |
| 39E_124E_145T_179E | 38R_131R_133G_176R |

In some embodiments, the antigen-binding polypeptide construct comprises a combination of one H1L1 heterodimer with one H2L2 heterodimer. In one embodiment, the combination of H1L1 heterodimer and H2L2 heterodimer is one of the following:

| H1 | L1 | H2 | L2 |
|---|---|---|---|
| 143K | 129T_133D | 124E_145T_179E | 131R_133G_176R |
| 186K_188T | 133D_178T | 124E_145T_179E | 131R_133G_176R |
| 139W_143K | 129T_133D | 124E_145T_179E | 131R_133G_135W_176R |

In some embodiments, the antigen-binding polypeptide construct comprises a combination of amino acid substitutions according to K-L cluster 12, having one or more of disulfide steering, steric 2, steric 3, variable domain electrostatic and variable domain steric driver sets.

In one embodiment, the amino acid combinations of K-L cluster 12 comprise one or more secondary substitutions selected from Table F.

In one embodiment, the antigen-binding polypeptide construct comprises a combination of amino acid substitutions according to K-L cluster 12, as set forth in one or more of the designs in Table 10-A12.

K-K Cluster 1:

In one embodiment, the antigen-binding polypeptide construct comprises a combination of amino acid substitutions according to K-K cluster 1 wherein: H1 comprises amino acid substitution at positions 143_179; L1 comprises amino acid substitution at positions 124_178; H2 comprises amino acid substitution at position 186, and L2 comprises amino acid substitution at positions 178_180 or 160_180. In some embodiments, H1 further comprises amino acid substitution at position 145.

In one embodiment, the antigen-binding polypeptide construct comprises a combination of amino acid substitutions according to K-K cluster 1 wherein: H1 comprises amino acid substitution at positions 143_145_179; L1 comprises amino acid substitution at positions 124_178; H2 comprises amino acid substitution at position 186, and L2 comprises amino acid substitution at position 180. In some embodiments, L2 further comprises amino acid substitutions at position 160 and/or 178.

In some embodiments, the antigen-binding polypeptide construct comprises a combination of amino acid substitutions according to K-K cluster 1 wherein H1 comprises amino acid substitutions at position 143_145_179; L1 comprises amino acid substitutions at positions 124_178; H2 comprises amino acid substitutions at position 186, and L2 comprises amino acid substitutions at positions 178_180 or 160_180.

In some embodiments, the antigen-binding polypeptide construct comprises a combination of amino acid substitutions according to K-K cluster 1 wherein the amino acid substitutions in H1 are selected from 143E, 145T, 179E, and conservative substitutions thereof; the amino acid substitutions in L1 are selected from 124K, 178R, and conservative substitutions thereof; the amino acid substitution in H2 is 186R, or conservative substitution thereof; the amino acid substitutions in L2 are selected from 160E, 178E, 180E, and conservative substitutions thereof.

In some embodiments, the antigen-binding polypeptide construct has an H1L1 heterodimer comprising a combination of amino acid substitutions according to K-K cluster 1, wherein the H1L1 heterodimer comprises the following set of amino acid substitutions: H1 comprises 143E_145T_179E and L1 comprises 124K_178R. In a further embodiment, the antigen-binding polypeptide construct has an H2L2 heterodimer comprising a combination of amino acid substitutions according to K-K cluster 1, wherein the H2L2 heterodimer comprises the following sets of amino acid substitutions: H2 comprises 124K_178R and L2 comprises 178E_180E or 160E_180E. In some embodiments, the antigen-binding polypeptide construct comprises a combination of these H1L1 and H2L2 heterodimers.

In one embodiment, the antigen-binding polypeptide construct comprises a combination of amino acid substitutions according to K-K cluster 1 as set forth in Table 10-B1.

K-K Cluster 2:

In one embodiment, the antigen-binding polypeptide construct comprises a combination of amino acid substitutions according to K-K cluster 2 wherein: H1 comprises amino acid substitution at position 143; L1 comprises amino acid substitution at position 124; H2 comprises amino acid substitution at position 179 or 186, and L2 comprises amino acid substitution at position 124_160_180. In some embodiments, H1 further comprises amino acid substitution at position 145, and/or H2 further comprises amino acid substitution at position 146.

In one embodiment, the antigen-binding polypeptide construct comprises a combination of amino acid substitutions according to K-K cluster 2 wherein: H1 comprises amino acid substitution at positions 143_145; L1 comprises amino acid substitution at position 124; and H2 comprises amino acid substitution at positions 179 or 186, and L2 comprises amino acid substitution at positions 124_160_180. In some embodiments, H2 further comprises amino acid substitution at position 146.

In some embodiments, the antigen-binding polypeptide construct comprises a combination of amino acid substitutions according to K-K cluster 2 wherein H1 comprises amino acid substitutions at positions 143_145; L1 comprises amino acid substitutions at position 124; H2 comprises amino acid substitutions at position 186, 179, or 146_179, and L2 comprises amino acid substitutions at positions 124_160_180.

In some embodiments, the antigen-binding polypeptide construct comprises a combination of amino acid substitutions according to K-K cluster 2 wherein the amino acid substitutions in H1 are selected from 143E, 145T, and conservative substitutions thereof; the amino acid substitutions in L1 is 124R, or conservative substitutions thereof; the amino acid substitutions in H2 are selected from 186R, 179K, 146G, and conservative substitutions thereof; the amino acid substitutions in L2 are selected from 124E, 160E, 180E, and conservative substitutions thereof.

In some embodiments, the antigen-binding polypeptide construct has an H1L1 heterodimer comprising a combination of amino acid substitutions according to K-K cluster 2, wherein the H1L1 heterodimer comprises the following set of amino acid substitutions: H1 comprises 143E_145T and L1 comprises 124R. In a further embodiment, the antigen-binding polypeptide construct has an H2L2 heterodimer comprising a combination of amino acid substitutions according to K-K cluster 2, wherein the H2L2 heterodimer comprises the following set of amino acid substitutions: H2 comprises 186R, 179K or 146G 179K and L2 comprises 124E_160E_180E. In some embodiments, the antigen-binding polypeptide construct comprises a combination of one H1L1 heterodimer with one H2L2 heterodimer. In one embodiment, the combination of H1L1 heterodimer and H2L2 heterodimer is one wherein H1 comprises 143E_145T, L1 comprises 124R, H2 comprises 179K, and L2 comprises 124E_160E_180E.

In one embodiment, the amino acid combination of K-K cluster 2 comprises one or more secondary substitutions selected from Table F.

In one embodiment, the antigen-binding polypeptide construct comprises a combination of amino acid substitutions according to K-K cluster 2, as set forth in one or more of the designs in Table 10-B2.

K-K Cluster 3:

In one embodiment, the antigen-binding polypeptide construct comprises a combination of amino acid substitutions according to K-K cluster 3 wherein:
H1 comprises amino acid substitution at position 186; L1 comprises amino acid substitution at positions 180 or 178_180; H2 comprises amino acid substitution at position 143 and/or 179, and L2 comprises amino acid substitution at positions 124_178 or 131. In some embodiments, H2 further comprises amino acid substitution at position 145.

In one embodiment, the antigen-binding polypeptide construct comprises a combination of amino acid substitutions according to K-K cluster 3 wherein: H1 comprises amino acid substitution at position 186; L1 comprises amino acid substitution at position 180; and H2 comprises amino acid substitution at position 145, and L2 comprises amino acid substitution at position 124 or 131. In some embodiments, L1 further comprises amino acid substitution at position 178, H2 further comprises amino acid substitution at positions 143 and/or 179, and/or L2 further comprises amino acid substitutions at position 178.

In some embodiments, the antigen-binding polypeptide construct comprises a combination of amino acid substitutions according to K-K cluster 3 wherein H1 comprises amino acid substitutions at position 186; L1 comprises amino acid substitutions at position 180 or 178_180; H2 comprises amino acid substitutions at positions 143_145, 143_145_179, or 145_179, and L2 comprises amino acid substitutions at positions 131 or 124_178.

In some embodiments, the antigen-binding polypeptide construct comprises a combination of amino acid substitutions according to K-K cluster 3 wherein the amino acid substitutions in H1 are selected from 186R, and conservative substitutions thereof; the amino acid substitutions in L1 are selected from 178E, 180E, and conservative substitutions thereof; the amino acid substitutions in H2 are selected from 143E, 145T, 179E, and conservative substitutions thereof; the amino acid substitutions in L2 are selected from 124K, 131K, 178R, and conservative substitutions thereof.

In some embodiments, the antigen-binding polypeptide construct has an H1L1 heterodimer comprising a combination of amino acid substitutions according to K-K cluster 3, wherein the H1L1 heterodimer comprises the following set of amino acid substitutions: H1 comprises 186R and L1 comprises 178E_180E or 180E. In further embodiments, the antigen-binding polypeptide construct has an H2L2 heterodimer comprising a combination of amino acid substitutions according to K-K cluster 3, wherein the H2L2 heterodimer comprises one of the following sets of amino acid substitutions:

| H2 | L2 |
|---|---|
| 143E_145T_179E | 124K_178R |
| 143E_145T | — |
| 145T_179E | 131K |

In some embodiments, the antigen-binding polypeptide construct comprises a combination of one H1L1 heterodimer with one H2L2 heterodimer. In one embodiment, the combination of H1L1 heterodimer and H2L2 heterodimer is one where H1 comprises 186R, L1 comprises 180E, H2 comprises 143E_145T_179E, and L2 comprises 124K_178R.

In one embodiment, the amino acid combinations of K-K cluster 3 comprise one or more secondary substitutions selected from Table F.

In one embodiment, the antigen-binding polypeptide construct comprises a combination of amino acid substitutions according to K-K cluster 3 as set forth in one or more of the designs in Table 10-B3.

K-K Cluster 4:

In one embodiment, the antigen-binding polypeptide construct comprises a combination of amino acid substitutions according to K-K cluster 4 wherein: H1 comprises amino acid substitution at position 179; L1 comprises amino acid substitution at position 180; H2 comprises amino acid substitution at position 143, and L2 comprises amino acid substitution at position 124. In some embodiments, H1 further comprises amino acid substitutions at position 146, H2 further comprises amino acid substitution at position 145, and/or L2 further comprises amino acid substitutions at position 160 and/or 178.

In one embodiment, the antigen-binding polypeptide construct comprises a combination of amino acid substitutions according to K-K cluster 4 wherein: H1 comprises amino acid substitution at position 179; L1 comprises amino acid substitution at position 180; H2 comprises amino acid substitution at positions 143_145, and L2 comprises amino acid substitution at position 124. In some embodiments, H1 further comprises amino acid substitutions at position 146, and/or L2 further comprises amino acid substitutions at position 160 and/or 178.

In some embodiments, the antigen-binding polypeptide construct comprises a combination of amino acid substitutions according to K-K cluster 4 wherein H1 comprises amino acid substitutions at positions 146_179 or 179; L1 comprises amino acid substitutions at position 180; H2 comprises amino acid substitutions at positions 143_145, and L2 comprises amino acid substitutions at positions 124 or 124_160_178.

In some embodiments, the antigen-binding polypeptide construct comprises a combination of amino acid substitutions according to K-K cluster 4 wherein the amino acid substitutions in H1 are selected from 146G, 179K, and conservative substitutions thereof; the amino acid substitutions in L1 is 180E, or conservative substitutions thereof; the amino acid substitutions in H2 are selected from 143E, 145T, and conservative substitutions thereof; the amino acid substitutions in L2 are selected from 124R, 160K, 178R, and conservative substitutions thereof.

In some embodiments, the antigen-binding polypeptide construct has an H1L1 heterodimer comprising a combination of amino acid substitutions according to K-K cluster 4, wherein the H1L1 heterodimer comprises the following set of amino acid substitutions: H1 comprises 179K or 146G_179K, and L1 comprises 180E. In further embodiments, the antigen-binding polypeptide construct has an H2L2 heterodimer comprising a combination of amino acid substitutions according to K-K cluster 4, wherein the H2L2 heterodimer comprises the following sets of amino acid substitutions: H2 comprises 143E_145T and L2 comprises Q124R_Q160K_T178R or Q124R. In some embodiments, the antigen-binding polypeptide construct comprises a combination of one H1L1 heterodimer with one H2L2 heterodimer. In one embodiment, the combination of H1L1 heterodimer and H2L2 heterodimer is one wherein H1 comprises 179K, L1 comprises 180E, H2 comprises 143E_145T, and L2 comprises 124R_160K_178R.

In one embodiment, the amino acid combinations of K-K cluster 4 comprise one or more secondary substitutions selected from Table F.

In one embodiment, the antigen-binding polypeptide construct comprises a combination of amino acid substitutions according to K-K cluster 4 as set forth in one or more of the designs in Table 10-B4.

K-K Cluster 5:

In one embodiment, the antigen-binding polypeptide construct comprises a combination of amino acid substitutions according to K-K cluster 5 wherein: H1 comprises amino acid substitution at position 143 or 186; L1 comprises amino acid substitution at position 180 or comprises no amino acid substitutions that promote preferential pairing; H2 comprises amino acid substitution at positions 143_145, and L2 comprises amino acid substitution at position 124. In some embodiments, L2 further comprises amino acid substitutions at one or more of positions 160 and/or 178. In an additional embodiment, L2 comprises amino acid substitutions at positions 124, 124_178 or 124_160_178.

In some embodiments, the antigen-binding polypeptide construct comprises a combination of amino acid substitutions according to K-K cluster 5 wherein the amino acid substitutions in H1 are selected from 186R, 143R, 143K, and conservative substitutions thereof; the amino acid substitution in L1 is 180E, and conservative substitutions thereof; the amino acid substitutions in H2 are selected from 143E, 145T, and conservative substitutions thereof; the amino acid substitutions in L2 are selected from 124R, 160K, 178R, and conservative substitutions thereof.

In some embodiments, the antigen-binding polypeptide construct has an H1L1 heterodimer comprising a combination of amino acid substitutions according to K-K cluster 5, wherein the H1L1 heterodimer comprises one of the following sets of amino acid substitutions:

| H1 | L1 |
|---|---|
| 186R | 180E |
| 186R | — |
| 143R/K | — |

In further embodiments, the antigen-binding polypeptide construct has an H2L2 heterodimer comprising a combination of amino acid substitutions according to K-K cluster 5, wherein the H2L2 heterodimer comprises one of the following sets of amino acid substitutions:

| H2 | L2 |
|---|---|
| 143E_145T | 124R_160K_178R |
| 143E_145T | 124R |
| 143E_145T | 124K_178R |

In some embodiments, the antigen-binding polypeptide construct comprises a combination of one H1L1 heterodimer with one H2L2 heterodimer.

In one embodiment, the amino acid combinations of K-K cluster 5 comprise one or more secondary substitutions selected from Table F.

In one embodiment, the antigen-binding polypeptide construct comprises a combination of amino acid substitutions according to K-K cluster 5 as set forth in one or more of the designs in Table 10-B5.

K-K Cluster 6:

In one embodiment, the antigen-binding polypeptide construct comprises a combination of amino acid substitutions according to K-K cluster 6 wherein: H1 comprises amino acid substitution at position 39 or comprises no amino acid substitutions that promote preferential pairing; L1 comprises amino acid substitution at position 38 or comprises no amino acid substitutions that promote preferential pairing; H2 comprises amino acid substitution at position 39, and L2 comprises amino acid substitution at position 38.

In some embodiments, the antigen-binding polypeptide construct comprises a combination of amino acid substitutions according to K-K cluster 6 wherein the amino acid substitutions in H1 are selected from 39D, 39E, 39K, 39R, and conservative substitutions thereof; the amino acid substitutions in L1 are selected from 38D, 38E, 38K, 38R, and conservative substitutions thereof; the amino acid substitutions in H2 are selected from 39D, 39E, 39K, 39R, and conservative substitutions thereof; the amino acid substitutions in L2 are selected from 38D, 38E, 38K, 38R, and conservative substitutions thereof.

In some embodiments, the antigen-binding polypeptide construct has an H1L1 heterodimer comprising a combination of amino acid substitutions according to K-K cluster 6, wherein the H1L1 heterodimer comprises one of the following sets of amino acid substitutions:

| H1 | L1 |
|---|---|
| — | — |
| 39R | 38D/E |
| 39K | 38E/D |
| 39E | 38R/K |
| 39D | 38R |

In further embodiments, the antigen-binding polypeptide construct has an H2L2 heterodimer comprising a combination of amino acid substitutions according to K-K cluster 6, wherein the H2L2 heterodimer comprises one of the following sets of amino acid substitutions:

| H2 | L2 |
|---|---|
| 39D | 38R/K |
| 39R | 38E/D |
| 39K | 38E |
| 39E | 38R/K |

In some embodiments, the antigen-binding polypeptide construct comprises a combination of one H1L1 heterodimer with one H2L2 heterodimer. In one embodiment, the combination of H1L1 heterodimer and H2L2 heterodimer is one where H1 comprises 39R, L1 comprises 38E, H2 comprises 39D, and L2 comprises 38R.

In one embodiment, the antigen-binding polypeptide construct comprises a combination of amino acid substitutions according to K-K cluster 6 as set forth in one or more of the designs in Table 10-B6. In one embodiment, the K-K cluster 6 design is not the design corresponding to LCCA unique identifier 10674-10749 or 10679-10744.

K-K Cluster 7:

In one embodiment, the antigen-binding polypeptide construct comprises a combination of amino acid substitutions according to K-K cluster 7 wherein: H1 comprises no amino acid substitutions that promote preferential pairing; L1 comprises amino acid substitution at position 135; H2 comprises amino acid substitution at position 139, and L2 comprises amino acid substitution at position 116. In some embodiments, L2 further comprises amino acid substitution at position 135.

In some embodiments, the antigen-binding polypeptide construct comprises a combination of amino acid substitutions according to K-K cluster 7 wherein the amino acid substitution in L1 is 135W, or conservative substitutions thereof; the amino acid substitution in H2 is 139W, or conservative substitutions thereof and the amino acid substitutions in L2 are selected from 116A, 135V, and conservative substitutions thereof.

In some embodiments, the antigen-binding polypeptide construct has an H1L1 heterodimer comprising a combination of amino acid substitutions according to K-K cluster 7, wherein the H1L1 heterodimer comprises the following set of amino acid substitutions: H1 comprises no amino acid substitutions that promote preferential pairing, and L1 comprises 135W. In a further embodiment, the antigen-binding polypeptide construct has an H2L2 heterodimer comprising a combination of amino acid substitutions according to K-K cluster 7, wherein the H2L2 heterodimer comprises the following set of amino acid substitutions: H2 comprises 139W, and L2 comprises 116A or 116A_1335V. In some embodiments, the antigen-binding polypeptide construct comprises a combination of one H1L1 heterodimer with one H2L2 heterodimer.

In one embodiment, the antigen-binding polypeptide construct comprises a combination of amino acid substitutions according to K-K cluster 7 as set forth in one or the other of the designs in Table 10-B7.

K-K cluster 8:

In one embodiment, the antigen-binding polypeptide construct comprises a combination of amino acid substitutions according to K-K cluster 8 wherein: H1 comprises no amino acid substitutions that promote preferential pairing or comprises amino acid substitution at position 45; L1 comprises no amino acid substitutions that promote preferential pairing; H2 comprises amino acid substitution at position 45, and L2 comprises amino acid substitution at position 44.

In some embodiments, the antigen-binding polypeptide construct comprises a combination of amino acid substitutions according to K-K cluster 8 wherein the amino acid substitution in H1 is 45F, or conservative substitutions thereof; the amino acid substitution in H2 is 45P, 45A, or conservative substitutions thereof; the amino acid substitution in L2 is 44F or conservative substitutions thereof.

In some embodiments, the antigen-binding polypeptide construct has an H1L1 heterodimer comprising a combination of amino acid substitutions according to K-K cluster 8, wherein the H1L1 heterodimer comprises one of the following sets of amino acid substitutions: H1 comprises no amino acid substitutions that promote preferential pairing or comprises 45F, and L1 comprises no amino acid substitutions that promote preferential pairing. In further embodiments, the antigen-binding polypeptide construct has an H2L2 heterodimer comprising a combination of amino acid substitutions according to K-K cluster 8, wherein the H2L2 heterodimer comprises the following set of amino acid substitutions: H2 comprises 45A or 45P, and L2 comprises 44F. In some embodiments, the antigen-binding polypeptide construct comprises a combination of H1L1 and H2L2 heterodimers, where H1 and L1 comprise no amino acid substitutions that promote preferential pairing, H2 comprises 45A and L2 comprises 44F.

In one embodiment, the antigen-binding polypeptide construct comprises a combination of amino acid substitutions according to K-K cluster 8 as set forth in one or more of the designs in Table 10-B8.

K-K Cluster 9:

In one embodiment, the antigen-binding polypeptide construct comprises a combination of amino acid substitutions according to K-K cluster 9 wherein: H1 comprises amino acid substitution at position 139; L1 comprises amino acid substitution at position 116; H2 comprises no amino acid substitutions that promote preferential pairing, and L2 comprises amino acid substitution at position 135.

In some embodiments, the antigen-binding polypeptide construct comprises a combination of amino acid substitutions according to K-K cluster 9 wherein the amino acid substitution in H1 is 139W or conservative substitutions thereof; the amino acid substitution in L1 is 116A or conservative substitutions thereof; and the amino acid substitution in L2 is 135W or conservative substitutions thereof.

In some embodiments, the antigen-binding polypeptide construct has an H1L1 heterodimer comprising a combination of amino acid substitutions according to K-K cluster 9, wherein the H1L1 heterodimer comprises the following set of amino acid substitutions: H1 comprises 139W, and L1 comprises 116A. In a further embodiment, the antigen-binding polypeptide construct has an H2L2 heterodimer comprising a combination of amino acid substitutions according to K-K cluster 9, wherein the H2L2 heterodimer comprises the following set of amino acid substitutions: H2 comprises no amino acid substitutions that promote preferential pairing, and L2 comprises 135W.

In one embodiment, the antigen-binding polypeptide construct comprises a combination of amino acid substitutions according to K-K cluster 9 as set forth in Table 10-B9.

K-K Cluster 10:

In one embodiment, the antigen-binding polypeptide construct comprises a combination of amino acid substitutions according to K-K cluster 10 wherein: H1 comprises amino acid substitution at position 124; L1 comprises amino acid substitution at position 176; H2 comprises amino acid substitution at position 124, and L2 comprises amino acid substitution at position 176. In some embodiments, L1 and/or L2 further comprise amino acid substitution at position 133.

In one embodiment, the antigen-binding polypeptide construct comprises a combination of amino acid substitutions according to K-K cluster 10 wherein: H1 comprises amino acid substitution at position 124; L1 comprises amino acid substitution at positions 133_176; H2 comprises amino acid substitution at position 124, and L2 comprises amino acid substitution at positions 133_176.

In some embodiments, the antigen-binding polypeptide construct comprises a combination of amino acid substitutions according to K-K cluster 10 wherein the amino acid substitution in H1 is 124E or conservative substitutions thereof the amino acid substitutions in L1 are selected from 133G, 176R or conservative substitutions thereof; the amino acid substitution in H2 is 124R, or conservative substitutions thereof; the amino acid substitutions in L2 are selected from 133G, 176D or conservative substitutions thereof.

In some embodiments, the antigen-binding polypeptide construct has an H1L1 heterodimer comprising a combination of amino acid substitutions according to K-K cluster 10, wherein the H1L1 heterodimer comprises the following set of amino acid substitutions: H1 comprises 124E, and L1 comprises 133G 176R. In further embodiments, the antigen-binding polypeptide construct has an H2L2 heterodimer comprising a combination of amino acid substitutions according to K-K cluster 10, wherein the H2L2 heterodimer comprises the following set of amino acid substitutions: H2 comprises 124R, and L2 comprises 133G 176D. In some embodiments, the antigen-binding polypeptide construct comprises a combination of these H1L1 and H2L2 heterodimers.

In one embodiment, the amino acid combinations of K-L cluster 9 comprise one or more secondary substitutions selected from Table F.

In one embodiment, the antigen-binding polypeptide construct comprises a combination of amino acid substitutions according to K-K cluster 10 as set forth in Table 10-B10.

Preferential Pairing in LCCA Design Sets

One or more of H1, L1, H2, and L2 comprise amino acid modifications that promote preferential pairing of H1 with L1 as compared to L2 and of H2 with L2 as compared to L1. In general, in the absence of the amino acid modifications and any naturally occurring bias, a wild type immunoglobulin heavy chain sequence (H1), when co-expressed with two different wild type immunoglobulin light chain sequences (L1 and L2), will statistically pair equally with both light chains, resulting in an approximate 50:50 mixture of H1 paired with L1 (H1L1, correctly paired) and H1 paired with L2 (H1L2, mispaired). Likewise, if wild type H2 is co-expressed with wild type L1 and L2, the heavy chain will statistically pair equally with both light chains, resulting in an approximate 50:50 mixture of H2 paired with L1 (H2L1, mispaired) and H2 paired with L2 (H2L2, correctly paired). The term "preferential pairing" is used herein to describe the pairing specificity or pairing preference of an immunoglobulin heavy chain polypeptide sequence with one immunoglobulin light chain polypeptide sequence as compared to another immunoglobulin light chain polypeptide sequence. In this context, preferential pairing would occur between, for example, H1 and L1, if the amount of the H1L1 heterodimer is greater than the amount of the H1L2 heterodimer when H1 is co-expressed with both L1 and L2. Similarly, preferential pairing would occur between, for example, H2 and L2, if the amount of the H2L2 heterodimer is greater than the amount of the H2L1 heterodimer when H2 is co-expressed with both L1 and L2.

However, in some cases, there is an inherent pairing bias observed in the wild-type heavy and light chain polypeptide sequences obtained from the parent antibodies. This inherent pairing bias can be observed in the context of an LCCA design set in which wild-type parental H1 or H2 are co-expressed with wild-type parental L1 and L2, where one of the light chains preferentially pairs with the heavy chains of both parent antibodies. In one embodiment, preferential pairing occurs when the amino acid modifications in one or more of H1, L1, H2 and L2 promote preferential pairing that is greater than the preferential pairing that occurs in the corresponding wild type system.

The degree of preferential pairing, or design strength, is a measure of the ability of the amino acid modifications to promote preferential pairing. The degree of preferential pairing can be assessed as described elsewhere herein, and in the examples, and is based on the measurement of correctly paired heterodimers (i.e. H1L1 and H2L2) compared to mispaired heterodimers (i.e. H1L2 and H2L1). The degree of preferential pairing can be assessed in the context of LCCA design sets (H1L1L2, or H2L1L2) where one heavy chain is co-expressed with two unique light chains, or a Mab design set (H1L1H2L2) where the heavy and light chains of the parent antibody are co-expressed.

The following embodiments relate to the context of LCCA design sets. In all of the embodiments in this section, the term "about" means ±5% of the specified ratio, and preferential pairing is compared with respect to wild-type, unless otherwise indicated. In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 60:40. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 60:40.

In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 65:35. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 65:35.

In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 70:30. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 70:30.

In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 75:25. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 75:25.

In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 80:20. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 80:20.

In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 85:15. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 85:15.

In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 90:10. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 90:10.

In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 95:5. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 95:5.

In one embodiment, one or more of H1, H2, L1 and L2 comprise amino acid modifications that promote preferential pairing of H1 with L1 as compared to L2 to form H1L1, or of H2 with L2 as compared to L1 to form H2L2, where the ratio of H1L1:H1L2 is at least about 40:60 and the ratio of H2L2:H2L1 is at least about 99:1. In one embodiment, one or more of H1, H2, L1 and L2 comprise amino acid modifications that promote preferential pairing of H1 with L1 as compared to L2 to form H1L1, or H2 with L2 as compared to L1 to form H2L2, where the ratio of H2L2:H2L1 is at least about 40:60 and the ratio of H1L1:H1L2 is at least about 99:1.

In other embodiments, one or more of H1, H2, L1 and L2 comprise amino acid modifications that promote preferential pairing of H1 with L1 as compared to L2 to form H1L1, or of H2 with L2 as compared to L1 to form H2L2, such that the amount of H1L1 or H2L2 is greater than about 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In one embodiment, preferential pairing is measured by LCCA as described in the examples. The LCCA results are generally predictive of the results in the context of preferential pairing in Mab design sets (described below) in which H1, L1, H2, and L2 are co-expressed.

In one embodiment, one or more of H1, H2, L1 and L2 comprise amino acid modifications that promote preferential pairing of H1 with L1 as compared to L2 to form H1L1, or H2 with L2 as compared to L1 to form H2L2, such that the relative pairing of at least one of H1L1 or H2L2 is at least about 10% greater relative to wild-type, and the relative pairing of the other is within about 10% of wild-type or at least about 10% greater relative to wild-type.

In one embodiment, one or more of H1, H2, L1 and L2 comprise amino acid modifications that promote preferential pairing of H1 with L1 as compared to L2 to form H1L1, or H2 with L2 as compared to L1 to form H2L2, such that the relative pairing of at least one of H1L1 or H2L2 is at least about 20% greater relative to wild-type, and the relative pairing of the other is within about 10% of wild-type or at least about 10% greater relative to wild-type.

In one embodiment, one or more of H1, H2, L1 and L2 comprise amino acid modifications that promote preferential pairing of H1 with L1 as compared to L2 to form H1L1, or H2 with L2 as compared to L1 to form H2L2, such that the relative pairing of at least one of H1L1 or H2L2 is at least about 30% greater relative to wild-type, and the relative pairing of the other is within about 10% of wild-type or at least about 10% greater relative to wild-type.

Preferential Pairing in Mab Design Sets

Figure 8:
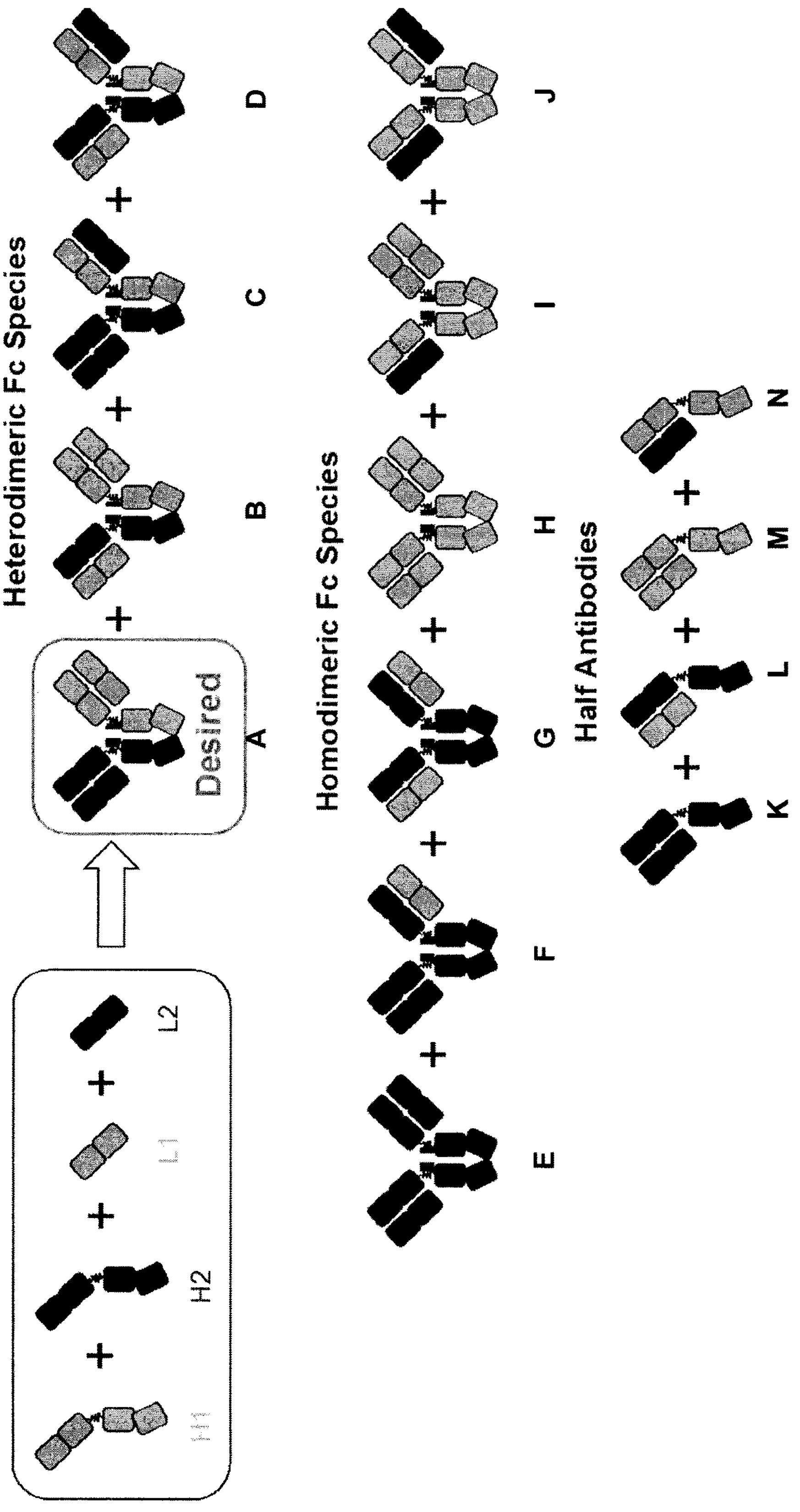
FIG. 8 depicts the potential heavy chain associated products that can be expected when two different light chains are co-expressed with two different heavy chains in a cell.

Preferential pairing can also be assessed in the context of Mab design sets where H1, L1, H2 and L2 are co-expressed and one or more of H1, L1, H2 and L2 comprise amino acid modifications that promote preferential pairing of H1 with L1 and of H2 with L2 to form a bispecific antigen-binding polypeptide construct that comprises a correctly paired first heterodimer (H1L1) and a correctly paired second heterodimer (H2L2). In this type of embodiment, as shown in FIG. 8, when the two distinct immunoglobulin heavy chain polypeptide sequences are co-expressed with two distinct immunoglobulin light chain polypeptide sequences, a number of potential products can result, fourteen of which are shown in FIG. 8, only one of which is the desired, or correctly paired, bispecific antibody H1L1H2L2 (antibody species A in FIG. 8). However, in the context of assessing correct pairing between heavy chains and light chain based on the Mab design sets, some of the additional products may also considered to exhibit correct pairing in the context of the Fab regions since they comprise correctly paired heterodimers at the Fab level (see for example antibody species E, H, K, and M in FIG. 8). In some embodiments, the Fc portion of the antigen-binding polypeptide construct comprises asymmetric amino acid modifications that promote formation of a heterodimeric Fc. In these embodiments, the number and amount of species E to J are expected to decrease.

As for the LCCA design sets, in the context of a Mab design set in which all four immunoglobulin polypeptide sequences H1, L1, H2, and L2 are co-expressed, in some cases there may be an inherent bias in pairing resulting in one of the light chains (either L1 or L2) preferentially pairing with both H1 and H2. Thus, when determining the strength of a Mab design in the context of a bispecific antigen-binding polypeptide construct, it may be necessary to assess the degree of pairing with the amino acid modifications of the Mab design compared to the amount of correct pairing observed in the corresponding wild-type parental system (H1, L1, H2, L2 polypeptide sequences without the amino acid modifications of the Mab design). Thus, in one embodiment, a Mab design is considered to show preferential pairing if the amount of correctly paired bispecific antigen-binding polypeptide construct is greater than the amount of correctly paired bispecific antibody obtained in the corresponding wild-type parental system. Alternatively, a Mab design is considered to show preferential pairing if the percentage of correctly paired bispecific antigen-binding polypeptide construct in the total expression product is greater than the percentage of correctly paired bispecific antibody obtained in the total expression product in the corresponding wild-type parental system. In one embodiment, the total expression product may comprise antibody species A to N in FIG. 8. In one embodiment, the total expression product may be only those antibody species that have two heavy chains and two light chains (antibody species A to J in FIG. 8). In the latter embodiment, preferential pairing is measured as a percentage of total bispecific antibody, excluding half-antibodies such as species K to N in FIG. 8).

In another embodiment, a Mab design is considered to show preferential pairing if the amount of correct pairing is increased in the heterodimer of the bispecific antigen-binding polypeptide construct that exhibits a high degree of mispairing in the corresponding wild-type parental system. In another embodiment, a Mab design is considered to show preferential pairing if the total amount of correct pairing between H1 and L1, and between H2 and L2, is greater than that observed in the corresponding wild-type parental system. For example, with reference to FIG. 8, species A, B, H, I, and M would be considered correctly paired with respect to H1L1, and species A, C, E, F, and K would be considered correctly paired with respect to H2L2. In this embodiment, preferential pairing is measured as a percentage of total pairing.

In one embodiment, the preferential pairing is measured by SMCA as described herein.

In some embodiments, a Mab design is considered to promote preferential pairing when the change in the amount of total correct pairing as measured by the sum of H1L1 and H2L2 pairing is greater than about 5%, 10%, 15%, 20%, 25%, 30%, 35%, 40%, or 45% compared to the pairing of corresponding H1, L1, H2 and L2 polypeptide chains without amino acid substitutions in the Fab region that promote preferential pairing.

In some embodiment, a Mab design is considered to promote preferential pairing when the change in the amount of total correct pairing, as measured by the amount of bispecific antibody produced as a percentage of species other than half-antibodies produced, is greater than about 5%, 10%, 20%, 30%, 40%, 50%, 60%, 70%, or 80%, compared to the pairing of corresponding H1, L1, H2 and L2 polypeptide chains without amino acid substitutions in the Fab region that promote preferential pairing.

In one embodiment, a Mab design is considered to promote preferential pairing when the change in the amount of total correct pairing, as measured by the amount of bispecific antibody produced as a percentage of all species produced, is greater than about 5%, 10%, 20%, 30%, 40%, 50%, 60%, 70%, or 80%, compared to the pairing of corresponding H1, L1, H2 and L2 polypeptide chains without amino acid substitutions in the Fab region that promote preferential pairing.

Thermal Stability of Fab Regions

The amino acid modifications in one or more of the H1, L1, H2 and L2 polypeptide sequences promote preferential pairing of H1 with L1 as compared to L2 and of H2 with L2 as compared to L1, and minimally affect the thermal stability of each heterodimer of the antigen-binding polypeptide construct. The effect of the amino acid modifications on each heterodimer is determined by measuring the thermal stability of the Fab regions formed by H1 and L1, or by H2 and L2, and comparing it to the thermal stability of a Fab region formed by the corresponding wild type H1 and L1 polypeptide sequences (wt first Fab region) or by the corresponding wild type H2 and L2 polypeptide sequences (wt second Fab region). The terms "corresponding wild type H1 and L1 polypeptide sequences," and "corresponding wild type H2 and L2 polypeptide sequences," are meant to describe corresponding H1, L1, H2, and L2 polypeptide sequences that do not have the amino acid modifications that promote preferential pairing as described herein.

Thermal stability can be measured by a variety of methods known in the art and described herein, including differential scanning calorimetry (DSC), or differential scanning fluorimetry (DSF). The latter methods provide a measure of thermal stability in terms of "melting temperature" or Tm.

In the context of the following embodiments, the term "about" means ±10% of the recited temperature. In one embodiment, the antigen-binding polypeptide construct comprises a first Fab region that has a Tm within about 20° C. of the Tm of the corresponding wt first Fab region. In one embodiment, the antigen-binding polypeptide construct comprises a first Fab region that has a Tm within about 15° C. of the Tm of the corresponding wt first Fab region. In one embodiment, the antigen-binding polypeptide construct comprises a first Fab region that has a Tm within about 10° C. of the Tm of the corresponding wt first Fab region. In one embodiment, the antigen-binding polypeptide construct comprises a first Fab region that has a Tm within about 9° C. of the Tm of the corresponding wt first Fab region. In one embodiment, the antigen-binding polypeptide construct comprises a first Fab region that has a Tm within about 8° C. of the Tm of the corresponding wt first Fab region. In one embodiment, the antigen-binding polypeptide construct comprises a first Fab region that has a Tm within about 7° C. of the Tm of the corresponding wt first Fab region. In one embodiment, the antigen-binding polypeptide construct comprises a first Fab region that has a Tm within about 6° C. of the Tm of the corresponding wt first Fab region. In one embodiment, the antigen-binding polypeptide construct comprises a first Fab region that has a Tm within about 5° C. of the Tm of the corresponding wt first Fab region. In one embodiment, the antigen-binding polypeptide construct comprises a first Fab region that has a Tm within about 4° C. of the Tm of the corresponding wt first Fab region. In one embodiment, the antigen-binding polypeptide construct comprises a first Fab region that has a Tm within about 3° C. of the Tm of the corresponding wt first Fab region. In one embodiment, the antigen-binding polypeptide construct comprises a first Fab region that has a Tm within about 2° C. of the Tm of the corresponding wt first Fab region. In one embodiment, the antigen-binding polypeptide construct comprises a first Fab region that has a Tm within about 1° C. of the Tm of the corresponding wt first Fab region. In one embodiment, the antigen-binding polypeptide construct comprises a first Fab region that has a Tm that is about the same as that of the corresponding wt first Fab region.

In one embodiment, the antigen-binding polypeptide construct comprises a second Fab region that has a Tm within about 20° C. of the Tm of the corresponding wt second Fab region. In one embodiment, the antigen-binding polypeptide construct comprises a second Fab region that has a Tm within about 15° C. of the Tm of the corresponding wt second Fab region. In one embodiment, the antigen-binding polypeptide construct comprises a second Fab region that has a Tm within about 10° C. of the Tm of the corresponding wt second Fab region. In one embodiment, the antigen-binding polypeptide construct comprises a second Fab region that has a Tm within about 9° C. of the Tm of the corresponding wt second Fab region. In one embodiment, the antigen-binding polypeptide construct comprises a second Fab region that has a Tm within about 8° C. of the Tm of the corresponding wt second Fab region. In one embodiment, the antigen-binding polypeptide construct comprises a second Fab region that has a Tm within about 7° C. of the Tm of the corresponding wt second Fab region. In one embodiment, the antigen-binding polypeptide construct comprises a second Fab region that has a Tm within about 6° C. of the Tm of the corresponding wt second Fab region. In one embodiment, the antigen-binding polypeptide construct comprises a second Fab region that has a Tm within about 5° C. of the Tm of the corresponding wt second Fab region. In one embodiment, the antigen-binding polypeptide construct comprises a second Fab region that has a Tm within about 4° C. of the Tm of the corresponding wt second Fab region. In one embodiment, the antigen-binding polypeptide construct comprises a second Fab region that has a Tm within about 3° C. of the Tm of the corresponding wt second Fab region. In one embodiment, the antigen-binding polypeptide construct comprises a second Fab region that has a Tm within about 2° C. of the Tm of the corresponding wt second Fab region. In one embodiment, the antigen-binding polypeptide construct comprises a second Fab region that has a Tm within about 1° C. of the Tm of the corresponding wt second Fab region. In one embodiment, the antigen-binding polypeptide construct comprises a second Fab region that has a Tm that is about the same as that of the corresponding wt second Fab region.

In one embodiment, the antigen-binding polypeptide construct comprises a first heterodimer and a second heterodimer wherein the melting temperature (Tm) of the first Fab region is within about 0, 1, 2, 3, 4, 5, 6, 7, 8, 9, 10, or 20° C. of the Tm of a Fab region formed by the corresponding wild type H1 and L1 polypeptide sequences for the first antigen (wt first Fab region), and/or the melting temperature (Tm) of the second Fab region is within about 0, 1, 2, 3, 4, 5, 6, 7, 8, 9, 10, or 20° C. of the Tm of a Fab region formed by the corresponding wild type H2 and L2 polypeptide sequences for the second antigen (wt second Fab region).

Furthermore, in some embodiments, the Tm of the first or second Fab region is greater than that of the corresponding wt first Fab or corresponding second wt second Fab. Thus, in one embodiment, the Tm of the first or second Fab region is increased by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 3.0, 3.1, 3.2, 3.3, 3.4, 3.5, 3.6, 3.7, 3.8, 3.9, 4.0, 4.5, 5.0° C. or more compared to the corresponding wt first Fab region or corresponding wt second Fab region.

In one embodiment, the antigen-binding polypeptide construct comprises amino acid substitutions corresponding to K-L design numbers 2979, 3018, 3041, 3102, 3898, and/or 3947. In one embodiment, the antigen-binding polypeptide construct comprises amino acid substitutions corresponding to K-L design numbers 3025, 3109, 3113, 3878, 3890, 3910, 3931, 3954, 3967, 4010, and/or 4040.

Ability of Fab Regions to Bind Antigen

The amino acid modifications in one or more of the H1, L1, H2 and L2 polypeptide sequences promote preferential pairing of H1 with L1 as compared to L2 and of H2 with L2 as compared to L1, and minimally affect the ability of each heterodimer of the antigen-binding polypeptide construct to bind to its antigen. The effect of the amino acid modifications on each heterodimer is determined by measuring the ability of the Fab regions formed by H1 and L1, or by H2 and L2, to bind to their respective antigens, and comparing it to the ability of the corresponding wt first Fab region, or corresponding wt second Fab region to bind to their respective antigens.

The ability of the Fab regions to bind to their respective antigens can be measured by a number of methods known in the art, some of which are described elsewhere herein. For example surface plasmon resonance (SPR), or whole cell binding assays may be used to assess the ability of the first Fab region to bind a first antigen and of the second Fab region to bind a second antigen. The latter two methods measure the ability of the Fab regions to bind to their respective antigens by determining the affinity of the Fab region for its antigen.

In one embodiment, the affinity of the first Fab region for the first antigen is within about 100-fold of the affinity of the wt first Fab region for the first antigen. In one embodiment, the affinity of the first Fab region for the first antigen is within about 50-fold of the affinity of the wt first Fab region for the first antigen. In one embodiment, the affinity of the first Fab region for the first antigen is within about 40-fold of the affinity of the wt first Fab region for the first antigen. In one embodiment, the affinity of the first Fab region for the first antigen is within about 30-fold of the affinity of the wt first Fab region for the first antigen. In one embodiment, the affinity of the first Fab region for the first antigen is within about 20-fold of the affinity of the wt first Fab region for the first antigen. In one embodiment, the affinity of the first Fab region for the first antigen is within about 10-fold of the affinity of the wt first Fab region for the first antigen. In one embodiment, the affinity of the first Fab region for the first antigen is within about 9-fold of the affinity of the wt first Fab region for the first antigen. In one embodiment, the affinity of the first Fab region for the first antigen is within about 8-fold of the affinity of the wt first Fab region for the first antigen. In one embodiment, the affinity of the first Fab region for the first antigen is within about 7-fold of the affinity of the wt first Fab region for the first antigen. In one embodiment, the affinity of the first Fab region for the first antigen is within about 6-fold of the affinity of the wt first Fab region for the first antigen. In one embodiment, the affinity of the first Fab region for the first antigen is within about 5-fold of the affinity of the wt first Fab region for the first antigen. In one embodiment, the affinity of the first Fab region for the first antigen is within 4-fold of the affinity of the wt first Fab region for the first antigen. In one embodiment, the affinity of the first Fab region for the first antigen is within about 3-fold of the affinity of the wt first Fab region for the first antigen. In one embodiment, the affinity of the first Fab region for the first antigen is within about 2-fold of the affinity of the wt first Fab region for the first antigen. In one embodiment, the affinity of the first Fab region for the first antigen is about the same as the affinity of the wt first Fab region for the first antigen.

In one embodiment, the affinity of the second Fab region for the second antigen is within about 100-fold of the affinity of the wt second Fab region for the second antigen. In one embodiment, the affinity of the second Fab region for the second antigen is within about 50-fold of the affinity of the wt second Fab region for the second antigen. In one embodiment, the affinity of the second Fab region for the second antigen is within about 40-fold of the affinity of the wt second Fab region for the second antigen. In one embodiment, the affinity of the second Fab region for the second antigen is within about 30-fold of the affinity of the wt second Fab region for the second antigen. In one embodiment, the affinity of the second Fab region for the second antigen is within about 20-fold of the affinity of the wt second Fab region for the second antigen. In one embodiment, the affinity of the second Fab region for the second antigen is within about 10-fold of the affinity of the wt second Fab region for the second antigen. In one embodiment, the affinity of the second Fab region for the second antigen is within about 9-fold of the affinity of the wt second Fab region for the second antigen. In one embodiment, the affinity of the second Fab region for the second antigen is within about 8-fold of the affinity of the wt second Fab region for the second antigen. In one embodiment, the affinity of the second Fab region for the second antigen is within about 7-fold of the affinity of the wt second Fab region for the second antigen. In one embodiment, the affinity of the second Fab region for the second antigen is within about 6-fold of the affinity of the wt second Fab region for the second antigen. In one embodiment, the affinity of the second Fab region for the second antigen is within about 5-fold of the affinity of the wt second Fab region for the second antigen. In one embodiment, the affinity of the second Fab region for the second antigen is within 4-fold of the affinity of the wt second Fab region for the second antigen. In one embodiment, the affinity of the second Fab region for the second antigen is within about 3-fold of the affinity of the wt second Fab region for the second antigen. In one embodiment, the affinity of the second Fab region for the second antigen is within about 2-fold of the affinity of the wt second Fab region for the second antigen. In one embodiment, the affinity of the second Fab region for the second antigen is about the same as the affinity of the wt second Fab region for the second antigen.

Transferability of Amino Acid Modifications or Design Sets

The amino acid modifications or design sets described herein can be used to prepare a bispecific antigen-binding polypeptide construct in which the immunoglobulin heavy chain polypeptide sequences and immunoglobulin light chain polypeptides of each heterodimer can be obtained from one or more parent antibodies, where at least one parent antibody comprises a kappa light chain, and at least one other parent antibody comprises a lambda light chain. Based on the following discussion, the Mab design sets can be applied to the majority of such bispecific antigen-binding polypeptide constructs.

The VH:VL and CH1:CL interface residues in the interface between immunoglobulin heavy and light chains are relatively well conserved (Padlan et al., 1986, Mol. Immunol. 23(9): 951-960). This sequence conservation, a result of evolutionary constraints, increases the likelihood that functionally active antibody binding domains will be formed during combinatorial pairing of light and heavy chains. As a result of this sequence conservation, it follows that the Mab design sets described herein and based on modeling of the structures of the D3H44 kappa Fab and CAT-2200 lambda Fab, which drive preferential pairing, can be transferred to the kappa Fabs and lambda Fabs of other parent antibodies to drive preferential pairing, since this region displays high sequence conservation across antibodies. Further, when sequence differences do occur, these usually lie distal to the CH1:CL interface. This is particularly the case for the CH1 and CL domains. In an embodiment, the antigen-binding polypeptide constructs described herein comprise heterodimers where the kappa Fab comprises one or more amino acid modifications in CL and/or CH1 domains that promote preferential pairing. In an embodiment, the antigen-binding polypeptide constructs described herein comprise heterodimers where the lambda Fab comprises one or more amino acid modifications in CL and/or CH1 domains that promote preferential pairing.

There is, however, some sequence variability at the antigen-binding site with respect to CDR (complementarity-determining regions) loop residues (and length), particularly for CDR-H3. Thus, in one embodiment, the antigen-binding polypeptide constructs described herein comprise heterodimers where the kappa Fab comprises one or more amino acid modifications in the VH and/or VL domains that lie distal to the CDR loops when the amino acid sequence of the antigen-binding site is significantly different from that of the D3H44 antibody. In another embodiment, the antigen-binding polypeptide constructs described herein comprise heterodimers where the lambda Fab comprises one or more amino acid modifications in the VH and/or VL domains that promote preferential pairing and that lie distal to the CDR loops when the amino acid sequence of the antigen-binding site is significantly different from that of the CAT-2200 antibody. In another embodiment, the antigen-binding polypeptide constructs described herein comprise heterodimers where the kappa Fab comprises one or more amino acid modifications that promote preferential pairing in the VH and/or VL domains that lie proximal or distal to the CDR loops, when the amino acid sequence of the antigen-binding site is substantially similar to that of the D3H44 antibody. In another embodiment, the antigen-binding polypeptide constructs described herein comprise heterodimers where the lambda Fab comprises one or more amino acid modifications in the VH and/or VL domains that promote preferential pairing and that lie proximal or distal to the CDR loops, when the amino acid sequence of the antigen-binding site is substantially similar to that of the CAT-2200 antibody. In an embodiment, the antigen-binding polypeptide constructs described herein comprise heterodimers where the kappa Fab comprises one or more amino acid modifications in CL and/or CH1 domains as well as modifications in the VH and/or VL domains that promote preferential pairing. In an embodiment, the antigen-binding polypeptide constructs described herein comprise heterodimers where the lambda Fab comprises one or more amino acid modifications in CL and/or CH1 domains as well as modifications in the VH and/or VL domains that promote preferential pairing.

In one embodiment, the amino acid modifications in one or more of H1, L1, H2, and L2 of the antigen-binding polypeptide construct can promote preferential pairing in an antigen-binding polypeptide construct where the kappa Fab of one parent antibody is a human or humanized IgG1/κ. Non-limiting examples of such parent antibodies include Ofatumumab (human) or Trastuzumab, or Bevacizumab (humanized). In one embodiment, the amino acid modifications in one or more of H1, L1, H2, and L2 of the antigen-binding polypeptide construct can promote preferential pairing in an antigen-binding polypeptide construct where the lambda Fab of one parent antibody is a human or humanized IgG1/lambda. Non-limiting examples of such human antibodies include Briakinumab or Sifalimumab, while an example of a humanized antibody is Brontictuzumab.

In another embodiment, the amino acid modifications described herein are transferable to the immunoglobulin heavy and light chains of antibodies utilizing commonly used VH and VL subgroups.

In one embodiment, the amino acid modifications described herein are transferable to the immunoglobulin heavy and light chains of antibodies having a framework close to germline. Examples of such antibodies include Obinutuzumab.

In one embodiment, the amino acid modifications described herein are transferable to the immunoglobulin heavy and light chains of antibodies having a VH:VL interdomain angle close to the average observed for heavy and light chain pairs. An example of this type of antibody includes, but is not limited to Pertuzumab. In another embodiment, the amino acid modifications described herein are transferable to the immunoglobulin heavy and light chains of antibodies having canonical CL and CH1 domains. Suitable examples of such antibodies include, but are not limited to Trastuzumab.

The Examples, Figures, and Tables demonstrate that the amino acid modifications (e.g., within one or more Fab fragments comprising a variable region and a constant region) that promote preferential pairing are transferable to other immunoglobulin heavy and light chains, resulting in similar patterns of preferential pairing of one immunoglobulin heavy chain with one of the two immunoglobulin light chains.

Scaffolds

The heterodimers of the antigen-binding polypeptide construct can be linked to a scaffold. A scaffold may be a peptide, polypeptide, polymer, nanoparticle or other chemical entity. The heterodimers of the antigen-binding polypeptide construct may be linked to either the N- or C-terminus of the scaffold, where the scaffold is a polypeptide. In one embodiment, the scaffold is an albumin polypeptide.

In another embodiment, the scaffold is an immunoglobulin Fc (Fc), or portion thereof. In some embodiments, the Fc comprises at least one or two CH3 domain sequences. In some embodiments, the Fc further comprises at least one or two CH2 domain sequences. In some embodiments the antigen-binding polypeptide construct comprises an Fc that is coupled, with or without one or more linkers, to the first heterodimer and/or the second heterodimer. In some embodiments, the Fc is a human Fc. In some embodiments, the Fc is a human IgG or IgG1 Fc. In some embodiments, the Fc is a heterodimeric Fc. In some embodiments, an Fc is a single polypeptide. In some embodiments, an Fc is multiple peptides, e.g., two polypeptides.

In some embodiments, the Fc comprises one or more amino acid modifications in at least one of the CH3 domain sequences. Amino acid modifications can be made to the immunoglobulin Fc in order to drive preferential pairing between heterodimeric CH3 domain sequences relative to homodimeric CH3 domain sequences. Such amino acid modifications are known in the art and include, for example, those described, in US Patent Publication No. 2012/0149876. Alternate strategies for driving preferential pairing between heterodimeric CH3 domain sequences relative to homodimeric CH3 sequences include, for example, "knobs into holes", charged residues with ionic interactions, and strand-exchange engineered domain (SEED) technologies can also be employed. The latter strategies have been described in the art and are reviewed in Klein et al, supra. Further discussion of Fc domains follows below.

In some aspects, Fc is an Fc described in patent applications PCT/CA2011/001238, filed Nov. 4, 2011 or PCT/CA2012/050780, filed Nov. 2, 2012, the entire disclosure of each of which is hereby incorporated by reference in its entirety for all purposes.

In some aspects, the antigen-binding polypeptide construct described herein comprises a heterodimeric Fc comprising a modified CH3 domain that has been asymmetrically modified.

The heterodimeric Fc can comprise two heavy chain constant domain polypeptides: a first heavy chain polypeptide and a second heavy chain polypeptide, which can be used interchangeably provided that Fc comprises one first heavy chain polypeptide and one second heavy chain polypeptide. Generally, the first heavy chain polypeptide comprises a first CH3 sequence and the second heavy chain polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table X provides the amino acid sequence of the human IgG1 Fc sequence, corresponding to amino acids 231 to 447 of the full-length human IgG1 heavy chain. The CH3 sequence comprises amino acid 341-447 of the full-length human IgG1 heavy chain.

Typically an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, an Fc includes a mutant sequence shown in Table X. In some aspects, an Fc includes the mutations of Variant 1 A-B. In some aspects, an Fc includes the mutations of Variant 2 A-B. In some aspects, an Fc includes the mutations of Variant 3 A-B. In some aspects, an Fc includes the mutations of Variant 4 A-B. In some aspects, an Fc includes the mutations of Variant 5 A-B.

TABLE X

| | | |
|---|---|---|
| Human IgG1 Fc sequence 231-447 (EU-numbering), SEQ ID NO: 11 | APELLGGPSVFLFPPKPKDTLMISRTPEVTCVVVDVSH EDPEVKFNWYVDGVEVHNAKTKPREEQYNSTYRVVS VLTVLHQDWLNGKEYKCKVSNKALPAPIEKTISKAKG QPREPQVYTLPPSRDELTKNQVSLTCLVKGFYPSDIAV EWESNGQPENNYKTTPPVLDSDGSFFLYSKLTVDKSR WQQGNVFSCSVMHEALHNHYTQKSLSLSPGK | |
| Variant IgG1 Fc sequence (231-447) | Chain | Mutations |
| 1 | A | L351Y_F405A_Y407V |
| 1 | B | T366L_K392M_T394W |
| 2 | A | L351Y_F405A_Y407V |
| 2 | B | T366L_K392L_T394W |

TABLE X-continued

| | | |
|---|---|---|
| 3 | A | T350V_L351Y_F405A_Y407V |
| 3 | B | T350V_T366L_K392L_T394W |
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L_N390R_K392M_T394W |

In some embodiments, the Fc can comprise one or more amino acid modifications in at least one of the CH2 domain sequences. A number of mutations in the heavy chain sequence of the Fc are known in the art for selectively altering the affinity of the antibody Fc for different Fcgamma receptors. In some embodiments, the Fc comprises one or more modifications to alter binding of Fc-gamma receptors to the antigen-binding polypeptide construct.

The CH2 domain corresponds to amino acids 231-340 of the sequence shown in Table X. Exemplary, non-limiting amino acid modifications that alter the ability of the Fc of the antigen-binding polypeptide construct to bind to Fc-gamma receptors are listed below:

S298A/E333A/K334A, S298A/E333A/K334A/K326A (Lu Y, Vernes J M, Chiang N, et al. J Immunol Methods. 2011 Feb. 28; 365(1-2); 132-41); F243L/R292P/Y300L/V305I/P396L, F243L/R292P/Y300L/L235V/P396L (Stavenhagen J B, Gorlatov S, Tuaillon N, et al. Cancer Res. 2007 Sep. 15; 67(18):8882-90; Nordstrom J L, Gorlatov S, Zhang W, et al. Breast Cancer Res. 2011 Nov. 30; 13(6): R123); F243L (Stewart R, Thorn G, Levens M, et al. Protein Eng Des Sel. 2011 September; 24(9):671-8.), S298A/E333A/K334A (Shields R L, Namenuk A K, Hong K, et al. J Biol Chem. 2001 Mar. 2; 276(9):6591-604), S239D/I332E/A330L, S239D/I332E (Lazar G A, Dang W, Karki S, et al. Proc Natl Acad Sci USA. 2006 Mar. 14; 103(11):4005-10); S239D/S267E, S267E/L328F (Chu S Y, Vostiar I, Karki S, et al. Mol Immunol. 2008 September; 45(15):3926-33); S239D/D265S/S298A/I332E, S239E/S298A/K326A/A327H, G237F/S298A/A330L/I332E, S239D/I332E/S298A, S239D/K326E/A330L/I332E/S298A, G236A/S239D/D270L/I332E, S239E/S267E/H268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) describes additional modifications to the Fc that affect binding of the Fc to Fc-gamma receptors on page 283.

Additional Modifications to Improve Effector Function.

In some embodiments the Fc of the antigen-binding polypeptide construct described herein can be modified to improve its effector function. Such modifications are known in the art and include afucosylation, or engineering of the affinity of the Fc portion of antibodies towards an activating receptor, mainly FCGR3a for ADCC, and towards C1q for CDC. The following Table Y summarizes various designs reported in the literature for effector function engineering.

TABLE Y

| Reference | Mutations | Effect |
|---|---|---|
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Thus, in one embodiment, an antigen-binding polypeptide construct described herein can include a dimeric Fc that comprises one or more amino acid modifications as noted in the above table that confer improved effector function. In another embodiment, the antigen-binding polypeptide construct can be afucosylated to improve effector function.

FcRn Binding and PK Parameters

As is known in the art, binding to FcRn recycles endocytosed antibody from the endosome back to the bloodstream (Raghavan et al., 1996, Annu Rev Cell Dev Biol 12:181-220; Ghetie et al., 2000, Annu Rev Immunol 18:739-766). This process, coupled with preclusion of kidney filtration due to the large size of the full-length molecule, results in favorable antibody serum half-lives ranging from one to three weeks. Binding of Fc to FcRn also plays a key role in antibody transport. Thus, in one embodiment, the Fc comprises one or more amino acid modifications that alter or promote the ability of the Fc to bind FcRn.

Linkers

The constructs described herein can include one or more heterodimers described herein operatively coupled to an Fc described herein. In some aspects, Fc is coupled to the one or more heterodimers with or without one or more linkers. In some aspects, Fc is directly coupled to the one or more heterodimers. In some aspects, Fc is coupled to the one or more heterodimers by one or more linkers. In some aspects, Fc is coupled to the heavy chain of each heterodimer by a linker.

In some aspects, the one or more linkers are one or more polypeptide linkers. In some aspects, the one or more linkers comprise one or more antibody hinge regions. In some aspects, the one or more linkers comprise one or more IgG1 hinge regions.

Additional Optional Modifications

In one embodiment, the immunoglobulin heavy and light chains of the antigen-binding polypeptide construct described herein can be further modified (i.e., by the covalent attachment of various types of molecules) such that covalent attachment does not interfere with the preferential pairing between heavy chain and light chains or affect the ability of the heterodimer to bind to its antigen, or affect its stability. Such modification include, for example, but not by way of limitation, glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc.

In another embodiment, the immunoglobulin heavy and light chains of the antigen-binding polypeptide construct described herein can be conjugated (directly or indirectly) to a therapeutic agent or drug moiety that modifies a given biological response. In certain embodiments an antigen-binding polypeptide construct is conjugated to a drug, e.g., a toxin, a chemotherapeutic agent, an immune modulator, or a radioisotope. Several methods of preparing ADCs (antibody-drug conjugates or antigen-binding polypeptide construct drug conjugates) are known in the art and are described in U.S. Pat. No. 8,624,003 (pot method), U.S. Pat. No. 8,163,888 (one-step), and U.S. Pat. No. 5,208,020 (two-step method) for example. In some embodiments, the drug is selected from a maytansine, auristatin, calicheamicin, or derivative thereof. In other embodiments, the drug is a maytansine selected from DM1 and DM4.

In some embodiments the antigen-binding polypeptide construct is conjugated to a cytotoxic agent. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32, and Lu177), chemotherapeutic agents, and toxins such as small molecule toxins or enzymatically active toxins of bacterial, fungal, plant or animal origin, including fragments and/or variants thereof.

Therapeutic agents or drug moieties are not to be construed as limited to classical chemical therapeutic agents. For example, the drug moiety can be a protein or polypeptide possessing a desired biological activity. Such proteins can include, for example, a toxin such as abrin, ricin A, Onconase (or another cytotoxic RNase), *pseudomonas* exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, in an alternate embodiment, the antigen-binding polypeptide construct can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N",N"-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

In some embodiments, the immunoglobulin heavy and light chains of the antigen-binding polypeptide construct are expressed as fusion proteins comprising a tag to facilitate purification and/or testing etc. As referred to herein, a "tag" is any added series of amino acids which are provided in a protein at either the C-terminus, the N-terminus, or internally that contributes to the identification or purification of the protein. Suitable tags include but are not limited to tags known to those skilled in the art to be useful in purification and/or testing such as albumin binding domain (ABD), His tag, FLAG tag, glutathione-s-transferase, hemagglutinin (HA) and maltose binding protein. Such tagged proteins can also be engineered to comprise a cleavage site, such as a thrombin, enterokinase or factor X cleavage site, for ease of removal of the tag before, during or after purification.

Methods of Preparing Antigen-Binding Polypeptide Constructs

As described above, the antigen-binding polypeptide constructs described herein can comprise a first heterodimer and a second heterodimer, the first heterodimer comprising an immunoglobulin heavy chain or fragment thereof having at least a VH and CH1 domain, and an immunoglobulin lambda light chain having a VL domain and a CL domain, and the second heterodimer comprising an immunoglobulin heavy chain or fragment thereof having at least a VH and CH1 domain, and an immunoglobulin kappa light chain having a VL domain and a CL domain. The immunoglobulin polypeptide sequences are engineered to incorporate amino acid modifications that promote preferential pairing as described herein. Accordingly, in the case of a bispecific antigen-binding polypeptide construct, there are typically four distinct polypeptide sequences, two immunoglobulin heavy chain polypeptide sequences or fragments thereof and two immunoglobulin light chain polypeptide sequences, that make up the antigen-binding polypeptide construct. The immunoglobulin heavy chain polypeptide sequences and immunoglobulin light chain polypeptide sequences of the antigen-binding polypeptide construct can readily be prepared using recombinant DNA technology known in the art. Standard techniques such as, for example, those described in Sambrook and Russell, Molecular Cloning: A Laboratory Manual (Cold Spring Harbor Laboratory Press, Cold Spring Harbor, N.Y., 3rd ed., 2001); Sambrook et al., Molecular Cloning: A Laboratory Manual (Cold Spring Harbor Laboratory Press, Cold Spring Harbor, N.Y., 2nd ed., 1989); Short Protocols in Molecular Biology (Ausubel et al., John Wiley and Sons, New York, 4th ed., 1999); and Glick and Pasternak, Molecular Biotechnology: Principles and Applications of Recombinant DNA (ASM Press, Washington, D.C., 2nd ed., 1998) can be used for recombinant nucleic acid methods, nucleic acid synthesis, cell culture, transgene incorporation, and recombinant protein expression.

The polynucleotide and amino acid sequences of the immunoglobulin heavy and light chains of the parent antibodies that make up the antigen-binding polypeptide construct are either known in the art or can be readily determined using nucleic acid and/or protein sequencing methods.

Accordingly, also provided are polynucleotides or a set of polynucleotides encoding the immunoglobulin heavy and light chains of the antigen-binding polypeptide construct. Such polynucleotides include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The polynucleotides include full-length genes or cDNA molecules as well as a combination of fragments thereof.

The polynucleotides encoding the engineered immunoglobulin heavy and light chain polypeptides described herein can be prepared by site specific mutagenesis of nucleotides in the DNA encoding the polypeptide, using cassette or PCR mutagenesis or other techniques well known in the art, to produce DNA encoding the engineered immunoglobulin heavy and light chain polypeptides, and thereafter expressing the recombinant DNA in cell culture as outlined herein. However, polynucleotides encoding the engineered immunoglobulin heavy and light chain polypeptides may also be prepared by in vitro gene synthesis using established techniques.

As will be appreciated by those in the art, due to the degeneracy of the genetic code, an extremely large number of polynucleotides may be made, all of which encode the engineered immunoglobulin heavy and light chain polypeptides described herein. Thus, having identified a particular amino acid sequence, those skilled in the art could make any number of different polynucleotides, by simply modifying the sequence of one or more codons in a way which does not change the amino acid sequence of the encoded protein.

Also provided are expression systems and constructs in the form of plasmids, expression vectors, transcription or expression cassettes which comprise at least one polynucleotide as above. Also provided are host cells comprising such expression systems or constructs.

Typically, expression vectors used in the host cells will contain sequences for plasmid maintenance and for cloning and expression of exogenous nucleotide sequences. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the polynucleotide encoding the polypeptide to be expressed, and a selectable marker element. The vector can be multicistronic i.e. expressing two or more of the polynucleotides encoding the immunoglobulin heavy and light chains of the antigen-binding polypeptide construct, or the antigen-binding polypeptide construct can be expressed by a set of vectors, each vector expressing one or more of the polynucleotides. The antigen-binding polypeptide construct can also be expressed using a set of vectors comprising a combination of multicistronic vectors and vectors that comprise a single polynucleotide encoding one of the immunoglobulin heavy and light chains.

In some embodiments, the vector may contain a "tag"-encoding sequence, i.e., an oligonucleotide molecule located at the 5' or 3' end of the polypeptide coding sequence; the oligonucleotide sequence encodes polyHis (such as hexa-His), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the polypeptide from the host cell. Affinity purification can be accomplished, for example, by column chromatography using antibodies against the tag as an affinity matrix. Optionally, the tag can subsequently be removed from the purified polypeptide by various means such as peptidase cleavage.

Vectors typically contain a promoter that is recognized by the host organism and operably linked to the polynucleotide encoding the polypeptide. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known.

Suitable promoters for use with yeast hosts, bacterial hosts, and insect hosts are well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

The vector may contain one or more elements that facilitate expression when the vector is integrated into the host cell genome. Examples include an EASE element (Aldrich et al. 2003 Biotechnol Prog. 19:1433-38) and a matrix attachment region (MAR). MARs mediate structural organization of the chromatin and may insulate the integrated vector from "position" effects. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

After the vector has been constructed and the polynucleotide has been inserted into the proper site of the vector, the completed vector may be inserted into a suitable host cell for amplification and/or polypeptide expression. The transformation of an expression vector into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. The host cells can be transfected transiently or the host cells can be transfected stably. These methods and other suitable methods are well known to the skilled artisan, and are set forth, for example, in Sambrook et al., 2001, supra.

For long-term, high-yield production of recombinant proteins, stable expression is often preferred. For example, cell lines that stably express the engineered heavy and light chains of the antigen-binding polypeptide construct can be prepared. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA or polynucleotide, engineered cells are allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines.

A number of selection systems can be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981,Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

A host cell, when cultured under appropriate conditions, produces the antigen-binding polypeptide construct that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product can be used.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides described herein. In general, host cells are transformed with a recombinant expression vector that comprises DNA encoding the antigen-binding polypeptide construct. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, C127 cells, 3T3 cells (ATCC CCL 163), Chinese hamster ovary (CHO) cells, or their derivatives such as Veggie CHO and related cell lines which grow in serum-free media (Rasmussen et al., 1998, Cytotechnology 28: 31), HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces* strains, *Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides.

If the antigen-binding polypeptide construct is produced in yeast or bacteria, it may be desirable to modify the product produced therein, for example by phosphorylation or glycosylation of the appropriate sites, in order to obtain a functional product. Such covalent attachments can be accomplished using known chemical or enzymatic methods. The antigen-binding polypeptide construct can also be produced by operably linking the set of polynucleotides to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac™ kit), and such methods are well known in the art, as described in Summers and Smith, Texas Agricultural Experiment Station Bulletin No. 1555 (1987), and Luckow and Summers, Bio/Technology 6:47 (1988). Appropriate cloning and expression vectors for use with bacterial, fungal, yeast, and mammalian cellular hosts are described by Pouwels et al. (Cloning Vectors: A Laboratory Manual, Elsevier, New York, 1985).

In certain embodiments, cell-free protein expression systems can be utilized to co-express polypeptides (e.g., heavy and light chain polypeptides) from the set of polynucleotides without the use of living cells. Instead, all components needed to transcribe DNA to RNA and translate the RNA to protein (e.g. ribosomes, tRNAs, enzymes, cofactors, amino acids) are provided in solution for use in vitro. In certain embodiments, the in vitro expression requires (1) the genetic template (mRNA or DNA) encoding the heavy and light chain polypeptides and (2) a reaction solution containing the necessary transcriptional and translational molecular machinery. In certain embodiments, cell extracts substantially supply components of the reaction solution, for instance: RNA polymerases for mRNA transcription, ribosomes for polypeptide translation, tRNA, amino acids, enzymatic cofactors, an energy source, and cellular components essential for proper protein folding. Cell-free protein expression systems can be prepared using lysates derived from bacterial cells, yeast cells, insect cells, plant cells, mammalian cells, human cells or combinations thereof. Such cell lysates can provide the correct composition and proportion of enzymes and building blocks required for translation. In some embodiments, cell membranes are removed to leave only the cytosolic and organelle components of the cell.

Several cell-free protein expression systems are known in the art as reviewed in Carlson et al. (2012) Biotechnol. Adv. 30:1185-1194. For example, cell-free protein expression systems are available based on prokaryotic or eukaryotic cells. Examples of prokaryotic cell-free expression systems include those from *E. coli*. Eukaryotic cell-free protein expression systems are available based on extracts from rabbit reticulocytes, wheat germ, and insect cells, for example. Such prokaryotic and eukaryotic cell-free protein expression systems are commercially available from companies such as Roche, Invitrogen, Qiagen, and Novagen. One skilled in the art would readily be able to select suitable cell-free protein expression systems that would produce polypeptides (e.g., heavy chain and light chain polypeptides) that are capable of pairing with each other. Further, the cell-free protein expression system can also be supplemented with chaperones (e.g. BiP) and isomerases (e.g. disulphide isomerase) to improve the efficiency of IgG folding.

Co-Expression of Heavy Chains and Light Chains

The engineered immunoglobulin heavy chains and light chains of the antigen-binding polypeptide construct described herein can be co-expressed in mammalian cells, as noted above. In one embodiment, the immunoglobulin heavy chains and immunoglobulin light chains of the antigen-binding polypeptide construct are co-expressed in a host cell. Thus, in the case of a bispecific antigen-binding polypeptide construct, two immunoglobulin heavy chains and two immunoglobulin light chains are co-expressed in a host cell. However, alternate methods of producing bispecific antigen-binding polypeptide constructs that do not rely on the use of a single clonal or transient cell line expressing all four chains are also known in the art (Gramer, et al. (2013) mAbs 5, 962; Strop et al. (2012) J Mol Biol 420, 204.). These methods rely on a post production arm exchange under redox conditions of the two pairs of light and heavy chain involved in the formation of bispecific antibody (Redox production). In this approach the H1L1 and H2L2 heterodimers can be expressed in two different cell lines to independently produce the two heterodimers. Subsequently, the two heterodimers are mixed under select redox conditions to achieve re-association of the two unique heavy chain H1 and H2 to form the bispecific antigen-binding polypeptide construct comprising H1L1H2L2.

Although preferential pairing is driven mainly by the incorporation of the Mab design set amino acid modifications into the immunoglobulin heavy and light chain polypeptides, the amount of correctly-paired heterodimers may further be optimized by varying the ratio of the polynucleotides encoding each polypeptide to each other, as shown in the Examples.

Testing of Antigen-Binding Polypeptide Constructs

As described above, the antigen-binding polypeptide constructs comprise a first heterodimer comprising H1 and L1, as well as a second heterodimer comprising H2 and L2, where L1 is a lambda light chain, and L2 is a kappa light chain, and H1 and H2 are distinct from each other. One or more of H1, L1, H2, and L2 comprise amino acid modifications that promote preferentially pairing of H1 with L1 as compared to L2 and of H2 with L2 as compared to L1. The first Fab region of the H1L1 heterodimer and the second Fab region of the H2L2 heterodimer are able to bind to antigen with an affinity that is similar to the corresponding wt first Fab region or wt second Fab region. The first Fab region of the H1L1 heterodimer and the second Fab region of the H2L2 heterodimer also exhibit thermal stability that is comparable to that of the corresponding wt first Fab region or wt second Fab region.

The affinity of each heterodimer of the heterodimer pair for its respective antigen can be tested as described below. The thermal stability of each heterodimer of the heterodimer pair can also be tested as described below.

In one embodiment, one heavy chain is co-expressed with two different light chains in a LCCA design set as described above, where the heavy chain preferentially pairs with one of the two light chains. In another embodiment, two unique heavy chains are co-expressed with two unique light chains, where each heavy chain preferentially pairs with one of the light chains.

Methods to Measure Preferential Pairing

The degree of preferential pairing can be assessed, for example, by using the methods described below and in the examples. Preferential pairing can be assessed in the context of LCCA design sets (H1L1L2, or H2L1L2) or Mab design sets (H1L1H2L2).

In one embodiment, a Light Chain Competition Assay (LCCA) can be used to assess preferential pairing in the context of LCCA design sets. Co-owned patent application PCT/US2013/063306, filed Oct. 3, 2013, describes various embodiments of LCCA and is herein incorporated by reference in its entirety for all purposes. The method allows quantitative analysis of the pairing of heavy chains with specific light chains within the mixture of co-expressed proteins and can be used to determine if one particular immunoglobulin heavy chain selectively associates with either one of two immunoglobulin light chains when the heavy chain and light chains are co-expressed. The method is briefly described as follows: At least one heavy chain and two different light chains are co-expressed in a cell, in ratios such that the heavy chain is the limiting pairing reactant. The heavy chains and light chains may be tagged to facilitate detection. The secreted proteins may be separated from the cell, and the immunoglobulin light chain polypeptides bound to heavy chain are isolated from other secreted proteins to produce an isolated heavy chain paired fraction. The amount of each different light chain in the isolated heavy chain fraction is then detected, and the relative amount of each different light chain in the isolated heavy chain fraction is analyzed to determine the ability of the heavy chain to selectively pair with one of the light chains. Further details regarding an embodiment of this method are provided in the Examples.

In another embodiment, preferential pairing is assessed in the context of Mab design sets, where H1, L1, H2 and L2 are co-expressed. In this embodiment, one or more of H1, L2, H2, and L2 may be tagged to facilitate detection and analysis. The resulting species of paired heavy chains and light chains are assessed using LCMS (Liquid chromatography-Mass spectrometry), based on differences in the molecular weight of each species. An antigen activity assay could also be used to quantify relative heterodimer populations containing each light chain whereby the degree of binding measured (relative to controls) would be used to estimate each respective heterodimer population.

Thermal Stability

The thermal stability of the heterodimers can be determined according to methods known in the art. The melting temperature of each heterodimer is indicative of its thermal stability. The melting point of the heterodimer can be measured using techniques such as differential scanning calorimetry (Chen et al (2003) Pharm Res 20:1952-60; Ghirlando et al (1999) Immunol Lett 68:47-52). Alternatively, the thermal stability of the heterodimer can be measured using circular dichroism (Murray et al. (2002) J. Chromatogr Sci 40:343-9).

Affinity for Antigen

The binding affinity of the heterodimers for their respective antigens and the off-rate of the interaction can be determined by competitive binding assays according to methods well known in the art. One example of a competitive binding assay is a radioimmunoassay comprising the incubation of labeled antigen (e.g., 3H or 1251 with a molecule of interest (e.g., heterodimers of described here) in the presence of increasing amounts of unlabeled antigen, and the detection of the molecule bound to the labeled ligand. The affinity of the heterodimers for the antigen and the binding off-rates can be determined from the saturation data by Scatchard analysis.

The kinetic parameters of a heterodimer described herein can also be determined using surface plasmon resonance (SPR) based assays known in the art (e.g., BIAcore kinetic analysis). For a review of SPR-based technology see Mullet et al., 2000, Methods 22: 77-91; Dong et al., 2002, Review in Mol. Biotech., 82: 303-23; Fivash et al., 1998, Current Opinion in Biotechnology 9: 97-101; Rich et al., 2000, Current Opinion in Biotechnology 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention. FACS can also be used to measured affinity, as is known in the art.

Pharmaceutical Compositions

Also provided herein are pharmaceutical compositions comprising the antigen-binding polypeptide constructs described herein. Such compositions comprise a therapeutically effective amount of the antigen-binding polypeptide construct, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the antigen-binding polypeptide construct is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a therapeutic protein can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Uses of Antigen-Binding Polypeptide Constructs

As described above, the antigen-binding polypeptide constructs described herein are obtained from parent antibodies where each heterodimer of the antigen-binding polypeptide construct corresponds to one of the parent antibodies, and has been engineered to incorporate amino acid modifications that promote preferential pairing of the immunoglobulin heavy and light chains that make up the heterodimers. Accordingly, the antigen-binding polypeptide constructs described herein can be used in the treatment or prevention of the same disease, disorder, or infection that the parent antibody or combination of parent antibodies is used for.

In another embodiment, the antigen-binding polypeptide constructs described herein can also be utilized in combination with other therapeutic agents known in the art for the treatment or prevention of a cancer, autoimmune disease, inflammatory disorders or infectious diseases. In a specific embodiment, the antigen-binding polypeptide constructs described herein can be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The antigen-binding polypeptide constructs described herein can also be utilized in combination with one or more drugs used to treat a disease, disorder, or infection such as, for example anti-cancer agents, anti-inflammatory agents or anti-viral agents.

Generation of Bispecific Antibodies Using a Mab Design Set Library

In one embodiment, the Mab design sets described herein can be employed to produce bispecific antigen-binding polypeptide constructs. The Mab design sets described herein can be utilized in the form of a Mab design set library, where the Mab design set library comprises Mab design sets that show utility in promoting preferential pairing to form bispecific antigen-binding polypeptide constructs. In one embodiment, Mab design set libraries are represented by Mab design sets included in Table 4A and Table 4B. In one embodiment, the Mab design set library is represented by the Mab design sets in one or more of Tables 10-A1 to 10-A12, and 10-B1 to 10-B10. In another embodiment, the Mab design set library is represented by one or more of Tables 10-A1 to 10-A12. In one embodiment, the Mab design set library is represented by one or more of Tables 10-B1, 10-B2, 10-B3, 10-B4, 10-B6, 10-B8, and 10-B10. The Mab design set library can be used to produce an antigen-binding polypeptide construct starting from two parent antibodies (i.e., Mab1 and Mab2) as follows. For the sake of illustration, Mab1 comprises a lambda Fab and comprises the immunoglobulin heavy chain polypeptide H1 and the immunoglobulin light chain polypeptide L1, while Mab2 comprises a kappa Fab and comprises the immunoglobulin heavy chain polypeptide H2 and the immunoglobulin light chain polypeptide L2.

The Mab design set amino acid modifications (H1L1H2L2) of the Mab design set library are introduced into the immunoglobulin heavy and light chain of Mab1 (H1 and L2) and the immunoglobulin heavy and light chain of Mab2 (H2 and L2). H1, L1, H2, and L2 are then co-expressed and the amount of the correctly paired bispecific antigen-binding polypeptide construct is determined. One or more Mab design sets of the Mab design set library may be individually tested or screened to determine which provides the desired amount of bispecific antigen-binding polypeptide construct. Each heterodimer of the bispecific antigen-binding polypeptide construct can be further tested to assess the ability of each heterodimer to bind to antigen or to assess its thermal stability, as described herein. Additional properties that can be assessed include solubility, aggregation, kon and koff rates, ability to withstand exposure to acids, bases, oxidation, freeze/thaw cycles, agitation, pressure etc. of the bispecific antigen-binding polypeptide construct compared to the parent antibodies or Fab regions of the parent antibodies. The latter properties can be impacted by the complementarity determining regions (CDRs) of an antibody of interest, and thus may be tested for each bispecific antigen-binding polypeptide construct generated.

Figure 9:
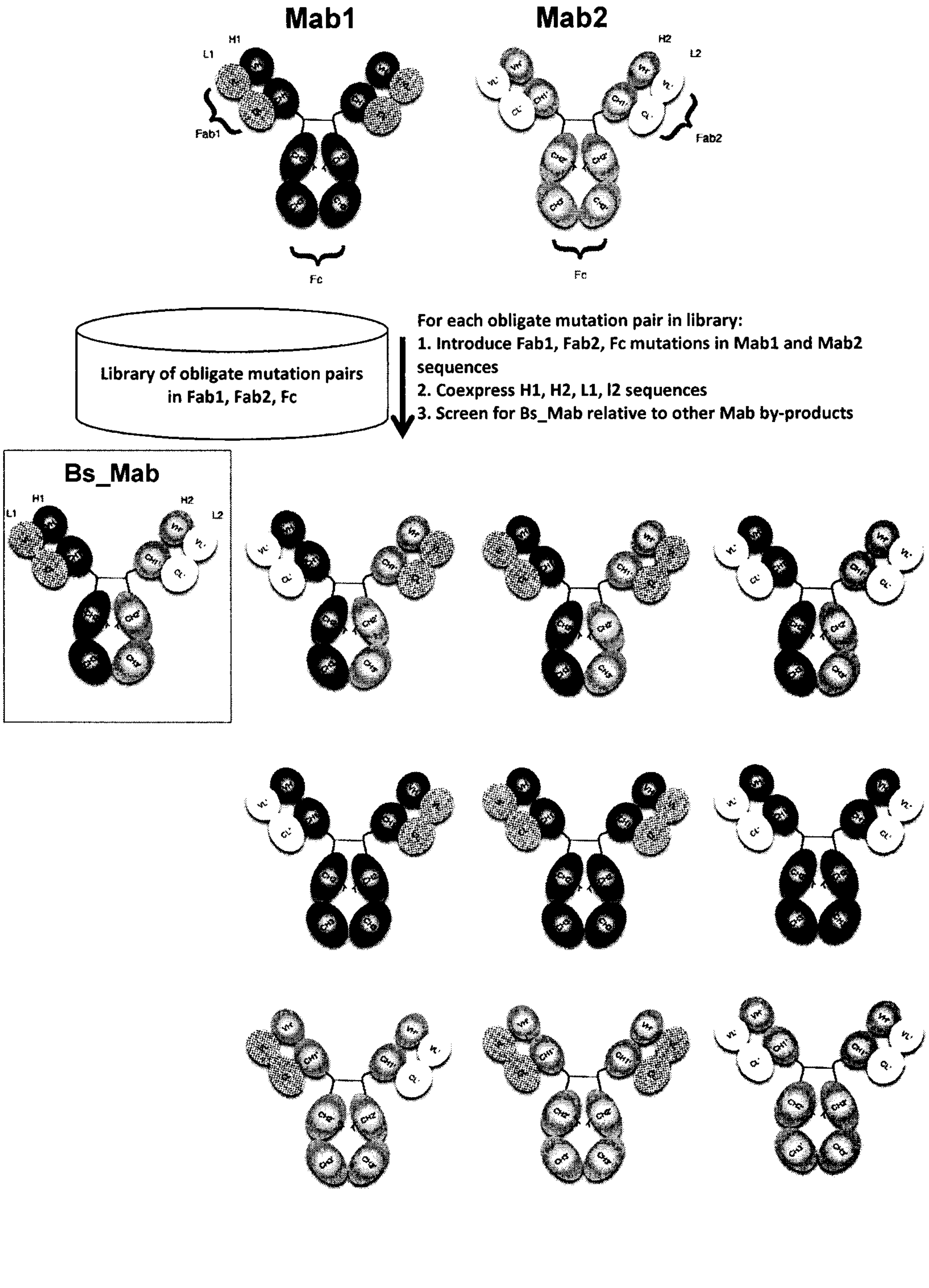
FIG. 9 depicts a general method of preparing a bispecific antigen-binding polypeptide construct using the Mab design set library provided herein.

In some embodiments the amount of correctly paired bispecific antigen-binding polypeptide construct is assessed by LCMS. In some embodiments the amount of correctly paired bispecific antigen-binding polypeptide construct is assessed by charge based separation techniques such as a capillary isoelectric focusing (cIEF) technique or a chromatographic technique. The procedure for preparation of a bispecific antigen-binding polypeptide construct from Mab1 and Mab2 using a library of Mab design sets is shown schematically in FIG. 9.

In one embodiment, the Mab design set library is stored on a computer-readable storage medium to facilitate use of the Mab design set library to design bispecific antigen-binding polypeptide constructs.

Computer Implementation

In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device can be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Below are examples of specific embodiments for making and using the antigen-binding polypeptide constructs described herein. The examples are offered for illustrative purposes only, and are not intended to limit the scope of the disclosure in any way. Efforts have been made to ensure accuracy with respect to numbers used (e.g., amounts, temperatures, etc.), but some experimental error and deviation should, of course, be allowed for.

The constructs and methods described herein can be prepared and carried out employing, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

EXAMPLES

Example 1: Molecular Modeling and Computer Guided Engineering of the Fab Interface A structure- and computational molecular modeling-guided approach was used to produce a kappa-lambda (K-L)

design library for the preparation of bispecific antibodies where one Fab has a kappa light chain and the other Fab has a lambda light chain (i.e. a kappa-lambda system, or K-L system). The K-L design library comprises designs with amino acid modifications in the heavy and light chains of the Fabs that promote preferential formation of the desired bispecific antibody when these heavy and light chains are co-expressed. The K-L design library takes advantage of inherent differences between kappa and lambda light chains in bispecific antibodies and is hence optimized for kappa-lambda systems. The K-L design library was generated by studying the structure of representative Fabs, with D3H44 (anti-tissue factor antibody) as a representative Fab containing a kappa light chain (kappa Fab), and CAT-2200 (anti-IL-17A antibody) as a representative Fab containing a lambda light chain (lambda Fab), but the library can be used in the context of other bispecific K-L system antibodies or fragments thereof to identify designs that exhibit the desired pairing specificity in the antibodies of interest.

The representative Fabs were chosen based on the criteria indicated in Table 1. These criteria included that the Fabs be human or humanized, have commonly used VH and VL subgroups and contain minimal framework region mutations. Also, pairwise 3D superposition with available non-redundant (90% sequence identity threshold) kappa and lambda structures was performed (structures obtained from the RSCB PDB, a database maintained by Rutgers University (Camden, N.J.) and the University of California at San Diego (San Diego, Calif.), see the internet at www.rcsb.org. Together with the other parameters described in Table 1, low H-L cross domain RMSDs (root-mean-square deviations) for VH-VL or CH1-CL was used to select a representative structure for each one of the kappa and lambda systems. After selection of D3H44 (PDB ID 1JPT) and CAT-2200 (PDB ID 2VXS) as representative Fabs, an in silico structural analysis of these Fab interfaces was carried out to identify and understand residues important for interactions between heavy and light chains, using a two-pronged approach.

Figure 1B:
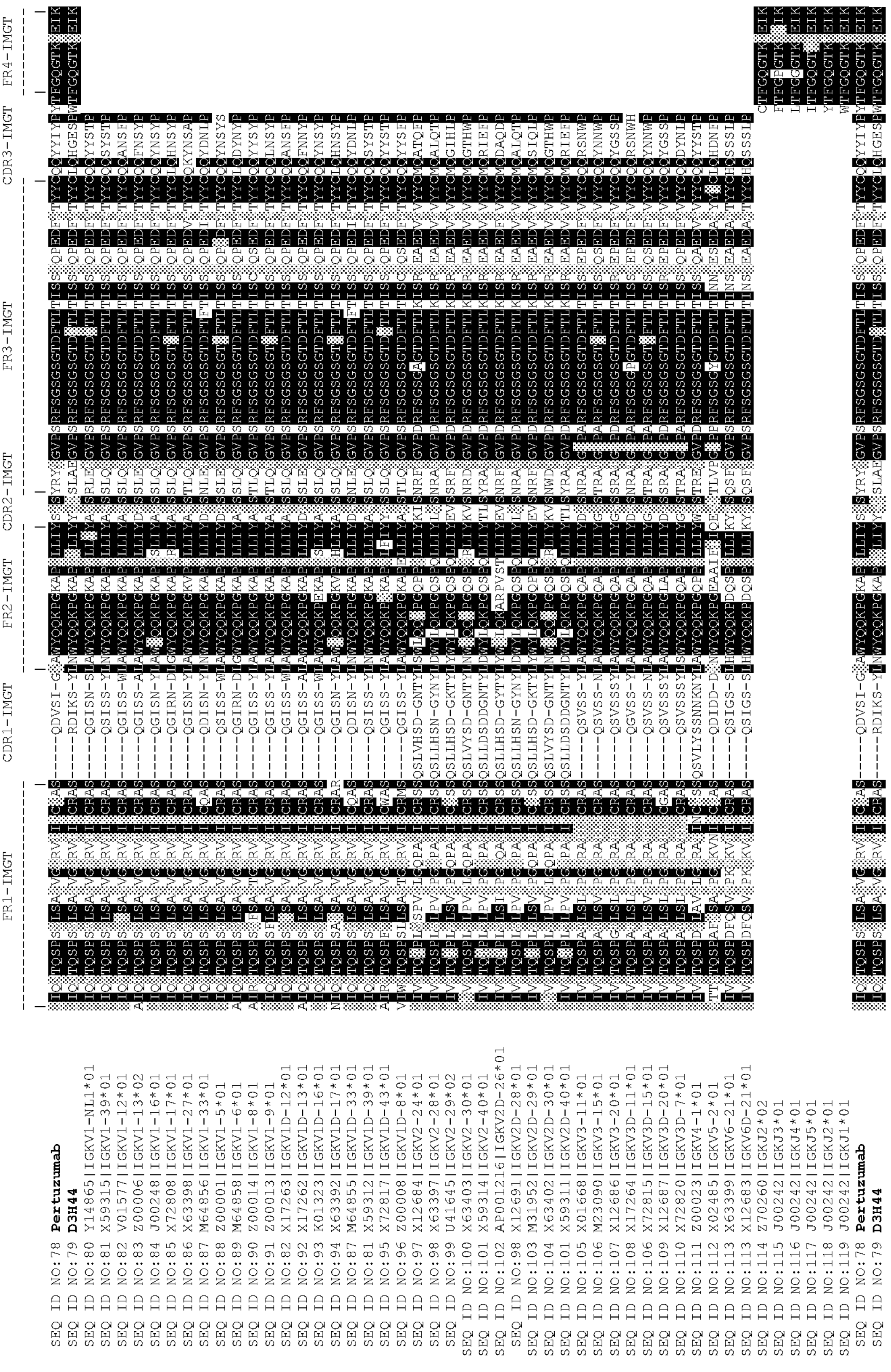
FIG. 1B depicts Pertuzumab and D3H44 variable light (VL) domains aligned against human kappa IGKV and IGKJ germline subgroups (one representative sequence is displayed from each gene and allele). The closest gene and allele sequences to Pertuzumab IGKV and IGKJ are Y14865|IGKV1-NL1*01 and J00242|IGKJ2*01, respectively. The closest gene and allele sequences to D3H44 IGKV and IGKJ are X59315|IGKV1-39*01 and J00242|IGKJ1*01, respectively.
Figure 1E:
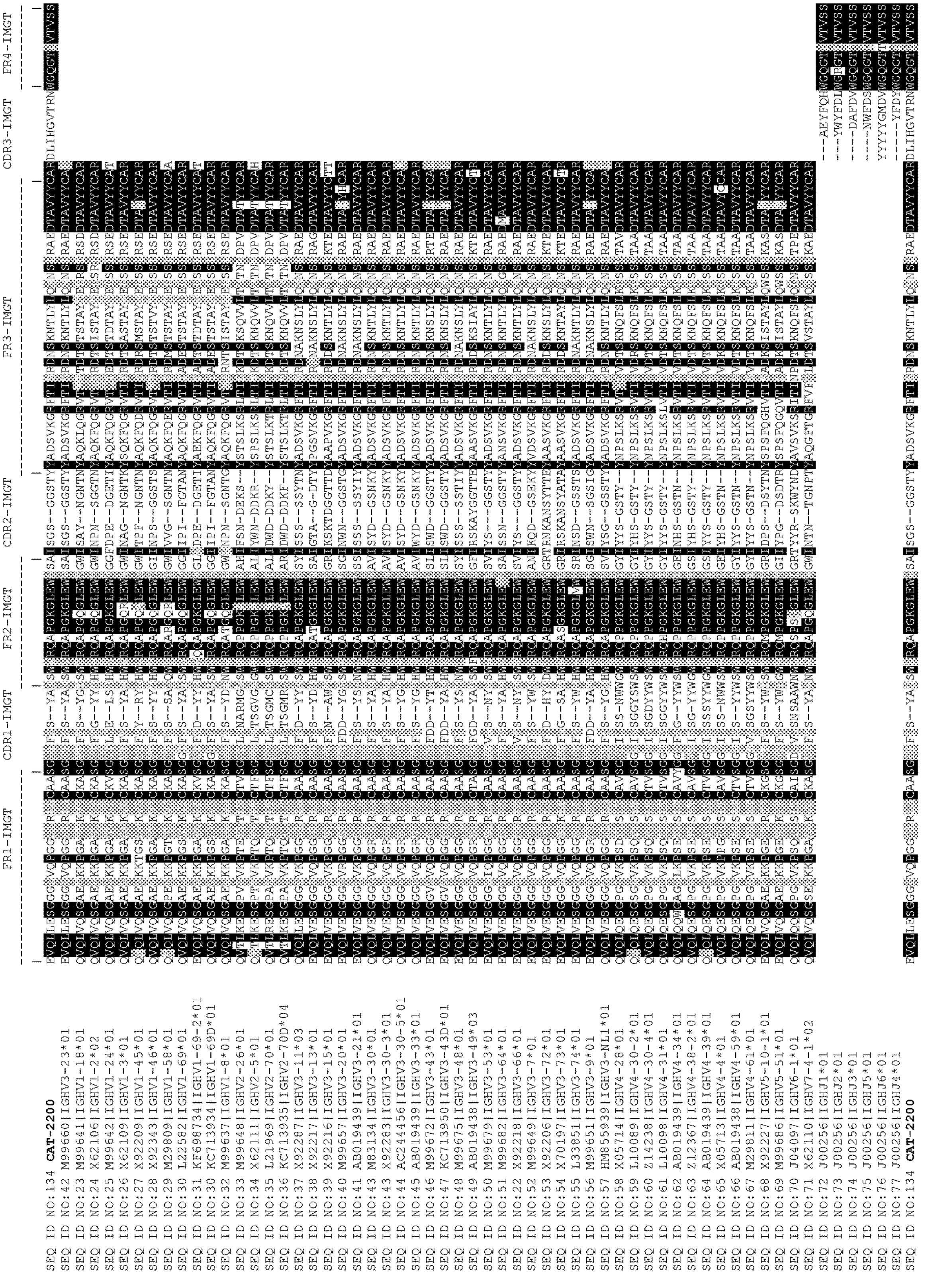
FIG. 1E depicts CAT-2200 VH domain aligned against human IGHV and IGHJ germline subgroups (one representative sequence is displayed for each gene and allele). The closest gene and allele sequences to CAT-2200 IGHV and IGHJ are M99660|IGHV3-23*01 and J00256|IGHJ4*01, respectively.

First, global analysis of the sequence conservation across the Fab variable and constant interfaces was carried out via sequence and structure alignments of known antibodies. An alignment of constant and variable domain sequences from various antibody subgroups, compared to the sequences of D3H44 and the anti-HER2 antibody pertuzumab (both containing kappa light chains) and CAT-2200 (containing a lambda light chain) is shown in FIG. 1. FIG. 1A and FIG. 1E depict an alignment comparing representative human VH germline subgroups with that of D3H44/Pertuzumab and CAT-2200, respectively. FIG. 1B depicts an alignment comparing D3H44/Pertuzumab with representative human kappa VL germline subgroups. FIG. 1C and FIG. 1G depict an alignment comparing human CH1 allele sequences with that of D3H44/Pertuzumab and CAT-2200, respectively. FIG. 1D depicts an alignment comparing D3H44/Pertuzumab with human kappa allele sequences. FIG. 1F depicts an alignment comparing CAT-2200 with representative human lambda VL germline subgroups. FIG. 1H depicts an alignment comparing CAT-2200 with human lambda allele sequences. This analysis revealed that pertuzumab and D3H44 show high degree of sequence conservation with kappa constant and variable domain germlines, while CAT-2200 shows high degree of sequence conservation with lambda constant and variable domain germlines. These alignments also exemplify the higher degree of conservation in the constant domains of both heavy and light chains, making designs in the constant domain interface more likely to be transferable to other antibodies.

Figure 2:
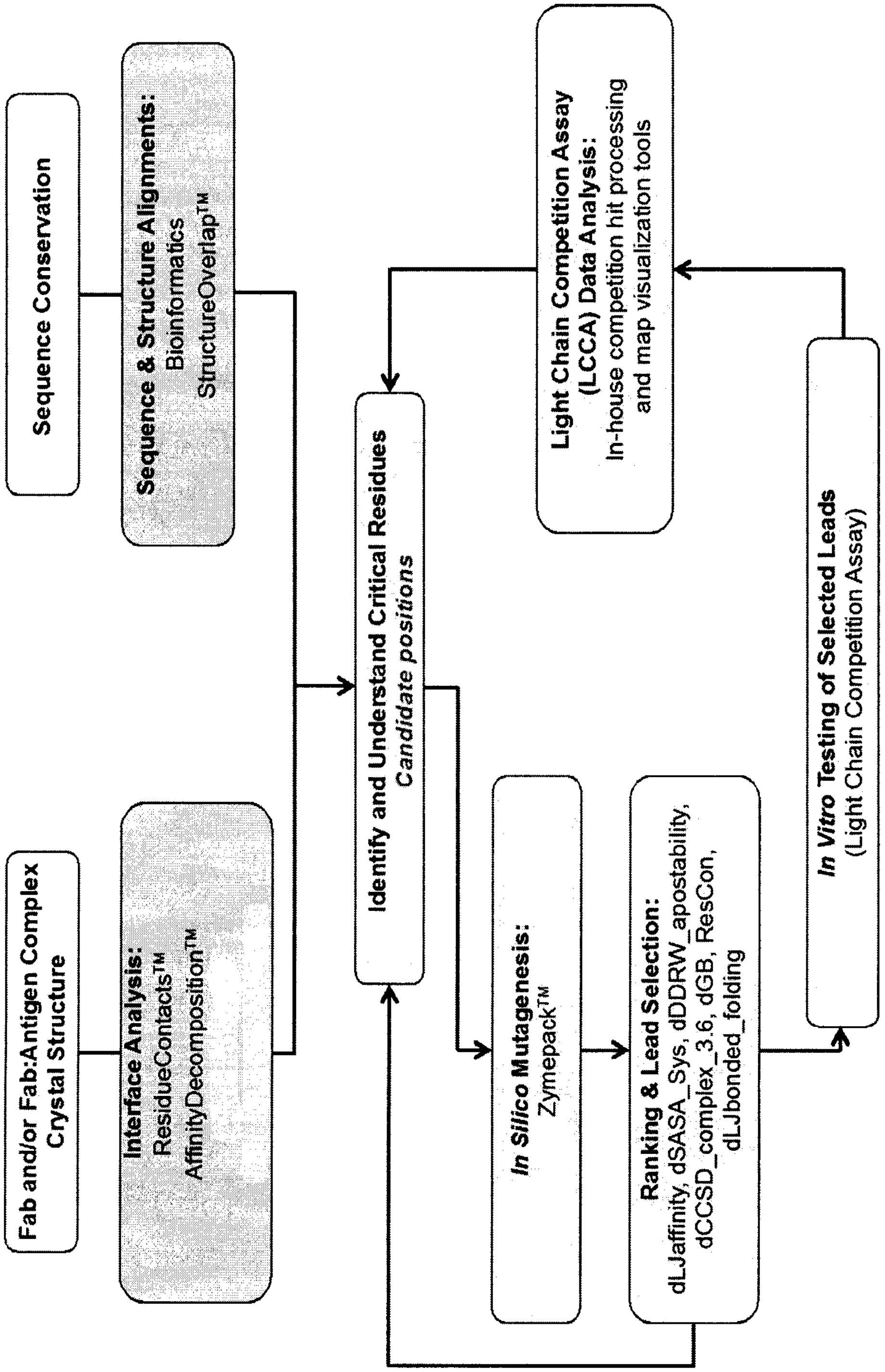
FIG. 2 depicts a flowchart for identifying interface residues and for computational modeling of designs with preferential heavy-light chain pairing.
Figure 3:
FIG. 3 depicts a 3D structural alignment between the constant domains of D3H44 (PDB ID 1JPT) and CAT-2200 (PDB-ID 2VXS).

The second approach involved the analysis of the D3H44 and CAT-2200 crystal structure interfaces using a number of molecular modeling tools as shown in FIG. 2 (e.g. RESIDUECONTACTS™ and AFFINITYDECOMPOSITION™). To improve transferability to other antibodies or fragments the analysis focused on the constant domain where sequence conservation is higher (see FIG. 1). These analyses were used to identify differences in hotspot positions (key interface residues) between the representative kappa Fab (D3H44) and lambda Fab (CAT-2200) structures, as shown in Table 2. There are noticeable conformational differences in the constant domain between CH1-CL (kappa) and CH1-CL (lambda) structures. Superposing available Fab structures on the CH1 domain showed that CL (kappa) structures adopt a very similar conformation and form a tight cluster. CL (lambda) conformations, however, tend to reside into two distinct clusters: one closer to the kappa orientation (kappa-like cluster) and one more discrepant orientation (lambda cluster). By this analysis D3H44 represents a typical kappa structure and CAT-2200 represents a typical lambda structure (lambda cluster). FIG. 3 exemplifies the typical constant domain kappa-lambda conformational difference using D3H44 and CAT-2200 as representative structures. These differences seem to stem mainly from a rigid body movement of the light constant domain relative to the CH1 domain, which changes the nature of the H-L interface in the constant domain of kappa when compared with a lambda system. The identified hotspot discrepancies (Table 2) as well as the above-mentioned conformational differences (FIG. 3) served as the starting point for the engineering of H-L pairing designs for a bispecific system containing a kappa Fab and a lambda Fab. The numbering of amino acids in the parent D3H44 and CAT-2200 sequences according to Kabat is provided in Table 3A and Table 3B.

Next, potential mutations at the hotspot positions as well as positions neighboring the hotspots of interest in the 3D crystal structure were simulated and identified via in silico mutagenesis and packing/modeling with ZYMEPACK™. ZYMEPACK™ is a software suite that, given an input structure and a set of mutations, will alter the residue types in the input structure according to the supplied mutations, and generate a new structure that is an approximation to the physical structure of the mutant protein. Additionally, ZYMEPACK™ evaluates the properties of the mutant protein by computing a variety of quantitative metrics. These metrics include measures of steric and electrostatic complementarity, which may correlate with the stability, binding affinity, or heterodimeric specificity of the mutant protein.

By exploiting interface discrepancies, mutations were introduced to promote selective pairing of the desired or preferred polypeptide chains or heterodimers while disfavoring the formation of incorrectly paired or mispaired polypeptide chains or heterodimers. For example, in order to prepare a bispecific antibody with one kappa Fab and one lambda Fab, four polypeptide chains are required. The kappa Fab comprises heavy chain 1 (H1) and kappa light chain 1 (L1), while the lambda Fab comprises heavy chain 2 (H2) and lambda light chain 2 (L2). In this case, the desired H-L pairs would be H1L1 and H2L2, while the incorrect pairs would be H1L2 and H2L1. Note that the designation/numbering of the polypeptide chains here is arbitrary. Thus, mutations that favor the paired CH1-CL (kappa) interface (H1L1) over the mispaired CH1-CL (lambda) interface (H1L2) and mutations that favor the paired CH1-CL (lambda) interface (H2L2) over the mispaired CH1-C L (kappa) interface (H2L1) were identified to generate kappa Fab-lambda Fab tailored designs in the constant domain. Using computational methods including ZYMEPACK™, steric complementarity was modeled and also computed on the basis of energy factors such as van der Waals packing, cavitation effects and close contact of hydrophobic groups. Similarly, electrostatic interaction energies were modeled and evaluated on the basis of coulomb interactions between charges, hydrogen bonds, and desolvation effects. Both the preferred heavy and light chain pair models H1L1 and H2L2, and the incorrect pair models H1L2 and H2L1 obtained by introducing the mutations of interest were simulated to compute the relative steric and electrostatic scores. This allowed the determination of whether a particular mutation set led to favorable energies i.e. greater steric and/or electrostatic complementarity for the preferred heavy-light chain pairs relative to the incorrect pairs. The computed steric and electrostatic energies are components of the free energy associated with the light and heavy chain pairing. Hence greater steric and electrostatic complementarity is indicative of a larger free energy change associated with the pairing of the desired pair relative to the pairing of the incorrect pair. The greater steric and/or electrostatic complementarity results in preferential (selective) pairing of the desired heavy and light chains relative to the steric penalty and/or electrostatic repulsion for the incorrect pair.

Example 2: Selection and Description of Designs

The approach described in Example 1 was used to design heavy chain-light chain heterodimer pairs (i.e. H1L1 and H2L2) that exhibit selective or preferential pairing when one of the H-L heterodimer pairs contains a kappa light chain and the other contains a lambda light chain. The heterodimers were designed in pairs, referred to as a "Mab design" or "Mab design set," and include a set of amino acid substitutions on H1, L1, H2, and L2 chains that promote preferential pairing. The Mab design sets were initially tested as "LCCA designs" where one heavy chain of the Mab design set was co-expressed with the two light chains of the Mab design set, one kappa and one lambda, in order to assess relative pairing. The amino acid substitutions described throughout the Examples are identified with reference to Table 3A and Table 3B (for pertuzumab and CAT-2200 Fabs), using the Kabat numbering system as described in Kabat and Wu, 1991; Kabat et al, Sequences of proteins of immunological interest. 5th Edition—US Department of Health and Human Services, NIH publication no, 91-3242, p 647 (1991), unless otherwise indicated. For reference, however, Tables 22A, 22B, and 22C provide an identification of selected amino acid positions in the heavy chain, kappa light chain, and lambda light chain using IMGT, 1JPT, and EU numbering systems as applicable.

The Mab designs were packed onto a molecular model of D3H44 and CAT-2200 and metrics were calculated as described in Example 1. The top designs were then selected based on risk (minimizing effects on stability as well as immunogenicity) and impact (which takes into account the proposed strength of the drive pairing specificity). The top designs were then tested by a light chain competition assay (LCCA) to experimentally determine their pairing specificity (see Example 4). Although the Mab designs were identified using D3H44 and CAT-2200 as representative Fabs, they were tested in a K-L system using Pertuzumab as the kappa Fab and CAT-2200 as the lambda Fab (pertuzumab-CAT-2200 K-L system). As shown in FIG. 1C and FIG. 1D, D3H44 and Pertuzumab have identical sequences in the constant domain, allowing for seamless interconversion between the two systems. These Mab designs are referred to as K-L designs.

A second set of designs was also tested in the pertuzumab/CAT-2200 K-L system. These designs were proposed using representative designs that reflected the diversity of the designs from the kappa-kappa (K-K) design library described in Table 30 of International Patent Application Number PCT/CA2013/050914 (International Patent Publication No. WO2014/082179) as a starting point. These representative K-K-derived designs included a subset of designs that were either ported without modification to the K-L system where possible, or adapted to the kappa-lambda-system by modifying amino acid residues as necessary to account for sequence and structural differences between kappa and lambda light chains. Both types of representative K-K-derived designs are referred to as K-K-derived K-L designs.

Pairing specificity for K-L designs and K-K-derived K-L designs was experimentally assessed as LCCA designs by LCCA in the kappa-lambda system, as described in Example 4.

Example 3:Preparation of Fab Constructs Encoding Pertuzumab IgG Heavy Chains, Pertuzumab IgG Light Chains, CAT-2200 IgG Heavy Chains, and CAT-2200 IgG Light Chains The wild-type Fab heavy and light chains of the anti-HER2 antibody Pertuzumab and for the anti-IL17 antibody CAT-2200 were prepared as follows. The protein sequences of the pertuzumab Fab light chain (GenBank Accession No. HC359025.1, SEQ ID NO:2) and heavy chain (GenBank Accession No. HC359024.1, SEQ ID NO:1) were reverse translated to DNA, codon optimized for mammalian expression, and gene synthesized (SEQ ID NOs: 8 and 7, respectively). The protein sequences of the CAT-2200 Fab light chain (2VXS chain L, SEQ ID NO:4) and heavy chain (2VXS chain H, SEQ ID NO:3) were taken from the PDB entry 2VXS, reverse translated to DNA, codon optimized for mammalian expression, and gene synthesized (SEQ ID NOs:10 and 9, respectively). The polypeptide and DNA sequences of these antibody heavy and light chains are shown in Table 3C.

Light chain vector inserts, consisting of a 5'-EcoRI cutsite—HLA-A signal peptide—HA or FLAG tag—Light chain Ig clone—'TGA or TAA stop'—BamH1 cutsite-3', were ligated into a pTT5 vector (Durocher Y et al., Nucl. Acids Res. 2002; 30, No. 2 e9) to produce light chain expression vectors. The resulting light chain expression vectors were sequenced to confirm correct reading frame and sequence of the coding DNA. Likewise, heavy chain vector inserts, consisting of a 5'-EcoR1 restriction site—HLA-A signal peptide—heavy chain clone (terminating at T238; see Table 3A)—$ABD_2$-His6tag—TGA stop—BamH1 cutsite-3', were ligated into a pTT5 vector ($ABD_2$=two copies of the albumin binding domain protein, in tandem) to produce heavy chain expression vectors. The resulting heavy chain expression vectors were also sequenced to confirm correct reading frame and sequence of the coding DNA. The various Pertuzumab or CAT-2200 Fab constructs containing amino acid substitutions for the Mab design sets were generated either by gene synthesis or by site-directed mutagenesis (Braman J, Papworth C & Greener A., Methods Mol. Biol. (1996) 57:31-44).

Heavy and light chains were tagged at the C- and N-termini respectively, in order to facilitate the assessment of preferential pairing via a competition assay-SPR screen (LCCA). The $ABD_2$-His6 heavy chain tag allowed H-L complexes to be captured on an anti-His tag SPR chip surface, whilst FLAG and HA light chain tags allowed the relative L1 and L2 populations to be quantified.

Example 4: Assessment of Preferential Pairing of Designed Fab Heterodimers by Light Chain Competition Assay (LCCA)

Constructs encoding CAT-2200 and Pertuzumab IgG heavy and light chains in the Fab format comprising amino acid modifications were prepared as described in Example 3. The ability of the constructs to preferentially pair to form the desired H-L heterodimer in the context of an LCCA design set (H1, L1, L2 or H2, L2, L1) was determined using a Light Chain Competition Assay (LCCA).

The LCCA quantifies the relative pairing of one heavy chain for at least two unique light chains, one kappa and one lambda, and can be summarized as follows. To determine pairing specificity for the lambda Fab, one CAT-2200 heavy chain Fab construct was co-expressed with one CAT-2200 light chain Fab construct (for the paired Fab product H1L1) and one Pertuzumab light chain Fab construct (for the mispaired Fab product H1L2) and the relative light chain pairing specificity (H1L1:H1L2) was determined from a competition assay-SPR screen, conducted in duplicate. Conversely, to determine pairing specificity for the kappa Fab, one Pertuzumab heavy chain Fab construct was co-expressed with one Pertuzumab light chain Fab construct (for the paired Fab product H2L2) and one CAT-2200 light chain Fab construct (for the mispaired Fab product H2L1) and the relative light chain pairing specificity (H2L2:H2L1) was determined from a competition assay-SPR screen, conducted in duplicate.

Figure 4:
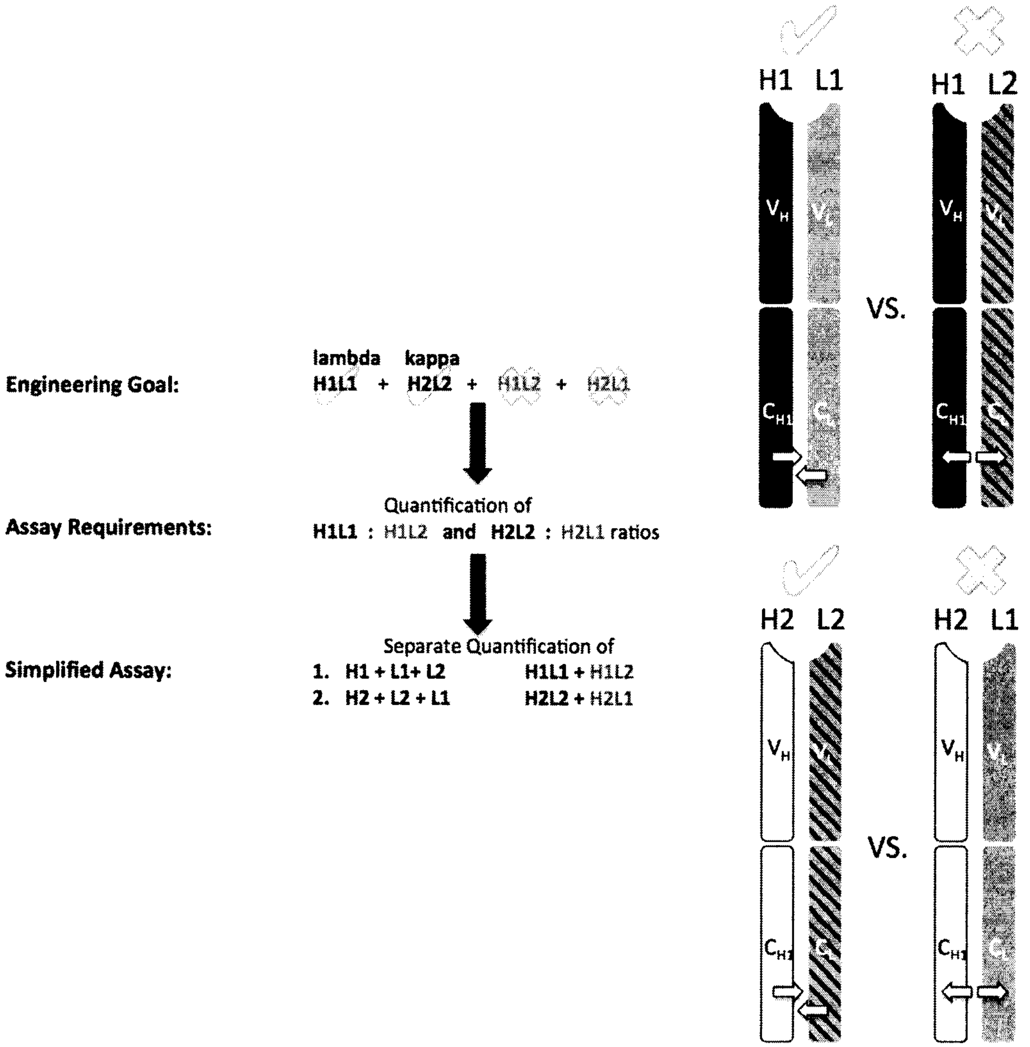
FIG. 4 illustrates a high level schematic overview of the engineering requirements for forming a bispecific antibody, and the assay requirements needed to quantify heavy chain light chain (H-L) pairs. The design goal of engineering a bispecific antibody with high purity (i.e., little or no mispaired H-L associations) can be achieved by rationally engineering (via the introduction of specific amino acid mutations) the preferential pairing of two unique heavy chains for their unique cognate light chains. This process is shown schematically; here H1 has been engineered to preferentially pair with L1 (indicated by a checkmark) and not L2 (indicated by an "X"). Likewise, H2 has been engineered to preferentially pair with L2 and not L1. The arrows on the H1L1 and H2L2 heterodimers represent facilitated pairing between these H-L pairs, while the arrows on the H1L2 and H2L1 heterodimers represent disruption of pairing between the latter H-L pairs. The experimental screening of designs to promote preferential pairing requires an assay capable of simultaneously quantifying H1L1:H1L2 and H2L2:H2L1. These assay requirements can be simplified by assuming that each bispecific Fab arm can be independently engineered. In this case, the assay would only need to quantify H1L1:H1L2 or H2L2:H2L1, and not both simultaneously.
Figure 5:
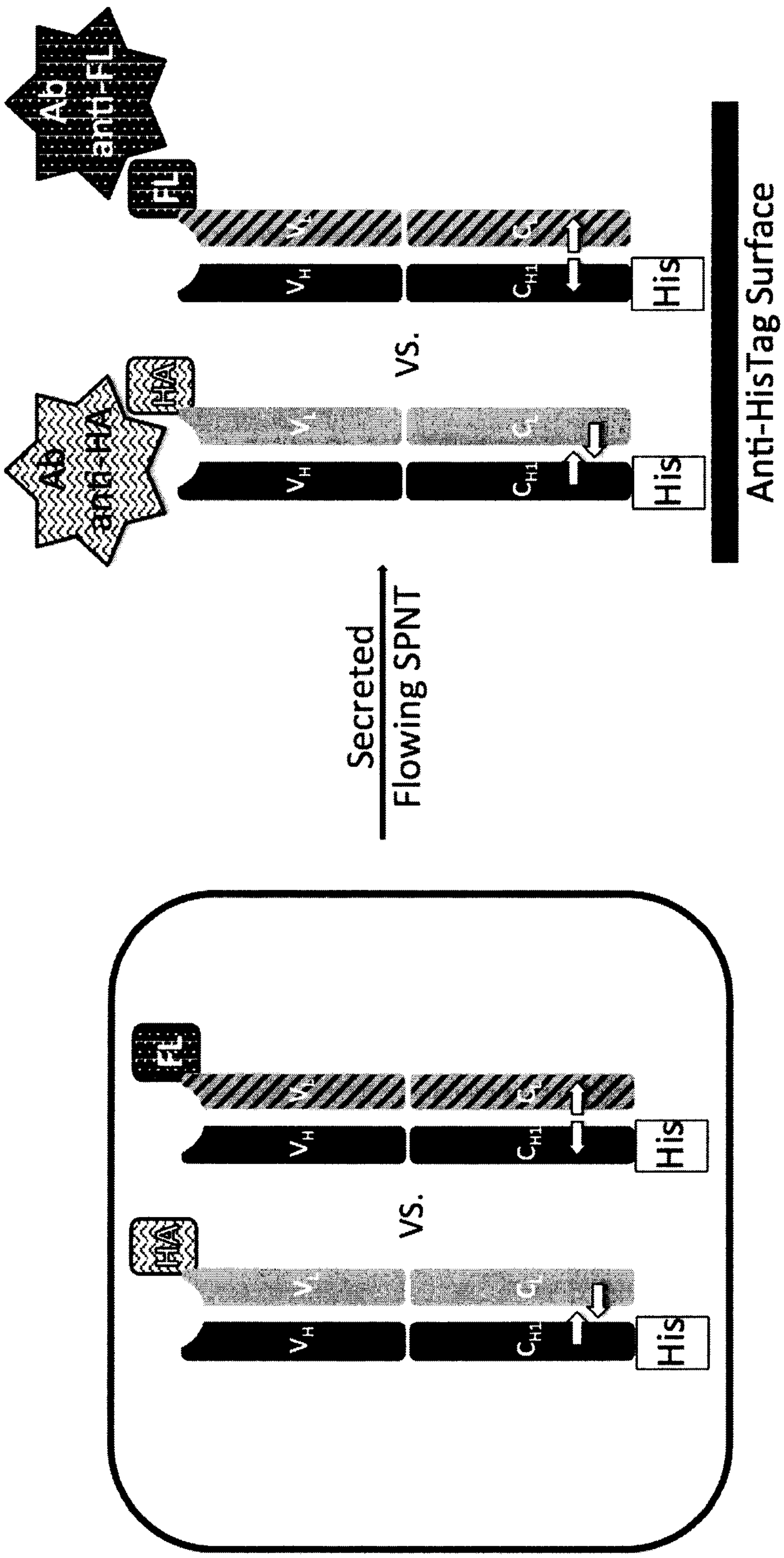
FIG. 5 provides a schematic depicting how heavy chains and light chains can be tagged and how preferential pairing is determined. In this schematic, the circular boundary represents a cell in which 3 constructs (one heavy chain and two unique light chains) are transfected. The expression products are secreted from the cell and the supernatant (SPNT) is passed over a detection device, in this case an SPR chip. Based on detection of the two different tags fused to the two light chains competing for heavy chain pairing, a quantitative estimate of the preferential pairing of the heavy chain to the two light chains can be obtained.

The LCCA assay was performed by concomitant expression of heavy and light chains at ratios of 1:1:1 (by weight) for H1:L1:L2 or H2:L2:L1, with the heavy chain being in limiting amounts. The amount of each heterodimer formed (i.e. H1L1 and H1L2 or H2L2 and H2L1) was determined by binding heavy chains to the SPR chip via a his-tag pull-down, followed by detection of the amount of each light chain tag (HA or FLAG) using antibodies specific for these tags. Subsequently, selected heterodimer hits were verified via a light chain competition assay verification whereby the L1:L2 DNA ratios were again checked for a 1:1 ratio, while keeping the heavy chain in limiting quantities. For these particular kappa-lambda system combinations the light chain tags can have an effect on the wild type LCCA pairing, leading to deviations from the expected neutral 50%:50% ratio. For that reason the arrangement with the least amount of deviation from neutral was chosen by fusing the Pertuzumab light chain with the HA tag and the CAT-2200 light chain with the FLAG tag. A schematic representing the design of the assay is shown in FIG. 4. FIG. 5 depicts how the heavy chains and light chains are tagged and how preferential pairing is assessed. The experimental details of the LCCA are provided below.

Transfection Method

LCCA designs comprising one heavy chain construct and two light chain constructs, prepared as described in Example 3, were transfected into CHO-3E7 cells as follows. CHO-3E7 cells, at a density of $1.7\text{-}2\times10^6$ cells/ml, were cultured at 37° C. in FREESTYLE™ F17 medium (Invitrogen cat #A-1383501) supplemented with 4 mM glutamine and 0.1% KoliphorP188 (Sigma #K4894). A total volume of 2 ml was transfected with a total of 2 μg DNA using PEI-pro (Polyplus transfection #115-375) at a DNA:PEI ratio of 1:2.5. All transfections were performed using 333 ng of each heavy chain and each light chain of (i.e. H1:L1:L2 or H2:L2:L1=1:1:1 ratio), 300 ng of AKTdd pTT22 (a vector containing a constitutively active protein kinase B mutant), and 700 ng of ssDNA (salmon sperm DNA). Twenty-four hours after the addition of the DNA-PEI mixture, 0.5 mM Valproic acid (final concentration) and 1% w/v Tryptone (final concentration) were added to the cells which were then transferred to 32° C. Supernatants were tested for expression on day 7 by non-reducing SDS-PAGE analysis followed by Coommassie blue staining to visualize the bands.

Competition Assay SPR Method

The degree of preferential heavy chain pairing to each of the two light chains in the LCCA designs was assessed using an SPR-based readout of unique epitope tags located at the N-terminus of each light chain. CAT-2200 LC construct contain a FLAG tag and Pertuzumab LC construct contain an HA tag.

Surface Plasmon resonance (SPR) supplies. GLC sensorchips, the Biorad ProteOn amine coupling kit (1-ethyl-3-(3-dimethylaminopropyl) carbodiimide hydrochloride (EDC), N-hydroxysulfosuccinimide (sNHS) and ethanolamine), and 10 mM sodium acetate buffers were purchased from Bio-Rad Laboratories (Canada) Ltd. (Mississauga, ON). 4-(2-hydroxyethyl)-1-piperazineethanesulfonic acid (HEPES) buffer, ethylenediaminetetraacetic acid (EDTA), and NaCl were purchased from Sigma-Aldrich (Oakville, ON). 10% Tween 20 solution was purchased from Teknova (Hollister, Calif.).

SPR biosensor assays. All surface plasmon resonance assays were carried out using a BioRad ProteOn XPR36 instrument (Bio-Rad Laboratories (Canada) Ltd. (Mississauga, ON)) with PB ST running buffer (PBS Teknova Inc with 0.05% Tween20) at a temperature of 25° C. The anti-penta His™ capture surface was generated using a GLC sensorchip activated by a 1:5 dilution of the standard Bio-Rad sNHS/EDC solutions injected for 140 s at 100 μL/min in the analyte (horizontal) direction. Immediately after the activation, a 25 μg/mL solution of anti-penta His™ antibody (Qiagen Inc.) in 10 mM NaOAc pH 4.5 was injected in the analyte (vertical) direction at a flow rate of 25 μL/min until approximately 3000 resonance units (RUs) are immobilized. Remaining active groups were quenched by a 140 s injection of 1M ethanolamine at 100 μL/min in the analyte direction, and this also ensures mock-activated interspots were created for blank referencing.

The screening of the heterodimers for binding to the anti-FLAG (Sigma Inc.) and anti-HA (Roche Inc.) monoclonal antibodies occurred in two steps: an indirect capture of the heterodimers onto the anti-penta His™ surface in the ligand direction followed by an anti-FLAG and anti-HA injection in the analyte direction. First, one injection of PBST for 30 s at 100 μL/min in the ligand direction was used to stabilize the baseline. For each heterodimer capture, unpurified heterodimers in cell-culture media were diluted to 4% in PBST. One to five heterodimers or controls (i.e. controls containing either 100% HA-light chain or 100% FLAG-light chain) were simultaneously injected in individual ligand channels for 240 s at flow 25 μL/min, resulting in a saturating heterodimer capture of approximately 300 to 400 RUs onto the anti-penta His surface. The first ligand channel was left empty to use as a blank control if required. This heterodimer capture step was immediately followed by two buffer injections in the analyte direction to stabilize the baseline, and then 5 nM anti-FLAG and 5 nM anti-HA were each injected in duplicate at 50 μL/min for 120 s with a 180 s dissociation phase, resulting in a set of binding sensorgrams with a buffer reference for each of the captured heterodimer. The heterodimers were regenerated by an 18 s pulse of 0.85% phosphoric acid for 18 sat 100 μL/min to prepare the anti-penta His™ surface for the next injection cycle. Sensorgrams were aligned and double-referenced using the buffer blank injection and interspots, and the resulting sensorgrams were analyzed using ProteOn Manager software v3.0.

Data Analysis and Description of LCCA Metrics

The assessment of preferential pairing for each design, present in the H1L1H2L2 format, was assessed by two complementary LCCA design sets, one for the H1L1L2 combination and the other for the H2L1L2 combination. Each LCCA design set is denoted with a 'unique identifier' (for example, 10629 or 10695). Each Mab design set (H1L1H2L2) is consequently identified by the LCCA design set numbers for the two constituent LCCAs (e.g. 10629-10695).

Figure 6:
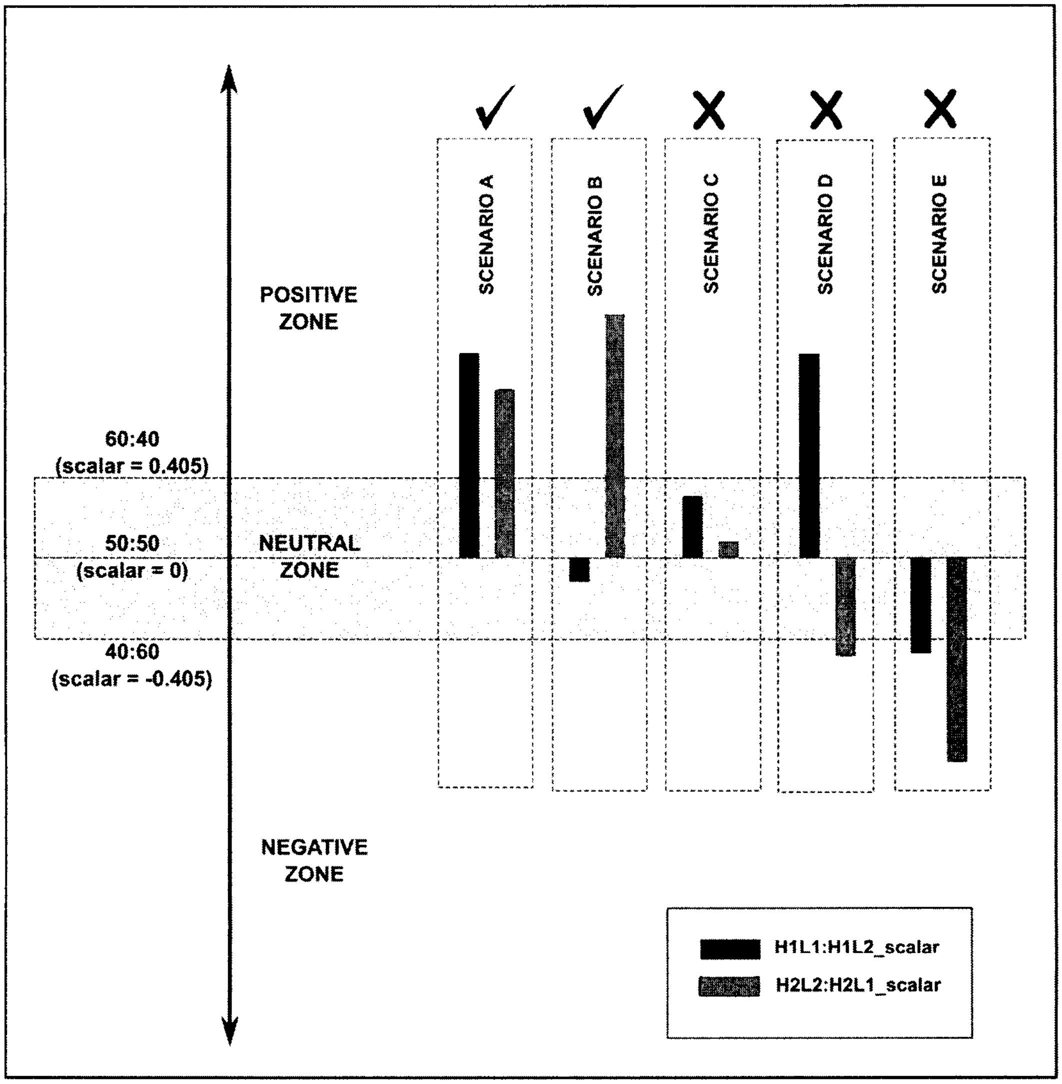
FIG. 6 depicts the performance filtering criteria based on the two LCCA results for each design. These performance filtering criteria were used to identify the K-L design library and the K-K-derived K-L design library. To be included, a design should contain a positive LCCA result above the neutral zone (neutral zone defined as the region between 40:60 and 60:40 paired:mispaired ratios) while the other LCCA has to be above the lower limit of the neutral zone (the 40:60 paired:mispaired ratio). Scenarios A and B represent designs that pass the filtering criteria. Note that Scenario B is included because H2L2:H2L1 LCCA is above the neutral zone and H1L1:H1L2 LCCA inside the neutral zone (not below it). Scenario C represents a design that is filtered out, where both LCCA results are positive, but neither are above the neutral zone. Scenarios D and E represent designs that are filtered out because at least one of the LCCA results is below the neutral zone, even if the other LCCA is above the neutral zone (see Scenario D). Designs where the designation of H1L1 and H2L2 are reversed are also included. This description of this Figure assumes that the wild-type pairing ratio is 50:50.

The LCCA design sets (H1L1L2 or H2L1L2) of each Mab design set were tested in the LCCA, and design sets of interest were identified based on the following inclusion criteria. In order to be considered a design of interest, the design must contain at least one positive LCCA result above the neutral zone (>60:40 correctly paired:mispaired ratio) while the other complementary LCCA had to be above the lower limit of the neutral zone (the 40:60 correctly paired: mispaired ratio) as illustrated by FIG. 6. The neutral zone was defined as the region between 40%:60% and 60%:40% correctly paired:mispaired ratios using the median normalized values for H1-L1:H1-L2 and H2-L2:H2-L1. For example, Scenarios A and B in FIG. 6 represent designs that pass the inclusion criteria. Scenario B is included because H2L2:H2L1 LCCA is above the neutral zone and H1L1: H1L2 LCCA inside the neutral zone (not below it). Scenario C represents a design where both LCCA results are positive, but neither are above the neutral zone, and hence is not included. Scenarios D and E represent designs that are filtered out because at least one of the LCCA results is below the neutral zone, even if the other LCCA is above the neutral zone (see Scenario D). Tables 4A (K-L designs) and 4B (K-K-derived K-L designs) list the Mab design sets that met these criteria, while Tables 5A and 5B show the results of the LCCA for these designs. In Tables 4A and 4B and all subsequent tables listing amino acid substitutions of the LCCA design sets or Mab design sets, the absence of a substitution in the table, or a "-" indicates that the polypeptide chain does not include an amino acid substitution that promotes preferential pairing.

The performance of each LCCA design set is described by two scalar values, ln(r1/f1) or ln(r2/f2), where r1 and r2 correspond to the median values of the ratios H1L1:H1L2 and H2L2:H2L1, respectively, and f1 and f2 correspond to the respective median values of ratios H1L1:H1L2 and H2L2:H2L1. The normalized scalar values are generated by subtracting the contribution of the WT (wild-type) system from the design; $\ln(r1/f1)_{design}-\ln(r1/f1)_{WT}$ or $\ln(r2/f2)_{design}-\ln(r2/f2)_{WT}$. For the wild type CAT-2200 (HC) competed against the CAT-2200 (LC-FLAG) plus the Pertuzumab (LC-HA) the $\ln(r1/f1)_{WT}=-0.48$. For the wild type Pertuzumab (HC) competed against the Pertuzumab (LC-HA) plus the CAT-2200 (LC-FLAG) the $\ln(r2/f2)_{WT}=0.66$. This procedure effectively removed any existing WT pairing bias and normalizes the specificity in comparison to a neutral 50%:50% L1:L2 WT system. These values are reported in columns 2 and 5 in Tables 5A and 5B.

In addition, the normalized scalar values were also converted back into a pure normalized median ratio H1L1:H1L2 and H2L2:H2L1. This conversion effectively normalized the LCCA ratios to 100% as it was observed for some designed Fabs that the total amount of H1L1 and H1L2, or H2L2 and H2L1 significantly differed from 100%. This discrepancy in total light chain percentage is believed to be due in part to the occurrence of variable non-specific binding during initial heterodimer capture on the SPR chip. These values are reported in columns 4 and 7 in Tables 5A and 5B.

Furthermore, the scalar range for each normalized LCCA of a design (H1L1:H1L2 and H2L2:H2L1 experiments) as well as the range for the normalized ratio of correctly paired to mispaired Fab heterodimers (the range is the same of percentage of L1 and percentage of L2 in the normalized ratio) is shown. For results reported from a single measurement the range values are marked NA (not applicable). These values are reported in columns 3 and 6 in Tables 5A and 5B.

For reference, Table 23 presents the correspondence between % of paired:mispaired heterodimers and the corresponding LCCA scalar value.

Results

The LCCA results are shown in Tables 5A and 5B in the context of Mab design sets. Table 5A provides the LCCA data relating to the K-L designs described in Example 2, while Table 5B provides the LCCA data relating to the K-K-derived K-L designs also described in Example 2. Note that all LCCA experiments were performed on constructs containing the inter-chain Fab disulfide bond located in the constant domain (H/C233-L/C214, Kabat numbering).

Table 4A lists 231 K-L designs that met the inclusion criteria. The LCCA data relating to these designs is shown in Table 5A. Table 4B lists 44 K-K-derived K-L designs that met the inclusion criteria and Table 5B shows the LCCA data relating to these designs. Designs that maintain 100% identity between the original K-K design library from Table 30 in the above-noted PCT Application No. PCT/CA2013/050914 and the new kappa-lambda system (i.e. were ported without modification) are identified with an asterisk (*) in Table 4B. Most of the designs in Table 4B have amino acid modifications in the constant region only, with a few of the designs also incorporating amino acid modifications in the variable region. These designs were proposed to further drive pairing specificity while also favoring transferability to other antibody systems.

Figure 7:
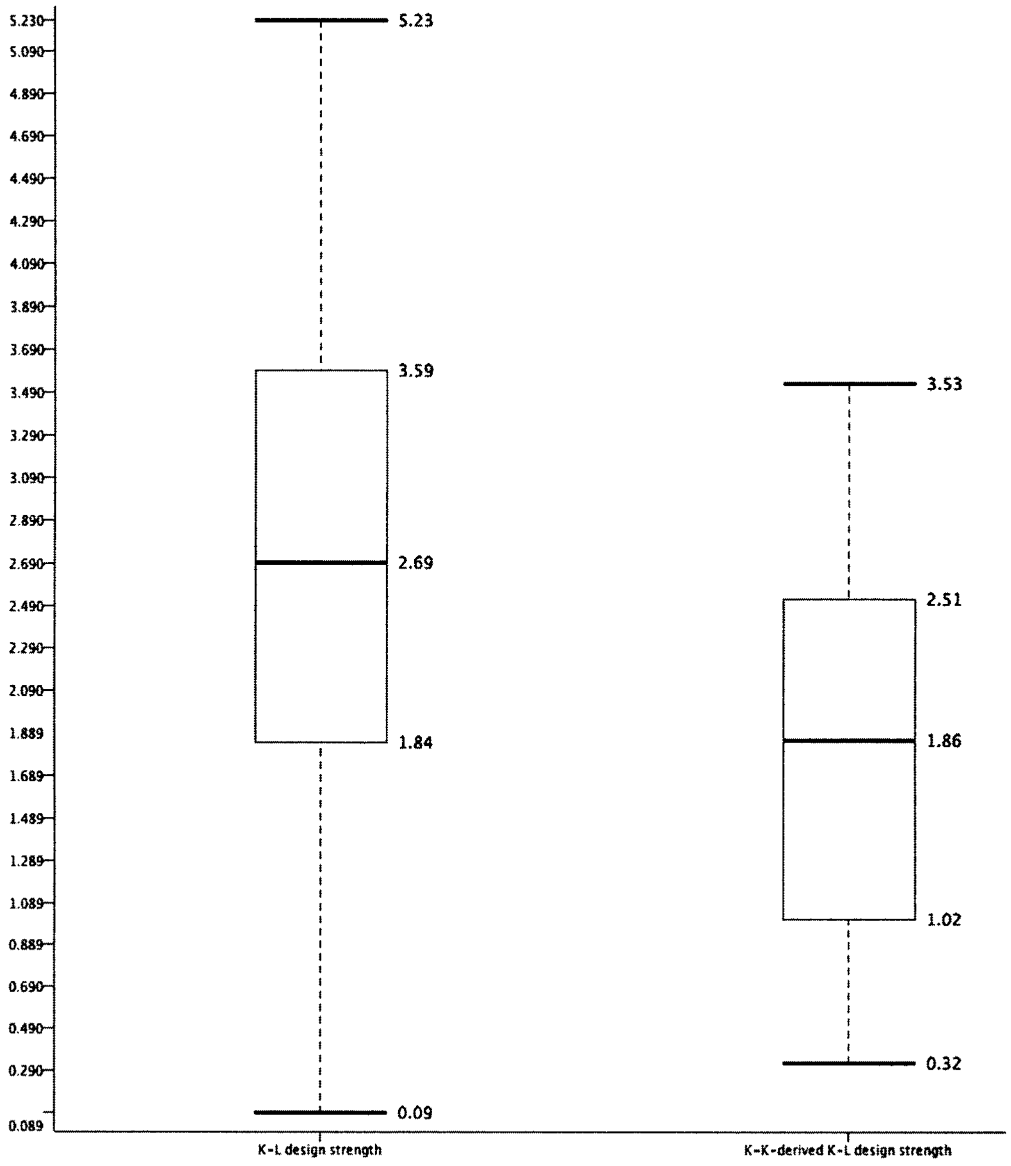
FIG. 7 depicts the performance of the selected K-L designs as well as K-K-derived L designs (based on LCCA data for Mab design set in Tables 4A and 4B) as defined by the design strength=ΔH1:L1:L2_scalar+ΔH2:L2:L1_scalar. This metric is an indicator of the overall pairing success at the design level.

Design strength can be defined as the sum of the two LCCA scalar values for a particular design. By comparing the design strength of K-K-derived K-L designs with the K-L designs it was apparent that those designs tailored specifically for the K-L system tended to show better pairing specificity than the K-K designs transferred into a K-L system, as summarized in FIG. 7. The median design strength for the K-K-derived K-L designs was 1.86, with a maximum design strength of 3.53. The median design strength for the K-L designs was 2.69, with a maximum design strength of 5.23.

Example 5: Scale Up of Designed Fab Heterodimers for Biophysical Characterization Correctly paired heterodimers H1L1 or H2L2, as indicated in the unique identifier sets (Tables 4A and 4B), were scaled up (typically to 20 ml) and purified as follows in order to test for thermal stability and antigen binding. For these experiments, the heavy chains of the Fabs were expressed without the $ABD_2$ tag, while the light chains were expressed with the same HA or FLAG tag used in the LCCA. The heavy and light chains of each heterodimer were expressed in 20 ml cultures of CHO-3E7 cells. CHO-3E7 cells, at a density of 1.7-2×$10^6$ cells/ml, were cultured at 37° C. in FREESTYLE™ F17 medium (Invitrogen cat #A-1383501) supplemented with 4 mM glutamine and 0.1% Koliphor P188 (Sigma #K4894). A total volume of 20 ml were transfected with a total of 20 μg DNA using PEI-pro (Polyplus cat #115-375) at a DNA:PEI ratio of 1:2.5. Twenty-four hours after the addition of the DNA-PEI mixture, 0.5 mM Valproic acid (final concentration) and 1% w/v Tryptone (final concentration) were added to the cells which were then transferred to 32° C.

Cells were centrifuged 7 days after transfection, and heterodimers were purified from supernatant by affinity capture using IgG-CH1 CaptureSelect™ (Life Technologies™, Catalog No.: 194-320-005) at 4° C. as follows. Supernatants were diluted to 20-25% cell culture supernatant in equilibration buffer (Dulbecco's phosphate buffered saline (DPBS) without Calcium, Magnesium, and phenol red (HyClone™#SH30028.02)) and then incubated with mixing for 16 hours with IgG-CH1 CaptureSelect™, also previously equilibrated with the equilibration buffer. The resin was then collected by centrifugation, transferred to a 96 well-fritted plate, washed with equilibration buffer three times. Bound samples were eluted with 1 to 4 bed volumes of elution buffer: 100 mM glycine pH 2.6. Eluted samples were collected by centrifugation into a 96-well UV-transparent receiver plate, each well containing neutralizing buffer: 1M Tris pH 9.0 at 10% of elution volume.

Following purification, heterodimer expression was assessed by non-reducing High Throughput Protein Express assay using Caliper LabChip GXII (Perkin Elmer #760499). Procedures were carried out according to HT Protein Express LabChip User Guide version2 LabChip GXII User Manual, with the following modifications. Heterodimer samples, at either 2 μl or 5 μl (concentration range 5-2000 ng/μl), were added to separate wells in 96 well plates (BioRad #HSP9601) along with 7 μl of HT Protein Express Sample Buffer (Perkin Elmer #760328). The heterodimer samples were then denatured at 70° C. for 15 mins. The LabChip instrument was operated using the HT Protein Express Chip (Perkin Elmer #760499) and the Ab-200 assay setting. After use, the chip was cleaned with MilliQ water and stored at 4° C.

Inclusion of Mab design set modifications did not have a significant impact on protein expression. Expression levels obtained for CAT-2200 Fabs containing design modifications are 0.45 mg/20 mL expression (SD of 0.16 mg), compared with 0.64 mg/20 mL expression (SD of 0.1 mg) for the wild type Fab. Pertuzumab Fabs bearing the design modifications express at 0.39 mg/20 mL expression (SD of 0.14 mg), compared with 0.4 mg/20 mL expression (SD of 0.03 mg) for the wild type Fab. Caliper analysis showed purity levels comparable to the WT Fab.

Example 6: Antigen Affinity Measurements of Designed Fab Heterodimers

The ability of CAT-2200 Fab heterodimers to bind to IL-17A and Pertuzumab Fab to bind to HER2-ECD was assessed in order to determine whether the amino acid substitutions had any effect on the ability of the heterodimer to bind to antigen. Fab heterodimers were prepared as described in Example 5. The affinity of each Fab heterodimer for its antigen was determined by SPR as follows.

SPR supplies. GLC sensorchips, the Biorad ProteOn amine coupling kit (EDC, sNHS and ethanolamine), and 10 mM sodium acetate buffers were purchased from Bio-Rad Laboratories (Canada) Ltd. (Mississauga, ON). PBS running buffer with 0.05% Tween20 (PBST) was purchased from Teknoca Inc. (Hollister, Calif.). Recombinant HER2 protein was purchased from eBioscience (San Diego, Calif.). Goat polyclonal anti-human Fc antibody was purchased from Jackson Immuno Research Laboratories Inc. (West Grove, Pa.). Recombinant human IL-17A was purchased from R&D Systems (Mineapolis, Minn.).

CAT-2200:IL-17A affinity determination. All surface plasmon resonance assays were carried out using a BioRad ProteOn XPR36 instrument (Bio-Rad Laboratories (Canada) Ltd. (Mississauga, ON)) with PBST running buffer at a temperature of 25° C. The IL-17A surface was generated using a GLC sensorchip activated by a 1:10 dilution of the standard BioRad sNHS/EDC solutions injected for 140 s at 100 μL/min in the ligand (vertical) direction. Immediately after the activation, a 2 microg/mL solution of IL-17A in 10 mM NaOAc pH 4.5 was injected in the ligand (vertical) direction at a flow rate of 25 microL/min until approximately 50 resonance units (RUs) were immobilized. Remaining active groups were quenched by a 140 s injection of 1M ethanolamine at 100 μL/min also in the ligand direction.

The screening of the designed Fabs for binding to IL-17A was performed by injection of purified CAT-2200 Fabs in the analyte (horizontal) direction. Firstly, two buffer injections for 30s at 100 microL/min in the analyte (horizontal) direction were used to stabilize the baseline. Five concentrations of a three-fold dilution series of each CAT-2200 designed Fab (60 nM, 20 nM, 6.7 nM, 2.2 nM, 0.74 nM) with a blank buffer control were simultaneously injected at 50 microL/min for 120 s with a 15 minute dissociation phase, resulting in a set of binding sensorgrams with a buffer reference. CAT-2200:IL-17A complexes on the SPR surface are dissociated and the IL-17A surface regenerated to prepare for the next injection cycle by two pulses of 0.85% phosphoric acid for 18 s at 100 microL/min. Sensorgrams were aligned and double-referenced using the buffer blank injection and interspots, and the resulting sensorgrams were analyzed using ProteOn Manager software v3.1. The double-referenced sensorgrams were fit to the Langmuir binding model.

Pertuzumab:HER2 affinity determination. All surface plasmon resonance assays were carried out using a BioRad ProteOn XPR36 instrument (Bio-Rad Laboratories (Canada) Ltd. (Mississauga, ON)) with PB ST running buffer at a temperature of 25° C. The anti-penta-His™ antibody (Qiagen) capture surface was generated using a GLC sensorchip activated by a 1:10 dilution of the standard BioRad sNHS/EDC solutions injected for 140 s at 100 μL/min in the analyte (horizontal) direction. Immediately after activation, a 10 microg/mL solution of anti-penta-His antibody in 10 mM NaOAc pH 4.5 was injected in the ligand (vertical) direction at a flow rate of 25 μL/min until approximately 3000 resonance units (RUs) were immobilized. Remaining active groups were quenched by a 140 s injection of 1M ethanolamine at 100 μL/min in the analyte direction to ensure mock-activated interspots are created for blank referencing.

The screening of the designed Fabs for binding to HER2 occurred in two steps: an indirect capture of the designed Fabs onto the anti-penta-His™ antibody surface in the ligand direction followed by the simultaneous injection of 5 concentrations of purified HER2 antigen and one buffer blank for double referencing in the analyte direction. Firstly, one buffer injection for 30 s at 100 microL/min in the ligand direction was used to stabilize the baseline. For each designed Fab capture, designed Fabs were diluted to 2 microg/mL in PB ST. One to five designed Fabs or controls were simultaneously injected in individual ligand channels for 240 s at flow 25 μL/min. This resulted in a capture of approximately 400 to 600 RUs onto the anti-human Fc surface. The first ligand channel was left empty to use as a blank control if required. This capture step was immediately followed by two buffer injections in the analyte direction to stabilize the baseline, and then 100 nM, 33.3 nM, 11.1 nM, 3.7 nM and 0.41 nM Her2 along with a buffer blank was simultaneously injected at 50 μL/min for 120 s with a 1200s dissociation phase. The captured antibody surfaces were regenerated by an 18 s pulse of 0.85% phosphoric acid at 100 μl/min to prepare for the next injection cycle. Sensorgrams were aligned and double-referenced using the buffer blank injection and interspots, and the resulting sensorgrams were analyzed using ProteOn Manager software v3.1. The double-referenced sensorgrams were fit to the 1:1 binding model.

Results. Antigen affinity (KD) values for designed Fab heterodimer samples are reported in Table 6A (K-L designs) and Table 6B (K-K-derived K-L designs) in the context of design pairs. The KD values of H1L1 and H2L2 Fabs are included in columns 2 and 4 (KD of H1L1 CAT-2200 Fab heterodimer and H2L2 Pertuzumab Fab heterodimer, respectively), and 3 and 5 (change in KD of H1L1 or H2L2 Fab heterodimer compared to its respective wild-type). KD values were determined only for Fab heterodimer samples that exhibited a Fab heterodimer capture of at least 100 RU. The reference KD value for wild-type CAT-2200 bound to IL-17A used for comparison to the designed heterodimers was 0.273 nM. This value is a median value based on multiple measurements of the wild-type CAT-2200 Fab heterodimer where the light chain contains a FLAG tag. Similarly, the reference KD value for wild-type pertuzumab bound to HER2 was 8.055 nM. This value is a median value based on multiple measurements of the wild-type pertuzumab Fab heterodimer where the light chain contains an HA tag. In Table 6, the difference in KD with respect to wild type antigen binding affinity is shown using the calculation −(log(KD_design)−log(KD_wt)), such that positive values indicate lower KD values whereas negative values indicate increased KD values of the Fab heterodimer compared with wild type binding affinity for antigen. NB indicates that no binding was detected. Note that some Fab heterodimers lack measured KD values and are hence marked as not determined (ND). In some of these cases, the Fab heterodimers were assessed but technical difficulties (such as low Fab heterodimer capture in the SPR experiment, i.e. less than 100 RU), prevented accurate determinations of KD values.

For the majority of the designed Fab heterodimers tested, amino acid substitutions had little or no impact on KD values. Three designs (Unique identifiers 10881-11412, 10883-11236, and 10888-11415) on the K-L design library showed a >5-fold decrease in KD on the CAT-2200 Fab. On the K-K-derived K-L design library, one of the Pertuzumab Fab heterodimers (designs containing the 10724 code in the Unique identifier) showed a >5-fold decrease in KD on the Pertuzumab side.

Example 7: Thermal Stability Measurements of Designed Fab Heterodimers by DSF Differential Scanning Fluorescence (DSF) was used to measure the thermal stability of correctly paired heterodimers in comparison to that of wild type, unmodified heavy chain-light chain pair. Although DSF is known to be a less precise method for measuring melting temperatures, it was used here because it is a high throughput method of measuring thermal stability and thus allowed for some measurement of thermal stability to be obtained for a large number of Fab heterodimers. Fab heterodimers were prepared as described in Example 5.

Measurement of Thermal Stability by DSF

The thermal stability of designed Fab heterodimer pairs was measured using DSF as follows. Each heterodimer was purified as described in Example 5 and diluted to 0.5 mg/mL in DPBS (Dulbecco's phosphate buffered saline, HyClone Cat #SH30028.02). For the majority of samples, a working stock of Sypro Orange gel stain (Life Technologies Cat #S-6650) was prepared by diluting 4 μL of Sypro Orange gel stain to 2 ml DPBS. The DSF samples were prepared by adding 14 μL of 0.5 mg/mL protein to 60 μL of the diluted Sypro Orange gel stain working stock. However, for proteins that had less than 0.5 mg/mL, each DSF sample were prepared by adding 14 μL of the undiluted protein to 60 μL of a working stock of Sypro Orange dye (that was diluted to 1:1500 in DPBS). DSF analysis was then conducted, in duplicate, on 20 μl aliquots using the Rotor-Gene 6000 qPCR instrument (QiaGen Inc). Each sample was scanned from 30° C. to 94° C. using 1° C. intervals with a 10 second equilibrium between each step and a 30 second wait time at the start. An excitation filter of 470 nM and emission filter of 610 nM with a gain of 9 was used. Data was analyzed with the Rotor-Gene 6000 software using the maxima value from the first derivative of the denaturation curve as the Tm. The remaining DSF samples were prepared and analyzed similarly, with the following protocol modifications that do not alter the measured Tm values: 1) the working stock was prepared by diluting 1 μL of Sypro Orange gel stain to 2 ml DPBS, 2) 30 μl aliquots were analyzed and 3) a gain of 10 was used.

DSF results for designed Fab heterodimer samples are reported in Tables 6A (K-L designs) and 6B (K-K-derived K-L designs), in the context of Mab design sets. Thermal stability of H1L1 and H2L2 Fabs are included in columns 6 and 8 (H1L1 refers to CAT-2200 Fab heterodimer and H2L2 to Pertuzumab Fab heterodimer) of Tables 6A and 6B. For Fab heterodimers where repeats were conducted, the reported Tm value is the median value. Comparisons of the designed Fab heterodimer Tm values with respect to the Tm value of the wild-type Fab heterodimer are reported in column 7 for the CAT-2200 H1L1 and in column 9 for the Pertuzumab H2L2. The median Tm for wild-type CAT-2200 Fab construct containing a FLAG tag was determined to be 76.9° C. The median Tm for wild-type Pertuzumab Fab heterodimer containing a HA tag, was determined to be 82.4° C. Given throughput limitations in the scale up procedure for the large number of Fab heterodimers generated by the Mab design sets, DSF measurements were performed by sampling a subset of designed Fab heterodimers. For that reason, some Fab heterodimers lack Tm values measured by DSF and are hence marked as not determined (ND). The majority of the designs tested showed good thermostability, within the range of expected Tm values commonly observed for wild-type Fabs. Designed Fab heterodimers containing the mutations K145T_V177D_S188D in the HC and S176K_Y178L in the lambda LC or S176K_T178L in the kappa LC, negatively affected the Tm values by >10° C. in the Fab heterodimer containing those mutations.

Example 8: Thermal Stability Measurements of Designed Fab Heterodimers by DSC

To complement the measurement of thermal stability by DSF, the more precise method of differential scanning calorimetry (DSC) was also used to measure the thermal stability of correctly paired, designed Fab heterodimers in comparison to that of wild type, unmodified heavy chain-light chain pair. Fab heterodimers were prepared as described in Example 5.

Measurement of Thermal Stability by DSC

The thermal stability of designed Fab heterodimer pairs was measured using DSC as follows. 400 μL of purified samples primarily at concentrations of either 0.2 mg/ml or 0.4 mg/mL in PBS were used for DSC analysis with a VP-Capillary DSC (GE Healthcare). At the start of each DSC run, 5 buffer blank injections were performed to stabilize the baseline, and a buffer injection was placed before each sample injection for referencing. Each sample was scanned from 20 to 100° C. at a 60° C./hr rate, with low feedback, 8 sec filter, 5 min preTstat, and 70 psi nitrogen pressure. The resulting thermograms were referenced and analyzed using Origin 7 software.

Thermal stability of H1L1 and H2L2 Fabs are included in columns 10 and 12 (H1L1 refers to CAT-2200 Fab heterodimer and H2L2 to Pertuzumab Fab heterodimer, respectively) of Table 6. For each Fab heterodimer where repeats were conducted, the reported Tm value is the median value. Comparisons of the designed Fab heterodimer Tm values with respect to the Tm value of the wild-type Fab heterodimer are reported in column 11 for the CAT-2200 H1L1 (wild type CAT-2200 Fab construct containing a FLAG tag, with a median Tm of 70.7° C.) and column 13 for the Pertuzumab H2L2 (wild type Pertuzumab Fab construct containing a HA tag, with a median Tm of 78.7° C.). Given the high sample amounts requirement and low throughput nature of DSC, measurements were performed by sampling a subset of designs. For this reason, some Fab heterodimers lack Tm values measured by DSC and are hence marked as not determined (ND). All of the designed Fab heterodimers assayed by DSC showed good thermostability. The DSC-derived Tm values were generally lower than those observed by DSF (Example 7).

Example 9: Optimization of Designs

The performance of the K-L designs and K-K-derived K-L designs in the pertuzumab/CAT-2200 system, as shown in Tables 5A and 5B, respectively, was examined in order to guide further understanding of the ability of the designs to drive selective pairing. This examination enabled a subsequent cycle of design optimization to improve pairing specificity where possible and/or increase the stability of the heterodimers. Design optimization included modification of the K-L designs and K-K-derived K-L designs at a particular substituted amino acid residue to assess the effect of alternate amino acid substitution at that residue, adding amino acid substitutions at additional amino acid residues, and/or removing amino acid substitution at a particular residue (i.e. converting it back to the wild-type residue). The design process and selection of designs was performed as described in Examples 1 and 2, and the resultant designs were tested in the pertuzumab/CAT-2200 K-L system.

An additional set of K-L designs was proposed using an alternate method of increasing the diversity of designs with improved pairing specificity, in which selected constant domain designs from Table 4A and 4B, as well as selected constant domain optimization design candidates described in the previous paragraph were combined with two K-K variable domain designs. The two K-K variable domain designs are included in Table 4B, and have the unique identifiers 10621-10733 and 10623-10745. These designs did not promote strong pairing specificity on their own and did not affect antigen binding, but have been shown to improve pairing specificity when combined with certain Fab constant domain designs in a kappa-kappa antibody system. This additional set of K-L designs also included combinations of constant domain designs only, where the constant domain designs are selected from Table 4A, 4B and optimization design candidates described in the previous paragraph.

Finally, a further additional set of K-K-derived K-L designs were proposed using representative designs from the K-K design library described in Table 5 of PCT Application No. PCT/M2015/054107 as a starting point, and tested in the pertuzumab/CAT-2200 K-L system. As described in Example 2, the representative K-K-derived designs were adapted to the kappa-lambda-system by modifying amino acid residues as necessary to account for sequence and structural differences between kappa and lambda light chains.

The pairing specificity of the additional K-L designs and K-K-derived K-L designs described in this Example was experimentally assessed by LCCA in the pertuzumab-CAT-2200 K-L system as described in Example 10.

Example 10: Preparation and Assessment of Preferential Pairing of Designed Fab Heterodimers by LCCA The pertuzumab and CAT-2200 Fab constructs comprising amino acid substitutions corresponding to the Mab design sets were prepared as described in Example 3. As described in Example 4, all LCCA experiments were performed on constructs containing the inter-chain Fab disulfide bond located in the constant domain (H/C233-L/C214, Kabat numbering). In order to assess preferential pairing exhibited by the Mab design sets, the preferential pairing exhibited by the corresponding LCCA design sets was measured as described in Example 4, with the following exceptions.

Assessment of preferential pairing in the LCCA design sets was carried out by LCCA as described in Example 4 except that transfection was carried out with heavy and light chains at ratio of 1:1:3 (by weight) for H1:L1:L2 or H2:L2:L1, instead of 1:1:1, with the heavy chain present in limiting amounts, and the mispaired light chain present in excess. Since the designs described in Example 9 were optimized versions of those described in Tables 4A and 4B, or constituted combinations of two designs, some of which already exhibit relatively high pairing specificity, it was possible that further improvement in such specificity (if attained) might not be detectable in the LCCA at the H1:L1:L2 or H2:L2:L1 of 1:1:1, due to limitation of the assay. Thus, the DNA ratio of 1:1:3 was used, rather than 1:1:1, in order to detect improvement in specificity. All transfections were performed using 300 ng of H1, 300 ng of L1 and 900 ng of L2 (i.e. H1:L1:L2 or H2:L2:L1=1:1:3 ratio), 100 ng of AKTdd pTT22 (a vector containing a constitutively active protein kinase B mutant), and 400 ng of ssDNA (salmon sperm DNA).

Data Analysis and Description of LCCA Metrics

Data analysis was carried out using a modified version of the analysis described in Example 4, as set forth below.

All LCCA design sets were tested in the LCCA, and designs of interest were identified based on the following inclusion criteria. In order to be considered a design of interest, the design had to contain at least one positive LCCA result above the upper limit of 95% WT scalar confidence interval, while the other complementary LCCA had to be above the lower limit of 95% WT scalar confidence interval. All designs that passed the above criteria were included in a second K-L design library as identified in Table 7A, or a second K-K derived K-L design library as identified in Table 7B.

Table 8A and Table 8B describe the LCCA data obtained for the second K-L design library and the second K-K-derived K-L library, respectively, in the context of Mab designs. The performance of each LCCA design set in this Example was described by two scalar values that corresponded to the natural logarithm of the ratio of H1L1:H1L2 (median value) and the ratio of H2L2:H2L1 (median value), respectively. Note that these scalar values are slightly different from the scalar values calculated in Example 4, but are similarly used to assess preferential pairing. These scalar values are reported in columns 2 and 5 in Table 8A for the second K-L design library, and in Table 8B for the second K-K-derived K-L library. For the wild type CAT-2200 (HC) competed against the CAT-2200 (LC-FLAG) plus the Pertuzumab (LC-HA) the 95% scalar confidence interval was −3.24 (lower limit) to −2.94 (upper limit). For the wild type Pertuzumab (HC) competed against the Pertuzumab (LC-HA) plus the CAT-2200 (LC-FLAG) the 95% scalar confidence interval was −0.9 (lower limit) to −0.6 (upper limit).

The scalar range for each LCCA of a design (H1L1L2 and H2L1L2 experiments) is shown in columns 3 and 6 in Tables 8A and 8B as a measure of the reproducibility of the results, and represents the difference between the highest and lowest scalar values measured for the design. For results reported from a single measurement the range values are marked NA (not applicable). In addition, scalar values were also converted back into a pure median ratio for H1L1:H1L2 and H2L2:H2L1. This conversion effectively normalized the LCCA ratios to 100% as it was observed in some cases that the total amount of H1L1 and H1L2, or H2L2 and H2L1 significantly differed from 100%. These values are reported in columns 4 and 7 in Tables 8A and 8B.

Results

As noted above, the LCCA results are shown in Tables 8A and 8B in the context of Mab design sets. Table 8A provides the LCCA data relating to the K-L designs described in Example 9. 151 K-L designs met the inclusion criteria, and most of the designs have amino acid modifications in the constant region only, with a few of the designs also incorporating amino acid modifications in the variable region (see Table 7A). These designs were proposed to further drive pairing specificity and stability while also favoring transferability to other antibody systems.

Table 8B provides the LCCA data relating to the K-K-derived K-L designs also described in Example 9. 21 K-K-derived K-L designs met the inclusion criteria. These designs include constant domain designs only.

Example 11: Scale Up of Designed Fab Heterodimers for Biophysical Characterization In order to examine the biophysical characteristics of correctly paired heterodimers, the preparation of selected correctly paired heterodimers H1L1 or H2L2 (designed Fabs) identified in the unique identifier sets shown in Tables 7A and 7B was scaled up as described in Example 5, with the exception that a 50 ml scale-up was performed instead of 20 ml. Expressed Fabs were purified as described in Example 5 in order to test for thermal stability and antigen binding. The purification protocol was modified to incubate supernatants with the IgG-CH1 CaptureSelect™ resin without any initial dilution in the equilibration buffer and elution of bound samples was performed with 4 bed volumes of elution buffer.

Following purification, heterodimer expression was assessed by non-reducing and reducing High Throughput Protein Express assay using Caliper LabChip GXII, as previously indicated in Example 5.

The data demonstrated that inclusion of Mab design set modifications in the designed Fabs did not have a significant impact on protein expression, judging by the post purification yield. Post-purification yield obtained for designed CAT-2200 Fabs was 1.3 mg/50 ml expression (SD of 0.6), compared with 1.9 mg/50 ml expression (SD of 0.5) for the wild type Fab. Designed pertuzumab Fabs were prepared with a yield of 0.9 mg/50 ml expression (SD of 0.4), compared with 1.1 mg/50 ml expression (SD of 0.2) for the wild type Fab. Caliper analysis showed a degree of purity comparable to WT Fab (data not shown). A number of designed Fabs had precipitate associated with them (noted with '*' in Tables 9A and 9B) post purification. Yield information provided above was measured following removal of the precipitate.

Example 12: Antigen Affinity Measurements of Designed Fab Heterodimers

The ability of CAT-2200 designed Fab heterodimers to bind to IL-17A and Pertuzumab designed Fab heterodimers to bind to HER2-ECD was assessed in order to determine whether the amino acid substitutions had any effect on the ability of the heterodimer to bind to antigen. Antigen-binding was assessed as described in Example 6, except that CAT-2200 designed Fabs were injected at 50 μL/min for 120s with a 600 to 800s dissociation phase, instead of a 900s dissociation phase. Furthermore, screening of designed pertuzumab Fabs for binding to HER2 was carried out as described in Example 6, with the following modifications: for each Fab capture, Fabs were diluted to 2.5 μg/ml instead of 2 μg/ml with an injection time of 120s instead of 240s. The lowest HER2 antigen concentration injected was 1.23 nM instead of 0.41 nM. The dissociation phase for the concentration series was 600s instead of 1200s.

Results. Antigen affinity (KD) values for designed Fab heterodimer samples are reported in Table 9A (K-L designs) and Table 9B (K-K-derived K-L designs) in the context of Mab design pairs. The KD values of H1L1 and H2L2 Fabs are included in columns 2 and 4 (KD of H1L1 CAT-2200 Fab heterodimer and H2L2 Pertuzumab Fab heterodimer, respectively), and 3 and 5 (change in KD of H1L1 or H2L2 Fab heterodimer compared to its respective wild-type). KD values were determined only for Fab heterodimer samples that exhibited a Fab heterodimer capture of at least 100 RU. The reference KD value for wild-type CAT-2200 Fab bound to IL-17A used for comparison to the designed heterodimers was 0.209 nM. This value is a median value based on multiple measurements of the wild-type CAT-2200 Fab heterodimer where the light chain contains a FLAG tag and does not differ significantly from the value reported in Example 6. Similarly, the reference KD value for wild-type pertuzumab bound to HER2 was 7.8 nM. This value is also a median value based on multiple measurements of the wild-type pertuzumab Fab heterodimer where the light chain contains an HA tag, and does not differ significantly from the value reported in Example 6. In Tables 9A and 9B, the difference in KD with respect to wild type antigen binding affinity is shown using the calculation −(log(KD_design)−log(KD_wt)), such that positive values indicate lower KD values whereas negative values indicate increased KD values of the Fab heterodimer compared with wild type binding affinity for antigen. As noted earlier, due to throughput limitations in the scale up procedure for the large number of Fab heterodimers generated by the Mab design sets, SPR measurements were performed by sampling a subset of designed Fab heterodimers. For that reason, some Fab heterodimers lack KD values measured by SPR and are hence marked as not determined (ND). For the designed Fab heterodimers tested, amino acid substitutions had little or no impact on KD values (within 2-fold of WT).

Example 13: Thermal Stability Measurements of Designed Fab Heterodimers by DSF Differential Scanning Fluorescence (DSF) was used to measure the thermal stability of correctly paired designed Fab heterodimers in comparison to that of wild type Fabs. Fab heterodimers were prepared as described in Example 11.

Measurement of Thermal Stability by DSF

The thermal stability of designed Fab heterodimer was measured using DSF as follows. Each purified heterodimer was diluted to 0.67 mg/mL in DPBS (Dulbecco's phosphate buffered saline, HyClone Cat #SH30028.02). A working stock of Sypro Orange gel stain (Life Technologies Cat #S-6650) was prepared by 1:1000 dilution in DPBS. The DSF samples were prepared by adding 15 μL of 0.67 mg/mL protein to 15 μL of the Sypro Orange gel stain working stock. However, for proteins that had a concentration less than 0.67 mg/mL, each DSF sample was prepared by adding 15 μL of the undiluted protein to 15 μL of a working stock of Sypro Orange dye. DSF analysis was then conducted on 30 μl aliquots using the Rotor-Gene 6000 qPCR instrument (QiaGen Inc). Each sample was scanned from 30° C. to 94° C. using 1° C. intervals with a 10 second equilibrium between each step and a 30 second wait time at the start. An excitation filter of 470 nM and emission filter of 610 nM with a gain of 8 was used. Data was analyzed with the Rotor-Gene 6000 software using the maxima value from the first derivative of the denaturation curve as the Tm.

DSF results for designed Fab heterodimer samples are reported in Tables 9A (K-L designs) and 9B (K-K-derived K-L designs), in the context of Mab design sets. Thermal stability of H1L1 and H2L2 Fabs are included in columns 6 and 8 (H1L1 refers to CAT-2200 Fab heterodimer and H2L2 to Pertuzumab Fab heterodimer) of Tables 9A and 9B. For Fab heterodimers where repeats were conducted, the reported Tm value is the median value. Comparisons of the designed Fab heterodimer Tm values with respect to the Tm value of the wild-type Fab heterodimer are reported in column 7 for the CAT-2200 H1L1 and in column 9 for the Pertuzumab H2L2. The median Tm for wild-type CAT-2200 Fab construct containing a FLAG tag was determined to be 77.0° C. The median Tm for wild-type Pertuzumab Fab heterodimer containing a HA tag, was determined to be 81.7° C. As mentioned earlier DSF measurements were performed by sampling a subset of designed Fab heterodimers, hence some Fab heterodimers lack Tm values measured by DSF and are marked as not determined (ND). The majority of the designs tested showed good thermostability (exhibiting a Tm decrease compared to WT of up to 4-5° C.), within the range of expected Tm values commonly observed for wild-type Fabs, with the following exception. The presence of the S131K L135K mutations in the kappa light chain in combination with L124E K145T mutations in kappa heavy chain in two Fab heterodimers appeared to negatively affect their Tm values by >10° C. Also of note, for some of the CAT-2200 designed Fabs, a shoulder to the main Fab peak was observed in the DSC spectra (these Fabs are marked with '#' in Tables 9A and 9B). Such a profile was also observed for the wild-type CAT-2200 Fab.

Example 14: Thermal Stability Measurements of Designed Fab Heterodimers by DSC To complement the measurement of thermal stability by DSF, the more precise method of differential scanning calorimetry (DSC) was also used to measure the thermal stability of correctly paired, designed Fab heterodimers in comparison to that of wild type, unmodified heavy chain-light chain pair. Fab heterodimers were prepared as described in Example 11 and thermal stability measure by DSC as described in Example 8. However, for Fab heterodimers that had sample concentrations lower than the ones indicated in the protocol, DSC was performed at the available concentration.

Thermal stability measurements for H1L1 and H2L2 Fabs are shown in columns 10 and 12 (H1L1 refers to CAT-2200 Fab heterodimer and H2L2 to Pertuzumab Fab heterodimer, respectively) of Table 9A and 9B. For each Fab heterodimer where repeats were conducted, the reported Tm value is the median value. Comparisons of the designed Fab heterodimer Tm values with respect to the Tm value of the wild-type Fab heterodimer are reported in column 11 for the CAT-2200 H1L1 (wild type CAT-2200 Fab construct containing a FLAG tag, with a median Tm of 70.7° C.) and column 13 for the Pertuzumab H2L2 (wild type Pertuzumab Fab construct containing a HA tag, with a median Tm of 78.1° C.). Given the high requirement for sample amounts and low throughput nature of DSC, measurements were performed by sampling a subset of designs that were characterized by DSF. For that reason, some Fab heterodimers lack Tm values measured by DSC and are hence marked as not determined (ND). All of the designed Fab heterodimers assayed by DSC showed good thermostability (Tm decrease compared to WT up to 2-3 C). The DSC-derived Tm values were generally lower than those observed by DSF (Example 13). Although the absolute difference in Tm of the designed Fabs compared to WT was observed to be dependent on the method used, whether DSF or DSC, the relative ranking of the designed Fabs with respect to the wild-type Fab was the same independent of the method used.

Example 15: Design Clustering and Selection of Representative Designs

Examples 2 to 14 described the design and testing of K-L designs and K-K-derived K-L designs. The ability of these designs to promote pairing was tested in the LCCA, in a Fab format where the ability of one heavy chain of each LCCA design set to pair with the appropriate light chain was determined. The effects of the amino acid substitutions on the stability and antigen-binding of the resulting correctly paired heterodimers (one heavy chain and one light chain) were also assessed.

In order to test whether the preferential pairing results for the Mab design sets (H1L1H2L2) obtained in LCCA format (co-expression of H1, L1, and L2, or of H2, L1, and L2) for the K-L designs and the K-K-derived K-L designs also applied when the polypeptide chains of a Mab design set were co-expressed (i.e. when H1, L1, H2 and L2 were co-expressed), a representative number of the over 400 designs described in Tables 4A, 4B, 7A, and 7B was selected, as it was not feasible to test all of the designs in this way. The representative designs were tested in an assay referred to as "SMCA" (described in detail in Example 16).

To select representative designs, the K-L designs identified in Tables 4A and 7A (n=404) were combined and clustered according to identity in the amino acid residue positions substituted. In some cases where a K-K-derived K-L design from Table 7B had been significantly modified from the original K-K design, it was also included in this K-L design group for clustering. Tables 10-A1 to 10-A12 show the resulting clusters 1 to 12 for the K-L designs. Likewise, the K-K-derived K-L designs reported in Tables 4B and 7B (n=43), excluding those moved to the K-L design group, were also combined and clustered. Tables 10-B1 to 10-B10 show the resulting clusters 1 to 10 for the K-K-derived K-L designs. Representative designs from each cluster were then selected as described below. The final set of selected representative designs is also included in Table 11A (K-L designs) and 11B (K-K derived K-L designs) including SMCA Design ID designation.

Representative Designs for SMCA

Representative designs were selected on the basis of primary criteria of demonstrating pairing specificity and having minimal or no impact on antigen binding, as well as taking into account secondary criteria such as: design stability, minimizing for the number of substitutions, comparable expression to WT. Maximal pairing specificity was assessed taking into account both Fabs as well as each Fab individually where one Fab paired less well than the other Fab in the heterodimer pair, but still demonstrated better than the wild-type pairing (Scenarios A and B as shown in FIG. 6). In addition, the diversity within a cluster and the number of designs in a cluster further guided the type and number of cluster representatives selected.

A total of 33 representative K-L designs were selected from clusters 1 through 12 for testing in SMCA format. Likewise, 7 K-K-derived K-L designs with high to medium average LCCA performance values were selected from 7 clusters of the 10 clusters identified. Three of the K-K-derived K-L design clusters did not include designs that met the criteria of a representative with respect to primary criteria such as LCCA performance criteria or lack of effect on antigen binding.

At least one representative design was chosen from each cluster. Clusters that were represented by only one representative design included K-L design clusters 5 and 11, and all of the 7 K-K-derived K-L design clusters. The remaining clusters had more than one representative design as the clusters were either large (i.e. clusters 2, 3, 4, 6, 7, 8) and/or had more design sub-diversity (minor clusters) (i.e. clusters 1, 9, 10, 12). Although the designs within each cluster shared sequence similarities, minor clusters within a cluster differed in at least one driver (amino acid substitution). The representative designs for each cluster are highlighted in bold in Tables 10-A1 to 10-A12 and 10-B1 to 10-B10. As noted elsewhere herein, "-" in these tables indicates that no amino acid substitutions that promote preferential pairing were present in that particular polypeptide chain.

Drivers and Secondary Substitutions

Clusters for which representatives were chosen are described here, with a focus on identifying the "drivers" or "driver sets" (amino acid positions and/or substitutions) that promoted the desired pairing specificity in each cluster, as assessed by the LCCA. The term "driver set" refers to a set of amino acid positions and substitutions that promote preferential pairing, while the term "driver" refers to a single position/substitution within a driver set. However, other residues and substitutions were sometimes associated with a design or set of designs in a cluster. These residues and substitutions are referred to as "secondary" substitutions, and were sometimes included in a Mab design set to improve the performance of the driver set or driver sets used. Mechanistically, these secondary substitutions may act to i) promote steric accommodation of drivers, ii) increase the number of contacts or substitute for contacts lost upon substitutions at driver set positions, at the interface between heavy and light chains, iii) optimize the hydrogen-bonding network based on driver sets, and/or iv) create an environment conducive to improved performance of driver sets. One or more of these mechanisms can be used/are intended to improve the performance of the drivers in each cluster.

Some of these secondary substitutions were common across several clusters. For example, the K145T substitution in the heavy chain was utilized in either H1L1 or H2L2 to remove the positive charge when a negatively charged driver or drivers were designed in its vicinity. In a number of clusters, the K129T substitution in the lambda light chain was sometimes utilized to remove the positive charge when a negatively charged driver or drivers were designed in its vicinity (e.g. K-L design cluster 4 and clusters 8-12). Furthermore, the E124Q substitution in the lambda light chain was utilized in some clusters to remove the negative charge in the vicinity of a positively charged driver or drivers (e.g. K-L design clusters 1-3). The V133G substitution was applied predominantly in the kappa light chain in some of the designs to sterically accommodate particular driver sets (e.g. predominantly in K-L design clusters 1, 3, 4, 6, 7, 10, 12 and K-K-derived K-L design cluster 10). Y178T in the lambda light chain was introduced in designs for steric accommodation of specific driver sets in the respective H1L1 (e.g. K-L clusters 4, 5, 8 and 12). V133S in the light chain was applied in yet another driver set (e.g. K-L clusters 1, 2 and 12) targeting improved hydrogen bonding network.

Description of K-L Design Clusters

For cluster 1, two designs (13175-13486 and 13180-13515) were chosen to represent the cluster as these designs utilized similar electrostatic drivers occupying similar space (see Table 10-A1). For all members of this cluster, a combination of two driver sets was utilized. A first electrostatic driver set was designed to allow negatively charged substitution (predominantly L143D) in H1 to form salt bridges with a positively charged substitution (T131K/R) in L1, while H2 was designed to allow for a) positively charged substitutions, S188K or L124R_S186R, to form salt bridges with negatively charged substitutions in L2 (S176D_T178E or S176D_T180E) orb) formation of salt bridges between L143R or S186K in H2 and Q124E_V133D in L2. A second electrostatic driver set, termed a "disulfide steering driver set," was added to disfavor formation of the H-L or heterodimer disulfide bond in mispaired heterodimers in the early stages of the H-L assembly process. The disulfide steering driver set used a positively charged substitution in H1 (A125R), a negatively charged substitution in L1 (S122D), a negatively charged substitution in H2 (K228D), and a positively charged substitution in L2 (S121K). These amino acid substitutions are located in the proximity of the disulfide bond, away from the buried (main) H-L interface where the majority of amino acid substitutions in the K-L designs are located. The two driver sets were designed to form salt bridges in the preferentially paired heterodimers while the mismatched pairs would be disfavored primarily due to electrostatic repulsion.

For cluster 2, four representative designs (13282-13484, 13287-13494, 13218-13482 and 10945-11377) were chosen to reflect the degree of diversity in this cluster (see Table 10-A2). All members of this cluster are based on H1 designed similarly as in the cluster 1 first electrostatic driver set, to allow negatively charged substitutions (L143D or L143D_Q179E) to form salt bridges with a positively charged substitution (T131K/R) in L1, while H2 was designed to allow for either a) positively charged substitution (S186K) to form salt bridges with negatively charged substitutions in L2, primarily V133D or V133D_Q160E; b) S188K to pair with S131D/E of L2; or c) L143R/K to pair with Q124E_V133D of L2. Some members of cluster 2 also contained a steric driver set in addition to the electrostatic driver set. Two steric driver sets were used, termed "steric 1" and "steric 2." The steric 1 driver set included F174G in H1, designed to be sterically complementary to S176F or T116F_S176F of L1, and V190F of H2 sterically complementary to L135A of L2. The steric 2 driver set included A139W in H1 sterically compatible with WT residues of L1 and WT of H2 sterically compatible with L135W of L2. Hence in this cluster, mismatched pairing of H1L2 and H2L1 would be disfavored primarily due to electrostatic repulsion or electrostatic repulsion in combination with the steric incompatibility. There are also two cluster members that in addition to the electrostatic driver set contain a variable design component ("variable domain driver set") in the H2 chain (Q39E or L45P) and L2 chain (Q38R or P44F, respectively) for which representatives were not chosen, but would be expected to improve pairing.

For cluster 3, five representative designs (10931-11263, 13221-13411, 10987-11257, 10983-11306 and 10947-11392) were chosen (see Table 10-A3). Members of this cluster utilized similar electrostatic driver sets in H1 (L143D or L143E_Q179E) and L1 (T131R/K) as in cluster 2, but differed with respect to the design of H2L2. The design of H2L2 was based primarily on a) L124R_S186R/K or L124R_Q179K or S188K of H2 pairing with S176D_T178E or S176D_T180E of L2; orb) L143R_S188K of H2 pairing with Q124E_V133D_S176D_T178D/E of L2, leading to disfavoring mismatched pairs primarily due to electrostatic repulsion. As in cluster 2, some members of the cluster also utilized a steric 1 or steric 2 driver set in addition to the electrostatic driver set. A representative of such a driver set combination is 13221-13411. This cluster also included two designs containing a 'variable domain driver set' in addition to the electrostatic driver set.

Three representative designs (13335-13361, 13209-13364 and 11100-11205) were chosen for cluster 4 (see Table 10-A4). Most members of this cluster utilized similar electrostatic drivers on H1 (S188K) and L1 (S176E/D_Y178E) with several variations in the H2L2 pair: a) V177D_S188D of H2 pairing with S176K_T178R/K of L2; orb) S186E or L124E or L124E_Q179E of H2 pairing with S176K/R or S131K/R_S176R/K of L2, which would allow for the formation of salt bridges in the preferentially paired heterodimers while the mismatched pairs would be disfavored primarily due to electrostatic repulsion. Some members of this cluster utilized only a steric driver set, i.e. a steric 3 driver set or some components of the steric 3 driver set, in addition to the electrostatic driver sets. The steric 3 driver set was based on WT residues in H1L1 or S188A in H1 and S176A_Y178W in L1 and S188W or S186I/L_S188W in H2 designed to be sterically complementary to S176V or S176A_T178A in L2. Furthermore, some members of this cluster also contained the disulfide steering driver set in addition to the electrostatic driver sets. In addition, a few cluster members contained the variable domain driver set(s) in addition to the electrostatic driver.

Cluster 5 was represented by unique identifier 11066-11181 (see Table 10-A5). All members of this cluster utilized electrostatic driver sets. A first set of electrostatic drivers was based on S186K in H1 pairing with V133D in L1 and S188D or V177D_S188D of H2 pairing with S131K or S176K_T178R/K respectively, in L2. A second set of drivers was of reversed charge orientation, primarily L124E_V190D in H1 pairing with L135K in L1 and L124R or S188K of H2 pairing with S176D or S176D_T178E of L2.

For cluster 6, two representative designs (10808-11308 and 10814-11233) were chosen (see Table 10-A6). All members of this cluster utilized similar electrostatic driver sets in the H1L1 pair: V177D_S188D of H1 with S176K_Y178K/R of L1 and a more diverse set of drivers in the H2L2 pair, namely a) S188K of H2 pairing with S176E/D_T178E or S131D/E of L2; b) S186K/R of H2 pairing with V133D or Q124E_Q160E_T180E of L2; c) L124R or L124R_Q179K of H2 pairing with S176D or S176D_T178D or S176D_T180E of L2; or d) L143K/R of H2 pairing with V133D or Q124E_V133D of L2. These substitutions allowed for formation of salt bridges in the preferentially paired heterodimers while the mismatched pairs would be disfavored primarily due to electrostatic repulsion.

For cluster 7, three designs (13167-13514, 13263-13493 and 12878-11240) were chosen to represent the cluster (see Table 10-A7). All cluster members utilized electrostatic driver sets based on a common driver set in H1L1: S188E in H1 and Y178K in L1, with some driver set diversity in the H2L2 pair: primarily L124R or S188K (also in combination with L143K or S186R or Q179K) of H2 pairing primarily with S176D/E_T178D/E or S176D/E_T180E or in combination with Q124E of L2. Some of the cluster members also contained the disulfide steering driver set, the steric 2 driver set or a variable domain driver set in addition to the electrostatic driver set.

For cluster 8, five designs (13320-13370, 12938-13469, 13226-13434, 11026-11270 and 13316-13451) were chosen to represent the cluster (see Table 10-A7). Members of this cluster had more variability in the H1L1 electrostatic pair while the H2L2 pair was based on L143E or L143E_Q179E drivers in H2 pairing primarily with Q124R/K_T178R or Q124R_Q160R/K_T178R drivers in L2. The H1L1 driver diversity was as follows: a) S186R or Q179K utilized as drivers in H1 paired primarily with the S180E driver of L1 (the S186K variation in H1 paired with the V133D driver in L1); b) the L143K driver of H1 paired with V133D or T131E/D_V133D of L1; or c) S188K of H1 paired primarily with S176D/E Y178E of L1. Some of the cluster members contained the steric 2 or steric 3 driver set or steric 4 driver set based on L124W in H2 engineered to be sterically complementary to V133A in L2 (some cluster members as part of the latter design also utilized an L143A substitution in H1 and a V133W in L1) in addition to the electrostatic driver set. Furthermore, a few cluster members contained a variable domain driver set in addition to the electrostatic set, for which one representative was chosen, or contained an engineered disulfide bond between F122C of H2 and Q124C of L2.

For cluster 9, two representative designs (13208-13455 and 13194-13427) were chosen (see Table 10-A9). Almost all members of this cluster utilized a combination of two electrostatic driver sets. A first driver set was predominantly composed of Q179K or S186R in H1 and S180E in L1 with L143E or L143E_Q179E in H2 and S131K or Q124R T178R or Q124R_Q160K_T178R in L2, and the second driver set was the disulfide steering driver set.

For cluster 10, two representative designs (13238-13463 and 13304-13466) were chosen (see Table 10-A10). Members of this cluster were based on steric 1 drivers alone, or in combination with the electrostatic driver sets used in cluster 9.

For cluster 11, one representative design (13306-13375) was chosen (see Table 10-All). All members of this cluster utilized electrostatic substitutions to drive preferential pairing of heterodimers, based on the following drivers: L143K_V190K in H1 and V133D in L1 and L124E in H2 and S131K L135K in L2.

For cluster 12, three representative designs (13227-13383, 11065-11206 and 11034-11204) were chosen (see Table 10-A12). Members of this cluster primarily utilized electrostatic substitutions to drive preferential pairing of heterodimers. These included L143K or S186K in H1 and V133D or T131D/E_V133D in L1 and predominantly L124E_Q179E in H2 and S131K/R_S176R in L2. Some cluster members additionally included the disulfide steering, steric 2, steric 3, or variable domain driver sets.

Description of K-K-Derived K-L Design Clusters

A significantly smaller set of K-K-derived K-L designs was tested (n=43) in the LCCA compared to the K-L designs. Hence, each of the ten kappa-kappa ported clusters was represented by a single design. Most of the clusters utilized electrostatic driver sets, except for two that utilized steric driver sets. Furthermore, two clusters were composed of designs in the variable domain only, while the rest of the clusters comprised constant domain designs.

Cluster 1 included electrostatic designs based on the following set of drivers: L143E_Q179E in H1, E124K_Y178R in L1, S186R in H2, and T178E_T180E or Q160E_T180E in L2 and is represented by design 10657-10760.

Cluster 2 included electrostatic driver sets featuring L143E in H1, E124R in L1 and S186R or Q179K in H2, Q124E_Q160E_T180E in L2 (design representative 10652-10734).

Cluster 3 contained a positively charged driver S186R in H1 complementary to a negatively charged driver S180E in L1, and a negatively charged driver L143E or Q179E or their combination in H2 complementary predominantly to a positively charged driver Q124K_T178R in L2 (design representative 10685-10726).

Cluster 4 utilized the following drivers: Q179K in H1, S180E in L1 and L143E in H2, Q124R or Q124R_Q160K_T178R in L2 (design representative 10665-10724).

Cluster 6 members contained variable domain designs based on the electrostatic pair of Q39K/R and Q38E/D in one arm and Q39E/D with Q38K/R in the other arm (both charge pair orientations were utilized in H1L1 and H2L2 arms) (design representative 10681-10741).

Cluster 8 members included a second set of variable domain drivers, steric in nature: WT or L45F in H1 complementary to WT in L1, and L45A/P in H2 complementary to P44F of L2 (design representative 10621-10733).

Cluster 10 included a single design based on L124E in H1, S176R in L1 and L124R in H2 and S176D in L2 (design 10640-10713).

Representatives for clusters 5, 7 and 9 were not selected as they did not meet performance criteria, such as moderate to strong driving or lack of impact on antigen binding relative to the parental Fab.

Example 16: Assessment of Preferential Pairing of Designed Heterodimers in Mab Design Sets in a Bispecific Antibody Format Examples 2 to 4, and 10 demonstrated the ability of the designed Fabs to preferentially pair in the context of an LCCA design (i.e. H1, L1, L2, or H2, L1, L2, where one heavy chain was co-expressed with two light chains in a Fab format). In this example, designed heterodimers in Mab design sets (H1, L1, H2, L2) were assessed to determine if they promoted preferential pairing in a bispecific antibody format (i.e. where H1, L1, H2, and L2 are co-expressed). In addition to the amino acid substitutions of the Mab design set, the Fc region of the full-length heavy chain of each heterodimer was asymmetrically modified such that one heavy chain comprised the amino acid substitutions T350V, L351Y, F405A and Y407V (Chain A) and the other heavy chain comprised the amino acid substitutions T350V, T366L, K392L and T394W (Chain B) where the amino acid numbering of the Fc is according to the EU numbering system. These asymmetric Fc modifications were included in order to promote heterodimerization of the unique heavy chains.

The ability of designed heterodimers in Mab sets to promote preferential pairing in the context of a bispecific antibody was assessed in 3 bispecific systems using combinations of the CAT-2200 and pertuzumab antibodies described in prior examples, and a CR8071 (anti-influenza B hemagglutinin protein) antibody and SGN-CD19a (anti-CD19). The 3 bispecific systems tested were: A) CAT-2200 (having a lambda light chain)/pertuzumab (having a kappa light chain), B) CAT-2200 (having a lambda light chain)/SGN-CD19a (having a kappa light chain), and C) CR8071 (having a lambda light chain)/SGN-CD19a (having a kappa light chain). CAT-2200 and CR8071 are human antibodies, while pertuzumab and SGN-CD19a are humanized antibodies.

Assay Format (SMCA)

The ability of heterodimers containing amino acid substitutions of a Mab design set to preferentially pair to form a correctly paired bispecific antibody was assessed as described below. The assay is based on co-expressing the four chains (H1 and L1 chains from one antibody with the H2 and L2 chains from the other antibody) and detecting the presence of correctly formed bispecific antibody using mass spectrometry (LC-MS). FIG. 8 provides a schematic depicting the four starting polypeptide chains and the potential products resulting from co-expression of these starting polypeptide chains in the absence of preferential pairing between heavy and light chains (in both Fab and Fc regions) of the heterodimer pairs. Two unique full-length heavy chain constructs were co-expressed with two unique light chain constructs, yielding ten possible antibody species (also referred to as Mab species): H1L1_H1L1, H1L2_H1L2, H1L1_H1L2, H2L1_H2L1, H2L2_H2L2, H2L1_H2L2, H1L1_H2L1, H1L2_H2L2, H1L2_H2L1 and H1L1_H2L2. The H1L1_H2L2 species is the correctly paired bispecific antibody (see FIG. 8). Four types of half-antibody (half-Ab) species are also possible, as shown in FIG. 8. When modifications are introduced into the Fc region to promote heterodimerization of the unique heavy chains, the number of potential Mab species decreases (i.e. less of species E to J are observed). The relative pairing specificity in terms of amount of correctly paired bispecific antibody species H1L1_H2L2 vs. other species was determined using LC-MS after protein A (pA) purification and deglycosylation. When possible, chains were left untagged, provided that all Mab species and half-Ab species differed from each other by at least 50 Da. When mass differences precluded this possibility, N-terminal tags (HA or FLAG) were added to the light chains in order to provide sufficient mass differentiation between species, with emphasis on the use of the FLAG tag where possible, as cleavage of HA tag was sometimes observed (in the case of constructs containing CR8071, only the FLAG tag was used).

This assay, involving the expression of H1, L1, H2, and L2 of a bispecific antibody, and subsequent analysis of paired products is referred to as SMCA.

Preparation of Constructs

Constructs encoding the CAT-2200, pertuzumab, CR8071 and SGN-CD19a IgG heavy and light chains comprising amino acid modifications according to the designs were prepared as follows. The CAT-2200 and pertuzumab light chain sequences were prepared as described in Example 3, while the full-length heavy chain sequences for these antibodies were created by appending the IgG1*01 DNA sequence encoding the partial hinge-CH2-CH3 domains [SEQ ID NO:6] and modified to promote heterodimerization, onto the C-terminus of the CH1 domain of the Fab heavy chains (containing a portion of the hinge and excluding the $ABD_2$ extension used for constructs in the LCCA) preparation of which was described in Example 3. The constructs containing amino acid substitutions for the Mab design sets were generated either by gene synthesis or by site-directed mutagenesis as noted in Example 3. Of note, the canonical C-terminal heavy chain lysine residue was removed in order to prevent LC-MS signal heterogeneity due to C-terminal lysine clipping (Lawrence W. Dick Jr. et al., Biotechnol. Bioeng. (2008) 100:1132-43).

The base DNA sequences for the Fab portion of the heavy chain (SEQ ID NO:18) and the DNA sequences of the light chain (SEQ ID NO:19) of CR8071 are shown in Table 3C. The CR8071 Fab amino acid sequences for heavy chain (SEQ ID NO:14) and light chain (SEQ ID NO:15) correspond to those in the PDB entry 4FQJ (complex of Fab CR8071 and hemagglutinin) where an R222K substitution in the heavy chain was made to convert to the most common IGHG1*01 sequence.

The base DNA sequences for the Fab portion of the heavy chain (SEQ ID NO:16) and the DNA sequences of the light chain (SEQ ID NO:17) of SGN-CD19a are also shown in Table 3C. The SGN-CD19a sequences correspond to SEQ ID NOs: 7 and 17 reported in U.S. Pat. No. 8,242,252 and are included here as SEQ ID NO:12 (heavy chain) and SEQ ID NO:13 (light chain).

As noted above, the CAT-2200, CR8071, pertuzumab and SGN-CD19a light chain sequences in some of the designed heterodimers in Mab sets were prepared with or without FLAG or HA tags in order to provide sufficient mass differentiation between species. Light chains with tags were prepared as described in Example 3.

Wild-type versions of these constructs were also prepared in order to assess natural bias in each system, discern potential effect of the HA or FLAG tags on pairing and for determining the effect of designed constructs on preferential pairing over wild-type.

Transfection, Expression and Purification of Constructs

Constructs encoding the two heavy chains and two light chains of each bispecific antibody system, either wild-type or with amino acid substitutions corresponding to each Mab design set tested were transfected into CHO-3E7 cells as follows. CHO-3E7 cells, at a density of 1.7-2×$10^6$ cells/ml, were cultured at 37° C. in FreeStyle™ F17 medium (Invitrogen cat #A-1383501) supplemented with 4 mM glutamine and 0.1% Koliphor P188 (Sigma #K4894). A total volume of 200 ml was transfected with a total of 200 □g DNA with varying ratios of H1:H2:L1:L2 (which consists of 100 □g of antibody DNA and 100 □□g of GFP/AKT/stuffer DNA) using PEI-max (Polysciences Cat #24765-2) at a DNA:PEI ratio of 1:4. Twenty-four hours after the addition of the DNA-PEI mixture, 0.5 mM Valproic acid (final concentration) and 1% w/v Tryptone N1 (final concentration) were added to the cells which were then transferred to 32° C. and incubated for 7 days prior to harvesting. Culture media was harvested by centrifugation and vacuum filtered using a Stericup 0.22 μm filter (Millipore Cat #SCGPU05RE). The filtered culture media was then purified using protein A Mab Select SuRe resin (GE Healthcare #17-5438-02) that was previously equilibrated with PBS pH 7.4. The antibody species bound to the resin was then washed with PBS pH 7.4 and eluted with 100 mM sodium citrate buffer pH 3.6. Eluted antibody species were concentrated and buffer exchanged in PBS pH 7.4 by centrifugation using Amicon ultra 15 centrifuge filter Ultracel 10K (Millipore #SCGP00525). The resulting protein A-purified SMCA samples containing the antibody species were assessed by Caliper prior to deglycosylation and LC-MS.

Mass Spectrometry Method

The degree of preferential pairing of heterodimers driven by the Mab design sets in the context of a bispecific antibody was assessed using mass spectrometry after protein A purification and non-denaturating deglycosylation. As the heterodimers contained Fc N-linked glycans only, the SMCA samples were treated with only one enzyme, N-glycosidase F (PNGase-F). The purified samples were de-glycosylated with PNGaseF as follows: 0.2U PNGaseF/μg of antibody in 50 mM Tris-HCl pH 7.0, overnight incubation at 37° C., final protein concentration of 0.5 mg/mL. After deglycosylation, the samples were stored at 4° C. prior to LC-MS analysis.

The deglycosylated protein samples were analyzed by intact LC-MS using an Agilent 1100 HPLC system coupled to an LTQ-Orbitrap XL mass spectrometer (ThermoFisher Scientific) via an Ion Max electrospray source (ThermoFisher). The samples (5 μg) were injected onto a 2.1×30 mm Poros R2 reverse phase column (Applied Biosystems) and resolved using the following gradient conditions: 0-3 min: 20% solvent B; 3-6 min: 20-90% solvent B; 6-7 min: 90-20% Solvent B; 7-9 min: 20% solvent B. Solvent A was degassed 0.1% formic acid aq. and solvent B was degassed acetonitrile. The flow rate was 3 mL/min. The flow was split post-column to direct 100 μL into the electrospray interface. The column was heated to 82.5° C. and solvents were heated pre-column to 80° C. to improve protein peak shape. The LTQ-Orbitrap XL was calibrated using ThermoFisher Scientific's LTQ Positive Ion ESI calibration solution (caffeine, MRFA and Ultramark 1621), and tuned using a 10 mg/mL solutions of CsI. The cone voltage (source fragmentation setting) was 48 V, the FT resolution was 7,500 and the scan range was m/z 400-4,000. The LTQ-Orbitrap XL was tuned for optimal detection of larger proteins (>50 kDa).

The ranges containing the multiply charged ions from the full-sized antibodies (m/z 2000-3800) and the half-antibodies (m/z 1400-2000) were separately deconvoluted into molecular weight profiles using MaxEnt 1 module of MassLynx, the instrument control and data analysis software (Waters). Briefly, the raw protein LC-MS data were first opened in QualBrower, the spectrum viewing module of Xcalibur (Thermo Scientific) and converted to be compatible with MassLynx using Databridge, a file conversion program provided by Waters. The converted protein spectra were viewed in the Spectrum module of MassLynx and deconvoluted using MaxEnt 1. The amount of each antibody species in each sample was determined directly from the resulting molecular weight profiles.

Analysis of LC-MS Results

Overall, in most cases, the deglycosylation treatments resulted in the ability to identify all of the possible different antibody species identified by LC-MS. In many cases, each antibody species was represented by a single LC-MS peak. Exceptions included side peaks that likely also correspond to the desired bispecific species (possibly adducts or heterogeneity in the cleavage of leader peptides); however, because identity of the species resulting in the side peaks was not clear, these side peaks were not considered in the contributions to the bispecific species. Furthermore, the desired bispecific species, H1L1 H2L2, cannot generally be distinguished experimentally from the mispaired type, H1L2 H2L1, on the basis of LC-MS. As such, when bispecific antibody content is reported in the tables, it cannot be completely excluded that it does not contain this type of mispaired species. However, the very low content observed for species such as H1L2_H1L2 and H2L1_H2L1 as well as H1L2 and H2L1 half antibodies is indicative that only minor, if any, contamination of the bispecific species with mispaired species occurred.

Assessment of Natural Bias and Effect of Tags on Pairing in Wild-Type Systems

As a first step, for each of the three bispecific systems tested, the wild-type (one of the light chains containing a tag if required for sufficient mass differentiation between species), unmodified heavy and light chains of the parent antibodies for each system were co-expressed using varying DNA ratios for H1:H2:L1:L2, and the resulting antibody species were identified and quantitated. This allowed for the identification of any inherent pairing bias (or that introduced by the presence of a tag) in each system (for example, if the light chain of one parent antibody in the bispecific system preferentially binds the heavy chain of the other parent antibody in the bispecific system), and also allowed for the identification of a DNA ratio for H1:H2:L1:L2 that provided the highest amount of bispecific antibody with the lowest amount of half-Abs. The DNA ratios were chosen to compensate for natural differences in expression levels and/or intrinsic pairing biases between heavy and light chains of the two parent antibodies and/or tag influence for each system. In tested wild-type bispecific systems A and B, L2 was tagged with a FLAG tag. In bispecific system C, neither of the light chains were tagged.

Table 12 shows the result of this assessment. The DNA ratio for H1:H2:L1:L2 that provided the highest amount of bispecific antibody with the lowest amount of half-Abs was 10:20:24:46 for System A, 15:15:35:35 for System B, and 15:15:35:35 for System C. Of note, in the CAT-2200/pertuzumab bispecific Ab system (System A), a bias was observed where the pertuzumab heavy chain (H2) preferentially paired with the CAT-2200 light chain (L1). This bias was evident when data for equivalent ratios of heavy chain 1 and heavy chain 2, but inverse ratios of light chain 1 and light chain 2 are considered (e.g. consider inverse L1:L2 DNA ratios in H1:H2:L1:L2 of 8:22:17:53 and 8:22:53:17 in Table 12). Under these conditions of H1:H2:L1:L2=8:22:53:17, prevalent mispaired Mab species of H1L1 H2L1 are much more abundant (79.6%) than in the case of H1:H2:L1:L2=8:22:17:53, where prevalent mispaired species of H1L2 H2L2 made up about 38.4%. This indicated that the pertuzumab heavy chain appeared to pair preferentially with the CAT-2200 light chain in this system, when the pertuzumab light chain had a FLAG tag.

Design SMCA constructs that contained N-terminal tags (HA or FLAG) on one of the light chains guided preparation of the analogous WT SMCA constructs that were investigated for possible influence of tags on the ability of the light chains to pair with the heavy chains. Table 13 shows the results of this experiment, and indicates that in some cases, the tag did have an impact on pairing of the light chains with heavy chains. For example, with respect to the System A case noted above, where there was preferential pairing of the pertuzumab heavy chain with the CAT-2200 light chain when the pertuzumab light chain contained the FLAG tag, when the CAT-2200 light chain contained the HA tag and the 4 polypeptide chains were expressed at the same DNA ratio, preferential pairing of the CAT-2200 heavy chain to the pertuzumab light chain was observed (see Table 13, 'System A, L1-HA' and compare 'System A, L1-HA' with 'System A, L2-FLAG' at the same ratio of 10:20:24:46). Furthermore, for the SGN-CD19a/CAT-2200 bispecific system (System B), the degree of mispairing between the heavy chain of SGN-CD19a with the CAT-2200 light chain in the system that contains FLAG-tagged SGN-CD19a light chain was greater than in the other two variations of the same system at the same ratio (Table 13, 'System B, L1-FLAG' and contrast 'System B, L1-FLAG with 'System B, L2-FLAG and L2-HA' at the same ratio of 15:15:35:35). Note that Table 13 reflects data accumulated for all repeats performed, hence species percentage may in some cases differ from the data at the initial assessment stage, provided in Table 12.

For testing each of the 40 representative designs within each bispecific system, the H1:H2:L1:L2 DNA ratios used were the ratios from the corresponding wild-type bispecific systems that yielded the highest amount of bispecific Ab species and the lowest amount of half-Ab. As indicated above, for the CAT-2200/pertuzumab system, the ratio used was 10:20:24:46 (H1:H2:L1:L2), where and 1, refer to CAT-2200 and H2 and L2 refer to pertuzumab. For the SGN-CD19a/CAT-2200 and SGN-CD19a/CR8071 systems, the ratio used was 15:15:35:35 (H1:H2:L1:L2).

Preferential Pairing Results in Bispecific Antibody Format

The results of the SMCA with the 40 representative designs tested are shown in Tables 14 to 17. Tables 14 to 17 refer to Mab design sets as "designs" and have been identified with a 4-digit number. Each 4-digit number corresponds to a Mab design set unique identifier (LCCA set unique identifiers) in Tables 10-A1 to A12 and 10-B1 to 10-B10. Table 24 provides a correspondence table between the designs tested in SMCA and the LCCA set unique identifiers. The analysis of preferential pairing was performed based on two types of calculations. The first type of calculation is noted as "% H1L1 and % H2L2 Pairing" in the Tables, and represents the amount of correct pairing between H1 and L1 and between H2 and L2 across all Mab species and half-Ab species observed, including Mab species that may have had only one correctly paired arm, as a percentage of total product (H1L1_H2L2_and_H1L2_H2L1+H1L1_H1L1+H2L2_H2L2+H1L1+H2L2+0.5×(H1L1_H2L1+H1L1_H1L2+H1L2_H2L2+H2L1_H2L2)). This calculation is referred to as the 'total pairing' calculation. The second type of calculation is noted as "H1L1_H2L2 and H1L2_H2L1**" in the Tables, and represents the amount of correct paired bispecific antibody as a percentage of all the Mab species (i.e. Mab species A-J in FIG. 8) observed (H1L1_H2L2_and_H1L2_H2L1/(H1L1_H2L2_and_H1L2_H2L1+H1L1_H1L1+H2L2_H2L2+H1L1_H2L1+H1L2_H2L2+H1L1_H1L2+H2L1_H2L2+H1L2_H1L2+H2L1_H2L1)). This calculation is referred to as the 'total bispecific' calculation. Half antibodies were not taken into account in this calculation, since if present, may be removed/minimized by preparative SEC or through further H1:H2:L1:L2 DNA titrations. Table 12 demonstrates that DNA titrations are effective in manipulating the percentage of half-Ab species expressed. The effectiveness of prep-SEC purification in reducing the amount of half-Ab of type Chain A' is demonstrated in Example 18.

Figure 16A:
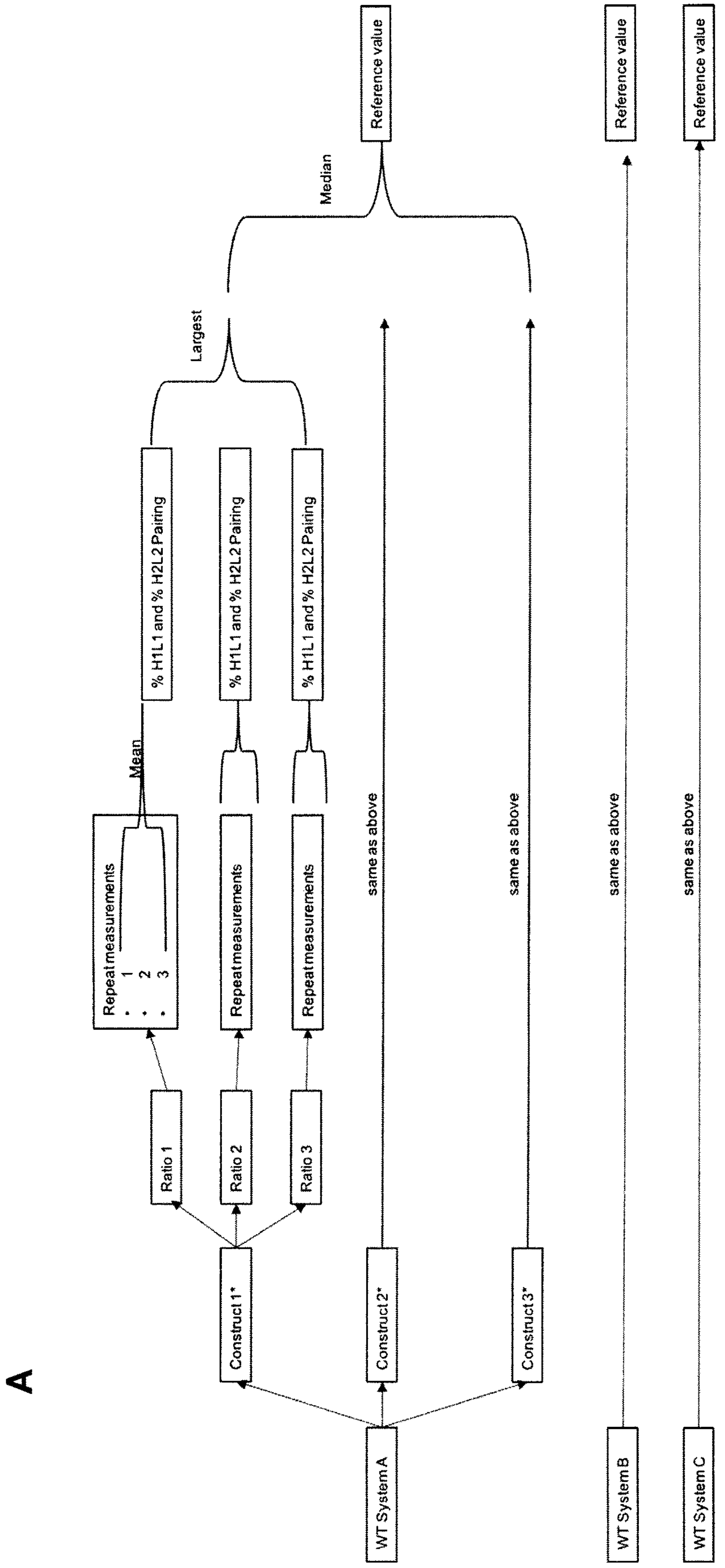
FIG. 16A shows the process for selecting wild-type reference values for 'total pairing' ("% H1L1 and % H2L2 Pairing") for each of the three bispecific systems.
Figure 16B:
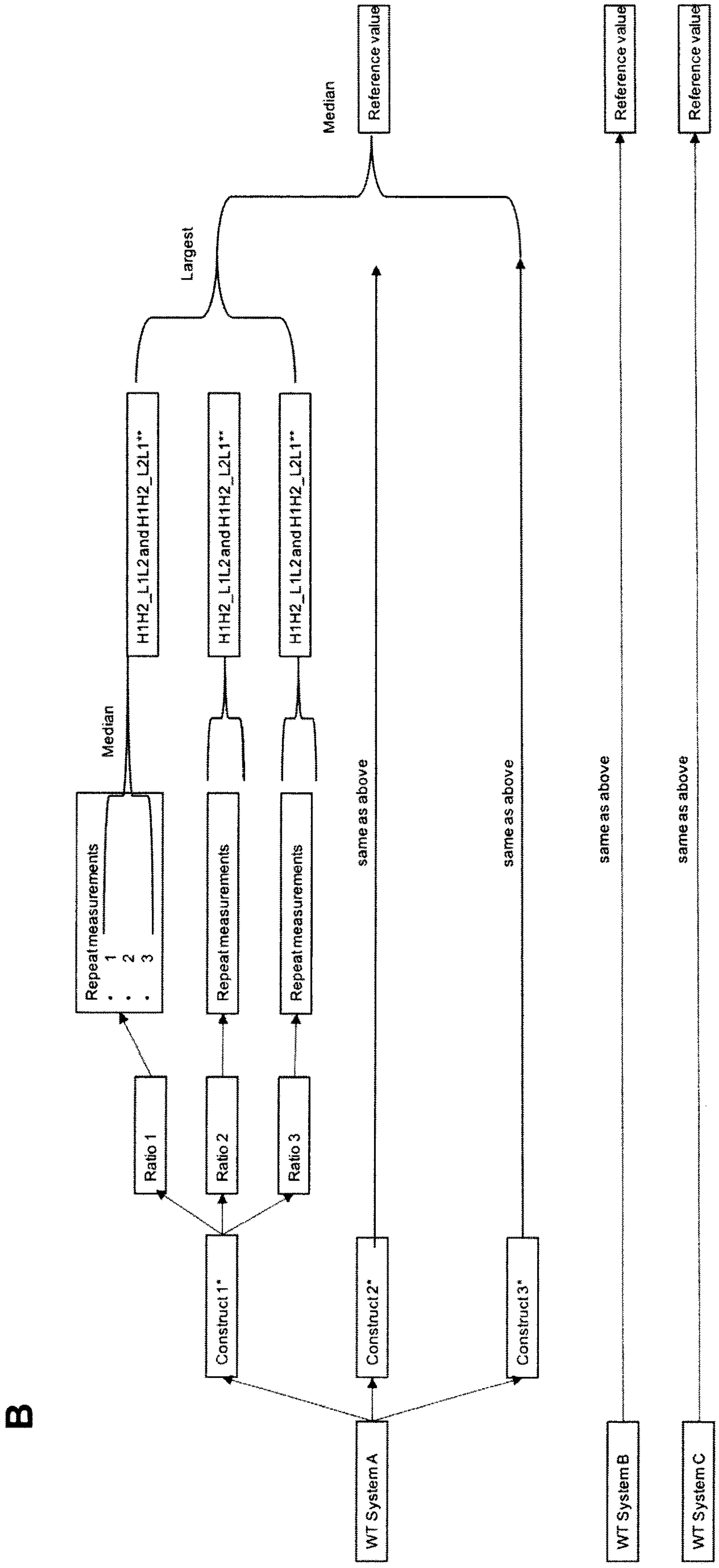
FIG. 16B shows the process for selecting wild-type reference values for 'total bispecific' ("H1L1_H2L2 and H1L2_H2L1**") for each of the three bispecific systems.

To account for biases that were observed in some wild-type bispecific systems, as described above, the preferential pairing data was reported as a comparison to the corresponding wild-type bispecific constructs at the same H1:H2:L1:L2 DNA ratio. This comparison was reported in the columns "Change in % H1L1 and % H2L2 Pairing with respect to wild-type" (i.e. change in total pairing with respect to WT) and "Change in H1L1_H2L2 and H1L2_H2L1 with respect to wild-type" (i.e. change in total bispecific with respect to WT). Where the corresponding wild-type bispecific construct had not been assessed by SMCA, a comparison was made to a similar wild-type construct. These cases are indicated by a "s" next to the values reported. The similar wild-type construct chosen for comparison was selected as follows. For each bispecific system and construct (with or without tags), median values for "H1L1 H2L2 and H1L2 H2L1" and the mean values for "% H1L1 and % H2L2 Pairing" from repeat SMCA experiments per DNA ratio were taken. The largest values from any ratio within each construct were taken, and the median across all constructs was used to represent the WT reference for particular system (see FIGS. 16A and 16B).

Tables 14 and 15 provide a summary of the SMCA results for the representative K-L designs tested, where designs were binned according to "Change in % H1L1 and % H2L2 Pairing with respect to wild-type" (Table 14) or "Change in H1L1_H2L2 and H1L2_H2L1** with respect to wild-type" (Table 15). Similarly, Tables 16 and 17 provide a summary of the SMCA results for the representative K-K-derived K-L designs tested, where designs were binned according to change in total pairing (Table 16) or change in total bispecific (Table 17) calculations.

Performance

The performance, or ability to promote preferential pairing of correct heavy and light chains, for each of the representative designs was assessed using the total pairing calculation and using the total bispecific calculation. First, a positive value in the column "Change in % H1L1 and % H2L2 Pairing with respect to wild-type" (change in total pairing with respect to WT) indicated that the Mab design set was able to promote preferential pairing. Second, a positive value in the column "Change in H1L1_H2L2 and H1L2_H2L1** with respect to wild-type" (change in total bispecific with respect to WT), was also indicative of a Mab design set that was able to promote preferential pairing.

All of the K-L designs and 18 out of 21 K-K-derived K-L designs showed reduced amounts of the primary mispaired species (H1L2_H2L2 or H1L1_H2L1) compared to wild-type although in some cases the amount of a different mispaired species was increased compared to wild-type. On average, both K-L and K-K-derived K-L designs generated the greatest increase of desired bispecific relative to wild-type (change in total bispecific with respect to WT) in system A (48.8%), followed by system B (31.1%), and system C (14.5%). On average, all of the designs tested resulted in a relatively minor increase in the total amount of half antibody compared to wild-type, from 24.1% to 27.9%, but improved the average ratio of paired to mispaired half antibody from 1.5 to 6.9.

Transferability

The ability of the representative set of Mab designs to promote preferential pairing in multiple systems was tested as a measure of the "transferability" of the designs. Using the 'change in total pairing with respect to WT' calculation, 29 out of 33 K-L designs were transferable in 3 of 3 tested systems and 3 designs were transferable in 2 of the 3 systems tested (Table 14). In other words, these designs showed a positive value of 'change in pairing with respect to WT". When preferential pairing was measured using the 'change in total bispecific with respect to WT' calculation, 24 out of 33 K-L designs were identified as transferable in 3 of 3 systems and 8 designs were transferable in 2 of 3 systems (Table 15). For the K-K-derived K-L designs, 2 out of 7 designs were transferable in 3 of 3 systems and 4 designs were transferable in 2 of 3 systems using the 'change in total pairing with respect to WT' calculation (Table 16). Using the 'change in total bispecific with respect to WT' calculation, 1 out of 7 designs was transferable in 3 of 3 systems and 5 designs were transferable in 2 of 3 systems (Table 17). 23 out of 33 K-L designs and 1 out of 7 K-K-derived K-L designs were transferable in 3 of 3 tested systems when assessed using both calculations.

Figure 10A:
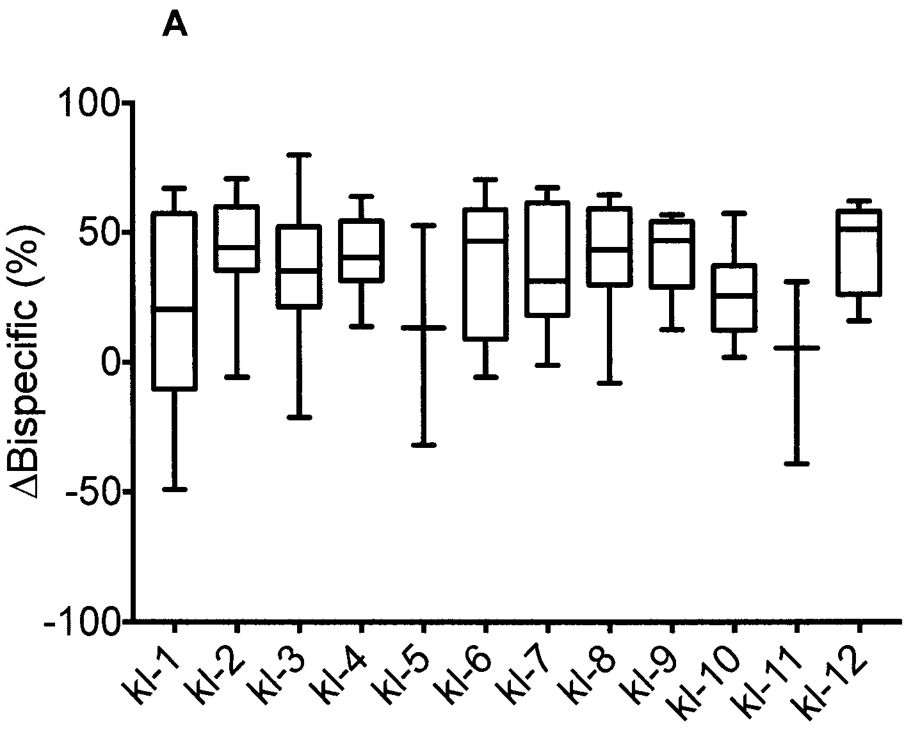
FIG. 10A shows performance as measured by the total bispecific calculation (ΔBispecific %).
Figure 10B:
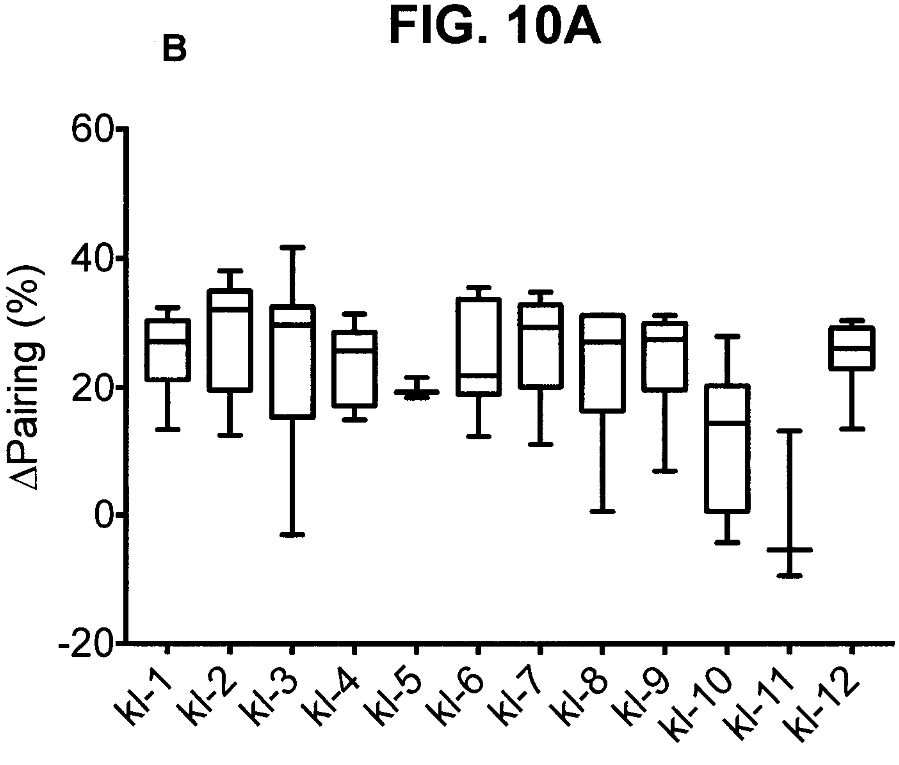
FIG. 10B shows performance as measured by the total pairing calculation (ΔPairing %).

With respect to performance of the clusters, all designs within 9 of 12 K-L clusters were transferable in 3/3 systems according to the 'change in total pairing with respect to WT' calculation, and 4 of 12 according to the 'change in total bispecific with respect to WT' calculation. All designs within clusters kl-4, kl-9, and kl-12 were transferable in 3/3 systems using both calculations. FIG. 10 shows box plots comparing the performance of the representative designs from each cluster, based on the 'change in total bispecific with respect to WT' calculation (FIG. 10A, change in bispecific %) or on the 'change in total pairing with respect to WT' calculation (FIG. 10B, change in pairing %). For the K-K-derived K-L clusters, only one design per cluster was tested and so cluster transferability was equivalent to the design transferability discussed above.

Figure 11:
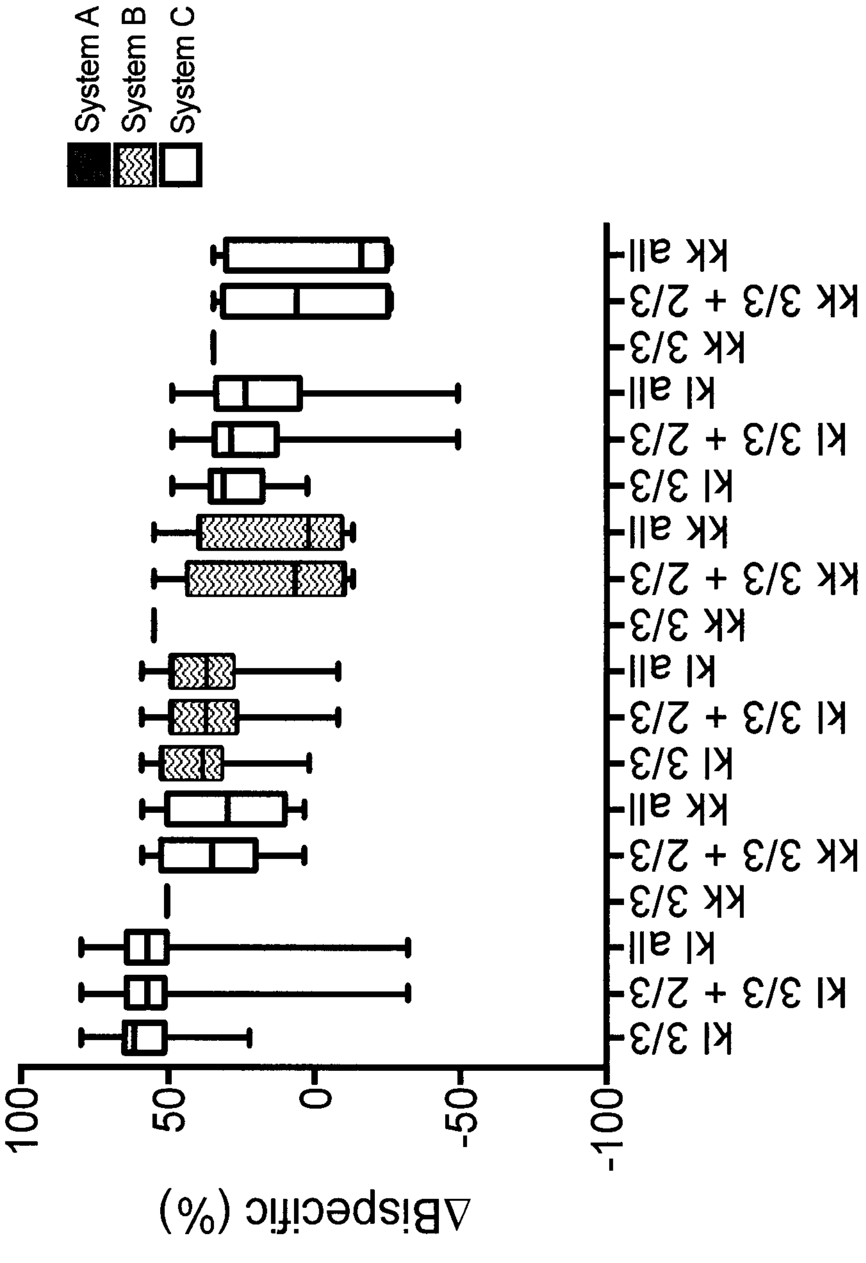
FIG. 11 depicts a min-max box plot graph summarizing the performance of K-L designs and K-K-derived K-L designs per bispecific system, by transferability group; "kl 3/3" indicates K-L designs transferable in 3/3 bispecific systems, "kl 3/3+2/3" indicates K-L designs transferable in at least 2 bispecific systems, and "kl all" indicates all K-L designs tested. Likewise, "kk 3/3" indicates K-K-derived K-L designs transferable in 3/3 bispecific systems, "kk 3/3+2/3" indicates K-K-derived K-L designs transferable in at least 2 bispecific systems, and "kk all" indicates all K-K-derived K-L designs tested; results are presented based on the total bispecific calculation (ΔBispecific %).

Overall, the K-L designs were able to promote preferential pairing more effectively than the K-K-derived K-L designs. FIG. 11 shows box plots depicting the ability of K-L designs and K-K-derived K-L designs to promote preferential pairing in each system tested, based on the 'change in total bispecific with respect to WT' calculation. For example, FIG. 11 shows that K-L designs generally promoted a larger increase in amount of bispecific antibody compared to WT than did the K-K-derived K-L designs (comparing the "kl all" value to the "kk all" value for each system). This is also true when considering only designs transferable in 2 or more or in all 3 systems.

Example 17: Preparative Size Exclusion Chromatography (SEC) of Selected SMCA Bispecific Antibodies and Parental Mabs for Biophysical Characterization To assess the biophysical characteristics of the bispecific antibodies generated in the SMCA described in Example 16, the protein A-purified SMCA samples from a subset of the representative designs tested were subjected to preparative SEC to remove half-Ab species. SMCA samples having at least 60% "H1L1_H2L2 and H1L2_H2L 1**" (total bispecific) were selected for this step (36 in total). Some SMCA samples not meeting this cutoff were also included for completeness. For example, in cases where the SMCA samples for a given design met this cutoff in two of the three bispecific systems tested, the SMCA sample met this cutoff, but not the third, the SMCA samples for all 3 systems were included. Preparative SEC was carried out as follows. Antibody species in the SMCA samples were separated using a Superdex 200 10/300 Increase (GE Healthcare) column mounted on a GE Healthcare ÄKTA Avant 25 system equipped with an ALIAS Bio Cool autosampler (Spark-Holland) used to inject samples on the column. SMCA samples (0.9 ml) in PBS pH 7.4 (Hyclone DPB S/modified, No Calcium, No Magnesium, Cat. No. SH-300028.02) were automatically loaded into a 2 ml loop filled with PBS. Samples were then automatically injected onto the column and resolved at 0.5 ml/min with a 1 CV elution volume. Protein elution was monitored at $OD_{280}$ and collected in 0.5 ml fractions. For each SMCA sample, fractions that comprised the main peak (fractions were assessed by Caliper) were pooled and further biophysically characterized as described in Examples 19 and 20.

Example 18: Removal of Half-Antibodies by Preparative Size Exclusion Chromatography In Example 16, it was noted that half-Abs were excluded from calculations of pairing according to the 'total bispecific' calculation, since the percentage of half-Abs produced can either be manipulated by DNA titrations or, in the case of half-Abs of type 'Fc Chain A,' that these can also be removed/minimized by preparative SEC purification of Protein-A purified SMCA samples. To demonstrate removal of "Fe Chain A half-Abs," purified SMCA samples from Example 17 for two K-L designs in all three bispecific systems were subjected to LC-MS analysis as described in Example 16. The two K-L designs selected were 2901 and 3972 (as identified in Table 11A). The results are shown in Table 18.

Comparing the LC-MS data in Table 18 to the respective LC-MS data for protein-A purified SMCA samples in Table 14 demonstrates that preparative SEC can be effective in the removal/minimization of half-Ab species of the type 'Fe Chain A' (H1L1 in 2901 and 3972). In all of the samples tested, there was enrichment in the percentage of the desired bispecific antibody species (H1L1_H2L2 and H1L2_H2L1) as well as a decrease in the percentage of half antibody species of type 'Fe Chain A' (H1L1 in Table 18).

Example 19: Thermal Stability of SMCA Bispecific Antibodies

Following preparative SEC, the thermal stability of the prep-SEC purified SMCA bispecific antibodies was measured and compared to parental CAT-2200, pertuzumab, CR8071 and SGN-CD19a monoclonal antibodies in order to determine whether the amino acid substitutions had any effects on thermal stability.

Measurement of Thermal Stability

The thermal stability of selected bispecific heterodimeric antibodies and wild-type controls was measured using differential scanning calorimetry (DSC) as follows. Following preparative SEC treatment, 400 μL samples primarily at concentrations of 0.4 mg/mL in PBS were used for DSC analysis with a VP-Capillary DSC (GE Healthcare). At the start of each DSC run, 5 buffer blank injections were performed to stabilize the baseline, and a buffer injection was placed before each sample injection for referencing. Each sample was scanned from 20 to 100° C. at a 60° C./hr rate, with low feedback, 8 sec filter, 3 min preTstat, and 70 psi nitrogen pressure. The resulting thermograms were referenced and analyzed using Origin 7 software.

Figure 12A:
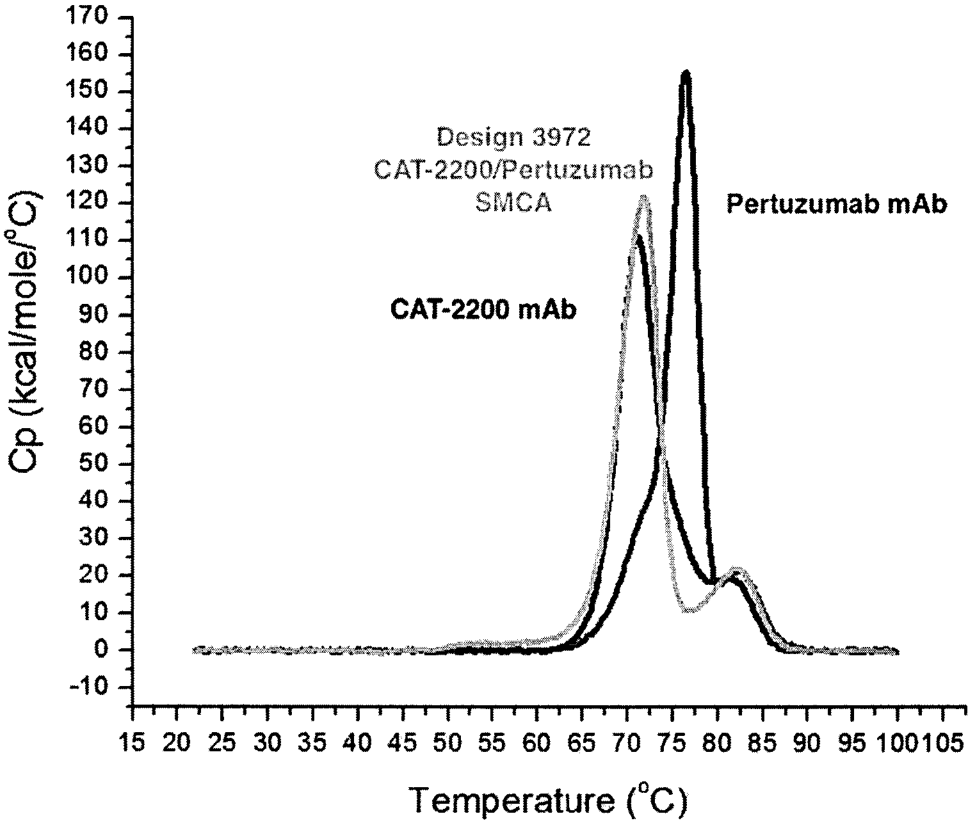
FIG. 12A depicts wild-type CAT-2200 mAb (dark grey), wild-type Pertuzumab mAb (medium grey), and Design 3972 CAT-2200/Pertuzumab SMCA (light grey)
Figure 12B:
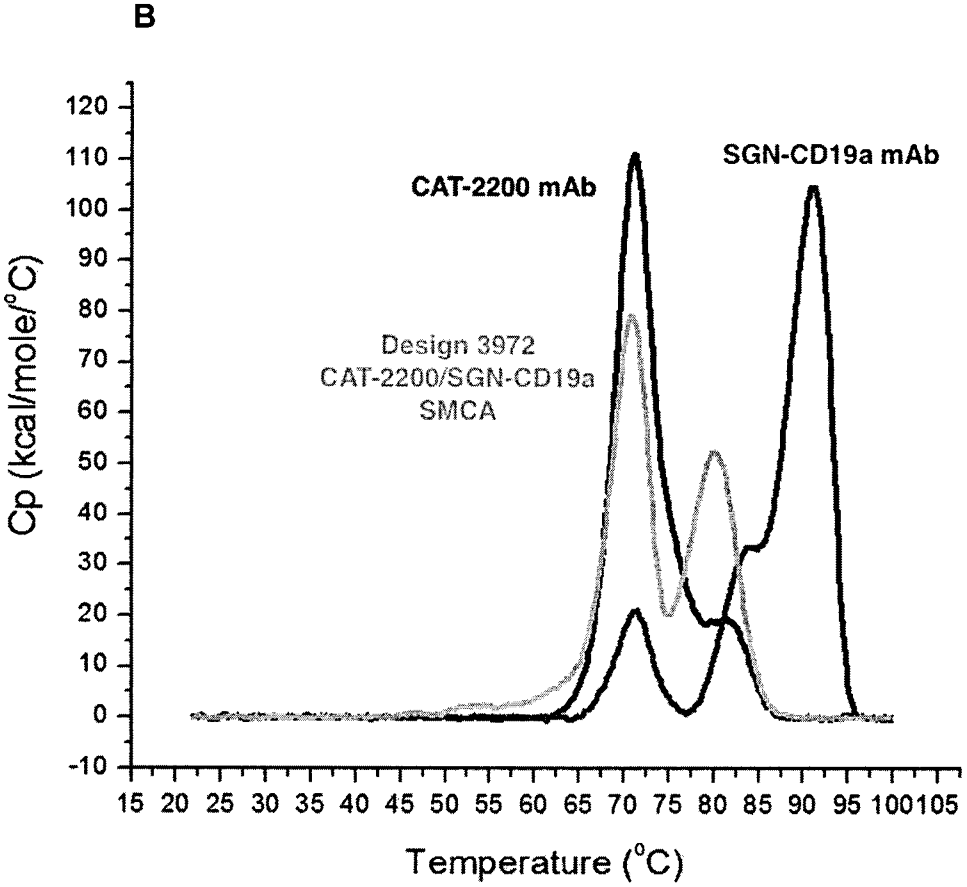
FIG. 12B depicts wild-type CAT-2200 mAb (dark grey), wild-type SGN-CD19a mAb (medium grey), and Design 3972 CAT-2200/SGN-CD19a SMCA (light grey)
Figure 12C:
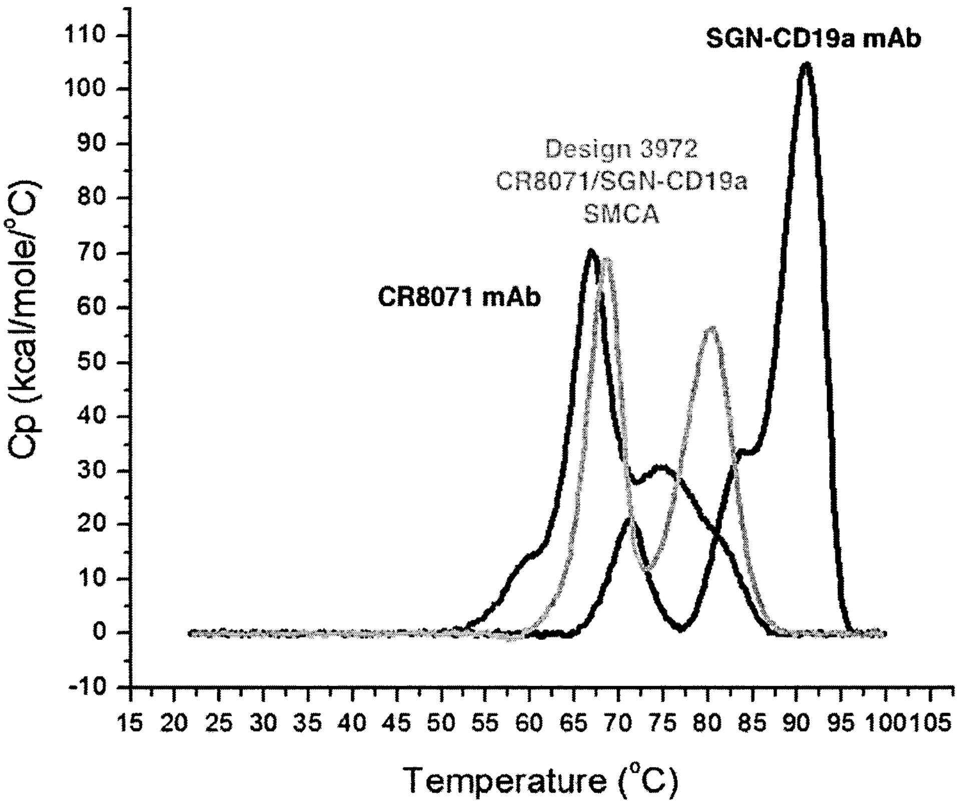
FIG. 12C depicts wild-type SGN-CD19a mAb (dark grey), wild-type CR8071 mAb (medium grey), and Design 3972 CR8071/SGN-CD19a SMCA (light grey).

The results are shown in Table 20 and Table 21. The wild-type Fab Tm values used to calculate "Average difference in Fab Tm from wild-type (° C.)" as reported in the tables were obtained from DSC thermograms of parental antibodies of CAT-2200 (71.2° C.), pertuzumab (76.7° C.), CR8071 (66.9° C., corresponding to the primary peak) and SGN-CD19a (91.0° C.). The CR8071 parental antibody displayed two Fab transitions. For parental antibodies, additional thermal transitions were observed for the CH2 and CH3 domains of the Fc (at approximately 71° C. and 82° C., respectively) where these did not overlap with the Fab transition (FIG. 12). Some designs with large amounts of H2L2 'Fe Chain B' half antibody displayed an additional thermal transition at approximately 60° C., likely due to the presence of non-covalent homodimers. In some cases, designs caused a reduction in the Tm of the pertuzumab Fab such that it led to overlap of the CAT-2200 Fab, pertuzumab Fab, and CH2 peaks in those samples (FIG. 12A, representative design 3972). Likewise, many designs reduced the Tm of SGN-CD19a Fab to such an extent that caused overlap with the CH3 peaks in those antibodies (FIGS. 12B and 12C, representative design 3972). These overlaps led to some ambiguity in Tm assignment of the contributing Fab components, and hence the Tm values reported in Tables 20 and 21 are considered approximations. Interestingly, CR8071/SGN-CD19a bispecific antibodies containing designs displayed a single CR8071 Fab transition instead of two transitions observed in the wild-type bispecific antibodies (e.g. FIG. 12C).

Figure 13:
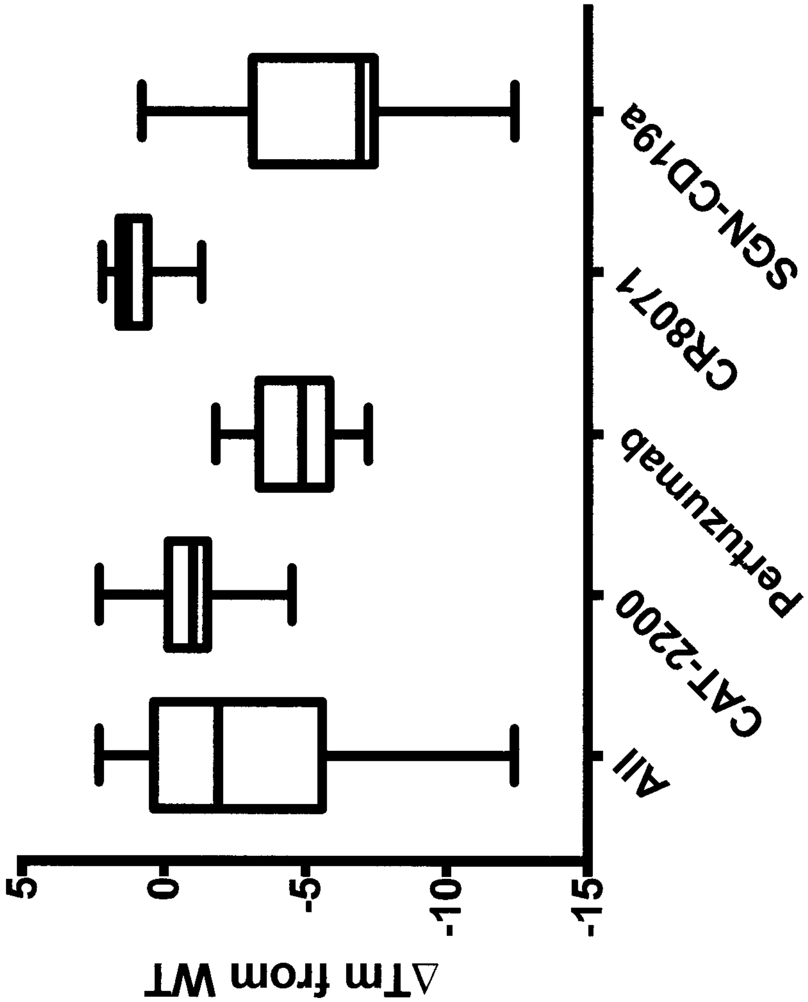
FIG. 13 depicts a min-max box plot summarizing the effect of the amino acid substitutions of Mab designs on the Tm of tested Fabs. The results are reported as the change in Fab Tm compared to WT and are shown for all the designs for which Tm was measured ("All"), and separated by paratope.

Out of all the tested K-L designs, the average difference in Fab Tm from wild-type across all systems was between 0° C. and −1.5° C. for 6 designs, between −1.5° C. and −3.0° C. for 11 designs, and between −3.0° C. and −4.5° C. for 15 designs (Table 20). Out of all tested K-K-derived K-L designs, the average difference was between 0° C. and −1.5° C. for 2 designs, between −1.5° C. and −3.0° C. for 1 design, and between −3.0° C. and −4.5° C. for 1 design (Table 21). The average differences in Fab Tm from wild-type across tested designs were −0.9° C. for CAT-2200 (STDEV=1.4), −4.6° C. for pertuzumab (STDEV=1.6), −5.8° C. for SGN-CD19a (STDEV=3.5), and +1.1° C. for CR8071 (STDEV=0.8). FIG. 13 depicts a box plot of the change in Fab Tm compared to parental antibody for the tested designs, for all designs tested ("All"), or by paratope (CAT-2200, pertuzumab, CR8071, or SGN-CD19a).

Example 20: Antigen Affinity Measurements of Bispecific Antibodies

The ability of the bispecific antibodies to bind the appropriate antigens was assessed in order to determine whether the amino acid substitutions had any effects on antigen binding. The antigen binding affinity was determined by SPR as follows.

SPR Biosensor Assays

For studies on Biacore T200: CM5 Series S sensor chip, Biacore amine coupling kit (NHS, EDC and 1 M ethanolamine), and 10 mM sodium acetate buffers were purchased from GE Healthcare Life Science (Mississauga, ON, Canada). For studies on Biorad ProteOn: GLC sensorchips, the Biorad ProteOn amine coupling kit (EDC, sNHS and ethanolamine), and 10 mM sodium acetate buffers were purchased from Bio-Rad Laboratories (Canada) Ltd. (Mississauga, ON). PBS running buffer with 0.05% Tween20 (PBST) was purchased from Teknova Inc. (Hollister, Calif.). Goat polyclonal anti-human Fc antibody was purchased from Jackson Immuno Research Laboratories Inc. (West Grove, Pa.). Antigens: His-tagged recombinant human CD-19 was purchased from Abcam (Cambridge, UK) and His-tagged Influenza B Hemagglutinin (B/Brisbane/60/2008) was purchased from Sino Biological (Beijing, China). Recombinant Her2 extracellular domain (ECD) protein was purchased from eBioscience (San Diego, Calif.). Recombinant human IL-17A was purchased from R&D Systems (Mineapolis, Minn.).

Surface plasmon resonance (SPR) assays with antigens Hemagglutinin and CD-19 were carried out using a Biacore T200 instrument (GE Healthcare) with PBST running buffer (with 0.5 M EDTA stock solution added to 3.4 mM final concentration) at a temperature of 25° C. Surface plasmon resonance assays with antigens HER2 ECD and IL-17 were carried out using BioRad ProteOn XPR36 instrument (Bio-Rad Laboratories (Canada) Ltd. (Mississauga, ON)) with PB ST running buffer at a temperature of 25C.

SGN-CD19a:CD-19 affinity determination was carried out as follows. The screening of antibodies (preparative SEC purified SMCA samples and OAA controls) for binding to CD-19 antigen occurred in two steps: an indirect capture of His-tagged CD-19 onto the anti-His IgG surface, followed by the injection of five concentrations of purified antibody for kinetic analysis using single cycle kinetics. The anti-His capture surface was prepared on a CMS Series S sensor chip by amine coupling approximately 12000 RUs of anti-His IgG (His Capture Kit, GE Healthcare) onto the active and reference flow cells, according to the manufacturer's instructions. CD-19 was injected at 10 μg/ml over the active flow cell for 60 s at a flow rate of 10 μl/min. In general, this resulted in the capture of approximately 250 RUs of CD-19 onto the anti-His IgG surface. CD-19 was not captured on the reference (blank) flow cell. The capture step was followed by five concentrations of purified antibody (200 nM and 2-fold dilutions, 80 nM and 2-fold dilutions, or 40 nM and 2-fold dilutions; depending on the antibody) that were sequentially injected over both the active and reference flow cells at 40 μl/min for 180 s with a dissociation phase of 600 s. The captured antibody surfaces were regenerated by 10 mM glycine pH 1.5 for 120 s at 30 μl/min to prepare the surfaces for the next injection cycle. At least two mock-buffer injections were performed for each analyte injection and used for referencing. The resulting single cycle kinetics sensorgrams were analyzed using Biacore T200 BiaEvaluation software version 3.0 and fit to the 1:1 binding model.

CR8071:Hemagglutinin affinity determination was carried out as follows. Hemagglutinin (HA) was diluted in 10 mM acetate buffer pH 5.5 and directly immobilized via amine coupling onto a CMS Series S sensor chip. This resulted in approximately 120-130 RUs of immobilized HA. The reference flow cell was left empty (ethanolamine blocked) to use as a blank control. Antibodies were injected over the HA surface for kinetic analysis using single cycle kinetics. Five concentrations (40 nM and 2-fold dilutions) of purified antibody (preparative SEC purified SMCA samples and OAA controls) were sequentially injected over both the active and reference flow cells at 50 μl/min for 300 s with a dissociation phase of 3600 s. HA surfaces were regenerated using 2 cycles of 10 mM glycine pH 1.5 for 120 s at 30 μl/min to prepare the surfaces for the next injection cycle. At least two mock-buffer injections were performed for each analyte injection to be used for referencing. The resulting single cycle kinetics sensorgrams were analyzed using Biacore T200 BiaEvaluation software version 3.0 and fit to the 1:1 binding model.

CAT-2200:IL-17 affinity determination was carried out as previously described in Example 6 with the following modifications: the antibodies tested were preparative SEC purified SMCA samples and OAA controls instead of CAT-2200 Fabs. One of the control antibodies 13612 was injected at starting at 10 nM instead of 60 nM.

Pertuzumab: HER2 affinity determination was carried out as follows. All lines were immobilized horizontally with 25 □g/ml Goat Anti-Human IgG, Fc□ Fragment specific (anti-human Fc). An average of 4058 resonance units (RUs) were immobilized. The anti-human Fc antibody capture surface was generated using a GLC sensorchip activated by a 1:10 dilution of the standard BioRad sNHS/EDC solutions injected for 140 s at 100 μl/min in the analyte (horizontal) direction. Immediately after activation, a 25 μg/ml solution of anti-human Fc antibody in 10 mM NaOAc pH4.5 was injected in the analyte (horizontal) direction at a flow rate of 25 μl/min for 240 s until approximately 4000 resonance units (RUs) were immobilized. Remaining active groups were quenched by a 140s injections of 1M ethanolamine at 30 μl/min for 300s also in the analyte direction to ensure mock-activated interspots are created for blank referencing. The screening of the antibodies for binding to HER2 occurred in two steps: an indirect capture of the antibodies (preparative SEC purified SMCA samples and OAA controls) onto the anti-human IgG (Fc□□Fragment specific) surface in the ligand direction followed by the simultaneous injection of 5 concentrations of purified HER2 ECD and one buffer blank for double referencing in the analyte direction. Firstly, one buffer injection for 30 s at 100 μl/min in the ligand direction was used to stabilize the baseline. For each antibody capture, antibodies were diluted to 2 μg/ml in PB ST. One to five antibodies or controls were simultaneously injected in individual ligand channels for 480 s at flow 25 μl/min. This resulted in a capture of approximately 800-1200 RUs onto the anti-human Fc surface. The first ligand channel was left empty to use as a blank control if required. This capture step was immediately followed by one buffer injection in the analyte direction to stabilize the baseline, and then 100 nM, 33.3 nM, 11.1 nM, 3.7 nM and 0.41 nM HER2 along with a buffer blank were simultaneously injected at 50 μl/min for 120 s with a 300 s dissociation phase. The captured antibody surfaces were regenerated by two 18 s pulse of 0.85% phosphoric acid at 100 μl/min to prepare for the next injection cycle. Sensorgrams were aligned and double-referenced using the buffer blank injection and interspots, and the resulting sensorgrams were analyzed using ProteOn Manager software v3.1. The double-referenced sensorgrams were fit to the Langmuir binding model.

Antigen affinities of the heterodimeric antibodies were assessed with reference to the respective OAA (one-armed) wild-type controls. Antigen affinities were also obtained for the wild-type bispecific antibodies; however, SPR capture of the WT bispecifics can be heterogeneous (e.g. involving capture of mispaired heterodimers), thereby interfering with KD determination. Furthermore, wild-type affinities were measured in OAA formats containing relevant light chain tags present in antibodies. The presence of tags was observed to reduce affinity of SGN-CD-19a for CD19 by as much as 4-5 fold (Table 19). For example, the measured binding affinity of SGN-CD-19a for CD19 decreased from 67.5 nM to 224.5 nM with the addition of a FLAG tag to the light chain (Table 19). Therefore, all calculations of change in affinity relative to wild-type were performed using the median values of matching tagged wild-type constructs.

When measuring binding to CD-19, the sensorgrams of some antibodies could not be fit to a 1:1 binding model. In these cases, antibodies contained large amounts of Chain B' half antibody that are prone to homodimerization, which caused avidity effects and obscured the Fab binding behavior. For the affected antibodies, binding affinities were further assessed in OAA format.

Figure 14:
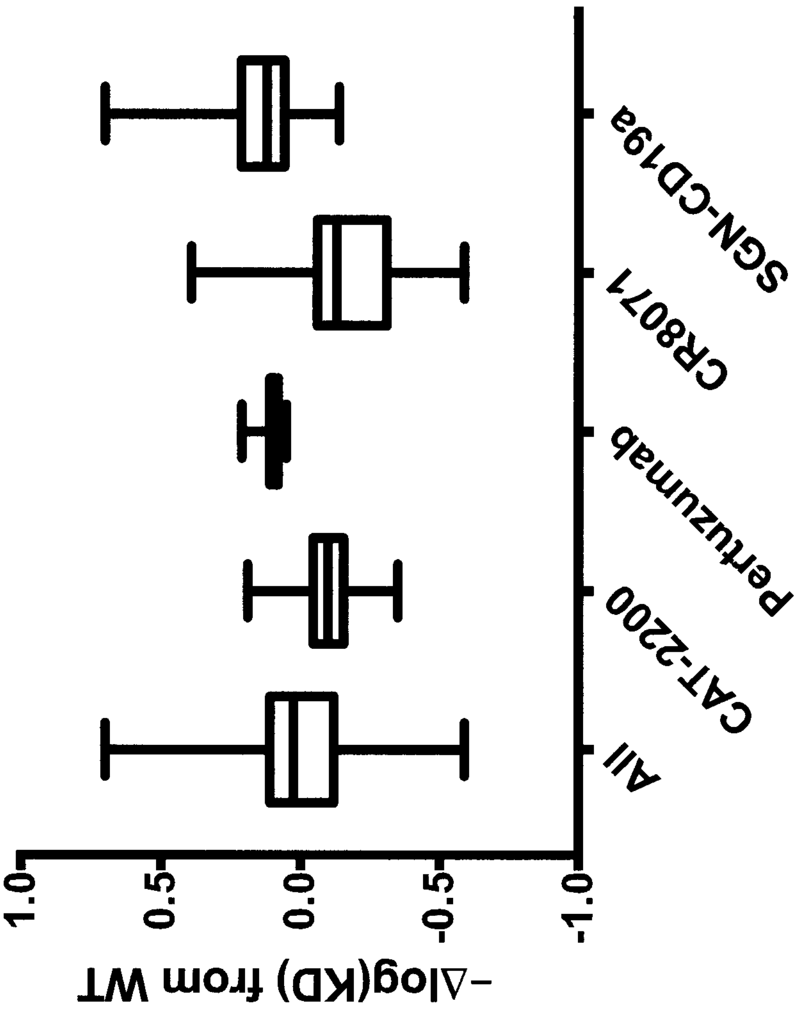
FIG. 14 depicts a min-max box plot summarizing the effect of the amino acid substitutions of Mab designs on the affinity of tested Fabs for its antigen. The results are reported as the difference in log(KD) of the appropriate Fab of the bispecific from WT (−(log(KD_variant)−log(KD_wt)). The results are shown for all designs for which affinity was measured ("All"), and separated by paratope.

The majority of tested designs (36 designs corresponding to 96 bispecific antibodies made) exhibited KD values comparable to those of respective wild-type (Table 20 and 21, FIG. 14). Nine designed Fabs exhibited reduced affinity, between 2- and 3-fold compared to WT, and in a single designed Fab a 4-fold reduction in affinity was observed. Of these 10 Fabs, only one design (#34) was present twice, and 8 out of 10 affected Fabs were CR8071. The average difference in log(KD) from WT (−(log KD_antibody−log KD_wt)) for all warheads possessing designs was 0.003 with a standard deviation of 0.187 (e.g. −0.3 corresponds to 2-fold decrease in affinity, −0.6 corresponds to 4-fold decrease in affinity). These results are summarized in FIG. 14, which depicts a box plot of the change in affinity compared to parental antibody for the tested designs, for all designs tested ("All"), or by paratope (CAT-2200, pertuzumab, CR8071, or SGN-CD19a).

Example 21: UltraPerformance Liquid Chromatography Size Exclusion Chromatography (UPLC-SEC) Profiles of Engineered Bispecific Antibodies Compared to Parental Antibodies To assess the quality of the engineered bispecific antibodies, antibodies purified by preparative SEC as in Example 17 were subjected to UPLC-SEC. UPLC-SEC was performed using a Waters BEH200 SEC column (2.5 mL, 4.6×150 mm, stainless steel, 1.7 μm particles) set to 30° C. and mounted on a Waters Acquity UPLC system with a PDA detector. Run times consisted of 7 min and a total volume per injection of 2.8 mL with a running buffer of PBS and 0.02% Tween 20 pH 7.4 at 0.4 ml/min. Elution was monitored by UV absorbance in the range 210-400 nm, and chromatograms were extracted at 280 nm. Peak integration was performed using Empower 3 software.

Figure 15A:
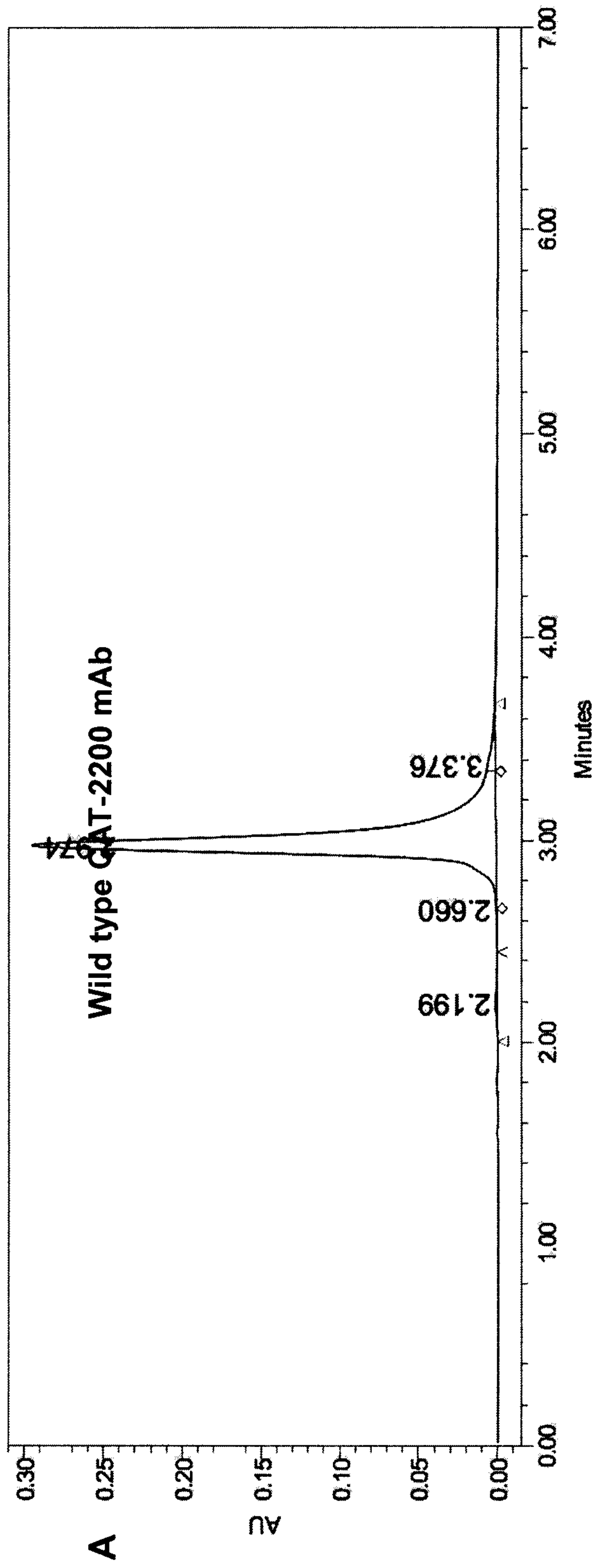
FIG. 15A shows wild-type parent CAT-2200 mAb.
Figure 15B:
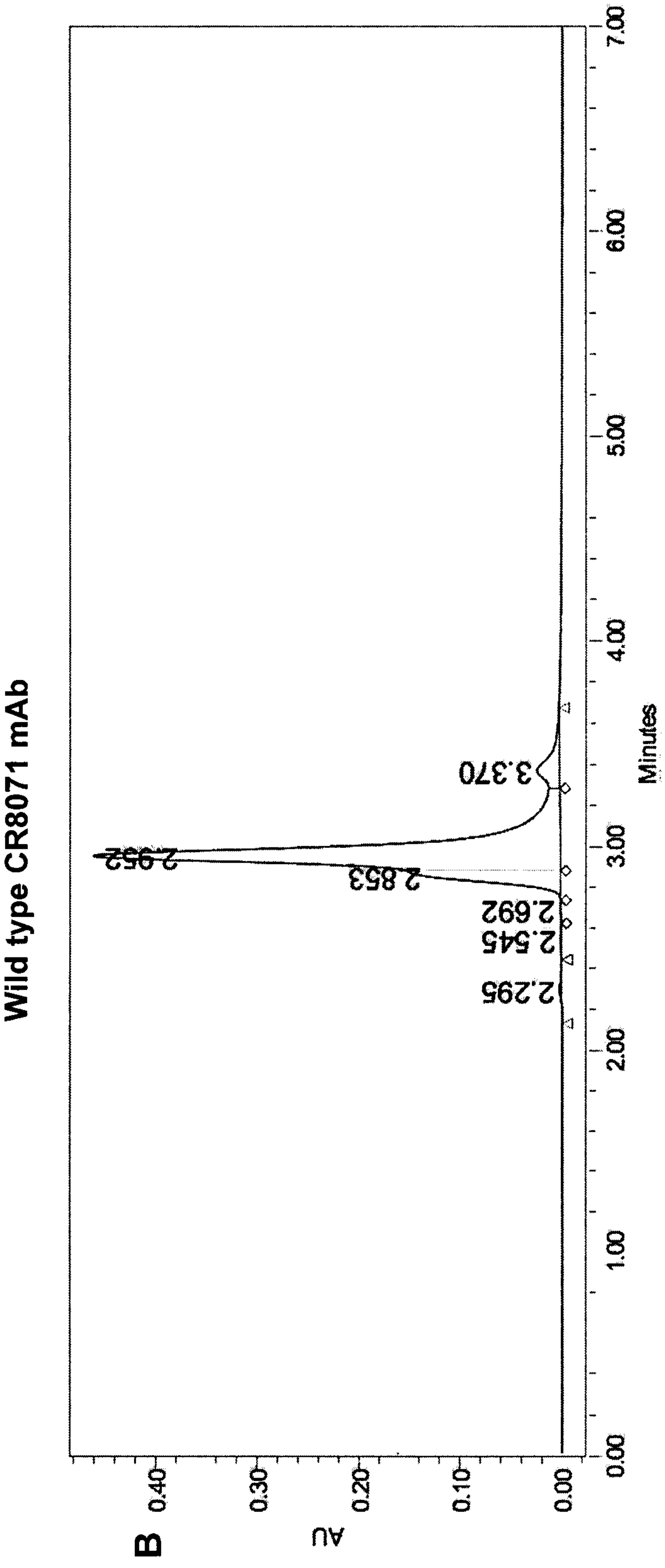
FIG. 15B shows wild-type parent CR8071 mAb.
Figure 15C:
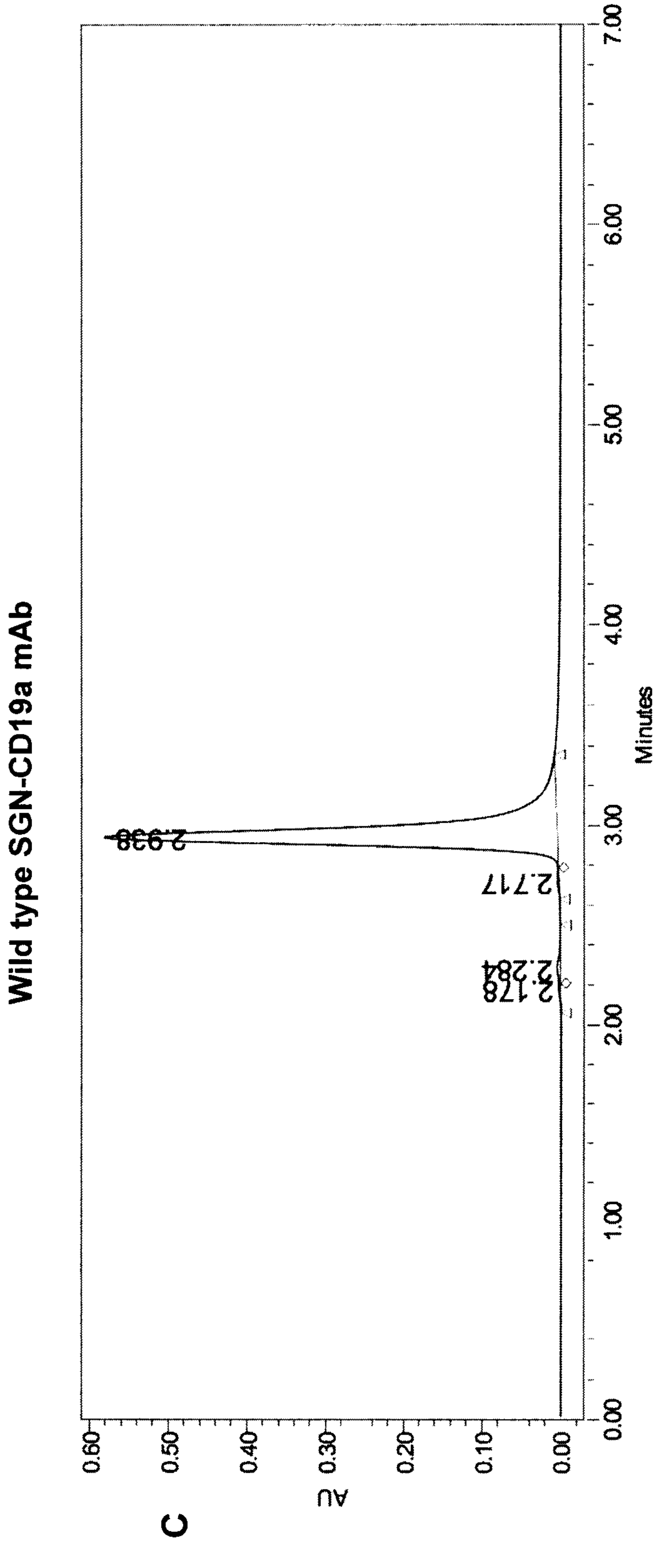
FIG. 15C shows wild-type parent SGN-CD19a mAb.
Figure 15D:
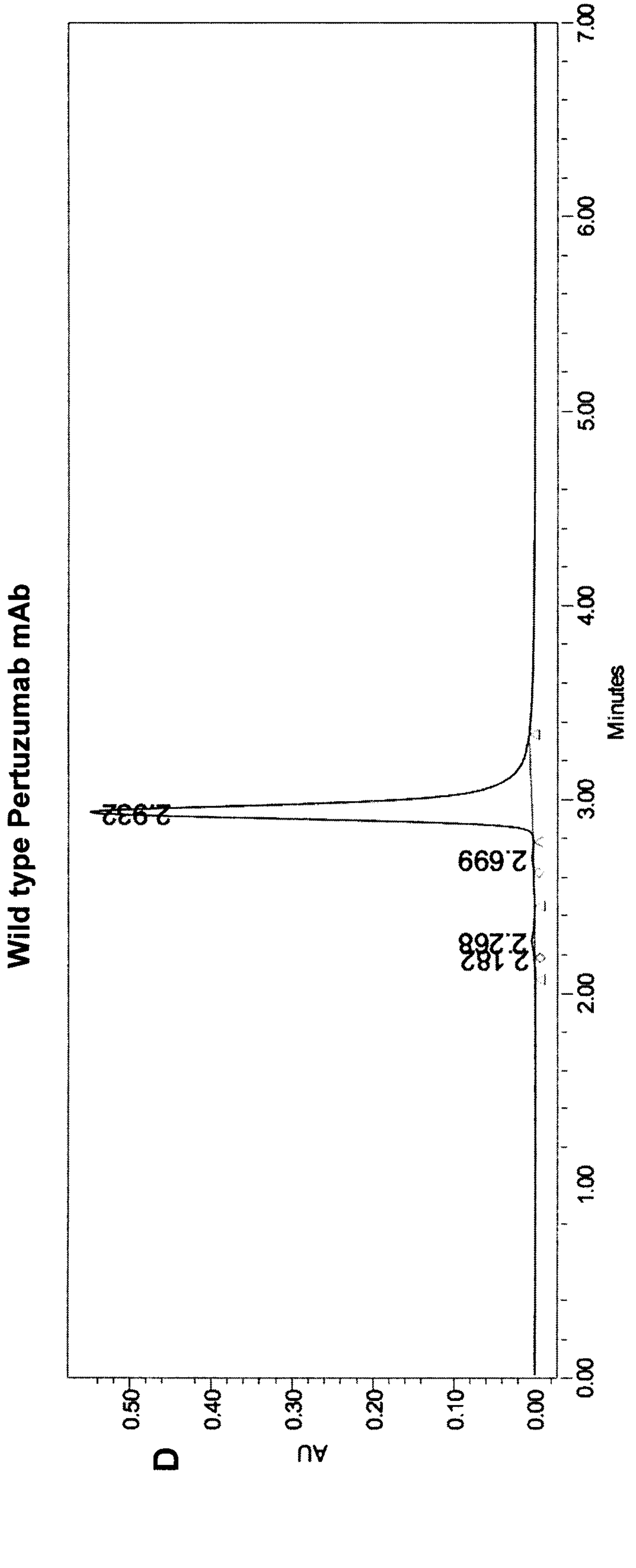
FIG. 15D shows wild-type parent Pertuzumab mAb.
Figure 15E:
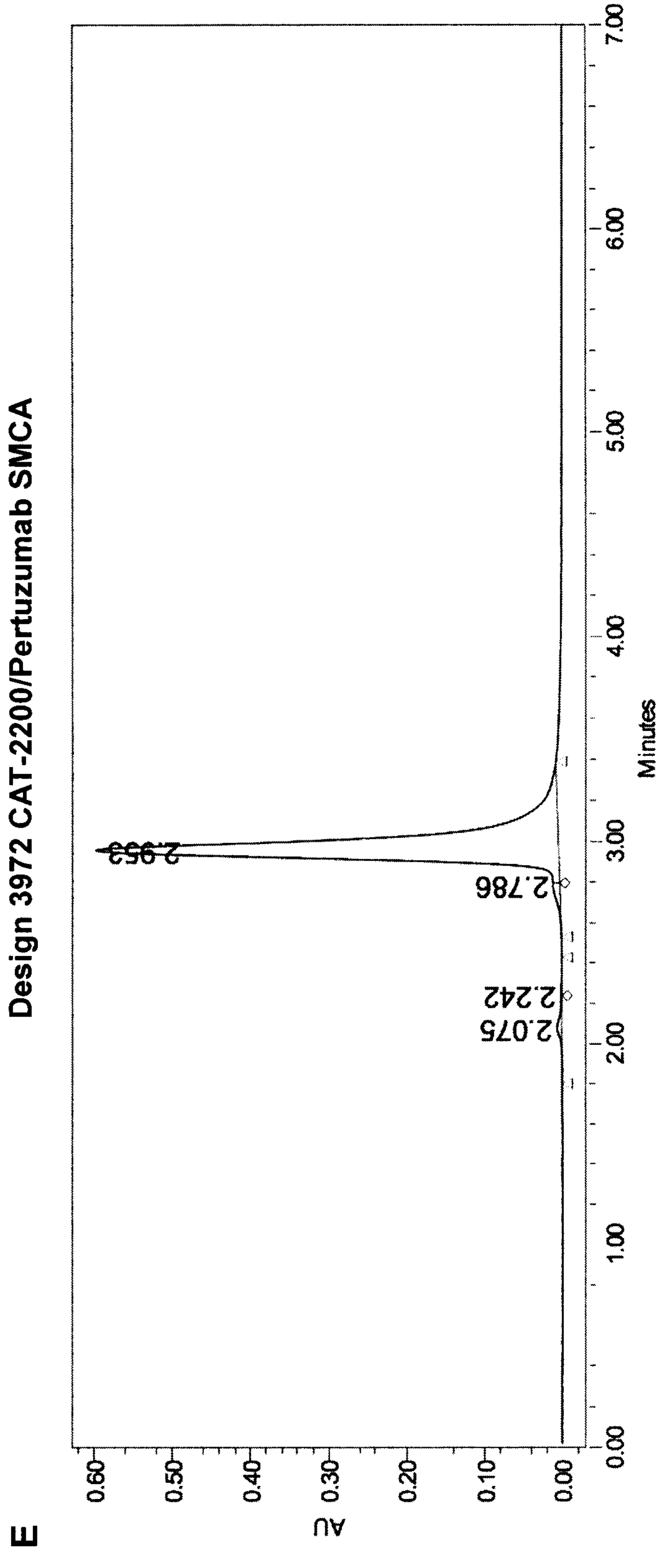
FIG. 15E shows the bispecific antibody generated using design 3972 CAT-2200/Pertuzumab SMCA.
Figure 15F:
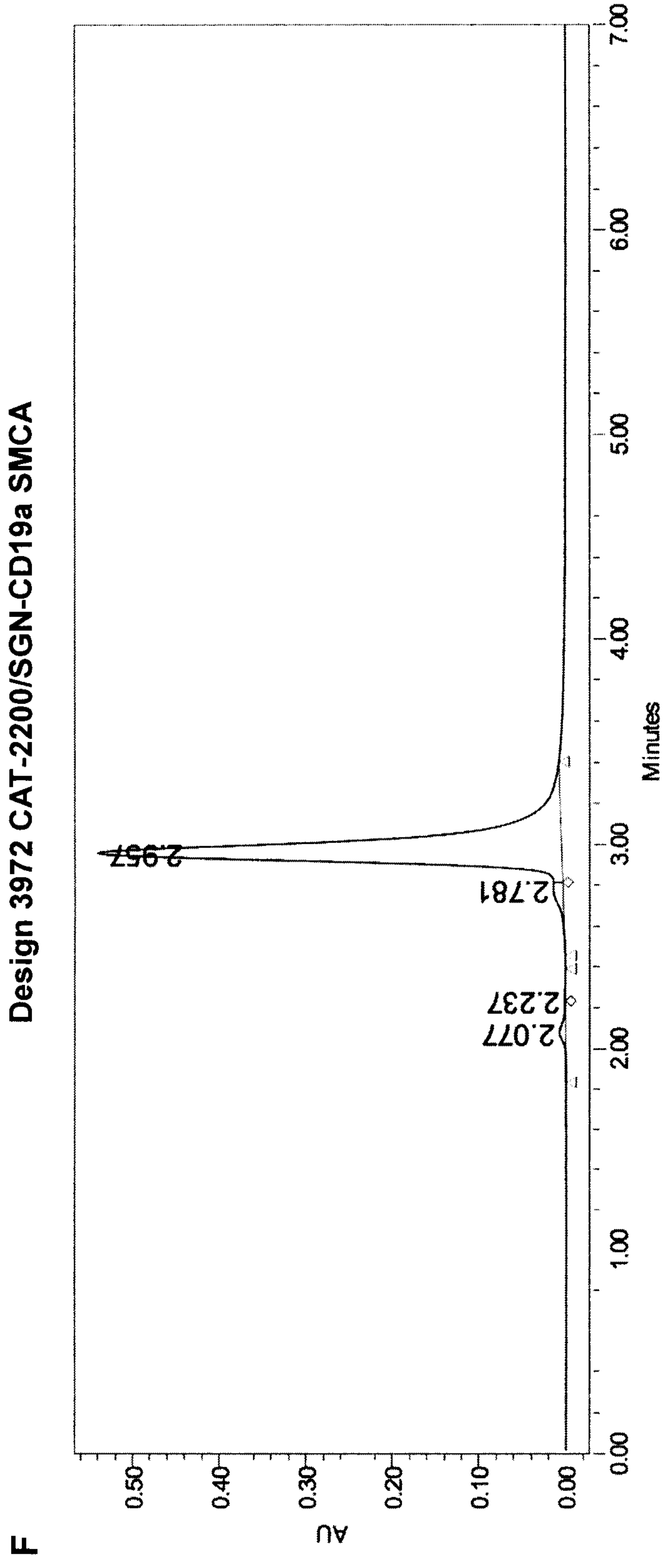
FIG. 15F shows the bispecific antibody generated using design 3972 CAT-2200/SGN-CD19a SMCA.
Figure 15G:
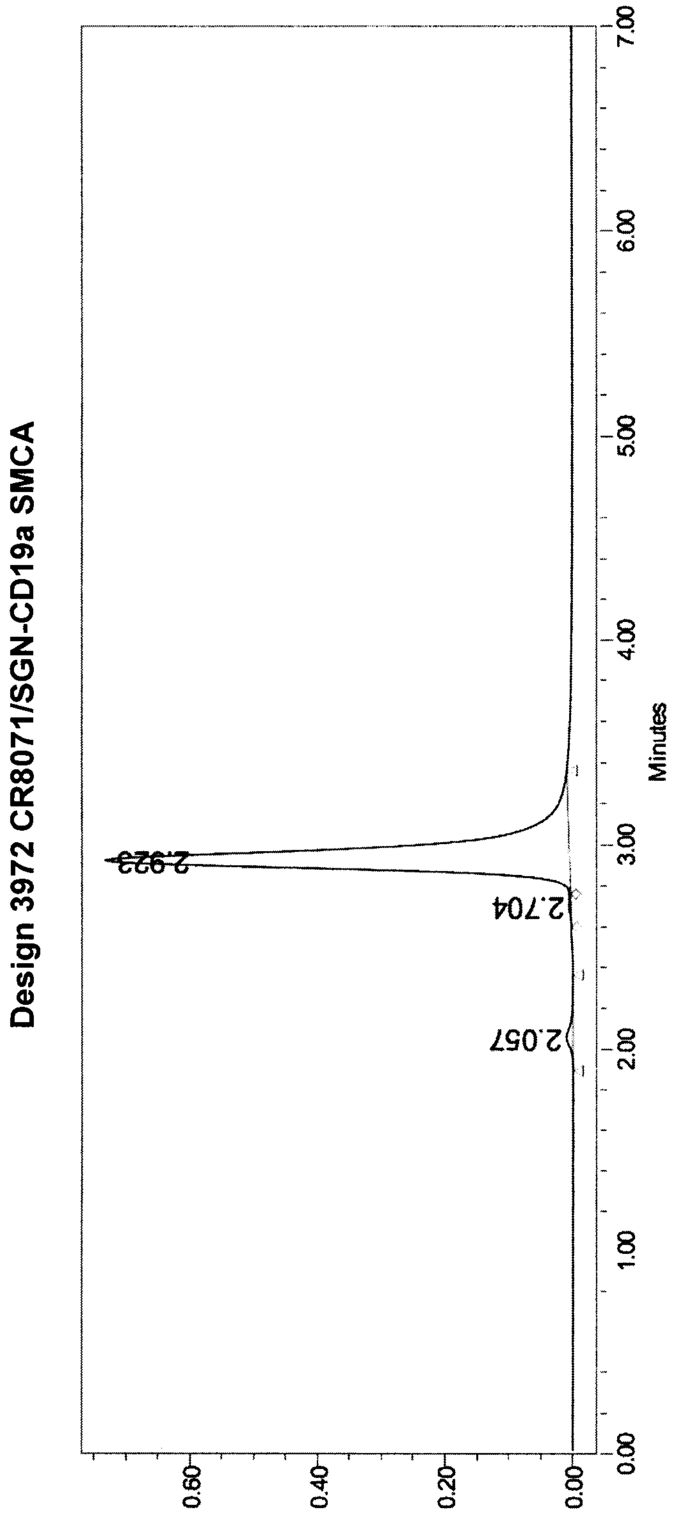
FIG. 15G shows the bispecific antibody generated using design 3972 CR8071/SGN-CD19a SMCA.

FIG. 15A-D depicts UPLC-SEC profiles of parental antibodies and FIG. 15E-G depicts those corresponding to design 3972 antibodies in three bispecific systems. Exemplary design 3972 was used here to demonstrate that the designed/engineered bispecific antibodies of high bispecific content (>80%) have UPLC-SEC profiles that are comparable to those of parental antibodies. For such engineered bispecific antibodies the median percentage of monomer species is 95.2% (i.e. little or no high molecular weight species were detected).

All references, issued patents, patent applications, and sequence accession numbers (e.g., Genbank accession numbers) cited within the body of the instant specification are hereby incorporated by reference in their entirety, for all purposes.

TABLE 1

Criteria for Fab model

| Criteria | Importance |
|---|---|
| Human or humanized IgGI/κ or IgGI/λ | Similarity |
| Has commonly used $V_H$ and $V_L$ subgroups | |
| Framework close to germline | |
| 3D Structure represents a typical kappa or lambda conformation (low pairwise computed RMSD) | |
| Structure available for apo- and complexed Fab | Design |
| No major structural changes observed upon binding antigen | |
| Antigen binding can be readily assayed | Assay |

TABLE 2

Hotspot amino acid positions (marked by asterisk) at the interface of the heavy and light chains in D3H44 (1JPT, a typical Fab containing a kappa light chain) and CAT-2200 (2VXS, a typical Fab containing a lambda light chain).

| 1JPT | 1JPT Hotspot | 2VXS Hotspot | 2VXS |
|---|---|---|---|
| Heavy Chain (Kabat numbering) | | | |
| F122 | * | * | F122 |
| S130 | * | | S130 |
| S134 | * | | S134 |
| A139 | * | | A139 |
| L143 | | * | L143 |
| K145 | * | * | K145 |
| H172 | * | * | H172 |
| F174 | * | * | F174 |
| P175 | * | | P175 |
| V177 | * | * | V177 |
| S188 | | * | S188 |
| K228 | * | * | K228 |
| Light Chain (Kabat numbering) | | | |
| F116 | * | | T116 |
| F118 | * | * | F118 |
| P119 | * | | P119 |
| E123 | * | * | E123 |
| L135 | * | * | L135 |
| N160 | * | * | E160 |
| E161 | | | T161 |
| S162 | * | * | T162 |
| T164 | * | | P164 |
| T178 | | * | Y178 |

TABLE 3A

Kabat numbering of the heavy chain amino acid sequences of D3H44, Pertuzumab, and CAT-2200 Fabs.
Table 3A
Heavy chain origin

| KABAT numbering | D3H44 | Pertuzumab (Seq ID No. 1) | CAT-2200 (Seq ID No. 3) |
|---|---|---|---|
| 1 | E | E | E |
| 2 | V | V | V |
| 3 | Q | Q | Q |
| 4 | L | L | L |
| 5 | V | V | L |
| 6 | E | E | E |
| 7 | S | S | S |
| 8 | G | G | G |
| 9 | G | G | G |
| 10 | G | G | G |
| 11 | L | L | L |
| 12 | V | V | V |
| 13 | Q | Q | Q |
| 14 | P | P | P |
| 15 | G | G | G |
| 16 | G | G | G |

TABLE 3A-continued

Kabat numbering of the heavy chain amino acid sequences of D3H44, Pertuzumab, and CAT-2200 Fabs.
Table 3A
Heavy chain origin

| KABAT numbering | D3H44 | Pertuzumab (Seq ID No. 1) | CAT-2200 (Seq ID No. 3) |
|---|---|---|---|
| 17 | S | S | S |
| 18 | L | L | L |
| 19 | R | R | R |
| 20 | L | L | L |
| 21 | S | S | S |
| 22 | C | C | C |
| 23 | A | A | A |
| 24 | A | A | A |
| 25 | S | S | S |
| 26 | G | G | G |
| 27 | F | F | F |
| 28 | N | T | T |
| 29 | I | F | F |
| 30 | K | T | S |
| 31 | E | D | S |
| 32 | Y | Y | Y |
| 33 | Y | T | A |
| 34 | M | M | M |
| 35 | H | D | S |
| 36 | W | W | W |
| 37 | V | V | V |
| 38 | R | R | R |
| 39 | Q | Q | Q |
| 40 | A | A | A |
| 41 | P | P | P |
| 42 | G | G | G |
| 43 | K | K | K |
| 44 | G | G | G |
| 45 | L | L | L |
| 46 | E | E | E |
| 47 | W | W | W |
| 48 | V | V | V |
| 49 | G | A | S |
| 50 | L | D | A |
| 51 | I | V | I |
| 52 | D | N | S |
| 52A | P | P | G |
| 53 | E | N | S |
| 54 | Q | S | G |
| 55 | G | G | G |
| 56 | N | G | S |
| 57 | T | S | T |
| 58 | I | I | Y |
| 59 | Y | Y | Y |
| 60 | D | N | A |
| 61 | P | Q | D |
| 62 | K | R | S |
| 63 | F | F | V |
| 64 | Q | K | K |
| 65 | D | G | G |
| 66 | R | R | R |
| 67 | A | F | F |
| 68 | T | T | T |
| 69 | I | L | I |
| 70 | S | S | S |
| 71 | A | V | R |
| 72 | D | D | D |
| 73 | N | R | N |
| 74 | S | S | S |
| 75 | K | K | K |
| 76 | N | N | N |
| 77 | T | T | T |
| 78 | A | L | L |
| 79 | Y | Y | Y |
| 80 | L | L | L |
| 81 | Q | Q | Q |
| 82 | M | M | M |
| 82A | N | N | N |
| 82B | S | S | S |
| 82C | L | L | L |
| 83 | R | R | R |
| 84 | A | A | A |

TABLE 3A-continued

Kabat numbering of the heavy chain amino acid sequences of D3H44, Pertuzumab, and CAT-2200 Fabs.
Table 3A
Heavy chain origin

| KABAT numbering | D3H44 | Pertuzumab (Seq ID No. 1) | CAT-2200 (Seq ID No. 3) |
|---|---|---|---|
| 85 | E | E | E |
| 86 | D | D | D |
| 87 | T | T | T |
| 88 | A | A | A |
| 89 | V | V | V |
| 90 | Y | Y | Y |
| 91 | Y | Y | Y |
| 92 | C | C | C |
| 93 | A | A | A |
| 94 | R | R | R |
| 95 | D | N | D |
| 96 | T | L | L |
| 97 | A | G | I |
| 98 | A | P | H |
| 99 | Y | S | G |
| 100 | F | F | V |
| 100A | — | Y | T |
| 100B | — | F | — |
| 101 | D | D | R |
| 102 | Y | Y | N |
| 103 | W | W | W |
| 104 | G | G | G |
| 105 | Q | Q | Q |
| 106 | G | G | G |
| 107 | T | T | T |
| 108 | L | L | L |
| 109 | V | V | V |
| 110 | T | T | T |
| 111 | V | V | V |
| 112 | S | S | S |
| 113 | S | S | S |
| 114 | A | A | A |
| 115 | S | S | S |
| 116 | T | T | T |
| 117 | K | K | K |
| 118 | G | G | G |
| 119 | P | P | P |
| 120 | S | S | S |
| 121 | V | V | V |
| 122 | F | F | F |
| 123 | P | P | P |
| 124 | L | L | L |
| 125 | A | A | A |
| 126 | P | P | P |
| 127 | S | S | S |
| 128 | S | S | S |
| 129 | K | K | K |
| 130 | S | S | S |
| 133 | T | T | T |
| 134 | S | S | S |
| 135 | G | G | G |
| 136 | G | G | G |
| 137 | T | T | T |
| 138 | A | A | A |
| 139 | A | A | A |
| 140 | L | L | L |
| 141 | G | G | G |
| 142 | C | C | C |
| 143 | L | L | L |
| 144 | V | V | V |
| 145 | K | K | K |
| 146 | D | D | D |
| 147 | Y | Y | Y |
| 148 | F | F | F |
| 149 | P | P | P |
| 150 | E | E | Q |
| 151 | P | P | P |
| 152 | V | V | V |
| 153 | T | T | T |
| 154 | V | V | V |
| 156 | S | S | S |
| 157 | W | W | W |

TABLE 3A-continued

Kabat numbering of the heavy chain amino acid sequences of D3H44, Pertuzumab, and CAT-2200 Fabs.
Table 3A
Heavy chain origin

| KABAT numbering | D3H44 | Pertuzumab (Seq ID No. 1) | CAT-2200 (Seq ID No. 3) |
|---|---|---|---|
| 162 | N | N | N |
| 163 | S | S | S |
| 164 | G | G | G |
| 165 | A | A | A |
| 166 | L | L | L |
| 167 | T | T | T |
| 168 | S | S | S |
| 169 | G | G | G |
| 171 | V | V | V |
| 172 | H | H | H |
| 173 | T | T | T |
| 174 | F | F | F |
| 175 | P | P | P |
| 176 | A | A | A |
| 177 | V | V | V |
| 178 | L | L | L |
| 179 | Q | Q | Q |
| 180 | S | S | S |
| 182 | S | S | S |
| 183 | G | G | G |
| 184 | L | L | L |
| 185 | Y | Y | Y |
| 186 | S | S | S |
| 187 | L | L | L |
| 188 | S | S | S |
| 189 | S | S | S |
| 190 | V | V | V |
| 191 | V | V | V |
| 192 | T | T | T |
| 193 | V | V | V |
| 194 | P | P | P |
| 195 | S | S | S |
| 196 | S | S | S |
| 197 | S | S | S |
| 198 | L | L | L |
| 199 | G | G | G |
| 200 | T | T | T |
| 203 | Q | Q | Q |
| 205 | T | T | T |
| 206 | Y | Y | Y |
| 207 | I | I | I |
| 208 | C | C | C |
| 209 | N | N | N |
| 210 | V | V | V |
| 211 | N | N | N |
| 212 | H | H | H |
| 213 | K | K | K |
| 214 | P | P | P |
| 215 | S | S | S |
| 216 | N | N | N |
| 217 | T | T | T |
| 218 | K | K | K |
| 219 | V | V | V |
| 220 | D | D | D |
| 221 | K | K | K |
| 222 | K | K | K |
| 223 | V | V | V |
| 226 | E | E | E |
| 227 | P | P | P |
| 228 | K | K | K |
| 232 | S | S | S |
| 233 | C | C | C |
| 234 | D | D | D |
| 235 | K | K | K |
| 236 | T | T | T |
| 237 | H | H | H |
| 238 | T | T | T |

TABLE 3B

Light chain origin

| KABAT numbering | D3H44 | Pertuzumab (Seq ID No. 2) | CAT-2200 (Seq ID No. 4) |
|---|---|---|---|
| 1 | D | D | N |
| 2 | I | I | F |
| 3 | Q | Q | M |
| 4 | M | M | L |
| 5 | T | T | T |
| 6 | Q | Q | Q |
| 7 | S | S | P |
| 8 | P | P | H |
| 9 | S | S | S |
| 10 | S | S | — |
| 11 | L | L | V |
| 12 | S | S | S |
| 13 | A | A | E |
| 14 | S | S | S |
| 15 | V | V | P |
| 16 | G | G | G |
| 17 | D | D | K |
| 18 | R | R | T |
| 19 | V | V | V |
| 20 | T | T | T |
| 21 | I | I | I |
| 22 | T | T | S |
| 23 | C | C | C |
| 24 | R | K | T |
| 25 | A | A | R |
| 26 | S | S | S |
| 27 | R | Q | S |
| 27A | — | — | G |
| 27B | — | — | S |
| 28 | D | D | L |
| 29 | I | V | A |
| 30 | K | S | N |
| 31 | S | I | Y |
| 32 | Y | G | Y |
| 33 | L | V | V |
| 34 | N | A | Q |
| 35 | W | W | W |
| 36 | Y | Y | Y |
| 37 | Q | Q | Q |
| 38 | Q | Q | Q |
| 39 | K | K | R |
| 40 | P | P | P |
| 41 | G | G | G |
| 42 | K | K | S |
| 43 | A | A | S |
| 44 | P | P | P |
| 45 | K | K | T |
| 46 | V | L | I |
| 47 | L | L | V |
| 48 | I | I | I |
| 49 | Y | Y | F |
| 50 | Y | S | A |
| 51 | A | A | N |
| 52 | T | S | N |
| 53 | S | Y | Q |
| 54 | L | R | R |
| 55 | A | Y | P |
| 56 | E | T | S |
| 57 | G | G | G |
| 58 | V | V | V |
| 59 | P | P | P |
| 60 | S | S | D |
| 61 | R | R | R |
| 62 | F | F | F |
| 63 | S | S | S |
| 64 | G | G | G |
| 65 | S | S | S |
| 66 | G | G | I |
| 66A | — | — | D |
| 66B | — | — | S |
| 67 | S | S | S |
| 68 | G | G | S |
| 69 | T | T | N |
| 70 | D | D | S |
| 71 | Y | F | A |

TABLE 3B-continued

| Light chain origin | | | |
|---|---|---|---|
| KABAT numbering | D3H44 | Pertuzumab (Seq ID No. 2) | CAT-2200 (Seq ID No. 4) |
| 72 | T | T | S |
| 73 | L | L | L |
| 74 | T | T | T |
| 75 | I | I | I |
| 76 | S | S | S |
| 77 | S | S | G |
| 78 | L | L | L |
| 79 | Q | Q | K |
| 80 | P | P | T |
| 81 | E | E | E |
| 82 | D | D | D |
| 83 | F | F | E |
| 84 | A | A | A |
| 85 | T | T | D |
| 86 | Y | Y | Y |
| 87 | Y | Y | Y |
| 88 | C | C | C |
| 89 | L | Q | Q |
| 90 | Q | Q | T |
| 91 | H | Y | Y |
| 92 | G | Y | D |
| 93 | E | I | P |
| 94 | S | Y | Y |
| 95 | P | P | S |
| 96 | W | Y | V |
| 97 | T | T | V |
| 98 | F | F | F |
| 99 | G | G | G |
| 100 | Q | Q | G |
| 101 | G | G | G |
| 102 | T | T | T |
| 103 | K | K | K |
| 104 | V | V | L |
| 105 | E | E | T |
| 106 | I | I | V |
| 106A | — | — | L |
| 107 | K | K | G |
| 108 | R | R | Q |
| 109 | T | T | P |
| 110 | V | V | K |
| 111 | A | A | A |
| 112 | A | A | A |
| 113 | P | P | P |
| 114 | S | S | S |
| 115 | V | V | V |
| 116 | F | F | T |
| 117 | I | I | L |
| 118 | F | F | F |
| 119 | P | P | P |
| 120 | P | P | P |
| 121 | S | S | S |
| 122 | D | D | S |
| 123 | E | E | E |
| 124 | Q | Q | E |
| 125 | L | L | L |
| 126 | K | K | Q |
| 127 | S | S | A |
| 128 | G | G | N |
| 129 | T | T | K |
| 130 | A | A | A |
| 131 | S | S | T |
| 132 | V | V | L |
| 133 | V | V | V |
| 134 | C | C | C |
| 135 | L | L | L |
| 136 | L | L | I |
| 137 | N | N | S |
| 138 | N | N | D |
| 139 | F | F | F |
| 140 | Y | Y | Y |
| 141 | P | P | P |
| 142 | R | R | G |
| 143 | E | E | A |
| 144 | A | A | V |
| 145 | K | K | T |

TABLE 3B-continued

| Light chain origin | | | |
|---|---|---|---|
| KABAT numbering | D3H44 | Pertuzumab (Seq ID No. 2) | CAT-2200 (Seq ID No. 4) |
| 146 | V | V | V |
| 147 | Q | Q | A |
| 148 | W | W | W |
| 149 | K | K | K |
| 150 | V | V | A |
| 151 | D | D | D |
| 152 | N | N | S |
| 153 | A | A | S |
| 154 | L | L | P |
| 155 | Q | Q | V |
| 156 | S | S | K |
| 157 | G | G | A |
| 158 | N | N | G |
| 159 | S | S | V |
| 160 | Q | Q | E |
| 161 | E | E | T |
| 162 | S | S | T |
| 163 | V | V | T |
| 164 | T | T | P |
| 165 | E | E | S |
| 166 | Q | Q | K |
| 167 | D | D | Q |
| 168 | S | S | S |
| 169 | K | K | — |
| 170 | D | D | N |
| 171 | S | S | N |
| 172 | T | T | K |
| 173 | Y | Y | Y |
| 174 | S | S | A |
| 175 | L | L | A |
| 176 | S | S | S |
| 177 | S | S | S |
| 178 | T | T | Y |
| 179 | L | L | L |
| 180 | T | T | S |
| 181 | L | L | L |
| 182 | S | S | T |
| 183 | K | K | P |
| 184 | A | A | E |
| 185 | D | D | Q |
| 186 | Y | Y | W |
| 187 | E | E | K |
| 188 | K | K | S |
| 189 | H | H | H |
| 190 | K | K | R |
| 191 | V | V | S |
| 192 | Y | Y | Y |
| 193 | A | A | S |
| 194 | C | C | C |
| 195 | E | E | Q |
| 196 | V | V | V |
| 197 | T | T | T |
| 198 | H | H | H |
| 199 | Q | Q | E |
| 200 | G | G | G |
| 201 | L | L | — |
| 202 | S | S | — |
| 203 | S | S | S |
| 204 | P | P | T |
| 205 | V | V | V |
| 206 | T | T | E |
| 207 | K | K | K |
| 208 | S | S | T |
| 209 | F | F | V |
| 210 | N | N | A |
| 211 | R | R | P |
| 212 | G | G | T |
| 213 | E | E | E |
| 214 | C | C | C |
| 215 | — | — | S |

TABLE 3C

Amino acid and DNA sequences

| SEQ ID NO: | DESCRIPTION (amino acid residues numbered with respect to sequence) | SEQUENCE |
|---|---|---|
| 1 | Pertuzumab heavy chain Fab (Domain boundaries: VH; E1-S119, CH1; A120-V217, Hinge (partial); E218-T227) | EVQLVESGGGLVQPGGSLRLSCAASGFTFTDYTMDWVRQAPGKGLEWVADVNPNSGGSIYNQRF<br>KGRFTLSVDRSKNTLYLQMNSLRAEDTAVYYCARNLGPSFYFDYWGQGTLVTVSSASTKGPSVFPLA<br>PSSKSTSGGTAALGCLVKDYFPEPVTVSWNSGALTSGVHTFPAVLQSSGLYSLSSVVTVPSSSLGTQ<br>TYICNVNHKPSNTKVDKKVEPKSCDKTHT |
| 2 | Pertuzumab light chain (kappa) (Domain boundaries: VL; D1-K107, CL; R108-C214) | DIQMTQSPSSLSASVGDRVTITCKASQDVSIGVAWYQQKPGKAPKLLIYSASYRYTGVPSRFSGSGS<br>GTDFTLTISSLQPEDFATYYCQQYYIYPYTFGQGTKVEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGL<br>SSPVTKSFNRGEC |
| 3 | CAT-2200 heavy chain Fab (Domain boundaries: VH; E1-S118, CH1; A119-V216, Hinge (partial); E217-T226) | EVQLLESGGGLVQPGGSLRLSCAASGFTFSSYAMSWVRQAPGKGLEWVSAISGSGGSTYYADSVKG<br>RFTISRDNSKNTLYLQMNSLRAEDTAVYYCARDLIHGVTRNWGQGTLVTVSSASTKGPSVFPLAPSS<br>KSTSGGTAALGCLVKDYFPQPVTVSWNSGALTSGVHTFPAVLQSSGLYSLSSVVTVPSSSLGTQTYI<br>CNVNHKPSNTKVDKKVEPKSCDKTHT |
| 4 | CAT-2200 light chain (lambda) (Domain boundaries: VL; N1-L110, CL; G111-S216) | NFMLTQPHSVSESPGKTVTISCTRSSGSLANYYVQWYQQRPGSSPTIVIFANNQRPSGVPDRFSGSI<br>DSSSNSASLTISGLKTEDEADYYCQTYDPYSVVFGGGTKLTVLGQPKAAPSVTLFPPSSEELQANKA<br>TLVCLISDFYPGAVTVAWKADSSPVKAGVETTTPSKQSNNKYAASSYLSLTPEQWKSHRSYSCQVTH<br>EGSTVEKTVAPTECS |
| 5 | IgG1 Fc (Domain boundaries: Hinge (partial); C1-P5, CH2; A6-K115, CH3; G116-K222) | CPPCPAPELLGGPSVFLFPPKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLTVDKSRWQQGNVFSCS<br>VMHEALHNHYTQKSLSLSPGK |
| 6 | IgG1 Fc | TGCCCTCCCTGTCCAGCTCCAGAACTGCTGGGAGGACCTAGCGTGTTCCTGTTTCCCCCTAAGCCA<br>AAAGACACTCTGATGATTTCCAGGACTCCCGAGGTGACCTGCGTGGTGGTGGACGTGTCTCACG<br>AGGACCCCGAAGTGAAGTTCAACTGGTACGTGGATGGCGTGGAAGTGCATAATGCTAAGACAA<br>AACCAAGAGAGGAACAGTACAACTCCACTTATCGCGTCGTGAGCGTGCTGACCGTGCTGCACCA<br>GGACTGGCTGAACGGGAAGGAGTATAAGTGCAAAGTCAGTAATAAGGCCCTGCCTGCTCCAATC<br>GAAAAAACCATCTCTAAGGCCAAAGGCCAGCCAAGGGAGCCCCAGGTGTACACACTGCCACCCA<br>GCAGAGACGAACTGACCAAGAACCAGGTGTCCCTGACATGTCTGGTGAAAGGCTTCTATCCTAG<br>TGATATTGCTGTGGAGTGGGAATCAAATGGACAGCCAGAGAACAATTACAAGACCACACCTCCA<br>GTGCTGGACAGCGATGGCAGCTTCTTCCTGTATTCCAAGCTGACAGTGGATAAATCTCGATGGCA<br>GCAGGGGAACGTGTTTAGTTGTTCAGTGATGCATGAAGCCCTGCACAATCATTACACTCAGAAG<br>AGCCTGTCCCTGTCTCCCGGCAAA |
| 7 | Pertuzumab heavy chain Fab | GAAGTGCAGCTGGTCGAATCTGGAGGAGGACTGGTGCAGCCAGGAGGGTCCCTGCGCCTGTCTT<br>GCGCCGCTAGTGGCTTCACTTTTACCGACTACACCATGGATTGGGTGCGACAGGCACCTGGAAA<br>GGGCCTGGAGTGGGTCGCCGATGTGAACCCAAATAGCGGAGGCTCCATCTACAACCAGCGGTTC<br>AAGGGCCGGTTCACCCTGTCAGTGGACCGGAGCAAAAACACCCTGTATCTGCAGATGAATAGCC<br>TGCGAGCCGAAGATACTGCTGTGTACTATTGCGCCCGGAATCTGGGGCCCTCCTTCTACTTTGACT<br>ATTGGGGGCAGGGAACTCTGGTCACCGTGAGCTCCGCCTCCACCAAGGGACCTTCTGTGTTCCCA<br>CTGGCTCCCTCTAGTAAATCCACATCTGGGGGAACTGCAGCCCTGGGCTGTCTGGTGAAGGACTA<br>CTTCCCAGAGCCCGTCACAGTGTCTTGGAACAGTGGCGCTCTGACTTCTGGGGTCCACACCTTTCC |

TABLE 3C-continued

Amino acid and DNA sequences

| SEQ ID NO: | DESCRIPTION (amino acid residues numbered with respect to sequence) | SEQUENCE |
|---|---|---|
| | | TGCAGTGCTGCAGTCAAGCGGGCTGTACAGCCTGTCCTCTGTGGTCACCGTGCCAAGTTCAAGCC TGGGAACACAGACTTATATCTGCAACGTGAATCACAAGCCATCCAATACAAAAGTCGACAAGAA AGTGGAACCCAAGTCTTGTGATAAAACCCATACA |
| 8 | Pertuzumab light chain (kappa) | GATATTCAGATGACCCAGTCCCCAAGCTCCCTGAGTGCCTCAGTGGGCGACCGAGTCACCATCAC ATGCAAGGCTTCCCAGGATGTGTCTATTGGAGTCGCATGGTACCAGCAGAAGCCAGGCAAAGCA CCCAAGCTGCTGATCTATAGCGCCTCCTACCGGTATACCGGCGTGCCCTCTAGATTCTCTGGCAGT GGGTCAGGAACAGACTTTACTCTGACCATCTCTAGTCTGCAGCCTGAGGATTTCGCTACCTACTAT TGCCAGCAGTACTATATCTACCCATATACCTTTGGCCAGGGGACAAAAGTGGAGATCAAGAGGA CTGTGGCCGCTCCCTCCGTCTTCATTTTTCCCCCTTCTGACGAACAGCTGAAAAGTGGCACAGCCA GCGTGGTCTGTCTGCTGAACAATTTCTACCCTCGCGAAGCCAAAGTGCAGTGGAAGGTCGATAA CGCTCTGCAGAGCGGCAACAGCCAGGAGTCTGTGACTGAACAGGACAGTAAAGATTCAACCTAT AGCCTGTCAAGCACACTGACTCTGAGCAAGGCAGACTACGAGAAGCACAAAGTGTATGCCTGCG AAGTCACACATCAGGGGCTGTCCTCTCCTGTGACTAAGAGCTTTAACAGAGGAGAGTGT |
| 9 | CAT-2200 heavy chain Fab | GAGGTGCAGCTGCTGGAATCTGGGGGGGGCCTGGTGCAGCCTGGGGGGTCCCTGAGACTGTCA TGTGCTGCCAGCGGGTTTACTTTCAGCTCCTACGCTATGTCCTGGGTGCGACAGGCACCCGGGAA GGGACTGGAGTGGGTCTCTGCAATCAGTGGGTCAGGCGGGAGTACTTACTATGCCGACAGCGT GAAGGGACGGTTCACTATCTCAAGAGATAACAGCAAGAACACCCTGTATCTGCAGATGAACAGC CTGAGAGCAGAAGACACAGCCGTGTACTATTGCGCCAGGGATCTGATCCACGGAGTCACTCGCA ATTGGGGCCAGGGGACTCTGGTGACCGTCTCTAGTGCTAGCACAAAGGGGCCCTCTGTGTTTCCA CTGGCCCCCTCAAGCAAAAGCACATCCGGAGGAACTGCAGCTCTGGGATGTCTGGTGAAGGACT ACTTCCCCCAGCCTGTGACCGTCTCTTGGAACAGTGGAGCCCTGACCAGCGGCGTGCACACATTT CCTGCTGTCCTGCAGTCCTCTGGCCTGTACTCCCTGAGTTCAGTGGTCACAGTGCCTAGCTCCTCTC TGGGGACCCAGACATATATTTGCAACGTGAATCATAAACCAAGCAACACTAAGGTCGACAAGAA AGTGGAGCCCAAGAGCTGTGATAAAACTCATACC |
| 10 | CAT-2200 light chain (lambda) | AACTTTATGCTGACTCAGCCCCACTCCGTGTCCGAGAGCCCTGGCAAAACTGTGACTATTTCATGT ACCCGATCATCTGGAAGCCTGGCCAACTACTATGTGCAGTGGTACCAGCAGAGGCCAGGCAGCT CCCCCACTATCGTGATTTTCGCTAACAATCAGCGGCCTTCCGGCGTCCCAGACAGATTTTCCGGGT CTATCGATTCTAGTTCAAATAGTGCATCACTGACTATTTCCGGGCTGAAGACCGAGGACGAAGCC GATTACTATTGCCAGACCTACGACCCCTATTCTGTGGTCTTCGGCGGGGGAACCAAGCTGACAGT GCTGGGACAGCCAAAAGCGGCGCCCAGTGTCACACTGTTTCCCCCTAGCTCCGAGGAACTGCAG GCTAACAAAGCAACACTGGTGTGTCTGATCAGCGACTTCTACCCTGGAGCTGTGACTGTCGCCTG GAAGGCTGATTCTAGTCCAGTGAAAGCAGGCGTCGAGACCACAACTCCCTCTAAGCAGAGTAAC AACAAGTACGCAGCCTCAAGCTATCTGTCACTGACCCCAGAACAGTGGAAGAGCCACCGGAGCT ATTCCTGCCAGGTCACTCACGAAGGCTCCACTGTCGAGAAAACCGTCGCTCCCACCGAATGTTCA |
| 11 | Human IgG1 Fc sequence 231-447 (EU-numbering), without hinge | APELLGGPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRDELTKNQV SLTCLVKGFYPSDIAVEWESNGQPENNYKTTPPVLDSDGSFFLYSKLTVDKSRWQQGNVFSCSVMH EALHNHYTQKSLSLSPGK |
| 12 | SGN-CD19a heavy chain Fab (Domain boundaries: VH; Q1-S120, CH1; A121-V218, Hinge (partial); E219-T228) | QVTLRESGPALVKPTQTLTLTCTFSGFSLSTSGMGVGWIRQPPGKALEWLAHIWWDDDKRYNPALK SRLTISKDTSKNQVVLTMTNMDPVDTAAYYCARMELWSYYFDYWGQGTLVTVSSASTKGPSVFPL APSSKSTSGGTAALGCLVKDYFPEPVTVSWNSGALTSGVHTFPAVLQSSGLYSLSSVVTVPSSSLGT QTYICNVNHKPSNTKVDKKVEPKSCDKTHT |
| 13 | SGN-CD19a light chain (kappa) (Domain boundaries: VL; E1-K106, CL; R107-C213) | EIVLTQSPATLSLSPGERATLSCSASSSVSYMHWYQQKPGQAPRLLIYDTSKLASGIPARFSGSGSG TDFTLTISSLEPEDFAVYYCFQGSVYPFTFGQGTKLEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLS SPVTKSFNRGEC |

TABLE 3C-continued

Amino acid and DNA sequences

| SEQ ID NO: | DESCRIPTION (amino acid residues numbered with respect to sequence) | SEQUENCE |
|---|---|---|
| 14 | CR8071 heavy chain Fab (Domain boundaries: VH; Q1-S125, CH1; A126-V223, Hinge (partial); E224-T233) | QVQLVQSGAEVKKPGASVRVSCRASGYIFTESGITWVRQAPGQGLEWMGWISGYSGDTKYAQKL QGRVTMTKDTSTTTAYMELRSLRYDDTAVYYCARDVQYSGSYLGAYYFDYWSPGTLVTVSSASTKG PSVFPLAPSSKSTSGGTAALGCLVKDYFPEPVTVSWNSGALTSGVHTFPAVLQSSGLYSLSSVVTVP SSSLGTQTYICNVNHKPSNTKVDKKVEPKSCDKTHT |
| 15 | CR8071 light chain (lambda) (Domain boundaries: VL; Q1-L110, CL; R111-S216) | QSVLTQPPSASGTPGQRVTISCSGSSSNIGTNYVYWYQQFPGTAPKLLIYRSYQRPSGVPDRFSGSK SGSSASLAISGLQSEDEADYYCATWDDSLDGWVFGGGTKLTVLRQPKAAPSVTLFPPSSEELQANKA TLVCLISDFYPGAVTVAWKADSSPVKAGVETTTPSKQSNNKYAASSYLSLTPEQWKSHRSYSCQVTH EGSTVEKTVAPTECS |
| 16 | SGN-CD19a heavy chain Fab | CAGGTGACACTGAGAGAATCCGGCCCAGCCCTGGTGAAGCCCACTCAGACCCTGACACTGACTT GCACCTTCTCTGGGTTTTCCCTGTCTACAAGTGGGATGGGAGTGGGATGGATCAGGCAGCCACCT GGAAAAGCCCTGGAGTGGCTGGCTCACATTTGGTGGGACGATGACAAGCGGTACAACCCAGCA CTGAAAAGCAGACTGACAATCAGCAAGGATACTTCCAAAAACCAGGTGGTCCTGACAATGACTA ATATGGACCCCGTGGACACAGCCGCTTACTATTGCGCCCGCATGGAACTGTGGAGCTACTATTTC GACTACTGGGGGCAGGGAACACTGGTCACTGTGAGCTCCGCTAGCACTAAGGGGCCTTCCGTGT TTCCACTGGCTCCCTCTAGTAAATCCACCTCTGGAGGCACAGCTGCACTGGGATGTCTGGTGAAG GATTACTTCCCTGAACCAGTCACAGTGAGTTGGAACTCAGGGGCTCTGACAAGTGGAGTCCATA CTTTTCCCGCAGTGCTGCAGTCAAGCGGACTGTACTCCCTGTCCTCTGTGGTCACCGTGCCTAGTT CAAGCCTGGGCACCCAGACATATATCTGCAACGTGAATCACAAGCCATCAAATACAAAAGTCGA CAAGAAAGTGGAGCCCAAGAGCTGTGATAAAACTCATACC |
| 17 | SGN-CD19a light chain (kappa) | GAGATCGTGCTGACCCAGTCTCCAGCCACACTGTCTCTGAGCCCAGGAGAGAGGGCCACCCTGTC CTGCTCTGCCAGCTCCAGCGTGAGCTACATGCACTGGTATCAGCAGAAGCCAGGACAGGCCCCT AGGCTGCTGATCTACGACACCAGCAAGCTGGCCTCCGGCATCCCCGCAAGATTCAGCGGCTCCG GCTCTGGCACAGACTTTACCCTGACAATCAGCTCCCTGGAGCCTGAGGATTTCGCCGTGTACTATT GTTTTCAGGGCAGCGTGTATCCATTCACCTTTGGCCAGGGCACAAAGCTGGAGATCAAGCGGAC AGTGGCGGCGCCCAGTGTCTTCATTTTTCCCCCTAGCGACGAACAGCTGAAGTCTGGGACAGCCA GTGTGGTCTGTCTGCTGAACAACTTCTACCCTAGAGAGGCTAAAGTGCAGTGGAAGGTCGATAA CGCACTGCAGTCCGGAAATTCTCAGGAGAGTGTGACTGAACAGGACTCAAAAGATAGCACCTAT TCCCTGTCAAGCACACTGACTCTGAGCAAGGCCGACTACGAGAAGCATAAAGTGTATGCTTGTG AAGTCACCCACCAGGGGCTGAGTTCACCAGTCACAAAATCATTCAACAGAGGGGAGTGC |
| 18 | CR8071 heavy chain Fab | CAGGTGCAGCTGGTCCAGTCCGGGGCTGAAGTGAAAAAACCTGGGGCATCCGTGCGGGTGTCA TGTCGGGCAAGCGGGTATATCTTTACTGAGTCTGGAATCACCTGGGTGAGGCAGGCTCCCGGAC AGGGACTGGAATGGATGGGATGGATTTCTGGATACAGTGGCGACACAAAGTATGCACAGAAAC TGCAGGGCCGCGTCACCATGACAAAGGATACTTCAACCACAACTGCCTACATGGAGCTGCGGAG CCTGAGATATGACGATACAGCCGTGTACTATTGCGCCCGGGACGTGCAGTACAGCGGGTCCTAC CTGGGGGCATACTACTTCGATTACTGGTCACCTGGAACTCTGGTCACCGTCTCTTCAGCTAGCACC AAGGGCCCTTCTGTGTTTCCACTGGCACCCTCAAGCAAAAGCACCTCCGGAGGAACAGCAGCACT GGGATGTCTGGTCAAGGACTATTTCCCCGAGCCTGTGACCGTCTCATGGAATAGCGGCGCACTG ACTAGTGGGGTGCACACCTTTCCCGCCGTCCTGCAGTCCTCTGGGCTGTACAGCCTGAGTTCAGT GGTCACAGTGCCAAGCTCCTCTCTGGGAACTCAGACCTATATCTGCAACGTCAATCATAAACCCA GCAACACAAAGGTCGACAAGAAAGTGGAGCCCAAGAGCTGTGATAAAACTCATACC |
| 19 | CR8071 light chain (lambda) | CAGAGCGTCCTGACTCAGCCTCCCTCCGCCTCCGGAACACCTGGGCAGAGAGTGACTATCTCCTG TAGCGGATCAAGCTCAAACATTGGAACCAACTACGTGTATTGGTACCAGCAGTTCCCCGGCACA GCTCCTAAGCTGCTGATCTATCGGAGCTACCAGAGACCAAGCGGGGTCCCCGACAGGTTTTCTGG CAGTAAATCAGGGAGCTCCGCCAGCCTGGCTATTTCCGGCCTGCAGTCTGAGGACGAAGCAGAT TACTATTGCGCCACCTGGGACGATTCCCTGGATGGATGGGTCTTCGGCGGCGGCACAAAACTGA CCGTCCTGAGGCAGCCAAAGGCGGCGCCCAGTGTCACACTGTTTCCCCCTAGCTCCGAGGAACTG CAGGCTAACAAAGCAACACTGGTGTGTCTGATCAGCGACTTCTACCCTGGAGCTGTGACTGTCGC CTGGAAGGCTGATTCTAGTCCAGTGAAAGCAGGCGTCGAGACCACAACTCCCTCTAAGCAGAGT AACAACAAGTACGCAGCCTCAAGCTATCTGTCACTGACCCCAGAACAGTGGAAGAGCCACCGGA GCTATTCCTGCCAGGTCACTCACGAAGGCTCCACTGTCGAGAAAACCGT CGCTCCCACCGAATGTTCA |

TABLE 4A

| K-L design libary | | | | | | |
|---|---|---|---|---|---|---|
| Unique identifier | H1 mutation (Kabat) | L1 mutation (Kabat) | H2 mutation (Kabat) | L2 mutation (Kabat) | H1L1 Fab | H2L2 Fab |
| 10771-11335 | — | — | S186I_S188W | S176V | CAT-2200 | Pertuzumab |
| 10771-11360 | — | — | S186L_S188W | S176V | CAT-2200 | Pertuzumab |
| 10776-11312 | D146T_V177D_S188D | S176K_Y178R | L143K | V133D | CAT-2200 | Pertuzumab |
| 10776-11321 | D146T_V177D_S188D | S176K_Y178R | L143S_S186K_S188T | V133D | CAT-2200 | Pertuzumab |
| 10776-11353 | D146T_V177D_S188D | S176K_Y178R | S186K_S188T | V133D | CAT-2200 | Pertuzumab |
| 10780-11417 | F174G | S176F | V190F | — | CAT-2200 | Pertuzumab |
| 10781-11300 | F174G | S176F | L143I_V190F | L135A | CAT-2200 | Pertuzumab |
| 10781-11419 | F174G | S176F | V190F | L135A | CAT-2200 | Pertuzumab |
| 10786-11299 | F174G | T116F_S176F | L143I_V190F | — | CAT-2200 | Pertuzumab |
| 10786-11418 | F174G | T116F_S176F | V190F | — | CAT-2200 | Pertuzumab |
| 10787-11301 | F174G | T116F_S176F | L143I_V190F | L135A | CAT-2200 | Pertuzumab |
| 10787-11420 | F174G | T116F_S176F | V190F | L135A | CAT-2200 | Pertuzumab |
| 10788-11422 | F174G | T116F_S176F | V190F | L135A_T178F | CAT-2200 | Pertuzumab |
| 10792-11305 | F174G | T116F_S176F | L143I_V190F | T178F | CAT-2200 | Pertuzumab |
| 10792-11424 | F174G | T116F_S176F | V190F | T178F | CAT-2200 | Pertuzumab |
| 10793-11375 | F174G | T116F_S176F | S188F | V133A | CAT-2200 | Pertuzumab |
| 10795-11390 | K145T_S188E | Y178K | S188K | S176D_T178E | CAT-2200 | Pertuzumab |
| 10796-11396 | K145T_S188E | Y178K | S188K | S176E_T178E | CAT-2200 | Pertuzumab |
| 10798-11256 | K145T_S188E | Y178K | L124R_Q179K | V133G_S176D_T180E | CAT-2200 | Pertuzumab |
| 10798-11268 | K145T_S188E | Y178K | L124R_S186R | V133G_S176D_T180E | CAT-2200 | Pertuzumab |
| 10800-11416 | K145T_S188E | Y178K | V177I_S188K | V133L_S176D_T178E | CAT-2200 | Pertuzumab |
| 10806-11326 | K145T_V177D_S188D | S176K_Y178K | Q179K | Q124E_Q160E_T180E | CAT-2200 | Pertuzumab |
| 10806-11369 | K145T_V177D_S188D | S176K_Y178K | S186R | Q124E_Q160E_T180E | CAT-2200 | Pertuzumab |
| 10808-11308 | K145T_V177D_S188D | S176K_Y178K | L143K | Q124E_V133D | CAT-2200 | Pertuzumab |
| 10808-11315 | K145T_V177D_S188D | S176K_Y178K | L143R | Q124E_V133D | CAT-2200 | Pertuzumab |
| 10809-11378 | K145T_V177D_S188D | S176K_Y178K | S188K | S131D_V133G_T178F | CAT-2200 | Pertuzumab |
| 10810-11383 | K145T_V177D_S188D | S176K_Y178K | S188K | S131E_V133G_T178F | CAT-2200 | Pertuzumab |
| 10811-11386 | K145T_V177D_S188D | S176K_Y178K | S188K | S176D_T178E | CAT-2200 | Pertuzumab |
| 10812-11393 | K145T_V177D_S188D | S176K_Y178K | S188K | S176E_T178E | CAT-2200 | Pertuzumab |
| 10813-11311 | K145T_V177D_S188D | S176K_Y178K | L143K | V133D | CAT-2200 | Pertuzumab |
| 10813-11320 | K145T_V177D_S188D | S176K_Y178K | L143S_S186K_S188T | V133D | CAT-2200 | Pertuzumab |
| 10813-11352 | K145T_V177D_S188D | S176K_Y178K | S186K_S188T | V133D | CAT-2200 | Pertuzumab |
| 10814-11233 | K145T_V177D_S188D | S176K_Y178K | L124R | V133G_S176D | CAT-2200 | Pertuzumab |
| 10816-11253 | K145T_V177D_S188D | S176K_Y178K | L124R_Q179K | V133G_S176D_T180E | CAT-2200 | Pertuzumab |
| 10816-11265 | K145T_V177D_S188D | S176K_Y178K | L124R_S186R | V133G_S176D_T180E | CAT-2200 | Pertuzumab |
| 10818-11404 | K145T_V177D_S188D | S176K_Y178K | V177I_S188K | V133I_S176D_T178E | CAT-2200 | Pertuzumab |
| 10819-11407 | K145T_V177D_S188D | S176K_Y178K | V177I_S188K | V133I_S176E_T178E | CAT-2200 | Pertuzumab |
| 10820-11413 | K145T_V177D_S188D | S176K_Y178K | V177I_S188K | V133L_S176D_T178E | CAT-2200 | Pertuzumab |
| 10827-11373 | K145T_V177D_S188D | S176K_Y178L | S186R_S188W | Q124E_Q160E_S176A_T178A_T180E | CAT-2200 | Pertuzumab |
| 10828-11327 | K145T_V177D_S188D | S176K_Y178L | Q179K | Q124E_Q160E_T180E | CAT-2200 | Pertuzumab |
| 10828-11370 | K145T_V177D_S188D | S176K_Y178L | S186R | Q124E_Q160E_T180E | CAT-2200 | Pertuzumab |
| 10830-11309 | K145T_V177D_S188D | S176K_Y178L | L143K | Q124E_V133D | CAT-2200 | Pertuzumab |
| 10830-11316 | K145T_V177D_S188D | S176K_Y178L | L143R | Q124E_V133D | CAT-2200 | Pertuzumab |
| 10831-11379 | K145T_V177D_S188D | S176K_Y178L | S188K | S131D_V133G_T178F | CAT-2200 | Pertuzumab |
| 10832-11384 | K145T_V177D_S188D | S176K_Y178L | S188K | S131E_V133G_T178F | CAT-2200 | Pertuzumab |
| 10833-11387 | K145T_V177D_S188D | S176K_Y178L | S188K | S176D_T178E | CAT-2200 | Pertuzumab |
| 10834-11394 | K145T_V177D_S188D | S176K_Y178L | S188K | S176E_T178E | CAT-2200 | Pertuzumab |
| 10835-11234 | K145T_V177D_S188D | S176K_Y178L | L124R | V133G_S176D | CAT-2200 | Pertuzumab |
| 10837-11254 | K145T_V177D_S188D | S176K_Y178L | L124R_Q179K | V133G_S176D_T180E | CAT-2200 | Pertuzumab |
| 10837-11266 | K145T_V177D_S188D | S176K_Y178L | L124R_S186R | V133G_S176D_T180E | CAT-2200 | Pertuzumab |
| 10840-11408 | K145T_V177D_S188D | S176K_Y178L | V177I_S188K | V133I_S176E_T178E | CAT-2200 | Pertuzumab |
| 10848-11328 | K145T_V177D_S188D | S176K_Y178R | Q179K | Q124E_Q160E_T180E | CAT-2200 | Pertuzumab |
| 10848-11371 | K145T_V177D_S188D | S176K_Y178R | S186R | Q124E_Q160E_T180E | CAT-2200 | Pertuzumab |
| 10850-11310 | K145T_V177D_S188D | S176K_Y178R | L143K | Q124E_V133D | CAT-2200 | Pertuzumab |
| 10850-11317 | K145T_V177D_S188D | S176K_Y178R | L143R | Q124E_V133D | CAT-2200 | Pertuzumab |
| 10851-11380 | K145T_V177D_S188D | S176K_Y178R | S188K | S131D_V133G_T178F | CAT-2200 | Pertuzumab |
| 10852-11385 | K145T_V177D_S188D | S176K_Y178R | S188K | S131E_V133G_T178F | CAT-2200 | Pertuzumab |
| 10853-11388 | K145T_V177D_S188D | S176K_Y178R | S188K | S176D_T178E | CAT-2200 | Pertuzumab |
| 10854-11395 | K145T_V177D_S188D | S176K_Y178R | S188K | S176E_T178E | CAT-2200 | Pertuzumab |
| 10855-11312 | K145T_V177D_S188D | S176K_Y178R | L143K | V133D | CAT-2200 | Pertuzumab |
| 10855-11321 | K145T_V177D_S188D | S176K_Y178R | L143S_S186K_S188T | V133D | CAT-2200 | Pertuzumab |
| 10855-11353 | K145T_V177D_S188D | S176K_Y178R | S186K_S188T | V133D | CAT-2200 | Pertuzumab |
| 10856-11235 | K145T_V177D_S188D | S176K_Y178R | L124R | V133G_S176D | CAT-2200 | Pertuzumab |
| 10857-11243 | K145T_V177D_S188D | S176K_Y178R | L124R | V133G_S176D_T178D | CAT-2200 | Pertuzumab |
| 10858-11255 | K145T_V177D_S188D | S176K_Y178R | L124R_Q179K | V133G_S176D_T180E | CAT-2200 | Pertuzumab |
| 10858-11267 | K145T_V177D_S188D | S176K_Y178R | L124R_S186R | V133G_S176D_T180E | CAT-2200 | Pertuzumab |
| 10860-11406 | K145T_V177D_S188D | S176K_Y178R | V177I_S188K | V133I_S176D_T178E | CAT-2200 | Pertuzumab |
| 10861-11409 | K145T_V177D_S188D | S176K_Y178R | V177I_S188K | V133I_S176E_T178E | CAT-2200 | Pertuzumab |
| 10862-11414 | K145T_V177D_S188D | S176K_Y178R | V177I_S188K | V133L_S176D_T178E | CAT-2200 | Pertuzumab |
| 10869-11390 | K145T_V177T_S188E | Y178K | S188K | S176D_T178E | CAT-2200 | Pertuzumab |
| 10870-11396 | K145T_V177T_S188E | Y178K | S188K | S176E_T178E | CAT-2200 | Pertuzumab |
| 10871-11240 | K145T_V177T_S188E | Y178K | L124R | V133G_S176D | CAT-2200 | Pertuzumab |
| 10873-11256 | K145T_V177T_S188E | Y178K | L124R_Q179K | V133G_S176D_T180E | CAT-2200 | Pertuzumab |
| 10873-11268 | K145T_V177T_S188E | Y178K | L124R_S186R | V133G_S176D_T180E | CAT-2200 | Pertuzumab |

TABLE 4A-continued

K-L design libary

| Unique identifier | H1 mutation (Kabat) | L1 mutation (Kabat) | H2 mutation (Kabat) | L2 mutation (Kabat) | H1L1 Fab | H2L2 Fab |
|---|---|---|---|---|---|---|
| 10875-11416 | K145T_V177T_S188E | Y178K | V177I_S188K | V133L_S176D_T178E | CAT-2200 | Pertuzumab |
| 10881-11412 | L124E_V190D | L135K_Y178F | V177I_S188K | V133L_S176D_T178E | CAT-2200 | Pertuzumab |
| 10883-11236 | L124E_V190D | V133I_L135K | L124R | V133G_S176D | CAT-2200 | Pertuzumab |
| 10888-11415 | L124E_V190D | V133I_L135K_Y178F | V177I_S188K | V133L_S176D_T178E | CAT-2200 | Pertuzumab |
| 10898-11239 | L124E_V190E | V133I_L135R_Y178F | L124R | V133G_S176D | CAT-2200 | Pertuzumab |
| 10923-11306 | L143D_K145T | E124Q_T131K | L143K | Q124E_V133D | CAT-2200 | Pertuzumab |
| 10924-11376 | L143D_K145T | E124Q_T131K | S188K | S131D_V133G_T178F | CAT-2200 | Pertuzumab |
| 10926-11391 | L143D_K145T | E124Q_T131K | S188K | S176E_T178E | CAT-2200 | Pertuzumab |
| 10927-11290 | L143D_K145T | E124Q_T131K | L143I_S186K | V133D | CAT-2200 | Pertuzumab |
| 10927-11344 | L143D_K145T | E124Q_T131K | S186K | V133D | CAT-2200 | Pertuzumab |
| 10928-11294 | L143D_K145T | E124Q_T131K | L143I_S186K | V133D_Q160E | CAT-2200 | Pertuzumab |
| 10928-11348 | L143D_K145T | E124Q_T131K | S186K | V133D_Q160E | CAT-2200 | Pertuzumab |
| 10929-11249 | L143D_K145T | E124Q_T131K | L124R_Q179K | V133G_S176D_T178E | CAT-2200 | Pertuzumab |
| 10929-11257 | L143D_K145T | E124Q_T131K | L124R_S186K | V133G_S176D_T178E | CAT-2200 | Pertuzumab |
| 10929-11261 | L143D_K145T | E124Q_T131K | L124R_S186R | V133G_S176D_T178E | CAT-2200 | Pertuzumab |
| 10931-11251 | L143D_K145T | E124Q_T131K | L124R_Q179K | V133G_S176D_T180E | CAT-2200 | Pertuzumab |
| 10931-11259 | L143D_K145T | E124Q_T131K | L124R_S186K | V133G_S176D_T180E | CAT-2200 | Pertuzumab |
| 10931-11263 | L143D_K145T | E124Q_T131K | L124R_S186R | V133G_S176D_T180E | CAT-2200 | Pertuzumab |
| 10934-11410 | L143D_K145T | E124Q_T131K | V177I_S188K | V133L_S176D_T178E | CAT-2200 | Pertuzumab |
| 10942-11291 | L143D_K145T | E124Q_T131K_V133S | L143I_S186K | V133D | CAT-2200 | Pertuzumab |
| 10942-11345 | L143D_K145T | E124Q_T131K_V133S | S186K | V133D | CAT-2200 | Pertuzumab |
| 10943-11295 | L143D_K145T | E124Q_T131K_V133S | L143I_S186K | V133D_Q160E | CAT-2200 | Pertuzumab |
| 10943-11349 | L143D_K145T | E124Q_T131K_V133S | S186K | V133D_Q160E | CAT-2200 | Pertuzumab |
| 10944-11307 | L143D_K145T | E124Q_T131R | L143K | Q124E_V133D | CAT-2200 | Pertuzumab |
| 10944-11314 | L143D_K145T | E124Q_T131R | L143R | Q124E_V133D | CAT-2200 | Pertuzumab |
| 10945-11377 | L143D_K145T | E124Q_T131R | S188K | S131D_V133G_T178F | CAT-2200 | Pertuzumab |
| 10946-11382 | L143D_K145T | E124Q_T131R | S188K | S131E_V133G_T178F | CAT-2200 | Pertuzumab |
| 10947-11392 | L143D_K145T | E124Q_T131R | S188K | S176E_T178E | CAT-2200 | Pertuzumab |
| 10948-11250 | L143D_K145T | E124Q_T131R | L124R_Q179K | V133G_S176D_T178E | CAT-2200 | Pertuzumab |
| 10948-11258 | L143D_K145T | E124Q_T131R | L124R_S186K | V133G_S176D_T178E | CAT-2200 | Pertuzumab |
| 10948-11262 | L143D_K145T | E124Q_T131R | L124R_S186R | V133G_S176D_T178E | CAT-2200 | Pertuzumab |
| 10950-11252 | L143D_K145T | E124Q_T131R | L124R_Q179K | V133G_S176D_T180E | CAT-2200 | Pertuzumab |
| 10950-11260 | L143D_K145T | E124Q_T131R | L124R_S186K | V133G_S176D_T180E | CAT-2200 | Pertuzumab |
| 10950-11264 | L143D_K145T | E124Q_T131R | L124R_S186R | V133G_S176D_T180E | CAT-2200 | Pertuzumab |
| 10952-11398 | L143D_K145T | E124Q_T131R | S188K | V133I_S176D_T178E | CAT-2200 | Pertuzumab |
| 10953-11411 | L143D_K145T | E124Q_T131R | V177I_S188K | V133L_S176D_T178E | CAT-2200 | Pertuzumab |
| 10962-11296 | L143D_K145T | T131K | L143I_S186K | V133D_Q160E | CAT-2200 | Pertuzumab |
| 10962-11350 | L143D_K145T | T131K | S186K | V133D_Q160E | CAT-2200 | Pertuzumab |
| 10965-11293 | L143D_K145T | T131K_V133S | L143I_S186K | V133D | CAT-2200 | Pertuzumab |
| 10965-11347 | L143D_K145T | T131K_V133S | S186K | V133D | CAT-2200 | Pertuzumab |
| 10966-11297 | L143D_K145T | T131K_V133S | L143I_S186K | V133D_Q160E | CAT-2200 | Pertuzumab |
| 10966-11351 | L143D_K145T | T131K_V133S | S186K | V133D_Q160E | CAT-2200 | Pertuzumab |
| 10969-11290 | L143D_K145T_Q179E | E124Q_T131K | L143I_S186K | V133D | CAT-2200 | Pertuzumab |
| 10969-11344 | L143D_K145T_Q179E | E124Q_T131K | S186K | V133D | CAT-2200 | Pertuzumab |
| 10970-11294 | L143D_K145T_Q179E | E124Q_T131K | L143I_S186K | V133D_Q160E | CAT-2200 | Pertuzumab |
| 10970-11348 | L143D_K145T_Q179E | E124Q_T131K | S186K | V133D_Q160E | CAT-2200 | Pertuzumab |
| 10973-11291 | L143D_K145T_Q179E | E124Q_T131K_V133S | L143I_S186K | V133D | CAT-2200 | Pertuzumab |
| 10973-11345 | L143D_K145T_Q179E | E124Q_T131K_V133S | S186K | V133D | CAT-2200 | Pertuzumab |
| 10974-11295 | L143D_K145T_Q179E | E124Q_T131K_V133S | L143I_S186K | V133D_Q160E | CAT-2200 | Pertuzumab |
| 10974-11349 | L143D_K145T_Q179E | E124Q_T131K_V133S | S186K | V133D_Q160E | CAT-2200 | Pertuzumab |
| 10977-11292 | L143D_K145T_Q179E | T131K | L143I_S186K | V133D | CAT-2200 | Pertuzumab |
| 10977-11346 | L143D_K145T_Q179E | T131K | S186K | V133D | CAT-2200 | Pertuzumab |
| 10978-11296 | L143D_K145T_Q179E | T131K | L143I_S186K | V133D_Q160E | CAT-2200 | Pertuzumab |
| 10978-11350 | L143D_K145T_Q179E | T131K | S186K | V133D_Q160E | CAT-2200 | Pertuzumab |
| 10981-11293 | L143D_K145T_Q179E | T131K_V133S | L143I_S186K | V133D | CAT-2200 | Pertuzumab |
| 10981-11347 | L143D_K145T_Q179E | T131K_V133S | S186K | V133D | CAT-2200 | Pertuzumab |
| 10982-11297 | L143D_K145T_Q179E | T131K_V133S | L143I_S186K | V133D_Q160E | CAT-2200 | Pertuzumab |
| 10982-11351 | L143D_K145T_Q179E | T131K_V133S | S186K | V133D_Q160E | CAT-2200 | Pertuzumab |
| 10983-11306 | L143E_K145T_Q179E | E124Q_T131K | L143K | Q124E_V133D | CAT-2200 | Pertuzumab |
| 10984-11376 | L143E_K145T_Q179E | E124Q_T131K | S188K | S131D_V133G_T178F | CAT-2200 | Pertuzumab |
| 10985-11381 | L143E_K145T_Q179E | E124Q_T131K | S188K | S131E_V133G_T178F | CAT-2200 | Pertuzumab |
| 10986-11391 | L143E_K145T_Q179E | E124Q_T131K | S188K | S176E_T178E | CAT-2200 | Pertuzumab |
| 10987-11249 | L143E_K145T_Q179E | E124Q_T131K | L124R_Q179K | V133G_S176D_T178E | CAT-2200 | Pertuzumab |
| 10987-11257 | L143E_K145T_Q179E | E124Q_T131K | L124R_S186K | V133G_S176D_T178E | CAT-2200 | Pertuzumab |
| 10987-11261 | L143E_K145T_Q179E | E124Q_T131K | L124R_S186R | V133G_S176D_T178E | CAT-2200 | Pertuzumab |
| 10989-11251 | L143E_K145T_Q179E | E124Q_T131K | L124R_Q179K | V133G_S176D_T180E | CAT-2200 | Pertuzumab |
| 10989-11259 | L143E_K145T_Q179E | E124Q_T131K | L124R_S186K | V133G_S176D_T180E | CAT-2200 | Pertuzumab |
| 10989-11263 | L143E_K145T_Q179E | E124Q_T131K | L124R_S186R | V133G_S176D_T180E | CAT-2200 | Pertuzumab |
| 10992-11410 | L143E_K145T_Q179E | E124Q_T131K | V177I_S188K | V133L_S176D_T178E | CAT-2200 | Pertuzumab |
| 10998-11307 | L143E_K145T_Q179E | E124Q_T131R | L143K | Q124E_V133D | CAT-2200 | Pertuzumab |
| 10998-11314 | L143E_K145T_Q179E | E124Q_T131R | L143R | Q124E_V133D | CAT-2200 | Pertuzumab |
| 10999-11377 | L143E_K145T_Q179E | E124Q_T131R | S188K | S131D_V133G_T178F | CAT-2200 | Pertuzumab |
| 11000-11382 | L143E_K145T_Q179E | E124Q_T131R | S188K | S131E_V133G_T178F | CAT-2200 | Pertuzumab |
| 11001-11392 | L143E_K145T_Q179E | E124Q_T131R | S188K | S176E_T178E | CAT-2200 | Pertuzumab |
| 11002-11250 | L143E_K145T_Q179E | E124Q_T131R | L124R_Q179K | V133G_S176D_T178E | CAT-2200 | Pertuzumab |

TABLE 4A-continued

K-L design libary

| Unique identifier | H1 mutation (Kabat) | L1 mutation (Kabat) | H2 mutation (Kabat) | L2 mutation (Kabat) | H1L1 Fab | H2L2 Fab |
|---|---|---|---|---|---|---|
| 11002-11258 | L143E_K145T_Q179E | E124Q_T131R | L124R_S186K | V133G_S176D_T178E | CAT-2200 | Pertuzumab |
| 11002-11262 | L143E_K145T_Q179E | E124Q_T131R | L124R_S186R | V133G_S176D_T178E | CAT-2200 | Pertuzumab |
| 11004-11252 | L143E_K145T_Q179E | E124Q_T131R | L124R_Q179K | V133G_S176D_T180E | CAT-2200 | Pertuzumab |
| 11004-11260 | L143E_K145T_Q179E | E124Q_T131R | L124R_S186K | V133G_S176D_T180E | CAT-2200 | Pertuzumab |
| 11004-11264 | L143E_K145T_Q179E | E124Q_T131R | L124R_S186R | V133G_S176D_T180E | CAT-2200 | Pertuzumab |
| 11006-11398 | L143E_K145T_Q179E | E124Q_T131R | S188K | V133I_S176D_T178E | CAT-2200 | Pertuzumab |
| 11007-11411 | L143E_K145T_Q179E | E124Q_T131R | V177I_S188K | V133L_S176D_T178E | CAT-2200 | Pertuzumab |
| 11025-11284 | L143K | K129T_V133D | L143E_K145T_Q179E_S188L | Q124K_T178R | CAT-2200 | Pertuzumab |
| 11026-11270 | L143K | K129T_V133D | L124W_L143E_K145T_Q179E | Q124K_V133A_T178R | CAT-2200 | Pertuzumab |
| 11027-11281 | L143K | K129T_V133D | L143E_K145T_Q179E_S1861_S188W | Q124R_Q160R_S176A_T178R | CAT-2200 | Pertuzumab |
| 11027-11287 | L143K | K129T_V133D | L143E_K145T_Q179E_S188W | Q124R_Q160R_S176A_T178R | CAT-2200 | Pertuzumab |
| 11028-11275 | L143K | K129T_V133D | L143E_K145T_Q179E | Q124R_Q160R_T178R | CAT-2200 | Pertuzumab |
| 11029-11282 | L143K | K129T_V133D | L143E_K145T_Q179E_S186I_S188W | Q124R_S176A_T178R | CAT-2200 | Pertuzumab |
| 11029-11288 | L143K | K129T_V133D | L143E_K145T_Q179E_S188W | Q124R_S176A_T178R | CAT-2200 | Pertuzumab |
| 11030-11276 | L143K | K129T_V133D | L143E_K145T_Q179E | Q124R_T178R | CAT-2200 | Pertuzumab |
| 11030-11285 | L143K | K129T_V133D | L143E_K145T_Q179E_S188L | Q124R_T178R | CAT-2200 | Pertuzumab |
| 11032-11199 | L143K | K129T_V133D | L124E_K145T_Q179E | S131K_V133G_S176R | CAT-2200 | Pertuzumab |
| 11033-11209 | L143K | K129T_V133D | L124E_K145T_Q179E_S1861_S188W | S131K_V133G_S176R_T178A | CAT-2200 | Pertuzumab |
| 11033-11215 | L143K | K129T_V133D | L124E_K145T_Q179E_S188W | S131K_V133G_S176R_T178A | CAT-2200 | Pertuzumab |
| 11034-11204 | L143K | K129T_V133D | L124E_K145T_Q179E | S131R_V133G_S176R | CAT-2200 | Pertuzumab |
| 11035-11212 | L143K | K129T_V133D | L124E_K145T_Q179E_S186I_S188W | S131R_V133G_S176R_T178A | CAT-2200 | Pertuzumab |
| 11035-11218 | L143K | K129T_V133D | L124E_K145T_Q179E_S188W | S131R_V133G_S176R_T178A | CAT-2200 | Pertuzumab |
| 11036-11221 | L143K | K129T_V133D | L124E_K145T_S186E | S131R_V133S_L135K | CAT-2200 | Pertuzumab |
| 11039-11224 | L143K | K129T_V133D | L124E_L143E_K145T | S131R_V133T_L135K_T178S | CAT-2200 | Pertuzumab |
| 11042-11273 | L143S_S186K_S188T | V133D_Y178T | L143E_K145T_Q179E | Q124R_Q160K_T178R | CAT-2200 | Pertuzumab |
| 11043-11181 | L143S_S186K_S188T | V133D_Y178T | K145T_V177D_S188D | S176K_T178K | CAT-2200 | Pertuzumab |
| 11044-11191 | L143S_S186K_S188T | V133D_Y178T | K145T_V177D_S188D | S176K_T178R | CAT-2200 | Pertuzumab |
| 11055-11322 | S186K_S188T | T131S_V133D_Y178T | L143T_S188D | S131K_S176A_T178S | CAT-2200 | Pertuzumab |
| 11056-11324 | S186K_S188T | T131S_V133D_Y178T | L143T_S188D | S131K_T178S | CAT-2200 | Pertuzumab |
| 11061-11273 | S186K_S188T | V133D_Y178T | L143E_K145T_Q179E | Q124R_Q160K_T178R | CAT-2200 | Pertuzumab |
| 11062-11323 | S186K_S188T | V133D_Y178T | L143T_S188D | S131K_S176A_T178S | CAT-2200 | Pertuzumab |
| 11063-11325 | S186K_S188T | V133D_Y178T | L143T_S188D | S131K_T178S | CAT-2200 | Pertuzumab |
| 11064-11201 | S186K_S188T | V133D_Y178T | L124E_K145T_Q179E | S131K_V133G_S176R | CAT-2200 | Pertuzumab |
| 11065-11206 | S186K_S188T | V133D_Y178T | L124E_K145T_Q179E | S131R_V133G_S176R | CAT-2200 | Pertuzumab |
| 11066-11181 | S186K_S188T | V133D_Y178T | K145T_V177D_S188D | S176K_T178K | CAT-2200 | Pertuzumab |
| 11076-11355 | S188A | S176A_Y178W | S186L_S188W | S176A_T178A | CAT-2200 | Pertuzumab |
| 11087-11179 | S188K | S176D_Y178E | K145T_V177D_S188D | S176K_T178K | CAT-2200 | Pertuzumab |
| 11088-11185 | S188K | S176D_Y178E | K145T_V177D_S188D | S176K_T178L | CAT-2200 | Pertuzumab |
| 11089-11189 | S188K | S176D_Y178E | K145T_V177D_S188D | S176K_T178R | CAT-2200 | Pertuzumab |
| 11096-11272 | S188K | S176E_Y178E | L143E_K145T_Q179E | Q124R_Q160K_T178R | CAT-2200 | Pertuzumab |
| 11097-11277 | S188K | S176E_Y178E | L143E_K145T_Q179E | Q124R_T178R | CAT-2200 | Pertuzumab |
| 11098-11200 | S188K | S176E_Y178E | L124E_K145T_Q179E | S131K_V133G_S176R | CAT-2200 | Pertuzumab |
| 11099-11210 | S188K | S176E_Y178E | L124E_K145T_Q179E_S186I_S188W | S131K_V133G_S176R_T178A | CAT-2200 | Pertuzumab |
| 11099-11216 | S188K | S176E_Y178E | L124E_K145T_Q179E_S188W | S131K_V133G_S176R_T178A | CAT-2200 | Pertuzumab |
| 11100-11205 | S188K | S176E_Y178E | L124E_K145T_Q179E | S131R_V133G_S176R | CAT-2200 | Pertuzumab |
| 11101-11213 | S188K | S176E_Y178E | L124E_K145T_Q179E_S186I_S188W | S131R_V133G_S176R_T178A | CAT-2200 | Pertuzumab |
| 11101-11219 | S188K | S176E_Y178E | L124E_K145T_Q179E_S188W | S131R_V133G_S176R_T178A | CAT-2200 | Pertuzumab |
| 11102-11180 | S188K | S176E_Y178E | K145T_V177D_S188D | S176K_T178K | CAT-2200 | Pertuzumab |
| 11103-11186 | S188K | S176E_Y178E | K145T_V177D_S188D | S176K_T178L | CAT-2200 | Pertuzumab |
| 11104-11190 | S188K | S176E_Y178E | K145T_V177D_S188D | S176K_T178R | CAT-2200 | Pertuzumab |
| 11105-11195 | S188K | S176E_Y178E | L124E | V133A_S176K | CAT-2200 | Pertuzumab |
| 11106-11225 | S188K | S176E_Y178E | L124E_S186I_S188W | V133A_S176K_T178A | CAT-2200 | Pertuzumab |
| 11106-11229 | S188K | S176E_Y178E | L124E_S188W | V133A_S176K_T178A | CAT-2200 | Pertuzumab |
| 11107-11197 | S188K | S176E_Y178E | L124E | V133G_S176R | CAT-2200 | Pertuzumab |
| 11108-11227 | S188K | S176E_Y178E | L124E_S186I_S188W | V133G_S176R_T178A | CAT-2200 | Pertuzumab |
| 11108-11231 | S188K | S176E_Y178E | L124E_S188W | V133G_S176R_T178A | CAT-2200 | Pertuzumab |
| 11124-11202 | S188K | V133I_S176D_Y178E | L124E_K145T_Q179E | S131K_V133G_S176R | CAT-2200 | Pertuzumab |
| 11125-11207 | S188K | V133I_S176D_Y178E | L124E_K145T_Q179E | S131R_V133G_S176R | CAT-2200 | Pertuzumab |
| 11140-11202 | V177I_S188K | V133I_S176D_Y178E | L124E_K145T_Q179E | S131K_V133G_S176R | CAT-2200 | Pertuzumab |
| 11141-11207 | V177I_S188K | V133I_S176D_Y178E | L124E_K145T_Q179E | S131R_V133G_S176R | CAT-2200 | Pertuzumab |
| 11142-11182 | V177I_S188K | V133I_S176D_Y178E | K145T_V177D_S188D | S176K_T178K | CAT-2200 | Pertuzumab |
| 11143-11187 | V177I_S188K | V133I_S176D_Y178E | K145T_V177D_S188D | S176K_T178L | CAT-2200 | Pertuzumab |
| 11144-11192 | V177I_S188K | V133I_S176D_Y178E | K145T_V177D_S188D | S176K_T178R | CAT-2200 | Pertuzumab |

TABLE 4A-continued

| K-L design libary | | | | | | |
|---|---|---|---|---|---|---|
| Unique identifier | H1 mutation (Kabat) | L1 mutation (Kabat) | H2 mutation (Kabat) | L2 mutation (Kabat) | H1L1 Fab | H2L2 Fab |
| 11148-11183 | V177I_S188K | V133I_S176E_Y178E | K145T_V177D_S188D | S176K_T178K | CAT-2200 | Pertuzumab |
| 11149-11188 | V177I_S188K | V133I_S176E_Y178E | K145T_V177D_S188D | S176K_T178L | CAT-2200 | Pertuzumab |
| 11150-11193 | V177I_S188K | V133I_S176E_Y178E | K145T_V177D_S188D | S176K_T178R | CAT-2200 | Pertuzumab |
| 11156-11274 | V177I_S188K | V133L_S176D_Y178E | L143E_K145T_Q179E | Q124R_Q160K_T178R | CAT-2200 | Pertuzumab |
| 11157-11279 | V177I_S188K | V133L_S176D_Y178E | L143E_K145T_Q179E | Q124R_T178R | CAT-2200 | Pertuzumab |
| 11158-11203 | V177I_S188K | V133L_S176D_Y178E | L124E_K145T_Q179E | S131K_V133G_S176R | CAT-2200 | Pertuzumab |
| 11159-11211 | V177I_S188K | V133L_S176D_Y178E | L124E_K145T_Q179E_ S186I_S188W | S131K_V133G_S176R_ T178A | CAT-2200 | Pertuzumab |
| 11159-11217 | V177I_S188K | V133L_S176D_Y178E | L124E_K145T_Q179E_ S188W | S131K_V133G_S176R_ T178A | CAT-2200 | Pertuzumab |
| 11160-11208 | V177I_S188K | V133L_S176D_Y178E | L124E_K145T_Q179E | S131R_V133G_S176R | CAT-2200 | Pertuzumab |
| 11161-11214 | V177I_S188K | V133L_S176D_Y178E | L124E_K145T_Q179E_ S186I_S188W | S131R_V133G_S176R_ T178A | CAT-2200 | Pertuzumab |
| 11161-11220 | V177I_S188K | V133L_S176D_Y178E | L124E_K145T_Q179E_ S188W | S131R_V133G_S176R_ T178A | CAT-2200 | Pertuzumab |
| 11162-11184 | V177I_S188K | V133L_S176D_Y178E | K145T_V177D_S188D | S176K_T178K | CAT-2200 | Pertuzumab |
| 11163-11194 | V177I_S188K | V133L_S176D_Y178E | K145T_V177D_S188D | S176K_T178R | CAT-2200 | Pertuzumab |
| 11164-11196 | V177I_S188K | V133L_S176D_Y178E | L124E | V133A_S176K | CAT-2200 | Pertuzumab |
| 11165-11226 | V177I_S188K | V133L_S176D_Y178E | L124E_S186I_S188W | V133A_S176K_T178A | CAT-2200 | Pertuzumab |
| 11165-11230 | V177I_S188K | V133L_S176D_Y178E | L124E_S188W | V133A_S176K_T178A | CAT-2200 | Pertuzumab |
| 11166-11198 | V177I_S188K | V133L_S176D_Y178E | L124E | V133G_S176R | CAT-2200 | Pertuzumab |
| 11167-11228 | V177I_S188K | V133L_S176D_Y178E | L124E_S186I_S188W | V133G_S176R_T178A | CAT-2200 | Pertuzumab |
| 11167-11232 | V177I_S188K | V133L_S176D_Y178E" | L124E_S188W | V133G_S176R_T178A | CAT-2200 | Pertuzumab |

TABLE 4B

| K-K derived K-L designs libarary | | | | | | |
|---|---|---|---|---|---|---|
| Unique identifier | H1 mutation (Kabat) | L1 mutation (Kabat) | H2 mutation (Kabat) | L2 mutation (Kabat) | H1L1 Fab | H2L2 Fab |
| 10629-10695 | A139W | T116A | — | L135W | CAT-2200 | Pertuzumab |
| 10631-10722 | D146G_Q179K | S180E | L143E_K145T | Q124R | CAT-2200 | Pertuzumab |
| 10632-10724 | D146G_Q179K | S180E | L143E_K145T | Q124R_Q160K_T178R | CAT-2200 | Pertuzumab |
| 10640-10713* | L124E | V133G_S176R | L124R | V133G_S176D | CAT-2200 | Pertuzumab |
| 10652-10734 | L143E_K145T | E124R | Q179K | Q124E_Q160E_T180E | CAT-2200 | Pertuzumab |
| 10652-10755 | L143E_K145T | E124R | S186R | Q124E_Q160E_T180E | CAT-2200 | Pertuzumab |
| 10656-10758 | L143E_K145T_Q179E | E124K_Y178R | S186R | Q160E_T180E | CAT-2200 | Pertuzumab |
| 10657-10760 | L143E_K145T_Q179E | E124K_Y178R | S186R | T178E_T180E | CAT-2200 | Pertuzumab |
| 10662-10733* | L45F | — | L45P | P44F | CAT-2200 | Pertuzumab |
| 10671-10751 | Q39D | Q38R | Q39R | Q38E | CAT-2200 | Pertuzumab |
| 10674-10749* | Q39E | Q38K | Q39K | Q38E | CAT-2200 | Pertuzumab |
| 10676-10750* | Q39E | Q38R | Q39R | Q38D | CAT-2200 | Pertuzumab |
| 10677-10751 | Q39E | Q38R | Q39R | Q38E | CAT-2200 | Pertuzumab |
| 10624-10700* | — | L135W | A139W | F116A | CAT-2200 | Pertuzumab |
| 10625-10701* | — | L135W | A139W | F116A_L135V | CAT-2200 | Pertuzumab |
| 10652-10702 | L143E_K145T | E124R | D146G_Q179K | Q124E_Q160E_T180E | CAT-2200 | Pertuzumab |
| 10684-10706 | S186R | K129T_S180E | K145T_Q179E | S131K | CAT-2200 | Pertuzumab |
| 10689-10707 | S186R | S180E | K145T_Q179E | S131K | CAT-2200 | Pertuzumab |
| 10682-10718 | S186R | — | L143E_K145T | Q124K_T178R | CAT-2200 | Pertuzumab |
| 10685-10719 | S186R | S180E | L143E_K145T | Q124K_T178R | CAT-2200 | Pertuzumab |
| 10658-10720 | L143K | — | L143E_K145T | Q124R | CAT-2200 | Pertuzumab |
| 10659-10720 | L143R | — | L143E_K145T | Q124R | CAT-2200 | Pertuzumab |
| 10683-10720 | S186R | — | L143E_K145T | Q124R | CAT-2200 | Pertuzumab |
| 10664-10722 | Q179K | S180E | L143E_K145T | Q124R | CAT-2200 | Pertuzumab |
| 10687-10722 | S186R | S180E | L143E_K145T | Q124R | CAT-2200 | Pertuzumab |
| 10665-10724 | Q179K | S180E | L143E_K145T | Q124R_Q160K_T178R | CAT-2200 | Pertuzumab |
| 10688-10724 | S186R | S180E | L143E_K145T | Q124R_Q160K_T178R | CAT-2200 | Pertuzumab |
| 10685-10726 | S186R | S180E | L143E_K145T_Q179E | Q124K_T178R | CAT-2200 | Pertuzumab |
| 10690-10727 | S186R | Y178E_S180E | L143E_K145T_Q179E | Q124K_T178R | CAT-2200 | Pertuzumab |
| 10621-10731* | — | — | L45A | P44F | CAT-2200 | Pertuzumab |
| 10662-10731* | L45F | — | L45A | P44F | CAT-2200 | Pertuzumab |
| 10621-10733* | — | — | L45P | P44F | CAT-2200 | Pertuzumab |
| 10622-10736 | — | — | Q39D | Q38K | CAT-2200 | Pertuzumab |
| 10678-10737 | Q39K | Q38D | Q39D | Q38K | CAT-2200 | Pertuzumab |
| 10679-10738 | Q39K | Q38E | Q39D | Q38K | CAT-2200 | Pertuzumab |
| 10623-10739 | — | — | Q39D | Q38R | CAT-2200 | Pertuzumab |
| 10680-10740* | Q39R | Q38D | Q39D | Q38R | CAT-2200 | Pertuzumab |
| 10681-10741 | Q39R | Q38E | Q39D | Q38R | CAT-2200 | Pertuzumab |
| 10622-10742 | — | — | Q39E | Q38K | CAT-2200 | Pertuzumab |
| 10678-10743 | Q39K | Q38D | Q39E | Q38K | CAT-2200 | Pertuzumab |
| 10679-10744 | Q39K | Q38E | Q39E | Q38K | CAT-2200 | Pertuzumab |

TABLE 4B-continued

| K-K derived K-L designs libarary | | | | | | |
|---|---|---|---|---|---|---|
| Unique identifier | H1 mutation (Kabat) | L1 mutation (Kabat) | H2 mutation (Kabat) | L2 mutation (Kabat) | H1L1 Fab | H2L2 Fab |
| 10623-10745 | — | — | Q39E | Q38R | CAT-2200 | Pertuzumab |
| 10680-10746 | Q39R | Q38D | Q39E | Q38R | CAT-2200 | Pertuzumab |
| 10681-10747 | Q39R | Q38E | Q39E | Q38R | CAT-2200 | Pertuzumab |

*Designs with exact match mutations to kappa-kappa library designs.

TABLE 5A

| LCCA results for K-L designs that passed the performance cut-off criteria | | | | | | | | |
|---|---|---|---|---|---|---|---|---|
| Column 1 Unique identifier | Column 2 H1L1:H1L2 normalized median scalar value ln(r1/f1) | Column 3 H1L1:H1L2 range of normalized scalar value ln(r1/f1) | Column 4 H1L1: H1L2 normalized median ratio | Column 5 H2L2:H2L1 normalized median scalar value ln(r1/f1) | Column 6 H2L2:H2L1 range of normalized scalar value ln(r1/f1) | Column 7 H2L2:H2L1 normalized median ratio | Column 8 H1L1 Fab | Column 9 H2L2 Fab |
| 10771-11335 | 0.48 | NA | 62:38 | −0.39 | NA | 40:60 | CAT-2200 | Pertuzumab |
| 10771-11360 | 0.48 | NA | 62:38 | −0.39 | NA | 40:60 | CAT-2200 | Pertuzumab |
| 10776-11312 | −0.19 | NA | 45:55 | 1.39 | 0.1 | 80:20 | CAT-2200 | Pertuzumab |
| 10776-11321 | −0.19 | NA | 45:55 | 0.54 | NA | 63:37 | CAT-2200 | Pertuzumab |
| 10776-11353 | −0.19 | NA | 45:55 | 0.85 | 0.03 | 70:30 | CAT-2200 | Pertuzumab |
| 10780-11417 | 0.03 | NA | 51:49 | 0.6 | 4.25 | 65:35 | CAT-2200 | Pertuzumab |
| 10781-11300 | 0.74 | NA | 68:32 | −0.16 | NA | 46:54 | CAT-2200 | Pertuzumab |
| 10781-11419 | 0.74 | NA | 68:32 | −0.34 | NA | 42:58 | CAT-2200 | Pertuzumab |
| 10786-11299 | −0.07 | NA | 48:52 | 0.49 | 0.43 | 62:38 | CAT-2200 | Pertuzumab |
| 10786-11418 | −0.07 | NA | 48:52 | 0.47 | NA | 62:38 | CAT-2200 | Pertuzumab |
| 10787-11301 | 1.15 | 0.37 | 76:24 | −0.04 | NA | 49:51 | CAT-2200 | Pertuzumab |
| 10787-11420 | 1.15 | 0.37 | 76:24 | −0.26 | NA | 44:56 | CAT-2200 | Pertuzumab |
| 10788-11422 | −0.01 | NA | 50:50 | 0.41 | NA | 60:40 | CAT-2200 | Pertuzumab |
| 10792-11305 | 0.04 | NA | 51:49 | 0.62 | NA | 65:35 | CAT-2200 | Pertuzumab |
| 10792-11424 | 0.04 | NA | 51:49 | 0.9 | NA | 71:29 | CAT-2200 | Pertuzumab |
| 10793-11375 | 0.24 | 0.14 | 56:44 | 0.93 | 0.18 | 72:28 | CAT-2200 | Pertuzumab |
| 10795-11390 | 1.27 | 0.55 | 78:22 | 1.41 | NA | 80:20 | CAT-2200 | Pertuzumab |
| 10796-11396 | 0.81 | 0.2 | 69:31 | 2.67 | NA | 94:6 | CAT-2200 | Pertuzumab |
| 10798-11256 | 2.12 | 0.81 | 89:11 | 0.63 | 0.12 | 65:35 | CAT-2200 | Pertuzumab |
| 10798-11268 | 2.12 | 0.81 | 89:11 | 1.21 | 0.31 | 77:23 | CAT-2200 | Pertuzumab |
| 10800-11416 | 1.12 | 0.42 | 75:25 | 0.55 | NA | 63:37 | CAT-2200 | Pertuzumab |
| 10806-11326 | 0.39 | 0.61 | 60:40 | 2.33 | 0.86 | 91:9 | CAT-2200 | Pertuzumab |
| 10806-11369 | 0.39 | 0.61 | 60:40 | 3.29 | 0.39 | 96:4 | CAT-2200 | Pertuzumab |
| 10808-11308 | 0.59 | NA | 64:36 | 1.78 | NA | 86:14 | CAT-2200 | Pertuzumab |
| 10808-11315 | 0.59 | NA | 64:36 | 1.3 | 0.22 | 79:21 | CAT-2200 | Pertuzumab |
| 10809-11378 | 1.29 | 0.73 | 78:22 | 1.85 | 0.12 | 86:14 | CAT-2200 | Pertuzumab |
| 10810-11383 | 0.8 | 0.22 | 69:31 | 2.77 | 0.55 | 94:6 | CAT-2200 | Pertuzumab |
| 10811-11386 | 1.71 | 0.38 | 85:15 | 1.83 | NA | 86:14 | CAT-2200 | Pertuzumab |
| 10812-11393 | 0.56 | 0.54 | 64:36 | 2.75 | 0.48 | 94:6 | CAT-2200 | Pertuzumab |
| 10813-11311 | 0.39 | NA | 60:40 | 1.2 | NA | 77:23 | CAT-2200 | Pertuzumab |
| 10813-11320 | 0.39 | NA | 60:40 | 0.58 | NA | 64:36 | CAT-2200 | Pertuzumab |
| 10813-11352 | 0.39 | NA | 60:40 | 0.49 | NA | 62:38 | CAT-2200 | Pertuzumab |
| 10814-11233 | 1.53 | 0.78 | 82:18 | 1.63 | 0.4 | 84:16 | CAT-2200 | Pertuzumab |
| 10816-11253 | 1.95 | 0.27 | 88:12 | 0.75 | 0.08 | 68:32 | CAT-2200 | Pertuzumab |
| 10816-11265 | 1.95 | 0.27 | 88:12 | 1.06 | 0.14 | 74:26 | CAT-2200 | Pertuzumab |
| 10818-11404 | 1.14 | 0.77 | 76:24 | 2.34 | NA | 91:9 | CAT-2200 | Pertuzumab |
| 10819-11407 | 0.35 | 0.46 | 59:41 | 2.83 | NA | 94:6 | CAT-2200 | Pertuzumab |
| 10820-11413 | 1.61 | 0.48 | 83:17 | 2.37 | NA | 91:9 | CAT-2200 | Pertuzumab |
| 10827-11373 | −0.02 | NA | 50:50 | 2.64 | NA | 93:7 | CAT-2200 | Pertuzumab |
| 10828-11327 | −0.35 | 0.61 | 41:59 | 1.88 | 0.41 | 87:13 | CAT-2200 | Pertuzumab |
| 10828-11370 | −0.35 | 0.61 | 41:59 | 2.07 | NA | 89:11 | CAT-2200 | Pertuzumab |
| 10830-11309 | 0.31 | NA | 58:42 | 2.64 | 0.73 | 93:7 | CAT-2200 | Pertuzumab |
| 10830-11316 | 0.31 | NA | 58:42 | 1.53 | NA | 82:18 | CAT-2200 | Pertuzumab |
| 10831-11379 | 0.71 | 0.56 | 67:33 | 1.77 | NA | 85:15 | CAT-2200 | Pertuzumab |
| 10832-11384 | 0.09 | 0.31 | 52:48 | 2.17 | 0.12 | 90:10 | CAT-2200 | Pertuzumab |
| 10833-11387 | 1.23 | 0.01 | 77:23 | 1.78 | NA | 86:14 | CAT-2200 | Pertuzumab |
| 10834-11394 | −0.29 | 0.48 | 43:57 | 2.96 | NA | 95:5 | CAT-2200 | Pertuzumab |
| 10835-11234 | 0.52 | NA | 63:37 | 1.06 | 0.39 | 74:26 | CAT-2200 | Pertuzumab |
| 10837-11254 | 1.5 | 0.38 | 82:18 | 0.67 | 0.19 | 66:34 | CAT-2200 | Pertuzumab |
| 10837-11266 | 1.5 | 0.38 | 82:18 | 0.98 | 0.09 | 73:27 | CAT-2200 | Pertuzumab |
| 10840-11408 | −0.38 | 0.47 | 41:59 | 2.79 | NA | 94:6 | CAT-2200 | Pertuzumab |
| 10848-11328 | −0.02 | 0.67 | 50:50 | 3.21 | 0.9 | 96:4 | CAT-2200 | Pertuzumab |
| 10848-11371 | −0.02 | 0.67 | 50:50 | 3.46 | 0.75 | 97:3 | CAT-2200 | Pertuzumab |
| 10850-11310 | 0.74 | 0.17 | 68:32 | 1.95 | 0.04 | 88:12 | CAT-2200 | Pertuzumab |
| 10850-11317 | 0.74 | 0.17 | 68:32 | 1.84 | 0.12 | 86:14 | CAT-2200 | Pertuzumab |
| 10851-11380 | 0.95 | 0.27 | 72:28 | 2.09 | 0.61 | 89:11 | CAT-2200 | Pertuzumab |
| 10852-11385 | 0.24 | 0.67 | 56:44 | 2.35 | 0.38 | 91:9 | CAT-2200 | Pertuzumab |

TABLE 5A-continued

LCCA results for K-L designs that passed the performance cut-off criteria

| Column 1 Unique identifier | Column 2 H1L1:H1L2 normalized median scalar value ln(r1/f1) | Column 3 H1L1:H1L2 range of normalized scalar value ln(r1/f1) | Column 4 H1L1: H1L2 normalized median ratio | Column 5 H2L2:H2L1 normalized median scalar value ln(r1/f1) | Column 6 H2L2:H2L1 range of normalized scalar value ln(r1/f1) | Column 7 H2L2:H2L1 normalized median ratio | Column 8 H1L1 Fab | Column 9 H2L2 Fab |
|---|---|---|---|---|---|---|---|---|
| 10853-11388 | 0.79 | 1 | 69:31 | 2.16 | NA | 90:10 | CAT-2200 | Pertuzumab |
| 10854-11395 | 0.1 | 0.15 | 52:48 | 2.87 | NA | 95:5 | CAT-2200 | Pertuzumab |
| 10855-11312 | 0.62 | 0.2 | 65:35 | 1.39 | 0.1 | 80:20 | CAT-2200 | Pertuzumab |
| 10855-11321 | 0.62 | 0.2 | 65:35 | 0.54 | NA | 63:37 | CAT-2200 | Pertuzumab |
| 10855-11353 | 0.62 | 0.2 | 65:35 | 0.85 | 0.03 | 70:30 | CAT-2200 | Pertuzumab |
| 10856-11235 | 1.24 | 0.26 | 78:22 | 1.75 | 0.78 | 85:15 | CAT-2200 | Pertuzumab |
| 10857-11243 | 0.43 | NA | 61:39 | 0.43 | 0.31 | 61:39 | CAT-2200 | Pertuzumab |
| 10858-11255 | 1.13 | 1.23 | 76:24 | 0.79 | 0.16 | 69:31 | CAT-2200 | Pertuzumab |
| 10858-11267 | 1.13 | 1.23 | 76:24 | 1.17 | 0.07 | 76:24 | CAT-2200 | Pertuzumab |
| 10860-11406 | 0.81 | 0.63 | 69:31 | 2.58 | NA | 93:7 | CAT-2200 | Pertuzumab |
| 10861-11409 | 0.18 | 0.16 | 54:46 | 2.63 | NA | 93:7 | CAT-2200 | Pertuzumab |
| 10862-11414 | 0.45 | 1.18 | 61:39 | 2.38 | NA | 92:8 | CAT-2200 | Pertuzumab |
| 10869-11390 | 1.07 | 0.67 | 74:26 | 1.41 | NA | 80:20 | CAT-2200 | Pertuzumab |
| 10870-11396 | 0.75 | 0.36 | 68:32 | 2.67 | NA | 94:6 | CAT-2200 | Pertuzumab |
| 10871-11240 | 0.87 | NA | 70:30 | 1.68 | 0.56 | 84:16 | CAT-2200 | Pertuzumab |
| 10873-11256 | 1.32 | 0.02 | 79:21 | 0.63 | 0.12 | 65:35 | CAT-2200 | Pertuzumab |
| 10873-11268 | 1.32 | 0.02 | 79:21 | 1.21 | 0.31 | 77:23 | CAT-2200 | Pertuzumab |
| 10875-11416 | 1.04 | 0.63 | 74:26 | 0.55 | NA | 63:37 | CAT-2200 | Pertuzumab |
| 10881-11412 | 0.39 | NA | 60:40 | 1.64 | NA | 84:16 | CAT-2200 | Pertuzumab |
| 10883-11236 | −0.25 | 0.64 | 44:56 | 1.8 | 1.06 | 86:14 | CAT-2200 | Pertuzumab |
| 10888-11415 | 0.27 | 0.28 | 57:43 | 1.83 | 0.08 | 86:14 | CAT-2200 | Pertuzumab |
| 10898-11239 | −0.14 | 0.52 | 47:53 | 1.56 | 0.38 | 83:17 | CAT-2200 | Pertuzumab |
| 10923-11306 | 1.11 | 0.12 | 75:25 | 2.48 | 0.22 | 92:8 | CAT-2200 | Pertuzumab |
| 10924-11376 | 0.51 | 0.14 | 62:38 | 1.5 | 0.39 | 82:18 | CAT-2200 | Pertuzumab |
| 10926-11391 | 0.21 | 0.45 | 55:45 | 2.71 | 0.33 | 94:6 | CAT-2200 | Pertuzumab |
| 10927-11290 | 0.72 | 0.39 | 67:33 | 0.36 | NA | 59:41 | CAT-2200 | Pertuzumab |
| 10927-11344 | 0.72 | 0.39 | 67:33 | 0.22 | NA | 55:45 | CAT-2200 | Pertuzumab |
| 10928-11294 | 1.23 | 0.36 | 77:23 | 0.81 | NA | 69:31 | CAT-2200 | Pertuzumab |
| 10928-11348 | 1.23 | 0.36 | 77:23 | 0.41 | NA | 60:40 | CAT-2200 | Pertuzumab |
| 10929-11249 | 1.46 | 0.91 | 81:19 | 0.77 | 0.24 | 68:32 | CAT-2200 | Pertuzumab |
| 10929-11257 | 1.46 | 0.91 | 81:19 | 1.12 | 0.28 | 75:25 | CAT-2200 | Pertuzumab |
| 10929-11261 | 1.46 | 0.91 | 81:19 | 1.04 | 0.26 | 74:26 | CAT-2200 | Pertuzumab |
| 10931-11251 | 1.17 | 0.41 | 76:24 | 0.95 | NA | 72:28 | CAT-2200 | Pertuzumab |
| 10931-11259 | 1.17 | 0.41 | 76:24 | 1.47 | NA | 81:19 | CAT-2200 | Pertuzumab |
| 10931-11263 | 1.17 | 0.41 | 76:24 | 1.5 | 0.7 | 82:18 | CAT-2200 | Pertuzumab |
| 10934-11410 | 1.23 | 0.34 | 77:23 | 2.15 | NA | 90:10 | CAT-2200 | Pertuzumab |
| 10942-11291 | 0.83 | 0.77 | 70:30 | 1.18 | NA | 76:24 | CAT-2200 | Pertuzumab |
| 10942-11345 | 0.83 | 0.77 | 70:30 | 0.82 | NA | 69:31 | CAT-2200 | Pertuzumab |
| 10943-11295 | 1.02 | 0.85 | 73:27 | 1.6 | NA | 83:17 | CAT-2200 | Pertuzumab |
| 10943-11349 | 1.02 | 0.85 | 73:27 | 1.27 | 0.16 | 78:22 | CAT-2200 | Pertuzumab |
| 10944-11307 | 1.02 | NA | 73:27 | 2.3 | 0.17 | 91:9 | CAT-2200 | Pertuzumab |
| 10944-11314 | 1.02 | NA | 73:27 | 3.06 | 0.45 | 96:4 | CAT-2200 | Pertuzumab |
| 10945-11377 | 0.97 | 0.39 | 73:27 | 2.22 | 0.65 | 90:10 | CAT-2200 | Pertuzumab |
| 10946-11382 | 0.53 | 0.18 | 63:37 | 1.67 | NA | 84:16 | CAT-2200 | Pertuzumab |
| 10947-11392 | 0.59 | 0.66 | 64:36 | 2.75 | 0.27 | 94:6 | CAT-2200 | Pertuzumab |
| 10948-11250 | 1.4 | 0.35 | 80:20 | 0.69 | NA | 67:33 | CAT-2200 | Pertuzumab |
| 10948-11258 | 1.4 | 0.35 | 80:20 | 1.22 | NA | 77:23 | CAT-2200 | Pertuzumab |
| 10948-11262 | 1.4 | 0.35 | 80:20 | 1.18 | 0.44 | 76:24 | CAT-2200 | Pertuzumab |
| 10950-11252 | 1.92 | 0.07 | 87:13 | 0.97 | 0.3 | 73:27 | CAT-2200 | Pertuzumab |
| 10950-11260 | 1.92 | 0.07 | 87:13 | 1.32 | NA | 79:21 | CAT-2200 | Pertuzumab |
| 10950-11264 | 1.92 | 0.07 | 87:13 | 1.47 | 0.18 | 81:19 | CAT-2200 | Pertuzumab |
| 10952-11398 | 1.08 | 1.48 | 75:25 | 2.33 | NA | 91:9 | CAT-2200 | Pertuzumab |
| 10953-11411 | 1.03 | 1.32 | 74:26 | 2.3 | 0.11 | 91:9 | CAT-2200 | Pertuzumab |
| 10962-11296 | 0.65 | 0.18 | 66:34 | 0.76 | NA | 68:32 | CAT-2200 | Pertuzumab |
| 10962-11350 | 0.65 | 0.18 | 66:34 | 0.22 | NA | 55:45 | CAT-2200 | Pertuzumab |
| 10965-11293 | 0.39 | 0.1 | 60:40 | 0.92 | NA | 72:28 | CAT-2200 | Pertuzumab |
| 10965-11347 | 0.39 | 0.1 | 60:40 | 0.77 | NA | 68:32 | CAT-2200 | Pertuzumab |
| 10966-11297 | 0.34 | 0.57 | 58:42 | 1.5 | NA | 82:18 | CAT-2200 | Pertuzumab |
| 10966-11351 | 0.34 | 0.57 | 58:42 | 1.05 | NA | 74:26 | CAT-2200 | Pertuzumab |
| 10969-11290 | 0.82 | 0.77 | 69:31 | 0.36 | NA | 59:41 | CAT-2200 | Pertuzumab |
| 10969-11344 | 0.82 | 0.77 | 69:31 | 0.22 | NA | 55:45 | CAT-2200 | Pertuzumab |
| 10970-11294 | 1.19 | 0.39 | 77:23 | 0.81 | NA | 69:31 | CAT-2200 | Pertuzumab |
| 10970-11348 | 1.19 | 0.39 | 77:23 | 0.41 | NA | 60:40 | CAT-2200 | Pertuzumab |
| 10973-11291 | 1.3 | 0.16 | 79:21 | 1.18 | NA | 76:24 | CAT-2200 | Pertuzumab |
| 10973-11345 | 1.3 | 0.16 | 79:21 | 0.82 | NA | 69:31 | CAT-2200 | Pertuzumab |
| 10974-11295 | 1.39 | 0.29 | 80:20 | 1.6 | NA | 83:17 | CAT-2200 | Pertuzumab |
| 10974-11349 | 1.39 | 0.29 | 80:20 | 1.27 | 0.16 | 78:22 | CAT-2200 | Pertuzumab |
| 10977-11292 | 0.59 | 0.16 | 64:36 | 0.26 | NA | 56:44 | CAT-2200 | Pertuzumab |
| 10977-11346 | 0.59 | 0.16 | 64:36 | 0.02 | NA | 50:50 | CAT-2200 | Pertuzumab |
| 10978-11296 | 0.76 | 0.24 | 68:32 | 0.76 | NA | 68:32 | CAT-2200 | Pertuzumab |
| 10978-11350 | 0.76 | 0.24 | 68:32 | 0.22 | NA | 55:45 | CAT-2200 | Pertuzumab |

TABLE 5A-continued

LCCA results for K-L designs that passed the performance cut-off criteria

| Column 1 Unique identifier | Column 2 H1L1:H1L2 normalized median scalar value ln(r1/f1) | Column 3 H1L1:H1L2 range of normalized scalar value ln(r1/f1) | Column 4 H1L1: H1L2 normalized median ratio | Column 5 H2L2:H2L1 normalized median scalar value ln(r1/f1) | Column 6 H2L2:H2L1 range of normalized scalar value ln(r1/f1) | Column 7 H2L2:H2L1 normalized median ratio | Column 8 H1L1 Fab | Column 9 H2L2 Fab |
|---|---|---|---|---|---|---|---|---|
| 10981-11293 | 0.41 | 0.06 | 60:40 | 0.92 | NA | 72:28 | CAT-2200 | Pertuzumab |
| 10981-11347 | 0.41 | 0.06 | 60:40 | 0.77 | NA | 68:32 | CAT-2200 | Pertuzumab |
| 10982-11297 | 0.58 | 0.1 | 64:36 | 1.5 | NA | 82:18 | CAT-2200 | Pertuzumab |
| 10982-11351 | 0.58 | 0.1 | 64:36 | 1.05 | NA | 74:26 | CAT-2200 | Pertuzumab |
| 10983-11306 | 1.21 | 0.36 | 77:23 | 2.48 | 0.22 | 92:8 | CAT-2200 | Pertuzumab |
| 10984-11376 | 0.65 | 0.2 | 66:34 | 1.5 | 0.39 | 82:18 | CAT-2200 | Pertuzumab |
| 10985-11381 | −0.04 | 0.01 | 49:51 | 1.7 | NA | 85:15 | CAT-2200 | Pertuzumab |
| 10986-11391 | 0.46 | 0.44 | 61:39 | 2.71 | 0.33 | 94:6 | CAT-2200 | Pertuzumab |
| 10987-11249 | 3.04 | 1.13 | 95:5 | 0.77 | 0.24 | 68:32 | CAT-2200 | Pertuzumab |
| 10987-11257 | 3.04 | 1.13 | 95:5 | 1.12 | 0.28 | 75:25 | CAT-2200 | Pertuzumab |
| 10987-11261 | 3.04 | 1.13 | 95:5 | 1.04 | 0.26 | 74:26 | CAT-2200 | Pertuzumab |
| 10989-11251 | 2.73 | 0.64 | 94:6 | 0.95 | NA | 72:28 | CAT-2200 | Pertuzumab |
| 10989-11259 | 2.73 | 0.64 | 94:6 | 1.47 | NA | 81:19 | CAT-2200 | Pertuzumab |
| 10989-11263 | 2.73 | 0.64 | 94:6 | 1.5 | 0.7 | 82:18 | CAT-2200 | Pertuzumab |
| 10992-11410 | 1.64 | 0.16 | 84:16 | 2.15 | NA | 90:10 | CAT-2200 | Pertuzumab |
| 10998-11307 | 1.24 | 0.55 | 78:22 | 2.3 | 0.17 | 91:9 | CAT-2200 | Pertuzumab |
| 10998-11314 | 1.24 | 0.55 | 78:22 | 3.06 | 0.45 | 96:4 | CAT-2200 | Pertuzumab |
| 10999-11377 | 0.8 | 0.41 | 69:31 | 2.22 | 0.65 | 90:10 | CAT-2200 | Pertuzumab |
| 11000-11382 | 0.28 | 0.03 | 57:43 | 1.67 | NA | 84:16 | CAT-2200 | Pertuzumab |
| 11001-11392 | 0.77 | 0.13 | 68:32 | 2.75 | 0.27 | 94:6 | CAT-2200 | Pertuzumab |
| 11002-11250 | 2.87 | 1.15 | 95:5 | 0.69 | NA | 67:33 | CAT-2200 | Pertuzumab |
| 11002-11258 | 2.87 | 1.15 | 95:5 | 1.22 | NA | 77:23 | CAT-2200 | Pertuzumab |
| 11002-11262 | 2.87 | 1.15 | 95:5 | 1.18 | 0.44 | 76:24 | CAT-2200 | Pertuzumab |
| 11004-11252 | 2.38 | 0.52 | 92:8 | 0.97 | 0.3 | 73:27 | CAT-2200 | Pertuzumab |
| 11004-11260 | 2.38 | 0.52 | 92:8 | 1.32 | NA | 79:21 | CAT-2200 | Pertuzumab |
| 11004-11264 | 2.38 | 0.52 | 92:8 | 1.47 | 0.18 | 81:19 | CAT-2200 | Pertuzumab |
| 11006-11398 | 1.7 | 0.54 | 85:15 | 2.33 | NA | 91:9 | CAT-2200 | Pertuzumab |
| 11007-11411 | 1.65 | 0.61 | 84:16 | 2.3 | 0.11 | 91:9 | CAT-2200 | Pertuzumab |
| 11025-11284 | 1.38 | 0.88 | 80:20 | 3.02 | 0.11 | 95:5 | CAT-2200 | Pertuzumab |
| 11026-11270 | 1.8 | 1.64 | 86:14 | 2.51 | 0.42 | 92:8 | CAT-2200 | Pertuzumab |
| 11027-11281 | 1.13 | 0.17 | 76:24 | 1.42 | 1.88 | 81:19 | CAT-2200 | Pertuzumab |
| 11027-11287 | 1.13 | 0.17 | 76:24 | 1.71 | 1.6 | 85:15 | CAT-2200 | Pertuzumab |
| 11028-11275 | 1.55 | 0.72 | 82:18 | 3.15 | 0.91 | 96:4 | CAT-2200 | Pertuzumab |
| 11029-11282 | 1.21 | NA | 77:23 | 2.8 | NA | 94:6 | CAT-2200 | Pertuzumab |
| 11029-11288 | 1.21 | NA | 77:23 | 2.83 | NA | 94:6 | CAT-2200 | Pertuzumab |
| 11030-11276 | 1.38 | 0.39 | 80:20 | 2.63 | 0.26 | 93:7 | CAT-2200 | Pertuzumab |
| 11030-11285 | 1.38 | 0.39 | 80:20 | 3 | 0.73 | 95:5 | CAT-2200 | Pertuzumab |
| 11032-11199 | 1.72 | 0.2 | 85:15 | 2.38 | 0.61 | 92:8 | CAT-2200 | Pertuzumab |
| 11033-11209 | 1.72 | 1.34 | 85:15 | 1.69 | NA | 84:16 | CAT-2200 | Pertuzumab |
| 11033-11215 | 1.72 | 1.34 | 85:15 | 2.31 | 0.42 | 91:9 | CAT-2200 | Pertuzumab |
| 11034-11204 | 1.43 | 0.25 | 81:19 | 3.12 | 0.61 | 96:4 | CAT-2200 | Pertuzumab |
| 11035-11212 | 1.81 | 0.46 | 86:14 | 2.04 | 0.12 | 88:12 | CAT-2200 | Pertuzumab |
| 11035-11218 | 1.81 | 0.46 | 86:14 | 3.12 | 0.48 | 96:4 | CAT-2200 | Pertuzumab |
| 11036-11221 | 1.35 | 0.18 | 79:21 | 1.38 | 0.52 | 80:20 | CAT-2200 | Pertuzumab |
| 11039-11224 | 0.9 | 0.46 | 71:29 | 0.62 | 0.2 | 65:35 | CAT-2200 | Pertuzumab |
| 11042-11273 | 0.83 | 1.03 | 70:30 | 1.75 | 0.25 | 85:15 | CAT-2200 | Pertuzumab |
| 11043-11181 | 1.09 | 0.21 | 75:25 | 1.68 | 0.67 | 84:16 | CAT-2200 | Pertuzumab |
| 11044-11191 | 0.93 | 0.18 | 72:28 | 1.5 | 0.61 | 82:18 | CAT-2200 | Pertuzumab |
| 11055-11322 | −0.34 | 0.5 | 42:58 | 1.51 | 0.2 | 82:18 | CAT-2200 | Pertuzumab |
| 11056-11324 | 0.42 | NA | 60:40 | 0.84 | NA | 70:30 | CAT-2200 | Pertuzumab |
| 11061-11273 | 1.23 | 0.45 | 77:23 | 1.75 | 0.25 | 85:15 | CAT-2200 | Pertuzumab |
| 11062-11323 | 0.54 | NA | 63:37 | 0.15 | NA | 54:46 | CAT-2200 | Pertuzumab |
| 11063-11325 | 0.83 | NA | 70:30 | −0.25 | NA | 44:56 | CAT-2200 | Pertuzumab |
| 11064-11201 | 1.64 | 0.68 | 84:16 | 2.18 | 0.61 | 90:10 | CAT-2200 | Pertuzumab |
| 11065-11206 | 1.84 | 0.08 | 86:14 | 2.72 | 0.33 | 94:6 | CAT-2200 | Pertuzumab |
| 11066-11181 | 0.91 | 0.15 | 71:29 | 1.68 | 0.67 | 84:16 | CAT-2200 | Pertuzumab |
| 11076-11355 | −0.4 | NA | 40:60 | 0.7 | NA | 67:33 | CAT-2200 | Pertuzumab |
| 11087-11179 | 1.98 | 0.49 | 88:12 | 1.83 | NA | 86:14 | CAT-2200 | Pertuzumab |
| 11088-11185 | 1.63 | 0.48 | 84:16 | 2.29 | 0.29 | 91:9 | CAT-2200 | Pertuzumab |
| 11089-11189 | 1.77 | 0.2 | 85:15 | 1.64 | NA | 84:16 | CAT-2200 | Pertuzumab |
| 11096-11272 | 1.75 | 0.63 | 85:15 | 2.62 | 0.05 | 93:7 | CAT-2200 | Pertuzumab |
| 11097-11277 | 1.87 | 0.16 | 87:13 | 2.22 | NA | 90:10 | CAT-2200 | Pertuzumab |
| 11098-11200 | 2.65 | 0.47 | 93:7 | 2.21 | 0.1 | 90:10 | CAT-2200 | Pertuzumab |
| 11099-11210 | 2.31 | 0.64 | 91:9 | 0.9 | NA | 71:29 | CAT-2200 | Pertuzumab |
| 11099-11216 | 2.31 | 0.64 | 91:9 | 1.77 | 0.35 | 85:15 | CAT-2200 | Pertuzumab |
| 11100-11205 | 2.58 | 0.19 | 93:7 | 2.51 | 0.72 | 92:8 | CAT-2200 | Pertuzumab |
| 11101-11213 | 2.44 | 0.37 | 92:8 | 1.24 | NA | 78:22 | CAT-2200 | Pertuzumab |
| 11101-11219 | 2.44 | 0.37 | 92:8 | 2.13 | 0.34 | 89:11 | CAT-2200 | Pertuzumab |
| 11102-11180 | 2.21 | 0.22 | 90:10 | 1.95 | 0.23 | 88:12 | CAT-2200 | Pertuzumab |
| 11103-11186 | 2.04 | 0.32 | 88:12 | 1.52 | 0.1 | 82:18 | CAT-2200 | Pertuzumab |
| 11104-11190 | 2.37 | 0.11 | 91:9 | 1.9 | NA | 87:13 | CAT-2200 | Pertuzumab |

TABLE 5A-continued

LCCA results for K-L designs that passed the performance cut-off criteria

| Column 1 Unique identifier | Column 2 H1L1:H1L2 normalized median scalar value ln(r1/f1) | Column 3 H1L1:H1L2 range of normalized scalar value ln(r1/f1) | Column 4 H1L1: H1L2 normalized median ratio | Column 5 H2L2:H2L1 normalized median scalar value ln(r1/f1) | Column 6 H2L2:H2L1 range of normalized scalar value ln(r1/f1) | Column 7 H2L2:H2L1 normalized median ratio | Column 8 H1L1 Fab | Column 9 H2L2 Fab |
|---|---|---|---|---|---|---|---|---|
| 11105-11195 | 1.93 | NA | 87:13 | −0.15 | 0.29 | 46:54 | CAT-2200 | Pertuzumab |
| 11106-11225 | 1.83 | NA | 86:14 | 0.65 | NA | 66:34 | CAT-2200 | Pertuzumab |
| 11106-11229 | 1.83 | NA | 86:14 | 0.18 | 0.06 | 54:46 | CAT-2200 | Pertuzumab |
| 11107-11197 | 1.92 | 0.25 | 87:13 | 0.25 | 0.18 | 56:44 | CAT-2200 | Pertuzumab |
| 11108-11227 | 2.4 | NA | 92:8 | 0.94 | NA | 72:28 | CAT-2200 | Pertuzumab |
| 11108-11231 | 2.4 | NA | 92:8 | 0.15 | 0.33 | 54:46 | CAT-2200 | Pertuzumab |
| 11124-11202 | 2.1 | 0.67 | 89:11 | 2.94 | 1.29 | 95:5 | CAT-2200 | Pertuzumab |
| 11125-11207 | 2.13 | 0.27 | 89:11 | 2.85 | 1.01 | 95:5 | CAT-2200 | Pertuzumab |
| 11140-11202 | 2.29 | 0.32 | 91:9 | 2.94 | 1.29 | 95:5 | CAT-2200 | Pertuzumab |
| 11141-11207 | 2.1 | NA | 89:11 | 2.85 | 1.01 | 95:5 | CAT-2200 | Pertuzumab |
| 11142-11182 | 1.93 | 0.21 | 87:13 | 2.4 | 0.71 | 92:8 | CAT-2200 | Pertuzumab |
| 11143-11187 | 1.4 | 0.57 | 80:20 | 2.11 | 0.33 | 89:11 | CAT-2200 | Pertuzumab |
| 11144-11192 | 1.96 | 0.32 | 88:12 | 2.3 | 0.38 | 91:9 | CAT-2200 | Pertuzumab |
| 11148-11183 | 2.25 | 0.2 | 90:10 | 1.93 | 1.9 | 87:13 | CAT-2200 | Pertuzumab |
| 11149-11188 | 1.99 | 0.29 | 88:12 | 1.59 | 0.29 | 83:17 | CAT-2200 | Pertuzumab |
| 11150-11193 | 2.13 | 0.7 | 89:11 | 1.59 | 0.3 | 83:17 | CAT-2200 | Pertuzumab |
| 11156-11274 | 0.42 | 0.77 | 60:40 | 3.21 | 0.22 | 96:4 | CAT-2200 | Pertuzumab |
| 11157-11279 | 0.38 | 0.09 | 59:41 | 3.16 | 0.59 | 96:4 | CAT-2200 | Pertuzumab |
| 11158-11203 | 2.02 | NA | 88:12 | 2.41 | 0.13 | 92:8 | CAT-2200 | Pertuzumab |
| 11159-11211 | 2.02 | 0.05 | 88:12 | 0.82 | NA | 69:31 | CAT-2200 | Pertuzumab |
| 11159-11217 | 2.02 | 0.05 | 88:12 | 1.98 | 0.27 | 88:12 | CAT-2200 | Pertuzumab |
| 11160-11208 | 2.02 | NA | 88:12 | 2.42 | 0.22 | 92:8 | CAT-2200 | Pertuzumab |
| 11161-11214 | 2.08 | 0.26 | 89:11 | 1.55 | NA | 82:18 | CAT-2200 | Pertuzumab |
| 11161-11220 | 2.08 | 0.26 | 89:11 | 2.4 | 0.71 | 92:8 | CAT-2200 | Pertuzumab |
| 11162-11184 | 1.13 | 0.65 | 76:24 | 1.09 | NA | 75:25 | CAT-2200 | Pertuzumab |
| 11163-11194 | 1.16 | 0.09 | 76:24 | 1.75 | NA | 85:15 | CAT-2200 | Pertuzumab |
| 11164-11196 | 0.93 | 0.3 | 72:28 | 1.69 | 0.58 | 84:16 | CAT-2200 | Pertuzumab |
| 11165-11226 | 0.92 | NA | 72:28 | 1.03 | NA | 74:26 | CAT-2200 | Pertuzumab |
| 11165-11230 | 0.92 | NA | 72:28 | 1.71 | 0.18 | 85:15 | CAT-2200 | Pertuzumab |
| 11166-11198 | 0.66 | 0.17 | 66:34 | 2.32 | 0.85 | 91:9 | CAT-2200 | Pertuzumab |
| 11167-11228 | 0.85 | NA | 70:30 | 1.19 | NA | 77:23 | CAT-2200 | Pertuzumab |
| 11167-11232 | 0.85 | NA | 70:30 | 1.84 | 0.11 | 86:14 | CAT-2200 | Pertuzumab |

TABLE 5B

LCCA results for K-K-derived K-L designs that passed the performance cut-off criteria

| Column 1 Unique identifier | Column 2 H1L1:H1L2 normalized median scalar value ln(r1/f1) | Column 3 H1L1:H1L2 range of normalized scalar value ln(r1/f1) | Column 4 H1L1:H1L2 normalized median ratio | Column 5 H2L2:H2L1 normalized median scalar value ln(r1/f1) | Column 6 H2L2:H2L1 range of normalized scalar value ln(r1/f1) | Column 7 H2L2:H2L1 normalized median ratio | Column 8 H1L1 Fab | Column 9 H2L2 Fab |
|---|---|---|---|---|---|---|---|---|
| 10621-10731 | 0.49 | 0.43 | 62:38 | 0.37 | 0.09 | 59:41 | CAT-2200 | Pertuzumab |
| 10621-10733 | 0.49 | 0.43 | 62:38 | 0.72 | 3.76 | 67:33 | CAT-2200 | Pertuzumab |
| 10622-10736 | 0.69 | NA | 67:33 | −0.11 | NA | 47:53 | CAT-2200 | Pertuzumab |
| 10622-10742 | 0.69 | NA | 67:33 | −0.11 | NA | 47:53 | CAT-2200 | Pertuzumab |
| 10623-10739 | 1.06 | NA | 74:26 | −0.03 | NA | 49:51 | CAT-2200 | Pertuzumab |
| 10623-10745 | 1.06 | NA | 74:26 | −0.08 | NA | 48:52 | CAT-2200 | Pertuzumab |
| 10624-10700 | −0.25 | NA | 44:56 | 0.57 | NA | 64:36 | CAT-2200 | Pertuzumab |
| 10625-10701 | 0.59 | 0.07 | 64:36 | −0.04 | 0.18 | 49:51 | CAT-2200 | Pertuzumab |
| 10629-10695 | 0.76 | NA | 68:32 | −0.36 | NA | 41:59 | CAT-2200 | Pertuzumab |
| 10631-10722 | 1.1 | 0.23 | 75:25 | 0.87 | 1.04 | 70:30 | CAT-2200 | Pertuzumab |
| 10632-10724 | 2.16 | 0.67 | 90:10 | 0.61 | 0.27 | 65:35 | CAT-2200 | Pertuzumab |
| 10640-10713 | 0.08 | 0.48 | 52:48 | 1.51 | 0.81 | 82:18 | CAT-2200 | Pertuzumab |
| 10652-10702 | −0.11 | 0.41 | 47:53 | 3.29 | 1.58 | 96:4 | CAT-2200 | Pertuzumab |
| 10652-10734 | −0.11 | 0.41 | 47:53 | 2.67 | 0.39 | 94:6 | CAT-2200 | Pertuzumab |
| 10652-10755 | −0.11 | 0.41 | 47:53 | 1.42 | NA | 81:19 | CAT-2200 | Pertuzumab |
| 10656-10758 | −0.13 | 0.61 | 47:53 | 2.54 | 0.65 | 93:7 | CAT-2200 | Pertuzumab |
| 10657-10760 | 0.53 | 0.46 | 63:37 | 2.85 | 1.28 | 95:5 | CAT-2200 | Pertuzumab |
| 10658-10720 | 0.07 | NA | 52:48 | 0.83 | 0.66 | 70:30 | CAT-2200 | Pertuzumab |
| 10659-10720 | 0.28 | 0.12 | 57:43 | 0.83 | 0.66 | 70:30 | CAT-2200 | Pertuzumab |
| 10662-10731 | 0.63 | 0.31 | 65:35 | 0.37 | 0.09 | 59:41 | CAT-2200 | Pertuzumab |
| 10662-10733 | 0.63 | 0.31 | 65:35 | 0.72 | 3.76 | 67:33 | CAT-2200 | Pertuzumab |
| 10664-10722 | 0.94 | 0.05 | 72:28 | 0.87 | 1.04 | 70:30 | CAT-2200 | Pertuzumab |
| 10665-10724 | 2.32 | 0.27 | 91:9 | 0.61 | 0.27 | 65:35 | CAT-2200 | Pertuzumab |
| 10671-10751 | 0.56 | NA | 64:36 | 0.15 | 0.32 | 54:46 | CAT-2200 | Pertuzumab |

TABLE 5B-continued

LCCA results for K-K-derived K-L designs that passed the performance cut-off criteria

| Column 1 Unique identifier | Column 2 H1L1:H1L2 normalized median scalar value ln(r1/f1) | Column 3 H1L1:H1L2 range of normalized scalar value ln(r1/f1) | Column 4 H1L1:H1L2 normalized median ratio | Column 5 H2L2:H2L1 normalized median scalar value ln(r1/f1) | Column 6 H2L2:H2L1 range of normalized scalar value ln(r1/f1) | Column 7 H2L2:H2L1 normalized median ratio | Column 8 H1L1 Fab | Column 9 H2L2 Fab |
|---|---|---|---|---|---|---|---|---|
| 10674-10749 | 1.13 | 0.18 | 76:24 | 0.18 | 0.21 | 54:46 | CAT-2200 | Pertuzumab |
| 10676-10750 | 0.81 | 0.23 | 69:31 | 0.23 | 0.19 | 56:44 | CAT-2200 | Pertuzumab |
| 10677-10751 | 0.78 | 0.39 | 69:31 | 0.15 | 0.32 | 54:46 | CAT-2200 | Pertuzumab |
| 10678-10737 | 0.91 | 0.37 | 71:29 | 1.09 | 0.39 | 75:25 | CAT-2200 | Pertuzumab |
| 10678-10743 | 0.91 | 0.37 | 71:29 | 1.09 | 0.91 | 75:25 | CAT-2200 | Pertuzumab |
| 10679-10738 | 0.61 | 0.08 | 65:35 | 1.35 | NA | 79:21 | CAT-2200 | Pertuzumab |
| 10679-10744 | 0.61 | 0.08 | 65:35 | 1.29 | 0.69 | 78:22 | CAT-2200 | Pertuzumab |
| 10680-10740 | 1.23 | 0.47 | 77:23 | 1.19 | 0.37 | 77:23 | CAT-2200 | Pertuzumab |
| 10680-10746 | 1.23 | 0.47 | 77:23 | 1.02 | 0.38 | 73:27 | CAT-2200 | Pertuzumab |
| 10681-10741 | 0.92 | 0.26 | 72:28 | 2.47 | 1.3 | 92:8 | CAT-2200 | Pertuzumab |
| 10681-10747 | 0.92 | 0.26 | 72:28 | 1.19 | 0.73 | 77:23 | CAT-2200 | Pertuzumab |
| 10682-10718 | 2.12 | 0.77 | 89:11 | 0.55 | 0.61 | 63:37 | CAT-2200 | Pertuzumab |
| 10683-10720 | 0.82 | 0.33 | 69:31 | 0.83 | 0.66 | 70:30 | CAT-2200 | Pertuzumab |
| 10684-10706 | 1.94 | 0.25 | 87:13 | 0.53 | 0.26 | 63:37 | CAT-2200 | Pertuzumab |
| 10685-10719 | 2.07 | 0.27 | 89:11 | 1.01 | 0.14 | 73:27 | CAT-2200 | Pertuzumab |
| 10685-10726 | 2.07 | 0.27 | 89:11 | 1.46 | 0.39 | 81:19 | CAT-2200 | Pertuzumab |
| 10687-10722 | 1.04 | 0.63 | 74:26 | 0.87 | 1.04 | 70:30 | CAT-2200 | Pertuzumab |
| 10688-10724 | 2.24 | 0.66 | 90:10 | 0.61 | 0.27 | 65:35 | CAT-2200 | Pertuzumab |
| 10689-10707 | 1.13 | 0.38 | 76:24 | 0.53 | 0.74 | 63:37 | CAT-2200 | Pertuzumab |
| 10690-10727 | 2.1 | 0.46 | 89:11 | 1.42 | 0.09 | 81:19 | CAT-2200 | Pertuzumab |
| 10621-10731 | 0.49 | 0.43 | 62:38 | 0.37 | 0.09 | 59:41 | CAT-2200 | Pertuzumab |

TABLE 6A

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 10771-11335 | 0.27 | 0.00 | ND | ND | 77.0 | 0.0 | ND | ND | 70.7 | 0.0 | ND | ND | CAT-2200 | Pertuzumab |
| 10771-11360 | 0.27 | 0.00 | ND | ND | 77.0 | 0.0 | ND | ND | 70.7 | 0.0 | ND | ND | CAT-2200 | Pertuzumab |
| 10776-11312 | ND | ND | ND | ND | ND | ND | ND | ND | ND | ND | ND | ND | CAT-2200 | Pertuzumab |
| 10776-11321 | ND | ND | ND | ND | ND | ND | ND | ND | ND | ND | ND | ND | CAT-2200 | Pertuzumab |
| 10776-11353 | ND | ND | ND | ND | ND | ND | ND | ND | ND | ND | ND | ND | CAT-2200 | Pertuzumab |
| 10780-11417 | 0.22 | 0.09 | ND | ND | 76.5 | −0.5 | ND | ND | ND | ND | ND | ND | CAT-2200 | Pertuzumab |
| 10781-11300 | 0.22 | 0.09 | ND | ND | 76.5 | −0.5 | ND | ND | ND | ND | ND | ND | CAT-2200 | Pertuzumab |
| 10781-11419 | 0.22 | 0.09 | 7.76 | 0.02 | 76.5 | −0.5 | 80.5 | −1.5 | ND | ND | ND | ND | CAT-2200 | Pertuzumab |
| 10786-11299 | 0.23 | 0.08 | ND | ND | 75.7 | −1.3 | ND | ND | ND | ND | ND | ND | CAT-2200 | Pertuzumab |
| 10786-11418 | 0.23 | 0.08 | ND | ND | 75.7 | −1.3 | ND | ND | ND | ND | ND | ND | CAT-2200 | Pertuzumab |
| 10787-11301 | 0.23 | 0.08 | ND | ND | 75.7 | −1.3 | ND | ND | ND | ND | ND | ND | CAT-2200 | Pertuzumab |
| 10787-11420 | 0.23 | 0.08 | 7.76 | 0.02 | 75.7 | −1.3 | 80.5 | −1.5 | ND | ND | ND | ND | CAT-2200 | Pertuzumab |
| 10788-11422 | 0.23 | 0.08 | ND | ND | 75.7 | −1.3 | ND | ND | ND | ND | ND | ND | CAT-2200 | Pertuzumab |
| 10791-11305 | 0.23 | 0.08 | ND | ND | 75.7 | −1.3 | ND | ND | ND | ND | ND | ND | CAT-2200 | Pertuzumab |
| 10792-11424 | 0.23 | 0.08 | ND | ND | 75.7 | −1.3 | ND | ND | ND | ND | ND | ND | CAT-2200 | Pertuzumab |
| 10793-11375 | 0.23 | 0.08 | 8.13 | 0.00 | 75.7 | −1.3 | 80.5 | −1.5 | ND | ND | ND | ND | CAT-2200 | Pertuzumab |
| 10795-11390 | 0.34 | −0.10 | 7.92 | 0.01 | 74.0 | −3.0 | 80.7 | −1.3 | 69.7 | −1.0 | ND | ND | CAT-2200 | Pertuzumab |
| 10796-11396 | 0.34 | −0.10 | 8.15 | 0.00 | 74.0 | −3.0 | 82.5 | 0.5 | 69.7 | −1.0 | ND | ND | CAT-2200 | Pertuzumab |
| 10798-11256 | 0.34 | −0.10 | 7.78 | 0.02 | 74.0 | −3.0 | 81.5 | −0.5 | 69.7 | −1.0 | ND | ND | CAT-2200 | Pertuzumab |
| 10798-11268 | 0.34 | −0.10 | 8.24 | −0.01 | 74.0 | −3.0 | 81.5 | −0.5 | 69.7 | −1.0 | ND | ND | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 10800-11416 | 0.34 | −0.10 | 8.26 | −0.01 | 74.0 | −3.0 | 78.0 | −4.0 | 69.7 | −1.0 | ND | ND | CAT-2200 | Pertuzumab |
| 10806-11326 | 0.27 | 0.00 | 7.65 | 0.02 | 69.7 | −7.3 | 83.2 | 1.3 | 65.5 | −5.2 | ND | ND | CAT-2200 | Pertuzumab |
| 10806-11369 | 0.27 | 0.00 | 6.98 | 0.06 | 69.7 | −7.3 | 81.7 | −0.3 | 65.5 | −5.2 | 78.4 | −0.3 | CAT-2200 | Pertuzumab |
| 10808-11308 | 0.27 | 0.00 | 7.41 | 0.04 | 69.7 | −7.3 | 81.0 | −1.0 | 65.5 | −5.2 | ND | ND | CAT-2200 | Pertuzumab |
| 10808-11315 | 0.27 | 0.00 | 7.91 | 0.01 | 69.7 | −7.3 | 80.3 | −1.7 | 65.5 | −5.2 | 77.1 | −1.6 | CAT-2200 | Pertuzumab |
| 10809-11378 | 0.27 | 0.00 | 8.46 | −0.02 | 69.7 | −7.3 | 80.2 | −1.8 | 65.5 | −5.2 | ND | ND | CAT-2200 | Pertuzumab |
| 10810-11383 | 0.27 | 0.00 | 8.31 | −0.01 | 69.7 | −7.3 | 78.8 | −3.2 | 65.5 | −5.2 | ND | ND | CAT-2200 | Pertuzumab |
| 10811-11386 | 0.27 | 0.00 | 7.92 | 0.01 | 69.7 | −7.3 | 80.7 | −1.3 | 65.5 | −5.2 | ND | ND | CAT-2200 | Pertuzumab |
| 10812-11393 | 0.27 | 0.00 | 8.15 | 0.00 | 69.7 | −7.3 | 82.5 | 0.5 | 65.5 | −5.2 | ND | ND | CAT-2200 | Pertuzumab |
| 10813-11311 | 0.27 | 0.00 | ND | ND | 69.7 | −7.3 | ND | ND | 65.5 | −5.2 | ND | ND | CAT-2200 | Pertuzumab |
| 10813-11320 | 0.27 | 0.00 | ND | ND | 69.7 | −7.3 | ND | ND | 65.5 | −5.2 | ND | ND | CAT-2200 | Pertuzumab |
| 10813-11352 | 0.27 | 0.00 | ND | ND | 69.7 | −7.3 | ND | ND | 65.5 | −5.2 | ND | ND | CAT-2200 | Pertuzumab |
| 10814-11233 | 0.27 | 0.00 | 8.28 | −0.01 | 69.7 | −7.3 | 80.8 | −1.1 | 65.5 | −5.2 | 78.2 | −0.5 | CAT-2200 | Pertuzumab |
| 10816-11253 | 0.27 | 0.00 | 7.78 | 0.02 | 69.7 | −7.3 | 81.5 | −0.5 | 65.5 | −5.2 | ND | ND | CAT-2200 | Pertuzumab |
| 10816-11265 | 0.27 | 0.00 | 8.25 | −0.01 | 69.7 | −7.3 | 81.5 | −0.5 | 65.5 | −5.2 | ND | ND | CAT-2200 | Pertuzumab |
| 10818-11404 | 0.27 | 0.00 | ND | ND | 69.7 | −7.3 | ND | ND | 65.5 | −5.2 | ND | ND | CAT-2200 | Pertuzumab |
| 10819-11407 | 0.27 | 0.00 | ND | ND | 69.7 | −7.3 | ND | ND | 65.5 | −5.2 | ND | ND | CAT-2200 | Pertuzumab |
| 10820-11413 | 0.27 | 0.00 | 8.26 | −0.01 | 69.7 | −7.3 | 78.0 | −4.0 | 65.5 | −5.2 | ND | ND | CAT-2200 | Pertuzumab |
| 10827-11373 | 0.25 | 0.04 | 7.57 | 0.03 | 60.0 | −17.0 | 82.2 | 0.3 | ND | ND | ND | ND | CAT-2200 | Pertuzumab |
| 10828-11327 | 0.25 | 0.04 | 7.65 | 0.02 | 60.0 | −17.0 | 83.2 | 1.3 | ND | ND | ND | ND | CAT-2200 | Pertuzumab |
| 10828-11370 | 0.25 | 0.04 | 6.98 | 0.06 | 60.0 | −17.0 | 81.7 | −0.3 | ND | ND | 78.4 | −0.3 | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 10830-11309 | 0.25 | 0.04 | 7.41 | 0.04 | 60.0 | −17.0 | 81.0 | −1.0 | ND | ND | ND | ND | CAT-2200 | Pertuzumab |
| 10830-11316 | 0.25 | 0.04 | 7.91 | 0.01 | 60.0 | −17.0 | 80.3 | −1.7 | ND | ND | 77.1 | −1.6 | CAT-2200 | Pertuzumab |
| 10831-11379 | 0.25 | 0.04 | 8.46 | −0.02 | 60.0 | −17.0 | 80.2 | −1.8 | ND | ND | ND | ND | CAT-2200 | Pertuzumab |
| 10832-11384 | 0.25 | 0.04 | 8.31 | −0.01 | 60.0 | −17.0 | 78.8 | −3.2 | ND | ND | ND | ND | CAT-2200 | Pertuzumab |
| 10833-11387 | 0.25 | 0.04 | 7.92 | 0.01 | 60.0 | −17.0 | 80.7 | −1.3 | ND | ND | ND | ND | CAT-2200 | Pertuzumab |
| 10834-11394 | 0.25 | 0.04 | 8.15 | 0.00 | 60.0 | −17.0 | 82.5 | 0.5 | ND | ND | ND | ND | CAT-2200 | Pertuzumab |
| 10835-11234 | 0.25 | 0.04 | 8.28 | −0.01 | 60.0 | −17.0 | 80.8 | −1.1 | ND | ND | 78.2 | −0.5 | CAT-2200 | Pertuzumab |
| 10837-11254 | 0.25 | 0.04 | 7.78 | 0.02 | 60.0 | −17.0 | 81.5 | −0.5 | ND | ND | ND | ND | CAT-2200 | Pertuzumab |
| 10837-11266 | 0.25 | 0.04 | 8.25 | −0.01 | 60.0 | −17.0 | 81.5 | −0.5 | ND | ND | ND | ND | CAT-2200 | Pertuzumab |
| 10840-11408 | 0.25 | 0.04 | ND | ND | 60.0 | −17.0 | ND | ND | ND | ND | ND | ND | CAT-2200 | Pertuzumab |
| 10848-11328 | 0.27 | 0.01 | 7.65 | 0.02 | 67.7 | −9.3 | 83.2 | 1.3 | ND | ND | ND | ND | CAT-2200 | Pertuzumab |
| 10848-11371 | 0.27 | 0.01 | 6.98 | 0.06 | 67.7 | −9.3 | 81.7 | −0.3 | ND | ND | 78.4 | −0.3 | CAT-2200 | Pertuzumab |
| 10850-11310 | 0.27 | 0.01 | 7.41 | 0.04 | 67.7 | −9.3 | 81.0 | −1.0 | ND | ND | ND | ND | CAT-2200 | Pertuzumab |
| 10850-11317 | 0.27 | 0.01 | 7.91 | 0.01 | 67.7 | −9.3 | 80.3 | −1.7 | ND | ND | 77.1 | −1.6 | CAT-2200 | Pertuzumab |
| 10851-11380 | 0.27 | 0.01 | 8.46 | −0.02 | 67.7 | −9.3 | 80.2 | −1.8 | ND | ND | ND | ND | CAT-2200 | Pertuzumab |
| 10852-11385 | 0.27 | 0.01 | 8.31 | −0.01 | 67.7 | −9.3 | 78.8 | −3.2 | ND | ND | ND | ND | CAT-2200 | Pertuzumab |
| 10853-11388 | 0.27 | 0.01 | 7.92 | 0.01 | 67.7 | −9.3 | 80.7 | −1.3 | ND | ND | ND | ND | CAT-2200 | Pertuzumab |
| 10854-11395 | 0.27 | 0.01 | 8.15 | 0.00 | 67.7 | −9.3 | 82.5 | 0.5 | ND | ND | ND | ND | CAT-2200 | Pertuzumab |
| 10855-11312 | 0.27 | 0.01 | ND | ND | 67.7 | −9.3 | ND | ND | ND | ND | ND | ND | CAT-2200 | Pertuzumab |
| 10855-11321 | 0.27 | 0.01 | ND | ND | 67.7 | −9.3 | ND | ND | ND | ND | ND | ND | CAT-2200 | Pertuzumab |
| 10855-11353 | 0.27 | 0.01 | ND | ND | 67.7 | −9.3 | ND | ND | ND | ND | ND | ND | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 10856-11235 | 0.27 | 0.01 | 8.28 | −0.01 | 67.7 | −9.3 | 80.8 | −1.1 | ND | ND | 78.2 | −0.5 | CAT-2200 | Pertuzumab |
| 10857-11243 | 0.27 | 0.01 | 10.65 | −0.12 | 67.7 | −9.3 | 78.8 | −3.2 | ND | ND | 75.5 | −3.2 | CAT-2200 | Pertuzumab |
| 10858-11255 | 0.27 | 0.01 | 7.78 | 0.02 | 67.7 | −9.3 | 81.5 | −0.5 | ND | ND | ND | ND | CAT-2200 | Pertuzumab |
| 10858-11267 | 0.27 | 0.01 | 8.25 | −0.01 | 67.7 | −9.3 | 81.5 | −0.5 | ND | ND | ND | ND | CAT-2200 | Pertuzumab |
| 10860-11406 | 0.27 | 0.01 | ND | ND | 67.7 | −9.3 | ND | ND | ND | ND | ND | ND | CAT-2200 | Pertuzumab |
| 10861-11409 | 0.27 | 0.01 | ND | ND | 67.7 | −9.3 | ND | ND | ND | ND | ND | ND | CAT-2200 | Pertuzumab |
| 10862-11414 | 0.27 | 0.01 | 8.26 | −0.01 | 67.7 | −9.3 | 78.0 | −4.0 | ND | ND | ND | ND | CAT-2200 | Pertuzumab |
| 10869-11390 | 0.21 | 0.11 | 7.92 | 0.01 | 73.7 | −3.3 | 80.7 | −1.3 | 68.9 | −1.8 | ND | ND | CAT-2200 | Pertuzumab |
| 10870-11396 | 0.21 | 0.11 | 8.15 | 0.00 | 73.7 | −3.3 | 82.5 | 0.5 | 68.9 | −1.8 | ND | ND | CAT-2200 | Pertuzumab |
| 10871-11240 | 0.21 | 0.11 | 8.28 | −0.01 | 73.7 | −3.3 | 80.8 | −1.1 | 68.9 | −1.8 | 78.2 | −0.5 | CAT-2200 | Pertuzumab |
| 10873-11256 | 0.21 | 0.11 | 7.78 | 0.02 | 73.7 | −3.3 | 81.5 | −0.5 | 68.9 | −1.8 | ND | ND | CAT-2200 | Pertuzumab |
| 10873-11268 | 0.21 | 0.11 | 8.25 | −0.01 | 73.7 | −3.3 | 81.5 | −0.5 | 68.9 | −1.8 | ND | ND | CAT-2200 | Pertuzumab |
| 10875-11416 | 0.21 | 0.11 | 8.26 | −0.01 | 73.7 | −3.3 | 78.0 | −4.0 | 68.9 | −1.8 | ND | ND | CAT-2200 | Pertuzumab |
| 10881-11412 | NB | −3.56 | 8.26 | −0.01 | ND | ND | 78.0 | −4.0 | ND | ND | ND | ND | CAT-2200 | Pertuzumab |
| 10883-11236 | NB | −3.56 | 8.28 | −0.01 | ND | ND | 80.8 | −1.1 | ND | ND | 78.2 | −0.5 | CAT-2200 | Pertuzumab |
| 10888-11415 | NB | −3.56 | 8.26 | −0.01 | ND | ND | 78.0 | −4.0 | ND | ND | ND | ND | CAT-2200 | Pertuzumab |
| 10898-11239 | ND | ND | 8.28 | −0.01 | ND | ND | 80.8 | −1.1 | ND | ND | 78.2 | −0.5 | CAT-2200 | Pertuzumab |
| 10923-11306 | 0.22 | 0.10 | 7.41 | 0.04 | 74.0 | −3.0 | 81.0 | −1.0 | ND | ND | ND | ND | CAT-2200 | Pertuzumab |
| 10924-11376 | 0.22 | 0.10 | 8.46 | −0.02 | 74.0 | −3.0 | 80.2 | −1.8 | ND | ND | ND | ND | CAT-2200 | Pertuzumab |
| 10926-11391 | 0.22 | 0.10 | 8.15 | 0.00 | 74.0 | −3.0 | 82.5 | 0.5 | ND | ND | ND | ND | CAT-2200 | Pertuzumab |
| 10927-11290 | 0.22 | 0.10 | ND | ND | 74.0 | −3.0 | ND | ND | ND | ND | ND | ND | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 10927-11344 | 0.22 | 0.10 | 8.01 | 0.00 | 74.0 | −3.0 | 78.0 | −4.0 | ND | ND | ND | ND | CAT-2200 | Pertuzumab |
| 10928-11294 | 0.22 | 0.10 | 7.13 | 0.05 | 74.0 | −3.0 | 78.0 | −4.0 | ND | ND | 74.9 | −3.8 | CAT-2200 | Pertuzumab |
| 10928-11348 | 0.22 | 0.10 | ND | ND | 74.0 | −3.0 | ND | ND | ND | ND | ND | ND | CAT-2200 | Pertuzumab |
| 10929-11249 | 0.22 | 0.10 | 8.64 | −0.03 | 74.0 | −3.0 | 80.0 | −2.0 | ND | ND | 76.6 | −2.1 | CAT-2200 | Pertuzumab |
| 10929-11257 | 0.22 | 0.10 | 8.53 | −0.02 | 74.0 | −3.0 | 80.0 | −2.0 | ND | ND | 76.8 | −1.9 | CAT-2200 | Pertuzumab |
| 10929-11261 | 0.22 | 0.10 | ND | ND | 74.0 | −3.0 | ND | ND | ND | ND | ND | ND | CAT-2200 | Pertuzumab |
| 10931-11251 | 0.22 | 0.10 | 7.78 | 0.02 | 74.0 | −3.0 | 81.5 | −0.5 | ND | ND | ND | ND | CAT-2200 | Pertuzumab |
| 10931-11259 | 0.22 | 0.10 | ND | ND | 74.0 | −3.0 | 79.0 | −3.0 | ND | ND | ND | ND | CAT-2200 | Pertuzumab |
| 10931-11263 | 0.22 | 0.10 | 8.25 | −0.01 | 74.0 | −3.0 | 81.5 | −0.5 | ND | ND | ND | ND | CAT-2200 | Pertuzumab |
| 10934-11410 | 0.22 | 0.10 | 8.26 | −0.01 | 74.0 | −3.0 | 78.0 | −4.0 | ND | ND | ND | ND | CAT-2200 | Pertuzumab |
| 10942-11291 | 0.33 | −0.08 | ND | ND | 74.0 | −3.0 | ND | ND | ND | ND | ND | ND | CAT-2200 | Pertuzumab |
| 10942-11345 | 0.33 | −0.08 | 8.01 | 0.00 | 74.0 | −3.0 | 78.0 | −4.0 | ND | ND | ND | ND | CAT-2200 | Pertuzumab |
| 10943-11295 | 0.33 | −0.08 | 7.13 | 0.05 | 74.0 | −3.0 | 78.0 | −4.0 | ND | ND | 74.9 | −3.8 | CAT-2200 | Pertuzumab |
| 10943-11349 | 0.33 | −0.08 | ND | ND | 74.0 | −3.0 | ND | ND | ND | ND | ND | ND | CAT-2200 | Pertuzumab |
| 10944-11307 | 0.35 | −0.10 | 7.41 | 0.04 | 74.2 | −2.8 | 81.0 | −1.0 | ND | ND | ND | ND | CAT-2200 | Pertuzumab |
| 10944-11314 | 0.35 | −0.10 | 7.91 | 0.01 | 74.2 | −2.8 | 80.3 | −1.7 | ND | ND | 77.1 | −1.6 | CAT-2200 | Pertuzumab |
| 10945-11377 | 0.35 | −0.10 | 8.46 | −0.02 | 74.2 | −2.8 | 80.2 | −1.8 | ND | ND | ND | ND | CAT-2200 | Pertuzumab |
| 10946-11382 | 0.35 | −0.10 | 8.31 | −0.01 | 74.2 | −2.8 | 78.8 | −3.2 | ND | ND | ND | ND | CAT-2200 | Pertuzumab |
| 10947-11392 | 0.35 | −0.10 | 8.15 | 0.00 | 74.2 | −2.8 | 82.5 | 0.5 | ND | ND | ND | ND | CAT-2200 | Pertuzumab |
| 10948-11250 | 0.35 | −0.10 | 8.64 | −0.03 | 74.2 | −2.8 | 80.0 | −2.0 | ND | ND | 76.6 | −2.1 | CAT-2200 | Pertuzumab |
| 10948-11258 | 0.35 | −0.10 | 8.53 | −0.02 | 74.2 | −2.8 | 80.0 | −2.0 | ND | ND | 76.8 | −1.9 | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 10948-11262 | 0.35 | −0.10 | ND | ND | 74.2 | −2.8 | ND | ND | ND | ND | ND | ND | CAT-2200 | Pertuzumab |
| 10950-11252 | 0.35 | −0.10 | 7.78 | 0.02 | 74.2 | −2.8 | 81.5 | −0.5 | ND | ND | ND | ND | CAT-2200 | Pertuzumab |
| 10950-11260 | 0.35 | −0.10 | ND | ND | 74.2 | −2.8 | 79.0 | −3.0 | ND | ND | ND | ND | CAT-2200 | Pertuzumab |
| 10950-11264 | 0.35 | −0.10 | 8.25 | −0.01 | 74.2 | −2.8 | 81.5 | −0.5 | ND | ND | ND | ND | CAT-2200 | Pertuzumab |
| 10952-11398 | 0.35 | −0.10 | 9.02 | −0.05 | 74.2 | −2.8 | 80.2 | −1.8 | ND | ND | 76.8 | −1.9 | CAT-2200 | Pertuzumab |
| 10953-11411 | 0.35 | −0.10 | 8.26 | −0.01 | 74.2 | −2.8 | 78.0 | −4.0 | ND | ND | ND | ND | CAT-2200 | Pertuzumab |
| 10962-11296 | ND | ND | 7.13 | 0.05 | ND | ND | 78.0 | −4.0 | ND | ND | 74.9 | −3.8 | CAT-2200 | Pertuzumab |
| 10962-11350 | ND | ND | ND | ND | ND | ND | ND | ND | ND | ND | ND | ND | CAT-2200 | Pertuzumab |
| 10965-11293 | ND | ND | ND | ND | ND | ND | ND | ND | ND | ND | ND | ND | CAT-2200 | Pertuzumab |
| 10965-11347 | ND | ND | 8.01 | 0.00 | ND | ND | 78.0 | −4.0 | ND | ND | ND | ND | CAT-2200 | Pertuzumab |
| 10966-11297 | ND | ND | 7.13 | 0.05 | ND | ND | 78.0 | −4.0 | ND | ND | 74.9 | −3.8 | CAT-2200 | Pertuzumab |
| 10966-11351 | ND | ND | ND | ND | ND | ND | ND | ND | ND | ND | ND | ND | CAT-2200 | Pertuzumab |
| 10969-11290 | ND | ND | ND | ND | ND | ND | ND | ND | ND | ND | ND | ND | CAT-2200 | Pertuzumab |
| 10969-11344 | ND | ND | 8.01 | 0.00 | ND | ND | 78.0 | −4.0 | ND | ND | ND | ND | CAT-2200 | Pertuzumab |
| 10970-11294 | ND | ND | 7.13 | 0.05 | ND | ND | 78.0 | −4.0 | ND | ND | 74.9 | −3.8 | CAT-2200 | Pertuzumab |
| 10970-11348 | ND | ND | ND | ND | ND | ND | ND | ND | ND | ND | ND | ND | CAT-2200 | Pertuzumab |
| 10973-11291 | 0.30 | −0.04 | ND | ND | 73.2 | −3.8 | ND | ND | 69.7 | −1.0 | ND | ND | CAT-2200 | Pertuzumab |
| 10973-11345 | 0.30 | −0.04 | 8.01 | 0.00 | 73.2 | −3.8 | 78.0 | −4.0 | 69.7 | −1.0 | ND | ND | CAT-2200 | Pertuzumab |
| 10974-11295 | 0.30 | −0.04 | 7.13 | 0.05 | 73.2 | −3.8 | 78.0 | −4.0 | 69.7 | −1.0 | 74.9 | −3.8 | CAT-2200 | Pertuzumab |
| 10974-11349 | 0.30 | −0.04 | ND | ND | 73.2 | −3.8 | ND | ND | 69.7 | −1.0 | ND | ND | CAT-2200 | Pertuzumab |
| 10977-11292 | ND | ND | ND | ND | ND | ND | ND | ND | ND | ND | ND | ND | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 10977-11346 | ND | ND | 8.01 | 0.00 | ND | ND | 78.0 | −4.0 | ND | ND | ND | ND | CAT-2200 | Pertuzumab |
| 10978-11296 | ND | ND | 7.13 | 0.05 | ND | ND | 78.0 | −4.0 | ND | ND | 74.9 | −3.8 | CAT-2200 | Pertuzumab |
| 10978-11350 | ND | ND | ND | ND | ND | ND | ND | ND | ND | ND | ND | ND | CAT-2200 | Pertuzumab |
| 10981-11293 | ND | ND | ND | ND | ND | ND | ND | ND | ND | ND | ND | ND | CAT-2200 | Pertuzumab |
| 10981-11347 | ND | ND | 8.01 | 0.00 | ND | ND | 78.0 | −4.0 | ND | ND | ND | ND | CAT-2200 | Pertuzumab |
| 10982-11297 | ND | ND | 7.13 | 0.05 | ND | ND | 78.0 | −4.0 | ND | ND | 74.9 | −3.8 | CAT-2200 | Pertuzumab |
| 10982-11351 | ND | ND | ND | ND | ND | ND | ND | ND | ND | ND | ND | ND | CAT-2200 | Pertuzumab |
| 10983-11306 | 0.32 | −0.06 | 7.41 | 0.04 | 73.0 | −4.0 | 81.0 | −1.0 | 68.3 | −2.4 | ND | ND | CAT-2200 | Pertuzumab |
| 10984-11376 | 0.32 | −0.06 | 8.46 | −0.02 | 73.0 | −4.0 | 80.2 | −1.8 | 68.3 | −2.4 | ND | ND | CAT-2200 | Pertuzumab |
| 10985-11381 | 0.32 | −0.06 | 8.31 | −0.01 | 73.0 | −4.0 | 78.8 | −3.2 | 68.3 | −2.4 | ND | ND | CAT-2200 | Pertuzumab |
| 10986-11391 | 0.32 | −0.06 | 8.15 | 0.00 | 73.0 | −4.0 | 82.5 | 0.5 | 68.3 | −2.4 | ND | ND | CAT-2200 | Pertuzumab |
| 10987-11249 | 0.32 | −0.06 | 8.64 | −0.03 | 73.0 | −4.0 | 80.0 | −2.0 | 68.3 | −2.4 | 76.6 | −2.1 | CAT-2200 | Pertuzumab |
| 10987-11257 | 0.32 | −0.06 | 8.53 | −0.02 | 73.0 | −4.0 | 80.0 | −2.0 | 68.3 | −2.4 | 76.8 | −1.9 | CAT-2200 | Pertuzumab |
| 10987-11261 | 0.32 | −0.06 | ND | ND | 73.0 | −4.0 | ND | ND | 68.3 | −2.4 | ND | ND | CAT-2200 | Pertuzumab |
| 10989-11251 | 0.32 | −0.06 | 7.78 | 0.02 | 73.0 | −4.0 | 81.5 | −0.5 | 68.3 | −2.4 | ND | ND | CAT-2200 | Pertuzumab |
| 10989-11259 | 0.32 | −0.06 | ND | ND | 73.0 | −4.0 | 79.0 | −3.0 | 68.3 | −2.4 | ND | ND | CAT-2200 | Pertuzumab |
| 10989-11263 | 0.32 | −0.06 | 8.25 | −0.01 | 73.0 | −4.0 | 81.5 | −0.5 | 68.3 | −2.4 | ND | ND | CAT-2200 | Pertuzumab |
| 10992-11410 | 0.32 | −0.06 | 8.26 | −0.01 | 73.0 | −4.0 | 78.0 | −4.0 | 68.3 | −2.4 | ND | ND | CAT-2200 | Pertuzumab |
| 10998-11307 | 0.29 | −0.03 | 7.41 | 0.04 | 73.0 | −4.0 | 81.0 | −1.0 | 69.1 | −1.6 | ND | ND | CAT-2200 | Pertuzumab |
| 10998-11314 | 0.29 | −0.03 | 7.91 | 0.01 | 73.0 | −4.0 | 80.3 | −1.7 | 69.1 | −1.6 | 77.1 | −1.6 | CAT-2200 | Pertuzumab |
| 10999-11377 | 0.29 | −0.03 | 8.46 | −0.02 | 73.0 | −4.0 | 80.2 | −1.8 | 69.1 | −1.6 | ND | ND | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 11000-11382 | 0.29 | −0.03 | 8.31 | −0.01 | 73.0 | −4.0 | 78.8 | −3.2 | 69.1 | −1.6 | ND | ND | CAT-2200 | Pertuzumab |
| 11001-11392 | 0.29 | −0.03 | 8.15 | 0.00 | 73.0 | −4.0 | 82.5 | 0.5 | 69.1 | −1.6 | ND | ND | CAT-2200 | Pertuzumab |
| 11002-11250 | 0.29 | −0.03 | 8.64 | −0.03 | 73.0 | −4.0 | 80.0 | −2.0 | 69.1 | −1.6 | 76.6 | −2.1 | CAT-2200 | Pertuzumab |
| 11002-11258 | 0.29 | −0.03 | 8.53 | −0.02 | 73.0 | −4.0 | 80.0 | −2.0 | 69.1 | −1.6 | 76.8 | −1.9 | CAT-2200 | Pertuzumab |
| 11002-11262 | 0.29 | −0.03 | ND | ND | 73.0 | −4.0 | ND | ND | 69.1 | −1.6 | ND | ND | CAT-2200 | Pertuzumab |
| 11004-11252 | 0.29 | −0.03 | 7.78 | 0.02 | 73.0 | −4.0 | 81.5 | −0.5 | 69.1 | −1.6 | ND | ND | CAT-2200 | Pertuzumab |
| 11004-11260 | 0.29 | −0.03 | ND | ND | 73.0 | −4.0 | 79.0 | −3.0 | 69.1 | −1.6 | ND | ND | CAT-2200 | Pertuzumab |
| 11004-11264 | 0.29 | −0.03 | 8.25 | −0.01 | 73.0 | −4.0 | 81.5 | −0.5 | 69.1 | −1.6 | ND | ND | CAT-2200 | Pertuzumab |
| 11006-11398 | 0.29 | −0.03 | 9.02 | −0.05 | 73.0 | −4.0 | 80.2 | −1.8 | 69.1 | −1.6 | 76.8 | −1.9 | CAT-2200 | Pertuzumab |
| 11007-11411 | 0.29 | −0.03 | 8.26 | −0.01 | 73.0 | −4.0 | 78.0 | −4.0 | 69.1 | −1.6 | ND | ND | CAT-2200 | Pertuzumab |
| 11025-11284 | 0.26 | 0.03 | 7.38 | 0.04 | 73.8 | −3.2 | 81.2 | −0.8 | ND | ND | 77.6 | −1.1 | CAT-2200 | Pertuzumab |
| 11026-11270 | 0.26 | 0.03 | 7.30 | 0.04 | 73.8 | −3.2 | 79.5 | −2.5 | ND | ND | 76.0 | −2.7 | CAT-2200 | Pertuzumab |
| 11027-11281 | 0.26 | 0.03 | ND | ND | 73.8 | −3.2 | ND | ND | ND | ND | ND | ND | CAT-2200 | Pertuzumab |
| 11027-11287 | 0.26 | 0.03 | 5.81 | 0.14 | 73.8 | −3.2 | 81.8 | −0.2 | ND | ND | ND | ND | CAT-2200 | Pertuzumab |
| 11028-11275 | 0.26 | 0.03 | 7.57 | 0.03 | 73.8 | −3.2 | 80.8 | −1.2 | ND | ND | 77.4 | −1.3 | CAT-2200 | Pertuzumab |
| 11029-11282 | 0.26 | 0.03 | ND | ND | 73.8 | −3.2 | ND | ND | ND | ND | ND | ND | CAT-2200 | Pertuzumab |
| 11029-11288 | 0.26 | 0.03 | 7.71 | 0.02 | 73.8 | −3.2 | 81.0 | −1.0 | ND | ND | 77.5 | −1.2 | CAT-2200 | Pertuzumab |
| 11030-11276 | 0.26 | 0.03 | 7.00 | 0.06 | 73.8 | −3.2 | 81.3 | −0.7 | ND | ND | 77.9 | −0.8 | CAT-2200 | Pertuzumab |
| 11030-11285 | 0.26 | 0.03 | 7.44 | 0.03 | 73.8 | −3.2 | 81.5 | −0.5 | ND | ND | ND | ND | CAT-2200 | Pertuzumab |
| 11032-11199 | 0.26 | 0.03 | 8.09 | 0.00 | 73.8 | −3.2 | 80.0 | −2.0 | ND | ND | 76.5 | −2.2 | CAT-2200 | Pertuzumab |
| 11033-11209 | 0.26 | 0.03 | ND | ND | 73.8 | −3.2 | ND | ND | ND | ND | ND | ND | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 11033-11215 | 0.26 | 0.03 | 7.98 | 0.00 | 73.8 | −3.2 | 75.5 | −6.5 | ND | ND | ND | ND | CAT-2200 | Pertuzumab |
| 11034-11204 | 0.26 | 0.03 | 8.11 | 0.00 | 73.8 | −3.2 | 80.8 | −1.2 | ND | ND | 77.5 | −1.2 | CAT-2200 | Pertuzumab |
| 11035-11212 | 0.26 | 0.03 | ND | ND | 73.8 | −3.2 | ND | ND | ND | ND | ND | ND | CAT-2200 | Pertuzumab |
| 11035-11218 | 0.26 | 0.03 | 8.06 | 0.00 | 73.8 | −3.2 | 77.0 | −5.0 | ND | ND | 74.3 | −4.4 | CAT-2200 | Pertuzumab |
| 11036-11221 | 0.26 | 0.03 | 7.72 | 0.02 | 73.8 | −3.2 | 75.5 | −6.5 | ND | ND | ND | ND | CAT-2200 | Pertuzumab |
| 11039-11224 | 0.26 | 0.03 | ND | ND | 73.8 | −3.2 | ND | ND | ND | ND | ND | ND | CAT-2200 | Pertuzumab |
| 11042-11273 | 0.18 | 0.19 | 7.19 | 0.05 | 72.7 | −4.3 | 81.2 | −0.8 | ND | ND | ND | ND | CAT-2200 | Pertuzumab |
| 11043-11181 | 0.18 | 0.19 | 7.30 | 0.04 | 72.7 | −4.3 | 75.8 | −6.2 | ND | ND | ND | ND | CAT-2200 | Pertuzumab |
| 11044-11191 | 0.18 | 0.19 | ND | ND | 72.7 | −4.3 | 76.0 | −6.0 | ND | ND | ND | ND | CAT-2200 | Pertuzumab |
| 11055-11322 | 0.12 | 0.02 | ND | ND | 71.8 | −4.5 | ND | ND | ND | ND | ND | ND | CAT-2200 | Pertuzumab |
| 11056-11324 | 0.12 | 0.02 | ND | ND | 71.8 | −4.5 | ND | ND | ND | ND | ND | ND | CAT-2200 | Pertuzumab |
| 11061-11273 | 0.28 | −0.02 | 7.19 | 0.05 | 72.3 | −4.7 | 81.2 | −0.8 | 68.6 | −2.1 | ND | ND | CAT-2200 | Pertuzumab |
| 11062-11323 | 0.28 | −0.02 | ND | ND | 72.3 | −4.7 | ND | ND | 68.6 | −2.1 | ND | ND | CAT-2200 | Pertuzumab |
| 11063-11325 | 0.28 | −0.02 | ND | ND | 72.3 | −4.7 | ND | ND | 68.6 | −2.1 | ND | ND | CAT-2200 | Pertuzumab |
| 11064-11201 | 0.28 | −0.02 | 8.09 | 0.00 | 72.3 | −4.7 | 80.0 | −2.0 | 68.6 | −2.1 | 76.5 | −2.2 | CAT-2200 | Pertuzumab |
| 11065-11206 | 0.28 | −0.02 | 8.11 | 0.00 | 72.3 | −4.7 | 80.8 | −1.2 | 68.6 | −2.1 | 77.5 | −1.2 | CAT-2200 | Pertuzumab |
| 11066-11181 | 0.28 | −0.02 | 7.30 | 0.04 | 72.3 | −4.7 | 75.8 | −6.2 | 68.6 | −2.1 | ND | ND | CAT-2200 | Pertuzumab |
| 11076-11355 | ND | ND | ND | ND | ND | ND | ND | ND | ND | ND | ND | ND | CAT-2200 | Pertuzumab |
| 11087-11179 | 0.37 | −0.13 | 7.30 | 0.04 | 72.2 | −4.8 | 75.8 | −6.2 | ND | ND | ND | ND | CAT-2200 | Pertuzumab |
| 11088-11185 | 0.37 | −0.13 | 7.40 | 0.04 | 72.2 | −4.8 | 67.7 | −14.3 | ND | ND | ND | ND | CAT-2200 | Pertuzumab |
| 11089-11189 | 0.37 | −0.13 | ND | ND | 72.2 | −4.8 | 76.0 | −6.0 | ND | ND | ND | ND | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 11096-11272 | 0.36 | −0.12 | 7.19 | 0.05 | 72.7 | −4.3 | 81.2 | −0.8 | 68.8 | −1.9 | ND | ND | CAT-2200 | Pertuzumab |
| 11097-11277 | 0.36 | −0.12 | 7.00 | 0.06 | 72.7 | −4.3 | 81.3 | −0.7 | 68.8 | −1.9 | 77.9 | −0.8 | CAT-2200 | Pertuzumab |
| 11098-11200 | 0.36 | −0.12 | 8.09 | 0.00 | 72.7 | −4.3 | 80.0 | −2.0 | 68.8 | −1.9 | 76.5 | −2.2 | CAT-2200 | Pertuzumab |
| 11099-11210 | 0.36 | −0.12 | ND | ND | 72.7 | −4.3 | ND | ND | 68.8 | −1.9 | ND | ND | CAT-2200 | Pertuzumab |
| 11099-11216 | 0.36 | −0.12 | 7.98 | 0.00 | 72.7 | −4.3 | 75.5 | −6.5 | 68.8 | −1.9 | ND | ND | CAT-2200 | Pertuzumab |
| 11100-11205 | 0.36 | −0.12 | 8.11 | 0.00 | 72.7 | −4.3 | 80.8 | −1.2 | 68.8 | −1.9 | 77.5 | −1.2 | CAT-2200 | Pertuzumab |
| 11101-11213 | 0.36 | −0.12 | ND | ND | 72.7 | −4.3 | ND | ND | 68.8 | −1.9 | ND | ND | CAT-2200 | Pertuzumab |
| 11101-11219 | 0.36 | −0.12 | 8.06 | 0.00 | 72.7 | −4.3 | 77.0 | −5.0 | 68.8 | −1.9 | 74.3 | −4.4 | CAT-2200 | Pertuzumab |
| 11102-11180 | 0.36 | −0.12 | 7.30 | 0.04 | 72.7 | −4.3 | 75.8 | −6.2 | 68.8 | −1.9 | ND | ND | CAT-2200 | Pertuzumab |
| 11103-11186 | 0.36 | −0.12 | 7.40 | 0.04 | 72.7 | −4.3 | 67.7 | −14.3 | 68.8 | −1.9 | ND | ND | CAT-2200 | Pertuzumab |
| 11104-11190 | 0.36 | −0.12 | ND | ND | 72.7 | −4.3 | 76.0 | −6.0 | 68.8 | −1.9 | ND | ND | CAT-2200 | Pertuzumab |
| 11105-11195 | 0.36 | −0.12 | ND | ND | 72.7 | −4.3 | ND | ND | 68.8 | −1.9 | ND | ND | CAT-2200 | Pertuzumab |
| 11106-11225 | 0.36 | −0.12 | ND | ND | 72.7 | −4.3 | ND | ND | 68.8 | −1.9 | ND | ND | CAT-2200 | Pertuzumab |
| 11106-11229 | 0.36 | −0.12 | 7.71 | 0.02 | 72.7 | −4.3 | 77.5 | −4.5 | 68.8 | −1.9 | ND | ND | CAT-2200 | Pertuzumab |
| 11107-11197 | 0.36 | −0.12 | 8.22 | −0.01 | 72.7 | −4.3 | 80.7 | −1.3 | 68.8 | −1.9 | ND | ND | CAT-2200 | Pertuzumab |
| 11108-11227 | 0.36 | −0.12 | ND | ND | 72.7 | −4.3 | ND | ND | 68.8 | −1.9 | ND | ND | CAT-2200 | Pertuzumab |
| 11108-11231 | 0.36 | −0.12 | 7.80 | 0.01 | 72.7 | −4.3 | 77.2 | −4.8 | 68.8 | −1.9 | ND | ND | CAT-2200 | Pertuzumab |
| 11124-11202 | 0.24 | 0.06 | 8.09 | 0.00 | 71.8 | −5.2 | 80.0 | −2.0 | ND | ND | 76.5 | −2.2 | CAT-2200 | Pertuzumab |
| 11125-11207 | 0.24 | 0.06 | 8.11 | 0.00 | 71.8 | −5.2 | 80.8 | −1.2 | ND | ND | 77.5 | −1.2 | CAT-2200 | Pertuzumab |
| 11140-11202 | 0.23 | 0.08 | 8.09 | 0.00 | 71.8 | −5.2 | 80.0 | −2.0 | 68.1 | −2.6 | 76.5 | −2.2 | CAT-2200 | Pertuzumab |
| 11141-11207 | 0.23 | 0.08 | 8.11 | 0.00 | 71.8 | −5.2 | 80.8 | −1.2 | 68.1 | −2.6 | 77.5 | −1.2 | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 11142-11182 | 0.23 | 0.08 | 7.30 | 0.04 | 71.8 | −5.2 | 75.8 | −6.2 | 68.1 | −2.6 | ND | ND | CAT-2200 | Pertuzumab |
| 1L143-11187 | 0.23 | 0.08 | 7.40 | 0.04 | 71.8 | −5.2 | 67.7 | −14.3 | 68.1 | −2.6 | ND | ND | CAT-2200 | Pertuzumab |
| 11144-11192 | 0.23 | 0.08 | ND | ND | 71.8 | −5.2 | 76.0 | −6.0 | 68.1 | −2.6 | ND | ND | CAT-2200 | Pertuzumab |
| 11148-11183 | 0.34 | −0.09 | 7.30 | 0.04 | 71.0 | −6.0 | 75.8 | −6.2 | ND | ND | ND | ND | CAT-2200 | Pertuzumab |
| 11149-11188 | 0.34 | −0.09 | 7.40 | 0.04 | 71.0 | −6.0 | 67.7 | −14.3 | ND | ND | ND | ND | CAT-2200 | Pertuzumab |
| 11150-11193 | 0.34 | −0.09 | ND | ND | 71.0 | −6.0 | 76.0 | −6.0 | ND | ND | ND | ND | CAT-2200 | Pertuzumab |
| 11156-11274 | 0.22 | 0.08 | 7.19 | 0.05 | 71.3 | −5.8 | 81.2 | −0.8 | ND | ND | ND | ND | CAT-2200 | Pertuzumab |
| 11157-11279 | 0.22 | 0.08 | 7.00 | 0.06 | 71.3 | −5.8 | 81.3 | −0.7 | ND | ND | 77.9 | −0.8 | CAT-2200 | Pertuzumab |
| 11158-11203 | 0.22 | 0.08 | 8.09 | 0.00 | 71.3 | −5.8 | 80.0 | −2.0 | ND | ND | 76.5 | −2.2 | CAT-2200 | Pertuzumab |
| 11159-11211 | 0.22 | 0.08 | ND | ND | 71.3 | −5.8 | ND | ND | ND | ND | ND | ND | CAT-2200 | Pertuzumab |
| 11159-11217 | 0.22 | 0.08 | 7.98 | 0.00 | 71.3 | −5.8 | 75.5 | −6.5 | ND | ND | ND | ND | CAT-2200 | Pertuzumab |
| 11160-11208 | 0.22 | 0.08 | 8.11 | 0.00 | 71.3 | −5.8 | 80.8 | −1.2 | ND | ND | 77.5 | −1.2 | CAT-2200 | Pertuzumab |
| 11161-11214 | 0.22 | 0.08 | ND | ND | 71.3 | −5.8 | ND | ND | ND | ND | ND | ND | CAT-2200 | Pertuzumab |
| 11161-11220 | 0.22 | 0.08 | 8.06 | 0.00 | 71.3 | −5.8 | 77.0 | −5.0 | ND | ND | 74.3 | −4.4 | CAT-2200 | Pertuzumab |
| 11162-11184 | 0.22 | 0.08 | 7.30 | 0.04 | 71.3 | −5.8 | 75.8 | −6.2 | ND | ND | ND | ND | CAT-2200 | Pertuzumab |
| 11163-11194 | 0.22 | 0.08 | ND | ND | 71.3 | −5.8 | 76.0 | −6.0 | ND | ND | ND | ND | CAT-2200 | Pertuzumab |
| 11164-11196 | 0.22 | 0.08 | ND | ND | 71.3 | −5.8 | ND | ND | ND | ND | ND | ND | CAT-2200 | Pertuzumab |
| 11165-11226 | 0.22 | 0.08 | ND | ND | 71.3 | −5.8 | ND | ND | ND | ND | ND | ND | CAT-2200 | Pertuzumab |
| 11165-11230 | 0.22 | 0.08 | 7.71 | 0.02 | 71.3 | −5.8 | 77.5 | −4.5 | ND | ND | ND | ND | CAT-2200 | Pertuzumab |
| 11166-11198 | 0.22 | 0.08 | 8.22 | −0.01 | 71.3 | −5.8 | 80.7 | −1.3 | ND | ND | ND | ND | CAT-2200 | Pertuzumab |

TABLE 6A-continued

Antigen binding and thermal stability assessment of the K-L designs that passed the LCCA performance cut-off criteria
K-L designs

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 11167-11228 | 0.22 | 0.08 | ND | ND | 71.3 | −5.8 | ND | ND | ND | ND | ND | ND | CAT-2200 | Pertuzumab |
| 11167-11232 | 0.22 | 0.08 | 7.80 | 0.01 | 71.3 | −5.8 | 77.2 | −4.8 | ND | ND | ND | ND | CAT-2200 | Pertuzumab |

TABLE 6B

Antigen binding and thermal stability assessment of the K-K-derived K-L designs that passed the LCCA performance cut-off criteria
K-K-derived K-L designs

| Column 1 Unique identifier | Column 2 KD of H1L1 Fab heterodimer (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
|---|---|---|---|---|---|---|---|---|---|---|---|---|---|---|
| 10621-10731 | 0.27 | 0.00 | 6.75 | 0.08 | 77.0 | 0.0 | 80.5 | −1.5 | 70.7 | 0.0 | ND | ND | CAT-2200 | Pertuzumab |
| 10621-10733 | 0.27 | 0.00 | 5.72 | 0.15 | 77.0 | 0.0 | 83.8 | 1.8 | 70.7 | 0.0 | 79.4 | 0.7 | CAT-2200 | Pertuzumab |
| 10622-10736 | 0.27 | 0.00 | ND | ND | 77.0 | 0.0 | ND | ND | 70.7 | 0.0 | ND | ND | CAT-2200 | Pertuzumab |
| 10622-10742 | 0.27 | 0.00 | ND | ND | 77.0 | 0.0 | ND | ND | 70.7 | 0.0 | ND | ND | CAT-2200 | Pertuzumab |
| 10623-10739 | 0.27 | 0.00 | 6.39 | 0.10 | 77.0 | 0.0 | 81.3 | −0.7 | 70.7 | 0.0 | ND | ND | CAT-2200 | Pertuzumab |
| 10623-10745 | 0.27 | 0.00 | 8.08 | 0.00 | 77.0 | 0.0 | 82.5 | 0.5 | 70.7 | 0.0 | 78.3 | −0.4 | CAT-2200 | Pertuzumab |
| 10624-10700 | ND | ND | ND | ND | ND | ND | ND | ND | ND | ND | ND | ND | CAT-2200 | Pertuzumab |
| 10625-10701 | ND | ND | ND | ND | ND | ND | ND | ND | ND | ND | ND | ND | CAT-2200 | Pertuzumab |
| 10629-10695 | ND | ND | ND | ND | ND | ND | 79.8 | −2.2 | ND | ND | ND | ND | CAT-2200 | Pertuzumab |
| 10631-10722 | 0.19 | 0.15 | ND | ND | 73.7 | −3.3 | ND | ND | ND | ND | 78.0 | −0.7 | CAT-2200 | Pertuzumab |
| 10632-10724 | 0.19 | 0.15 | NB | −2.09 | 73.7 | −3.3 | 74.0 | −7.9 | ND | ND | 77.8 | −0.9 | CAT-2200 | Pertuzumab |
| 10640-10713 | 0.23 | 0.08 | 8.28 | −0.01 | 73.3 | −3.7 | 80.8 | −1.1 | 69.1 | −1.6 | 78.2 | −0.5 | CAT-2200 | Pertuzumab |
| 10652-10702 | 0.28 | −0.01 | 7.78 | 0.02 | 73.0 | −4.0 | 81.3 | −0.7 | ND | ND | ND | ND | CAT-2200 | Pertuzumab |
| 10652-10734 | 0.28 | −0.01 | 7.65 | 0.02 | 73.0 | −4.0 | 83.2 | 1.3 | ND | ND | ND | ND | CAT-2200 | Pertuzumab |
| 10652-10755 | 0.28 | −0.01 | 6.98 | 0.06 | 73.0 | −4.0 | 81.7 | −0.3 | ND | ND | 78.4 | −0.3 | CAT-2200 | Pertuzumab |
| 10656-10758 | ND | ND | ND | ND | ND | ND | ND | ND | ND | ND | ND | ND | CAT-2200 | Pertuzumab |
| 10657-10760 | ND | ND | ND | ND | ND | ND | ND | ND | ND | ND | ND | ND | CAT-2200 | Pertuzumab |
| 10658-10720 | ND | ND | ND | ND | ND | ND | ND | ND | ND | ND | 78.0 | −0.7 | CAT-2200 | Pertuzumab |
| 10659-10720 | ND | ND | ND | ND | ND | ND | ND | ND | ND | ND | 78.0 | −0.7 | CAT-2200 | Pertuzumab |
| 10662-10731 | 0.29 | −0.02 | 6.75 | 0.08 | 75.0 | −2.0 | 80.5 | −1.5 | ND | ND | ND | ND | CAT-2200 | Pertuzumab |
| 10662-10733 | 0.29 | −0.02 | 5.72 | 0.15 | 75.0 | −2.0 | 83.8 | 1.8 | ND | ND | 79.4 | 0.7 | CAT-2200 | Pertuzumab |
| 10664-10722 | 0.29 | −0.03 | ND | ND | 77.3 | 0.3 | ND | ND | 70.7 | 0.0 | 78.0 | −0.7 | CAT-2200 | Pertuzumab |
| 10665-10724 | 0.29 | −0.03 | NB | −2.09 | 77.3 | 0.3 | 74.0 | −7.9 | 70.7 | 0.0 | 77.8 | −0.9 | CAT-2200 | Pertuzumab |
| 10671-10751 | ND | ND | ND | ND | ND | ND | ND | ND | ND | ND | ND | ND | CAT-2200 | Pertuzumab |
| 10674-10749 | 0.21 | 0.12 | 6.09 | 0.12 | 74.5 | −2.5 | 81.0 | −1.0 | ND | ND | ND | ND | CAT-2200 | Pertuzumab |
| 10676-10750 | ND | ND | ND | ND | ND | ND | ND | ND | ND | ND | ND | ND | CAT-2200 | Pertuzumab |
| 10677-10751 | ND | ND | ND | ND | ND | ND | ND | ND | ND | ND | ND | ND | CAT-2200 | Pertuzumab |
| 10678-10737 | ND | ND | ND | ND | ND | ND | ND | ND | ND | ND | ND | ND | CAT-2200 | Pertuzumab |
| 10678-10743 | ND | ND | ND | ND | ND | ND | ND | ND | ND | ND | ND | ND | CAT-2200 | Pertuzumab |
| 10679-10738 | ND | ND | ND | ND | ND | ND | ND | ND | ND | ND | ND | ND | CAT-2200 | Pertuzumab |
| 10679-10744 | ND | ND | ND | ND | ND | ND | ND | ND | ND | ND | ND | ND | CAT-2200 | Pertuzumab |
| 10680-10740 | 0.39 | −0.16 | 6.39 | 0.10 | 72.0 | −5.0 | 81.3 | −0.7 | 74.2 | 3.5 | ND | ND | CAT-2200 | Pertuzumab |

TABLE 6B-continued

| Antigen binding and thermal stability assessment of the K-K-derived K-L designs that passed the LCCA performance cut-off criteria K-K-derived K-L designs | | | | | | | | | | | | | | |
|---|---|---|---|---|---|---|---|---|---|---|---|---|---|---|
| Column 1 Unique identifier | Column 2 KD of H1L1 Fab heterodimer (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type | Column 14 H1L1 Fab | Column 15 H2L2 Fab |
| 10680-10746 | 0.39 | −0.16 | 8.08 | 0.00 | 72.0 | −5.0 | 82.5 | 0.5 | 74.2 | 3.5 | 78.3 | −0.4 | CAT-2200 | Pertuzumab |
| 10681-10741 | 0.35 | −0.11 | 6.39 | 0.10 | 71.5 | −5.5 | 81.3 | −0.7 | ND | ND | ND | ND | CAT-2200 | Pertuzumab |
| 10681-10747 | 0.35 | −0.11 | 8.08 | 0.00 | 71.5 | −5.5 | 82.5 | 0.5 | ND | ND | 78.3 | −0.4 | CAT-2200 | Pertuzumab |
| 10682-10718 | ND | ND | 7.43 | 0.04 | ND | ND | 81.7 | −0.3 | ND | ND | ND | ND | CAT-2200 | Pertuzumab |
| 10683-10720 | ND | ND | ND | ND | ND | ND | ND | ND | ND | ND | 78.0 | −0.7 | CAT-2200 | Pertuzumab |
| 10684-10706 | 0.26 | 0.03 | 7.28 | 0.04 | 75.2 | −1.8 | 81.5 | −0.5 | 69.6 | −1.1 | 77.2 | −1.5 | CAT-2200 | Pertuzumab |
| 10685-10719 | 0.22 | 0.09 | 7.43 | 0.04 | 75.0 | −2.0 | 81.7 | −0.3 | 70.3 | −0.4 | ND | ND | CAT-2200 | Pertuzumab |
| 10685-10726 | 0.22 | 0.09 | 7.24 | 0.05 | 75.0 | −2.0 | 80.3 | −1.7 | 70.3 | −0.4 | 77.4 | −1.3 | CAT-2200 | Pertuzumab |
| 10687-10722 | 0.22 | 0.09 | ND | ND | 75.0 | −2.0 | ND | ND | 70.3 | −0.4 | 78.0 | −0.7 | CAT-2200 | Pertuzumab |
| 10688-10724 | 0.22 | 0.09 | NB | −2.09 | 75.0 | −2.0 | 74.0 | −7.9 | 70.3 | −0.4 | 77.8 | −0.9 | CAT-2200 | Pertuzumab |
| 10689-10707 | 0.22 | 0.09 | 7.28 | 0.04 | 75.0 | −2.0 | 81.5 | −0.5 | 70.3 | −0.4 | 77.2 | −1.5 | CAT-2200 | Pertuzumab |
| 10690-10727 | 0.24 | 0.05 | 7.24 | 0.05 | 73.5 | −3.5 | 80.3 | −1.7 | ND | ND | 77.4 | −1.3 | CAT-2200 | Pertuzumab |
| 10621-10731 | 0.27 | 0.00 | 6.75 | 0.08 | 77.0 | 0.0 | 80.5 | −1.5 | 70.7 | 0.0 | ND | ND | CAT-2200 | Pertuzumab |

TABLE 7A

| Second K-L Design Library | | | | | | |
|---|---|---|---|---|---|---|
| Unique identifier | H1 mutation (Kabat) | L1 mutation (Kabat) | H2 mutations (Kabat) | L2 mutation (Kabat) | H1L1 Fab | H2L2 Fab |
| 12944-13093 | Q179K | K129T_S180E | L143E_K145T_Q179E | Q124R_T178R | CAT-2200 | Pertuzumab |
| 12958-13064 | S186R | K129T_S180E | L143E_K145T | Q124R_Q160K_T178R | CAT-2200 | Pertuzumab |
| 12958-13106 | S186R | K129T_S180E | L143E_K145T_ Q179E_S188L | Q124R_Q160K_T178R | CAT-2200 | Pertuzumab |
| 12958-13469 | S186R | K129T_S180E | L143E_K145T_S188L | Q124R_Q160K_T178R | CAT-2200 | Pertuzumab |
| 12961-13108 | S186R | K129T_S180E | L143E_K145T_ Q179E_S188L | Q124R_T178R | CAT-2200 | Pertuzumab |
| 12961-13471 | S186R | K129T_S180E | L143E_K145T_S188L | Q124R_T178R | CAT-2200 | Pertuzumab |
| 13200-13421 | A125R_S186R | S122D_K129T_S180E | L143E_K145T | Q124R_L135W_Q160K_T178R | CAT-2200 | Pertuzumab |
| 13202-13426 | A125R_S186R | S122D_K129T_S180E | L143E_K145T_K228D | S121K_Q124R_Q160K_T178R | CAT-2200 | Pertuzumab |
| 13203-13427 | A125R_S186R | S122D_K129T_S180E | L143E_K145T_K228D | S121K_Q124R_T178R | CAT-2200 | Pertuzumab |
| 13248-13475 | F174G_S186R | T116F_K129T_ S176F_S180E | L143E_K145T_V190F | Q124R_L135A_Q160K_T178R | CAT-2200 | Pertuzumab |
| 13309-13443 | Q179K | K129T_S180E | L143E_K145T_Q179E | Q124R_T129K_Q160K_T178R | CAT-2200 | Pertuzumab |
| 13322-13425 | S186R | K129T_S180E | L143E_K145T | Q124R_T129K_Q160K_T178R | CAT-2200 | Pertuzumab |
| 13204-13351 | A125R_S186R | S122D_K129T_S180E | K145T_Q179E_K228D | S121K_S131K | CAT-2200 | Pertuzumab |
| 13205-13353 | A125R_S186R | S122D_K129T_S180E | K145T_Q179E_K228D | S121K_T129K_S131K | CAT-2200 | Pertuzumab |
| 13196-13351 | A125R_Q179K | S122D_K129T_S180E | K145T_Q179E_K228D | S121K_S131K | CAT-2200 | Pertuzumab |
| 13197-13353 | A125R_Q179K | S122D_K129T_S180E | K145T_Q179E_K228D | S121K_T129K_S131K | CAT-2200 | Pertuzumab |
| 13250-13355 | F174G_S186R | T116F_K129T_ S176F_S180E | K145T_Q179E_ S188F_V190F | S131K_L135A | CAT-2200 | Pertuzumab |
| 13277-13420 | L143A_S186R | K129T_V133W_S180E | L124W_L143E_K145T | Q124K_V133A_T178R | CAT-2200 | Pertuzumab |
| 13319-13473 | S186R | K129T_5176A_ Y178W_S180E | L143E_K145T_S188W | Q124K_5176A_T178R | CAT-2200 | Pertuzumab |
| 13188-13421 | A125R_Q179K | S122D_K129T_S180E | L143E_K145T | Q124R_L135W_Q160K_T178R | CAT-2200 | Pertuzumab |
| 13190-13422 | A125R_Q179K | S122D_K129T_S180E | L143E_K145T | Q124R_L135W_T178R | CAT-2200 | Pertuzumab |
| 13242-13475 | F174G_Q179K | T116F_K129T_ S176F_S180E | L143E_K145T_V190F | Q124R_L135A_Q160K_T178R | CAT-2200 | Pertuzumab |

TABLE 7A-continued

| Second K-L Design Library | | | | | | |
|---|---|---|---|---|---|---|
| Unique identifier | H1 mutation (Kabat) | L1 mutation (Kabat) | H2 mutations (Kabat) | L2 mutation (Kabat) | H1L1 Fab | H2L2 Fab |
| 13192-13426 | A125R_Q179K | S122D_K129T_S180E | L143E_K145T_K228D | S121K_Q124R_Q160K_T178R | CAT-2200 | Pertuzumab |
| 13194-13427 | A125R_Q179K | S122D_K129T_S180E | L143E_K145T_K228D | S121K_Q124R_T178R | CAT-2200 | Pertuzumab |
| 13317-13423 | Q179K_V190K | K129T_V133D_ L1355_S180E | L143E_K145T | Q124R_Q160K_T178R | CAT-2200 | Pertuzumab |
| 13188-13430 | A125R_Q179K | S122D_K129T_S180E | L143E_K145T_Q179E | Q124R_L135W_Q160K_T178R | CAT-2200 | Pertuzumab |
| 13200-13430 | A125R_S186R | S122D_K129T_S180E | L143E_K145T_Q179E | Q124R_L135W_Q160K_T178R | CAT-2200 | Pertuzumab |
| 13246-13463 | F174G_S186R | T116F_K129T_ S176F_S180E | L143E_K145T_ Q179E_V190F | Q124K_L135A_T178R | CAT-2200 | Pertuzumab |
| 13238-13463 | F174G_Q179K | T116F_K129T_ S176F_S180E | L143E_K145T_ Q179E_V190F | Q124K_L135A_T178R | CAT-2200 | Pertuzumab |
| 13248-13465 | F174G_S186R | T116F_K129T_ S176F_S180E | L143E_K145T_ Q179E_V190F | Q124R_L135A_Q160K_T178R | CAT-2200 | Pertuzumab |
| 13242-13465 | F174G_Q179K | T116F_K129T_ S176F_S180E | L143E_K145T_ Q179E_V190F | Q124R_L135A_Q160K_T178R | CAT-2200 | Pertuzumab |
| 13246-13459 | F174G_S186R | T116F_K129T_ S176F_S180E | L143E_K145T_Q179E_ S188F_V190F | Q124K_L135A_T178R | CAT-2200 | Pertuzumab |
| 13238-13459 | F174G_Q179K | T116F_K129T_ S176F_S180E | L143E_K145T_Q179E_ S188F_V190F | Q124K_L135A_T178R | CAT-2200 | Pertuzumab |
| 13192-13452 | A125R_Q179K | S122D_K129T_S180E | L143E_K145T_ Q179E_K228D | S121K_Q124R_Q160K_T178R | CAT-2200 | Pertuzumab |
| 13194-13456 | A125R_Q179K | S122D_K129T_S180E | L143E_K145T_ Q179E_K228D | S121K_Q124R_T178R | CAT-2200 | Pertuzumab |
| 13202-13452 | A125R_S186R | S122D_K129T_S180E | L143E_K145T_ Q179E_K228D | S121K_Q124R_Q160K_T178R | CAT-2200 | Pertuzumab |
| 13203-13456 | A125R_S186R | S122D_K129T_S180E | L143E_K145T_ Q179E_K228D | S121K_Q124R_T178R | CAT-2200 | Pertuzumab |
| 13254-13508 | K145T_S188E | Y178K | S186R_S188K | Q124E_Q160E_S176D_T178D | CAT-2200 | Pertuzumab |
| 13255-13509 | K145T_S188E | Y178K | S186R_S188K | Q124E_Q160E_S176D_ T178D_T180E | CAT-2200 | Pertuzumab |
| 13262-13481 | K145T_S188E | Y178K | L143K_S188K | Q124E_V133D_S176E_T180E | CAT-2200 | Pertuzumab |
| 13261-13480 | K145T_S188E | Y178K | L143K_S188K | Q124E_V133D_S176E_ T178E_T180E | CAT-2200 | Pertuzumab |
| 13258-13504 | K145T_S188E | Y178K | Q179K_S188K | Q124E_S176E_T180E | CAT-2200 | Pertuzumab |
| 13256-13502 | K145T_S188E | Y178K | Q179K_S188K | Q124E_S176E_T178D_T180E | CAT-2200 | Pertuzumab |
| 13257-13503 | K145T_S188E | Y178K | Q179K_S188K | Q124E_S176E_T178E_T180E | CAT-2200 | Pertuzumab |
| 13269-13403 | K145T_S188E | Y178K | L124R_L143K | Q124E_V133G_S176D_T180E | CAT-2200 | Pertuzumab |
| 13268-13401 | K145T_S188E | Y178K | L124R_L143K | Q124E_V133G_S176D_ T178E_T180E | CAT-2200 | Pertuzumab |
| 12878-11240 | K145T_S188E | Y178K | L124R | V133G_S176D | CAT-2200 | Pertuzumab |
| 10798-13036 | K145T_S188E | Y178K | L124R | V133G_S176D_T180E | CAT-2200 | Pertuzumab |
| 13265-13392 | K145T_S188E | Y178K | L124K_S188K | Q124E_V133G_S176D_T178D | CAT-2200 | Pertuzumab |
| 13265-13419 | K145T_S188E | Y178K | L124R_S188K | Q124E_V133G_S176D_T178D | CAT-2200 | Pertuzumab |
| 13212-13396 | A139W_K145T_S188E | Y178K | L124R | V1338_L135W_S176D_T180E | CAT-2200 | Pertuzumab |
| 13211-13395 | A139W_K145T_S188E | Y178K | L124R | V1338_L135W_S176D | CAT-2200 | Pertuzumab |
| 13168-13397 | A125R_K145T_S188E | S122D_Y178K | L124R_K228D | S121K_V133G_S176D | CAT-2200 | Pertuzumab |
| 13296-13399 | L143E_K145T_Q179E | E124Q_T131R | L124R_L143K | Q124E_V133G_S176D | CAT-2200 | Pertuzumab |
| 13297-13402 | L143E_K145T_Q179E | E124Q_T131R | L124R_L143K | Q124E_V133G_S176D_T180E | CAT-2200 | Pertuzumab |
| 13264-13400 | K145T_S188E | Y178K | L124R_L143K | Q124E_V133G_S176D | CAT-2200 | Pertuzumab |
| 13332-13360 | S188K | K129T_S176E_Y178E | K145T_S186E | S131K_S176K | CAT-2200 | Pertuzumab |
| 13328-13359 | S188K | K129T_S176D_Y178T | K145T_S186E | S131K_S176K | CAT-2200 | Pertuzumab |
| 13335-13361 | S188K | K129T_Y178D | K145T_S186E | S131K_S176K | CAT-2200 | Pertuzumab |
| 13337-13362 | S188K | K129T_Y178E | K145T_S186E | S131K_S176K | CAT-2200 | Pertuzumab |
| 13237-13358 | A139W_S188K | K129T_S176E_Y178E | K145T_S186E | S131K_L135W_S176K | CAT-2200 | Pertuzumab |
| 13235-13357 | A139W_S188K | K129T_S176D_Y178T | K145T_S186E | S131K_L135W_S176K | CAT-2200 | Pertuzumab |
| 13209-13364 | A125R_S188K | S122D_K129T_ S176E_Y178E | K145T_S186E_K228D | S121K_S131K_S176K | CAT-2200 | Pertuzumab |
| 13207-13363 | A125R_S188K | S122D_K129T_ S176D_Y178T | K145T_S186E_K228D | S121K_S131K_S176K | CAT-2200 | Pertuzumab |
| 13210-13510 | A139W_K145T_S188E | Y178K | S188K | L135W_S176E_T178E | CAT-2200 | Pertuzumab |
| 13167-13514 | A125R_K145T_S188E | S122D_Y178K | S188K_K228D | S121K_S176E_T178E | CAT-2200 | Pertuzumab |
| 13294-13492 | L143E_K145T_Q179E | E124Q_T131R | L143R_S188K | Q124E_V133D_T178E | CAT-2200 | Pertuzumab |
| 13292-13489 | L143E_K145T_Q179E | E124Q_T131R | L143R_S188K | Q124E_V133D_S176D_T178E | CAT-2200 | Pertuzumab |
| 13263-13493 | K145T_S188E | Y178K | L143R_S188K | Q124E_V133D_T178E | CAT-2200 | Pertuzumab |
| 13259-13491 | K145T_S188E | Y178K | L143R_S188K | Q124E_V133D_S176D_T178E | CAT-2200 | Pertuzumab |
| 13212-13415 | A139W_K145T_S188E | Y178K | L124R_S186R | V133G_L135W_S176D_T180E | CAT-2200 | Pertuzumab |
| 13169-13418 | A125R_K145T_S188E | S122D_Y178K | L124R_S186R_K228D | S121K_V133G_S176D_T180E | CAT-2200 | Pertuzumab |
| 13331-13447 | S188K | K129T_S176E_Y178E | L143E_K145T_Q179E | Q124R_T178R | CAT-2200 | Pertuzumab |
| 13327-13446 | S188K | K129T_S176D_Y178T | L143E_K145T_Q179E | Q124R_T178R | CAT-2200 | Pertuzumab |
| 13334-13449 | S188K | K129T_Y178D | L143E_K145T_Q179E | Q124R_T178R | CAT-2200 | Pertuzumab |
| 13336-13450 | S188K | K129T_Y178E | L143E_K145T_Q179E | Q124R_T178R | CAT-2200 | Pertuzumab |
| 13236-13433 | A139W_S188K | K129T_S176E_Y178E | L143E_K145T_Q179E | Q124R_L135W_T178R | CAT-2200 | Pertuzumab |
| 13234-13432 | A139W_S188K | K129T_S176D_Y178T | L143E_K145T_Q179E | Q124R_L135W_T178R | CAT-2200 | Pertuzumab |
| 13208-13455 | A125R_S188K | S122D_K129T_ S176E_Y178E | L143E_K145T_ Q179E_K228D | S121K_Q124R_T178R | CAT-2200 | Pertuzumab |

TABLE 7A-continued

| Second K-L Design Library | | | | | | |
|---|---|---|---|---|---|---|
| Unique identifier | H1 mutation (Kabat) | L1 mutation (Kabat) | H2 mutations (Kabat) | L2 mutation (Kabat) | H1L1 Fab | H2L2 Fab |
| 13206-13454 | A125R_S188K | S122D_K129T_ S176D_Y178T | L143E_K145T_ Q179E_K228D | S121K_Q124R_T178R | CAT-2200 | Pertuzumab |
| 13333-13387 | S188K | K129T_S176E_Y178E | L124E_K145T_Q179E | S131R_V133G_5176R | CAT-2200 | Pertuzumab |
| 13295-13484 | L143E_K145T_Q179E | E124Q_T131R | L143R | Q124E_V133D_T180D | CAT-2200 | Pertuzumab |
| 13282-13484 | L143D_K145T | E124Q_T131R | L143R | Q124E_V133D_T180D | CAT-2200 | Pertuzumab |
| 13218-13482 | A139W_L143D_K145T | E124Q_T131R | L143R | Q124E_V133D_L135W | CAT-2200 | Pertuzumab |
| 13219-13483 | A139W_L143D_K145T | E124Q_T131R | L143R | Q124E_V133D_L135W_T180D | CAT-2200 | Pertuzumab |
| 13175-13486 | A125R_L143D_K145T | S122D_E124Q_T131R | L143R_K228D | S121K_Q124E_V133D | CAT-2200 | Pertuzumab |
| 13176-13487 | A125R_L143D_K145T | S122D_E124Q_T131R | L143R_K228D | S121K_Q124E_V133D_T180D | CAT-2200 | Pertuzumab |
| 13280-13488 | L143D_K145T | E124Q_T131R | L143R_S188K | Q124E_V133D_S176D_T178D | CAT-2200 | Pertuzumab |
| 13281-13489 | L143D_K145T | E124Q_T131R | L143R_S188K | Q124E_V133D_S176D_T178E | CAT-2200 | Pertuzumab |
| 13291-13488 | L143E_K145T_Q179E | E124Q_T131R | L143R_S188K | Q124E_V133D_S176D_T178D | CAT-2200 | Pertuzumab |
| 13287-13494 | L143D_K145T_F1748 | T116F_E124Q_ T131R_S176F | L143R_V190F | Q124E_V133D_L135A | CAT-2200 | Pertuzumab |
| 13214-13405 | A139W_L143D_K145T | E124Q_T131K | L124R_Q179K | V1338_L135W_S176D_T180E | CAT-2200 | Pertuzumab |
| 13221-13406 | A139W_L143D_K145T | E124Q_T131R | L124R_Q179K | V1338_L135W_S176D_T180E | CAT-2200 | Pertuzumab |
| 13214-13410 | A139W_L143D_K145T | E124Q_T131K | L124R_S186K | V1338_L135W_S176D_T180E | CAT-2200 | Pertuzumab |
| 13221-13411 | A139W_L143D_K145T | E124Q_T131R | L124R_S186K | V1338_L135W_S176D_T180E | CAT-2200 | Pertuzumab |
| 13285-13414 | L143D_K145T_F1748 | T116F_E124Q_ T131K_S176F | L124R_S186K_V190F | V1338_L135A_S176D_T180E | CAT-2200 | Pertuzumab |
| 13171-13416 | A125R_L143D_K145T | S122D_E124Q_T131K | L124R_S186R_K228D | S121K_V133G_S176D_T180E | CAT-2200 | Pertuzumab |
| 13178-13417 | A125R_L143D_K145T | S122D_E124Q_T131R | L124R_S186R_K228D | S121K_V133G_S176D_T180E | CAT-2200 | Pertuzumab |
| 13220-13511 | A139W_L143D_K145T | E124Q_T131R | S188K | S131D_V1338_L135W_T178F | CAT-2200 | Pertuzumab |
| 13177-13513 | A125R_L143D_K145T | S122D_E124Q_T131R | S188K_K228D | S121K_S131D_V133G_T178F | CAT-2200 | Pertuzumab |
| 13288-13516 | L143E_K145T_ F174G_Q179E | T116F_E124Q_ T131R_S176F | S188K_V190F | V1331_L135A_S176D_T178E | CAT-2200 | Pertuzumab |
| 13223-13512 | A139W_L143E_ K145T_Q179E | E124Q_T131R | S188K | V1331_L135W_S176D_T178E | CAT-2200 | Pertuzumab |
| 13180-13515 | A125R_L143E_ K145T_Q179E | S122D_E124Q_T131R | S188K_K228D | S121K_V133I_S176D_T178E | CAT-2200 | Pertuzumab |
| 13298-13439 | L143K | K129T_T131D_V133D | L143E_K145T_Q179E | Q124R_Q160R_T178R | CAT-2200 | Pertuzumab |
| 13300-13441 | L143K | K129T_T131E_V133D | L143E_K145T_Q179E | Q124R_Q160R_T178R | CAT-2200 | Pertuzumab |
| 13271-13439 | L124K_L143K | K129T_T131D_V133D | L143E_K145T_Q179E | Q124R_Q160R_T178R | CAT-2200 | Pertuzumab |
| 13273-13441 | L124K_L143K | K129T_T131E_V133D | L143E_K145T_Q179E | Q124R_Q160R_T178R | CAT-2200 | Pertuzumab |
| 13299-13379 | L143K | K129T_T131D_V133D | L124E_K145T_Q179E | S131K_V133G_S176R | CAT-2200 | Pertuzumab |
| 13301-13381 | L143K | K129T_T131E_V133D | L124E_K145T_Q179E | S131K_V133G_S176R | CAT-2200 | Pertuzumab |
| 13272-13379 | L124K_L143K | K129T_T131D_V133D | L124E_K145T_Q179E | S131K_V133G_S176R | CAT-2200 | Pertuzumab |
| 13274-13381 | L124K_L143K | K129T_T131E_V133D | L124E_K145T_Q179E | S131K_V133G_S176R | CAT-2200 | Pertuzumab |
| 13305-13448 | L143K_V190K | K129T_V133D_L135S | L143E_K145T_Q179E | Q124R_T178R | CAT-2200 | Pertuzumab |
| 13304-13466 | L143K_F174G | T116F_K129T_ V133D_S176F | L143E_K145T_ Q179E_V190F | Q124R_L135A_T178R | CAT-2200 | Pertuzumab |
| 13226-13434 | A139W_L143K | K129T_V133D | L143E_K145T_Q179E | Q124R_L135W_T178R | CAT-2200 | Pertuzumab |
| 13182-13458 | A125R_L143K | S122D_K129T_V133D | L143E_K145T_ Q179E_K228D | S121K_Q124R_T178R | CAT-2200 | Pertuzumab |
| 13227-13383 | A139W_L143K | K129T_V133D | L124E_K145T_Q179E | S131R_V133G_L135W_S176R | CAT-2200 | Pertuzumab |
| 13184-13388 | A125R_L143K | S122D_K129T_V133D | L124E_K145T_ Q179E_K228D | S121K_S131R_V133G_S176R | CAT-2200 | Pertuzumab |
| 13229-13428 | A139W_S186K | K129T_V133D_Y178T | L143E_K145T_Q179E | Q124R_L135W_Q160K_T178R | CAT-2200 | Pertuzumab |
| 13224-13428 | A139W_L143I_S186K | K129T_V133D_Y178T | L143E_K145T_Q179E | Q124R_L135W_Q160K_T178R | CAT-2200 | Pertuzumab |
| 13231-13386 | A139W_S186K_S188T | V133D_Y178T | L124E_K145T_Q179E | S131R_V133G_L135W_S176R | CAT-2200 | Pertuzumab |
| 13199-13391 | A125R_S186K_S188T | S122D_V133D_Y178T | L124E_K145T_ Q179E_K228D | S121K_S131R_V133G_S176R | CAT-2200 | Pertuzumab |
| 13230-13384 | A139W_S186K | K129T_V133D_Y178T | L124E_K145T_Q179E | S131R_V133G_L135W_S176R | CAT-2200 | Pertuzumab |
| 13198-13389 | A125R_S186K | S122D_K129T_ V133D_Y178T | L124E_K145T_ Q179E_K228D | S121K_S131R_V133G_S176R | CAT-2200 | Pertuzumab |
| 13225-13384 | A139W_L143I_S186K | K129T_V133D_Y178T | L124E_K145T_Q179E | S131R_V133G_L135W_S176R | CAT-2200 | Pertuzumab |
| 13181-13389 | A125R_L143I_S186K | S122D_K129T_ V133D_Y178T | L124E_K145T_ Q179E_K228D | S121K_S131R_V133G_S176R | CAT-2200 | Pertuzumab |
| 13306-13375 | L143K_V190K | K129T_V133D_L135S | L124E_K145T | S131K_L135K | CAT-2200 | Pertuzumab |
| 13306-13373 | L143K_V190K | K129T_V133D_L135S | L124E_A139I_ K145T_V190I | S131K_L135K | CAT-2200 | Pertuzumab |
| 13185-13374 | A125R_L143K_V190K | S122D_K129T_ V133D_L135S | L124E_A139I_K145T_ V190I_K228D | S121K_S131K_L135K | CAT-2200 | Pertuzumab |
| 13283-13507 | L143D_K145T_F174G | E124Q_T131K_ V133S_S176F | S186K_V190F | Q124E_V133D_L135A | CAT-2200 | Pertuzumab |
| 13216-13505 | A139W_L143D_K145T | E124Q_T131K_V133S | S186K | Q124E_V133D_L135W | CAT-2200 | Pertuzumab |
| 13173-13506 | A125R_L143D_K145T | S122D_E124Q_ T131K_V133S | S186K_K228D | S121K_Q124E_V133D | CAT-2200 | Pertuzumab |
| 13283-13478 | L143D_K145T_F174G | E124Q_T131K_ V133S_S176F | L143I_S186K_V190F | Q124E_V133D_L135A | CAT-2200 | Pertuzumab |
| 13216-13476 | A139W_L143D_K145T | E124Q_T131K_V133S | L143I_S186K | Q124E_V133D_L135W | CAT-2200 | Pertuzumab |
| 13173-13477 | A125R_L143D_K145T | S122D_E124Q_ T131K_V133S | L143I_S186K_K228D | S121K_Q124E_V133D | CAT-2200 | Pertuzumab |
| 13329-13366 | S188K | K129T_S176E_Y178E | L45P_L124E_ K145T_Q179E | P44F_S131R_V133G_S176R | CAT-2200 | Pertuzumab |

TABLE 7A-continued

| Second K-L Design Library | | | | | | |
|---|---|---|---|---|---|---|
| Unique identifier | H1 mutation (Kabat) | L1 mutation (Kabat) | H2 mutations (Kabat) | L2 mutation (Kabat) | H1L1 Fab | H2L2 Fab |
| 13252-13369 | K145T_S188E | Y178K | L45P_L124R_Q179K | P44F_V133G_S176D_T180E | CAT-2200 | Pertuzumab |
| 13289-13368 | L143E_K145T_Q179E | E124Q_T131R | L45P_L124R_Q179K | P44F_V133G_S176D_T180E | CAT-2200 | Pertuzumab |
| 13338-13371 | S188K | S176E_Y178E | L45P_L143E_K145T_Q179E | P44F_Q124R_T178R | CAT-2200 | Pertuzumab |
| 13278-13372 | L143D_K145T | E124Q_T131R | L45P_L143R | P44F_Q124E_V133D | CAT-2200 | Pertuzumab |
| 13320-13370 | S186R | K129T_S180E | L45P_L143E_K145T_Q179E | P44F_Q124K_T178R | CAT-2200 | Pertuzumab |
| 13302-13367 | L143K | K129T_V133D | L45P_L124E_K145T_Q179E | P44F_S131R_V133G_S176R | CAT-2200 | Pertuzumab |
| 13330-13495 | S188K | K129T_S176E_Y178E | Q39E_L124E_K145T_Q179E | Q38R_S131R_V133G_S176R | CAT-2200 | Pertuzumab |
| 13253-13498 | K145T_S188E | Y178K | Q39E_L124R_Q179K | Q38R_V133G_S176D_T180E | CAT-2200 | Pertuzumab |
| 13290-13497 | L143E_K145T_Q179E | E124Q_T131R | Q39E_L124R_Q179K | Q38R_V133G_S176D_T180E | CAT-2200 | Pertuzumab |
| 13339-13500 | S188K | S176E_Y178E | Q39E_L143E_K145T_Q179E | Q38R_Q124R_T178R | CAT-2200 | Pertuzumab |
| 13279-13501 | L143D_K145T | E124Q_T131R | Q39E_L143R | Q38R_Q124E_V133D | CAT-2200 | Pertuzumab |
| 13321-13499 | S186R | K129T_S180E | Q39E_L143E_K145T_Q179E | Q38R_Q124K_T178R | CAT-2200 | Pertuzumab |
| 13303-13496 | L143K | K129T_V133D | Q39E_L124E_K145T_Q179E | Q38R_S131R_V133G_S176R | CAT-2200 | Pertuzumab |
| 12957-13061 | S186R | K129T_S180E | L143E_K145T | Q124K_T178R | CAT-2200 | Pertuzumab |
| 12906-13152 | L143D_K145T | E124Q_T131K_V133S | S186K | Q124E_V133D | CAT-2200 | Pertuzumab |
| 13318-13437 | S186K | K129T_V133D_Y178T | L143E_K145T_Q179E | Q124R_Q160K_T178R | CAT-2200 | Pertuzumab |

TABLE 7B

| Second K-K derived K-L design libarary<br>Second K-K derived K-L designs libarary | | | | | | |
|---|---|---|---|---|---|---|
| Unique identifier | H1 mutation (Kabat) | L1 mutation (Kabat) | H2 mutation (Kabat) | L2 mutation (Kabat) | H1L1 Fab | H2L2 Fab |
| 12938-13064 | Q179K | K129T_S180E | L143E_K145T | Q124R_Q160K_T178R | CAT-2200 | Pertuzumab |
| 13309-13425 | Q179K | K129T_S180E | L143E_K145T | Q124R_T129K_Q160K_T178R | CAT-2200 | Pertuzumab |
| 13314-13424 | Q179K | K129T_Y178E_S180E | L143E_K145T | Q124R_Q160K_T178R | CAT-2200 | Pertuzumab |
| 12938-13469 | Q179K | K129T_S180E | L143E_K145T_S188L | Q124R_Q160K_T178R | CAT-2200 | Pertuzumab |
| 12944-13471 | Q179K | K129T_S180E | L143E_K145T_S188L | Q124R_T178R | CAT-2200 | Pertuzumab |
| 13275-13470 | L143A_Q179K | K129T_V133W_S180E | L143E_K145T_S188L | Q124R_Q160K_T178R | CAT-2200 | Pertuzumab |
| 13276-13472 | L143A_Q179K | K129T_V133W_S180E | L143E_K145T_S188L | Q124R_T178R | CAT-2200 | Pertuzumab |
| 13308-13340 | Q179K | K129T_S180E | F122C_L143E_K145T | Q124C_Q160K_T178R | CAT-2200 | Pertuzumab |
| 12961-13093 | S186R | K129T_S180E | L143E_K145T_Q179E | Q124R_T178R | CAT-2200 | Pertuzumab |
| 12958-13079 | S186R | K129T_S180E | L143E_K145T_Q179E | Q124R_Q160K_T178R | CAT-2200 | Pertuzumab |
| 12938-13079 | Q179K | K129T_S180E | L143E_K145T_Q179E | Q124R_Q160K_T178R | CAT-2200 | Pertuzumab |
| 13323-13444 | S186R | K129T_S180E | L143E_K145T_Q179E | Q124R_T129K_T178R | CAT-2200 | Pertuzumab |
| 13310-13444 | Q179K | K129T_S180E | L143E_K145T_Q179E | Q124R_T129K_T178R | CAT-2200 | Pertuzumab |
| 13322-13443 | S186R | K129T_S180E | L143E_K145T_Q179E | Q124R_T129K_Q160K_T178R | CAT-2200 | Pertuzumab |
| 13316-13451 | Q179K | K129T_Y178E_S180E | L143E_K145T_Q179E | Q124R_T178R | CAT-2200 | Pertuzumab |
| 13314-13438 | Q179K | K129T_Y178E_S180E | L143E_K145T_Q179E | Q124R_Q160K_T178R | CAT-2200 | Pertuzumab |
| 12938-13106 | Q179K | K129T_S180E | L143E_K145T_Q179E_S188L | Q124R_Q160K_T178R | CAT-2200 | Pertuzumab |
| 12944-13108 | Q179K | K129T_S180E | L143E_K145T_Q179E_S188L | Q124R_T178R | CAT-2200 | Pertuzumab |
| 13275-13461 | L143A_Q179K | K129T_V133W_S180E | L143E_K145T_Q179E_S188L | Q124R_Q160K_T178R | CAT-2200 | Pertuzumab |
| 13276-13462 | L143A_Q179K | K129T_V133W_S180E | L143E_K145T_Q179E_S188L | Q124R_T178R | CAT-2200 | Pertuzumab |
| 13308-13341 | Q179K | K129T_S180E | F122C_L143E_K145T_Q179E | Q124C_Q160K_T178R | CAT-2200 | Pertuzumab |

TABLE 8A

LCCA results for K-L designs from the second K-L design library that passed the performance cut off criteria

| Column 1 Unique identifier | Column 2 H1L1: H1L2 median scalar value | Column 3 H1L1: H1L2 range of scalar value | Column 4 H1L1: H1L2 normalized median ratio | Column 5 H2L2: H2L1 median scalar value | Column 6 H2L2: H2L1 range of scalar value | Column 7 H1L2: H2L1 noramlized median ratio | Column 8 H1L1 Fab | Column 9 H2L2 Fab |
|---|---|---|---|---|---|---|---|---|
| 12944-13093 | 1.41 | 1.04 | 79:21 | 1.39 | 0.27 | 80:20 | CAT-2200 | Pertuzumab |
| 12958-13064 | 1.29 | 1.13 | 77:23 | 0.86 | NA | 70:30 | CAT-2200 | Pertuzumab |
| 12958-13106 | 1.29 | 1.13 | 77:23 | 3.06 | 0.1 | 95:5 | CAT-2200 | Pertuzumab |
| 12958-13469 | 1.29 | 1.13 | 77:23 | 1.83 | 0.02 | 86:14 | CAT-2200 | Pertuzumab |
| 12961-13108 | 2 | NA | 88:12 | 1.82 | NA | 86:14 | CAT-2200 | Pertuzumab |
| 12961-13471 | 2 | NA | 88:12 | 1.16 | NA | 76:24 | CAT-2200 | Pertuzumab |
| 13200-13421 | −2.46 | NA | 7:93 | −0.26 | 0.35 | 44:56 | CAT-2200 | Pertuzumab |
| 13202-13426 | −2.18 | NA | 10:90 | −0.24 | NA | 44:56 | CAT-2200 | Pertuzumab |
| 13203-13427 | −2.68 | NA | 6:94 | 2.19 | 4.71 | 72:28 | CAT-2200 | Pertuzumab |
| 13248-13475 | 1.72 | NA | 84:16 | −0.23 | NA | 44:56 | CAT-2200 | Pertuzumab |
| 13309-13443 | 0.98 | NA | 72:28 | 1.35 | NA | 79:21 | CAT-2200 | Pertuzumab |
| 13322-13425 | 1.1 | 0.72 | 74:26 | −0.13 | 0.03 | 47:53 | CAT-2200 | Pertuzumab |
| 13204-13351 | 1.71 | 0.98 | 84:16 | −0.1 | 0.21 | 48:52 | CAT-2200 | Pertuzumab |
| 13205-13353 | 2.28 | NA | 90:10 | 0.07 | NA | 51:49 | CAT-2200 | Pertuzumab |
| 13196-13351 | 1 | NA | 73:27 | −0.1 | 0.21 | 48:52 | CAT-2200 | Pertuzumab |
| 13197-13353 | 0.37 | NA | 59:41 | 0.07 | NA | 51:49 | CAT-2200 | Pertuzumab |
| 13250-13355 | 1.38 | 0.6 | 79:21 | −0.45 | NA | 39:61 | CAT-2200 | Pertuzumab |
| 13277-13420 | 1.08 | 0.17 | 75:25 | 0.73 | 0.12 | 67:33 | CAT-2200 | Pertuzumab |
| 13319-13473 | −0.88 | 0.71 | 30:70 | 0.43 | 0.43 | 60:40 | CAT-2200 | Pertuzumab |
| 13188-13421 | 1.6 | 0.53 | 83:17 | −0.26 | 0.35 | 44:56 | CAT-2200 | Pertuzumab |
| 13190-13422 | 1.5 | NA | 81:19 | −0.32 | NA | 42:58 | CAT-2200 | Pertuzumab |
| 13242-13475 | 1.48 | NA | 81:19 | −0.23 | NA | 44:56 | CAT-2200 | Pertuzumab |
| 13192-13426 | 1.96 | NA | 87:13 | −0.24 | NA | 44:56 | CAT-2200 | Pertuzumab |
| 13194-13427 | 1.22 | 0.18 | 77:23 | 2.19 | 4.71 | 72:28 | CAT-2200 | Pertuzumab |
| 13317-13423 | −1.42 | NA | 19:81 | 3.09 | 1.62 | 94:6 | CAT-2200 | Pertuzumab |
| 13188-13430 | 1.6 | 0.53 | 83:17 | 0.77 | 0.25 | 68:32 | CAT-2200 | Pertuzumab |
| 13200-13430 | −2.46 | NA | 7:93 | 0.77 | 0.25 | 68:32 | CAT-2200 | Pertuzumab |
| 13246-13463 | 1.98 | 0.9 | 87:13 | −0.51 | 0.09 | 37:63 | CAT-2200 | Pertuzumab |
| 13238-13463 | 2.26 | 0.73 | 90:10 | −0.51 | 0.09 | 37:63 | CAT-2200 | Pertuzumab |
| 13248-13465 | 1.72 | NA | 84:16 | −0.29 | NA | 42:58 | CAT-2200 | Pertuzumab |
| 13242-13465 | 1.48 | NA | 81:19 | −0.29 | NA | 42:58 | CAT-2200 | Pertuzumab |
| 13246-13459 | 1.98 | 0.9 | 87:13 | −0.51 | NA | 37:63 | CAT-2200 | Pertuzumab |
| 13238-13459 | 2.26 | 0.73 | 90:10 | −0.51 | NA | 37:63 | CAT-2200 | Pertuzumab |
| 13192-13452 | 1.96 | NA | 87:13 | 1.15 | NA | 75:25 | CAT-2200 | Pertuzumab |
| 13194-13456 | 1.22 | 0.18 | 77:23 | 0.72 | 0.02 | 67:33 | CAT-2200 | Pertuzumab |
| 13202-13452 | −2.18 | NA | 10:90 | 1.15 | NA | 75:25 | CAT-2200 | Pertuzumab |
| 13203-13456 | −2.68 | NA | 6:94 | 0.72 | 0.02 | 67:33 | CAT-2200 | Pertuzumab |
| 13254-13508 | 1.68 | 0.94 | 83:17 | 0.8 | 0.08 | 69:31 | CAT-2200 | Pertuzumab |
| 13255-13509 | 1.67 | NA | 84:16 | 0 | NA | 49:51 | CAT-2200 | Pertuzumab |
| 13262-13481 | 2.41 | 0.41 | 91:9 | 1.01 | 0.15 | 73:27 | CAT-2200 | Pertuzumab |
| 13261-13480 | 1.91 | NA | 87:13 | 0.61 | NA | 64:36 | CAT-2200 | Pertuzumab |
| 13258-13504 | −0.25 | NA | 43:57 | 2.76 | NA | 94:6 | CAT-2200 | Pertuzumab |
| 13256-13502 | 0.53 | NA | 62:38 | 2.01 | NA | 88:12 | CAT-2200 | Pertuzumab |
| 13257-13503 | 0.85 | 0.63 | 70:30 | 2.48 | 0.41 | 92:8 | CAT-2200 | Pertuzumab |
| 13269-13403 | 2.58 | 1.35 | 92:8 | 0.35 | 0.23 | 58:42 | CAT-2200 | Pertuzumab |
| 13268-13401 | 2.25 | NA | 90:10 | 0.07 | NA | 51:49 | CAT-2200 | Pertuzumab |
| 12878-11240 | 1.85 | 0.37 | 86:14 | 2.2 | 0.04 | 90:10 | CAT-2200 | Pertuzumab |
| 10798-13036 | 2.29 | 0.65 | 90:10 | 2.34 | NA | 91:9 | CAT-2200 | Pertuzumab |
| 13265-13392 | 2.97 | 0.72 | 95:5 | −0.29 | NA | 42:58 | CAT-2200 | Pertuzumab |
| 13265-13419 | 2.97 | 0.72 | 95:5 | 0.54 | 0.12 | 63:37 | CAT-2200 | Pertuzumab |
| 13212-13396 | 3 | 0.15 | 95:5 | 0.29 | 0.2 | 57:43 | CAT-2200 | Pertuzumab |
| 13211-13395 | 2.12 | NA | 89:11 | 0.55 | NA | 63:37 | CAT-2200 | Pertuzumab |
| 13168-13397 | 3.03 | 0.12 | 95:5 | 1.97 | 5.15 | 67:33 | CAT-2200 | Pertuzumab |
| 13296-13399 | 1.05 | 0.04 | 74:26 | 0.55 | 0.45 | 63:37 | CAT-2200 | Pertuzumab |
| 13297-13402 | 1.21 | NA | 77:23 | 0.25 | NA | 56:44 | CAT-2200 | Pertuzumab |
| 13264-13400 | 1.14 | NA | 75:25 | 0.45 | NA | 61:39 | CAT-2200 | Pertuzumab |
| 13332-13360 | 1.69 | 0.38 | 84:16 | 2.25 | 0.47 | 90:10 | CAT-2200 | Pertuzumab |
| 13328-13359 | 2.12 | NA | 89:11 | 0.9 | NA | 71:29 | CAT-2200 | Pertuzumab |
| 13335-13361 | 2.01 | NA | 88:12 | 1.58 | NA | 82:18 | CAT-2200 | Pertuzumab |
| 13337-13362 | 2.14 | NA | 89:11 | 0.53 | NA | 63:37 | CAT-2200 | Pertuzumab |
| 13237-13358 | 2.33 | 0.56 | 91:9 | 0.59 | 0.22 | 64:36 | CAT-2200 | Pertuzumab |
| 13235-13357 | 1.96 | NA | 87:13 | −0.33 | NA | 41:59 | CAT-2200 | Pertuzumab |
| 13209-13364 | 2.54 | 0.19 | 92:8 | 1.21 | 0.05 | 77:23 | CAT-2200 | Pertuzumab |
| 13207-13363 | 2.09 | NA | 89:11 | 0.33 | NA | 58:42 | CAT-2200 | Pertuzumab |
| 13210-13510 | 1.5 | 0.14 | 81:19 | 2.55 | 0.51 | 92:8 | CAT-2200 | Pertuzumab |
| 13167-13514 | 2.61 | NA | 93:7 | 2.83 | 1.01 | 94:6 | CAT-2200 | Pertuzumab |
| 13294-13492 | 1.48 | 0.67 | 81:19 | 1.45 | 0.28 | 81:19 | CAT-2200 | Pertuzumab |
| 13292-13489 | 1.18 | 0.48 | 76:24 | 1.21 | 0.25 | 77:23 | CAT-2200 | Pertuzumab |
| 13263-13493 | 2 | 0.48 | 88:12 | 1.31 | 0.59 | 78:22 | CAT-2200 | Pertuzumab |

TABLE 8A-continued

LCCA results for K-L designs from the second K-L design library that passed the performance cut off criteria

| Column 1 Unique identifier | Column 2 H1L1: H1L2 median scalar value | Column 3 H1L1: H1L2 range of scalar value | Column 4 H1L1: H1L2 normalized median ratio | Column 5 H2L2: H2L1 median scalar value | Column 6 H2L2: H2L1 range of scalar value | Column 7 H1L2: H2L1 noramlized median ratio | Column 8 H1L1 Fab | Column 9 H2L2 Fab |
|---|---|---|---|---|---|---|---|---|
| 13259-13491 | 2.34 | NA | 91:9 | −0.02 | NA | 49:51 | CAT-2200 | Pertuzumab |
| 13212-13415 | 3 | 0.15 | 95:5 | 0.23 | 0.29 | 56:44 | CAT-2200 | Pertuzumab |
| 13169-13418 | 3.25 | 0.6 | 96:4 | 1.83 | 4.92 | 66:34 | CAT-2200 | Pertuzumab |
| 13331-13447 | 0.49 | NA | 61:39 | 3.52 | NA | 97:3 | CAT-2200 | Pertuzumab |
| 13327-13446 | 0.7 | NA | 66:34 | 3.01 | NA | 95:5 | CAT-2200 | Pertuzumab |
| 13334-13449 | 0.46 | NA | 61:39 | 2.74 | NA | 93:7 | CAT-2200 | Pertuzumab |
| 13336-13450 | 0.81 | 0.4 | 69:31 | 3.1 | 0.75 | 95:5 | CAT-2200 | Pertuzumab |
| 13236-13433 | 2.45 | 1.02 | 91:9 | 2.64 | NA | 93:7 | CAT-2200 | Pertuzumab |
| 13234-13432 | 2 | NA | 88:12 | 2.54 | NA | 92:8 | CAT-2200 | Pertuzumab |
| 13208-13455 | 1.54 | 0.48 | 82:18 | 3.5 | 1.89 | 95:5 | CAT-2200 | Pertuzumab |
| 13206-13454 | 1.2 | NA | 76:24 | 2.56 | NA | 92:8 | CAT-2200 | Pertuzumab |
| 13333-13387 | 1.64 | 0.38 | 83:17 | 4.11 | 1.06 | 98:2 | CAT-2200 | Pertuzumab |
| 13295-13484 | 1.44 | NA | 80:20 | 1.72 | 0.08 | 85:15 | CAT-2200 | Pertuzumab |
| 13282-13484 | 1.68 | 0.37 | 84:16 | 1.72 | 0.08 | 85:15 | CAT-2200 | Pertuzumab |
| 13218-13482 | 1.92 | 0.12 | 87:13 | 2.13 | 0.09 | 89:11 | CAT-2200 | Pertuzumab |
| 13219-13483 | 2.2 | NA | 89:11 | 0.87 | NA | 70:30 | CAT-2200 | Pertuzumab |
| 13175-13486 | 3.12 | 2.77 | 91:9 | 1.08 | 0.22 | 74:26 | CAT-2200 | Pertuzumab |
| 13176-13487 | 2.73 | NA | 93:7 | −0.2 | NA | 44:56 | CAT-2200 | Pertuzumab |
| 13280-13488 | 0.49 | NA | 62:38 | 0.02 | NA | 50:50 | CAT-2200 | Pertuzumab |
| 13281-13489 | 0.25 | NA | 56:44 | 1.21 | 0.25 | 77:23 | CAT-2200 | Pertuzumab |
| 13291-13488 | 1.41 | NA | 80:20 | 0.02 | NA | 50:50 | CAT-2200 | Pertuzumab |
| 13287-13494 | 1.73 | 0.28 | 85:15 | 1.25 | 0.13 | 77:23 | CAT-2200 | Pertuzumab |
| 13214-13405 | 2.08 | NA | 88:12 | −0.52 | NA | 37:63 | CAT-2200 | Pertuzumab |
| 13221-13406 | 2.38 | 0.29 | 91:9 | −0.41 | 0.26 | 40:60 | CAT-2200 | Pertuzumab |
| 13214-13410 | 2.08 | NA | 88:12 | 0 | NA | 49:51 | CAT-2200 | Pertuzumab |
| 13221-13411 | 2.38 | 0.29 | 91:9 | 0 | 0 | 50:50 | CAT-2200 | Pertuzumab |
| 13285-13414 | 1.63 | 0.18 | 83:17 | −0.44 | 0.1 | 39:61 | CAT-2200 | Pertuzumab |
| 13171-13416 | 3.11 | NA | 95:5 | −0.52 | NA | 37:63 | CAT-2200 | Pertuzumab |
| 13178-13417 | 2.74 | 1.26 | 93:7 | −0.49 | 0.1 | 38:62 | CAT-2200 | Pertuzumab |
| 13220-13511 | 1.56 | 1.08 | 81:19 | 1.72 | 0.22 | 85:15 | CAT-2200 | Pertuzumab |
| 13177-13513 | 1.58 | 0.73 | 82:18 | −0.08 | 0.07 | 47:53 | CAT-2200 | Pertuzumab |
| 13288-13516 | 1.41 | 0.68 | 80:20 | 0.88 | 0.26 | 70:30 | CAT-2200 | Pertuzumab |
| 13223-13512 | 0.95 | 1.17 | 70:30 | 2.03 | 0.22 | 88:12 | CAT-2200 | Pertuzumab |
| 13180-13515 | 1.56 | 0.75 | 82:18 | 1.74 | 0.42 | 85:15 | CAT-2200 | Pertuzumab |
| 13298-13439 | −1.21 | NA | 23:77 | 2.79 | NA | 94:6 | CAT-2200 | Pertuzumab |
| 13300-13441 | −0.72 | NA | 32:68 | 2.58 | 0 | 92:8 | CAT-2200 | Pertuzumab |
| 13271-13439 | −0.6 | NA | 35:65 | 2.79 | NA | 94:6 | CAT-2200 | Pertuzumab |
| 13273-13441 | −0.31 | 0.18 | 42:58 | 2.58 | 0 | 92:8 | CAT-2200 | Pertuzumab |
| 13299-13379 | −0.53 | NA | 37:63 | 3.26 | NA | 96:4 | CAT-2200 | Pertuzumab |
| 13301-13381 | −0.28 | 0.2 | 43:57 | 3.71 | 0.93 | 97:3 | CAT-2200 | Pertuzumab |
| 13272-13379 | −0.51 | NA | 37:63 | 3.26 | NA | 96:4 | CAT-2200 | Pertuzumab |
| 13274-13381 | −0.57 | NA | 36:64 | 3.71 | 0.93 | 97:3 | CAT-2200 | Pertuzumab |
| 13305-13448 | −1.5 | 0.06 | 18:82 | 3.63 | 1.65 | 96:4 | CAT-2200 | Pertuzumab |
| 13304-13466 | 0.63 | 0.22 | 65:35 | 0.99 | 0.24 | 73:27 | CAT-2200 | Pertuzumab |
| 13226-13434 | 1.82 | 0.08 | 86:14 | 2.68 | 0.36 | 93:7 | CAT-2200 | Pertuzumab |
| 13182-13458 | 1.53 | 0.76 | 81:19 | 1.1 | 2.96 | 66:34 | CAT-2200 | Pertuzumab |
| 13227-13383 | 2.47 | 1.62 | 90:10 | 2.31 | 0.51 | 90:10 | CAT-2200 | Pertuzumab |
| 13184-13388 | 1.4 | 0.79 | 79:21 | 3.08 | 0.13 | 95:5 | CAT-2200 | Pertuzumab |
| 13229-13428 | 1.44 | 1.12 | 79:21 | 2.02 | 0.28 | 88:12 | CAT-2200 | Pertuzumab |
| 13224-13428 | 1.48 | NA | 81:19 | 2.02 | 0.28 | 88:12 | CAT-2200 | Pertuzumab |
| 13231-13386 | 2.02 | 0.97 | 87:13 | 1.7 | 0.42 | 84:16 | CAT-2200 | Pertuzumab |
| 13199-13391 | 2.04 | NA | 88:12 | 1.9 | NA | 86:14 | CAT-2200 | Pertuzumab |
| 13230-13384 | 1.63 | NA | 83:17 | 1.71 | NA | 84:16 | CAT-2200 | Pertuzumab |
| 13198-13389 | 1.16 | 0.33 | 75:25 | 2.42 | 0.43 | 92:8 | CAT-2200 | Pertuzumab |
| 13225-13384 | 0.87 | NA | 70:30 | 1.71 | NA | 84:16 | CAT-2200 | Pertuzumab |
| 13181-13389 | 1.75 | NA | 85:15 | 2.42 | 0.43 | 92:8 | CAT-2200 | Pertuzumab |
| 13306-13375 | −1.45 | 0.02 | 19:81 | 0.85 | 0.33 | 70:30 | CAT-2200 | Pertuzumab |
| 13306-13373 | −1.45 | 0.02 | 19:81 | 0.48 | NA | 61:39 | CAT-2200 | Pertuzumab |
| 13185-13374 | −1.11 | 0.12 | 24:76 | 0.25 | NA | 56:44 | CAT-2200 | Pertuzumab |
| 13283-13507 | 1.09 | 0.31 | 74:26 | −0.45 | 0.26 | 39:61 | CAT-2200 | Pertuzumab |
| 13216-13505 | 1.39 | 1.28 | 78:22 | 0.96 | 0.05 | 72:28 | CAT-2200 | Pertuzumab |
| 13173-13506 | 1.33 | 0.47 | 78:22 | −0.5 | 0.02 | 37:63 | CAT-2200 | Pertuzumab |
| 13283-13478 | 1.09 | 0.31 | 74:26 | −0.49 | NA | 37:63 | CAT-2200 | Pertuzumab |
| 13216-13476 | 1.39 | 1.28 | 78:22 | 1.69 | NA | 84:16 | CAT-2200 | Pertuzumab |
| 13173-13477 | 1.33 | 0.47 | 78:22 | −0.18 | NA | 45:55 | CAT-2200 | Pertuzumab |
| 13329-13366 | 1.54 | 0.47 | 82:18 | 3.9 | 0.89 | 97:3 | CAT-2200 | Pertuzumab |
| 13252-13369 | 2.39 | 0.94 | 91:9 | 1.45 | 0.42 | 81:19 | CAT-2200 | Pertuzumab |
| 13289-13368 | 1.6 | 0.48 | 83:17 | 1.84 | 0.15 | 86:14 | CAT-2200 | Pertuzumab |
| 13338-13371 | 1.05 | 0.91 | 73:27 | 3.81 | 0.37 | 98:2 | CAT-2200 | Pertuzumab |

TABLE 8A-continued

LCCA results for K-L designs from the second K-L design library that passed the performance cut off criteria

| Column 1 Unique identifier | Column 2 H1L1: H1L2 median scalar value | Column 3 H1L1: H1L2 range of scalar value | Column 4 H1L1: H1L2 normalized median ratio | Column 5 H2L2: H2L1 median scalar value | Column 6 H2L2: H2L1 range of scalar value | Column 7 H1L2: H2L1 noramlized median ratio | Column 8 H1L1 Fab | Column 9 H2L2 Fab |
|---|---|---|---|---|---|---|---|---|
| 13278-13372 | 0.66 | 0.18 | 65:35 | 3.71 | 0.33 | 97:3 | CAT-2200 | Pertuzumab |
| 13320-13370 | 1.6 | 1.11 | 82:18 | 2.43 | 0.35 | 92:8 | CAT-2200 | Pertuzumab |
| 13302-13367 | 0.69 | 0.01 | 66:34 | 4.3 | 0.94 | 98:2 | CAT-2200 | Pertuzumab |
| 13330-13495 | 1.8 | 0.22 | 86:14 | 2.65 | 0.21 | 93:7 | CAT-2200 | Pertuzumab |
| 13253-13498 | 1.6 | 0.57 | 82:18 | 1.2 | 0.06 | 77:23 | CAT-2200 | Pertuzumab |
| 13290-13497 | 1.58 | 0.34 | 83:17 | 1.36 | 0.06 | 80:20 | CAT-2200 | Pertuzumab |
| 13339-13500 | 1.01 | 0.73 | 72:28 | 2.77 | 0.05 | 94:6 | CAT-2200 | Pertuzumab |
| 13279-13501 | 0.79 | 0.12 | 69:31 | 3.24 | 0.61 | 96:4 | CAT-2200 | Pertuzumab |
| 13321-13499 | 1.84 | 0.5 | 85:15 | 2.37 | 0.38 | 91:9 | CAT-2200 | Pertuzumab |
| 13303-13496 | 0.83 | NA | 69:31 | 3 | NA | 95:5 | CAT-2200 | Pertuzumab |
| 12957-13061 | 1.73 | 0.84 | 84:16 | 0.4 | 0.26 | 59:41 | CAT-2200 | Pertuzumab |
| 12906-13152 | 0.54 | 0.45 | 63:37 | 1.89 | 0.22 | 87:13 | CAT-2200 | Pertuzumab |
| 13318-13437 | 0.06 | 0.18 | 51:49 | 3.31 | 1.11 | 96:4 | CAT-2200 | Pertuzumab |

TABLE 8B

LCCA results for K-K-derived K-L designs from the second K-K derived K-L design library that passed the performance cut-off criteria
LCCA results for K-K-derived K-L designs from the second K-K derived design library that passed the performance cut-off criteria

| Column 1 Unique identifier | Column 2 H1L1: H1L2 median scalar value | Column 3 H1L1: H1L2 range of scalar value | Column 4 H1L1: H1L2 normalized median ratio | Column 5 H2L2: H2L1 median scalar value | Column 6 H2L2: H2L1 range of scalar value | Column 7 H1L2: H2L1 normalized median ratio | Column 8 H1L1 Fab | Column 9 H2L2 Fab |
|---|---|---|---|---|---|---|---|---|
| 12938-13064 | 1.96 | 0.19 | 87:13 | 0.86 | NA | 70:30 | CAT-2200 | Pertuzumab |
| 13309-13425 | 0.98 | NA | 72:28 | −0.13 | 0.03 | 47:53 | CAT-2200 | Pertuzumab |
| 13314-13424 | 0.89 | 0.3 | 70:30 | 2.02 | 1.32 | 86:14 | CAT-2200 | Pertuzumab |
| 12938-13469 | 1.96 | 0.19 | 87:13 | 1.83 | 0.02 | 86:14 | CAT-2200 | Pertuzumab |
| 12944-13471 | 1.41 | 1.04 | 79:21 | 1.16 | NA | 76:24 | CAT-2200 | Pertuzumab |
| 13275-13470 | 1.51 | 1.16 | 80:20 | 1.94 | NA | 87:13 | CAT-2200 | Pertuzumab |
| 13276-13472 | 0.88 | 0.11 | 70:30 | 2.16 | 0.12 | 90:10 | CAT-2200 | Pertuzumab |
| 13308-13340 | 0.98 | 0.32 | 72:28 | 2.34 | 0.8 | 90:10 | CAT-2200 | Pertuzumab |
| 12961-13093 | 2 | NA | 88:12 | 1.39 | 0.27 | 80:20 | CAT-2200 | Pertuzumab |
| 12958-13079 | 1.29 | 1.13 | 77:23 | 1.87 | NA | 86:14 | CAT-2200 | Pertuzumab |
| 12938-13079 | 1.96 | 0.19 | 87:13 | 1.87 | NA | 86:14 | CAT-2200 | Pertuzumab |
| 13323-13444 | 1.31 | NA | 78:22 | 1.29 | NA | 78:22 | CAT-2200 | Pertuzumab |
| 13310-13444 | 1.37 | NA | 79:21 | 1.29 | NA | 78:22 | CAT-2200 | Pertuzumab |
| 13322-13443 | 1.1 | 0.72 | 74:26 | 1.35 | NA | 79:21 | CAT-2200 | Pertuzumab |
| 13316-13451 | 1.22 | 0.26 | 77:23 | 3.71 | 1.94 | 96:4 | CAT-2200 | Pertuzumab |
| 13314-13438 | 0.89 | 0.3 | 70:30 | 2.81 | NA | 94:6 | CAT-2200 | Pertuzumab |
| 12938-13106 | 1.96 | 0.19 | 87:13 | 3.06 | 0.1 | 95:5 | CAT-2200 | Pertuzumab |
| 12944-13108 | 1.41 | 1.04 | 79:21 | 1.82 | NA | 86:14 | CAT-2200 | Pertuzumab |
| 13275-13461 | 1.51 | 1.16 | 80:20 | 2.23 | 0.45 | 90:10 | CAT-2200 | Pertuzumab |
| 13276-13462 | 0.88 | 0.11 | 70:30 | 2.29 | NA | 90:10 | CAT-2200 | Pertuzumab |
| 13308-13341 | 0.98 | 0.32 | 72:28 | 2.04 | 0.71 | 88:12 | CAT-2200 | Pertuzumab |

TABLE 9A

Antigen binding and thermal stability assessment of the K-L designs that passed the LCCA performance cut-off criteria

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 Change in DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type |
|---|---|---|---|---|---|---|---|---|---|---|---|---|
| 10798-13036 | 0.34 | −0.22 | ND | ND | 74 | −3 | ND | ND | 69.7 | −1 | ND | ND |
| 11240-12878 | 0.34 | −0.22 | 7.9 | −0.0068 | 74 | −3 | 80.8 | −0.9 | 69.7 | −1 | 78.2 | 0.1 |
| 12906-13152 | 0.33 | −0.19 | 7 | 0.044 | 74 | −3 | 78.5 | −3.2 | ND | ND | ND | ND |
| 12944-13093 | 0.24 | −0.056 | 7 | 0.046 | 78 | 1 | 81.3 | −0.4 | #70.7 | 0 | 77.9 | −0.2 |
| 12957-13061 | 0.26 | −0.088 | 7.4 | 0.02 | 75.2 | −1.8 | 81.7 | 0 | 69.6 | −1.1 | ND | ND |
| 12958-13064 | 0.26 | −0.088 | 7.9 | −0.007 | 75.2 | −1.8 | 81.3 | −0.4 | 69.6 | −1.1 | 77.8 | −0.3 |
| 12958-13106 | 0.26 | −0.088 | 6.9 | 0.051 | 75.2 | −1.8 | 81 | −0.7 | 69.6 | −1.1 | 78.2 | 0.1 |
| 12958-13469 | 0.26 | −0.088 | 7.7 | 0.0027 | 75.2 | −1.8 | 80 | −1.7 | 69.6 | −1.1 | 77.2 | −0.9 |
| 12961-13108 | 0.26 | −0.088 | 7.4 | 0.02 | 75.2 | −1.8 | 81.5 | −0.2 | 69.6 | −1.1 | ND | ND |
| 12961-13471 | 0.26 | −0.088 | 8 | −0.012 | 75.2 | −1.8 | 81.3 | −0.4 | 69.6 | −1.1 | 77.9 | −0.2 |
| 13167-13514* | 0.19 | 0.037 | 8.3 | −0.029 | 74.5 | −2.5 | 80 | −1.7 | 70 | −0.7 | 77.2 | −0.9 |
| 13168-13397‡ | 0.19 | 0.037 | 7.8 | 4.80E−04 | 74.5 | −2.5 | 76.8 | −4.9 | 70 | −0.7 | ND | ND |
| 13169-13418* | 0.19 | 0.037 | 7.6 | 0.0089 | 74.5 | −2.5 | 78.3 | −3.4 | 70 | −0.7 | ND | ND |
| 13171-13416 | ND | ND | 7.6 | 0.0089 | ND | ND | 78.3 | −3.4 | ND | ND | ND | ND |
| 13173-13477* | 0.088 | 0.38 | ND | ND | 75.3 | −1.7 | ND | ND | ND | ND | ND | ND |
| 13173-13506‡ | 0.088 | 0.38 | 9.7 | −0.096 | 75.3 | −1.7 | 72.7 | −9 | ND | ND | ND | ND |
| 13175-13486‡ | 0.16 | 0.11 | 9.1 | −0.07 | 74.8 | −2.2 | 77.5 | −4.2 | 70 | −0.7 | 74.7 | −3.4 |
| 13176-13487* | 0.16 | 0.11 | ND | ND | 74.8 | −2.2 | ND | ND | 70 | −0.7 | ND | ND |
| 13177-13513‡ | 0.16 | 0.11 | 9.7 | −0.096 | 74.8 | −2.2 | 76.8 | −4.9 | 70 | −0.7 | 73.6 | −4.5 |
| 13178-13417* | 0.16 | 0.11 | 7.6 | 0.0089 | 74.8 | −2.2 | 78.3 | −3.4 | 70 | −0.7 | ND | ND |
| 13180-13515† | 0.028 | 0.88 | 7.5 | 0.015 | 73.3 | −3.7 | 75.5 | −6.2 | ND | ND | ND | ND |
| 13181-13389 | ND | ND | 7.6 | 0.0078 | ND | ND | 79.8 | −1.9 | ND | ND | 76.3 | −1.8 |
| 13182-13458‡ | 0.11 | 0.3 | 7.5 | 0.014 | 74 | −3 | 79.5 | −2.2 | 69.5 | −1.2 | 76.2 | −1.9 |
| 13184-13388* | 0.11 | 0.3 | 7.6 | 0.0078 | 74 | −3 | 79.8 | −1.9 | 69.5 | −1.2 | 76.3 | −1.8 |
| 13185-13374 | ND | ND | 9.2 | −0.07 | ND | ND | ND | ND | ND | ND | ND | ND |
| 13188-13421 | 0.22 | −0.028 | 7.4 | 0.024 | 77.5 | 0.5 | 77 | −4.7 | #70.7 | 0 | ND | ND |
| 13188-13430 | 0.22 | −0.028 | 8 | −0.011 | 77.5 | 0.5 | 78.8 | −2.9 | #70.7 | 0 | 76.1 | −2 |
| 13190-13422 | 0.22 | −0.028 | 7.7 | 0.005 | 77.5 | 0.5 | 78.5 | −3.2 | #70.7 | 0 | 75.8 | −2.3 |
| 13192-13426 | 0.22 | −0.028 | ND | ND | 77.5 | 0.5 | ND | ND | #70.7 | 0 | ND | ND |
| 13192-13452 | 0.22 | −0.028 | ND | ND | 77.5 | 0.5 | ND | ND | #70.7 | 0 | ND | ND |
| 13194-13427† | 0.22 | −0.028 | 7.6 | 0.012 | 77.5 | 0.5 | 79.3 | −2.4 | #70.7 | 0 | 76.5 | −1.6 |
| 13194-13456† | 0.22 | −0.028 | 7.5 | 0.014 | 77.5 | 0.5 | 79.5 | −2.2 | #70.7 | 0 | 76.2 | −1.9 |
| 13196-13351† | 0.22 | −0.028 | 7.1 | 0.043 | 77.5 | 0.5 | 80 | −1.7 | #70.7 | 0 | 76.8 | −1.3 |
| 13197-13353 | 0.22 | −0.028 | ND | ND | 77.5 | 0.5 | ND | ND | #70.7 | 0 | ND | ND |
| 13198-13389* | 0.13 | 0.2 | 7.6 | 0.0078 | 73.3 | −3.7 | 79.8 | −1.9 | 69.2 | −1.5 | 76.3 | −1.8 |
| 13199-13391 | ND | ND | 7.6 | 0.0078 | ND | ND | 79.8 | −1.9 | ND | ND | 76.3 | −1.8 |
| 13200-13421 | 0.21 | −0.0041 | 7.4 | 0.024 | 75 | −2 | 77 | −4.7 | ND | ND | ND | ND |
| 13200-13430 | 0.21 | −0.0041 | 8 | −0.011 | 75 | −2 | 78.8 | −2.9 | ND | ND | 76.1 | −2 |
| 13202-13426 | 0.21 | −0.0041 | ND | ND | 75 | −2 | ND | ND | ND | ND | ND | ND |
| 13202-13452 | 0.21 | −0.0041 | ND | ND | 75 | −2 | ND | ND | ND | ND | ND | ND |
| 13203-13427† | 0.21 | −0.0041 | 7.6 | 0.012 | 75 | −2 | 79.3 | −2.4 | ND | ND | 76.5 | −1.6 |
| 13203-13456† | 0.21 | −0.0041 | 7.5 | 0.014 | 75 | −2 | 79.5 | −2.2 | ND | ND | 76.2 | −1.9 |
| 13204-13351† | 0.21 | −0.0041 | 7.1 | 0.043 | 75 | −2 | 80 | −1.7 | ND | ND | 76.8 | −1.3 |
| 13205-13353 | 0.21 | −0.0041 | ND | ND | 75 | −2 | ND | ND | ND | ND | ND | ND |
| 13206-13454† | ND | ND | 7.5 | 0.014 | ND | ND | 79.5 | −2.2 | ND | ND | 76.2 | −1.9 |
| 13207-13363 | ND | ND | 7.9 | −0.0084 | ND | ND | 79 | −2.7 | ND | ND | 76.1 | −2 |
| 13208-13455‡ | 0.19 | 0.046 | 7.5 | 0.014 | 72.7 | −4.3 | 79.5 | −2.2 | 68.8 | −1.9 | 76.2 | −1.9 |
| 13209-13364* | 0.19 | 0.046 | 7.9 | −0.0084 | 72.7 | −4.3 | 79 | −2.7 | 68.8 | −1.9 | 76.1 | −2 |
| 13210-13510* | 0.18 | 0.067 | 7.5 | 0.015 | 74.2 | −2.8 | 80.5 | −1.2 | 69.8 | −0.9 | 77 | −1.1 |
| 13211-13395* | 0.18 | 0.067 | ND | ND | 74.2 | −2.8 | ND | ND | 69.8 | −0.9 | ND | ND |
| 13212-13396* | 0.18 | 0.067 | 8.1 | −0.017 | 74.2 | −2.8 | 78 | −3.7 | 69.8 | −0.9 | 75.3 | −2.8 |
| 13212-13415* | 0.18 | 0.067 | 8.8 | −0.053 | 74.2 | −2.8 | 78.3 | −3.4 | 69.8 | −0.9 | 74.6 | −3.5 |
| 13214-13405* | 0.17 | 0.095 | 8.1 | −0.018 | 74 | −3 | 78 | −3.7 | ND | ND | ND | ND |
| 13214-13410* | 0.17 | 0.095 | 8.4 | −0.034 | 74 | −3 | 77.5 | −4.2 | ND | ND | ND | ND |
| 13216-13476* | 0.078 | 0.43 | 7.6 | 0.01 | 73.7 | −3.3 | 74.5 | −7.2 | 69.9 | −0.8 | 71.2 | −6.9 |
| 13216-13505* | 0.078 | 0.43 | 9.6 | −0.093 | 73.7 | −3.3 | 75 | −6.7 | 69.9 | −0.8 | ND | ND |
| 13218-13482* | 0.19 | 0.044 | 7.6 | 0.01 | 74.5 | −2.5 | 77.8 | −3.9 | 70.3 | −0.4 | 75.2 | −2.9 |
| 13219-13483* | 0.19 | 0.044 | ND | ND | 74.5 | −2.5 | ND | ND | 70.3 | −0.4 | ND | ND |
| 13220-13511* | 0.19 | 0.044 | 7 | 0.044 | 74.5 | −2.5 | 76.7 | −5 | 70.3 | −0.4 | ND | ND |
| 13221-13406* | 0.19 | 0.044 | 8.1 | −0.018 | 74.5 | −2.5 | 78 | −3.7 | 70.3 | −0.4 | ND | ND |
| 13221-13411* | 0.19 | 0.044 | 8.4 | −0.034 | 74.5 | −2.5 | 77.5 | −4.2 | 70.3 | −0.4 | ND | ND |
| 13223-13512 | 0.12 | 0.25 | 7.3 | 0.028 | 73 | −4 | 76.8 | −4.9 | ND | ND | ND | ND |
| 13224-13428 | ND | ND | 8 | −0.011 | ND | ND | 78.8 | −2.9 | ND | ND | 76.1 | −2 |
| 13225-13384 | ND | ND | 7.4 | 0.02 | ND | ND | 77.5 | −4.2 | ND | ND | 75.3 | −2.8 |
| 13226-13434* | 0.15 | 0.15 | 8 | −0.011 | 73.5 | −3.5 | 79 | −2.7 | 69.5 | −1.2 | 76.1 | −2 |
| 13227-13383* | 0.15 | 0.15 | 7.4 | 0.02 | 73.5 | −3.5 | 77.5 | −4.2 | 69.5 | −1.2 | 75.3 | −2.8 |
| 13229-13428 | 0.13 | 0.2 | 8 | −0.011 | 72.3 | −4.7 | 78.8 | −2.9 | ND | ND | 76.1 | −2 |

TABLE 9A-continued

Antigen binding and thermal stability assessment of the K-L designs that passed the LCCA performance cut-off criteria

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 Change in DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type |
|---|---|---|---|---|---|---|---|---|---|---|---|---|
| 13230-13384 | 0.13 | 0.2 | 7.4 | 0.02 | 72.3 | −4.7 | 77.5 | −4.2 | ND | ND | 75.3 | −2.8 |
| 13231-13386* | 0.12 | 0.24 | 7.4 | 0.02 | 72 | −5 | 77.5 | −4.2 | 68.2 | −2.5 | 75.3 | −2.8 |
| 13234-13432* | 0.16 | 0.1 | 8 | −0.011 | 73 | −4 | 79 | −2.7 | ND | ND | 76.1 | −2 |
| 13235-13357‡ | 0.16 | 0.1 | 7.3 | 0.029 | 73 | −4 | 78.5 | −3.2 | ND | ND | 75.1 | −3 |
| 13236-13433* | 0.13 | 0.19 | 8 | −0.011 | 72.5 | −4.5 | 79 | −2.7 | 69.1 | −1.6 | 76.1 | −2 |
| 13237-13358‡ | 0.13 | 0.19 | 7.3 | 0.029 | 72.5 | −4.5 | 78.5 | −3.2 | 69.1 | −1.6 | 75.1 | −3 |
| 13238-13459 | 0.36 | −0.24 | ND | ND | 77 | 0 | ND | ND | #70.1 | −0.6 | ND | ND |
| 13238-13463† | 0.36 | −0.24 | 7.8 | −8.10E−05 | 77 | 0 | 78.8 | −2.9 | #70.1 | −0.6 | ND | ND |
| 13242-13465 | 0.36 | −0.24 | ND | ND | 77 | 0 | ND | ND | #70.1 | −0.6 | ND | ND |
| 13242-13475 | 0.36 | −0.24 | ND | ND | 77 | 0 | ND | ND | #70.1 | −0.6 | ND | ND |
| 13246-13459 | 0.32 | −0.19 | ND | ND | 75.5 | −1.5 | ND | ND | ND | ND | ND | ND |
| 13246-13463† | 0.32 | −0.19 | 7.8 | −8.10E−05 | 75.5 | −1.5 | 78.8 | −2.9 | ND | ND | ND | ND |
| 13248-13465 | 0.32 | −0.19 | ND | ND | 75.5 | −1.5 | ND | ND | ND | ND | ND | ND |
| 13248-13475 | 0.32 | −0.19 | ND | ND | 75.5 | −1.5 | ND | ND | ND | ND | ND | ND |
| 13250-13355 | 0.32 | −0.19 | ND | ND | 75.5 | −1.5 | ND | ND | ND | ND | ND | ND |
| 13252-13369 | 0.34 | −0.22 | 6.7 | 0.065 | 74 | −3 | 81 | −0.7 | 69.7 | −1 | 77.4 | −0.7 |
| 13253-13498 | 0.34 | −0.22 | 7.5 | 0.016 | 74 | −3 | 79.5 | −2.2 | 69.7 | −1 | 76.3 | −1.8 |
| 13254-13508 | 0.34 | −0.22 | 8.2 | −0.022 | 74 | −3 | 74.5 | −7.2 | 69.7 | −1 | ND | ND |
| 13255-13509 | 0.34 | −0.22 | ND | ND | 74 | −3 | ND | ND | 69.7 | −1 | ND | ND |
| 13256-13502 | 0.34 | −0.22 | ND | ND | 74 | −3 | ND | ND | 69.7 | −1 | ND | ND |
| 13257-13503 | 0.34 | −0.22 | 8.4 | −0.035 | 74 | −3 | 81.3 | −0.4 | 69.7 | −1 | 78.4 | 0.3 |
| 13258-13504 | 0.34 | −0.22 | 7.2 | 0.032 | 74 | −3 | 82 | 0.3 | 69.7 | −1 | ND | ND |
| 13259-13491 | 0.34 | −0.22 | 7.9 | −0.0078 | 74 | −3 | 77.3 | −4.4 | 69.7 | −1 | ND | ND |
| 13261-13480 | 0.34 | −0.22 | ND | ND | 74 | −3 | ND | ND | 69.7 | −1 | ND | ND |
| 13262-13481 | 0.34 | −0.22 | 7.2 | 0.034 | 74 | −3 | 75.7 | −6 | 69.7 | −1 | 73.2 | −4.9 |
| 13263-13493 | 0.34 | −0.22 | 8.1 | −0.015 | 74 | −3 | 79.7 | −2 | 69.7 | −1 | 76.2 | −1.9 |
| 13264-13400 | 0.34 | −0.22 | 8.2 | −0.024 | 74 | −3 | 79.3 | −2.4 | 69.7 | −1 | ND | ND |
| 13265-13392 | 0.34 | −0.22 | ND | ND | 74 | −3 | ND | ND | 69.7 | −1 | ND | ND |
| 13265-13419 | 0.34 | −0.22 | 7.6 | 0.011 | 74 | −3 | 76.5 | −5.2 | 69.7 | −1 | 75.3 | −2.8 |
| 13268-13401 | 0.34 | −0.22 | ND | ND | 74 | −3 | ND | ND | 69.7 | −1 | ND | ND |
| 13269-13403 | 0.34 | −0.22 | 7.8 | 0.0016 | 74 | −3 | 79.8 | −1.9 | 69.7 | −1 | 76.1 | −2 |
| 13271-13439 | ND | ND | 7.6 | 0.012 | ND | ND | 80.8 | −0.9 | ND | ND | 77.4 | −0.7 |
| 13272-13379 | ND | ND | 8.1 | −0.016 | ND | ND | 80 | −1.7 | ND | ND | 76.5 | −1.6 |
| 13273-13441 | 0.099 | 0.32 | 7.6 | 0.012 | 74.5 | −2.5 | 80.8 | −0.9 | 70.6 | −0.1 | 77.4 | −0.7 |
| 13274-13381 | 0.099 | 0.32 | 8.1 | −0.016 | 74.5 | −2.5 | 80 | −1.7 | 70.6 | −0.1 | 76.5 | −1.6 |
| 13277-13420* | 0.17 | 0.085 | 7.3 | 0.028 | 73 | −4 | 78.2 | −3.5 | ND | ND | ND | ND |
| 13278-13372 | 0.35 | −0.22 | 5.9 | 0.12 | 74.2 | −2.8 | 80.5 | −1.2 | ND | ND | ND | ND |
| 13279-13501 | 0.35 | −0.22 | 7.5 | 0.015 | 74.2 | −2.8 | 79.3 | −2.4 | ND | ND | ND | ND |
| 13280-13488 | 0.35 | −0.22 | ND | ND | 74.2 | −2.8 | ND | ND | ND | ND | ND | ND |
| 13281-13489 | 0.35 | −0.22 | 7.9 | −0.0078 | 74.2 | −2.8 | 77.3 | −4.4 | ND | ND | ND | ND |
| 13282-13484 | 0.35 | −0.22 | 7.9 | −0.0045 | 74.2 | −2.8 | 77.3 | −4.4 | ND | ND | 74.6 | −3.5 |
| 13283-13478* | 0.098 | 0.33 | ND | ND | 73.5 | −3.5 | ND | ND | ND | ND | ND | ND |
| 13283-13507* | 0.098 | 0.33 | 7.3 | 0.026 | 73.5 | −3.5 | 75.3 | −6.4 | ND | ND | ND | ND |
| 13285-13414† | 0.16 | 0.12 | 7.2 | 0.035 | 75.5 | −1.5 | 77.8 | −3.9 | 69.7 | −1 | 74.5 | −3.6 |
| 13287-13494 | 0.15 | 0.15 | 7.6 | 0.012 | 76.3 | −0.7 | 78.5 | −3.2 | #69.6 | −1.1 | 75.4 | −2.7 |
| 13288-13516† | 0.16 | 0.11 | 7.3 | 0.026 | 73.7 | −3.3 | 77.8 | −3.9 | 69 | −1.7 | 74.6 | −3.5 |
| 13289-13368 | 0.29 | −0.14 | 6.7 | 0.065 | 73 | −4 | 81 | −0.7 | 69.1 | −1.6 | 77.4 | −0.7 |
| 13290-13497 | 0.29 | −0.14 | 7.5 | 0.016 | 73 | −4 | 79.5 | −2.2 | 69.1 | −1.6 | 76.3 | −1.8 |
| 13291-13488 | 0.29 | −0.14 | ND | ND | 73 | −4 | ND | ND | 69.1 | −1.6 | ND | ND |
| 13292-13489 | 0.29 | −0.14 | 7.9 | −0.0078 | 73 | −4 | 77.3 | −4.4 | 69.1 | −1.6 | ND | ND |
| 13294-13492 | 0.29 | −0.14 | 8.1 | −0.015 | 73 | −4 | 79.7 | −2 | 69.1 | −1.6 | 76.2 | −1.9 |
| 13295-13484 | 0.29 | −0.14 | 7.9 | −0.0045 | 73 | −4 | 77.3 | −4.4 | 69.1 | −1.6 | 74.6 | −3.5 |
| 13296-13399 | 0.29 | −0.14 | 8.2 | −0.024 | 73 | −4 | 79.3 | −2.4 | 69.1 | −1.6 | ND | ND |
| 13297-13402 | 0.29 | −0.14 | 7.8 | 0.0016 | 73 | −4 | 79.8 | −1.9 | 69.1 | −1.6 | 76.1 | −2 |
| 13298-13439 | 0.12 | 0.26 | 7.6 | 0.012 | 72.2 | −4.8 | 80.8 | −0.9 | ND | ND | 77.4 | −0.7 |
| 13299-13379 | 0.12 | 0.26 | 8.1 | −0.016 | 72.2 | −4.8 | 80 | −1.7 | ND | ND | 76.5 | −1.6 |
| 13300-13441 | 0.11 | 0.29 | 7.6 | 0.012 | 72.8 | −4.2 | 80.8 | −0.9 | ND | ND | 77.4 | −0.7 |
| 13301-13381 | 0.11 | 0.29 | 8.1 | −0.016 | 72.8 | −4.2 | 80 | −1.7 | ND | ND | 76.5 | −1.6 |
| 13302-13367 | 0.26 | −0.09 | 5.8 | 0.13 | 73.8 | −3.2 | 80.7 | −1 | 69.5 | −1.2 | 77.3 | −0.8 |
| 13303-13496 | 0.26 | −0.09 | 7.9 | −0.0084 | 73.8 | −3.2 | 79.5 | −2.2 | 69.5 | −1.2 | ND | ND |
| 13304-13466‡ | 0.15 | 0.14 | 8.2 | −0.024 | 72.5 | −4.5 | 79.7 | −2 | 68.3 | −2.4 | 76.5 | −1.6 |
| 13305-13448* | 0.097 | 0.33 | 7 | 0.046 | ND | ND | 81.3 | −0.4 | ND | ND | 77.9 | −0.2 |
| 13306-13373* | 0.097 | 0.33 | ND | ND | ND | ND | ND | ND | ND | ND | ND | ND |
| 13306-13375‡ | 0.097 | 0.33 | 8 | −0.012 | ND | ND | 64.7 | −17 | ND | ND | ND | ND |
| 13309-13443 | 0.24 | −0.056 | ND | ND | 78 | 1 | ND | ND | #70.7 | 0 | ND | ND |
| 13317-13423 | 0.12 | 0.23 | 7.9 | −0.007 | 73.3 | −3.7 | 81.3 | −0.4 | ND | ND | 77.8 | −0.3 |
| 13318-13437* | 0.1 | 0.3 | 7.2 | 0.035 | 72.5 | −4.5 | 81.2 | −0.5 | ND | ND | ND | ND |

TABLE 9A-continued

Antigen binding and thermal stability assessment of the K-L designs that passed the LCCA performance cut-off criteria

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 Change in DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type |
|---|---|---|---|---|---|---|---|---|---|---|---|---|
| 13319-13473* | 0.18 | 0.072 | 8.1 | −0.02 | 73.5 | −3.5 | 80.7 | −1 | 69.5 | −1.2 | 78.3 | 0.2 |
| 13320-13370 | 0.26 | −0.088 | 6 | 0.11 | 75.2 | −1.8 | 80.5 | −1.2 | 69.6 | −1.1 | 76.9 | −1.2 |
| 13321-13499 | 0.26 | −0.088 | 7.4 | 0.023 | 75.2 | −1.8 | 79 | −2.7 | 69.6 | −1.1 | 76 | −2.1 |
| 13322-13425 | 0.26 | −0.088 | ND | ND | 75.2 | −1.8 | ND | ND | 69.6 | −1.1 | ND | ND |
| 13327-13446 | ND | ND | 7 | 0.046 | ND | ND | 81.3 | −0.4 | ND | ND | 77.9 | −0.2 |
| 13328-13359 | ND | ND | 7.5 | 0.019 | ND | ND | 80.2 | −1.5 | ND | ND | 77.3 | −0.8 |
| 13329-13366* | 0.23 | −0.049 | 5.8 | 0.13 | 72.3 | −4.7 | 80.7 | −1 | ND | ND | 77.3 | −0.8 |
| 13330-13495* | 0.23 | −0.049 | 7.9 | −0.0084 | 72.3 | −4.7 | 79.5 | −2.2 | ND | ND | ND | ND |
| 13331-13447* | 0.23 | −0.049 | 7 | 0.046 | 72.3 | −4.7 | 81.3 | −0.4 | ND | ND | 77.9 | −0.2 |
| 13332-13360* | 0.23 | −0.049 | 7.5 | 0.019 | 72.3 | −4.7 | 80.2 | −1.5 | ND | ND | 77.3 | −0.8 |
| 13333-13387* | 0.23 | −0.049 | 8.1 | −0.018 | 72.3 | −4.7 | 80.8 | −0.9 | ND | ND | 77.5 | −0.6 |
| 13334-13449* | 0.14 | 0.16 | 7 | 0.046 | 73.5 | −3.5 | 81.3 | −0.4 | 69.7 | −1 | 77.9 | −0.2 |
| 13335-13361* | 0.14 | 0.16 | 7.5 | 0.019 | 73.5 | −3.5 | 80.2 | −1.5 | 69.7 | −1 | 77.3 | −0.8 |
| 13336-13450* | 0.12 | 0.26 | 7 | 0.046 | 72.7 | −4.3 | 81.3 | −0.4 | ND | ND | 77.9 | −0.2 |
| 13337-13362* | 0.12 | 0.26 | 7.5 | 0.019 | 72.7 | −4.3 | 80.2 | −1.5 | ND | ND | 77.3 | −0.8 |
| 13338-13371 | 0.36 | −0.24 | 5.9 | 0.12 | 72.7 | −4.3 | 81.5 | −0.2 | 68.8 | −1.9 | ND | ND |
| 13339-13500 | 0.36 | −0.24 | 7.4 | 0.023 | 72.7 | −4.3 | 80 | −1.7 | 68.8 | −1.9 | ND | ND |

H1L1 Fab is CAT-2200 and the H2L2 Fab is Pertuzumab.

A number of heterodimers had precipitate associated with them, noted with "*" in Tables 9A and 9B if the precipitate was associated with the H1L1 Fab; noted with "†" in Tables 9A and 9B is the precipitate was associated with H2L2 Fab;

and noted with "‡" in Tables 9A and 913 if the precipitate was associated with both the H1L1 and H2L2 Fabs.

#-denotes the presence of a shoulder to the main Fab peak (transition) in DSC thermogram

TABLE 9B

Antigen binding and thermal stablity assessment of the K-K derived K-L designs that passed the LCCA performance cut-off criteria

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type |
|---|---|---|---|---|---|---|---|---|---|---|---|---|
| 12938-13064 | 0.24 | −0.056 | 7.9 | −0.007 | 78 | 1 | 81.3 | −0.4 | #70.7 | 0 | 77.8 | −0.3 |
| 12938-13079 | 0.24 | −0.056 | 7.2 | 0.035 | 78 | 1 | 81.2 | −0.5 | #70.7 | 0 | ND | ND |
| 12938-13106 | 0.24 | −0.056 | 6.9 | 0.051 | 78 | 1 | 81 | −0.7 | #70.7 | 0 | 78.2 | 0.1 |
| 12938-13469 | 0.24 | −0.056 | 7.7 | 0.0027 | 78 | 1 | 80 | −1.7 | #70.7 | 0 | 77.2 | −0.9 |
| 12944-13108 | 0.24 | −0.056 | 7.4 | 0.02 | 78 | 1 | 81.5 | −0.2 | #70.7 | 0 | ND | ND |
| 12944-13471 | 0.24 | −0.056 | 8 | −0.012 | 78 | 1 | 81.3 | −0.4 | #70.7 | 0 | 77.9 | −0.2 |
| 12958-13079 | 0.26 | −0.088 | 7.2 | 0.035 | 75.2 | −1.8 | 81.2 | −0.5 | 69.6 | −1.1 | ND | ND |
| 12961-13093 | 0.26 | −0.088 | 7 | 0.046 | 75.2 | −1.8 | 81.3 | −0.4 | 69.6 | −1.1 | 77.9 | −0.2 |
| 13275-13461* | 0.094 | 0.35 | 6.9 | 0.051 | 75 | −2 | 81 | −0.7 | 70.4 | −0.3 | 78.2 | 0.1 |
| 13275-13470* | 0.094 | 0.35 | 7.7 | 0.0027 | 75 | −2 | 80 | −1.7 | 70.4 | −0.3 | 77.2 | −0.9 |

TABLE 9B-continued

Antigen binding and thermal stablity assessment of the K-K derived K-L designs that passed the LCCA performance cut-off criteria

| Column 1 Unique identifier | Column 2 KD of H1L1 Fab (nM) | Column 3 Change in KD of H1L1 Fab vs wild type | Column 4 KD of H2L2 Fab (nM) | Column 5 Change in KD of H2L2 Fab vs wild type | Column 6 DSF values of H1L1 Fab (° C.) | Column 7 Change in DSF values of H1L1 Fab vs wild type | Column 8 DSF values of H2L2 Fab (° C.) | Column 9 Change in DSF values of H2L2 Fab vs wild type | Column 10 DSC values of H1L1 Fab (° C.) | Column 11 Change in DSC values of H1L1 Fab vs wild type | Column 12 DSC values of H2L2 Fab (° C.) | Column 13 Change in DSC values of H2L2 Fab vs wild type |
|---|---|---|---|---|---|---|---|---|---|---|---|---|
| 13276-13462* | 0.094 | 0.35 | 7.4 | 0.02 | 75 | −2 | 81.5 | −0.2 | 70.4 | −0.3 | ND | ND |
| 13276-13472* | 0.094 | 0.35 | 8 | −0.012 | 75 | −2 | 81.3 | −0.4 | 70.4 | −0.3 | 77.9 | −0.2 |
| 13308-13340 | 0.24 | −0.056 | 8 | −0.013 | 78 | 1 | 79 | −2.7 | #70.7 | 0 | 75.9 | −2.2 |
| 13308-13341 | 0.24 | −0.056 | 7.8 | −6.40E−04 | 78 | 1 | 78.8 | −2.9 | #70.7 | 0 | 76.1 | -2 |
| 13309-13425 | 0.24 | −0.056 | ND | ND | 78 | 1 | ND | ND | #70.7 | 0 | ND | ND |
| 13310-13444 | 0.24 | −0.056 | 8.1 | −0.015 | 78 | 1 | 80.2 | −1.5 | #70.7 | 0 | ND | ND |
| 13314-13424 | 0.18 | 0.075 | 7.9 | −0.007 | 75.7 | −1.3 | 81.3 | −0.4 | 70.8 | 0.1 | 77.8 | −0.3 |
| 13314-13438 | 0.18 | 0.075 | 7.2 | 0.035 | 75.7 | −1.3 | 81.2 | −0.5 | 70.8 | 0.1 | ND | ND |
| 13316-13451 | 0.18 | 0.075 | 7 | 0.046 | 75.7 | −1.3 | 81.3 | −0.4 | 70.8 | 0.1 | 77.9 | −0.2 |
| 13322-13443 | 0.26 | −0.088 | ND | ND | 75.2 | −1.8 | ND | ND | 69.6 | −1.1 | ND | ND |
| 13323-13444 | 0.26 | −0.088 | 8.1 | −0.015 | 75.2 | −1.8 | 80.2 | −1.5 | 69.6 | −1.1 | ND | ND |

H1L1 Fab is CAT-2200 and the H2L2 Fab is Pertuzumab.
A number of heterodimers had precipitate associated with them, noted with
*in Tables 9A and 9B if the precipitate was associated with the H1L1 Fab; noted with
"†" in Tables 9A and 9B is the precipitate was associated with H2L1 Fab: and noted with
"‡" in Tables 9A and 9B if the precipitate was associated with both the H1L1 and H2L2 Fabs.
#denotes the presence of a shoulder to the main Fab peak (transition) in DSC thermogram

TABLE 10-A1

Cluster 1 K-L designs

| Unique identifier | H1 mutation (Kabat) | L1 mutation (Kabat) |
|---|---|---|
| 13173-13477 | A125R_L143D_K145T | S122D_E124Q_T131K_V133S |
| 13173-13506 | A125R_L143D_K145T | S122D_E124Q_T131K_V133S |
| 13180-13515 | A125R_L143E_K145T_Q179E | S122D_E124Q_T131R |
| 13177-13513 | A125R_L143D_K145T | S122D_E124Q_T131R |
| 13178-13417 | A125R_L143D_K145T | S122D_E124Q_T131R |
| 13171-13416 | A125R_L143D_K145T | S122D_E124Q_T131K |
| 13176-13487 | A125R_L143D_K145T | S122D_E124Q_T131R |
| 13175-13486 | A125R_L143D_K145T | S122D_E124Q_T131R |

| Unique identifier | H2 mutation (Kabat) | L2 mutation (Kabat) |
|---|---|---|
| 13173-13477 | L143I_S186K_K228D | S121K_Q124E_V133D |
| 13173-13506 | S186K_K228D | S121K_Q124E_V133D |
| 13180-13515 | S188K_K228D | S121K_V133I_S176D_T178E |
| 13177-13513 | S188K_K228D | S121K_S131D_V133G_T178F |
| 13178-13417 | L124R_S186R_K228D | S121K_V133G_S176D_T180E |
| 13171-13416 | L124R_S186R_K228D | S121K_V133G_S176D_T180E |
| 13176-13487 | L143R_K228D | S121K_Q124E_V133D_T180D |
| 13175-13486 | L143R_K228D | S121K_Q124E_V133D |

TABLE 10-A2

| Cluster 2 K-L designs | | | | |
|---|---|---|---|---|
| Unique identifier | H1 mutation (Kabat) | L1 mutation (Kabat) | H2 mutation (Kabat) | L2 mutation (Kabat) |
| 12906-13152 | L143D_K145T | E124Q_T131K_V133S | S186K | Q124E_V133D |
| 10970-11348 | L143D_K145T_Q179E | E124Q_T131K | S186K | V133D_Q160E |
| 10969-11344 | L143D_K145T_Q179E | E124Q_T131K | S186K | V133D |
| 10969-11290 | L143D_K145T_Q179E | E124Q_T131K | L143I_S186K | V133D |
| 10966-11351 | L143D_K145T | T131K_V133S | S186K | V133D_Q160E |
| 10966-11297 | L143D_K145T | T131K_V133S | L143I_S186K | V133D_Q160E |
| 10965-11347 | L143D_K145T | T131K_V133S | S186K | V133D |
| 10965-11293 | L143D_K145T | T131K_V133S | L143I_S186K | V133D |
| 10962-11350 | L143D_K145T | T131K | S186K | V133D_Q160E |
| 10962-11296 | L143D_K145T | T131K | L143I_S186K | V133D_Q160E |
| 10946-11382 | L143D_K145T | E124Q_T131R | S188K | S131E_V133G_T178F |
| 10945-11377 | L143D_K145T | E124Q_T131R | S188K | S131D_V133G_T178F |
| 10944-11314 | L143D_K145T | E124Q_T131R | L143R | Q124E_V133D |
| 10944-11307 | L143D_K145T | E124Q_T131R | L143K | Q124E_V133D |
| 10943-11349 | L143D_K145T | E124Q_T131K_V133S | S186K | V133D_Q160E |
| 10943-11295 | L143D_K145T | E124Q_T131K_V133S | L143I_S186K | V133D_Q160E |
| 10942-11345 | L143D_K145T | E124Q_T131K_V133S | S186K | V133D |
| 10942-11291 | L143D_K145T | E124Q_T131K_V133S | L143I_S186K | V133D |
| 10928-11348 | L143D_K145T | E124Q_T131K | S186K | V133D_Q160E |
| 10928-11294 | L143D_K145T | E124Q_T131K | L143I_S186K | V133D_Q160E |
| 10927-11344 | L143D_K145T | E124Q_T131K | S186K | V133D |
| 10927-11290 | L143D_K145T | E124Q_T131K | L143I_S186K | V133D |
| 10924-11376 | L143D_K145T | E124Q_T131K | S188K | S131D_V133G_T178F |
| 10970-11294 | L143D_K145T_Q179E | E124Q_T131K | L143I_S186K | V133D_Q160E |
| 10973-11291 | L143D_K145T_Q179E | E124Q_T131K_V133S | L143I_S186K | V133D |
| 13279-13501 | L143D_K145T | E124Q_T131R | Q39E_L143R | Q38R_Q124E_V133D |
| 10973-11345 | L143D_K145T_Q179E | E124Q_T131K_V133S | S186K | V133D |
| 13278-13372 | L143D_K145T | E124Q_T131R | L45P_L143R | P44F_Q124E_V133D |
| 13216-13476 | A139W_L143D_K145T | E124Q_T131K_V133S | L143I_S186K | Q124E_V133D_L135W |
| 13283-13478 | L143D_K145T_F174G | E124Q_T131K_V133S_S176F | L143I_S186K_V190F | Q124E_V133D_L135A |
| 13216-13505 | A139W_L143D_K145T | E124Q_T131K_V133S | S186K | Q124E_V133D_L135W |
| 13283-13507 | L143D_K145T_F174G | E124Q_T131K_V133S_S176F | S186K_V190F | Q124E_V133D_L135A |
| 13220-13511 | A139W_L143D_K145T | E124Q_T131R | S188K | S131D_V133G_L135W_T178F |
| 13285-13414 | L143D_K145T_F174G | T116F_E124Q_T131K_S176F | L124R_S186K_V190F | V133G_L135A_S176D_T180E |
| 13287-13494 | L143D_K145T_F174G | T116F_E124Q_T131R_S176F | L143R_V190F | Q124E_V133D_L135A |
| 13219-13483 | A139W_L143D_K145T | E124Q_T131R | L143R | Q124E_V133D_L135W_T180D |
| 13218-13482 | A139W_L143D_K145T | E124Q_T131R | L143R | Q124E_V133D_L135W |
| 13282-13484 | L143D_K145T | E124Q_T131R | L143R | Q124E_V133D_T180D |
| 10982-11351 | L143D_K145T_Q179E | T131K_V133S | S186K | V133D_Q160E |
| 10982-11297 | L143D_K145T_Q179E | T131K_V133S | L143I_S186K | V133D_Q160E |
| 10981-11347 | L143D_K145T_Q179E | T131K_V133S | S186K | V133D |
| 10981-11293 | L143D_K145T_Q179E | T131K_V133S | L143I_S186K | V133D |
| 10978-11350 | L143D_K145T_Q179E | T131K | S186K | V133D_Q160E |
| 10978-11296 | L143D_K145T_Q179E | T131K | L143I_S186K | V133D_Q160E |
| 10977-11346 | L143D_K145T_Q179E | T131K | S186K | V133D |
| 10977-11292 | L143D_K145T_Q179E | T131K | L143I_S186K | V133D |
| 10974-11349 | L143D_K145T_Q179E | E124Q_T131K_V133S | S186K | V133D_Q160E |
| 10974-11295 | L143D_K145T_Q179E | E124Q_T131K_V133S | L143I_S186K | V133D_Q160E |
| 10923-11306 | L143D_K145T | E124Q_T131K | L143K | Q124E_V133D |

TABLE 10-A3

| Cluster 3 K-L designs | | |
|---|---|---|
| Unique identifier | H1 mutation (Kabat) | L1 mutation (Kabat) |
| 13290-13497 | L143E_K145T_Q179E | E124Q_T131R |
| 10992-11410 | L143E_K145T_Q179E | E124Q_T131K |
| 10989-11259 | L143E_K145T_Q179E | E124Q_T131K |
| 10987-11261 | L143E_K145T_Q179E | E124Q_T131K |
| 10987-11257 | L143E_K145T_Q179E | E124Q_T131K |
| 10987-11249 | L143E_K145T_Q179E | E124Q_T131K |
| 10986-11391 | L143E_K145T_Q179E | E124Q_T131K |
| 10985-11381 | L143E_K145T_Q179E | E124Q_T131K |
| 10984-11376 | L143E_K145T_Q179E | E124Q_T131K |
| 10983-11306 | L143E_K145T_Q179E | E124Q_T131K |
| 10953-11411 | L143D_K145T | E124Q_T131R |
| 10952-11398 | L143D_K145T | E124Q_T131R |
| 10950-11264 | L143D_K145T | E124Q_T131R |
| 10950-11260 | L143D_K145T | E124Q_T131R |
| 10950-11252 | L143D_K145T | E124Q_T131R |
| 10948-11262 | L143D_K145T | E124Q_T131R |
| 10948-11258 | L143D_K145T | E124Q_T131R |

TABLE 10-A3-continued

| Cluster 3 K-L designs | | |
|---|---|---|
| 10948-11250 | L143D_K145T | E124Q_T131R |
| 10947-11392 | L143D_K145T | E124Q_T131R |
| 10934-11410 | L143D_K145T | E124Q_T131K |
| 10931-11263 | L143D_K145T | E124Q_T131K |
| 10931-11259 | L143D_K145T | E124Q_T131K |
| 10931-11251 | L143D_K145T | E124Q_T131K |
| 10929-11261 | L143D_K145T | E124Q_T131K |
| 10929-11257 | L143D_K145T | E124Q_T131K |
| 10929-11249 | L143D_K145T | E124Q_T131K |
| 10926-11391 | L143D_K145T | E124Q_T131K |
| 10989-11263 | L143E_K145T_Q179E | E124Q_T131K |
| 10998-11307 | L143E_K145T_Q179E | E124Q_T131R |
| 13289-13368 | L143E_K145T_Q179E | E124Q_T131R |
| 10998-11314 | L143E_K145T_Q179E | E124Q_T131R |
| 13223-13512 | A139W_L143E_K145T_Q179E | E124Q_T131R |
| 13288-13516 | L143E_K145T_F174G_Q179E | T116F_E124Q_T131R_S176F |
| 13221-13411 | A139W_L143D_K145T | E124Q_T131R |
| 13214-13410 | A139W_L143D_K145T | E124Q_T131K |
| 13221-13406 | A139W_L143D_K145T | E124Q_T131R |
| 13214-13405 | A139W_L143D_K145T | E124Q_T131K |
| 13291-13488 | L143E_K145T_Q179E | E124Q_T131R |
| 13281-13489 | L143D_K145T | E124Q_T131R |
| 13280-13488 | L143D_K145T | E124Q_T131R |
| 13295-13484 | L143E_K145T_Q179E | E124Q_T131R |
| 13292-13489 | L143E_K145T_Q179E | E124Q_T131R |
| 13294-13492 | L143E_K145T_Q179E | E124Q_T131R |
| 13297-13402 | L143E_K145T_Q179E | E124Q_T131R |
| 13296-13399 | L143E_K145T_Q179E | E124Q_T131R |
| 11007-11411 | L143E_K145T_Q179E | E124Q_T131R |
| 11006-11398 | L143E_K145T_Q179E | E124Q_T131R |
| 11004-11264 | L143E_K145T_Q179E | E124Q_T131R |
| 11004-11260 | L143E_K145T_Q179E | E124Q_T131R |
| 11004-11252 | L143E_K145T_Q179E | E124Q_T131R |
| 11002-11262 | L143E_K145T_Q179E | E124Q_T131R |
| 11002-11258 | L143E_K145T_Q179E | E124Q_T131R |
| 11002-11250 | L143E_K145T_Q179E | E124Q_T131R |
| 11001-11392 | L143E_K145T_Q179E | E124Q_T131R |
| 11000-11382 | L143E_K145T_Q179E | E124Q_T131R |
| 10999-11377 | L143E_K145T_Q179E | E124Q_T131R |
| 10989-11251 | L143E_K145T_Q179E | E124Q_T131K |

| Unique identifier | H2 mutation (Kabat) | L2 mutation (Kabat) |
|---|---|---|
| 13290-13497 | Q39E_L124R_Q179K | Q38R_V133G_S176D_T180E |
| 10992-11410 | V177I_S188K | V133L_S176D_T178E |
| 10989-11259 | L124R_S186K | V133G_S176D_T180E |
| 10987-11261 | L124R_S186R | V133G_S176D_T178E |
| 10987-11257 | L124R_S186K | V133G_S176D_T178E |
| 10987-11249 | L124R_Q179K | V133G_S176D_T178E |
| 10986-11391 | S188K | S176E_T178E |
| 10985-11381 | S188K | S131E_V133G_T178F |
| 10984-11376 | S188K | S131D_V133G_T178F |
| 10983-11306 | L143K | Q124E_V133D |
| 10953-11411 | V177I_S188K | V133L_S176D_T178E |
| 10952-11398 | S188K | V133I_S176D_T178E |
| 10950-11264 | L124R_S186R | V133G_S176D_T180E |
| 10950-11260 | L124R_S186K | V133G_S176D_T180E |
| 10950-11252 | L124R_Q179K | V133G_S176D_T180E |
| 10948-11262 | L124R_S186R | V133G_S176D_T178E |
| 10948-11258 | L124R_S186K | V133G_S176D_T178E |
| 10948-11250 | L124R_Q179K | V133G_S176D_T178E |
| 10947-11392 | S188K | S176E_T178E |
| 10934-11410 | V177I_S188K | V133L_S176D_T178E |
| 10931-11263 | L124R_S186R | V133G_S176D_T180E |
| 10931-11259 | L124R_S186K | V133G_S176D_T180E |
| 10931-11251 | L124R_Q179K | V133G_S176D_T180E |
| 10929-11261 | L124R_S186R | V133G_S176D_T178E |
| 10929-11257 | L124R_S186K | V133G_S176D_T178E |
| 10929-11249 | L124R_Q179K | V133G_S176D_T178E |
| 10926-11391 | S188K | S176E_T178E |
| 10989-11263 | L124R_S186R | V133G_S176D_T180E |
| 10998-11307 | L143K | Q124E_V133D |
| 13289-13368 | L45P_L124R_Q179K | P44F_V133G_S176D_T180E |
| 10998-11314 | L143R | Q124E_V133D |
| 13223-13512 | S188K | V133I_L135W_S176D_T178E |
| 13288-13516 | S188K_V190F | V133I_L135A_S176D_T178E |
| 13221-13411 | L124R_S186K | V133G_L135W_S176D_T180E |
| 13214-13410 | L124R_S186K | V133G_L135W_S176D_T180E |

TABLE 10-A3-continued

| Cluster 3 K-L designs | | |
|---|---|---|
| 13221-13406 | L124R_Q179K | V133G_L135W_S176D_T180E |
| 13214-13405 | L124R_Q179K | V133G_L135W_S176D_T180E |
| 13291-13488 | L143R_S188K | Q124E_V133D_S176D_T178D |
| 13281-13489 | L143R_S188K | Q124E_V133D_S176D_T178E |
| 13280-13488 | L143R_S188K | Q124E_V133D_S176D_T178D |
| 13295-13484 | L143R | Q124E_V133D_T180D |
| 13292-13489 | L143R_S188K | Q124E_V133D_S176D_T178E |
| 13294-13492 | L143R_S188K | Q124E_V133D_T178E |
| 13297-13402 | L124R_L143K | Q124E_V133G_S176D_T180E |
| 13296-13399 | L124R_L143K | Q124E_V133G_S176D |
| 11007-11411 | V177I_S188K | V133L_S176D_T178E |
| 11006-11398 | S188K | V133I_S176D_T178E |
| 11004-11264 | L124R_S186R | V133G_S176D_T180E |
| 11004-11260 | L124R_S186K | V133G_S176D_T180E |
| 11004-11252 | L124R_Q179K | V133G_S176D_T180E |
| 11002-11262 | L124R_S186R | V133G_S176D_T178E |
| 11002-11258 | L124R_S186K | V133G_S176D_T178E |
| 11002-11250 | L124R_Q179K | V133G_S176D_T178E |
| 11001-11392 | S188K | S176E_T178E |
| 11000-11382 | S188K | S131E_V133G_T178F |
| 10999-11377 | S188K | S131D_V133G_T178F |
| 10989-11251 | L124R_Q179K | V133G_S176D_T180E |

TABLE 10-A4

| Cluster 4 K-L designs | | | |
|---|---|---|---|
| Unique identifier | H1 mutation (Kabat) | L1 mutation (Kabat) | H2 mutation (Kabat) |
| 13330-13495 | S188K | K129T_S176E_Y178E | Q39E_L124E_K145T_Q179E |
| 13329-13366 | S188K | K129T_S176E_Y178E | L45P_L124E_K145T_Q179E |
| 11108-11231 | S188K | S176E_Y178E | L124E_S188W |
| 11108-11227 | S188K | S176E_Y178E | L124E_S186I_S188W |
| 11107-11197 | S188K | S176E_Y178E | L124E |
| 11106-11229 | S188K | S176E_Y178E | L124E_S188W |
| 11106-11225 | S188K | S176E_Y178E | L124E_S186I_S188W |
| 11105-11195 | S188K | S176E_Y178E | L124E |
| 11104-11190 | S188K | S176E_Y178E | K145T_V177D_S188D |
| 11103-11186 | S188K | S176E_Y178E | K145T_V177D_S188D |
| 11102-11180 | S188K | S176E_Y178E | K145T_V177D_S188D |
| 11101-11219 | S188K | S176E_Y178E | L124E_K145T_Q179E_S188W |
| 11101-11213 | S188K | S176E_Y178E | L124E_K145T_Q179E_S186I_S188W |
| 11100-11205 | S188K | S176E_Y178E | L124E_K145T_Q179E |
| 11099-11216 | S188K | S176E_Y178E | L124E_K145T_Q179E_S188W |
| 11099-11210 | S188K | S176E_Y178E | L124E_K145T_Q179E_S186I_S188W |
| 11098-11200 | S188K | S176E_Y178E | L124E_K145T_Q179E |
| 11076-11355 | S188A | S176A_Y178W | S186L_S188W |
| 10771-11360 | — | — | S186L_S188W |
| 10771-11335 | — | — | S186I_S188W |
| 11163-11194 | V177I_S188K | V133L_S176D_Y178E | K145T_V177D_S188D |
| 11162-11184 | V177I_S188K | V133L_S176D_Y178E | K145T_V177D_S188D |
| 11144-11192 | V177I_S188K | V133I_S176D_Y178E | K145T_V177D_S188D |
| 11143-11187 | V177I_S188K | V133I_S176D_Y178E | K145T_V177D_S188D |
| 11142-11182 | V177I_S188K | V133I_S176D_Y178E | K145T_V177D_S188D |
| 11089-11189 | S188K | S176D_Y178E | K145T_V177D_S188D |
| 11088-11185 | S188K | S176D_Y178E | K145T_V177D_S188D |
| 11124-11202 | S188K | V133I_S176D_Y178E | L124E_K145T_Q179E |
| 11125-11207 | S188K | V133I_S176D_Y178E | L124E_K145T_Q179E |
| 11140-11202 | V177I_S188K | V133I_S176D_Y178E | L124E_K145T_Q179E |
| 11166-11198 | V177I_S188K | V133L_S176D_Y178E | L124E |
| 13333-13387 | S188K | K129T_S176E_Y178E | L124E_K145T_Q179E |
| 13207-13363 | A125R_S188K | S122D_K129T_S176D_Y178T | K145T_S186E_K228D |
| 13209-13364 | A125R_S188K | S122D_K129T_S176E_Y178E | K145T_S186E_K228D |
| 13235-13357 | A139W_S188K | K129T_S176D_Y178T | K145T_S186E |
| 13237-13358 | A139W_S188K | K129T_S176E_Y178E | K145T_S186E |
| 13337-13362 | S188K | K129T_Y178E | K145T_S186E |
| 13335-13361 | S188K | K129T_Y178D | K145T_S186E |
| 13328-13359 | S188K | K129T_S176D_Y178T | K145T_S186E |
| 13332-13360 | S188K | K129T_S176E_Y178E | K145T_S186E |
| 11167-11232 | V177I_S188K | V133L_S176D_Y178E | L124E_S188W |
| 11167-11228 | V177I_S188K | V133L_S176D_Y178E | L124E_S186I_S188W |
| 11165-11230 | V177I_S188K | V133L_S176D_Y178E | L124E_S188W |
| 11141-11207 | V177I_S188K | V133I_S176D_Y178E | L124E_K145T_Q179E |
| 11165-11226 | V177I_S188K | V133L_S176D_Y178E | L124E_S186I_S188W |
| 11164-11196 | V177I_S188K | V133L_S176D_Y178E | L124E |

TABLE 10-A4-continued

| Cluster 4 K-L designs | | | |
|---|---|---|---|
| 11161-11220 | V177I_S188K | V133L_S176D_Y178E | L124E_K145T_Q179E_S188W |
| 11161-11214 | V177I_S188K | V133L_S176D_Y178E | L124E_K145T_Q179E_S186I_S188W |
| 11160-11208 | V177I_S188K | V133L_S176D_Y178E | L124E_K145T_Q179E |
| 11159-11217 | V177I_S188K | V133L_S176D_Y178E | L124E_K145T_Q179E_S188W |
| 11159-11211 | V177I_S188K | V133L_S176D_Y178E | L124E_K145T_Q179E_S186I_S188W |
| 11158-11203 | V177I_S188K | V133L_S176D_Y178E | L124E_K145T_Q179E |
| 11150-11193 | V177I_S188K | V133I_S176E_Y178E | K145T_V177D_S188D |
| 11149-11188 | V177I_S188K | V133I_S176E_Y178E | K145T_V177D_S188D |
| 11148-11183 | V177I_S188K | V133I_S176E_Y178E | K145T_V177D_S188D |
| 11087-11179 | S188K | S176D_Y178E | K145T_V177D_S188D |

| Unique identifier | L2 mutation (Kabat) |
|---|---|
| 13330-13495 | Q38R_S131R_V133G_S176R |
| 13329-13366 | P44F_S131R_V133G_S176R |
| 11108-11231 | V133G_S176R_T178A |
| 11108-11227 | V133G_S176R_T178A |
| 11107-11197 | V133G_S176R |
| 11106-11229 | V133A_S176K_T178A |
| 11106-11225 | V133A_S176K_T178A |
| 11105-11195 | V133A_S176K |
| 11104-11190 | S176K_T178R |
| 11103-11186 | S176K_T178L |
| 11102-11180 | S176K_T178K |
| 11101-11219 | S131R_V133G_S176R_T178A |
| 11101-11213 | S131R_V133G_S176R_T178A |
| 11100-11205 | S131R_V133G_S176R |
| 11099-11216 | S131K_V133G_S176R_T178A |
| 11099-11210 | S131K_V133G_S176R_T178A |
| 11098-11200 | S131K_V133G_S176R |
| 11076-11355 | S176A_T178A |
| 10771-11360 | S176V |
| 10771-11335 | S176V |
| 11163-11194 | S176K_T178R |
| 11162-11184 | S176K_T178K |
| 11144-11192 | S176K_T178R |
| 11143-11187 | S176K_T178L |
| 11142-11182 | S176K_T178K |
| 11089-11189 | S176K_T178R |
| 11088-11185 | S176K_T178L |
| 11124-11202 | S131K_V133G_S176R |
| 11125-11207 | S131R_V133G_S176R |
| 11140-11202 | S131K_V133G_S176R |
| 11166-11198 | V133G_S176R |
| 13333-13387 | S131R_V133G_S176R |
| 13207-13363 | S121K_S131K_S176K |
| 13209-13364 | S121K_S131K_S176K |
| 13235-13357 | S131K_L135W_S176K |
| 13237-13358 | S131K_L135W_S176K |
| 13337-13362 | S131K_S176K |
| 13335-13361 | S131K_S176K |
| 13328-13359 | S131K_S176K |
| 13332-13360 | S131K_S176K |
| 11167-11232 | V133G_S176R_T178A |
| 11167-11228 | V133G_S176R_T178A |
| 11165-11230 | V133A_S176K_T178A |
| 11141-11207 | S131R_V133G_S176R |
| 11165-11226 | V133A_S176K_T178A |
| 11164-11196 | V133A_S176K |
| 11161-11220 | S131R_V133G_S176R_T178A |
| 11161-11214 | S131R_V133G_S176R_T178A |
| 11160-11208 | S131R_V133G_S176R |
| 11159-11217 | S131K_V133G_S176R_T178A |
| 11159-11211 | S131K_V133G_S176R_T178A |
| 11158-11203 | S131K_V133G_S176R |
| 11150-11193 | S176K_T178R |
| 11149-11188 | S176K_T178L |
| 11148-11183 | S176K_T178K |
| 11087-11179 | S176K_T178K |

TABLE 10-A5

| Cluster 5 K-L designs | | | | |
|---|---|---|---|---|
| Unique identifier | H1 mutation (Kabat) | L1 mutation (Kabat) | H2 mutation (Kabat) | L2 mutation (Kabat) |
| 11066-11181 | S186K_S188T | V133D_Y178T | K145T_V177D_S188D | S176K_T178K |
| 11063-11325 | S186K_S188T | V133D_Y178T | L143T_S188D | S131K_T178S |
| 11062-11323 | S186K_S188T | V133D_Y178T | L143T_S188D | S131K_S176A_T178S |
| 11056-11324 | S186K_S188T | T131S_V133D_Y178T | L143T_S188D | S131K_T178S |
| 11055-11322 | S186K_S188T | T131S_V133D_Y178T | L143T_S188D | S131K_S176A_T178S |
| 11044-11191 | L143S_S186K_S188T | V133D_Y178T | K145T_V177D_S188D | S176K_T178R |
| 11043-11181 | L143S_S186K_S188T | V133D_Y178T | K145T_V177D_S188D | S176K_T178K |
| 10898-11239 | L124E_V190E | V133I_L135R_Y178F | L124R | V133G_S176D |
| 10888-11415 | L124E_V190D | V133I_L135K_Y178F | V177I_S188K | V133L_S176D_T178E |
| 10883-11236 | L124E_V190D | V133I_L135K | L124R | V133G_S176D |
| 10881-11412 | L124E_V190D | L135K_Y178F | V177I_S188K | V133L_S176D_T178E |

TABLE 10-A6

| Cluster 6 K-L designs | | | | |
|---|---|---|---|---|
| Unique identifier | H1 mutation (Kabat) | L1 mutation (Kabat) | H2 mutation (Kabat) | L2 mutation (Kabat) |
| 10861-11409 | K145T_V177D_S188D | S176K_Y178R | V177I_S188K | V133I_S176E_T178E |
| 10776-11353 | D146T_V177D_S188D | S176K_Y178R | S186K_S188T | V133D |
| 10814-11233 | K145T_V177D_S188D | S176K_Y178K | L124R | V133G_S176D |
| 10813-11352 | K145T_V177D_S188D | S176K_Y178K | S186K_S188T | V133D |
| 10813-11320 | K145T_V177D_S188D | S176K_Y178K | L143S_S186K_S188T | V133D |
| 10813-11311 | K145T_V177D_S188D | S176K_Y178K | L143K | V133D |
| 10812-11393 | K145T_V177D_S188D | S176K_Y178K | S188K | S176E_T178E |
| 10810-11383 | K145T_V177D_S188D | S176K_Y178K | S188K | S131E_V133G_T178F |
| 10808-11315 | K145T_V177D_S188D | S176K_Y178K | L143R | Q124E_V133D |
| 10808-11308 | K145T_V177D_S188D | S176K_Y178K | L143K | Q124E_V133D |
| 10806-11369 | K145T_V177D_S188D | S176K_Y178K | S186R | Q124E_Q160E_T180E |
| 10806-11326 | K145T_V177D_S188D | S176K_Y178K | Q179K | Q124E_Q160E_T180E |
| 10776-11321 | D146T_V177D_S188D | S176K_Y178R | L143S_S186K_S188T | V133D |
| 10816-11265 | K145T_V177D_S188D | S176K_Y178K | L124R_S186R | V133G_S176D_T180E |
| 10776-11312 | D146T_V177D_S188D | S176K_Y178R | L143K | V133D |
| 10862-11414 | K145T_V177D_S188D | S176K_Y178R | V177I_S188K | V133L_S176D_T178E |
| 10860-11406 | K145T_V177D_S188D | S176K_Y178R | V177I_S188K | V133I_S176D_T178E |
| 10853-11388 | K145T_V177D_S188D | S176K_Y178R | S188K | S176D_T178E |
| 10851-11380 | K145T_V177D_S188D | S176K_Y178R | S188K | S131D_V133G_T178F |
| 10833-11387 | K145T_V177D_S188D | S176K_Y178L | S188K | S176D_T178E |
| 10831-11379 | K145T_V177D_S188D | S176K_Y178L | S188K | S131D_V133G_T178F |
| 10820-11413 | K145T_V177D_S188D | S176K_Y178K | V177I_S188K | V133L_S176D_T178E |
| 10818-11404 | K145T_V177D_S188D | S176K_Y178K | V177I_S188K | V133I_S176D_T178E |
| 10811-11386 | K145T_V177D_S188D | S176K_Y178K | S188K | S176D_T178E |
| 10816-11253 | K145T_V177D_S188D | S176K_Y178K | L124R_Q179K | V133G_S176D_T180E |
| 10819-11407 | K145T_V177D_S188D | S176K_Y178K | V177I_S188K | V133I_S176E_T178E |
| 10858-11267 | K145T_V177D_S188D | S176K_Y178R | L124R_S186R | V133G_S176D_T180E |
| 10848-11371 | K145T_V177D_S188D | S176K_Y178R | S186R | Q124E_Q160E_T180E |
| 10858-11255 | K145T_V177D_S188D | S176K_Y178R | L124R_Q179K | V133G_S176D_T180E |
| 10857-11243 | K145T_V177D_S188D | S176K_Y178R | L124R | V133G_S176D_T178D |
| 10856-11235 | K145T_V177D_S188D | S176K_Y178R | L124R | V133G_S176D |
| 10855-11353 | K145T_V177D_S188D | S176K_Y178R | S186K_S188T | V133D |
| 10855-11321 | K145T_V177D_S188D | S176K_Y178R | L143S_S186K_S188T | V133D |
| 10855-11312 | K145T_V177D_S188D | S176K_Y178R | L143K | V133D |
| 13330-13495 | K145T_V177D_S188D | S176K_Y178R | S188K | S176E_T178E |
| 10852-11385 | K145T_V177D_S188D | S176K_Y178R | S188K | S131E_V133G_T178F |
| 10850-11317 | K145T_V177D_S188D | S176K_Y178R | L143R | Q124E_V133D |
| 10850-11310 | K145T_V177D_S188D | S176K_Y178R | L143K | Q124E_V133D |
| 10848-11328 | K145T_V177D_S188D | S176K_Y178R | Q179K | Q124E_Q160E_T180E |
| 10827-11373 | K145T_V177D_S188D | S176K_Y178L | S186R_S188W | Q124E_Q160E_S176A_T178A_T180E |
| 10840-11408 | K145T_V177D_S188D | S176K_Y178L | V177I_S188K | V133I_S176E_T178E |
| 10837-11266 | K145T_V177D_S188D | S176K_Y178L | L124R_S186R | V133G_S176D_T180E |
| 10837-11254 | K145T_V177D_S188D | S176K_Y178L | L124R_Q179K | V133G_S176D_T180E |
| 10835-11234 | K145T_V177D_S188D | S176K_Y178L | L124R | V133G_S176D |
| 10834-11394 | K145T_V177D_S188D | S176K_Y178L | S188K | S176E_T178E |
| 10832-11384 | K145T_V177D_S188D | S176K_Y178L | S188K | S131E_V133G_T178F |
| 10830-11316 | K145T_V177D_S188D | S176K_Y178L | L143R | Q124E_V133D |
| 10830-11309 | K145T_V177D_S188D | S176K_Y178L | L143K | Q124E_V133D |
| 10828-11370 | K145T_V177D_S188D | S176K_Y178L | S186R | Q124E_Q160E_T180E |
| 10828-11327 | K145T_V177D_S188D | S176K_Y178L | Q179K | Q124E_Q160E_T180E |
| 10809-11378 | K145T_V177D_S188D | S176K_Y178K | S188K | S131D_V133G_T178F |

TABLE 10-A7

| Cluster 7 K-L designs | | | | |
|---|---|---|---|---|
| Unique identifier | H1 mutation (Kabat) | L1 mutation (Kabat) | H2 mutation (Kabat) | L2 mutation (Kabat) |
| 13253-13498 | K145T_S188E | Y178K | Q39E_L124R_Q179K | Q38R_V133G_S176D_T180E |
| 13252-13369 | K145T_S188E | Y178K | L45P_L124R_Q179K | P44F_V133G_S176D_T180E |
| 13258-13504 | K145T_S188E | Y178K | Q179K_S188K | Q124E_S176E_T180E |
| 13261-13480 | K145T_S188E | Y178K | L143K_S188K | Q124E_V133D_S176E_T178E_T180E |
| 13262-13481 | K145T_S188E | Y178K | L143K_S188K | Q124E_V133D_S176E_T180E |
| 13255-13509 | K145T_S188E | Y178K | S186R_S188K | Q124E_Q160E_S176D_T178D_T180E |
| 13254-13508 | K145T_S188E | Y178K | S186R_S188K | Q124E_Q160E_S176D_T178D |
| 10875-11416 | K145T_V177T_S188E | Y178K | V177I_S188K | V133L_S176D_T178E |
| 10873-11268 | K145T_V177T_S188E | Y178K | L124R_S186R | V133G_S176D_T180E |
| 10873-11256 | K145T_V177T_S188E | Y178K | L124R_Q179K | V133G_S176D_T180E |
| 10871-11240 | K145T_V177T_S188E | Y178K | L124R | V133G_S176D |
| 10870-11396 | K145T_V177T_S188E | Y178K | S188K | S176E_T178E |
| 10869-11390 | K145T_V177T_S188E | Y178K | S188K | S176D_T178E |
| 10800-11416 | K145T_S188E | Y178K | V177I_S188K | V133L_S176D_T178E |
| 10798-11268 | K145T_S188E | Y178K | L124R_S186R | V133G_S176D_T180E |
| 10798-11256 | K145T_S188E | Y178K | L124R_Q179K | V133G_S176D_T180E |
| 10796-11396 | K145T_S188E | Y178K | S188K | S176E_T178E |
| 13256-13502 | K145T_S188E | Y178K | Q179K_S188K | Q124E_S176E_T178D_T180E |
| 13257-13503 | K145T_S188E | Y178K | Q179K_S188K | Q124E_S176E_T178E_T180E |
| 13269-13403 | K145T_S188E | Y178K | L124R_L143K | Q124E_V133G_S176D_T180E |
| 13264-13400 | K145T_S188E | Y178K | L124R_L143K | Q124E_V133G_S176D |
| 13169-13418 | A125R_K145T_S188E | S122D_Y178K | L124R_S186R_K228D | S121K_V133G_S176D_T180E |
| 13212-13415 | A139W_K145T_S188E | Y178K | L124R_S186R | V133G_L135W_S176D_T180E |
| 13259-13491 | K145T_S188E | Y178K | L143R_S188K | Q124E_V133D_S176D_T178E |
| 13263-13493 | K145T_S188E | Y178K | L143R_S188K | Q124E_V133D_T178E |
| 13167-13514 | A125R_K145T_S188E | S122D_Y178K | S188K_K228D | S121K_S176E_T178E |
| 13210-13510 | A139W_K145T_S188E | Y178K | S188K | L135W_S176E_T178E |
| 13168-13397 | A125R_K145T_S188E | S122D_Y178K | L124R_K228D | S121K_V133G_S176D |
| 13268-13401 | K145T_S188E | Y178K | L124R_L143K | Q124E_V133G_S176D_T178E_T180E |
| 13211-13395 | A139W_K145T_S188E | Y178K | L124R | V133G_L135W_S176D |
| 13212-13396 | A139W_K145T_S188E | Y178K | L124R | V133G_L135W_S176D_T180E |
| 13265-13419 | K145T_S188E | Y178K | L124R_S188K | Q124E_V133G_S176D_T178D |
| 13265-13392 | K145T_S188E | Y178K | L124K_S188K | Q124E_V133G_S176D_T178D |
| 10798-13036 | K145T_S188E | Y178K | L124R | V133G_S176D_T180E |
| 12878-11240 | K145T_S188E | Y178K | L124R | V133G_S176D |
| 10795-11390 | K145T_S188E | Y178K | S188K | S176D_T178E |

TABLE 10-A8

| Cluster 8 K-L designs | | | |
|---|---|---|---|
| Unique identifier | H1 mutation (Kabat) | L1 mutation (Kabat) | H2 mutation (Kabat) |
| 13318-13437 | S186K | K129T_V133D_Y178T | L143E_K145T_Q179E |
| 11061-11273 | S186K_S188T | V133D_Y178T | L143E_K145T_Q179E |
| 12938-13064 | Q179K | K129T_S180E | L143E_K145T |
| 13319-13473 | S186R | K129T_S176A_Y178W_S180E | L143E_K145T_S188W |
| 13277-13420 | L143A_S186R | K129T_V133W_S180E | L124W_L143E_K145T |
| 13322-13425 | S186R | K129T_S180E | L143E_K145T |
| 12961-13471 | S186R | K129T_S180E | L143E_K145T_S188L |
| 12961-13108 | S186R | K129T_S180E | L143E_K145T_Q179E_S188L |
| 12958-13469 | S186R | K129T_S180E | L143E_K145T_S188L |
| 12958-13106 | S186R | K129T_S180E | L143E_K145T_Q179E_S188L |
| 12958-13064 | S186R | K129T_S180E | L143E_K145T |
| 12944-13093 | Q179K | K129T_S180E | L143E_K145T_Q179E |
| 11157-11279 | V177I_S188K | V133L_S176D_Y178E | L143E_K145T_Q179E |
| 11156-11274 | V177I_S188K | V133L_S176D_Y178E | L143E_K145T_Q179E |
| 11097-11277 | S188K | S176E_Y178E | L143E_K145T_Q179E |
| 11096-11272 | S188K | S176E_Y178E | L143E_K145T_Q179E |
| 11042-11273 | L143S_S186K_S188T | V133D_Y178T | L143E_K145T_Q179E |
| 13314-13424 | Q179K | K129T_Y178E_S180E | L143E_K145T |
| 11030-11285 | L143K | K129T_V133D | L143E_K145T_Q179E_S188L |
| 11030-11276 | L143K | K129T_V133D | L143E_K145T_Q179E |
| 11029-11288 | L143K | K129T_V133D | L143E_K145T_Q179E_S188W |
| 11029-11282 | L143K | K129T_V133D | L143E_K145T_Q179E_S186I_S188W |
| 11028-11275 | L143K | K129T_V133D | L143E_K145T_Q179E |
| 11027-11287 | L143K | K129T_V133D | L143E_K145T_Q179E_S188W |
| 11027-11281 | L143K | K129T_V133D | L143E_K145T_Q179E_S186I_S188W |
| 11026-11270 | L143K | K129T_V133D | L124W_L143E_K145T_Q179E |
| 11025-11284 | L143K | K129T_V133D | L143E_K145T_Q179E_S188L |
| 13308-13341 | Q179K | K129T_S180E | F122C_L143E_K145T_Q179E |
| 13275-13461 | L143A_Q179K | K129T_V133W_S180E | L143E_K145T_Q179E_S188L |
| 12938-13106 | Q179K | K129T_S180E | L143E_K145T_Q179E_S188L |

TABLE 10-A8-continued

| Cluster 8 K-L designs | | | |
|---|---|---|---|
| 13314-13438 | Q179K | K129T_Y178E_S180E | L143E_K145T_Q179E |
| 12938-13079 | Q179K | K129T_S180E | L143E_K145T_Q179E |
| 13309-13425 | Q179K | K129T_S180E | L143E_K145T |
| 12938-13469 | Q179K | K129T_S180E | L143E_K145T_S188L |
| 12957-13061 | S186R | K129T_S180E | L143E_K145T |
| 13336-13450 | S188K | K129T_Y178E | L143E_K145T_Q179E |
| 13321-13499 | S186R | K129T_S180E | Q39E_L143E_K145T_Q179E |
| 13339-13500 | S188K | S176E_Y178E | Q39E_L143E_K145T_Q179E |
| 13320-13370 | S186R | K129T_S180E | L45P_L143E_K145T_Q179E |
| 13338-13371 | S188K | S176E_Y178E | L45P_L143E_K145T_Q179E |
| 13224-13428 | A139W_L143I_S186K | K129T_V133D_Y178T | L143E_K145T_Q179E |
| 13229-13428 | A139W_S186K | K129T_V133D_Y178T | L143E_K145T_Q179E |
| 13226-13434 | A139W_L143K | K129T_V133D | L143E_K145T_Q179E |
| 13305-13448 | L143K_V190K | K129T_V133D_L135S | L143E_K145T_Q179E |
| 13273-13441 | L124K_L143K | K129T_T131E_V133D | L143E_K145T_Q179E |
| 13271-13439 | L124K_L143K | K129T_T131D_V133D | L143E_K145T_Q179E |
| 13300-13441 | L143K | K129T_T131E_V133D | L143E_K145T_Q179E |
| 13298-13439 | L143K | K129T_T131D_V133D | L143E_K145T_Q179E |
| 13234-13432 | A139W_S188K | K129T_S176D_Y178T | L143E_K145T_Q179E |
| 13236-13433 | A139W_S188K | K129T_S176E_Y178E | L143E_K145T_Q179E |
| 13334-13449 | S188K | K129T_Y178D | L143E_K145T_Q179E |
| 12944-13471 | Q179K | K129T_S180E | L143E_K145T_S188L |
| 13327-13446 | S188K | K129T_S176D_Y178T | L143E_K145T_Q179E |
| 13331-13447 | S188K | K129T_S176E_Y178E | L143E_K145T_Q179E |
| 13276-13462 | L143A_Q179K | K129T_V133W_S180E | L143E_K145T_Q179E_S188L |
| 12944-13108 | Q179K | K129T_S180E | L143E_K145T_Q179E_S188L |
| 13316-13451 | Q179K | K129T_Y178E_S180E | L143E_K145T_Q179E |
| 13322-13443 | S186R | K129T_S180E | L143E_K145T_Q179E |
| 13310-13444 | Q179K | K129T_S180E | L143E_K145T_Q179E |
| 13323-13444 | S186R | K129T_S180E | L143E_K145T_Q179E |
| 12958-13079 | S186R | K129T_S180E | L143E_K145T_Q179E |
| 12961-13093 | S186R | K129T_S180E | L143E_K145T_Q179E |
| 13317-13423 | Q179K_V190K | K129T_V133D_L135S_S180E | L143E_K145T |
| 13308-13340 | Q179K | K129T_S180E | F122C_L143E_K145T |
| 13276-13472 | L143A_Q179K | K129T_V133W_S180E | L143E_K145T_S188L |
| 13275-13470 | L143A_Q179K | K129T_V133W_S180E | L143E_K145T_S188L |
| 13309-13443 | Q179K | K129T_S180E | L143E_K145T_Q179E |

| Unique identifier | L2 mutation (Kabat) |
|---|---|
| 13318-13437 | Q124R_Q160K_T178R |
| 11061-11273 | Q124R_Q160K_T178R |
| 12938-13064 | Q124R_Q160K_T178R |
| 13319-13473 | Q124K_S176A_T178R |
| 13277-13420 | Q124K_V133A_T178R |
| 13322-13425 | Q124R_T129K_Q160K_T178R |
| 12961-13471 | Q124R_T178R |
| 12961-13108 | Q124R_T178R |
| 12958-13469 | Q124R_Q160K_T178R |
| 12958-13106 | Q124R_Q160K_T178R |
| 12958-13064 | Q124R_Q160K_T178R |
| 12944-13093 | Q124R_T178R |
| 11157-11279 | Q124R_T178R |
| 11156-11274 | Q124R_Q160K_T178R |
| 11097-11277 | Q124R_T178R |
| 11096-11272 | Q124R_Q160K_T178R |
| 11042-11273 | Q124R_Q160K_T178R |
| 13314-13424 | Q124R_Q160K_T178R |
| 11030-11285 | Q124R_T178R |
| 11030-11276 | Q124R_T178R |
| 11029-11288 | Q124R_S176A_T178R |
| 11029-11282 | Q124R_S176A_T178R |
| 11028-11275 | Q124R_Q160R_T178R |
| 11027-11287 | Q124R_Q160R_S176A_T178R |
| 11027-11281 | Q124R_Q160R_S176A_T178R |
| 11026-11270 | Q124K_V133A_T178R |
| 11025-11284 | Q124K_T178R |
| 13308-13341 | Q124C_Q160K_T178R |
| 13275-13461 | Q124R_Q160K_T178R |
| 12938-13106 | Q124R_Q160K_T178R |
| 13314-13438 | Q124R_Q160K_T178R |
| 12938-13079 | Q124R_Q160K_T178R |
| 13309-13425 | Q124R_T129K_Q160K_T178R |
| 12938-13469 | Q124R_Q160K_T178R |
| 12957-13061 | Q124K_T178R |
| 13336-13450 | Q124R_T178R |
| 13321-13499 | Q38R_Q124K_T178R |
| 13339-13500 | Q38R_Q124R_T178R |

TABLE 10-A8-continued

| Cluster 8 K-L designs | |
|---|---|
| 13320-13370 | P44F_Q124K_T178R |
| 13338-13371 | P44F_Q124R_T178R |
| 13224-13428 | Q124R_L135W_Q160K_T178R |
| 13229-13428 | Q124R_L135W_Q160K_T178R |
| 13226-13434 | Q124R_L135W_T178R |
| 13305-13448 | Q124R_T178R |
| 13273-13441 | Q124R_Q160R_T178R |
| 13271-13439 | Q124R_Q160R_T178R |
| 13300-13441 | Q124R_Q160R_T178R |
| 13298-13439 | Q124R_Q160R_T178R |
| 13234-13432 | Q124R_L135W_T178R |
| 13236-13433 | Q124R_L135W_T178R |
| 13334-13449 | Q124R_T178R |
| 12944-13471 | Q124R_T178R |
| 13327-13446 | Q124R_T178R |
| 13331-13447 | Q124R_T178R |
| 13276-13462 | Q124R_T178R |
| 12944-13108 | Q124R_T178R |
| 13316-13451 | Q124R_T178R |
| 13322-13443 | Q124R_T129K_Q160K_T178R |
| 13310-13444 | Q124R_T129K_T178R |
| 13323-13444 | Q124R_T129K_T178R |
| 12958-13079 | Q124R_Q160K_T178R |
| 12961-13093 | Q124R_T178R |
| 13317-13423 | Q124R_Q160K_T178R |
| 13308-13340 | Q124C_Q160K_T178R |
| 13276-13472 | Q124R_T178R |
| 13275-13470 | Q124R_Q160K_T178R |
| 13309-13443 | Q124R_T129K_Q160K_T178R |

TABLE 10-A9

| Cluster 9 K-L designs | | | | |
|---|---|---|---|---|
| Unique identifier | H1 mutation (Kabat) | L1 mutation (Kabat) | H2 mutation (Kabat) | L2 mutation (Kabat) |
| 13182-13458 | A125R_L143K | S122D_K129T_V133D | L143E_K145T_Q179E_K228D | S121K_Q124R_T178R |
| 13206-13454 | A125R_S188K | S122D_K129T_S176D_Y178T | L143E_K145T_Q179E_K228D | S121K_Q124R_T178R |
| 13197-13353 | A125R_Q179K | S122D_K129T_S180E | K145T_Q179E_K228D | S121K_T129K_S131K |
| 13188-13430 | A125R_Q179K | S122D_K129T_S180E | L143E_K145T_Q179E | Q124R_L135W_Q160K_T178R |
| 13192-13452 | A125R_Q179K | S122D_K129T_S180E | L143E_K145T_Q179E_K228D | S121K_Q124R_Q160K_T178R |
| 13200-13421 | A125R_S186R | S122D_K129T_S180E | L143E_K145T | Q124R_L135W_Q160K_T178R |
| 13202-13426 | A125R_S186R | S122D_K129T_S180E | L143E_K145T_K228D | S121K_Q124R_Q160K_T178R |
| 13203-13427 | A125R_S186R | S122D_K129T_S180E | L143E_K145T_K228D | S121K_Q124R_T178R |
| 13204-13351 | A125R_S186R | S122D_K129T_S180E | K145T_Q179E_K228D | S121K_S131K |
| 13205-13353 | A125R_S186R | S122D_K129T_S180E | K145T_Q179E_K228D | S121K_T129K_S131K |
| 13188-13421 | A125R_Q179K | S122D_K129T_S180E | L143E_K145T | Q124R_L135W_Q160K_T178R |
| 13190-13422 | A125R_Q179K | S122D_K129T_S180E | L143E_K145T | Q124R_L135W_T178R |
| 13192-13426 | A125R_Q179K | S122D_K129T_S180E | L143E_K145T_K228D | S121K_Q124R_Q160K_T178R |
| 13194-13427 | A125R_Q179K | S122D_K129T_S180E | L143E_K145T_K228D | S121K_Q124R_T178R |
| 13200-13430 | A125R_S186R | S122D_K129T_S180E | L143E_K145T_Q179E | Q124R_L135W_Q160K_T178R |
| 13194-13456 | A125R_Q179K | S122D_K129T_S180E | L143E_K145T_Q179E_K228D | S121K_Q124R_T178R |
| 13202-13452 | A125R_S186R | S122D_K129T_S180E | L143E_K145T_Q179E_K228D | S121K_Q124R_Q160K_T178R |
| 13203-13456 | A125R_S186R | S122D_K129T_S180E | L143E_K145T_Q179E_K228D | S121K_Q124R_T178R |
| 13208-13455 | A125R_S188K | S122D_K129T_S176E_Y178E | L143E_K145T_Q179E_K228D | S121K_Q124R_T178R |
| 13196-13351 | A125R_Q179K | S122D_K129T_S180E | K145T_Q179E_K228D | S121K_S131K |

TABLE 10-A10

| Cluster 10 K-L designs | | | |
|---|---|---|---|
| Unique identifier | H1 mutation (Kabat) | L1 mutation (Kabat) | H2 mutation (Kabat) |
| 13304-13466 | L143K_F174G | T116F_K129T_V133D_S176F | L143E_K145T_Q179E_V190F |
| 13238-13459 | F174G_Q179K | T116F_K129T_S176F_S180E | L143E_K145T_Q179E_S188F_V190F |
| 10780-11417 | F174G | S176F | V190F |
| 10781-11300 | F174G | S176F | L143I_V190F |
| 10781-11419 | F174G | S176F | V190F |
| 10786-11299 | F174G | T116F_S176F | L143I_V190F |

TABLE 10-A10-continued

| Cluster 10 K-L designs | | | |
|---|---|---|---|
| 10786-11418 | F174G | T116F_S176F | V190F |
| 10787-11301 | F174G | T116F_S176F | L143I_V190F |
| 10787-11420 | F174G | T116F_S176F | V190F |
| 10788-11422 | F174G | T116F_S176F | V190F |
| 10792-11305 | F174G | T116F_S176F | L143I_V190F |
| 10792-11424 | F174G | T116F_S176F | V190F |
| 10793-11375 | F174G | T116F_S176F | S188F |
| 10684-10706 | S186R | K129T_S180E | K145T_Q179E |
| 13248-13475 | F174G_S186R | T116F_K129T_S176F_S180E | L143E_K145T_V190F |
| 13250-13355 | F174G_S186R | T116F_K129T_S176F_S180E | K145T_Q179E_S188F_V190F |
| 13242-13475 | F174G_Q179K | T116F_K129T_S176F_S180E | L143E_K145T_V190F |
| 13246-13463 | F174G_S186R | T116F_K129T_S176F_S180E | L143E_K145T_Q179E_V190F |
| 13238-13463 | F174G_Q179K | T116F_K129T_S176F_S180E | L143E_K145T_Q179E_V190F |
| 13248-13465 | F174G_S186R | T116F_K129T_S176F_S180E | L143E_K145T_Q179E_V190F |
| 13246-13459 | F174G_S186R | T116F_K129T_S176F_S180E | L143E_K145T_Q179E_S188F_V190F |
| 13242-13465 | F174G_Q179K | T116F_K129T_S176F_S180E | L143E_K145T_Q179E_V190F |

| Unique identifier | L2 mutation (Kabat) |
|---|---|
| 13304-13466 | Q124R_L135A_T178R |
| 13238-13459 | Q124K_L135A_T178R |
| 10780-11417 | |
| 10781-11300 | L135A |
| 10781-11419 | L135A |
| 10786-11299 | — |
| 10786-11418 | — |
| 10787-11301 | L135A |
| 10787-11420 | L135A |
| 10788-11422 | L135A_T178F |
| 10792-11305 | T178F |
| 10792-11424 | T178F |
| 10793-11375 | V133A |
| 10684-10706 | S131K |
| 13248-13475 | Q124R_L135A_Q160K_T178R |
| 13250-13355 | S131K_L135A |
| 13242-13475 | Q124R_L135A_Q160K_T178R |
| 13246-13463 | Q124K_L135A_T178R |
| 13238-13463 | Q124K_L135A_T178R |
| 13248-13465 | Q124R_L135A_Q160K_T178R |
| 13246-13459 | Q124K_L135A_T178R |
| 13242-13465 | Q124R_L135A_Q160K_T178R |

TABLE 10-A11

| Cluster 11 K-L designs | | | | |
|---|---|---|---|---|
| Unique identifier | H1 mutation (Kabat) | L1 mutation (Kabat) | H2 mutation (Kabat) | L2 mutation (Kabat) |
| 13185-13374 | A125R_L143K_V190K | S122D_K129T_V133D_L135S | L124E_A139I_K145T_V190I_K228D | S121K_S131K_L135K |
| 13306-13373 | L143K_V190K | K129T_V133D_L135S | L124E_A139I_K145T_V190I | S131K_L135K |
| 13306-13375 | L143K_V190K | K129T_V133D_L135S | L124E_K145T | S131K_L135K |

TABLE 10-A12

| Cluster 12 K-L designs | | | |
|---|---|---|---|
| Unique identifier | H1 mutation (Kabat) | L1 mutation (Kabat) | H2 mutation (Kabat) |
| 13303-13496 | L143K | K129T_V133D | Q39E_L124E_K145T_Q179E |
| 13302-13367 | L143K | K129T_V133D | L45P_L124E_K145T_Q179E |
| 11033-11209 | L143K | K129T_V133D | L124E_K145T_Q179E_S186I_S188W |
| 11033-11215 | L143K | K129T_V133D | L124E_K145T_Q179E_S188W |
| 11034-11204 | L143K | K129T_V133D | L124E_K145T_Q179E |
| 11035-11212 | L143K | K129T_V133D | L124E_K145T_Q179E_S186I_S188W |
| 11035-11218 | L143K | K129T_V133D | L124E_K145T_Q179E_S188W |
| 11036-11221 | L143K | K129T_V133D | L124E_K145T_S186E |
| 11039-11224 | L143K | K129T_V133D | L124E_L143E_K145T |
| 11064-11201 | S186K_S188T | V133D_Y178T | L124E_K145T_Q179E |
| 11065-11206 | S186K_S188T | V133D_Y178T | L124E_K145T_Q179E |
| 13299-13379 | L143K | K129T_T131D_V133D | L124E_K145T_Q179E |
| 13301-13381 | L143K | K129T_T131E_V133D | L124E_K145T_Q179E |

TABLE 10-A12-continued

| Cluster 12 K-L designs | | | |
|---|---|---|---|
| 13272-13379 | L124K_L143K | K129T_T131D_V133D | L124E_K145T_Q179E |
| 13274-13381 | L124K_L143K | K129T_T131E_V133D | L124E_K145T_Q179E |
| 13227-13383 | A139W_L143K | K129T_V133D | L124E_K145T_Q179E |
| 13184-13388 | A125R_L143K | S122D_K129T_V133D | L124E_K145T_Q179E_K228D |
| 13231-13386 | A139W_S186K_S188T | V133D_Y178T | L124E_K145T_Q179E |
| 13199-13391 | A125R_S186K_S188T | S122D_V133D_Y178T | L124E_K145T_Q179E_K228D |
| 13230-13384 | A139W_S186K | K129T_V133D_Y178T | L124E_K145T_Q179E |
| 13198-13389 | A125R_S186K | S122D_K129T_V133D_Y178T | L124E_K145T_Q179E_K228D |
| 13225-13384 | A139W_L143I_S186K | K129T_V133D_Y178T | L124E_K145T_Q179E |
| 13181-13389 | A125R_L143I_S186K | S122D_K129T_V133D_Y178T | L124E_K145T_Q179E_K228D |
| 11032-11199 | L143K | K129T_V133D | L124E_K145T_Q179E |

| Unique identifier | L2 mutation (Kabat) |
|---|---|
| 13303-13496 | Q38R_S131R_V133G_S176R |
| 13302-13367 | P44F_S131R_V133G_S176R |
| 11033-11209 | S131K_V133G_S176R_T178A |
| 11033-11215 | S131K_V133G_S176R_T178A |
| 11034-11204 | S131R_V133G_S176R |
| 11035-11212 | S131R_V133G_S176R_T178A |
| 11035-11218 | S131R_V133G_S176R_T178A |
| 11036-11221 | S131R_V133S_L135K |
| 11039-11224 | S131R_V133T_L135K_T178S |
| 11064-11201 | S131K_V133G_S176R |
| 11065-11206 | S131R_V133G_S176R |
| 13299-13379 | S131K_V133G_S176R |
| 13301-13381 | S131K_V133G_S176R |
| 13272-13379 | S131K_V133G_S176R |
| 13274-13381 | S131K_V133G_S176R |
| 13227-13383 | S131R_V133G_L135W_S176R |
| 13184-13388 | S121K_S131R_V133G_S176R |
| 13231-13386 | S131R_V133G_L135W_S176R |
| 13199-13391 | S121K_S131R_V133G_S176R |
| 13230-13384 | S131R_V133G_L135W_S176R |
| 13198-13389 | S121K_S131R_V133G_S176R |
| 13225-13384 | S131R_V133G_L135W_S176R |
| 13181-13389 | S121K_S131R_V133G_S176R |
| 11032-11199 | S131K_V133G_S176R |

In Tables 10-A1 to 10-A12, H1L1 Fab is CAT-2200 and H2L2 Fab is Pertuzumab

TABLE 10-B1

| Cluster 1 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10657-10760 | L143E_K145T_Q179E | E124K_Y178R | S186R | T178E_T180E |
| 10656-10758 | L143E_K145T_Q179E | E124K_Y178R | S186R | Q160E_T180E |

TABLE 10-B2

| Cluster 2 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10652-10755 | L143E_K145T | E124R | S186R | Q124E_Q160E_T180E |
| 10652-10734 | L143E_K145T | E124R | Q179K | Q124E_Q160E_T180E |
| 10652-10702 | L143E_K145T | E124R | D146G_Q179K | Q124E_Q160E_T180E |

TABLE 10-B3

| Cluster 3 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10690-10727 | S186R | Y178E_S180E | L143E_K145T_Q179E | Q124K_T178R |
| 10689-10707 | S186R | S180E | K145T_Q179E | S131K |
| 10685-10726 | S186R | S180E | L143E_K145T_Q179E | Q124K_T178R |
| 10685-10719 | S186R | S180E | L143E_K145T | Q124K_T178R |

TABLE 10-B4

| Cluster 4 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10665-10724 | Q179K | S180E | L143E_K145T | Q124R_Q160K_T178R |
| 10664-10722 | Q179K | S180E | L143E_K145T | Q124R |
| 10632-10724 | D146G_Q179K | S180E | L143E_K145T | Q124R_Q160K_T178R |
| 10631-10722 | D146G_Q179K | S180E | L143E_K145T | Q124R |

TABLE 10-B5

| Cluster 5 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10688-10724 | S186R | S180E | L143E_K145T | Q124R_Q160K_T178R |
| 10687-10722 | S186R | S180E | L143E_K145T | Q124R |
| 10683-10720 | S186R | | L143E_K145T | Q124R |
| 10682-10718 | S186R | | L143E_K145T | Q124K_T178R |
| 10659-10720 | L143R | | L143E_K145T | Q124R |
| 10658-10720 | L143K | | L143E_K145T | Q124R |

TABLE 10-B6

| Cluster 6 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10681-10747 | Q39R | Q38E | Q39E | Q38R |
| 10681-10741 | Q39R | Q38E | Q39D | Q38R |
| 10680-10746 | Q39R | Q38D | Q39E | Q38R |
| 10680-10740 | Q39R | Q38D | Q39D | Q38R |
| 10679-10738 | Q39K | Q38E | Q39D | Q38K |
| 10678-10743 | Q39K | Q38D | Q39E | Q38K |
| 10677-10751 | Q39E | Q38R | Q39R | Q38E |
| 10676-10750 | Q39E | Q38R | Q39R | Q38D |
| 10671-10751 | Q39D | Q38R | Q39R | Q38E |
| 10623-10745 | — | — | Q39E | Q38R |
| 10623-10739 | — | — | Q39D | Q38R |

TABLE 10-B6-continued

| Cluster 6 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10622-10742 | — | — | Q39E | Q38K |
| 10622-10736 | — | — | Q39D | Q38K |
| 10679-10744 | Q39K | Q38E | Q39E | Q38K |
| 10678-10737 | Q39K | Q38D | Q39D | Q38K |
| 10674-10749 | Q39E | Q38K | Q39K | Q38E |

TABLE 10-B7

| Cluster 7 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10625-10701 | — | L135W | A139W | F116A_L135V |
| 10624-10700 | — | L135W | A139W | F116A |

TABLE 10-B8

| Cluster 8 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10662-10733 | L45F | — | L45P | P44F |
| 10662-10731 | L45F | — | L45A | P44F |
| 10621-10733 | — | — | L45P | P44F |
| 10621-10731 | — | — | L45A | P44F |

TABLE 10-B9

| Cluster 9 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10629-10695 | A139W | T116A | | L135W |

TABLE 10-B10

| Cluster 10 K-K-derived K-L designs | | | | |
|---|---|---|---|---|
| Unique identifier | H1 mutation (Kabat) | L1 mutation (Kabat) | H2 mutation (Kabat) | L2 mutation (Kabat) |
| 10640-10713 | L124E | V133G_S176R | L124R | V133G_S176D |

In Tables 10-B1 to 10-B10, H1L1 Fab is CAT-2200 and H2L2 Fab is Pertuzumab

TABLE 11A

Amino acid mutations in the Fab regions of H1, L1, H2 and L2 for K-L designs tested in SMCA format (Kabat numbering).

| Cluster | Design | H1 mutation (lambda) | L1 mutation (lambda) |
|---|---|---|---|
| kl-6 | 2892 | K145T_V177D_S188D | S176K_Y178K |
| kl-6 | 2901 | K145T_V177D_S188D | S176K_Y178K |
| kl-4 | 2979 | S188K | S176E_Y178E |
| kl-3 | 2994 | L143E_K145T_Q179E | E124Q_T131K |
| kl-3 | 3008 | L143E_K145T_Q179E | E124Q_T131K |
| kl-3 | 3018 | L143D_K145T | E124Q_T131K |
| kl-2 | 3025 | L143D_K145T | E124Q_T131R |
| kl-3 | 3041 | L143D_K145T | E124Q_T131R |
| kl-12 | 3102 | L143K | K129T_V133D |
| kl-8 | 3109 | L143K | K129T_V133D |
| kl-12 | 3113 | S186K_S188T | V133D_Y178T |
| kl-5 | 3122 | S186K_S188T | V133D_Y178T |
| kl-8 | 3878 | Q179K | K129T_S180E |
| kl-9 | 3890 | A125R_Q179K | S122D_K129T_S180E |
| kl-8 | 3898 | Q179K | K129T_Y178E_S180E |
| kl-10 | 3910 | F174G_Q179K | T116F_K129T_S176F_S180E |
| kl-7 | 3931 | K145T_S188E | Y178K |
| kl-4 | 3947 | S188K | K129T_Y178D |
| kl-4 | 3951 | A125R_S188K | S122D_K129T_S176E_Y178E |
| kl-7 | 3954 | A125R_K145T_S188E | S122D_Y178K |
| kl-7 | 3957 | K145T_S188E | Y178K |
| kl-9 | 3967 | A125R_S188K | S122D_K129T_S176E_Y178E |
| kl-2 | 3971 | L143D_K145T | E124Q_T131R |
| kl-2 | 3972 | A139W_L143D_K145T | E124Q_T131R |
| kl-1 | 3974 | A125R_L143D_K145T | S122D_E124Q_T131R |
| kl-2 | 3980 | L143D_K145T_F174G | T116F_E124Q_T131R_S176F |
| kl-3 | 3987 | A139W_L143D_K145T | E124Q_T131R |
| kl-1 | 3997 | A125R_L143E_K145T_Q179E | S122D_E124Q_T131R |
| kl-8 | 4008 | A139W_L143K | K129T_V133D |
| kl-12 | 4010 | A139W_L143K | K129T_V133D |
| kl-11 | 4022 | L143K_V190K | K129T_V133D_L135S |
| kl-8 | 4040 | S186R | K129T_S180E |
| kl-10 | 4320 | L143K_F174G | T116F_K129T_V133D_S176F |
| Cluster | Design | H2 mutation (kappa) | L2 mutation (kappa) |
| kl-6 | 2892 | L143K | Q124E_V133D |
| kl-6 | 2901 | L124R | V133G_S176D |
| kl-4 | 2979 | L124E_K145T_Q179E | S131R_V133G_S176R |
| kl-3 | 2994 | L143K | Q124E_V133D |
| kl-3 | 3008 | L124R_S186K | V133G_S176D_T178E |
| kl-3 | 3018 | L124R_S186R | V133G_S176D_T180E |
| kl-2 | 3025 | S188K | S131D_V133G_T178F |
| kl-3 | 3041 | S188K | S176E_T178E |
| kl-12 | 3102 | L124E_K145T_Q179E | S131R_V133G_S176R |
| kl-8 | 3109 | L124W_L143E_K145T_Q179E | Q124K_V133A_T178R |
| kl-12 | 3113 | L124E_K145T_Q179E | S131R_V133G_S176R |
| kl-5 | 3122 | K145T_V177D_S188D | S176K_T178K |

TABLE 11A-continued

Amino acid mutations in the Fab regions of H1, L1, H2 and L2 for K-L designs tested in SMCA format (Kabat numbering).

| | | | |
|---|---|---|---|
| kl-8 | 3878 | L143E_K145T_S188L | Q124R_Q160K_T178R |
| kl-9 | 3890 | L143E_K145T_K228D | S121K_Q124R_T178R |
| kl-8 | 3898 | L143E_K145T_Q179E | Q124R_T178R |
| kl-10 | 3910 | L143E_K145T_Q179E_V190F | Q124K_L135A_T178R |
| kl-7 | 3931 | L124R | V133G_S176D |
| kl-4 | 3947 | K145T_S186E | S131K_S176K |
| kl-4 | 3951 | K145T_S186E_K228D | S121K_S131K_S176K |
| kl-7 | 3954 | S188K_K228D | S121K_S176E_T178E |
| kl-7 | 3957 | L143R_S188K | Q124E_V133D_T178E |
| kl-9 | 3967 | L143E_K145T_Q179E_K228D | S121K_Q124R_T178R |
| kl-2 | 3971 | L143R | Q124E_V133D_T180D |
| kl-2 | 3972 | L143R | Q124E_V133D_L135W |
| kl-1 | 3974 | L143R_K228D | S121K_Q124E_V133D |
| kl-2 | 3980 | L143R_V190F | Q124E_V133D_L135A |
| kl-3 | 3987 | L124R_S186K | V133G_L135W_S176D_T180E |
| kl-1 | 3997 | S188K_K228D | S121K_V133I_S176D_T178E |
| kl-8 | 4008 | L143E_K145T_Q179E | Q124R_L135W_T178R |
| kl-12 | 4010 | L124E_K145T_Q179E | S131R_V133G_L135W_S176R |
| kl-11 | 4022 | L124E_K145T | S131K_L135K |
| kl-8 | 4040 | L45P_L143E_K145T_Q179E | P44F_Q124K_T178R |
| kl-10 | 4320 | L143E_K145T_Q179E_V190F | Q124K_L135A_T178R |

TABLE 11B

Amino acid mutations in the Fab regions of H1, L1, H2 and L2 for K-K-derived K-L designs tested in SMCA format (Kabat numbering).

| Cluster | Design | H1 mutation (lambda) | L1 mutation (lambda) | H2 mutation (kappa) | L2 mutation (kappa) |
|---|---|---|---|---|---|
| kk-6 | 34 | Q39R | Q38E | Q39D | Q38R |
| kk-10 | 2188 | L124E | V133G_S176R | L124R | V133G_S176D |
| kk-8 | 2798 | — | — | L45P | P44F |
| kk-4 | 2816 | Q179K | S180E | L143E_K145T | Q124R_Q160K_T178R |
| kk-2 | 2826 | L143E_K145T | E124R | Q179K | Q124E_Q160E_T180E |
| kk-3 | 2827 | S186R | S180E | L143E_K145T_Q179E | Q124K_T178R |
| kk-1 | 2830 | L143E_K145T_Q179E | E124K_Y178R | S186R | T178E_T180E |

TABLE 12

Effect of DNA ratio titration on the percentage of antibody species, as assessed by LC-MS, of select wild-type systems

| System* | Tag | H1:H2: L1:L2 DNA ratio | H1L2_ H1L2 and H1L2_ H2L1 | H1L1_ H1L1 | H1L1_ H1L2 | H1L2_ H1L2 | H2L1_ H2L1 | H2L1_ H2L2 | H2L2_ H2L2 | H1L1_ H2L1 | H1L2_ H2L2 | H1L1 | H1L2 | H2L1 | H2L2 |
|---|---|---|---|---|---|---|---|---|---|---|---|---|---|---|---|
| A | L2 FLAG | 10:20:24:46 | 40 | 0.2 | 0.3 | 0.1 | 0.5 | 0.4 | 0.6 | 20.3 | 26.2 | 0.8 | 0.5 | 3.9 | 6.1 |
| A | L2 FLAG | 8:22:17:53 | 36.3 | 0.1 | 0.2 | 0.2 | 0.2 | 0.5 | 1.4 | 7.6 | 38.4 | 0.2 | 0.1 | 3.7 | 11.1 |
| A | L2 FLAG | 8:22:13:57 | 33.8 | 0.1 | 0.3 | 0.1 | 0.3 | 0.4 | 1.9 | 5.1 | 39.9 | 0.3 | 0.1 | 3.8 | 13.9 |
| A | L2 FLAG | 10:20:35:35 | 30.4 | 0.3 | 0.1 | 0.1 | 0.5 | 0.2 | 0.3 | 50.9 | 6.7 | 14 | 0 | 6 | 2.9 |
| A | L2 FLAG | 15:15:35:35 | 19.5 | 1.8 | 1.8 | 0.9 | 0.1 | 0 | 0 | 7.5 | 18.2 | 32.9 | 16.5 | 0.2 | 0.5 |
| A | L2 FLAG | 8:22:35:35 | 16.7 | 0.2 | 0.1 | 0.1 | 0.7 | 0.2 | 0.2 | 61.9 | 3.2 | 0.8 | 0.1 | 11.6 | 4.3 |
| A | L2 FLAG | 10:20:46:24 | 11 | 0.8 | 0.1 | 0 | 0.3 | 0.1 | 0.1 | 78.6 | 1.3 | 4 | 0.1 | 3 | 0.4 |
| A | L2 FLAG | 8:22:53:17 | 3.2 | 0.5 | 0.1 | 0 | 1.3 | 0.1 | 0.1 | 79.6 | 0.4 | 1.9 | 0 | 11.8 | 1 |
| B† | L2 FLAG | 20:10:37:33 | 36.8 | 0.5 | 1.1 | 1.6 | 0.1 | 0.2 | 0 | 19.6 | 22.4 | 8 | 9.5 | 0.3 | 0.1 |
| B† | L2 FLAG | 20:10:24:46 | 34.7 | 0.1 | 0.5 | 1.6 | 0.2 | 0.1 | 0.1 | 12.2 | 33.9 | 6.2 | 9.9 | 0.3 | 0.3 |
| B† | L2 FLAG | 20:10:46:24 | 33 | 1.1 | 0.8 | 0.6 | 0.1 | 0 | 0.1 | 40.6 | 9 | 9.3 | 5.2 | 0.2 | 0.1 |
| B† | L2 FLAG | 22:8:35:35 | 31.1 | 0.8 | 1.5 | 2.2 | 0.1 | 0 | 0 | 20.1 | 21.5 | 9.6 | 13 | 0 | 0 |
| B† | L2 FLAG | 20:10:35:35 | 29 | 0.3 | 2 | 2.1 | 0.1 | 0 | 0.1 | 14.5 | 20.4 | 13.5 | 17.5 | 0.3 | 0.1 |
| B† | L2 FLAG | 22:8:53:17 | 26.8 | 2.4 | 2.1 | 0.8 | 0.1 | 0.1 | 0 | 39.7 | 7.5 | 13.3 | 6.8 | 0.2 | 0.1 |
| B† | L2 FLAG | 15:15:35:35 | 43.7 | 0 | 0 | 0.5 | 0.2 | 0.5 | 0.3 | 22.6 | 24.8 | 0.4 | 0.4 | 2.9 | 3.7 |

TABLE 12-continued

Effect of DNA ratio titration on the percentage of antibody species, as assessed by LC-MS, of select wild-type systems

| System* | Tag | H1:H2: L1:L2 DNA ratio | H1L2_ H1L2 and H1L2_ H2L1 | H1L1_ H1L1 | H1L1_ H1L2 | H1L2_ H1L2 | H2L1_ H2L1 | H2L1_ H2L2 | H2L2_ H2L2 | H1L1_ H2L1 | H1L2_ H2L2 | H1L1 | H1L2 | H2L1 | H2L2 |
|---|---|---|---|---|---|---|---|---|---|---|---|---|---|---|---|
| B† | L2 FLAG | 22:8:17:53 | 13.3 | 0.0 | 1.0 | 5.7 | 0.3 | 0.1 | 0.0 | 1.7 | 36.8 | 8.4 | 32.5 | 0.1 | 0.1 |
| C† | NO TAGS | 17:13:35:35 | 45.4 | 0.2 | 0.8 | 0.3 | 0 | 0 | 0 | 24.7 | 16.1 | 5.8 | 5.8 | 0.5 | 0.2 |
| C† | NO TAGS | 15:15:35:35 | 47.8 | 0 | 0.2 | 0.1 | 0.2 | 0.2 | 0.1 | 28.1 | 17.1 | 1.9 | 2.2 | 1.4 | 0.8 |

*System A: CAT-2200 H1/L1 & Pertuzumab H2/L2; System B: SGN-CD19a H1/L1 & CAT-2200 H2/L2; System C: SGN-CD19a H1/L1 & CR8071 H2/L2

†Systems B† and C† for wild type controls differ from Systems B and C of designs in the orientation of H1L1 vs H2L2 warheads.

TABLE 13

LC-MS pairing data and post pA yields (mg/L) for wild type antibody constructs, and effect of tags on pairing

| System* | Tag | Post pA yield (mg/L A280) | % H1L1 Pairing (over all H1 species) | % H2L2 Pairing (over all H2 species) | % H1L1 and % H2L2 Pairing (over all species) | H1L1_ H2L2 and H1L2_ H2L1** | H1L1_ H2L2 and H1L2_ H2L1 | H1L1_ H1L1 | H1L1_ H1L2 | H1L2_ H1L2 | H2L1_ H2L1 |
|---|---|---|---|---|---|---|---|---|---|---|---|
| A | L2 FLAG | 41 | 57.4 | 79.9 | 70.6 | 47 | 36.5 | 0.3 | 0.3 | 0.1 | 0.2 |
| A | L1 HA | 45 | 19.1 | 93.1 | 61 | 16.9 | 14.3 | 0.2 | 0.3 | 0.3 | 0.2 |
| B† | L2 FLAG | 44 | 64.1 | 64.8 | 60 | 34.4 | 26.3 | 0 | 0 | 0.5 | 0.3 |
| B† | L1 FLAG | 58 | 37.6 | 92 | 71.2 | 32.1 | 23.5 | 0.2 | 0 | 0 | 0.1 |
| B† | L2 HA | 72 | 54.2 | 70.1 | 66.7 | 35.1 | 17 | 0 | 0 | 0 | 1 |
| C† | NO TAGS | 38 | 71.3 | 68.1 | 68.9 | 51.9 | 45.2 | 0 | 0 | 0 | 0.2 |
| C† | L1 FLAG | 56 | 59.9 | 82.3 | 71.8 | 48.1 | 43.7 | 0.1 | 0 | 0.1 | 0.3 |
| C† | L2 FLAG | 63 | 79.6 | 48.4 | 57.5 | 46.8 | 30.1 | 0 | 0 | 0.1 | 3.2 |

| System* | H2L1_ H2L2 | H2L2_ H2L2 | H1L1_ H2L1 | H1L2_ H2L2 | H1L1 | H1L2 | H2L1 | H2L2 |
|---|---|---|---|---|---|---|---|---|
| A | 0.3 | 0.6 | 14.6 | 23.9 | 1.7 | 1.9 | 4.3 | 12.3 |
| A | 0.1 | 0.4 | 1.4 | 67.8 | 0.1 | 0.7 | 3 | 11.1 |
| B† | 0.6 | 1.1 | 15.9 | 24.8 | 0.4 | 0.4 | 4.9 | 14.1 |
| B† | 0.4 | 2.1 | 3.1 | 43.7 | 1 | 2 | 3.1 | 20.9 |
| B† | 2.2 | 3.1 | 5.8 | 19.2 | 0.3 | 0.2 | 18.5 | 32.7 |
| C† | 0.2 | 0.1 | 15.2 | 18.9 | 1.7 | 1.5 | 7.3 | 4.1 |
| C† | 0.2 | 0.3 | 11.4 | 34.8 | 0.5 | 1.4 | 3.2 | 4 |
| C† | 2.6 | 0.8 | 16.3 | 11.2 | 0.2 | 0.3 | 23.8 | 11.4 |

*System A: CAT-2200 H1/L1 & Perhtzumab H2/L2 (with 10:20:24:46 ratio H1:H2:L1:L2 DNA); System B: SGN-CD19a H1/L1 & CAT-2200 H2/L2 (with 15:15:35:35 ratio H1:H2:L1:L2 DNA); System C: SGN-CD19a H1/L1 & CR8071 H2/L2 (with 15:15:35:35 ratio H1:H2:L1:L2 DNA)

Multiple LCMS SMCA experiments were performed for some constructs In those cases, the mean pairing values and median amounts of each SMCA species are reported.

**considering full Ab species only

†Systems B† and C† for wild type controls differ from Systems B and C of designs in the orientation of H1L1 vs H2L2 warheads.

TABLE 14

| LC-MS pairing data and post pA yields (mg/L) for K-L designs total pairing) | | | | | | | | | | | | | |
|---|---|---|---|---|---|---|---|---|---|---|---|---|---|
| Design§ | Cluster | System* | Post pA yield (mg per L expression) | % H1L1 Pairing | Change in % H1L1 Pairing with respect to wild type | % H2L2 Pairing | Change in % H2L2 Pairing with respect to wild type | % H1L1 and % H2L2 Pairing | Change in % H1L1 and % H2L2 Pairing with respect to wild type | H1L1_ H2L2 and H1L2_ H2L1** | Change in H1L1_ H2L2 and H1L2_ H2L1** with respect to wild type | H1L1_ H2L2 and H1L2_ H2L1 | H1L1_ H1L1 |
| Transferable in 3/3 systems | | | | | | | | | | | | | |
| 2892 | kl-6 | A | 28 | 81.3 | 62.2 | 98.3 | 5.2 | 94.1 | 33.1 | 71.8 | 54.9 | 39.1 | 0.1 |
| | | B | 34 | 84.7 | 14.6 | 94.3 | 40.1 | 88.7 | 22 | 84.2 | 49.1 | 63.4 | 0.6 |
| | | C | 32 | 41.5 | −6.9 | 99.6 | 20 | 69.9 | 12.4 | 41 | −5.8 | 34.3 | 0.1 |
| 2901 | kl-6 | A | 20 | 94.3 | 75.2 | 97.9 | 4.8 | 96.6 | 35.6 | 87 | 70.2 | 64.1 | 0.2 |
| | | B | 18 | 85.7 | 15.6 | 94.6 | 40.4 | 88.8 | 22.1 | 79.2 | 44.1 | 48.2 | 1.6 |
| | | C | 19 | 62.6 | 14.2 | 99.5 | 19.9 | 78.7 | 21.2 | 60.6 | 13.8 | 46.6 | 1.4 |
| 2979 | kl-4 | A | 20 | 99.4 | 47.6‡ | 98.3 | 27.2‡ | 98.8 | 31.5‡ | 95.7 | 63.8‡ | 83.8 | 1.5 |
| | | B | 30 | 98 | 6 | 77.3 | 39.7 | 86.7 | 15.5 | 72.4 | 40.3 | 63.7 | 0.2 |
| | | C | 14 | 94.5 | 12.2 | 99.5 | 39.6 | 98.5 | 26.7 | 79.9 | 31.8 | 34.3 | 0 |
| 3008 | kl-3 | A | 27 | 98.8 | 79.7 | 98.3 | 5.2 | 98.5 | 37.5 | 96.7 | 79.8 | 75.9 | 0 |
| | | B | 26 | 98.3 | 28.2 | 98.8 | 44.6 | 98.4 | 31.7 | 93.2 | 58.1 | 57 | 2.1 |
| | | C | 17 | 84.7 | 36.3 | 99.6 | 20 | 90.1 | 32.6 | 78.2 | 31.4 | 56.5 | 2.9 |
| 3018 | kl-3 | A | 23 | 97.1 | 78 | 98.7 | 5.6 | 98 | 37 | 95.3 | 78.4 | 72.4 | 0 |
| | | B | 33 | 96 | 25.9 | 98.6 | 44.4 | 96.5 | 29.8 | 77.9 | 42.8 | 33.9 | 7.1 |
| | | C | 18 | 79.7 | 11.6 | 99.5 | 28.2 | 84.3 | 15.4 | 70 | 18.1 | 34.3 | 3.4 |
| 3025 | kl-2 | A | 35 | 83.6 | 64.5 | 99.1 | 6 | 93.9 | 33 | 72.7 | 55.9 | 54.9 | 0.1 |
| | | B | 30 | 80.2 | 10.1 | 87.9 | 33.7 | 85.5 | 18.8 | 71.4 | 36.3 | 44.9 | 0 |
| | | C | 37 | 43.9 | −4.5 | 99.7 | 20.1 | 70.1 | 12.6 | 41.1 | −5.7 | 40.4 | 1.8 |
| 3102 | kl-12 | A | 28 | 96.5 | 44.7‡ | 97.6 | 26.5‡ | 97.1 | 29.8‡ | 93.1 | 61.2‡ | 81.3 | 0.1 |
| | | B | 33 | 96.6 | 4.6 | 92.8 | 55.2 | 94.4 | 23.2 | 86.9 | 54.8 | 74.7 | 0.2 |
| | | C | 27 | 88.7 | 6.4 | 99.8 | 39.9 | 98.1 | 26.3 | 65.2 | 17.1 | 27.1 | 0.1 |
| 3109 | kl-8 | A | 16 | 99.7 | 47.9‡ | 97.4 | 26.3‡ | 98.6 | 31.3‡ | 96.4 | 64.5‡ | 81.3 | 0.8 |
| | | B | 35 | 99.1 | 29‡ | 97.1 | 42.9‡ | 98 | 31.3‡ | 94.1 | 59‡ | 78.4 | 0.3 |
| | | C | 21 | 84 | 15.9‡ | 99.6 | 28.3‡ | 97.9 | 29‡ | 66.8 | 18.7‡ | 17.6 | 0.1 |
| 3113 | kl-12 | A | 33 | 97 | 45.2‡ | 98.4 | 27.3‡ | 97.8 | 30.5‡ | 93.8 | 61.9‡ | 74.7 | 0.2 |
| | | B | 43 | 98.9 | 6.9 | 90.9 | 53.3 | 94.3 | 23.1 | 85.6 | 53.5 | 72.8 | 0.3 |
| | | C | 28 | 76.7 | −5.6 | 99.6 | 39.7 | 95.2 | 23.4 | 64 | 15.9 | 28.3 | 0 |
| 3122 | kl-5 | A | 16 | 85.9 | 34.1‡ | 23.4 | −47.7‡ | 85.8 | 18.5‡ | 0 | −31.9‡ | 0 | 10.4 |
| | | B | 38 | 96.9 | 4.9 | 89.7 | 52.1 | 92.9 | 21.7 | 84.7 | 52.6 | 72.7 | 0.2 |
| | | C | 45 | 65.8 | −16.5 | 99.8 | 39.9 | 91.1 | 19.3 | 61.5 | 13.4 | 32.6 | 0.1 |
| 3878 | kl-8 | A | 21 | 99.7 | 47.9‡ | 89.7 | 18.6‡ | 94.6 | 27.3‡ | 87.6 | 55.7‡ | 78.1 | 0.6 |
| | | B | 31 | 97.7 | 5.7 | 28.7 | −8.9 | 71.8 | 0.6 | 24.2 | −7.9 | 17.3 | 3.6 |
| | | C | 30 | 99.3 | 17 | 67.4 | 7.5 | 88.2 | 16.4 | 61.3 | 13.2 | 42.6 | 6 |
| 3890 | kl-9 | A | 29 | 99.8 | 48‡ | 87.5 | 16.4‡ | 93.3 | 26‡ | 85.1 | 53.2‡ | 70.7 | 1.7 |
| | | B | 24 | 99.7 | 29.6‡ | 51.3 | −2.9‡ | 73.7 | 7‡ | 47.7 | 12.6‡ | 41.4 | 1.1 |
| | | C | 27 | 98.4 | 30.3 | 88.5 | 17.2 | 92.8 | 23.9 | 86.3 | 34.4 | 72.3 | 0.7 |
| 3898 | kl-8 | A | 15 | 98.7 | 46.9‡ | 98.7 | 27.6† | 98.7 | 31.4‡ | 93.9 | 62‡ | 81.4 | 2.3 |
| | | B | 21 | 97.3 | 5.3 | 74.5 | 36.9 | 85.9 | 14.7 | 71.1 | 39 | 68.7 | 0.5 |
| | | C | 11 | 97.4 | 15.1 | 95.2 | 35.3 | 96.3 | 24.5 | 91.4 | 43.3 | 87.4 | 0.4 |
| 3931 | kl-7 | A | 30 | 92.2 | 73.1 | 94.9 | 1.8 | 93.6 | 32.6 | 83.9 | 67.1 | 70.7 | 0.5 |
| | | B | 39 | 85.5 | 15.4 | 83.6 | 29.4 | 85 | 18.3 | 60.7 | 25.6 | 35.4 | 6.8 |
| | | C | 40 | 57.1 | 8.7 | 99.5 | 19.9 | 68.6 | 11.1 | 45.7 | −1.1 | 27.3 | 4.6 |
| 3947 | kl-4 | A | 16 | 99.6 | 47.8‡ | 92.8 | 21.7‡ | 96.3 | 29‡ | 89.1 | 57.2‡ | 73.2 | 2.3 |
| | | B | 24 | 98.8 | 28.7‡ | 70.3 | 16.1‡ | 81.7 | 15‡ | 66.1 | 31‡ | 53.4 | 0.2 |
| | | C | 11 | 91.3 | 23.2 | 94.5 | 23.2 | 94 | 25.1 | 65.7 | 13.8 | 23.4 | 0.2 |
| 3951 | kl-4 | A | 14 | 98.7 | 46.9‡ | 89.5 | 18.4‡ | 93.2 | 25.9‡ | 83.5 | 51.6‡ | 63.3 | 0.2 |
| | | B | 23 | 99.8 | 29.7‡ | 77.5 | 23.3‡ | 85.6 | 18.9‡ | 72.8 | 37.7‡ | 52.5 | 0.1 |
| | | C | 23 | 97.5 | 29.4 | 97.1 | 25.8 | 97.3 | 28.4 | 92.2 | 40.3 | 73.6 | 0 |
| 3954 | kl-7 | A | 35 | 99.1 | 47.3‡ | 97.7 | 26.6‡ | 98.3 | 31‡ | 92.7 | 60.8‡ | 71.9 | 1 |
| | | B | 38 | 98.4 | 28.3‡ | 61.8 | 7.6‡ | 88.6 | 21.9‡ | 46 | 10.9‡ | 27.3 | 12.9 |
| | | C | 39 | 89 | 40.6 | 98.7 | 19.1 | 92.4 | 34.9 | 78.1 | 31.3 | 55.4 | 8.9 |
| 3957 | kl-7 | A | 32 | 90.2 | 71.1 | 90.6 | −2.5 | 90.4 | 29.5 | 78.8 | 61.9 | 66.8 | 0.6 |
| | | B | 34 | 99 | 28.9 | 85.4 | 31.2 | 95.6 | 28.9 | 70.9 | 35.8 | 36.5 | 7.9 |
| | | C | 41 | 87.2 | 38.8 | 99.7 | 20.1 | 90.8 | 33.3 | 75.5 | 28.7 | 45.7 | 8 |
| 3967 | kl-9 | A | 12 | 100 | 42.6 | 99.9 | 20 | 99.9 | 29.3 | 97.2 | 50.2 | 68.3 | 1.8 |
| | | B | 18 | 97.1 | 27‡ | 98.6 | 44.4‡ | 98 | 31.3‡ | 91.8 | 56.7‡ | 69.4 | 0.3 |
| | | C | 14 | 96.7 | 28.6 | 100 | 28.7 | 98.6 | 29.7 | 95.2 | 43.3 | 80 | 0.8 |
| 3971 | kl-2 | A | 27 | 98.9 | 79.8 | 99.1 | 6 | 99.1 | 38.1 | 87.4 | 70.6 | 45.6 | 0.2 |
| | | B | 27 | 97.9 | 27.8 | 99.3 | 45.1 | 98.9 | 32.2 | 93.2 | 58.1 | 62.3 | 0 |
| | | C | 30 | 89 | 40.6 | 99.8 | 20.2 | 92.5 | 35 | 82.6 | 35.8 | 54.2 | 3.9 |
| 3972 | kl-2 | A | 25 | 99.9 | 48.1‡ | 99.5 | 28.4‡ | 99.7 | 32.4‡ | 96.9 | 65‡ | 79.4 | 1.2 |
| | | B | 36 | 98.1 | 28‡ | 99.7 | 45.5‡ | 98.5 | 31.8‡ | 84 | 48.9‡ | 46.5 | 8.1 |
| | | C | 38 | 92.8 | 44.4 | 99.8 | 20.2 | 95.2 | 37.7 | 81.3 | 34.5 | 57.4 | 5.7 |

TABLE 14-continued

| | | | | | | | | | | | | | |
|---|---|---|---|---|---|---|---|---|---|---|---|---|---|
| 3974 | kl-1 | A | 22 | 91.8 | 72.7 | 94.7 | 1.6 | 93.5 | 32.5 | 83.7 | 66.8 | 62.3 | 0.4 |
| | | B | 38 | 97.6 | 27.5 | 92.6 | 38.4 | 96.5 | 29.8 | 72.9 | 37.8 | 34 | 8.3 |
| | | C | 36 | 59.9 | 11.5 | 99.8 | 20.2 | 71 | 13.5 | 49.5 | 2.7 | 31.4 | 5.6 |
| 3980† | kl-2 | A | 26 | 99.7 | 47.9‡ | 74.8 | 3.7‡ | 86.9 | 19.6‡ | 71.4 | 39.5‡ | 59 | 1.9 |
| | | B | 37 | 99.8 | 29.7‡ | 82.6 | 28.4‡ | 95.1 | 28.4‡ | 69.6 | 34.5‡ | 39.6 | 8.3 |
| 3987 | kl-3 | A | 25 | 99.7 | 47.9‡ | 83 | 11.9‡ | 93.9 | 26.6‡ | 80.7 | 48.8‡ | 51.6 | 2.7 |
| | | B | 27 | 97.5 | 27.4‡ | 98.1 | 43.9‡ | 97.6 | 30.9‡ | 66.4 | 31.3‡ | 24.8 | 11.1 |
| | | C | 21 | 99.2 | 50.8 | 99.3 | 19.7 | 99.2 | 41.7 | 78.9 | 32.1 | 37.4 | 9.2 |
| 3997 | kl-1 | A | 14 | 99.8 | 48‡ | 90.7 | 19.6‡ | 94.9 | 27.6‡ | 85.9 | 54‡ | 69 | 0.6 |
| | | B | 25 | 98.8 | 28.7‡ | 53 | −1.2‡ | 90.6 | 23.9‡ | 38 | 2.9‡ | 16 | 12.2 |
| | | C | 6 | 96 | 27.9 | 99.9 | 28.6 | 96 | 27.1 | 2.9 | −49 | 0.4 | 11.2 |
| 4008 | kl-8 | A | 22 | 100 | 42.6 | 99.3 | 19.4 | 99.7 | 29.1 | 96.5 | 49.5 | 81.6 | 1.2 |
| | | B | 30 | 99.6 | 7.6 | 70.9 | 33.3 | 84.6 | 13.4 | 68.7 | 36.6 | 60.2 | 0.6 |
| | | C | 26 | 99.6 | 17.3 | 98.3 | 38.4 | 98.9 | 27.1 | 96.8 | 48.7 | 85.5 | 0.1 |
| 4010 | kl-12 | A | 29 | 99.9 | 42.5 | 98.9 | 19 | 99.5 | 28.9 | 98.1 | 51.1 | 76.7 | 0.2 |
| | | B | 27 | 99.5 | 7.5 | 71.5 | 33.9 | 84.8 | 13.6 | 67.1 | 35 | 59.9 | 0.5 |
| | | C | 23 | 99.3 | 17 | 98.6 | 38.7 | 98.9 | 27.1 | 96.7 | 48.6 | 83.6 | 0.2 |
| 4040 | kl-8 | A | 29 | 99.8 | 48‡ | 97.7 | 26.6‡ | 98.7 | 31.4‡ | 94.6 | 62.7‡ | 85.8 | 1.2 |
| | | B | 41 | 99.2 | 29.1‡ | 75.8 | 21.6‡ | 86 | 19.3‡ | 73.7 | 38.6‡ | 62.7 | 0.6 |
| | | C | 19 | 98.7 | 30.6 | 98.6 | 27.3 | 98.7 | 29.8 | 81.8 | 29.9 | 51.2 | 1.2 |
| 4320 | kl-10 | A | 14 | 99.7 | 47.9‡ | 91.4 | 20.3‡ | 95.4 | 28.1‡ | 89.1 | 57.2‡ | 77.7 | 0.6 |
| | | B | 35 | 99.8 | 7.8 | 55.5 | 17.9 | 73.4 | 2.2 | 47.9 | 15.8 | 38.9 | 0.3 |
| | | C | 22 | 96.6 | 14.3 | 81.4 | 21.5 | 89 | 17.2 | 77.1 | 29 | 75 | 0.6 |
| Transferable in 2/3 systems | | | | | | | | | | | | | |
| 2994 | kl-3 | A | 35 | 78.3 | 59.2 | 98.9 | 5.8 | 92 | 31 | 70.1 | 53.2 | 50 | 0.7 |
| | | B | 42 | 84.8 | 14.7 | 99.2 | 45 | 90.9 | 24.2 | 80.9 | 45.8 | 64.6 | 3.5 |
| | | C | 33 | 26.3 | −22.1 | 99.7 | 20.1 | 57.4 | −0.1 | 25.5 | −21.3 | 19.9 | 0.3 |
| 3041 | kl-3 | A | 8 | 66.7 | 47.6 | 23.5 | −69.6 | 66.6 | 5.6 | 0 | −16.9 | 0 | 5.4 |
| | | B | 29 | 75.6 | 5.5 | 99.6 | 45.4 | 92.2 | 25.5 | 71 | 35.9 | 46.3 | 0.1 |
| | | C | 26 | 27.2 | −21.2 | 99.9 | 20.3 | 54.4 | −3.1 | 29 | −17.8 | 20.9 | 0.8 |
| 3910 | kl-10 | A | 20 | 99.6 | 47.8‡ | 57 | −14.1‡ | 79.1 | 11.8‡ | 54.1 | 22.2‡ | 43.9 | 1.8 |
| | | B | 41 | 99.6 | 7.6 | 39.7 | 2.1 | 66.9 | −4.3 | 34 | 1.9 | 29.9 | 0.5 |
| | | C | 52 | 99.3 | 17 | 81 | 21.1 | 89.5 | 17.7 | 78.7 | 30.6 | 73.2 | 0.3 |
| Transferable in 1/3 systems | | | | | | | | | | | | | |
| 4022 | kl-11 | A | 10 | 70.4 | 18.6‡ | 90.4 | 19.3‡ | 80.6 | 13.3‡ | 62.9 | 31‡ | 57.3 | 1.3 |
| | | B | 20 | 35.4 | −34.7‡ | 90.4 | 36.2‡ | 61.3 | −5.4‡ | 40.6 | 5.5‡ | 27 | 0.4 |
| | | C | 21 | 10 | −38.4 | 87.6 | 8 | 48 | −9.5 | 7.7 | −39.1 | 7 | 0.5 |

| | | | LC-MS pairing data and post pA yields (mg/L) for K-L designs total pairing) | | | | | | | | | | |
|---|---|---|---|---|---|---|---|---|---|---|---|---|---|
| | | | H1L1_H1L2 | H1L2_H1L2 | H2L1_H2L1 | H2L1_H2L2 | H2L2_H2L2 | H1L1_H2L1 | H1L2_H2L2 | H1L1 | H1L2 | H2L1 | H2L2 |
| Transferable in 3/3 systems | | | | | | | | | | | | | |
| 2892 | kl-6 | A | 0.2 | 0.2 | 0.3 | 1 | 5 | 0.2 | 8.3 | 0.4 | 0.2 | 0.3 | 44.6 |
| | | B | 0.1 | 0.5 | 0.3 | 0.2 | 0.1 | 3.2 | 7 | 15.8 | 4.9 | 0.3 | 3.7 |
| | | C | 0.6 | 0.8 | 0 | 0 | 0.1 | 0.2 | 47.5 | 3.6 | 5.1 | 0 | 7.6 |
| 2901 | kl-6 | A | 0.3 | 0.1 | 0.3 | 1.5 | 3.5 | 0.4 | 3.4 | 2.3 | 0.2 | 0.1 | 23.7 |
| | | B | 0.3 | 0.3 | 0.3 | 0.2 | 0.2 | 2.2 | 7.7 | 29 | 5 | 0.4 | 4.7 |
| | | C | 1.2 | 1.4 | 0.1 | 0 | 0.5 | 0 | 25.7 | 10 | 6.3 | 0.1 | 6.7 |
| 2979 | kl-4 | A | 0 | 0.2 | 0.9 | 0 | 1 | 0 | 0.2 | 5.4 | 0 | 0 | 7.1 |
| | | B | 0.1 | 0.8 | 0.1 | 0 | 0.8 | 22.1 | 0 | 1.2 | 0 | 1.2 | 9.6 |
| | | C | 0.7 | 0 | 0.1 | 0 | 6 | 0.5 | 1.3 | 0 | 0 | 0.1 | 56.9 |
| 3008 | kl-3 | A | 0.1 | 0.2 | 0.1 | 0.3 | 0.2 | 1.3 | 0.5 | 2.1 | 0.1 | 0.1 | 19.3 |
| | | B | 0 | 0.2 | 0.1 | 0 | 0.1 | 0.2 | 1.4 | 35.8 | 0.3 | 0.1 | 2.7 |
| | | C | 3.8 | 0.5 | 0 | 0.1 | 0.3 | 0.1 | 8.1 | 20.8 | 3.4 | 0 | 3.5 |
| 3018 | kl-3 | A | 0 | 0.1 | 0.1 | 0 | 1 | 0.6 | 1.7 | 3.1 | 0.2 | 0.4 | 20.3 |
| | | B | 0.1 | 0.2 | 0.1 | 0 | 0 | 0.2 | 1.8 | 52.9 | 2.1 | 0.1 | 1.4 |
| | | C | 0.8 | 0.3 | 0 | 0 | 0 | 0.2 | 10.1 | 40.4 | 9.8 | 0 | 0.8 |
| 3025 | kl-2 | A | 0 | 0 | 0.1 | 0.4 | 8.9 | 0.4 | 10.7 | 0.1 | 0.1 | 0.1 | 24.1 |
| | | B | 0 | 0.1 | 0.1 | 0.1 | 2 | 3.6 | 12 | 0.6 | 0 | 6.4 | 30.1 |
| | | C | 1.4 | 2.3 | 0.1 | 0 | 0.2 | 0.1 | 52.1 | 0.6 | 0.7 | 0 | 0.3 |
| 3102 | kl-12 | A | 0 | 0.5 | 1.2 | 0.2 | 1.8 | 0 | 2.1 | 2.8 | 0 | 0 | 9.9 |
| | | B | 0.1 | 1.3 | 0.1 | 0 | 2 | 7.4 | 0 | 0.1 | 0 | 0.3 | 13.7 |
| | | C | 0.4 | 0 | 0.1 | 0 | 11 | 0.1 | 2.9 | 0 | 0.1 | 0 | 58.2 |
| 3109 | kl-8 | A | 0.1 | 0 | 0.5 | 1.2 | 0.3 | 0 | 0.2 | 10.7 | 0 | 0.1 | 4.8 |
| | | B | 0.1 | 0 | 0 | 0 | 1.1 | 2.8 | 0.6 | 0.2 | 0 | 0.2 | 16.2 |
| | | C | 0.3 | 0.1 | 0.1 | 0 | 5.6 | 0 | 2.6 | 0.1 | 0.2 | 0.2 | 73.1 |
| 3113 | kl-12 | A | 0 | 0 | 0.9 | 0 | 1.3 | 0.1 | 2.4 | 2.1 | 0 | 0 | 18.2 |
| | | B | 0.2 | 0.1 | 0 | 0 | 1.7 | 9.5 | 0.4 | 1.1 | 0 | 0.4 | 13.4 |
| | | C | 0.6 | 0.1 | 0.2 | 0 | 7.8 | 0.3 | 7 | 0.1 | 0.6 | 0 | 55 |
| 3122 | kl-5 | A | 2.5 | 0.5 | 0 | 0 | 0 | 0.2 | 0 | 74 | 12.3 | 0 | 0 |
| | | B | 0.2 | 0.5 | 0.1 | 0 | 0.8 | 10.2 | 1 | 1.6 | 0.3 | 0.5 | 11.8 |
| | | C | 0.4 | 0.5 | 0.1 | 0 | 3.4 | 0.2 | 15.9 | 0.2 | 0.1 | 0 | 46.7 |

TABLE 14-continued

| | | | | | | | | | | | | | |
|---|---|---|---|---|---|---|---|---|---|---|---|---|---|
| 3878 | kl-8 | A | 0 | 0 | 0.2 | 0.3 | 1 | 8.7 | 0.2 | 4.7 | 0 | 0.6 | 5.5 |
| | | B | 0.7 | 1 | 0.9 | 0.1 | 0.2 | 47.8 | 0.1 | 24.5 | 0 | 2 | 1.9 |
| | | C | 0.6 | 0.1 | 0 | 0.2 | 0.1 | 19.7 | 0.1 | 27.3 | 0 | 1.4 | 1.9 |
| 3890 | kl-9 | A | 0 | 0 | 0 | 0 | 1.2 | 9.2 | 0.1 | 5.4 | 0 | 1.9 | 9.5 |
| | | B | 0 | 0 | 0.2 | 0.1 | 0.4 | 43.4 | 0.1 | 2.7 | 0 | 4.2 | 6.4 |
| | | C | 0.3 | 0.3 | 0 | 0.2 | 0.9 | 8.5 | 0.5 | 2.1 | 0 | 2 | 12.1 |
| 3898 | kl-8 | A | 0 | 0 | 0.6 | 0 | 1 | 0 | 1.3 | 9.1 | 0 | 0 | 4.3 |
| | | B | 0.3 | 1 | 0 | 0 | 0.8 | 25 | 0.2 | 1.1 | 0 | 0.2 | 2.1 |
| | | C | 0.8 | 0 | 0 | 0.1 | 0.6 | 4.8 | 1.6 | 1 | 0.1 | 0 | 3.2 |
| 3931 | kl-7 | A | 0.2 | 0 | 0.2 | 1.7 | 1.5 | 3 | 6.5 | 7.2 | 0.4 | 0.1 | 8 |
| | | B | 1.7 | 0.2 | 0.2 | 0 | 0 | 7.9 | 6 | 32.6 | 6.4 | 0.3 | 2.3 |
| | | C | 3.5 | 2.2 | 0 | 0 | 0 | 0.1 | 22 | 21.6 | 16.3 | 0.1 | 2.2 |
| 3947 | kl-4 | A | 0 | 0 | 0.1 | 0.1 | 1.2 | 5 | 0.4 | 9.5 | 0 | 0.9 | 7.4 |
| | | B | 0.3 | 0 | 0.3 | 0.5 | 1.9 | 23.6 | 0.6 | 0.7 | 0 | 5.5 | 13 |
| | | C | 0.2 | 0.1 | 0 | 0.1 | 8 | 17 | 2 | 2.4 | 0.3 | 3.7 | 57.9 |
| 3951 | kl-4 | A | 0 | 0.3 | 1.7 | 0 | 3 | 6.8 | 0.3 | 4.2 | 0 | 1.1 | 18.8 |
| | | B | 0 | 0 | 0.1 | 0.2 | 1.5 | 17.7 | 0.1 | 0.9 | 0 | 5.3 | 21.6 |
| | | C | 0.2 | 0 | 0 | 0 | 2.6 | 16 | 1.8 | 0.5 | 0 | 0.9 | 18.8 |
| 3954 | kl-7 | A | 0 | 0 | 0.5 | 0 | 2.1 | 1.2 | 0.8 | 4.2 | 0 | 0.2 | 18 |
| | | B | 0.1 | 0.1 | 0 | 0 | 0.1 | 17.6 | 1.1 | 36.6 | 0.4 | 1.4 | 2.2 |
| | | C | 1.1 | 0.1 | 0 | 0 | 0.2 | 0.6 | 4.6 | 20.5 | 4.2 | 0.1 | 4.3 |
| 3957 | kl-7 | A | 0.1 | 0 | 0.1 | 0.1 | 0.4 | 7.9 | 86 | 8.9 | 0.7 | 0.4 | 5.3 |
| | | B | 0.1 | 0.1 | 0.1 | 0 | 0 | 6.4 | 0.3 | 44.4 | 0.4 | 0.4 | 3.3 |
| | | C | 0.9 | 0.2 | 0 | 0 | 0.2 | 0 | 5.5 | 31.2 | 5.8 | 0.1 | 2.4 |
| 3967 | kl-9 | A | 0 | 0 | 0 | 0 | 0 | 0 | 0 | 21.8 | 0 | 0 | 7.9 |
| | | B | 0.1 | 0 | 0 | 0.1 | 2 | 1.7 | 2.1 | 1.1 | 0 | 0 | 23.3 |
| | | C | 1.3 | 0 | 0 | 0 | 0.7 | 0 | 1.3 | 0.6 | 02 | 0 | 15.3 |
| 3971 | kl-2 | A | 0 | 0 | 0.1 | 0.3 | 5.1 | 0.7 | 0.1 | 0.2 | 0.2 | 0.1 | 47.4 |
| | | B | 0 | 0.2 | 0.1 | 0 | 3 | 0.3 | 1 | 0.7 | 0 | 0.2 | 32.2 |
| | | C | 0.7 | 0.2 | 0 | 0 | 0.1 | 0.1 | 6.5 | 28.4 | 3.6 | 0 | 2.3 |
| 3972 | kl-2 | A | 0 | 0 | 0.1 | 0 | 0.9 | 0.2 | 0.1 | 12.1 | 0 | 0 | 6 |
| | | B | 0.1 | 0.1 | 0 | 0 | 0.3 | 0.1 | 0.2 | 40 | 1.1 | 0 | 3.5 |
| | | C | 1.1 | 0 | 0 | 0 | 0.2 | 0.1 | 6 | 25.2 | 1.1 | 0 | 3.1 |
| 3974 | kl-1 | A | 4.4 | 0 | 0.3 | 0.4 | 1.9 | 2.8 | 2 | 4.1 | 0.3 | 1.1 | 20 |
| | | B | 0.3 | 0.2 | 0.2 | 0 | 0 | 2.7 | 1 | 49.3 | 1.1 | 0.1 | 3 |
| | | C | 4.5 | 1.8 | 0 | 0 | 0.1 | 0 | 20.1 | 19.7 | 14.9 | 0 | 19 |
| 3980† | kl-2 | A | 0.1 | 0 | 1.1 | 0.1 | 1.4 | 18.9 | 0.1 | 78 | 0.1 | 2.3 | 7.2 |
| | | B | 0 | 0 | 0.1 | 0.1 | 0.2 | 8.6 | 0.1 | 40.2 | 0.1 | 0.3 | 2.4 |
| 3987 | kl-3 | A | 0 | 0.1 | 1.2 | 0.4 | 0.1 | 7.7 | 0.1 | 33 | 0.1 | 0.6 | 2.3 |
| | | B | 0.3 | 0.2 | 0 | 0 | 0.1 | 0.4 | 0.4 | 60.4 | 1.6 | 0 | 0.7 |
| | | C | 0.4 | 0 | 0 | 0 | 0.1 | 0 | 0.2 | 51.8 | 0.3 | 0.1 | 0.4 |
| 3997 | kl-1 | A | 0 | 0.1 | 0.4 | 0 | 1.1 | 9.1 | 0.1 | 6.6 | 0 | 0 | 13 |
| | | B | 0.2 | 0.1 | 0 | 0 | 0 | 13.6 | 0 | 54 | 0.8 | 1.6 | 1.4 |
| | | C | 0.7 | 0.1 | 0 | 0 | 0 | 0 | 0.4 | 83.8 | 3.3 | 0 | 0.1 |
| 4008 | kl-8 | A | 0 | 0 | 0 | 0 | 1 | 0.6 | 0 | 8.7 | 0 | 0 | 6.9 |
| | | B | 0 | 0.1 | 0.1 | 0.1 | 0.7 | 25.7 | 0.1 | 4.1 | 0 | 2.2 | 6.1 |
| | | C | 0.3 | 0 | 0 | 0 | 0.7 | 1.7 | 0 | 1.3 | 0 | 0.1 | 10.3 |
| 4010 | kl-12 | A | 0 | 0 | 0.1 | 0.1 | 0.4 | 0.7 | 0 | 15.3 | 0 | 0 | 6.6 |
| | | B | 0.1 | 0.1 | 0.1 | 0.3 | 0.4 | 27.7 | 0.1 | 3 | 0 | 0.9 | 6.9 |
| | | C | 0.4 | 0 | 0 | 0 | 0.8 | 1.4 | 0 | 0.8 | 0 | 0.1 | 12.6 |
| 4040 | kl-8 | A | 0 | 0 | 0.9 | 0 | 2 | 0.7 | 0.1 | 3.7 | 0 | 0 | 5.5 |
| | | B | 0 | 0 | 0.1 | 0.1 | 0.6 | 20.4 | 0.6 | 1.3 | 0 | 3.3 | 10.3 |
| | | C | 0.1 | 0 | 0 | 0.3 | 8.2 | 1 | 0.5 | 0.5 | 0 | 0.3 | 36.7 |
| 4320 | kl-10 | A | 0 | 0 | 0.1 | 0.1 | 1.3 | 7.3 | 0.2 | 5 | 0 | 0.7 | 7.1 |
| | | B | 0.1 | 0 | 1 | 0.3 | 0.7 | 39.8 | 0.1 | 0.8 | 0 | 5.4 | 12.6 |
| | | C | 3.2 | 0 | 0.1 | 0.7 | 0.9 | 16.8 | 0.1 | 0.2 | 0.1 | 0.5 | 2 |
| Transferable in 2/3 systems | | | | | | | | | | | | | |
| 2994 | kl-3 | 2994 | 0 | 0 | 0.2 | 1 | 5.1 | 0.1 | 14.2 | 0.6 | 0.1 | 0 | 28 |
| | | | 0.3 | 0.3 | 0.2 | 0 | 0.1 | 0.2 | 10.6 | 12.9 | 3 | 0 | 4.2 |
| | | | 1.6 | 3.1 | 0 | 0 | 0.1 | 0 | 53.1 | 4.1 | 12 | 0.1 | 5.7 |
| 3041 | kl-3 | 3041 | 2.1 | 1.4 | 0 | 0 | 0 | 0 | 0 | 60.2 | 30.7 | 0.2 | 0.1 |
| | | | 0 | 0.3 | 0.2 | 0 | 3.8 | 0.1 | 14.5 | 0.1 | 0 | 0.1 | 34.6 |
| | | | 1.9 | 4 | 0 | 0 | 0.1 | 0 | 44.3 | 4.8 | 18.5 | 0 | 4.6 |
| 3910 | kl-10 | 3910 | 0 | 0 | 0 | 0.2 | 0.4 | 34.6 | 0.4 | 10.6 | 0 | 3.3 | 4.8 |
| | | | 0.1 | 0 | 0.9 | 0.4 | 0.5 | 55.4 | 0.3 | 2 | 0 | 4.1 | 6 |
| | | | 0.2 | 0.1 | 0.3 | 0.7 | 0.7 | 17.4 | 0 | 0.1 | 0.1 | 0.9 | 5.9 |
| Transferable in 1/3 systems | | | | | | | | | | | | | |
| 4022 | kl-11 | A | 0.2 | 0.1 | 1.5 | 0.8 | 0.4 | 4.8 | 24.7 | 2 | 1.9 | 0.6 | 4.5 |
| | | B | 0.5 | 1.2 | 0.6 | 4.1 | 1.1 | 0.4 | 31.3 | 4.4 | 17.1 | 1.6 | 10.3 |
| | | C | 1 | 1.7 | 2.7 | 6 | 0.9 | 0.7 | 70.9 | 0.3 | 8.3 | 0 | 0.1 |

*System A: CAT-2200 H1/L1 & Pertuzumab H2/L2 (with 10:20:24:46 ratio H1:H2:L1:L2 DNA); System B: CAT-2200 H1/L1 & SGN-CD19a H2/L2 (w.th 15:15:35:35 ratio H1:H2:L1 L2 DNA). System C: CR8071 H1/L1 & SGN-CD19a H2/L2 with 15:15:35:35 ratio H1:H2:L1:L2 DNA)

**Considering full Ab species only

§Designs are shaded with increasing grey according to their transferability in 3/3 (not shaded), 2/3, or 1/3 systems, based on a positive Change in % H1L1 and % H2L2 Pairing with respect to wild type ‡Estimated change with respect to wild type †Design 3980 was assessed only in 2 systems

TABLE 15

LC-MS pairing data and post pA yields (nng/L) for K-L designs total bispecific)

| Design§ | Cluster | System* | Post pA yield (mg/L A280) | % H1L1 Pairing | Change in % H1L1 Pairing with respect to wild type | % H2L2 Pairing | Change in % H2L2 Pairing with respect to wild type | % H2L2 Pairing | Change in % H1L1 and H2L2 Pairing with respect to wild type | H1L1_H2L2 and H1L2_H2L1** | Change in H1L1_H2L2 and H1L2_H2L1** with respect to wild type | H1L1_H2L2 and H1L2_H2L1 | H1L1_H1L1 |
|---|---|---|---|---|---|---|---|---|---|---|---|---|---|
| Transferable in 3/3 sytems: | | | | | | | | | | | | | |
| 2901 | kl-6 | A | 20 | 94.3 | 75.2 | 97.9 | 4.8 | 96.6 | 35.6 | 87 | 70.2 | 64.1 | 0.2 |
| | | B | 18 | 85.7 | 15.6 | 94.6 | 40.4 | 88.8 | 22.1 | 79.2 | 44.1 | 48.2 | 1.6 |
| | | C | 19 | 62.6 | 14.2 | 99.5 | 19.9 | 78.7 | 21.2 | 60.6 | 13.8 | 46.6 | 1.4 |
| 2979 | kl-4 | A | 20 | 99.4 | 47.6‡ | 98.3 | 27.2‡ | 98.8 | 31.5‡ | 95.7 | 63.8‡ | 83.8 | 1.5 |
| | | B | 30 | 98 | 6 | 77.3 | 39.7 | 86.7 | 15.5 | 72.4 | 40.3 | 63.7 | 0.2 |
| | | C | 14 | 94.5 | 12.2 | 99.5 | 39.6 | 98.5 | 26.7 | 79.9 | 31.8 | 34.3 | 0 |
| 3008 | kl-3 | A | 27 | 98.8 | 79.7 | 98.3 | 5.2 | 98.5 | 37.5 | 96.7 | 79.8 | 75.9 | 0 |
| | | B | 26 | 98.3 | 28.2 | 98.8 | 44.6 | 98.4 | 31.7 | 93.2 | 58.1 | 57 | 2.1 |
| | | C | 17 | 84.7 | 36.3 | 99.6 | 20 | 90.1 | 32.6 | 78.2 | 31.4 | 56.5 | 2.9 |
| 3018 | kl-3 | A | 23 | 97.1 | 78 | 98.7 | 5.6 | 98 | 37 | 95.3 | 78.4 | 72.4 | 0 |
| | | B | 33 | 96 | 25.9 | 98.6 | 44.4 | 96.5 | 29.8 | 77.9 | 42.8 | 33.9 | 7.1 |
| | | C | 18 | 79.7 | 11.6 | 99.5 | 28.2 | 84.3 | 15.4 | 70 | 18.1 | 34.3 | 3.4 |
| 3102 | kl-12 | A | 28 | 96.5 | 44.7‡ | 97.6 | 26.5‡ | 97.1 | 29.8‡ | 93.1 | 61.2‡ | 81.3 | 0.1 |
| | | B | 33 | 96.6 | 4.6 | 92.8 | 55.2 | 94.4 | 23.2 | 86.9 | 54.8 | 74.7 | 0.2 |
| | | C | 27 | 88.7 | 6.4 | 99.8 | 39.9 | 98.1 | 26.3 | 65.2 | 17.1 | 27.1 | 0.1 |
| 3109 | kl-8 | A | 16 | 99.7 | 47.9‡ | 97.4 | 26.3‡ | 98.6 | 31.3‡ | 96.4 | 64.5‡ | 81.3 | 0.8 |
| | | B | 35 | 99.1 | 29‡ | 97.1 | 42.9‡ | 98 | 31.3‡ | 94.1 | 59‡ | 78.4 | 0.3 |
| | | C | 21 | 84 | 15.9‡ | 99.6 | 28.3‡ | 97.9 | 29‡ | 66.8 | 18.7‡ | 17.6 | 0.1 |
| 3113 | kl-12 | A | 33 | 97 | 45.2‡ | 98.4 | 27.3‡ | 97.8 | 30.5‡ | 93.8 | 61.9‡ | 74.7 | 0.2 |
| | | B | 43 | 98.9 | 6.9 | 90.9 | 53.3 | 94.3 | 23.1 | 85.6 | 53.5 | 72.8 | 0.3 |
| | | C | 28 | 76.7 | −5.6 | 99.6 | 39.7 | 95.2 | 23.4 | 64 | 15.9 | 28.3 | 0 |
| 3890 | kl-9 | A | 29 | 99.8 | 48‡ | 87.5 | 16.4‡ | 93.3 | 26‡ | 85.1 | 53.2‡ | 70.7 | 1.7 |
| | | B | 24 | 99.7 | 29.6‡ | 51.3 | −2.9‡ | 73.7 | 7‡ | 47.7 | 12.6‡ | 41.4 | 1.1 |
| | | C | 27 | 98.4 | 30.3 | 88.5 | 17.2 | 92.8 | 23.9 | 86.3 | 34.4 | 72.3 | 0.7 |
| 3898 | kl-8 | A | 15 | 98.7 | 46.9‡ | 98.7 | 27.6‡ | 98.7 | 31.4‡ | 93.9 | 62‡ | 81.4 | 2.3 |
| | | B | 21 | 97.3 | 5.3 | 74.5 | 36.9 | 85.9 | 14.7 | 71.1 | 39 | 68.7 | 0.5 |
| | | C | 11 | 97.4 | 15.1 | 95.2 | 35.3 | 96.3 | 24.5 | 91.4 | 43.3 | 87.4 | 0.4 |
| 3910 | kl-10 | A | 20 | 99.6 | 47.8‡ | 57 | −14.1‡ | 79.1 | 11.8‡ | 54.1 | 22.2‡ | 43.9 | 1.8 |
| | | B | 41 | 99.6 | 7.6 | 39.7 | 2.1 | 66.9 | −4.3 | 34 | 1.9 | 29.9 | 0.5 |
| | | C | 52 | 99.3 | 17 | 81 | 21.1 | 89.5 | 17.7 | 78.7 | 30.6 | 73.2 | 0.3 |
| 3947 | kl-4 | A | 16 | 99.6 | 47.8‡ | 92.8 | 21.7‡ | 96.3 | 29‡ | 89.1 | 57.2‡ | 73.2 | 2.3 |
| | | B | 24 | 98.8 | 28.7‡ | 70.3 | 16.1‡ | 81.7 | 15‡ | 66.1 | 31‡ | 53.4 | 0.2 |
| | | C | 11 | 91.3 | 23.2 | 94.5 | 23.2 | 94 | 25.1 | 65.7 | 13.8 | 23.4 | 0.2 |
| 3951 | kl-4 | A | 14 | 98.7 | 46.9‡ | 89.5 | 18.4‡ | 93.2 | 25.9‡ | 83.5 | 51.6‡ | 63.3 | 0.2 |
| | | B | 23 | 99.8 | 29.7‡ | 77.5 | 23.3‡ | 85.6 | 18.9‡ | 72.8 | 37.7‡ | 52.5 | 0.1 |
| | | C | 23 | 97.5 | 29.4 | 97.1 | 25.8 | 97.3 | 28.4 | 92.2 | 40.3 | 73.6 | 0 |
| 3954 | kl-7 | A | 35 | 99.1 | 47.3‡ | 97.7 | 26.6‡ | 98.3 | 31‡ | 92.7 | 60.8‡ | 71.9 | 1 |
| | | B | 38 | 98.4 | 28.3‡ | 61.8 | 7.6‡ | 88.6 | 21.9‡ | 46 | 10.9‡ | 27.3 | 12.9 |
| | | C | 39 | 89 | 40.6 | 98.7 | 19.1 | 92.4 | 34.9 | 78.1 | 31.3 | 55.4 | 8.9 |
| 3957 | kl-7 | A | 32 | 90.2 | 71.1 | 90.6 | −2.5 | 90.4 | 29.5 | 78.8 | 61.9 | 66.8 | 0.6 |
| | | B | 34 | 99 | 28.9 | 85.4 | 31.2 | 95.6 | 28.9 | 70.9 | 35.8 | 36.5 | 7.9 |
| | | C | 41 | 87.2 | 38.8 | 99.7 | 20.1 | 90.8 | 33.3 | 75.5 | 28.7 | 45.7 | 8 |
| 3967 | kl-9 | A | 12 | 100 | 42.6 | 99.9 | 20 | 99.9 | 29.3 | 97.2 | 50.2 | 68.3 | 1.8 |
| | | B | 18 | 97.1 | 27‡ | 98.6 | 44.4‡ | 98 | 31.3‡ | 91.8 | 56.7‡ | 69.4 | 0.3 |
| | | C | 14 | 96.7 | 28.6 | 100 | 28.7 | 98.6 | 29.7 | 95.2 | 43.3 | 80 | 0.8 |
| 3971 | kl-2 | A | 27 | 98.9 | 79.8 | 99.1 | 6 | 99.1 | 38.1 | 87.4 | 70.6 | 45.6 | 0.2 |
| | | B | 27 | 97.9 | 27.8 | 99.3 | 45.1 | 98.9 | 32.2 | 93.2 | 58.1 | 62.3 | 0 |
| | | C | 30 | 89 | 40.6 | 99.8 | 20.2 | 92.5 | 35 | 82.6 | 35.8 | 54.2 | 3.9 |
| 3972 | kl-2 | A | 25 | 99.9 | 48.1‡ | 99.5 | 28.4‡ | 99.7 | 32.4‡ | 96.9 | 65‡ | 79.4 | 1.2 |
| | | B | 36 | 98.1 | 28‡ | 99.7 | 45.5‡ | 98.5 | 31.8‡ | 84 | 48.9‡ | 46.5 | 8.1 |
| | | C | 38 | 92.8 | 44.4 | 99.8 | 20.2 | 95.2 | 37.7 | 81.3 | 34.5 | 57.4 | 5.7 |
| 3974 | kl-1 | A | 22 | 91.8 | 72.7 | 94.7 | 1.6 | 93.5 | 32.5 | 83.7 | 66.8 | 62.3 | 0.4 |
| | | B | 38 | 97.6 | 27.5 | 92.6 | 38.4 | 96.5 | 29.8 | 72.9 | 37.8 | 34 | 8.3 |
| | | C | 36 | 59.9 | 11.5 | 99.8 | 20.2 | 71 | 13.5 | 49.5 | 2.7 | 31.4 | 5.6 |
| 3980† | kl-2 | A | 26 | 99.7 | 47.9‡ | 74.8 | 3.7‡ | 86.9 | 19.6‡ | 71.4 | 39.5‡ | 59 | 1.9 |
| | | B | 37 | 99.8 | 29.7‡ | 82.6 | 28.4‡ | 95.1 | 28.4‡ | 69.6 | 34.5‡ | 39.6 | 8.3 |
| 3987 | kl-3 | A | 25 | 99.7 | 47.9‡ | 83 | 11.9‡ | 93.9 | 26.6‡ | 80.7 | 48.8‡ | 51.6 | 2.7 |
| | | B | 27 | 97.5 | 27.4‡ | 98.1 | 43.9‡ | 97.6 | 30.9‡ | 66.4 | 31.3‡ | 24.8 | 11.1 |
| | | C | 21 | 99.2 | 50.8 | 99.3 | 19.7 | 99.2 | 41.7 | 78.9 | 32.1 | 37.4 | 9.2 |
| 4008 | kl-8 | A | 22 | 100 | 42.6 | 99.3 | 19.4 | 99.7 | 29.1 | 96.5 | 49.5 | 81.6 | 1.2 |
| | | B | 30 | 99.6 | 7.6 | 70.9 | 33.3 | 84.6 | 13.4 | 68.7 | 36.6 | 60.2 | 0.6 |
| | | C | 26 | 99.6 | 17.3 | 98.3 | 38.4 | 98.9 | 27.1 | 96.8 | 48.7 | 85.5 | 0.1 |

TABLE 15-continued

| | | | | | | | | | | | | | |
|---|---|---|---|---|---|---|---|---|---|---|---|---|---|
| 4010 | kl-12 | A | 29 | 99.9 | 42.5 | 98.9 | 19 | 99.5 | 28.9 | 98.1 | 51.1 | 76.7 | 0.2 |
| | | B | 27 | 99.5 | 7.5 | 71.5 | 33.9 | 84.8 | 13.6 | 67.1 | 35 | 59.9 | 0.5 |
| | | C | 23 | 99.3 | 17 | 98.6 | 38.7 | 98.9 | 27.1 | 96.7 | 48.6 | 83.6 | 0.2 |
| 4040 | kl-8 | A | 29 | 99.8 | 48‡ | 97.7 | 26.6‡ | 98.7 | 31.4‡ | 94.6 | 62.7‡ | 85.8 | 1.2 |
| | | B | 41 | 99.2 | 29.1‡ | 75.8 | 21.6‡ | 86 | 19.3‡ | 73.7 | 38.6‡ | 62.7 | 0.6 |
| | | C | 19 | 98.7 | 30.6 | 98.6 | 27.3 | 98.7 | 29.8 | 81.8 | 29.9 | 51.2 | 1.2 |
| 4320 | kl-10 | A | 14 | 99.7 | 47.9‡ | 91.4 | 20.3‡ | 95.4 | 28.1‡ | 89.1 | 57.2‡ | 77.7 | 0.6 |
| | | B | 35 | 99.8 | 7.8 | 55.5 | 17.9 | 73.4 | 2.2 | 47.9 | 15.8 | 38.9 | 0.3 |
| | | C | 22 | 96.6 | 14.3 | 81.4 | 21.5 | 89 | 17.2 | 77.1 | 29 | 75 | 0.6 |
| Transferable in 2/3 systems | | | | | | | | | | | | | |
| 2892 | kl-6 | A | 28 | 81.3 | 62.2 | 98.3 | 5.2 | 94.1 | 33.1 | 71.8 | 54.9 | 39.1 | 0.1 |
| | | B | 34 | 84.7 | 14.6 | 94.3 | 40.1 | 88.7 | 22 | 84.2 | 49.1 | 63.4 | 0.6 |
| | | C | 32 | 41.5 | −6.9 | 99.6 | 20 | 69.9 | 12.4 | 41 | −5.8 | 34.3 | 0.1 |
| 2994 | kl-3 | A | 35 | 78.3 | 59.2 | 98.9 | 5.8 | 92 | 31 | 70.1 | 53.2 | 50 | 0.7 |
| | | B | 42 | 84.8 | 14.7 | 99.2 | 45 | 90.9 | 24.2 | 80.9 | 45.8 | 64.6 | 3.5 |
| | | C | 33 | 26.3 | −22.1 | 99.7 | 20.1 | 57.4 | −0.1 | 25.5 | −21.3 | 19.9 | 0.3 |
| 3025 | kl-2 | A | 35 | 83.6 | 64.5 | 99.1 | 6 | 93.9 | 33 | 72.7 | 55.9 | 54.9 | 0.1 |
| | | B | 30 | 80.2 | 10.1 | 87.9 | 33.7 | 85.5 | 18.8 | 71.4 | 36.3 | 44.9 | 0 |
| | | C | 37 | 43.9 | −4.5 | 99.7 | 20.1 | 70.1 | 12.6 | 41.1 | −5.7 | 40.4 | 1.8 |
| 3122 | kl-5 | A | 16 | 85.9 | 34.1‡ | 23.4 | −47.7‡ | 85.8 | 18.5‡ | 0 | −31.9‡ | 0 | 10.4 |
| | | B | 38 | 96.9 | 4.9 | 89.7 | 52.1 | 92.9 | 21.7 | 84.7 | 52.6 | 72.7 | 0.2 |
| | | C | 45 | 65.8 | −16.5 | 99.8 | 39.9 | 91.1 | 19.3 | 61.5 | 13.4 | 32.6 | 0.1 |
| 3878 | kl-8 | A | 21 | 99.7 | 47.9‡ | 89.7 | 18.6‡ | 94.6 | 27.3‡ | 87.6 | 55.7‡ | 78.1 | 0.6 |
| | | B | 31 | 97.7 | 5.7 | 28.7 | −8.9 | 71.8 | 0.6 | 24.2 | −7.9 | 17.3 | 3.6 |
| | | C | 30 | 99.3 | 17 | 67.4 | 7.5 | 88.2 | 16.4 | 61.3 | 13.2 | 42.6 | 6 |
| 3931 | kl-7 | A | 30 | 92.2 | 73.1 | 94.9 | 1.8 | 93.6 | 32.6 | 83.9 | 67.1 | 70.7 | 0.5 |
| | | B | 39 | 85.5 | 15.4 | 83.6 | 29.4 | 85 | 18.3 | 60.7 | 25.6 | 35.4 | 6.8 |
| | | C | 40 | 57.1 | 8.7 | 99.5 | 19.9 | 68.6 | 11.1 | 45.7 | −1.1 | 27.3 | 4.6 |
| 3997 | kl-1 | A | 14 | 99.8 | 48‡ | 90.7 | 19.6‡ | 94.9 | 27.6‡ | 85.9 | 54‡ | 69 | 0.6 |
| | | B | 25 | 98.8 | 28.7‡ | 53 | −1.2‡ | 90.6 | 23.9‡ | 38 | 2.9‡ | 16 | 12.2 |
| | | C | 6 | 96 | 27.9 | 99.9 | 28.6 | 96 | 27.1 | 2.9 | −49 | 0.4 | 11.2 |
| 4022 | kl-11 | A | 10 | 70.4 | 18.6‡ | 90.4 | 19.3‡ | 80.6 | 13.3‡ | 62.9 | 31‡ | 57.3 | 1.3 |
| | | B | 20 | 35.4 | −34.7‡ | 90.4 | 36.2‡ | 61.3 | −5.4‡ | 40.6 | 5.5‡ | 27 | 0.4 |
| | | C | 21 | 10 | −38.4 | 87.6 | 8 | 48 | −9.5 | 7.7 | −39.1 | 7 | 0.5 |
| Transferable in 1/3 systems | | | | | | | | | | | | | |
| 3041 | kl-3 | A | 8 | 66.7 | 47.6 | 23.5 | −69.6 | 66.6 | 5.6 | 0 | −16.9 | 0 | 5.4 |
| | | B | 29 | 75.6 | 5.5 | 99.6 | 45.4 | 92.2 | 25.5 | 71 | 35.9 | 46.3 | 0.1 |
| | | C | 26 | 27.2 | −21.2 | 99.9 | 20.3 | 54.4 | −3.1 | 29 | −17.8 | 209 | 0.8 |

LC-MS pairing data and post pA yields (mg/L) for K-L designs total bispecific)

| | | | H1L1_ H1L2 | H1L2_ H1L2 | H2L1_ H2L1 | H2L1_ H2L2 | H1L2_ H1L2 | H1L1_ H2L1 | H1L2_ H2L2 | H1L1 | H1L2 | H2L1 | H2L2 |
|---|---|---|---|---|---|---|---|---|---|---|---|---|---|
| Transferable in 3/3 sytems: | | | | | | | | | | | | | |
| 2901 | kl-6 | A | 0.3 | 0.1 | 0.3 | 1.5 | 3.5 | 0.4 | 3.4 | 2.3 | 0.2 | 0.1 | 23.7 |
| | | B | 0.3 | 0.3 | 0.3 | 0.2 | 0.2 | 2.2 | 7.7 | 29 | 5 | 0.4 | 4.7 |
| | | C | 1.2 | 1.4 | 0.1 | 0 | 0.5 | 0 | 25.7 | 10 | 6.3 | 0.1 | 6.7 |
| 2979 | kl-4 | A | 0 | 0.2 | 0.9 | 0 | 1 | 0 | 0.2 | 5.4 | 0 | 0 | 7.1 |
| | | B | 0.1 | 0.8 | 0.1 | 0 | 0.8 | 22.1 | 0 | 1.2 | 0 | 1.2 | 9.6 |
| | | C | 0.7 | 0 | 0.1 | 0 | 6 | 0.5 | 1.3 | 0 | 0 | 0.1 | 56.9 |
| 3008 | kl-3 | A | 0.1 | 0.2 | 0.1 | 0.3 | 0.2 | 1.3 | 0.5 | 2.1 | 0.1 | 0.1 | 19.3 |
| | | B | 0 | 0.2 | 0.1 | 0 | 0.1 | 0.2 | 1.4 | 35.8 | 0.3 | 0.1 | 2.7 |
| | | C | 3.8 | 0.5 | 0 | 0.1 | 0.3 | 0.1 | 8.1 | 20.8 | 3.4 | 0 | 3.5 |
| 3018 | kl-3 | A | 0 | 0.1 | 0.1 | 0 | 1 | 0.6 | 1.7 | 3.1 | 0.2 | 0.4 | 20.3 |
| | | B | 0.1 | 0.2 | 0.1 | 0 | 0 | 0.2 | 1.8 | 52.9 | 2.1 | 0.1 | 1.4 |
| | | C | 0.8 | 0.3 | 0 | 0 | 0 | 0.2 | 10.1 | 40.4 | 9.8 | 0 | 0.8 |
| 3102 | kl-12 | A | 0 | 0.5 | 1.2 | 0.2 | 1.8 | 0 | 2.1 | 2.8 | 0 | 0 | 9.9 |
| | | B | 0.1 | 1.3 | 0.1 | 0 | 2 | 7.4 | 0 | 0.1 | 0 | 0.3 | 13.7 |
| | | C | 0.4 | 0 | 0.1 | 0 | 11 | 0.1 | 2.9 | 0 | 0.1 | 0 | 58.2 |
| 3109 | kl-8 | A | 0.1 | 0 | 0.5 | 1.2 | 0.3 | 0 | 0.2 | 10.7 | 0 | 0.1 | 4.8 |
| | | B | 0.1 | 0 | 0 | 0 | 1.1 | 2.8 | 0.6 | 0.2 | 0 | 0.2 | 16.2 |
| | | C | 0.3 | 0.1 | 0.1 | 0 | 5.6 | 0 | 2.6 | 0.1 | 0.2 | 0.2 | 73.1 |
| 3113 | kl-12 | A | 0 | 0 | 0.9 | 0 | 1.3 | 0.1 | 2.4 | 2.1 | 0 | 0 | 18.2 |
| | | B | 0.2 | 0.1 | 0 | 0 | 1.7 | 9.5 | 0.4 | 1.1 | 0 | 0.4 | 13.4 |
| | | C | 0.6 | 0.1 | 0.2 | 0 | 7.8 | 0.3 | 7 | 0.1 | 0.6 | 0 | 55 |
| 3890 | kl-9 | A | 0 | 0 | 0 | 0 | 1.2 | 9.2 | 0.1 | 5.4 | 0 | 1.9 | 9.5 |
| | | B | 0 | 0 | 0.2 | 0.1 | 0.4 | 43.4 | 0.1 | 2.7 | 0 | 4.2 | 6.4 |
| | | C | 0.3 | 0.3 | 0 | 0.2 | 0.9 | 8.5 | 0.5 | 2.1 | 0 | 2 | 12.1 |
| 3898 | kl-8 | A | 0 | 0 | 0.6 | 0 | 1 | 0 | 1.3 | 9.1 | 0 | 0 | 4.3 |
| | | B | 0.3 | 1 | 0 | 0 | 0.8 | 25 | 0.2 | 1.1 | 0 | 0.2 | 2.1 |
| | | C | 0.8 | 0 | 0 | 0.1 | 0.6 | 4.8 | 1.6 | 1 | 0.1 | 0 | 3.2 |
| 3910 | kl-10 | A | 0 | 0 | 0 | 0.2 | 0.4 | 34.6 | 0.4 | 10.6 | 0 | 3.3 | 4.8 |
| | | B | 0.1 | 0 | 0.9 | 0.4 | 0.5 | 55.4 | 0.3 | 2 | 0 | 4.1 | 6 |
| | | C | 0.2 | 0.1 | 0.3 | 0.7 | 0.7 | 17.4 | 0 | 0.1 | 0.1 | 0.9 | 5.9 |

TABLE 15-continued

| | | | | | | | | | | | | | |
|---|---|---|---|---|---|---|---|---|---|---|---|---|---|
| 3947 | kl-4 | A | 0 | 0 | 0.1 | 0.1 | 1.2 | 5 | 0.4 | 9.5 | 0 | 0.9 | 7.4 |
| | | B | 0.3 | 0 | 0.3 | 0.5 | 1.9 | 23.6 | 0.6 | 0.7 | 0 | 5.5 | 13 |
| | | C | 0.2 | 0.1 | 0 | 0.1 | 8 | 1.7 | 2 | 2.4 | 0.3 | 3.7 | 57.9 |
| 3951 | kl-4 | A | 0 | 0.3 | 1.7 | 0 | 3 | 6.8 | 0.3 | 4.2 | 0 | 1.1 | 18.8 |
| | | B | 0 | 0 | 0.1 | 0.2 | 15 | 17.7 | 0.1 | 0.9 | 0 | 5.3 | 21.6 |
| | | C | 0.2 | 0 | 0 | 0 | 26 | 1.6 | 18 | 0.5 | 0 | 0.9 | 18.8 |
| 3954 | kl-7 | A | 0 | 0 | 0.5 | 0 | 2.1 | 12 | 0.8 | 4.2 | 0 | 0.2 | 18 |
| | | B | 0.1 | 0.1 | 0 | 0 | 0.1 | 17.6 | 1.1 | 36.6 | 0.4 | 1.4 | 2.2 |
| | | C | 1.1 | 0.1 | 0 | 0 | 0.2 | 0.6 | 4.6 | 20.5 | 4.2 | 0.1 | 4.3 |
| 3957 | kl-7 | A | 0.1 | 0 | 0.1 | 0.1 | 0.4 | 7.9 | 8.6 | 8.9 | 0.7 | 0.4 | 5.3 |
| | | B | 0.1 | 0.1 | 0.1 | 0 | 0 | 6.4 | 0.3 | 44.4 | 0.4 | 0.4 | 3.3 |
| | | C | 0.9 | 0.2 | 0 | 0 | 0.2 | 0 | 5.5 | 31.2 | 5.8 | 0.1 | 2.4 |
| 3967 | kl-9 | A | 0 | 0 | 0 | 0 | 0 | 0 | 0 | 21.8 | 0 | 0 | 7.9 |
| | | B | 0.1 | 0 | 0 | 0.1 | 2 | 1.7 | 2.1 | 1.1 | 0 | 0 | 23.3 |
| | | C | 1.3 | 0 | 0 | 0 | 0.7 | 0 | 1.3 | 0.6 | 0.2 | 0 | 15.3 |
| 3971 | kl-2 | A | 0 | 0 | 0.1 | 0.3 | 5.1 | 0.7 | 0.1 | 0.2 | 0.2 | 0.1 | 17.4 |
| | | B | 0 | 0.2 | 0.1 | 0 | 3 | 0.3 | 1 | 0.7 | 0 | 0.2 | 12.2 |
| | | C | 0.7 | 0.2 | 0 | 0 | 0.1 | 0.1 | 6.5 | 28.4 | 3.6 | 0 | 2.3 |
| 3972 | kl-2 | A | 0 | 0 | 0.1 | 0 | 0.9 | 0.2 | 0.1 | 12.1 | 0 | 0 | 6 |
| | | B | 0.1 | 0.1 | 0 | 0 | 0.3 | 0.1 | 0.2 | 40 | 1.1 | 0 | 3.5 |
| | | C | 1.1 | 0 | 0 | 0 | 0.2 | 0.1 | 6 | 25.2 | 1.1 | 0 | 3.1 |
| 3974 | kl-1 | A | 4.4 | 0 | 0.3 | 0.4 | 1.9 | 28 | 2 | 4.1 | 0.3 | 1.1 | 20 |
| | | B | 0.3 | 0.2 | 0.2 | 0 | 0 | 2.7 | 1 | 49.3 | 1.1 | 0.1 | 3 |
| | | C | 4.5 | 1.8 | 0 | 0 | 0.1 | 0 | 20.1 | 19.7 | 14.9 | 0 | 1.9 |
| 3980† | kl-2 | A | 0.1 | 0 | 1.1 | 0.1 | 1.4 | 18.9 | 0.1 | 7.8 | 0.1 | 2.3 | 7.2 |
| | | B | 0 | 0 | 0.1 | 0.1 | 0.2 | 8.6 | 0.1 | 40.2 | 0.1 | 0.3 | 2.4 |
| 3987 | kl-3 | A | 0 | 0.1 | 1.2 | 0.4 | 0.1 | 7.7 | 0.1 | 33 | 0.1 | 0.6 | 2.3 |
| | | B | 0.3 | 0.2 | 0 | 0 | 0.1 | 0.4 | 0.4 | 60.4 | 1.6 | 0 | 0.7 |
| | | C | 0.4 | 0 | 0 | 0 | 0.1 | 0 | 0.2 | 51.8 | 0.3 | 0.1 | 0.4 |
| 4008 | kl-8 | A | 0 | 0 | 0 | 0 | 1 | 0.6 | 0 | 87 | 0 | 0 | 6.9 |
| | | B | 0 | 0.1 | 0.1 | 0.1 | 0.7 | 25.7 | 0.1 | 4.1 | 0 | 2.2 | 6.1 |
| | | C | 0.3 | 0 | 0 | 0 | 0.7 | 1.7 | 0 | 1.3 | 0 | 0.1 | 10.3 |
| 4010 | kl-12 | A | 0 | 0 | 0.1 | 0.1 | 0.4 | 0.7 | 0 | 15.3 | 0 | 0 | 6.6 |
| | | B | 0.1 | 0.1 | 0.1 | 0.3 | 0.4 | 27.7 | 0.1 | 3 | 0 | 0.9 | 6.9 |
| | | C | 0.4 | 0 | 0 | 0 | 0.8 | 1.4 | 0 | 0.8 | 0 | 0.1 | 12.6 |
| 4040 | kl-8 | A | 0 | 0 | 0.9 | 0 | 2 | 0.7 | 0.1 | 3.7 | 0 | 0 | 5.5 |
| | | B | 0 | 0 | 0.1 | 0.1 | 0.6 | 20.4 | 0.6 | 1.3 | 0 | 3.3 | 10.3 |
| | | C | 0.1 | 0 | 0 | 0.3 | 8.2 | 1 | 0.5 | 0.5 | 0 | 0.3 | 16.7 |
| 4320 | kl-10 | A | 0 | 0 | 0.1 | 0.1 | 1.3 | 7.3 | 0.2 | 5 | 0 | 0.7 | 7.1 |
| | | B | 0.1 | 0 | 1 | 0.3 | 0.7 | 39.8 | 0.1 | 0.8 | 0 | 5.4 | 12.6 |
| | | C | 3.2 | 0 | 0.1 | 0.7 | 0.9 | 16.8 | 0.1 | 0.2 | 0.1 | 0.5 | 2 |
| Transferable in 2/3 systems | | | | | | | | | | | | | |
| 2892 | kl-6 | A | 0.2 | 0.2 | 0.3 | 1 | 5 | 0.2 | 8.3 | 0.4 | 0.2 | 0.3 | 14.6 |
| | | B | 0.1 | 0.5 | 0.3 | 0.2 | 0.1 | 3.2 | 7 | 15.8 | 4.9 | 0.3 | 3.7 |
| | | C | 0.6 | 0.8 | 0 | 0 | 0.1 | 0.2 | 47.5 | 3.6 | 5.1 | 0 | 7.6 |
| 2994 | kl-3 | A | 0 | 0 | 0.2 | 1 | 5.1 | 0.1 | 14.2 | 0.6 | 0.1 | 0 | 28 |
| | | B | 0.3 | 0.3 | 0.2 | 0 | 0.1 | 0.2 | 10.6 | 12.9 | 3 | 0 | 4.2 |
| | | C | 1.6 | 3.1 | 0 | 0 | 0.1 | 0 | 53.1 | 4.1 | 12 | 0.1 | 5.7 |
| 3025 | kl-2 | A | 0 | 0 | 0.1 | 0.4 | 8.9 | 0.4 | 10.7 | 0.1 | 0.1 | 0.1 | 24.1 |
| | | B | 0 | 0.1 | 0.1 | 0.1 | 2 | 3.6 | 12 | 0.6 | 0 | 6.4 | 30.1 |
| | | C | 1.4 | 2.3 | 0.1 | 0 | 0.2 | 0.1 | 52.1 | 0.6 | 0.7 | 0 | 0.3 |
| 3122 | kl-5 | A | 2.5 | 0.5 | 0 | 0 | 0 | 0.2 | 0 | 74 | 12.3 | 0 | 0 |
| | | B | 0.2 | 0.5 | 0.1 | 0 | 0.8 | 10.2 | 1 | 1.6 | 0.3 | 0.5 | 11.8 |
| | | C | 0.4 | 0.5 | 0.1 | 0 | 3.4 | 0.2 | 15.9 | 0.2 | 0.1 | 0 | 46.7 |
| 3878 | kl-8 | A | 0 | 0 | 0.2 | 0.3 | 1 | 8.7 | 0.2 | 4.7 | 0 | 0.6 | 5.5 |
| | | B | 0.7 | 1 | 0.9 | 0.1 | 0.2 | 47.8 | 0.1 | 24.5 | 0 | 2 | 1.9 |
| | | C | 0.6 | 0.1 | 0 | 0.2 | 0.1 | 19.7 | 0.1 | 27.3 | 0 | 1.4 | 1.9 |
| 3931 | kl-7 | A | 0.2 | 0 | 0.2 | 1.7 | 1.5 | 3 | 6.5 | 7.2 | 0.4 | 0.1 | 8 |
| | | B | 1.7 | 0.2 | 0.2 | 0 | 0 | 7.9 | 6 | 32.6 | 6.4 | 0.3 | 2.3 |
| | | C | 3.5 | 2.2 | 0 | 0 | 0 | 0.1 | 22 | 21.6 | 16.3 | 0.1 | 2.2 |
| 3997 | kl-1 | A | 0 | 0.1 | 0.4 | 0 | 1.1 | 9.1 | 0.1 | 6.6 | 0 | 0 | 13 |
| | | B | 0.2 | 0.1 | 0 | 0 | 0 | 13.6 | 0 | 54 | 0.8 | 1.6 | 1.4 |
| | | C | 0.7 | 0.1 | 0 | 0 | 0 | 0 | 0.4 | 83.8 | 3.3 | 0 | 0.1 |
| 4022 | kl-11 | A | 0.2 | 0.1 | 1.5 | 0.8 | 0.4 | 4.8 | 24.7 | 2 | 1.9 | 0.6 | 4.5 |
| | | B | 0.5 | 1.2 | 0.6 | 4.1 | 1.1 | 0.4 | 31.3 | 4.4 | 17.1 | 1.6 | 10.3 |
| | | C | 1 | 1.7 | 2.7 | 6 | 0.9 | 0.7 | 70.9 | 0.3 | 8.3 | 0 | 0.1 |
| Transferable in 1/3 systems | | | | | | | | | | | | | |
| 3041 | kl-3 | A | 2.1 | 1.4 | 0 | 0 | 0 | 0 | 0 | 60.2 | 30.7 | 0.2 | 0.1 |
| | | B | 0 | 0.3 | 0.2 | 0 | 3.8 | 0.1 | 14.5 | 0.1 | 0 | 0.1 | 34.6 |
| | | C | 1.9 | 4 | 0 | 0 | 0.1 | 0 | 44.3 | 4.8 | 18.5 | 0 | 4.6 |

*System B: CAT-2200 H1/L1 & SGN-CD19a H2/L2 (with 15:15:35:35 ratio H1:H2:L1:L2 DNA); System C: CR8071 H1/L1 & SGN-CD19a H2/L2 (with 15:15:35:35 ratio H1:H2:L1:L2 DNA)

**Considering full Ab species only

§Designs are shaded according to their transferability in 3/3 (not shaded), or 2/3 (light grey) systems, based on a positive Change in H1L1_H2L2 and H1L2_H2L1** with respect to wild type ‡Estimated change with respect to wild type †Design 3980 was assessed only in 2 systems

TABLE 16

LC-MS pairing data and post pA yields (mg/L) for K-K-derived K-L designs (total pairing)

| Design§ | Cluster | System* | Post pA yield (mg/L A280) | % H1L1 Pairing | Change in % H1L1 Pairing with respect to wild type | % H2L2 Pairing | Change in % H2L2 Pairing with respect to wild type | H1L1 and % H2L2 Pairing | Change in % H1L1 and % H2L2 Pairing with respect to wild type | H1L1_H2L2 and H1L2_H2L1** | Change in H1L1_H2L2 and H1L2 H2L1** with respect to wild type | H1L1_H2L2 and H1L2_H2L1 | H1L1_H1L1 | H1L1_H1L2 | H1L2_H1L2 | H2L1_H2L1 | H2L1_H2L2 | H1L2_H1L2 | H1L1_H2L1 | H1L2_H2L2 | H1L1 | H1L2 | H2L1 | H2L2 |
|---|---|---|---|---|---|---|---|---|---|---|---|---|---|---|---|---|---|---|---|---|---|---|---|---|
| Transferable in 3/3 systems: | | | | | | | | | | | | | | | | | | | | | | | | |
| 34 | kk- | A | 37 | 85.9 | 34.1‡ | 98.8 | 27.7‡ | 92.8 | 25.5‡ | 82.3 | 50.4‡ | 71.9 | 0.6 | 0.2 | 0 | 0.1 | 0.2 | 1.9 | 0.6 | 11.8 | 2.5 | 0.5 | 0.1 | 9.5 |
| | 6 | B | 56 | 94.6 | 24.5‡ | 93.8 | 39.6‡ | 94.1 | 27.4‡ | 90.1 | 55.1 | 73.3 | 0.1 | 0.1 | 0 | 0.1 | 0.1 | 2 | 1.6 | 4.1 | 0.4 | 0.1 | 2.8 | 15.4 |
| | | C | 45 | 92.6 | 24.5 | 99.1 | 27.8 | 96.6 | 27.7 | 86.4 | 34.5 | 66.1 | 1 | 1.1 | 0 | 0 | 0.1 | 3.4 | 0.3 | 4.4 | 0 | 0 | 0.4 | 23 |
| 2826 | kk- | A | 38 | 23.1 | 4 | 99.6 | 6.5 | 67.8 | 6.8 | 20.5 | 3.6 | 16.5 | 0.4 | 0.1 | 0 | 0.1 | 0.1 | 2.4 | 0 | 61 | 0.9 | 1.4 | 0 | 17 |
| | 2 | B | 44 | 53.7 | −16.4 | 89.7 | 35.5 | 75.3 | 8.6 | 48.3 | 13.2 | 38.8 | 0 | 0.1 | 0.1 | 0.4 | 0.2 | 1.3 | 3.6 | 35.9 | 0.2 | 0.4 | 4 | 15.1 |
| | | C | 28 | 27.8 | −40.3 | 98 | 26.7 | 69.6 | 0.7 | 25.9 | −26 | 20.4 | 0.2 | 0.7 | 1 | 0 | 0 | 1.3 | 0.2 | 55.1 | 0.4 | 0.4 | 1.1 | 19.3 |
| Transferable in 2/3 systems: | | | | | | | | | | | | | | | | | | | | | | | | |
| 2188 | kk- | A | 19 | 28.5 | 9.4 | 98 | 4.9 | 69.8 | 8.8 | 27.3 | 10.4 | 22 | 0 | 0.1 | 0.1 | 0.2 | 0.6 | 3.5 | 0.3 | 53.6 | 0.4 | 2.1 | 0.5 | 16.6 |
| | 10 | B | 21 | 31 | −39.1 | 92.9 | 38.7 | 54 | −12.7 | 31.2 | −3.9 | 21.1 | 0.4 | 0.9 | 1.8 | 0.1 | 0 | 0.1 | 3.1 | 40.3 | 6.6 | 20.9 | 0.9 | 3.7 |
| | | C | 16 | 24.9 | −23.5 | 99.5 | 19.9 | 66.2 | 8.7 | 24.6 | −22.2 | 21.3 | 0.1 | 0.4 | 1.5 | 0 | 0 | 1 | 0.1 | 62.2 | 0.1 | 0.7 | 0.2 | 12.3 |
| 2816 | kk- | A | 37 | 99.6 | 47.8‡ | 63.1 | −8‡ | 72.1 | 4.8‡ | 58 | 26.1‡ | 32.2 | 0 | 0 | 0.1 | 1 | 1.8 | 3.6 | 16.8 | 0 | 0.1 | 0 | 17.5 | 26.8 |
| | 4 | B | 41 | 94.4 | 2.4 | 25.1 | −12.5 | 55.6 | −15.6 | 23.1 | −9 | 19.5 | 0.4 | 1.4 | 1.7 | 1.3 | 0.2 | 0.2 | 59.7 | 0.2 | 0.9 | 0 | 10.6 | 3.8 |
| | | C | 47 | 99.3 | 17 | 79.7 | 19.8 | 88.5 | 16.7 | 78.5 | 30.4 | 69.4 | 0.2 | 0.3 | 0 | 0.1 | 0.2 | 0.6 | 17.4 | 0.2 | 0.7 | 0 | 2.3 | 8.5 |
| 2827 | kk- | A | 37 | 97.9 | 46.1‡ | 93.6 | 22.5‡ | 95.5 | 28.2‡ | 90.8 | 58.9‡ | 75 | 0.3 | 0 | 0 | 0.8 | 0 | 2.2 | 4 | 0.4 | 2.5 | 0.7 | 0.8 | 13.4 |
| | 3 | B | 43 | 98.9 | 6.9 | 22.3 | −15.3 | 56 | −15.2 | 19.1 | −13 | 15.9 | 0.5 | 0.5 | 0.1 | 0.3 | 0.1 | 0.4 | 65.3 | 0.2 | 2.2 | 0 | 10.5 | 3.9 |
| | | C | 41 | 98.2 | 15.9 | 85 | 25.1 | 88.5 | 16.7 | 76.2 | 28.1 | 44.4 | 0.1 | 0.2 | 0.1 | 0.1 | 0.8 | 5.2 | 7.3 | 0.2 | 0.1 | 0.2 | 6.9 | 34.6 |
| 2830 | kk- | A | 24 | 76.8 | 25.1 | 99.6 | 28.5‡ | 90.9 | 23.6‡ | 72.2 | 40.3‡ | 56.6 | 0.1 | 0.1 | 0 | 0.2 | 0.1 | 4.2 | 0 | 17.1 | 0.7 | 0.2 | 0 | 20.6 |
| | 1 | B | 23 | 83.8 | 13.7‡ | 98.5 | 44.3‡ | 88.7 | 22‡ | 74.7 | 39.6‡ | 49.7 | 3.7 | 1.5 | 1.4 | 0.1 | 0 | 0.2 | 0.7 | 9.2 | 26 | 4 | 0.1 | 3.4 |
| | | C | 25 | 28 | −20.4 | 99.6 | 20 | 46.5 | −11 | 22 | −24.8 | 12.8 | 0.7 | 3.7 | 5.7 | 0 | 0 | 0 | 0 | 35.2 | 11.8 | 28.3 | 0.1 | 1.7 |
| Transferable in 1/3 systems: | | | | | | | | | | | | | | | | | | | | | | | | |
| 2798 | kk- | A | 64 | 89.5 | 37.7‡ | 88 | 16.9‡ | 88.3 | 21‡ | 61.6 | 29.7‡ | 36.1 | 0 | 0 | 0 | 0.5 | 1.7 | 10.9 | 4.6 | 4.8 | 0.1 | 0 | 5.6 | 35.6 |
| | 8 | B | 54 | 94 | 2 | 37.8 | 0.2 | 61.4 | −9.8 | 33.8 | 1.7 | 28 | 0.2 | 0.9 | 0.9 | 1.6 | 0.2 | 0.5 | 48.2 | 2.3 | 0.7 | 0 | 10.3 | 6.2 |
| | | C | 51 | 97.6 | 15.3 | 34.5 | −25.4 | 66.1 | −5.7 | 32.4 | −15.7 | 30.6 | 1.2 | 0.1 | 0.2 | 0.3 | 0.1 | 0.2 | 60 | 1.4 | 2.3 | 0.2 | 2.3 | 0.9 |

*System A: CAT-2200 H1/L1 & Pertuzumab H2/L2 (with 10:20:24:46 ratio H1:H2:L1:L2 DNA); System B: CAT-2200 H1/L1 & SGN-CD19a H2/L2 (with 15:15:35:35 ratio H1:H2:L1:L2 DNA) System C: CR8071 H1/L1 & SGN-CD19a H2/L2 (with 15:15:35:35 ratio H1:H2:L1:L2 DNA)

**Considering full Ab species only

§Designs are shaded with increasing grey according to their transferability in 3/3 (not shaded), 2/3, or 1/3 systems, based on a positive Change in % H1L1 and % H2L2 Pairing with respect to wild type ‡Estimated change with respect to wild type

TABLE 17

LC-MS pairing data and post pA yields mg/L) for K-K-derived K-L designs (total bispecific)

| Design[§] | Cluster | System* | Post pA yield (mg/L A280) | % H1L1 Pairing | Change in % H1L1 Pairing with respect to wild type | % H2L2 Pairing | Change in % H2L2 Pairing with respect to wild type | % H1L1 and % H2L2 Pairing | Change in % H1L1 and % H2L2 Pairing with respect to wild type | H1L1_H2L2 and H1L2_H2L1** | Change in H1L1_H2L2 and H1L2_H2L1** with respect to wild type | H1L1_H2L2 and H1L2_H2L1 | H1L1_H1L1 | H1L1_H1L2 | H1L2_H1L2 | H2L1_H2L1 | H2L1_H2L2 | H1L2_H1L2 | H1L1_H2L1 | H1L2_H2L2 | H1L1 | H1L2 | H2L1 | H2L2 |
|---|---|---|---|---|---|---|---|---|---|---|---|---|---|---|---|---|---|---|---|---|---|---|---|---|
| Transferable in 3/3 systems: | | | | | | | | | | | | | | | | | | | | | | | | |
| 34 | kk-6 | A | 37 | 85.9 | 34.1‡ | 98.8 | 27.7‡ | 92.8 | 25.5‡ | 82.3 | 50.4‡ | 71.9 | 0.6 | 0.2 | 0 | 0.1 | 0.2 | 1.9 | 0.6 | 11.8 | 2.5 | 0.5 | 0.1 | 9.5 |
| | | B | 56 | 94.6 | 24.5‡ | 93.8 | 39.6‡ | 94.1 | 27.4‡ | 90.1 | 55‡ | 73.3 | 0.1 | 0.1 | 0 | 0.1 | 0.1 | 2 | 1.6 | 4.1 | 0.4 | 0.1 | 2.8 | 15.4 |
| | | C | 45 | 92.6 | 24.5 | 99.1 | 27.8 | 96.6 | 27.7 | 86.4 | 34.5 | 66.1 | 1 | 1.1 | 0 | 0 | 0.1 | 3.4 | 0.3 | 4.4 | 0 | 0 | 0.4 | 23 |
| Transferable in 2/3 systems: | | | | | | | | | | | | | | | | | | | | | | | | |
| 2798 | kk-8 | A | 64 | 89.5 | 37.7‡ | 88 | 16.9‡ | 88.3 | 21‡ | 61.6 | 29.7‡ | 36.1 | 0 | 0 | 0 | 0.5 | 1.7 | 10.9 | 46 | 48 | 0.1 | 0 | 56 | 35.6 |
| | | B | 54 | 94 | 2 | 37.8 | 0.2 | 61.4 | −9.8 | 33.8 | 1.7 | 28 | 0.2 | 0.9 | 0.9 | 1.6 | 0.2 | 0.5 | 48.2 | 2.3 | 0.7 | 0 | 10.3 | 6.2 |
| | | C | 51 | 97.6 | 15.3 | 34.5 | −25.4 | 66.1 | −5.7 | 32.4 | −15.7 | 30.6 | 1.2 | 0.1 | 0.2 | 0.3 | 0.1 | 0.2 | 60 | 1.4 | 2.3 | 0.2 | 2.3 | 0.9 |
| 2816 | kk-4 | A | 37 | 99.6 | 47.8‡ | 63.1 | −8‡ | 72.1 | 4.8‡ | 58 | 26.1‡ | 32.2 | 0 | 0 | 0.1 | 1 | 1.8 | 3.6 | 16.8 | 0 | 0.1 | 0 | 17.5 | 26.8 |
| | | B | 41 | 94.4 | 2.4 | 25.1 | −12.5 | 55.6 | −15.6 | 23.1 | −9 | 19.5 | 0.4 | 1.4 | 1.7 | 1.3 | 0.2 | 0.2 | 59.7 | 0.2 | 0.9 | 0 | 10.6 | 3.8 |
| | | C | 47 | 99.3 | 17 | 79.7 | 19.8 | 88.5 | 16.7 | 78.5 | 30.4 | 69.4 | 0.2 | 0.3 | 0 | 0.1 | 0.2 | 0.6 | 17.4 | 0.2 | 0.7 | 0 | 2.3 | 8.5 |
| 2826 | kk-2 | A | 38 | 23.1 | 4 | 99.6 | 6.5 | 67.8 | 6.8 | 20.5 | 3.6 | 16.5 | 0.4 | 0.1 | 0 | 0.1 | 0.1 | 2.4 | 0 | 61 | 0.9 | 1.4 | 0 | 17 |
| | | B | 44 | 53.7 | −16.4 | 89.7 | 35.5 | 75.3 | 8.6 | 48.3 | 13.2 | 38.8 | 0 | 0.1 | 0.1 | 0.4 | 0.2 | 1.3 | 3.6 | 35.9 | 0.2 | 0.4 | 4 | 15.1 |
| | | C | 28 | 27.8 | −40.3 | 98 | 26.7 | 69.6 | 0.7 | 25.9 | −26 | 20.4 | 0.2 | 0.7 | 1 | 0 | 0 | 1.3 | 0.2 | 55.1 | 0.4 | 0.4 | 1.1 | 19.3 |
| 2827 | kk-3 | A | 37 | 97.9 | 46.1‡ | 93.6 | 22.5‡ | 95.5 | 28.2‡ | 90.8 | 58.9‡ | 75 | 0.3 | 0 | 0 | 0.8 | 0 | 2.2 | 4 | 0.4 | 2.5 | 0.7 | 0.8 | 13.4 |
| | | B | 43 | 98.9 | 6.9 | 22.3 | −15.3 | 56 | −15.2 | 19.1 | −13 | 15.9 | 0.5 | 0.5 | 0.1 | 0.3 | 0.1 | 0.4 | 65.3 | 0.2 | 2.2 | 0 | 10.5 | 3.9 |
| | | C | 41 | 98.2 | 15.9 | 85 | 25.1 | 88.5 | 16.7 | 76.2 | 28.1 | 44.4 | 0.1 | 0.2 | 0.1 | 0.1 | 0.8 | 5.2 | 7.3 | 0.2 | 0.1 | 0.2 | 6.9 | 34.6 |
| 2830 | kk-1 | A | 24 | 76.8 | 25‡ | 99.6 | 28.5‡ | 90.9 | 23.6‡ | 72.2 | 40.3‡ | 56.6 | 0.1 | 0.1 | 0 | 0.2 | 0.1 | 4.2 | 0 | 17.1 | 0.7 | 0.2 | 0 | 20.6 |
| | | B | 23 | 83.8 | 13.7‡ | 98.5 | 44.3‡ | 88.7 | 22‡ | 74.7 | 39.6‡ | 49.7 | 3.7 | 1.5 | 1.4 | 0.1 | 0 | 0.2 | 0.7 | 9.2 | 26 | 4 | 0.1 | 3.4 |
| | | C | 25 | 28 | −20.4 | 99.6 | 20 | 46.5 | −11 | 22 | −24.8 | 12.8 | 0.7 | 3.7 | 5.7 | 0 | 0 | 0 | 0 | 35.2 | 11.8 | 28.3 | 0.1 | 1.7 |
| Transferable in 1/3 systems: | | | | | | | | | | | | | | | | | | | | | | | | |
| 2188 | kk-10 | A | 19 | 28.5 | 9.4 | 98 | 4.9 | 69.8 | 8.8 | 27.3 | 10.4 | 22 | 0 | 0.1 | 0.1 | 0.2 | 0.6 | 3.5 | 0.3 | 53.6 | 0.4 | 2.1 | 0.5 | 16.6 |
| | | B | 21 | 31 | −39.1 | 92.9 | 38.7 | 54 | −12.7 | 31.2 | −3.9 | 21.1 | 0.4 | 0.9 | 1.8 | 0.1 | 0 | 0.1 | 3.1 | 40.3 | 6.6 | 20.9 | 0.9 | 3.7 |
| | | C | 16 | 24.9 | −23.5 | 99.5 | 19.9 | 66.2 | 8.7 | 24.6 | −22.2 | 21.3 | 0.1 | 0.4 | 1.5 | 0 | 0 | 1 | 0.1 | 62.2 | 0.1 | 0.7 | 0.2 | 12.3 |

*System A: CAT-2200 H1/L1 & Pertuzurriab H2/L2 (with 10:20:24:46 ratio H1:H2:L1:L2 DNA); System B: CAT-2200 H1/L1 & SGN-CD19a H2/L2 (with 15:15:35:35 ratio H1:H2:L1:L2 DNA); System C: CR8071 H1/L1 & SGN-CD19a H2/L2 (with 15:15:35:35 ratio H1:H2:L1:L2 DNA)

**Considering full Ab species only

[§]Designs are shaded with increasing grey according to their transferability in 3/3 (not shaded), 2/3, or 1/3 systems, based on a positive Change in H1L1_H2L2 and H1L2_H2L1** with respect to wild type ‡Estimated change with respect to wild type

TABLE 18

Post prep-SEC LC-MS pairing data for selected designs in three systems

| Design | Cluster | System* | % H1L1 Pairing | Change in % H1L1 Pairing with respect to wild type | % H2L2 Pairing | Change in % H2L2 Pairing with respect to wild type | % H1L1 and % H2L2 Pairing | Change in % H1L1 and % H2L2 Pairing with respect to wild type | H1L1_H2L2 and H1L2_H2L1** | Change in H1L1_H2L2 and H1L2_H2L1** with respect to wild type | H1L1_H2L2 and H1L2_H2L1 | H1L1_H1L1 | H1L1_H1L2 | H1L2_H1L2 | H2L1_H2L1 | H2L1_H2L2 | H2L2_H2L2 | H1L1_H2L1 | H1L2_H2L2 | H1L1 | H1L2 | H2L1 | H2L2 |
|---|---|---|---|---|---|---|---|---|---|---|---|---|---|---|---|---|---|---|---|---|---|---|---|
| 2901 | kl-6 | A | 95.4 | 76.3 | 98.6 | 5.5 | 97.3 | 36.3 | 90.8 | 73.9 | 74.1 | 0 | 0.1 | 0.1 | 0.1 | 1.2 | 2.3 | 0.2 | 3.5 | 2.7 | 0.1 | 0 | 15.5 |
| | | B | 88.1 | 18 | 95.7 | 41.5 | 92.1 | 25.4 | 84.7 | 49.6 | 76.1 | 0.3 | 0.3 | 0.2 | 0.2 | 0 | 0 | 2.8 | 9.8 | 2.3 | 0.5 | 0.6 | 6.9 |
| | | C | 63.3 | 14.9 | 99.8 | 20.2 | 81.9 | 24.4 | 62.9 | 16.1 | 56.5 | 0.3 | 1 | 1 | 0 | 0 | 0 | 0 | 30.9 | 2 | 1.1 | 0 | 7.1 |
| 3972 | kl-2 | A | 100 | 48.2‡ | 98.4 | 27.3‡ | 99.2 | 31.9‡ | 98.7 | 66.8‡ | 86.5 | 0.2 | 0 | 0 | 0.8 | 0.1 | 0.1 | 0 | 0 | 5.9 | 0 | 0 | 6.5 |
| | | B | 99.2 | 29.1‡ | 97.7 | 43.5‡ | 98.5 | 31.8‡ | 92.7 | 57.6‡ | 83.7 | 4.9 | 0.1 | 0 | 0.1 | 0 | 0 | 0.8 | 0.6 | 3.3 | 0 | 0.6 | 5.7 |
| | | C | 92.3 | 43.9 | 99.9 | 20.3 | 96.1 | 38.6 | 88.5 | 41.7 | 82.3 | 3.2 | 1 | 0.1 | 0 | 0 | 0 | 0 | 6.2 | 1.7 | 0.2 | 0 | 5.2 |

System A: CAT-2200 H1/L1 & Pertuzumab H2/L2 (with 10:20:24:46 ratio H1:H2:L1:L2 DNA); System B: CAT-2200 H1/L1 & SGN-CD19a H2/L2 (with 15:15:35:35 ratio H1:H2:L1:L2 DNA); System C: CR8071 H1/L1 & SGN-CD19a H2/L2 (with 15:15:35:35 ratio H1:H2:L1:L2 DNA)
**Considering full Ab species only
‡Estimated change with respect to wild type

TABLE 19

Antigen binding data for wild type paratopes in OAA format

| Warhead | Tag | Antigen | Count | Median KD (nM) | Mean KD (nM) | Standard Deviation (nM) |
|---|---|---|---|---|---|---|
| CAT-2200 | NO TAGS | IL-17A | 6 | 0.282 | 0.287 | 0.040 |
| CAT-2200 | /FLAG | IL-17A | 6 | 0.375 | 0.366 | 0.063 |
| CAT-2200 | /HA | IL-17A | 6 | 0.373 | 0.350 | 0.061 |
| CR8071 | NO TAGS | HEMAGGLUTININ | 3 | 0.385 | 0.379 | 0.013 |
| CR8071 | /FLAG | HEMAGGLUTININ | 3 | 0.332 | 0.332 | 0.007 |
| Pertuzumab | /FLAG | HERZ | 1 | 7.010 | | NA |
| Pertuzumab | NO TAGS | HERZ | 1 | 3.710 | | NA |
| SGN-CD19a | NO TAGS | CD19 | 2 | 67.535 | | 6.951 |
| SGN-CD19a* | NO TAGS | CD19 | 1 | 71.280 | | NA |
| SGN-CD19a* | /HA | CD19 | 1 | 137.000 | | NA |
| SGN-CD19a | /HA | CD19 | 2 | 150.100 | | 1.273 |
| SGN-CD19a | /FLAG | CD19 | 2 | 224.550 | | 22.981 |
| SGN-CD19a* | /FLAG | CD19 | 1 | 321.500 | | NA |

*Denotes a different capture method

TABLE 20

Antigen binding affinity and thermal stability assessment for select K-L designs

| Design§ | Cluster | System* | H1L1 KD (nM) | Difference in H1L1 log(KD) from wild type | H2L2 KD (nM) | Difference in H2L2 log(KD) from wild type | Tm H1L1 Fab (° C.)†† | Tm H2L2 Fab (° C.)†† | Average difference in Fab Tm (across systems) wild type from (° C.)‡‡ |
|---|---|---|---|---|---|---|---|---|---|
| 2979 | kl-4 | A | 0.31 | −0.03 | 3.06 | 0.08 | 70.4 | 74.0 | −0.4 |
| | | B | 0.39 | −0.14 | 148.80 | 0.18 | 70.1 | 91.4 | |
| | | C | 0.93 | −0.38 | 45.06 | 0.70 | 68.5 | 91.5 | |
| 3018 | kl-3 | A | 0.53 | −0.16 | 2.89 | 0.11 | 69.9 | 74.3 | −1.4 |
| | | B | 0.35 | 0.03 | 47.97 | 0.15 | 69.5 | 88.8 | |
| | | C | 0.16 | 0.39 | 93.89 | −0.14 | 67.1 | 89.2 | |
| 3041 | kl-3 | A | ND† | ND | ND | ND | ND | ND | −0.5 |
| | | B | 0.42 | −0.06 | MVB‡, 62.0** | MVB, 0.11** | 69.6 | 91.7 | |
| | | C | ND | ND | ND | ND | ND | ND | |
| 3102 | kl-12 | A | 0.37 | −0.12 | 3.14 | 0.07 | 71.1 | 71.1 | −1.0 |
| | | B | 0.41 | −0.16 | 215.20 | 0.17 | 70.4 | 91.8 | |
| | | C | 0.87 | −0.35 | MVB | MVB | 67.8 | 91.7 | |
| 3898 | kl-8 | A | 0.33 | −0.06 | 2.87 | 0.11 | 72.2 | 74.0 | −0.4 |
| | | B | 0.44 | −0.19 | 188.10 | 0.23 | 71.6 | 89.6 | |
| | | C | 0.50 | −0.12 | 220.60 | 0.16 | 68.3 | 89.8 | |
| 3947 | kl-4 | A | 0.31 | −0.04 | 3.28 | 0.05 | 70.9 | 73.1 | −1.4 |
| | | B | 0.36 | −0.10 | MVB, 65.4** | MVB, 0.09** | 70.4 | 88.0 | |
| | | C | 1.14 | −0.47 | MVB, 65.4** | MVB, 0.09** | 68.3 | 87.8 | |
| 3025 | kl-2 | A | 0.47 | −0.10 | 3.28 | 0.05 | 70.6 | 72.1 | −2.6 |
| | | B | 0.45 | −0.08 | MVB | MVB | 69.4 | 83.8 | |
| | | C | 0.68 | −0.31 | 61.05 | 0.07 | 68.9 | 84.4 | |
| 3109 | kl-8 | A | 0.37 | −0.12 | 2.96 | 0.10 | 71.6 | 71.6 | −3.0 |
| | | B | 0.47 | −0.22 | MVB, 140** | MVB, 0.06** | 70.5 | 83.5 | |
| | | C | 1.50 | −0.59 | MVB, 140** | MVB, 0.06** | 67.4 | 83.7 | |
| 3113 | kl-12 | A | 0.39 | −0.14 | 3.05 | 0.09 | 70.6 | 70.6 | −1.6 |
| | | B | 0.44 | −0.20 | 216.00 | 0.02 | 70.0 | 91.7 | |
| | | C | 0.99 | −0.41 | MVB | MVB | 66.8 | 91.6 | |
| 3878 | kl-8 | A | 0.36 | −0.10 | 3.03 | 0.09 | 73.5 | 73.5 | −1.6 |
| | | B | ND | ND | ND | ND | ND | ND | |
| | | C | 0.32 | 0.08 | 306.30 | −0.14 | 68.3 | 83.9 | |
| 3890 | kl-9 | A | 0.44 | −0.19 | 2.80 | 0.12 | 73.2 | 73.2 | −1.9 |
| | | B | 0.44 | −0.19 | 54.83 | 0.09 | 71.4 | 83.7 | |
| | | C | 0.44 | −0.06 | 40.94 | 0.22 | 68.5 | 84.3 | |
| 3910 | kl-10 | A | 0.37 | −0.11 | 2.88 | 0.11 | 71.3 | 71.3 | −2.7 |
| | | B | ND | ND | ND | ND | ND | ND | |
| | | C | 0.47 | −0.09 | 294.00 | −0.12 | 68.2 | 83.9 | |
| 3931 | kl-7 | A | 0.44 | −0.07 | 2.90 | 0.11 | 69.7 | 73.7 | −1.6 |
| | | B | 0.29 | 0.11 | 54.93 | 0.09 | 69.5 | 87.2 | |
| | | C | 0.45 | −0.13 | 64.37 | 0.04 | 68.6 | 87.1 | |
| 3954 | kl-7 | A | 0.34 | −0.09 | 3.10 | 0.08 | 71.8 | 72.9 | −2.2 |
| | | B | 0.26 | 0.04 | 76.38 | −0.03 | 70.6 | 83.6 | |
| | | C | 0.30 | 0.04 | 70.76 | 0.00 | 68.4 | 84.8 | |

TABLE 20-continued

Antigen binding affinity and thermal stability assessment for select K-L designs

| Design§ | Cluster | System* | H1L1 KD (nM) | Difference in H1L1 log(KD) from wild type | H2L2 KD (nM) | Difference in H2L2 log(KD) from wild type | Tm H1L1 Fab (° C.)†† | Tm H2L2 Fab (° C.)†† | Average difference in Fab Tm (across systems) wild type from (° C.)‡‡ |
|---|---|---|---|---|---|---|---|---|---|
| 3967 | kl-9 | A | 0.37 | −0.11 | 5.29 | 0.12 | 70.0 | 70.0 | −2.9 |
| | | B | 0.38 | −0.13 | 36.12 | 0.27 | 69.8 | 86.1 | |
| | | C | 0.52 | −0.13 | 43.33 | 0.19 | 68.0 | 86.6 | |
| 4010 | kl-12 | A | 0.42 | −0.17 | 5.41 | 0.11 | 71.4 | 71.4 | −2.9 |
| | | B | 0.36 | −0.11 | 131.70 | 0.23 | 70.3 | 83.2 | |
| | | C | 0.49 | −0.10 | 227.50 | −0.01 | 68.2 | 84.1 | |
| 4040 | kl-8 | A | 0.33 | −0.06 | 2.30 | 0.21 | 71.5 | 72.5 | −2.0 |
| | | B | 0.31 | −0.04 | 16.97, 22.4** | 0.62, 0.55** | 70.7 | 84.0 | |
| | | C | 0.66 | −0.24 | 3.53, 22.4** | 1.30, 0.55** | 69.1 | 86.2 | |
| 2892 | kl-6 | A | 0.65 | −0.24 | 3.24 | 0.06 | 67.7 | 74.8 | −3.6 |
| | | B | 0.53 | −0.15 | 49.74 | 0.13 | 65.8 | 84.1 | |
| | | C | 0.95 | −0.46 | 39.69 | 0.25 | 65.6 | 84.3 | |
| 2901 | kl-6 | A | 0.54 | −0.16 | 3.12 | 0.08 | 67.1 | 71.5 | −3.4 |
| | | B | 0.52 | −0.14 | 47.05 | 0.16 | 66.2 | 88.1 | |
| | | C | 0.64 | −0.29 | 41.91 | 0.21 | 66.1 | 87.6 | |
| 2994 | kl-3 | A | 0.45 | −0.08 | 3.20 | 0.06 | 69.0 | 73.5 | −4.3 |
| | | B | 0.28 | 0.12 | 49.69 | 0.16 | 68.3 | 83.7 | |
| | | C | ND | ND | ND | ND | ND | ND | |
| 3008 | kl-3 | A | 0.35 | 0.02 | 3.10 | 0.08 | 69.4 | 69.4 | −4.0 |
| | | B | 0.31 | 0.08 | 41.12 | 0.21 | 68.8 | 83.7 | |
| | | C | 0.47 | −0.15 | 48.01 | 0.15 | 67.5 | 83.9 | |
| 3122 | kl-5 | A | ND | ND | ND | ND | ND | ND | −4.1 |
| | | B | 0.43 | −0.19 | 195.60 | 0.06 | 69.9 | 80.1 | |
| | | C | 0.84 | −0.34 | MVB | MVB | 67.0 | 79.8 | |
| 3951 | kl-4 | A | 0.36 | −0.11 | 2.98 | 0.10 | 69.9 | 69.9 | −3.4 |
| | | B | 0.34 | −0.08 | 42.33 | 0.20 | 69.7 | 84.2 | |
| | | C | 0.55 | −0.16 | 38.35 | 0.24 | 68.1 | 84.3 | |
| 3957 | kl-7 | A | 0.37 | 0.00 | 2.83 | 0.12 | 69.4 | 69.4 | −3.8 |
| | | B | 0.24 | 0.19 | 54.58 | 0.09 | 69.0 | 82.8 | |
| | | C | 0.32 | 0.02 | 56.65 | 0.08 | 68.4 | 83.8 | |
| 3971 | kl-2 | A | 0.47 | −0.10 | 3.02 | 0.09 | 70.8 | 70.8 | −4.4 |
| | | B | 0.47 | −0.10 | 37.65 | 0.25 | 70.1 | 78.8 | |
| | | C | 0.40 | −0.08 | 53.08 | 0.10 | 68.5 | 78.3 | |
| 3972 | kl-2 | A | 0.32 | −0.05 | 3.11 | 0.08 | 71.9 | 71.9 | −3.3 |
| | | B | 0.29 | −0.02 | 53.63 | 0.12 | 70.9 | 80.2 | |
| | | C | 0.38 | −0.06 | 30.18 | 0.37 | 68.6 | 80.6 | |
| 3974 | kl-1 | A | 0.46 | −0.09 | 2.92 | 0.10 | 70.9 | 70.9 | −3.9 |
| | | B | 0.27 | 0.13 | 50.95 | 0.12 | 69.9 | 81.6 | |
| | | C | 0.44 | −0.12 | 62.40 | 0.03 | 67.5 | 81.0 | |
| 3980 | kl-2 | A | 0.32 | −0.05 | 2.82 | 0.12 | 71.1 | 71.1 | −4.9 |
| | | B | 0.25 | 0.05 | 55.39 | 0.08 | 70.9 | 82.0 | |
| | | C | ND | ND | ND | ND | ND | ND | |
| 3987 | kl-3 | A | 0.30 | −0.02 | 3.22 | 0.06 | 70.9 | 70.9 | −3.9 |
| | | B | 0.23 | 0.08 | 48.45 | 0.17 | 70.6 | 80.1 | |
| | | C | 0.23 | 0.16 | 63.74 | 0.05 | 68.4 | 80.3 | |
| 3997 | kd-1 | A | 0.33 | −0.07 | 2.95 | 0.10 | 69.7 | 69.7 | −4.2 |
| | | B | ND | ND | ND | ND | ND | ND | |
| | | C | ND | ND | ND | ND | ND | ND | |
| 4008 | kl-8 | A | 0.43 | −0.18 | 5.57 | 0.10 | 70.7 | 70.7 | −3.2 |
| | | B | 0.39 | −0.14 | 217.50 | 0.01 | 69.8 | 83.5 | |
| | | C | 0.48 | −0.09 | 272.90 | −0.09 | 68.0 | 84.6 | |
| 4320 | kl-10 | A | 0.36 | −0.10 | 2.90 | 0.11 | 69.9 | 69.9 | −3.5 |
| | | B | 0.38 | −0.13 | 306.70 | −0.14 | 69.9 | 83.3 | |
| | | C | 0.49 | −0.11 | 257.90 | −0.06 | 67.9 | 84.2 | |

*System A: CAT-2200 H1/L1 & Pertuzumab H2/L2 (with 10:20:24:46 ratio H1:H2:L1:L2 DNA); System B: CAT-2200 H1/L1 & SGN-CD19a H2/L2 (with 15:15:35:35 ratio H1:H2:L1:L2 DNA); System C: CR8071 H1/L1 & SGN-CD19a H2/L2 (with 15:15:35:35 ratio H1:H2:L1:L2 DNA)

§Designs are grouped and shaded in three bins with "Average difference in Fab Tm from wild type (° C.)" from 0 to −1.5, −1.5 to −3.0, and less than −3.

†ND = Not determined

‡MVB = Mixed valency binding in SMCA format

**KD determined in OAA format

††DSC for antibodies was pmformed in SMCA format, and thermal transitions attributable to each Fab arm are given.

‡‡Wild type Fab Tms were obtained from DSC experiments in Mab format

TABLE 21

Antigen binding affinity and thermal stability assessment for select K-K-derived K-L designs

| Design§ | Cluster | System* | H1L1 KD (nm) | Difference in H1L1 log(KD) from wild type | H2L2 KD (nM) | Difference in H2L2 log(KD) from wild type | Tm H1L1 (° C.) †† | Tm H2L2 (° C.) †† | Average difference in Fab Tm (across systems) from wild type (° C.) ‡‡ |
|---|---|---|---|---|---|---|---|---|---|
| 34 | kk-6 | A | 0.63 | −0.35 | 2.63 | 0.15 | 69.6 | 72.9 | −1.5 |
| | | B | 0.63 | −0.35 | 17.07 | 0.60 | 68.3 | 90.3 | |
| | | C | 0.66 | −0.23 | 24.18 | 0.44 | 67.2 | 90.9 | |
| 2827 | kk-3 | A | 0.38 | −0.13 | 2.93 | 0.10 | 72.0 | 73.1 | −1.2 |
| | | B | ND† | ND | ND | ND | ND | ND | |
| | | C | 0.72 | −0.27 | 111.90 | 0.30 | 68.8 | 86.9 | |
| 2816 | kk-4 | A | 0.51 | −0.26 | 3.08 | 0.08 | 72.5 | 72.5 | −2.3 |
| | | B | ND | ND | ND | ND | ND | ND | |
| | | C | 0.42 | −0.04 | 281.40 | 0.06 | 68.2 | 83.3 | |
| 2830 | kk-1 | A | 0.45 | −0.20 | 3.08 | 0.08 | 70.1 | 73.7 | −3.7 |
| | | B | 0.32 | −0.06 | 50.84 | 0.15 | 69.3 | 84.3 | |
| | | C | ND | ND | ND | ND | ND | ND | |

*System A: CAT-2200 H1/L1 & Pertuzumab H2/L2 (with 10:20:24:46 ratio H1:H2:L1:L2 DNA); System B: CAT-2200 H1/L1 & SGN-CD19a H2/L2 (with 15:15:35:35 ratio H1:H2:L1:L2 DNA); System C: CR8071 H1/L1 & SGN-CD19a H2/L2 (with 15:15:35:35 ratio H1:H2:L1:L2 DNA)

§Designs are grouped and shaded in three bins with "Average difference in Fab Tm from wild type (° C.)" from 0 to −1.5, −1.5 to −3.0, and less than −3.

†ND = Not determined

†† DSC for antibodies was pmformed in SMCA format, and thermal transitions attributable to each Fab arm are given.

‡‡ Mild type Fab Tms were obtained from DSC experiments in Mab format

TABLE 22A

IgG1 heavy chain amino acid residue numbering according to IMGT, Kabat, 1JPT, and EU numbering systems

| IMGT | Kabat | 1JPT | EU |
|---|---|---|---|
| 1044 | 39 | 39 | Not applicable |
| 1050 | 45 | 45 | Not applicable |
| 3005 | 122 | 126 | 126 |
| 3007 | 124 | 128 | 128 |
| 3008 | 125 | 129 | 129 |
| 3020 | 139 | 141 | 141 |
| 3024 | 143 | 145 | 145 |
| 3026 | 145 | 147 | 147 |
| 3027 | 146 | 148 | 148 |
| 3081 | 174 | 170 | 170 |
| 3084 | 177 | 173 | 173 |
| 3084B | 179 | 175 | 175 |
| 3085Y | 186 | 181 | 181 |
| 3086 | 188 | 183 | 183 |
| 3088 | 190 | 185 | 185 |
| 4003 | 228 | 218 | 218 |

TABLE 22B

Lambda light chain amino acid residue numbering according to IMGT, and Kabat numbering systems

| IMGT | Kabat |
|---|---|
| 1044 | 38 |
| 3005 | 116 |
| 3011 | 122 |
| 3013 | 124 |
| 3018 | 129 |
| 3020 | 131 |
| 3022 | 133 |
| 3024 | 135 |

TABLE 22B-continued

Lambda light chain amino acid residue numbering according to IMGT, and Kabat numbering systems

| IMGT | Kabat |
|---|---|
| 3086 | 176 |
| 3088 | 178 |
| 3090 | 180 |

TABLE 22C

Kappa light chain amino acid residue numbering according to IMGT, Kabat, and 1JPT numbering systems

| IMGT | Kabat | 1JPT |
|---|---|---|
| 1044 | 38 | 38 |
| 1050 | 44 | 44 |
| 3005 | 116 | 116 |
| 3010 | 121 | 121 |
| 3013 | 124 | 124 |
| 3018 | 129 | 129 |
| 3020 | 131 | 131 |
| 3022 | 133 | 133 |
| 3024 | 135 | 135 |
| 3079 | 160 | 160 |
| 3086 | 176 | 176 |
| 3088 | 178 | 178 |
| 3090 | 180 | 180 |

TABLE 23

Correspondence table for % Paired/ % Mispaired species and LCCA Scalar Values

| Paired species (%) | Mispaired species (%) | lcca_scalar |
|---|---|---|
| 99 | 1 | 4.60 |
| 98 | 2 | 3.89 |
| 97 | 3 | 3.48 |
| 96 | 4 | 3.18 |
| 95 | 5 | 2.94 |
| 94 | 6 | 2.75 |
| 93 | 7 | 2.59 |
| 92 | 8 | 2.44 |
| 91 | 9 | 2.31 |
| 90 | 10 | 2.20 |
| 89 | 11 | 2.09 |
| 88 | 12 | 1.99 |
| 87 | 13 | 1.90 |
| 86 | 14 | 1.82 |
| 85 | 15 | 1.73 |
| 84 | 16 | 1.66 |
| 83 | 17 | 1.59 |
| 82 | 18 | 1.52 |
| 81 | 19 | 1.45 |
| 80 | 20 | 1.39 |
| 79 | 21 | 1.32 |
| 78 | 22 | 1.27 |
| 77 | 23 | 1.21 |
| 76 | 24 | 1.15 |
| 75 | 25 | 1.10 |
| 74 | 26 | 1.05 |
| 73 | 27 | 0.99 |
| 72 | 28 | 0.94 |
| 71 | 29 | 0.90 |
| 70 | 30 | 0.85 |
| 69 | 31 | 0.80 |
| 68 | 32 | 0.75 |
| 67 | 33 | 0.71 |
| 66 | 34 | 0.66 |
| 65 | 35 | 0.62 |
| 64 | 36 | 0.58 |
| 63 | 37 | 0.53 |
| 62 | 38 | 0.49 |
| 61 | 39 | 0.45 |
| 60 | 40 | 0.41 |
| 59 | 41 | 0.36 |
| 58 | 42 | 0.32 |
| 57 | 43 | 0.28 |
| 56 | 44 | 0.24 |
| 55 | 45 | 0.20 |
| 54 | 46 | 0.16 |
| 53 | 47 | 0.12 |
| 52 | 48 | 0.08 |
| 51 | 49 | 0.04 |
| 50 | 50 | 0.00 |
| 49 | 51 | −0.04 |
| 48 | 52 | −0.08 |
| 47 | 53 | −0.12 |
| 46 | 54 | −0.16 |
| 45 | 55 | −0.20 |
| 44 | 56 | −0.24 |
| 43 | 57 | −0.28 |
| 42 | 58 | −0.32 |
| 41 | 59 | −0.36 |
| 40 | 60 | −0.41 |
| 39 | 61 | −0.45 |
| 38 | 62 | −0.49 |
| 37 | 63 | −0.53 |
| 36 | 64 | −0.58 |
| 35 | 65 | −0.62 |
| 34 | 66 | −0.66 |
| 33 | 67 | −0.71 |
| 32 | 68 | −0.75 |
| 31 | 69 | −0.80 |
| 30 | 70 | −0.85 |
| 29 | 71 | −0.90 |
| 28 | 72 | −0.94 |
| 27 | 73 | −0.99 |
| 26 | 74 | −1.05 |
| 25 | 75 | −1.10 |

TABLE 23-continued

Correspondence table for % Paired/ % Mispaired species and LCCA Scalar Values

| Paired species (%) | Mispaired species (%) | lcca_scalar |
|---|---|---|
| 24 | 76 | −1.15 |
| 23 | 77 | −1.21 |
| 22 | 78 | −1.27 |
| 21 | 79 | −1.32 |
| 20 | 80 | −1.39 |
| 19 | 81 | −1.45 |
| 18 | 82 | −1.52 |
| 17 | 83 | −1.59 |
| 16 | 84 | −1.66 |
| 15 | 85 | −1.73 |
| 14 | 86 | −1.82 |
| 13 | 87 | −1.90 |
| 12 | 88 | −1.99 |
| 11 | 89 | −2.09 |
| 10 | 90 | −2.20 |
| 9 | 91 | −2.31 |
| 8 | 92 | −2.44 |
| 7 | 93 | −2.59 |
| 6 | 94 | −2.75 |
| 5 | 95 | −2.94 |
| 4 | 96 | −3.18 |
| 3 | 97 | −3.48 |
| 2 | 98 | −3.89 |
| 1 | 99 | −4.60 |

TABLE 24

SMCA design numbers and corresponding LCCA set unique identifiers

| SMCA Design ID | LCCA Unique identifier |
|---|---|
| 34 | 10681-10741 |
| 2188 | 10640-10713 |
| 2798 | 10621-10733 |
| 2816 | 10665-10724 |
| 2826 | 10652-10734 |
| 2827 | 10685-10726 |
| 2830 | 10657-10760 |
| 2892 | 10808-11308 |
| 2901 | 10814-11233 |
| 2979 | 11100-11205 |
| 2994 | 10983-11306 |
| 3008 | 10987-11257 |
| 3018 | 10931-11263 |
| 3025 | 10945-11377 |
| 3041 | 10947-11392 |
| 3102 | 11034-11204 |
| 3109 | 11026-11270 |
| 3113 | 11065-11206 |
| 3122 | 11066-11181 |
| 3878 | 12938-13469 |
| 3890 | 13194-13427 |
| 3898 | 13316-13451 |
| 3910 | 13238-13463 |
| 3931 | 12878-11240 |
| 3947 | 13335-13361 |
| 3951 | 13209-13364 |
| 3954 | 13167-13514 |
| 3957 | 13263-13493 |
| 3967 | 13208-13455 |
| 3971 | 13282-13484 |
| 3972 | 13218-13482 |

TABLE 24-continued

SMCA design numbers and corresponding LCCA set unique identifiers

| SMCA Design ID | LCCA Unique identifier |
|---|---|
| 3974 | 13175-13486 |
| 3980 | 13287-13494 |
| 3987 | 13221-13411 |
| 3997 | 13180-13515 |
| 4008 | 13226-13434 |
| 4010 | 13227-13383 |
| 4022 | 13306-13375 |
| 4040 | 13320-13370 |
| 4320* | 13304-13466 |

*design was identical to LCCA design 13304-13466, except that Q124 position in L2 was tested as Q124

We claim:

1. An antigen-binding polypeptide construct comprising a first heterodimer and a second heterodimer, the first heterodimer (H1L1) comprising a first immunoglobulin G (IgG) heavy chain polypeptide sequence (H1), and an immunoglobulin lambda light chain polypeptide sequence (L1) that form a first Fab region that specifically binds to a first antigen; and the second heterodimer (H2L2) comprising a second immunoglobulin G (IgG) heavy chain polypeptide sequence (H2), and an immunoglobulin kappa light chain polypeptide sequence (L2) that form a second Fab region that specifically binds to a second antigen, wherein:

H1 is distinct from H2, and H1 and H2 each comprise a heavy chain variable domain (VH domain) and a heavy chain constant domain 1 (CH1 domain);

L1 comprises a lambda light chain variable (VL-lambda) domain and a lambda light chain constant (CL-lambda) domain, and L2 comprises a kappa light chain variable (VL-kappa) domain and a kappa light chain constant (CL-kappa) domain;

H1, H2, L1, and L2 comprise amino acid substitutions that promote preferential pairing of H1 with L1 as compared to L2, and/or that promote preferential pairing of H2 with L2 as compared to L1, at positions identified according to the Kabat numbering system; and a) H1 comprises amino acid substitution 186K, L1 comprises amino acid substitutions 129T, 133D and 178T, H2 comprises amino acid substitutions 143E, 145T, and 179E, and L2 comprises amino acid substitutions 124R, 160K, and 178R;

b) H1 comprises amino acid substitutions 186K and 188T, L1 comprises amino acid substitutions 133D and 178T, H2 comprises amino acid substitutions 143E, 145T, and 179E, and L2 comprises amino acid substitutions 124R, 160K, and 178R;

c) H1 comprises amino acid substitution 179K, L1 comprises amino acid substitutions 129T and 180E, H2 comprises amino acid substitutions 143E, and 145T, and L2 comprises amino acid substitutions 124R, 160K, and 178R;

d) H1 comprises amino acid substitution 186R, L1 comprises amino acid substitutions 129T, 176A, 178W and 180E, H2 comprises amino acid substitutions 143E, 145T, and 188W, and L2 comprises amino acid substitutions 124K, 176A, and 178R;

e) H1 comprises amino acid substitutions 143A and 186R, L1 comprises amino acid substitutions 129T, 133W and 180E, H2 comprises amino acid substitutions 124W, 143E, and 145T, and L2 comprises amino acid substitutions 124K, 133A, and 178R;

f) H1 comprises amino acid substitution 186R, L1 comprises amino acid substitutions 129T and 180E, H2 comprises amino acid substitutions 143E, and 145T, and L2 comprises amino acid substitutions 124R, 129K, 160K, and 178R;

g) H1 comprises amino acid substitution 186R, L1 comprises amino acid substitutions 129T and 180E, H2 comprises amino acid substitutions 143E, 145T, and 188L, and L2 comprises amino acid substitutions 124R and 178R;

h) H1 comprises amino acid substitution 186R, L1 comprises amino acid substitutions 129T and 180E, H2 comprises amino acid substitutions 143E, 145T, 179E, and 188L, and L2 comprises amino acid substitutions 124R and 178R;

i) H1 comprises amino acid substitution 186R, L1 comprises amino acid substitutions 129T and 180E, H2 comprises amino acid substitutions 143E, 145T, and 188L, and L2 comprises amino acid substitutions 124R, 160K, and 178R;

j) H1 comprises amino acid substitution 186R, L1 comprises amino acid substitutions 129T and 180E, H2 comprises amino acid substitutions 143E, 145T, 179E, and 188L, and L2 comprises amino acid substitutions 124R, 160K, and 178R;

k) H1 comprises amino acid substitution 186R, L1 comprises amino acid substitutions 129T and 180E, H2 comprises amino acid substitutions 143E, and 145T, and L2 comprises amino acid substitutions 124R, 160K, and 178R;

l) H1 comprises amino acid substitution 179K, L1 comprises amino acid substitutions 129T and 180E, H2 comprises amino acid substitutions 143E, 145T, and 179E, and L2 comprises amino acid substitutions 124R and 178R;

m) H1 comprises amino acid substitutions 177I and 188K, L1 comprises amino acid substitutions 133L, 176D and 178E, H2 comprises amino acid substitutions 143E, 145T, and 179E, and L2 comprises amino acid substitutions 124R and 178R;

n) H1 comprises amino acid substitutions 177I and 188K, L1 comprises amino acid substitutions 133L, 176D and 178E, H2 comprises amino acid substitutions 143E, 145T, and 179E, and L2 comprises amino acid substitutions 124R, 160K, and 178R;

o) H1 comprises amino acid substitution 188K, L1 comprises amino acid substitutions 176E and 178E, H2 comprises amino acid substitutions 143E, 145T, and 179E, and L2 comprises amino acid substitutions 124R and 178R;

p) H1 comprises amino acid substitution 188K, L1 comprises amino acid substitutions 176E and 178E, H2 comprises amino acid substitutions 143E, 145T, and 179E, and L2 comprises amino acid substitutions 124R, 160K, and 178R;

q) H1 comprises amino acid substitutions 143S, 186K and 188T, L1 comprises amino acid substitutions 133D and 178T, H2 comprises amino acid substitutions 143E, 145T, and 179E, and L2 comprises amino acid substitutions 124R, 160K, and 178R;

r) H1 comprises amino acid substitution 179K, L1 comprises amino acid substitutions 129T, 178E and 180E, H2 comprises amino acid substitutions 143E, and 145T, and L2 comprises amino acid substitutions 124R, 160K, and 178R;

s) H1 comprises amino acid substitution 143K, L1 comprises amino acid substitutions 129T and 133D, H2 comprises amino acid substitutions 143E, 145T, 179E, and 188L, and L2 comprises amino acid substitutions 124R and 178R;

t) H1 comprises amino acid substitution 143K, L1 comprises amino acid substitutions 129T and 133D, H2 comprises amino acid substitutions 143E, 145T, and 179E, and L2 comprises amino acid substitutions 124R and 178R;

u) H1 comprises amino acid substitution 143K, L1 comprises amino acid substitutions 129T and 133D, H2 comprises amino acid substitutions 143E, 145T, 179E, and 188W, and L2 comprises amino acid substitutions 124R, 176A, and 178R;

v) H1 comprises amino acid substitution 143K, L1 comprises amino acid substitutions 129T and 133D, H2 comprises amino acid substitutions 143E, 145T, 179E, 186I, and 188W, and L2 comprises amino acid substitutions 124R, 176A, and 178R;

w) H1 comprises amino acid substitution 143K, L1 comprises amino acid substitutions 129T and 133D, H2 comprises amino acid substitutions 143E, 145T, and 179E, and L2 comprises amino acid substitutions 124R, 160R, and 178R;

x) H1 comprises amino acid substitution 143K, L1 comprises amino acid substitutions 129T and 133D, H2 comprises amino acid substitutions 143E, 145T, 179E, and 188W, and L2 comprises amino acid substitutions 124R, 160R, 176A, and 178R;

y) H1 comprises amino acid substitution 143K, L1 comprises amino acid substitutions 129T and 133D, H2 comprises amino acid substitutions 143E, 145T, 179E, 186I, and 188W, and L2 comprises amino acid substitutions 124R, 160R, 176A, and 178R;

z) H1 comprises amino acid substitution 143K, L1 comprises amino acid substitutions 129T and 133D, H2 comprises amino acid substitutions 124W, 143E, 145T, and 179E, and L2 comprises amino acid substitutions 124K, 133A, and 178R;

aa) H1 comprises amino acid substitution 143K, L1 comprises amino acid substitutions 129T and 133D, H2 comprises amino acid substitutions 143E, 145T, 179E, and 188L, and L2 comprises amino acid substitutions 124K and 178R;

bb) H1 comprises amino acid substitution 179K, L1 comprises amino acid substitutions 129T and 180E, H2 comprises amino acid substitutions 122C, 143E, 145T, and 179E, and L2 comprises amino acid substitutions 124C, 160K, and 178R;

cc) H1 comprises amino acid substitutions 143A and 179K, L1 comprises amino acid substitutions 129T, 133W and 180E, H2 comprises amino acid substitutions 143E, 145T, 179E, and 188L, and L2 comprises amino acid substitutions 124R, 160K, and 178R;

dd) H1 comprises amino acid substitution 179K, L1 comprises amino acid substitutions 129T and 180E, H2 comprises amino acid substitutions 143E, 145T, 179E, and 188L, and L2 comprises amino acid substitutions 124R, 160K, and 178R;

ee) H1 comprises amino acid substitution 179K, L1 comprises amino acid substitutions 129T, 178E and 180E, H2 comprises amino acid substitutions 143E, 145T, and 179E, and L2 comprises amino acid substitutions 124R, 160K, and 178R;

ff) H1 comprises amino acid substitution 179K, L1 comprises amino acid substitutions 129T and 180E, H2 comprises amino acid substitutions 143E, 145T, and 179E, and L2 comprises amino acid substitutions 124R, 160K, and 178R;

gg) H1 comprises amino acid substitution 179K, L1 comprises amino acid substitutions 129T and 180E, H2 comprises amino acid substitutions 143E, and 145T, and L2 comprises amino acid substitutions 124R, 129K, 160K, and 178R;

hh) H1 comprises amino acid substitution 179K, L1 comprises amino acid substitutions 129T and 180E, H2 comprises amino acid substitutions 143E, 145T, and 188L, and L2 comprises amino acid substitutions 124R, 160K, and 178R;

ii) H1 comprises amino acid substitution 186R, L1 comprises amino acid substitutions 129T and 180E, H2 comprises amino acid substitutions 143E, and 145T, and L2 comprises amino acid substitutions 124K and 178R;

jj) H1 comprises amino acid substitution 188K, L1 comprises amino acid substitutions 129T and 178E, H2 comprises amino acid substitutions 143E, 145T, and 179E, and L2 comprises amino acid substitutions 124R and 178R;

kk) H1 comprises amino acid substitution 186R, L1 comprises amino acid substitutions 129T and 180E, H2 comprises amino acid substitutions 39E, 143E, 145T, and 179E, and L2 comprises amino acid substitutions 38R, 124K, and 178R;

ll) H1 comprises amino acid substitution 188K, L1 comprises amino acid substitutions 176E and 178E, H2 comprises amino acid substitutions 39E, 143E, 145T, and 179E, and L2 comprises amino acid substitutions 38R, 124R, and 178R;

mm) H1 comprises amino acid substitution 186R, L1 comprises amino acid substitutions 129T and 180E, H2 comprises amino acid substitutions 45P, 143E, 145T, and 179E, and L2 comprises amino acid substitutions 44F, 124K, and 178R;

nn) H1 comprises amino acid substitution 188K, L1 comprises amino acid substitutions 176E and 178E, H2 comprises amino acid substitutions 45P, 143E, 145T, and 179E, and L2 comprises amino acid substitutions 44F, 124R, and 178R;

oo) H1 comprises amino acid substitutions 139W, 143I and 186K, L1 comprises amino acid substitutions 129T, 133D and 178T, H2 comprises amino acid substitutions 143E, 145T, and 179E, and L2 comprises amino acid substitutions 124R, 135W, 160K, and 178R;

pp) H1 comprises amino acid substitutions 139W and 186K, L1 comprises amino acid substitutions 129T, 133D and 178T, H2 comprises amino acid substitutions 143E, 145T, and 179E, and L2 comprises amino acid substitutions 124R, 135W, 160K, and 178R;

qq) H1 comprises amino acid substitutions 139W and 143K, L1 comprises amino acid substitutions 129T and 133D, H2 comprises amino acid substitutions 143E, 145T, and 179E, and L2 comprises amino acid substitutions 124R, 135W, and 178R;

rr) H1 comprises amino acid substitutions 143K and 190K, L1 comprises amino acid substitutions 129T, 133D and 135S, H2 comprises amino acid substitutions 143E, 145T, and 179E, and L2 comprises amino acid substitutions 124R and 178R;

ss) H1 comprises amino acid substitutions 124K and 143K, L1 comprises amino acid substitutions 129T, 131E and 133D, H2 comprises amino acid substitutions 143E, 145T, and 179E, and L2 comprises amino acid substitutions 124R, 160R, and 178R;

tt) H1 comprises amino acid substitutions 124K and 143K, L1 comprises amino acid substitutions 129T, 131D and 133D, H2 comprises amino acid substitutions 143E, 145T, and 179E, and L2 comprises amino acid substitutions 124R, 160R, and 178R;

uu) H1 comprises amino acid substitution 143K, L1 comprises amino acid substitutions 129T, 131E and 133D, H2 comprises amino acid substitutions 143E, 145T, and 179E, and L2 comprises amino acid substitutions 124R, 160R, and 178R;

vv) H1 comprises amino acid substitution 143K, L1 comprises amino acid substitutions 129T, 131D and 133D, H2 comprises amino acid substitutions 143E, 145T, and 179E, and L2 comprises amino acid substitutions 124R, 160R, and 178R;

ww) H1 comprises amino acid substitutions 139W and 188K, L1 comprises amino acid substitutions 129T, 176D and 178T, H2 comprises amino acid substitutions 143E, 145T, and 179E, and L2 comprises amino acid substitutions 124R, 135W, and 178R;

xx) H1 comprises amino acid substitutions 139W and 188K, L1 comprises amino acid substitutions 129T, 176E and 178E, H2 comprises amino acid substitutions 143E, 145T, and 179E, and L2 comprises amino acid substitutions 124R, 135W, and 178R;

yy) H1 comprises amino acid substitution 188K, L1 comprises amino acid substitutions 129T and 178D, H2 comprises amino acid substitutions 143E, 145T, and 179E, and L2 comprises amino acid substitutions 124R and 178R;

zz) H1 comprises amino acid substitution 179K, L1 comprises amino acid substitutions 129T and 180E, H2 comprises amino acid substitutions 143E, 145T, and 188L, and L2 comprises amino acid substitutions 124R and 178R;

aaa) H1 comprises amino acid substitution 188K, L1 comprises amino acid substitutions 129T, 176D and 178T, H2 comprises amino acid substitutions 143E, 145T, and 179E, and L2 comprises amino acid substitutions 124R and 178R;

bbb) H1 comprises amino acid substitution 188K, L1 comprises amino acid substitutions 129T, 176E and 178E, H2 comprises amino acid substitutions 143E, 145T, and 179E, and L2 comprises amino acid substitutions 124R and 178R;

ccc) H1 comprises amino acid substitutions 143A and 179K, L1 comprises amino acid substitutions 129T, 133W and 180E, H2 comprises amino acid substitutions 143E, 145T, 179E, and 188L, and L2 comprises amino acid substitutions 124R and 178R;

ddd) H1 comprises amino acid substitution 179K, L1 comprises amino acid substitutions 129T and 180E, H2 comprises amino acid substitutions 143E, 145T, 179E, and 188L, and L2 comprises amino acid substitutions 124R and 178R;

eee) H1 comprises amino acid substitution 179K, L1 comprises amino acid substitutions 129T, 178E and 180E, H2 comprises amino acid substitutions 143E, 145T, and 179E, and L2 comprises amino acid substitutions 124R and 178R;

fff) H1 comprises amino acid substitution 186R, L1 comprises amino acid substitutions 129T and 180E, H2 comprises amino acid substitutions 143E, 145T, and 179E, and L2 comprises amino acid substitutions 124R, 129K, 160K, and 178R;

ggg) H1 comprises amino acid substitution 179K, L1 comprises amino acid substitutions 129T and 180E, H2 comprises amino acid substitutions 143E, 145T, and 179E, and L2 comprises amino acid substitutions 124R, 129K, and 178R;

hhh) H1 comprises amino acid substitution 186R, L1 comprises amino acid substitutions 129T and 180E, H2 comprises amino acid substitutions 143E, 145T, and 179E, and L2 comprises amino acid substitutions 124R, 129K, and 178R;

iii) H1 comprises amino acid substitution 186R, L1 comprises amino acid substitutions 129T and 180E, H2 comprises amino acid substitutions 143E, 145T, and 179E, and L2 comprises amino acid substitutions 124R, 160K, and 178R;

jjj) H1 comprises amino acid substitution 186R, L1 comprises amino acid substitutions 129T and 180E, H2 comprises amino acid substitutions 143E, 145T, and 179E, and L2 comprises amino acid substitutions 124R, and 178R;

kkk) H1 comprises amino acid substitutions 179K and 190K, L1 comprises amino acid substitutions 129T, 133D, 135S and 180E, H2 comprises amino acid substitutions 143E, and 145T, and L2 comprises amino acid substitutions 124R, 160K, and 178R;

lll) H1 comprises amino acid substitution 179K, L1 comprises amino acid substitutions 129T and 180E, H2 comprises amino acid substitutions 122C, 143E, and 145T, and L2 comprises amino acid substitutions 124C, 160K, and 178R;

mmm) H1 comprises amino acid substitutions 143A and 179K, L1 comprises amino acid substitutions 129T, 133W and 180E, H2 comprises amino acid substitutions 143E, 145T, and 188L, and L2 comprises amino acid substitutions 124R and 178R;

nnn) H1 comprises amino acid substitutions 143A and 179K, L1 comprises amino acid substitutions 129T and 133W and 180E, H2 comprises amino acid substitutions 143E, 145T, and 188L, and L2 comprises amino acid substitutions 124R, 160K, and 178R; or ooo) H1 comprises amino acid substitution 179K, L1 comprises amino acid substitutions 129T and 180E, H2 comprises amino acid substitutions 143E, 145T, and 179E, and L2 comprises amino acid substitutions 124R, 129K, 160K, and 178R.

2. The construct of claim 1, wherein the amino acid substitutions promote preferential pairing of H1 with L1 as compared to L2, and/or that promote preferential pairing of H2 with L2 as compared to L1, when H1, H2, L1 and L2 are co-expressed in a cell or a mammalian cell, or when H1, H2, L1 and L2 are co-expressed in a cell-free expression system, or when H1 and L1 are produced in a cell and H2 and L2 are produced in a different cell and the products of the two cells are mixed via a redox production method, or when H1 and L1 are produced in a cell-free expression system and H2 and L2 are produced in a different cell-free expression system and the products of the two cell-free expression systems are mixed.

3. The construct according to claim 1, wherein the sequences of each of H1, H2, L1, and L2 are derived from human sequences or humanized sequences.

4. The construct of claim 3, wherein the construct further comprises a dimeric Fc having two Fc polypeptides each comprising a CH2 domain sequence and a CH3 domain sequence and coupled with or without linkers to one of the first Fab region and second Fab region.

5. The construct of claim 4, wherein the Fc is a human Fc, a human IgG1 Fc, a human IgA Fc, a human IgG Fc, a human IgD Fc, a human IgE Fc, a human IgM Fc, a human IgG2 Fc, a human IgG3 Fc, or a human IgG4 Fc.

6. The construct of claim 5, wherein the Fc comprises one or more substitutions as compared to wild type in at least one of the CH3 domain sequences that promote preferential pairing between heterodimeric CH3 domain sequences relative to homodimeric CH3 domain sequences.

7. The construct of claim 6, wherein the Fc comprises:

i) a heterodimeric IgG1 Fc having the substitutions L351Y_F405A_Y407V in the first Fc polypeptide, and the substitutions T366L_K392M_T394W in the second Fc polypeptide;

ii) a heterodimeric IgG1 Fc having the substitutions L351Y_F405A_Y407V in the first Fc polypeptide, and the substitutions T366L_K392L_T394W in the second Fc polypeptide;

iii) a heterodimeric IgG1 Fc having the substitutions T350V_L351Y_F405A_Y407V in the first Fc polypeptide, and the substitutions T350V_T366L_K392L_T394W in the second Fc polypeptide;

iv) a heterodimeric IgG1 Fc having the substitutions T350V_L351Y_F405A_Y407V in the first Fc polypeptide, and the substitutions T350V_T366L_K392M_T394W in the second Fc polypeptide; or v) a heterodimeric IgG1 Fc having the substitutions T350V_L351Y_S400E_F405A_Y407V in the first Fc polypeptide, and the substitutions T350V_T366L_N390R_K392M_T394W in the second Fc polypeptide, wherein the numbering of amino acid residues in the Fc is according to EU numbering.

8. The construct of claim 4, wherein when H1, L1, H2 and L2 are co-expressed, a) the change in the amount of total correct pairing as measured by the sum of H1L1 and H2L2 pairing is greater than about 5%, 10%, 15%, 20%, 25%, 30%, 35%, 40%, or 45% compared to the pairing of corresponding H1, L1, H2 and L2 polypeptide chains without the amino acid substitutions that promote preferential pairing;

b) the change in the amount of total correct pairing, as measured by the amount of bispecific antibody produced as a percentage of species other than half-antibodies produced, is greater than about 5%, 10%, 20%, 30%, 40%, 50%, 60%, 70%, or 80%, compared to the pairing of corresponding H1, L1, H2 and L2 polypeptide chains without the amino acid substitutions that promote preferential pairing, or c) the change in the amount of total correct pairing, as measured by the amount of bispecific antibody produced as a percentage of all species produced, is greater than about 5%, 10%, 20%, 30%, 40%, 50%, 60%, 70%, or 80%, compared to the pairing of corresponding H1, L1, H2 and L2 polypeptide chains without the amino acid substitutions that promote preferential pairing.

9. The construct of claim 4, wherein the Fc comprises one or more modifications to promote selective binding of Fc-gamma receptors, to reduce or eliminate binding to Fc-gamma receptors, or to promote binding to FcRn.

10. The construct of claim 4, wherein the linkers are one or more polypeptide linkers.

11. The construct according to claim 1, conjugated to a therapeutic agent or drug.

12. The construct according to claim 1, wherein:

(a) H1 comprises amino acid substitution 143K, L1 comprises amino acid substitutions 129T and 133D, H2 comprises amino acid substitutions 124W, 143E, 145T, and 179E, and L2 comprises amino acid substitutions 124K, 133A, and 178R;

(b) H1 comprises amino acid substitution 186R, L1 comprises amino acid substitutions 129T and 180E, H2 comprises amino acid substitutions 45P, 143E, 145T, and 179E, and L2 comprises amino acid substitutions 44F, 124K, and 178R; or (c) H1 comprises amino acid substitution 179K, L1 comprises amino acid substitutions 129T, 178E and 180E, H2 comprises amino acid substitutions 143E, 145T, and 179E, and L2 comprises amino acid substitutions 124R and 178R.

13. The construct of claim 12, wherein the amino acid substitutions promote preferential pairing of H1 with L1 as compared to L2, and/or that promote preferential pairing of H2 with L2 as compared to L1, when H1, H2, L1 and L2 are co-expressed in a cell or a mammalian cell, or when H1, H2, L1 and L2 are co-expressed in a cell-free expression system, or when H1 and L1 are produced in a cell and H2 and L2 are produced in a different cell and the products of the two cells are mixed via a redox production method, or when H1 and L1 are produced in a cell-free expression system and H2 and L2 are produced in a different cell-free expression system and the products of the two cell-free expression systems are mixed.

14. The construct according to claim 13, wherein the sequences of each of H1, H2, L1, and L2 are derived from human sequences or humanized sequences.

15. The construct of claim 14, wherein the construct further comprises a dimeric Fc having two Fc polypeptides each comprising a CH2 domain sequence and a CH3 domain sequence and coupled with or without linkers to one of the first Fab region and second Fab region.

16. The construct of claim 15, wherein the PC is a human PC, a human IgG1 PC, a human IgA PC, a human IgG PC, a human IgD PC, a human IgE PC, a human IgM PC, a human IgG2 PC, a human IgG3 PC, or a human IgG4 Fc.

17. The construct of claim 16, wherein the Fc comprises one or more substitutions as compared to wild type in at least one of the CH3 domain sequences that promote-preferential pairing between heterodimeric CH3 domain sequences relative to homodimeric CH3 domain sequences.

18. The construct of claim 17, wherein the Fc comprises:

i) a heterodimeric IgG1 Fc having the substitutions L351Y_F405A_Y407V in the first PC polypeptide, and the substitutions T366L_K3 92M_T394W in the second Fc polypeptide;

ii) a heterodimeric IgG1 Fc having the substitutions L351Y_F405A_Y407V in the first PC polypeptide, and the substitutions T366L_K3 92L_T394W in the second Fc polypeptide;

iii) a heterodimeric IgG1 Fc having the substitutions T3 50V_L35 1Y_F405A_Y407V in the first PC polypeptide, and the substitutions T350V_T3 66L_K3 92L_T394W in the second Fc polypeptide;

iv) a heterodimeric IgG1 Fc having the substitutions T350V_L35 1Y_F405A_Y407V in the first PC polypeptide, and the substitutions_T350V_T366L_K392M_T394W in the second Fc polypeptide; or v) a heterodimeric IgG1 Fc having the substitutions T350V_L351Y_S400E_F405A_Y407V in the first PC polypeptide, and the substitutions T350V_T366L_N3 90R_K3 92M_T394W in the second Fc polypeptide, wherein the numbering of amino acid residues in the PC is according to EU numbering.

19. The construct of claim 15, wherein the Fc comprises one or more modifications to promote selective binding of Fc-gamma receptors, to reduce or eliminate binding to Fc-gamma receptors, or to promote binding to FcRn.

20. The construct of claim 15, wherein the linkers are one or more polypeptide linkers.

21. The construct according to claim 18, conjugated to a therapeutic agent or drug.

22. A pharmaceutical composition comprising the antigen-binding polypeptide construct of claim 1 and a pharmaceutically acceptable carrier.

23. A polynucleotide or set of polynucleotides that encodes the construct of claim 1.

24. A vector or set of vectors comprising one or more of the polynucleotides or sets of polynucleotides according to claim 23.

25. An isolated cell comprising the polynucleotide or set of polynucleotides according to claim 23.

26. A method of preparing the construct according to claim 1, comprising the steps of:

(a) obtaining a host cell comprising a polynucleotide or set of polynucleotides encoding the antigen-binding polypeptide construct;

(b) culturing the host cell in a host cell culture under conditions that allow expression of the antigen-binding polypeptide construct, and (c) collecting the antigen-binding polypeptide construct from the host cell culture.

* * * * *

SEQUENCE LISTING

```
<160> NUMBER OF SEQ ID NOS: 182

<210> SEQ ID NO 1
<211> LENGTH: 227
<212> TYPE: PRT
<213> ORGANISM: Artificial Sequence
<220> FEATURE:
<223> OTHER INFORMATION: synthetic Pertuzumab heavy chain Fab (Domain
      boundaries: VH; E1 - S119, CH1; A120 - V217, Hinge (partial);
      E218 - T227)

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225


<210> SEQ ID NO 2
<211> LENGTH: 214
<212> TYPE: PRT
<213> ORGANISM: Artificial Sequence
```

<220> FEATURE:
<223> OTHER INFORMATION: synthetic Pertuzumab light chain (kappa)
(Domain boundaries: VL; D1 - K107, CL; R108 - C214)

<400> SEQUENCE: 2

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 3
<211> LENGTH: 226
<212> TYPE: PRT
<213> ORGANISM: Artificial Sequence
<220> FEATURE:
<223> OTHER INFORMATION: CAT-2200 heavy chain Fab (Domain boundaries:
VH; E1 - S118, CH1; A119 - V216, Hinge(partial); E217 - T226)

<400> SEQUENCE: 3

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Leu Ile His Gly Val Thr Arg Asn Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Gln Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr
225

<210> SEQ ID NO 4
<211> LENGTH: 216
<212> TYPE: PRT
<213> ORGANISM: Artificial Sequence
<220> FEATURE:
<223> OTHER INFORMATION: CAT-2200 light chain (lambda) (Domain boundaries: VL; N1 - L110, CL; G111 - S216)

<400> SEQUENCE: 4

Asn Phe Met Leu Thr Gln Pro His Ser Val Ser Glu Ser Pro Gly Lys
1 5 10 15

Thr Val Thr Ile Ser Cys Thr Arg Ser Ser Gly Ser Leu Ala Asn Tyr
20 25 30

Tyr Val Gln Trp Tyr Gln Gln Arg Pro Gly Ser Ser Pro Thr Ile Val
35 40 45

Ile Phe Ala Asn Asn Gln Arg Pro Ser Gly Val Pro Asp Arg Phe Ser
50 55 60

Gly Ser Ile Asp Ser Ser Ser Asn Ser Ala Ser Leu Thr Ile Ser Gly
65 70 75 80

Leu Lys Thr Glu Asp Glu Ala Asp Tyr Tyr Cys Gln Thr Tyr Asp Pro
85 90 95

Tyr Ser Val Val Phe Gly Gly Gly Thr Lys Leu Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

```
<210> SEQ ID NO 5
<211> LENGTH: 222
<212> TYPE: PRT
<213> ORGANISM: Artificial Sequence
<220> FEATURE:
<223> OTHER INFORMATION: IgG1 Fc (Domain boundaries: Hinge (partial);
      C1 - P5, CH2; A6 - K115, CH3; G116 - K222)

<400> SEQUENCE: 5
```

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

```
<210> SEQ ID NO 6
<211> LENGTH: 666
<212> TYPE: DNA
<213> ORGANISM: Artificial Sequence
<220> FEATURE:
<223> OTHER INFORMATION: IgG1 Fc

<400> SEQUENCE: 6
```

| | | | | | |
|---|---|---|---|---|---|
| tgccctccct | gtccagctcc | agaactgctg | ggaggaccta | gcgtgttcct | gtttccccct | 60 |
| aagccaaaag | acactctgat | gatttccagg | actcccgagg | tgacctgcgt | ggtggtggac | 120 |
| gtgtctcacg | aggaccccga | agtgaagttc | aactggtacg | tggatggcgt | ggaagtgcat | 180 |
| aatgctaaga | caaaaccaag | agaggaacag | tacaactcca | cttatcgcgt | cgtgagcgtg | 240 |
| ctgaccgtgc | tgcaccagga | ctggctgaac | gggaaggagt | ataagtgcaa | agtcagtaat | 300 |
| aaggccctgc | ctgctccaat | cgaaaaaacc | atctctaagg | ccaaaggcca | gccaagggag | 360 |
| ccccaggtgt | acacactgcc | acccagcaga | gacgaactga | ccaagaacca | ggtgtccctg | 420 |
| acatgtctgg | tgaaaggctt | ctatcctagt | gatattgctg | tggagtggga | atcaaatgga | 480 |
| cagccagaga | acaattacaa | gaccacacct | ccagtgctgg | acagcgatgg | cagcttcttc | 540 |

ctgtattcca agctgacagt ggataaatct cgatggcagc aggggaacgt gtttagttgt 600
tcagtgatgc atgaagccct gcacaatcat tacactcaga agagcctgtc cctgtctccc 660
ggcaaa 666

<210> SEQ ID NO 7
<211> LENGTH: 681
<212> TYPE: DNA
<213> ORGANISM: Artificial Sequence
<220> FEATURE:
<223> OTHER INFORMATION: Pertuzumab heavy chain Fab

<400> SEQUENCE: 7
gaagtgcagc tggtcgaatc tggaggagga ctggtgcagc caggagggtc cctgcgcctg 60
tcttgcgccg ctagtggctt cacttttacc gactacacca tggattgggt gcgacaggca 120
cctggaaagg gcctggagtg ggtcgccgat gtgaacccaa atagcggagg ctccatctac 180
aaccagcggt tcaagggccg gttcaccctg tcagtggacc ggagcaaaaa caccctgtat 240
ctgcagatga atagcctgcg agccgaagat actgctgtgt actattgcgc ccggaatctg 300
gggccctcct tctactttga ctattggggg cagggaactc tggtcaccgt gagctccgcc 360
tccaccaagg gaccttctgt gttcccactg gctccctcta gtaaatccac atctgggga 420 actgcagccc tgggctgtct ggtgaaggac tacttcccag agcccgtcac agtgtcttgg 480
aacagtggcg ctctgacttc tggggtccac acctttcctg cagtgctgca gtcaagcggg 540
ctgtacagcc tgtcctctgt ggtcaccgtg ccaagttcaa gcctgggaac acagacttat 600
atctgcaacg tgaatcacaa gccatccaat acaaaagtcg acaagaaagt ggaacccaag 660
tcttgtgata aaacccatac a 681

<210> SEQ ID NO 8
<211> LENGTH: 642
<212> TYPE: DNA
<213> ORGANISM: Artificial Sequence
<220> FEATURE:
<223> OTHER INFORMATION: Pertuzumab light chain (kappa)

<400> SEQUENCE: 8
gatattcaga tgacccagtc cccaagctcc ctgagtgcct cagtgggcga ccgagtcacc 60
atcacatgca aggcttccca ggatgtgtct attggagtcg catggtacca gcagaagcca 120
ggcaaagcac ccaagctgct gatctatagc gcctcctacc ggtataccgg cgtgccctct 180
agattctctg gcagtgggtc aggaacagac tttactctga ccatctctag tctgcagcct 240
gaggatttcg ctacctacta ttgccagcag tactatatct acccatatac ctttggccag 300
gggacaaaag tggagatcaa gaggactgtg gccgctccct ccgtcttcat tttccccct 360 tctgacgaac agctgaaaag tggcacagcc agcgtggtct gtctgctgaa caatttctac 420
cctcgcgaag ccaaagtgca gtggaaggtc gataacgctc tgcagagcgg caacagccag 480
gagtctgtga ctgaacagga cagtaaagat tcaacctata gcctgtcaag cacactgact 540
ctgagcaagg cagactacga gaagcacaaa gtgtatgcct gcgaagtcac acatcagggg 600
ctgtcctctc ctgtgactaa gagctttaac agaggagagt gt 642

<210> SEQ ID NO 9
<211> LENGTH: 678
<212> TYPE: DNA
<213> ORGANISM: Artificial Sequence
<220> FEATURE:

<223> OTHER INFORMATION: CAT-2200 heavy chain Fab

<400> SEQUENCE: 9
gaggtgcagc tgctggaatc tgggggggc ctggtgcagc ctggggggtc cctgagactg 60
tcatgtgctg ccagcgggtt tactttcagc tcctacgcta tgtcctgggt gcgacaggca 120
cccgggaagg gactggagtg ggtctctgca atcagtgggt caggcgggag tacttactat 180
gccgacagcg tgaagggacg gttcactatc tcaagagata acagcaagaa caccctgtat 240
ctgcagatga acagcctgag agcagaagac acagccgtgt actattgcgc cagggatctg 300
atccacggag tcactcgcaa ttggggccag ggactctgg tgaccgtctc tagtgctagc 360 acaaagggc cctctgtgtt tccactggcc ccctcaagca aaagcacatc cggaggaact 420
gcagctctgg gatgtctggt gaaggactac ttcccccagc ctgtgaccgt ctcttggaac 480
agtggagccc tgaccagcgg cgtgcacaca tttcctgctg tcctgcagtc ctctggcctg 540
tactccctga gttcagtggt cacagtgcct agctcctctc tggggaccca gacatatatt 600
tgcaacgtga atcataaacc aagcaacact aaggtcgaca agaaagtgga gcccaagagc 660
tgtgataaaa ctcatacc 678

<210> SEQ ID NO 10
<211> LENGTH: 648
<212> TYPE: DNA
<213> ORGANISM: Artificial Sequence
<220> FEATURE:
<223> OTHER INFORMATION: CAT-2200 light chain (lambda)

<400> SEQUENCE: 10
aactttatgc tgactcagcc ccactccgtg tccgagagcc ctggcaaaac tgtgactatt 60
tcatgtaccc gatcatctgg aagcctggcc aactactatg tgcagtggta ccagcagagg 120
ccaggcagct cccccactat cgtgattttc gctaacaatc agcggccttc cggcgtccca 180
gacagatttt ccgggtctat cgattctagt tcaaatagtg catcactgac tatttccggg 240
ctgaagaccg aggacgaagc cgattactat tgccagacct acgaccccta ttctgtggtc 300
ttcggcgggg gaaccaagct gacagtgctg ggacagccaa aagcggcgcc cagtgtcaca 360
ctgtttcccc ctagctccga ggaactgcag gctaacaaag caacactggt gtgtctgatc 420
agcgacttct accctggagc tgtgactgtc gcctggaagg ctgattctag tccagtgaaa 480
gcaggcgtcg agaccacaac tccctctaag cagagtaaca acaagtacgc agcctcaagc 540
tatctgtcac tgaccccaga acagtggaag agccaccgga gctattcctg ccaggtcact 600
cacgaaggct ccactgtcga gaaaaccgtc gctcccaccg aatgttca 648

<210> SEQ ID NO 11
<211> LENGTH: 217
<212> TYPE: PRT
<213> ORGANISM: Artificial Sequence
<220> FEATURE:
<223> OTHER INFORMATION: Human IgG1 Fc sequence 231-447 (EU-numbering), without hinge

<400> SEQUENCE: 11

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Asp Glu Leu
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 12
<211> LENGTH: 228
<212> TYPE: PRT
<213> ORGANISM: Artificial Sequence
<220> FEATURE:
<223> OTHER INFORMATION: SGN-CD19a heavy chain Fab (Domain boundaries: VH; Q1 - S120, CH1; A121 - V218, Hinge (partial); E219 - T228)

<400> SEQUENCE: 12

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Ser
20 25 30

Gly Met Gly Val Gly Trp Ile Arg Gln Pro Pro Gly Lys Ala Leu Glu
35 40 45

Trp Leu Ala His Ile Trp Trp Asp Asp Asp Lys Arg Tyr Asn Pro Ala
50 55 60

Leu Lys Ser Arg Leu Thr Ile Ser Lys Asp Thr Ser Lys Asn Gln Val
65 70 75 80

Val Leu Thr Met Thr Asn Met Asp Pro Val Asp Thr Ala Ala Tyr Tyr
85 90 95

Cys Ala Arg Met Glu Leu Trp Ser Tyr Tyr Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225


<210> SEQ ID NO 13
<211> LENGTH: 213
<212> TYPE: PRT
<213> ORGANISM: Artificial Sequence
<220> FEATURE:
<223> OTHER INFORMATION: SGN-CD19a light chain (kappa) (Domain
      boundaries: VL; E1 - K106, CL; R107 - C213)

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 14
<211> LENGTH: 233
<212> TYPE: PRT
<213> ORGANISM: Artificial Sequence
<220> FEATURE:
<223> OTHER INFORMATION: CR8071 heavy chain Fab (Domain boundaries: VH;
      Q1 - S125, CH1; A126 - V223, Hinge (partial); E224 - T233)

<400> SEQUENCE: 14

Gln Val Gln Leu Val Gln Ser Gly Ala Glu Val Lys Lys Pro Gly Ala
1               5                   10                  15

Ser Val Arg Val Ser Cys Arg Ala Ser Gly Tyr Ile Phe Thr Glu Ser
```

```
            20                  25                  30

Gly Ile Thr Trp Val Arg Gln Ala Pro Gly Gln Gly Leu Glu Trp Met
        35                  40                  45

Gly Trp Ile Ser Gly Tyr Ser Gly Asp Thr Lys Tyr Ala Gln Lys Leu
    50                  55                  60

Gln Gly Arg Val Thr Met Thr Lys Asp Thr Ser Thr Thr Thr Ala Tyr
65                  70                  75                  80

Met Glu Leu Arg Ser Leu Arg Tyr Asp Asp Thr Ala Val Tyr Tyr Cys
                85                  90                  95

Ala Arg Asp Val Gln Tyr Ser Gly Ser Tyr Leu Gly Ala Tyr Tyr Phe
            100                 105                 110

Asp Tyr Trp Ser Pro Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230


<210> SEQ ID NO 15
<211> LENGTH: 216
<212> TYPE: PRT
<213> ORGANISM: Artificial Sequence
<220> FEATURE:
<223> OTHER INFORMATION: CR8071 light chain (lambda) (Domain boundaries:
      VL; Q1 - L110, CL; R111 - S216)

<400> SEQUENCE: 15

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Asn
            20                  25                  30

Tyr Val Tyr Trp Tyr Gln Gln Phe Pro Gly Thr Ala Pro Lys Leu Leu
        35                  40                  45

Ile Tyr Arg Ser Tyr Gln Arg Pro Ser Gly Val Pro Asp Arg Phe Ser
    50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asp Gly Trp Val Phe Gly Gly Gly Thr Lys Leu Thr Val Leu Arg Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140
```

-continued

```
Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 16
<211> LENGTH: 684
<212> TYPE: DNA
<213> ORGANISM: Artificial Sequence
<220> FEATURE:
<223> OTHER INFORMATION: SGN-CD19a heavy chain Fab

<400> SEQUENCE: 16

```
caggtgacac tgagagaatc cggcccagcc ctggtgaagc ccactcagac cctgacactg     60

acttgcacct tctctgggtt ttccctgtct acaagtggga tgggagtggg atggatcagg    120

cagccacctg gaaaagccct ggagtggctg gctcacattt ggtgggacga tgacaagcgg    180

tacaacccag cactgaaaag cagactgaca atcagcaagg atacttccaa aaaccaggtg    240

gtcctgacaa tgactaatat ggaccccgtg gacacagccg cttactattg cgcccgcatg    300

gaactgtgga gctactattt cgactactgg gggcagggaa cactggtcac tgtgagctcc    360

gctagcacta aggggccttc cgtgtttcca ctggctccct ctagtaaatc cacctctgga    420

ggcacagctg cactgggatg tctggtgaag gattacttcc ctgaaccagt cacagtgagt    480

tggaactcag gggctctgac aagtggagtc catacttttc ccgcagtgct gcagtcaagc    540

ggactgtact ccctgtcctc tgtggtcacc gtgcctagtt caagcctggg cacccagaca    600

tatatctgca acgtgaatca caagccatca aatacaaaag tcgacaagaa agtggagccc    660

aagagctgtg ataaaactca tacc                                           684
```

<210> SEQ ID NO 17
<211> LENGTH: 639
<212> TYPE: DNA
<213> ORGANISM: Artificial Sequence
<220> FEATURE:
<223> OTHER INFORMATION: SGN-CD19a light chain (kappa)

<400> SEQUENCE: 17

```
gagatcgtgc tgacccagtc tccagccaca ctgtctctga gcccaggaga gagggccacc     60

ctgtcctgct ctgccagctc cagcgtgagc tacatgcact ggtatcagca gaagccagga    120

caggccccta ggctgctgat ctacgacacc agcaagctgg cctccggcat ccccgcaaga    180

ttcagcggct ccggctctgg cacagacttt accctgacaa tcagctccct ggagcctgag    240

gatttcgccg tgtactattg ttttcagggc agcgtgtatc cattcacctt tggccagggc    300

acaaagctgg agatcaagcg gacagtggcg gcgcccagtg tcttcatttt tccccctagc    360

gacgaacagc tgaagtctgg gacagccagt gtggtctgtc tgctgaacaa cttctaccct    420

agagaggcta aagtgcagtg gaaggtcgat aacgcactgc agtccggaaa ttctcaggag    480

agtgtgactg aacaggactc aaaagatagc acctattccc tgtcaagcac actgactctg    540

agcaaggccg actacgagaa gcataaagtg tatgcttgtg aagtcaccca ccaggggctg    600
```

agttcaccag tcacaaaatc attcaacaga ggggagtgc 639

<210> SEQ ID NO 18
<211> LENGTH: 699
<212> TYPE: DNA
<213> ORGANISM: Artificial Sequence
<220> FEATURE:
<223> OTHER INFORMATION: CR8071 heavy chain Fab

<400> SEQUENCE: 18
caggtgcagc tggtccagtc cggggctgaa gtgaaaaaac ctggggcatc cgtgcgggtg 60
tcatgtcggg caagcgggta tatctttact gagtctggaa tcacctgggt gaggcaggct 120
cccggacagg gactggaatg gatgggatgg atttctggat acagtggcga cacaaagtat 180
gcacagaaac tgcagggccg cgtcaccatg acaaaggata cttcaaccac aactgcctac 240
atggagctgc ggagcctgag atatgacgat acagccgtgt actattgcgc ccgggacgtg 300
cagtacagcg ggtcctacct gggggcatac tacttcgatt actggtcacc tggaactctg 360
gtcaccgtct cttcagctag caccaagggc ccttctgtgt ttccactggc accctcaagc 420
aaaagcacct ccggaggaac agcagcactg ggatgtctgg tcaaggacta tttccccgag 480
cctgtgaccg tctcatggaa tagcggcgca ctgactagtg gggtgcacac ctttcccgcc 540
gtcctgcagt cctctgggct gtacagcctg agttcagtgg tcacagtgcc aagctcctct 600
ctgggaactc agacctatat ctgcaacgtc aatcataaac ccagcaacac aaaggtcgac 660
aagaaagtgg agcccaagag ctgtgataaa actcatacc 699

<210> SEQ ID NO 19
<211> LENGTH: 648
<212> TYPE: DNA
<213> ORGANISM: Artificial Sequence
<220> FEATURE:
<223> OTHER INFORMATION: CR8071 light chain (lambda)

<400> SEQUENCE: 19
cagagcgtcc tgactcagcc tccctccgcc tccggaacac ctgggcagag agtgactatc 60
tcctgtagcg gatcaagctc aaacattgga accaactacg tgtattggta ccagcagttc 120
cccggcacag ctcctaagct gctgatctat cggagctacc agagaccaag cggggtcccc 180
gacaggtttt ctggcagtaa atcagggagc tccgccagcc tggctatttc cggcctgcag 240
tctgaggacg aagcagatta ctattgcgcc acctgggacg attccctgga tggatgggtc 300
ttcggcggcg gcacaaaact gaccgtcctg aggcagccaa aggcggcgcc cagtgtcaca 360
ctgtttcccc ctagctccga ggaactgcag gctaacaaag caacactggt gtgtctgatc 420
agcgacttct accctggagc tgtgactgtc gcctggaagg ctgattctag tccagtgaaa 480
gcaggcgtcg agaccacaac tccctctaag cagagtaaca acaagtacgc agcctcaagc 540
tatctgtcac tgaccccaga acagtggaag agccaccgga gctattcctg ccaggtcact 600
cacgaaggct ccactgtcga gaaaaccgtc gctcccaccg aatgttca 648

<210> SEQ ID NO 20
<211> LENGTH: 119
<212> TYPE: PRT
<213> ORGANISM: Artificial Sequence
<220> FEATURE:
<223> OTHER INFORMATION: Pertuzumab

<400> SEQUENCE: 20

Glu Val Gln Leu Val Glu Ser Gly Gly Gly Leu Val Gln Pro Gly Gly

```
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115


<210> SEQ ID NO 21
<211> LENGTH: 117
<212> TYPE: PRT
<213> ORGANISM: Artificial Sequence
<220> FEATURE:
<223> OTHER INFORMATION: D3H44

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30

Tyr Met His Trp Val Arg Gln Ala Pro Gly Lys Gly Leu Glu Trp Val
        35                  40                  45

Gly Leu Ile Asp Pro Glu Gln Gly Asn Thr Ile Tyr Asp Pro Lys Phe
    50                  55                  60

Gln Asp Arg Ala Thr Ile Ser Ala Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Thr Ala Ala Tyr Phe Asp Tyr Trp Gly Gln Gly Thr Leu
            100                 105                 110

Val Thr Val Ser Ser
        115


<210> SEQ ID NO 22
<211> LENGTH: 97
<212> TYPE: PRT
<213> ORGANISM: Artificial Sequence
<220> FEATURE:
<223> OTHER INFORMATION: X92218HV3-66*01

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60
```

-continued

```
Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

<210> SEQ ID NO 23
<211> LENGTH: 98
<212> TYPE: PRT
<213> ORGANISM: Artificial Sequence
<220> FEATURE:
<223> OTHER INFORMATION: M99641HV1-18*01

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg
```

<210> SEQ ID NO 24
<211> LENGTH: 98
<212> TYPE: PRT
<213> ORGANISM: Artificial Sequence
<220> FEATURE:
<223> OTHER INFORMATION: X62106HV1-2*02

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg
```

<210> SEQ ID NO 25
<211> LENGTH: 98
<212> TYPE: PRT
<213> ORGANISM: Artificial Sequence
<220> FEATURE:
<223> OTHER INFORMATION: M99642HV1-24*01

<400> SEQUENCE: 25

```
Gln Val Gln Leu Val Gln Ser Gly Ala Glu Val Lys Lys Pro Gly Ala
```

```
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr


<210> SEQ ID NO 26
<211> LENGTH: 98
<212> TYPE: PRT
<213> ORGANISM: Artificial Sequence
<220> FEATURE:
<223> OTHER INFORMATION: X62109HV1-3*01

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg


<210> SEQ ID NO 27
<211> LENGTH: 98
<212> TYPE: PRT
<213> ORGANISM: Artificial Sequence
<220> FEATURE:
<223> OTHER INFORMATION: X92209HV1-45*01

<400> SEQUENCE: 27

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg
```

<210> SEQ ID NO 28
<211> LENGTH: 98
<212> TYPE: PRT
<213> ORGANISM: Artificial Sequence
<220> FEATURE:
<223> OTHER INFORMATION: X92343HV1-46*01

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 29
<211> LENGTH: 98
<212> TYPE: PRT
<213> ORGANISM: Artificial Sequence
<220> FEATURE:
<223> OTHER INFORMATION: M29809HV1-58*01

<400> SEQUENCE: 29

```
Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala
```

<210> SEQ ID NO 30
<211> LENGTH: 98
<212> TYPE: PRT
<213> ORGANISM: Artificial Sequence
<220> FEATURE:
<223> OTHER INFORMATION: L22582HV1-69*01, KC713934HV1-69D*01

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 31
<211> LENGTH: 98
<212> TYPE: PRT
<213> ORGANISM: Artificial Sequence
<220> FEATURE:
<223> OTHER INFORMATION: KF698734HV1-69-2*01

<400> SEQUENCE: 31

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 32
<211> LENGTH: 98
<212> TYPE: PRT
<213> ORGANISM: Artificial Sequence
<220> FEATURE:
<223> OTHER INFORMATION: M99637HV1-8*01

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 33
<211> LENGTH: 99
<212> TYPE: PRT
<213> ORGANISM: Artificial Sequence
<220> FEATURE:
<223> OTHER INFORMATION: M99648HV2-26*01

<400> SEQUENCE: 33

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg

<210> SEQ ID NO 34
<211> LENGTH: 99
<212> TYPE: PRT
<213> ORGANISM: Artificial Sequence
<220> FEATURE:
<223> OTHER INFORMATION: X62111HV2-5*01

<400> SEQUENCE: 34

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His

<210> SEQ ID NO 35
<211> LENGTH: 99
<212> TYPE: PRT
<213> ORGANISM: Artificial Sequence
<220> FEATURE:
<223> OTHER INFORMATION: L21969HV2-70*01

<400> SEQUENCE: 35

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg

<210> SEQ ID NO 36
<211> LENGTH: 99
<212> TYPE: PRT
<213> ORGANISM: Artificial Sequence
<220> FEATURE:
<223> OTHER INFORMATION: KC713935HV2-70D*04

<400> SEQUENCE: 36

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg
```

<210> SEQ ID NO 37
<211> LENGTH: 98
<212> TYPE: PRT
<213> ORGANISM: Artificial Sequence
<220> FEATURE:
<223> OTHER INFORMATION: X92287HV3-11*03

<400> SEQUENCE: 37

```
Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 38
<211> LENGTH: 97
<212> TYPE: PRT
<213> ORGANISM: Artificial Sequence
<220> FEATURE:
<223> OTHER INFORMATION: X92217HV3-13*01

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg


<210> SEQ ID NO 39
<211> LENGTH: 100
<212> TYPE: PRT
<213> ORGANISM: Artificial Sequence
<220> FEATURE:
<223> OTHER INFORMATION: X92216HV3-15*01

<400> SEQUENCE: 39

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100


<210> SEQ ID NO 40
<211> LENGTH: 98
<212> TYPE: PRT
<213> ORGANISM: Artificial Sequence
<220> FEATURE:
<223> OTHER INFORMATION: M99657HV3-20*01

<400> SEQUENCE: 40

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg


<210> SEQ ID NO 41
<211> LENGTH: 98
<212> TYPE: PRT
```

<213> ORGANISM: Artificial Sequence
<220> FEATURE:
<223> OTHER INFORMATION: AB019439HV3-21*01

<400> SEQUENCE: 41

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 42
<211> LENGTH: 98
<212> TYPE: PRT
<213> ORGANISM: Artificial Sequence
<220> FEATURE:
<223> OTHER INFORMATION: M99660HV3-23*01

<400> SEQUENCE: 42

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys

<210> SEQ ID NO 43
<211> LENGTH: 98
<212> TYPE: PRT
<213> ORGANISM: Artificial Sequence
<220> FEATURE:
<223> OTHER INFORMATION: M83134HV3-30*01, X92283HV3-30-3*01

<400> SEQUENCE: 43

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr

```
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 44
<211> LENGTH: 98
<212> TYPE: PRT
<213> ORGANISM: Artificial Sequence
<220> FEATURE:
<223> OTHER INFORMATION: AC244456HV3-30-5*01

<400> SEQUENCE: 44

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 45
<211> LENGTH: 98
<212> TYPE: PRT
<213> ORGANISM: Artificial Sequence
<220> FEATURE:
<223> OTHER INFORMATION: AB019439HV3-33*01

<400> SEQUENCE: 45

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 46
<211> LENGTH: 98
<212> TYPE: PRT
<213> ORGANISM: Artificial Sequence
<220> FEATURE:
<223> OTHER INFORMATION: M99672HV3-43*01

<400> SEQUENCE: 46

```
Glu Val Gln Leu Val Glu Ser Gly Gly Val Val Val Gln Pro Gly Gly
1               5                   10                  15
```

```
Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys


<210> SEQ ID NO 47
<211> LENGTH: 98
<212> TYPE: PRT
<213> ORGANISM: Artificial Sequence
<220> FEATURE:
<223> OTHER INFORMATION: KC713950HV3-43D*01

<400> SEQUENCE: 47

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys


<210> SEQ ID NO 48
<211> LENGTH: 98
<212> TYPE: PRT
<213> ORGANISM: Artificial Sequence
<220> FEATURE:
<223> OTHER INFORMATION: M99675HV3-48*01

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 49
<211> LENGTH: 100
<212> TYPE: PRT
<213> ORGANISM: Artificial Sequence
<220> FEATURE:
<223> OTHER INFORMATION: AB019438HV3-49*03

<400> SEQUENCE: 49

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100
```

<210> SEQ ID NO 50
<211> LENGTH: 97
<212> TYPE: PRT
<213> ORGANISM: Artificial Sequence
<220> FEATURE:
<223> OTHER INFORMATION: M99679HV3-53*01

<400> SEQUENCE: 50

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

<210> SEQ ID NO 51
<211> LENGTH: 98
<212> TYPE: PRT
<213> ORGANISM: Artificial Sequence
<220> FEATURE:
<223> OTHER INFORMATION: M99682HV3-64*01

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45
```

Ser Ala Ile Ser Ser Asn Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 52
<211> LENGTH: 98
<212> TYPE: PRT
<213> ORGANISM: Artificial Sequence
<220> FEATURE:
<223> OTHER INFORMATION: M99649HV3-7*01

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 53
<211> LENGTH: 100
<212> TYPE: PRT
<213> ORGANISM: Artificial Sequence
<220> FEATURE:
<223> OTHER INFORMATION: X92206HV3-72*01

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 54
<211> LENGTH: 100
<212> TYPE: PRT
<213> ORGANISM: Artificial Sequence
<220> FEATURE:
<223> OTHER INFORMATION: X70197HV3-73*01

<400> SEQUENCE: 54

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 55
<211> LENGTH: 98
<212> TYPE: PRT
<213> ORGANISM: Artificial Sequence
<220> FEATURE:
<223> OTHER INFORMATION: L33851HV3-74*01

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 56
<211> LENGTH: 98
<212> TYPE: PRT
<213> ORGANISM: Artificial Sequence
<220> FEATURE:
<223> OTHER INFORMATION: M99651HV3-9*01

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
85 90 95

Ala Lys

<210> SEQ ID NO 57
<211> LENGTH: 98
<212> TYPE: PRT
<213> ORGANISM: Artificial Sequence
<220> FEATURE:
<223> OTHER INFORMATION: HM855939HV3-NL1*01

<400> SEQUENCE: 57

Gln Val Gln Leu Val Glu Ser Gly Gly Gly Val Val Gln Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ser Val Ile Tyr Ser Gly Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys

<210> SEQ ID NO 58
<211> LENGTH: 98
<212> TYPE: PRT
<213> ORGANISM: Artificial Sequence
<220> FEATURE:
<223> OTHER INFORMATION: X05714HV4-28*01

<400> SEQUENCE: 58

Gln Val Gln Leu Gln Glu Ser Gly Pro Gly Leu Val Lys Pro Ser Asp
1 5 10 15

Thr Leu Ser Leu Thr Cys Ala Val Ser Gly Tyr Ser Ile Ser Ser Ser
20 25 30

Asn Trp Trp Gly Trp Ile Arg Gln Pro Pro Gly Lys Gly Leu Glu Trp
35 40 45

Ile Gly Tyr Ile Tyr Tyr Ser Gly Ser Thr Tyr Tyr Asn Pro Ser Leu
50 55 60

Lys Ser Arg Val Thr Met Ser Val Asp Thr Ser Lys Asn Gln Phe Ser
65 70 75 80

Leu Lys Leu Ser Ser Val Thr Ala Val Asp Thr Ala Val Tyr Tyr Cys
85 90 95

Ala Arg

<210> SEQ ID NO 59
<211> LENGTH: 99
<212> TYPE: PRT
<213> ORGANISM: Artificial Sequence
<220> FEATURE:
<223> OTHER INFORMATION: L10089HV4-30-2*01

<400> SEQUENCE: 59

Gln Leu Gln Leu Gln Glu Ser Gly Ser Gly Leu Val Lys Pro Ser Gln
1 5 10 15

Thr Leu Ser Leu Thr Cys Ala Val Ser Gly Gly Ser Ile Ser Ser Gly

```
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg


<210> SEQ ID NO 60
<211> LENGTH: 99
<212> TYPE: PRT
<213> ORGANISM: Artificial Sequence
<220> FEATURE:
<223> OTHER INFORMATION: Z14238HV4-30-4*01

<400> SEQUENCE: 60

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg


<210> SEQ ID NO 61
<211> LENGTH: 99
<212> TYPE: PRT
<213> ORGANISM: Artificial Sequence
<220> FEATURE:
<223> OTHER INFORMATION: L10098HV4-31*01

<400> SEQUENCE: 61

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg


<210> SEQ ID NO 62
<211> LENGTH: 97
```

<212> TYPE: PRT
<213> ORGANISM: Artificial Sequence
<220> FEATURE:
<223> OTHER INFORMATION: AB019439HV4-34*01

<400> SEQUENCE: 62

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

<210> SEQ ID NO 63
<211> LENGTH: 98
<212> TYPE: PRT
<213> ORGANISM: Artificial Sequence
<220> FEATURE:
<223> OTHER INFORMATION: Z12367HV4-38-2*01

<400> SEQUENCE: 63

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg
```

<210> SEQ ID NO 64
<211> LENGTH: 99
<212> TYPE: PRT
<213> ORGANISM: Artificial Sequence
<220> FEATURE:
<223> OTHER INFORMATION: AB019439HV4-39*01

<400> SEQUENCE: 64

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60
```

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg

<210> SEQ ID NO 65
<211> LENGTH: 98
<212> TYPE: PRT
<213> ORGANISM: Artificial Sequence
<220> FEATURE:
<223> OTHER INFORMATION: X05713HV4-4*01

<400> SEQUENCE: 65

Gln Val Gln Leu Gln Glu Ser Gly Pro Gly Leu Val Lys Pro Pro Gly
1 5 10 15

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Cys Cys
85 90 95

Ala Arg

<210> SEQ ID NO 66
<211> LENGTH: 97
<212> TYPE: PRT
<213> ORGANISM: Artificial Sequence
<220> FEATURE:
<223> OTHER INFORMATION: AB019438HV4-59*01

<400> SEQUENCE: 66

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Pro Gly Lys Gly Leu Glu Trp Ile
35 40 45

Gly Tyr Ile Tyr Tyr Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg

<210> SEQ ID NO 67
<211> LENGTH: 99
<212> TYPE: PRT
<213> ORGANISM: Artificial Sequence
<220> FEATURE:
<223> OTHER INFORMATION: M29811HV4-61*01

<400> SEQUENCE: 67

Gln Val Gln Leu Gln Glu Ser Gly Pro Gly Leu Val Lys Pro Ser Glu

-continued

```
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg


<210> SEQ ID NO 68
<211> LENGTH: 98
<212> TYPE: PRT
<213> ORGANISM: Artificial Sequence
<220> FEATURE:
<223> OTHER INFORMATION: X92227HV5-10-1*01

<400> SEQUENCE: 68

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg


<210> SEQ ID NO 69
<211> LENGTH: 98
<212> TYPE: PRT
<213> ORGANISM: Artificial Sequence
<220> FEATURE:
<223> OTHER INFORMATION: M99686HV5-51*01

<400> SEQUENCE: 69

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

<210> SEQ ID NO 70
<211> LENGTH: 101
<212> TYPE: PRT
<213> ORGANISM: Artificial Sequence
<220> FEATURE:
<223> OTHER INFORMATION: J04097HV6-1*01

<400> SEQUENCE: 70

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg
100

<210> SEQ ID NO 71
<211> LENGTH: 98
<212> TYPE: PRT
<213> ORGANISM: Artificial Sequence
<220> FEATURE:
<223> OTHER INFORMATION: X62110HV7-4-1*02

<400> SEQUENCE: 71

Gln Val Gln Leu Val Gln Ser Gly Ser Glu Leu Lys Lys Pro Gly Ala
1 5 10 15

Ser Val Lys Val Ser Cys Lys Ala Ser Gly Tyr Thr Phe Thr Ser Tyr
20 25 30

Ala Met Asn Trp Val Arg Gln Ala Pro Gly Gln Gly Leu Glu Trp Met
35 40 45

Gly Trp Ile Asn Thr Asn Thr Gly Asn Pro Thr Tyr Ala Gln Gly Phe
50 55 60

Thr Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg

<210> SEQ ID NO 72
<211> LENGTH: 17
<212> TYPE: PRT
<213> ORGANISM: Artificial Sequence
<220> FEATURE:
<223> OTHER INFORMATION: J00256HJ1*01

<400> SEQUENCE: 72

Ala Glu Tyr Phe Gln His Trp Gly Gln Gly Thr Leu Val Thr Val Ser
1 5 10 15

Ser

<210> SEQ ID NO 73
<211> LENGTH: 17

<212> TYPE: PRT
<213> ORGANISM: Artificial Sequence
<220> FEATURE:
<223> OTHER INFORMATION: J00256HJ2*01

<400> SEQUENCE: 73

Tyr Trp Tyr Phe Asp Leu Trp Gly Arg Gly Thr Leu Val Thr Val Ser
1 5 10 15

Ser

<210> SEQ ID NO 74
<211> LENGTH: 16
<212> TYPE: PRT
<213> ORGANISM: Artificial Sequence
<220> FEATURE:
<223> OTHER INFORMATION: J00256HJ3*01

<400> SEQUENCE: 74

Asp Ala Phe Asp Val Trp Gly Gln Gly Thr Met Val Thr Val Ser Ser
1 5 10 15

<210> SEQ ID NO 75
<211> LENGTH: 16
<212> TYPE: PRT
<213> ORGANISM: Artificial Sequence
<220> FEATURE:
<223> OTHER INFORMATION: J00256HJ5*01

<400> SEQUENCE: 75

Asn Trp Phe Asp Ser Trp Gly Gln Gly Thr Leu Val Thr Val Ser Ser
1 5 10 15

<210> SEQ ID NO 76
<211> LENGTH: 20
<212> TYPE: PRT
<213> ORGANISM: Artificial Sequence
<220> FEATURE:
<223> OTHER INFORMATION: J00256HJ6*01

<400> SEQUENCE: 76

Tyr Tyr Tyr Tyr Tyr Gly Met Asp Val Trp Gly Gln Gly Thr Thr Val
1 5 10 15

Thr Val Ser Ser
20

<210> SEQ ID NO 77
<211> LENGTH: 15
<212> TYPE: PRT
<213> ORGANISM: Artificial Sequence
<220> FEATURE:
<223> OTHER INFORMATION: J00256HJ4*01

<400> SEQUENCE: 77

Tyr Phe Asp Tyr Trp Gly Gln Gly Thr Leu Val Thr Val Ser Ser
1 5 10 15

<210> SEQ ID NO 78
<211> LENGTH: 107
<212> TYPE: PRT
<213> ORGANISM: Artificial Sequence
<220> FEATURE:
<223> OTHER INFORMATION: Pertuzumab

<400> SEQUENCE: 78

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Gln Gly Thr Lys Val Glu Ile Lys
100 105

<210> SEQ ID NO 79
<211> LENGTH: 107
<212> TYPE: PRT
<213> ORGANISM: Artificial Sequence
<220> FEATURE:
<223> OTHER INFORMATION: D3H44

<400> SEQUENCE: 79

Asp Ile Gln Met Thr Gln Ser Pro Ser Ser Leu Ser Ala Ser Val Gly
1 5 10 15

Asp Arg Val Thr Ile Thr Cys Arg Ala Ser Arg Asp Ile Lys Ser Tyr
20 25 30

Leu Asn Trp Tyr Gln Gln Lys Pro Gly Lys Ala Pro Lys Val Leu Ile
35 40 45

Tyr Tyr Ala Thr Ser Leu Ala Glu Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Leu Gln His Gly Glu Ser Pro Trp
85 90 95

Thr Phe Gly Gln Gly Thr Lys Val Glu Ile Lys
100 105

<210> SEQ ID NO 80
<211> LENGTH: 95
<212> TYPE: PRT
<213> ORGANISM: Artificial Sequence
<220> FEATURE:
<223> OTHER INFORMATION: Y14865KV1-NL1*01

<400> SEQUENCE: 80

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Asn Ser
20 25 30

Leu Ala Trp Tyr Gln Gln Lys Pro Gly Lys Ala Pro Lys Leu Leu Leu
35 40 45

Tyr Ala Ala Ser Arg Leu Glu Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln Tyr Tyr Ser Thr Pro
85 90 95

<210> SEQ ID NO 81
<211> LENGTH: 95
<212> TYPE: PRT
<213> ORGANISM: Artificial Sequence
<220> FEATURE:
<223> OTHER INFORMATION: X59315KV1-39*01, X59312KV1D-39*01

<400> SEQUENCE: 81

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro
85 90 95

<210> SEQ ID NO 82
<211> LENGTH: 95
<212> TYPE: PRT
<213> ORGANISM: Artificial Sequence
<220> FEATURE:
<223> OTHER INFORMATION: X17263KV1D-12*01, V01577KV1-12*01

<400> SEQUENCE: 82

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro
85 90 95

<210> SEQ ID NO 83
<211> LENGTH: 95
<212> TYPE: PRT
<213> ORGANISM: Artificial Sequence
<220> FEATURE:
<223> OTHER INFORMATION: Z00006KV1-13*02

<400> SEQUENCE: 83

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Thr Tyr Tyr Cys Gln Gln Phe Asn Ser Tyr Pro
                85                  90                  95


<210> SEQ ID NO 84
<211> LENGTH: 95
<212> TYPE: PRT
<213> ORGANISM: Artificial Sequence
<220> FEATURE:
<223> OTHER INFORMATION: J00248KV1-16*01

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95


<210> SEQ ID NO 85
<211> LENGTH: 95
<212> TYPE: PRT
<213> ORGANISM: Artificial Sequence
<220> FEATURE:
<223> OTHER INFORMATION: X72808KV1-17*01

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95


<210> SEQ ID NO 86
<211> LENGTH: 95
<212> TYPE: PRT
<213> ORGANISM: Artificial Sequence
<220> FEATURE:
<223> OTHER INFORMATION: X63398KV1-27*01

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45
```

```
Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95


<210> SEQ ID NO 87
<211> LENGTH: 95
<212> TYPE: PRT
<213> ORGANISM: Artificial Sequence
<220> FEATURE:
<223> OTHER INFORMATION: M64856KV1-33*01, M64855KV1D-33*01

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95


<210> SEQ ID NO 88
<211> LENGTH: 95
<212> TYPE: PRT
<213> ORGANISM: Artificial Sequence
<220> FEATURE:
<223> OTHER INFORMATION: Z00001KV1-5*01

<400> SEQUENCE: 88

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95


<210> SEQ ID NO 89
<211> LENGTH: 95
<212> TYPE: PRT
<213> ORGANISM: Artificial Sequence
<220> FEATURE:
<223> OTHER INFORMATION: M64858KV1-6*01

<400> SEQUENCE: 89

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
```

```
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95


<210> SEQ ID NO 90
<211> LENGTH: 95
<212> TYPE: PRT
<213> ORGANISM: Artificial Sequence
<220> FEATURE:
<223> OTHER INFORMATION: Z00014KV1-8*01

<400> SEQUENCE: 90

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95


<210> SEQ ID NO 91
<211> LENGTH: 95
<212> TYPE: PRT
<213> ORGANISM: Artificial Sequence
<220> FEATURE:
<223> OTHER INFORMATION: Z00013KV1-9*01

<400> SEQUENCE: 91

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95


<210> SEQ ID NO 92
<211> LENGTH: 95
<212> TYPE: PRT
<213> ORGANISM: Artificial Sequence
<220> FEATURE:
<223> OTHER INFORMATION: X17262KV1D-13*01

<400> SEQUENCE: 92
```

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro
                85                  90                  95


<210> SEQ ID NO 93
<211> LENGTH: 95
<212> TYPE: PRT
<213> ORGANISM: Artificial Sequence
<220> FEATURE:
<223> OTHER INFORMATION: K01323KV1D-16*01

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95


<210> SEQ ID NO 94
<211> LENGTH: 95
<212> TYPE: PRT
<213> ORGANISM: Artificial Sequence
<220> FEATURE:
<223> OTHER INFORMATION: X63392KV1D-17*01

<400> SEQUENCE: 94

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95


<210> SEQ ID NO 95
<211> LENGTH: 95
<212> TYPE: PRT
```

<213> ORGANISM: Artificial Sequence
<220> FEATURE:
<223> OTHER INFORMATION: X72817KV1D-43*01

<400> SEQUENCE: 95

```
Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95
```

<210> SEQ ID NO 96
<211> LENGTH: 95
<212> TYPE: PRT
<213> ORGANISM: Artificial Sequence
<220> FEATURE:
<223> OTHER INFORMATION: Z00008KV1D-8*01

<400> SEQUENCE: 96

```
Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro
                85                  90                  95
```

<210> SEQ ID NO 97
<211> LENGTH: 100
<212> TYPE: PRT
<213> ORGANISM: Artificial Sequence
<220> FEATURE:
<223> OTHER INFORMATION: X12684KV2-24*01

<400> SEQUENCE: 97

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

Thr Gln Phe Pro
100

<210> SEQ ID NO 98
<211> LENGTH: 100
<212> TYPE: PRT
<213> ORGANISM: Artificial Sequence
<220> FEATURE:
<223> OTHER INFORMATION: X12691KV2D-28*01, X63397KV2-28*01

<400> SEQUENCE: 98

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro
100

<210> SEQ ID NO 99
<211> LENGTH: 100
<212> TYPE: PRT
<213> ORGANISM: Artificial Sequence
<220> FEATURE:
<223> OTHER INFORMATION: U41645KV2-29*02

<400> SEQUENCE: 99

Asp Ile Val Met Thr Gln Thr Pro Leu Ser Leu Ser Val Thr Pro Gly
1 5 10 15

Gln Pro Ala Ser Ile Ser Cys Lys Ser Ser Gln Ser Leu Leu His Ser
20 25 30

Asp Gly Lys Thr Tyr Leu Tyr Trp Tyr Leu Gln Lys Pro Gly Gln Ser
35 40 45

Pro Gln Leu Leu Ile Tyr Glu Val Ser Ser Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Ile His Leu Pro
100

<210> SEQ ID NO 100
<211> LENGTH: 100
<212> TYPE: PRT
<213> ORGANISM: Artificial Sequence
<220> FEATURE:
<223> OTHER INFORMATION: X63403KV2-30*01

<400> SEQUENCE: 100

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro
100

<210> SEQ ID NO 101
<211> LENGTH: 101
<212> TYPE: PRT
<213> ORGANISM: Artificial Sequence
<220> FEATURE:
<223> OTHER INFORMATION: X59311KV2D-40*01, X59314KV2-40*01

<400> SEQUENCE: 101

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Asp Ser
20 25 30

Asp Asp Gly Asn Thr Tyr Leu Asp Trp Tyr Leu Gln Lys Pro Gly Gln
35 40 45

Ser Pro Gln Leu Leu Ile Tyr Thr Leu Ser Tyr Arg Ala Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Val Tyr Tyr Cys Met Gln
85 90 95

Arg Ile Glu Phe Pro
100

<210> SEQ ID NO 102
<211> LENGTH: 100
<212> TYPE: PRT
<213> ORGANISM: Artificial Sequence
<220> FEATURE:
<223> OTHER INFORMATION: AP001216KV2D-26*01

<400> SEQUENCE: 102

Glu Ile Val Met Thr Gln Thr Pro Leu Ser Leu Ser Ile Thr Pro Gly
1 5 10 15

Glu Gln Ala Ser Ile Ser Cys Arg Ser Ser Gln Ser Leu Leu His Ser
20 25 30

Asp Gly Tyr Thr Tyr Leu Tyr Trp Phe Leu Gln Lys Ala Arg Pro Val
35 40 45

Ser Thr Leu Leu Ile Tyr Glu Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Phe Gly Val Tyr Tyr Cys Met Gln Asp
85 90 95

Ala Gln Asp Pro
100

<210> SEQ ID NO 103
<211> LENGTH: 100
<212> TYPE: PRT
<213> ORGANISM: Artificial Sequence
<220> FEATURE:
<223> OTHER INFORMATION: M31952KV2D-29*01

<400> SEQUENCE: 103

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100
```

<210> SEQ ID NO 104
<211> LENGTH: 100
<212> TYPE: PRT
<213> ORGANISM: Artificial Sequence
<220> FEATURE:
<223> OTHER INFORMATION: X63402KV2D-30*01

<400> SEQUENCE: 104

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100
```

<210> SEQ ID NO 105
<211> LENGTH: 95
<212> TYPE: PRT
<213> ORGANISM: Artificial Sequence
<220> FEATURE:
<223> OTHER INFORMATION: X01668KV3-11*01

<400> SEQUENCE: 105

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95


<210> SEQ ID NO 106
<211> LENGTH: 95
<212> TYPE: PRT
<213> ORGANISM: Artificial Sequence
<220> FEATURE:
<223> OTHER INFORMATION: X72815KV3D-15*01, M23090KV3-15*01

<400> SEQUENCE: 106

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95


<210> SEQ ID NO 107
<211> LENGTH: 96
<212> TYPE: PRT
<213> ORGANISM: Artificial Sequence
<220> FEATURE:
<223> OTHER INFORMATION: X12686KV3-20*01

<400> SEQUENCE: 107

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95


<210> SEQ ID NO 108
<211> LENGTH: 95
<212> TYPE: PRT
<213> ORGANISM: Artificial Sequence
<220> FEATURE:
<223> OTHER INFORMATION: X17264KV3D-11*01

<400> SEQUENCE: 108

Glu Ile Val Leu Thr Gln Ser Pro Ala Thr Leu Ser Leu Ser Pro Gly
```

-continued

```
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95


<210> SEQ ID NO 109
<211> LENGTH: 96
<212> TYPE: PRT
<213> ORGANISM: Artificial Sequence
<220> FEATURE:
<223> OTHER INFORMATION: X12687KV3D-20*01

<400> SEQUENCE: 109

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95


<210> SEQ ID NO 110
<211> LENGTH: 96
<212> TYPE: PRT
<213> ORGANISM: Artificial Sequence
<220> FEATURE:
<223> OTHER INFORMATION: X72820KV3D-7*01

<400> SEQUENCE: 110

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95


<210> SEQ ID NO 111
<211> LENGTH: 101
<212> TYPE: PRT
<213> ORGANISM: Artificial Sequence
<220> FEATURE:
```

<223> OTHER INFORMATION: Z00023KV4-1*01

<400> SEQUENCE: 111

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro
100

<210> SEQ ID NO 112
<211> LENGTH: 95
<212> TYPE: PRT
<213> ORGANISM: Artificial Sequence
<220> FEATURE:
<223> OTHER INFORMATION: X02485KV5-2*01

<400> SEQUENCE: 112

Glu Thr Thr Leu Thr Gln Ser Pro Ala Phe Met Ser Ala Thr Pro Gly
1 5 10 15

Asp Lys Val Asn Ile Ser Cys Lys Ala Ser Gln Asp Ile Asp Asp Asp
20 25 30

Met Asn Trp Tyr Gln Gln Lys Pro Gly Glu Ala Ala Ile Phe Ile Ile
35 40 45

Gln Glu Ala Thr Thr Leu Val Pro Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Leu Gln His Asp Asn Phe Pro
85 90 95

<210> SEQ ID NO 113
<211> LENGTH: 95
<212> TYPE: PRT
<213> ORGANISM: Artificial Sequence
<220> FEATURE:
<223> OTHER INFORMATION: X12683KV6D-21*01, X63399KV6-21*01

<400> SEQUENCE: 113

Glu Ile Val Leu Thr Gln Ser Pro Asp Phe Gln Ser Val Thr Pro Lys
1 5 10 15

Glu Lys Val Thr Ile Thr Cys Arg Ala Ser Gln Ser Ile Gly Ser Ser
20 25 30

Leu His Trp Tyr Gln Gln Lys Pro Asp Gln Ser Pro Lys Leu Leu Ile
35 40 45

Lys Tyr Ala Ser Gln Ser Phe Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Thr Tyr Tyr Cys His Gln Ser Ser Ser Leu Pro 85 90 95

<210> SEQ ID NO 114
<211> LENGTH: 12
<212> TYPE: PRT
<213> ORGANISM: Artificial Sequence
<220> FEATURE:
<223> OTHER INFORMATION: Z70260KJ2*02

<400> SEQUENCE: 114

Cys Thr Phe Gly Gln Gly Thr Lys Leu Glu Ile Lys
1 5 10

<210> SEQ ID NO 115
<211> LENGTH: 12
<212> TYPE: PRT
<213> ORGANISM: Artificial Sequence
<220> FEATURE:
<223> OTHER INFORMATION: J00242KJ3*01

<400> SEQUENCE: 115

Phe Thr Phe Gly Pro Gly Thr Lys Val Asp Ile Lys
1 5 10

<210> SEQ ID NO 116
<211> LENGTH: 12
<212> TYPE: PRT
<213> ORGANISM: Artificial Sequence
<220> FEATURE:
<223> OTHER INFORMATION: J00242KJ4*01

<400> SEQUENCE: 116

Leu Thr Phe Gly Gly Gly Thr Lys Val Glu Ile Lys
1 5 10

<210> SEQ ID NO 117
<211> LENGTH: 12
<212> TYPE: PRT
<213> ORGANISM: Artificial Sequence
<220> FEATURE:
<223> OTHER INFORMATION: J00242KJ5*01

<400> SEQUENCE: 117

Ile Thr Phe Gly Gln Gly Thr Arg Leu Glu Ile Lys
1 5 10

<210> SEQ ID NO 118
<211> LENGTH: 12
<212> TYPE: PRT
<213> ORGANISM: Artificial Sequence
<220> FEATURE:
<223> OTHER INFORMATION: J00242KJ2*01

<400> SEQUENCE: 118

Tyr Thr Phe Gly Gln Gly Thr Lys Leu Glu Ile Lys
1 5 10

<210> SEQ ID NO 119
<211> LENGTH: 12
<212> TYPE: PRT
<213> ORGANISM: Artificial Sequence
<220> FEATURE:
<223> OTHER INFORMATION: J00242KJ1*01

<400> SEQUENCE: 119

Trp Thr Phe Gly Gln Gly Thr Lys Val Glu Ile Lys
1 5 10

<210> SEQ ID NO 120
<211> LENGTH: 98
<212> TYPE: PRT
<213> ORGANISM: Artificial Sequence
<220> FEATURE:
<223> OTHER INFORMATION: JN582178HG1*04, Z17370HG1*02, Pertuzumab, D3H44, AL122127HG1*05, J00228HG1*01

<400> SEQUENCE: 120

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 121
<211> LENGTH: 98
<212> TYPE: PRT
<213> ORGANISM: Artificial Sequence
<220> FEATURE:
<223> OTHER INFORMATION: Y14737HG1*03

<400> SEQUENCE: 121

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val
```

<210> SEQ ID NO 122
<211> LENGTH: 98
<212> TYPE: PRT
<213> ORGANISM: Artificial Sequence
<220> FEATURE:
<223> OTHER INFORMATION: J00230HG2*01, AF449616HG2*03, AF449618HG2*05, AL928742HG2*06

<400> SEQUENCE: 122

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val

<210> SEQ ID NO 123
<211> LENGTH: 98
<212> TYPE: PRT
<213> ORGANISM: Artificial Sequence
<220> FEATURE:
<223> OTHER INFORMATION: AJ250170HG2*02

<400> SEQUENCE: 123

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Thr Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val

<210> SEQ ID NO 124
<211> LENGTH: 98
<212> TYPE: PRT
<213> ORGANISM: Artificial Sequence
<220> FEATURE:
<223> OTHER INFORMATION: AF449617HG2*04

<400> SEQUENCE: 124

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Thr Cys Asn Val Asp His Lys Pro Ser Asn Thr Lys Val Asp Lys
85 90 95

Thr Val

<210> SEQ ID NO 125
<211> LENGTH: 98
<212> TYPE: PRT
<213> ORGANISM: Artificial Sequence
<220> FEATURE:
<223> OTHER INFORMATION: X99549HG3*04,AJ390244HG3*13,
X16110HG3*03,AJ390236HG3*05,AJ390242HG3*09,
AL122127HG3*10,AJ390279HG3*19,AJ390260HG3*15,
AJ390237HG3*06,AJ390238HG3*07,AJ390247HG3*11,
AJ390252HG3*12,AJ390262HG3*16,AJ390241HG3*08,
X03604HG3*01,AJ390254HG3*14

<400> SEQUENCE: 125

Ala Ser Thr Lys Gly Pro Ser Val Phe Pro Leu Ala Pro Cys Ser Arg
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Thr Cys Asn Val Asn His Lys Pro Ser Asn Thr Lys Val Asp Lys
85 90 95

Arg Val

<210> SEQ ID NO 126
<211> LENGTH: 98
<212> TYPE: PRT
<213> ORGANISM: Artificial Sequence
<220> FEATURE:
<223> OTHER INFORMATION: AJ390272HG3*17

<400> SEQUENCE: 126

Ala Ser Thr Lys Gly Pro Ser Val Phe Pro Leu Ala Pro Cys Ser Arg
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asn His Lys Pro Ser Asn Thr Lys Val Asp Lys
85 90 95

Arg Val

<210> SEQ ID NO 127
<211> LENGTH: 98
<212> TYPE: PRT
<213> ORGANISM: Artificial Sequence
<220> FEATURE:
<223> OTHER INFORMATION: AJ390276HG3*18

<400> SEQUENCE: 127

Ala Ser Thr Lys Gly Pro Ser Val Phe Pro Leu Ala Pro Cys Ser Arg
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Tyr Ser Gly Leu Tyr Ser
50 55 60

Leu Ser Ser Val Val Thr Val Pro Ser Ser Ser Leu Gly Thr Gln Thr
65 70 75 80

Tyr Thr Cys Asn Val Asn His Lys Pro Ser Asn Thr Lys Val Asp Lys
85 90 95

Arg Val

<210> SEQ ID NO 128
<211> LENGTH: 98
<212> TYPE: PRT
<213> ORGANISM: Artificial Sequence
<220> FEATURE:
<223> OTHER INFORMATION: K01316HG4*01, AL928742HG4*04

<400> SEQUENCE: 128

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val

<210> SEQ ID NO 129
<211> LENGTH: 107
<212> TYPE: PRT
<213> ORGANISM: Artificial Sequence
<220> FEATURE:
<223> OTHER INFORMATION: D3H44, J00241KC*01, Pertuzumab

<400> SEQUENCE: 129

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 130
<211> LENGTH: 107
<212> TYPE: PRT
<213> ORGANISM: Artificial Sequence
<220> FEATURE:
<223> OTHER INFORMATION: M11736KC*02

<400> SEQUENCE: 130

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105
```

<210> SEQ ID NO 131
<211> LENGTH: 107
<212> TYPE: PRT
<213> ORGANISM: Artificial Sequence
<220> FEATURE:
<223> OTHER INFORMATION: M11737KC*03

<400> SEQUENCE: 131

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 132
<211> LENGTH: 107
<212> TYPE: PRT
<213> ORGANISM: Artificial Sequence
<220> FEATURE:
<223> OTHER INFORMATION: AF017732KC*04

<400> SEQUENCE: 132

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

```
Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 133
<211> LENGTH: 107
<212> TYPE: PRT
<213> ORGANISM: Artificial Sequence
<220> FEATURE:
<223> OTHER INFORMATION: AF113887KC*05

<400> SEQUENCE: 133

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 134
<211> LENGTH: 118
<212> TYPE: PRT
<213> ORGANISM: Artificial Sequence
<220> FEATURE:
<223> OTHER INFORMATION: CAT-2200

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile His Gly Val Thr Arg Asn Trp Gly Gln Gly Thr
            100                 105                 110

Leu Val Thr Val Ser Ser
        115


<210> SEQ ID NO 135
<211> LENGTH: 110
<212> TYPE: PRT
<213> ORGANISM: Artificial Sequence
<220> FEATURE:
<223> OTHER INFORMATION: CAT-2200
```

<400> SEQUENCE: 135

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ser Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Pro
                85                  90                  95

Tyr Ser Val Val Phe Gly Gly Gly Thr Lys Leu Thr Val Leu
            100                 105                 110

<210> SEQ ID NO 136
<211> LENGTH: 98
<212> TYPE: PRT
<213> ORGANISM: Artificial Sequence
<220> FEATURE:
<223> OTHER INFORMATION: Z73673LV6-57*01

<400> SEQUENCE: 136

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 137
<211> LENGTH: 98
<212> TYPE: PRT
<213> ORGANISM: Artificial Sequence
<220> FEATURE:
<223> OTHER INFORMATION: Z73653LV1-36*01

<400> SEQUENCE: 137

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
85 90 95

Asn Gly

<210> SEQ ID NO 138
<211> LENGTH: 99
<212> TYPE: PRT
<213> ORGANISM: Artificial Sequence
<220> FEATURE:
<223> OTHER INFORMATION: M94116LV1-40*01

<400> SEQUENCE: 138

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly

<210> SEQ ID NO 139
<211> LENGTH: 98
<212> TYPE: PRT
<213> ORGANISM: Artificial Sequence
<220> FEATURE:
<223> OTHER INFORMATION: Z73654LV1-44*01

<400> SEQUENCE: 139

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly

<210> SEQ ID NO 140
<211> LENGTH: 98
<212> TYPE: PRT
<213> ORGANISM: Artificial Sequence
<220> FEATURE:
<223> OTHER INFORMATION: Z73663LV1-47*01

<400> SEQUENCE: 140

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn

```
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly


<210> SEQ ID NO 141
<211> LENGTH: 98
<212> TYPE: PRT
<213> ORGANISM: Artificial Sequence
<220> FEATURE:
<223> OTHER INFORMATION: Z73661LV1-51*01

<400> SEQUENCE: 141

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala


<210> SEQ ID NO 142
<211> LENGTH: 99
<212> TYPE: PRT
<213> ORGANISM: Artificial Sequence
<220> FEATURE:
<223> OTHER INFORMATION: Z73657LV2-11*01

<400> SEQUENCE: 142

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe


<210> SEQ ID NO 143
<211> LENGTH: 99
```

<212> TYPE: PRT
<213> ORGANISM: Artificial Sequence
<220> FEATURE:
<223> OTHER INFORMATION: Z73664LV2-14*01

<400> SEQUENCE: 143

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Leu

<210> SEQ ID NO 144
<211> LENGTH: 99
<212> TYPE: PRT
<213> ORGANISM: Artificial Sequence
<220> FEATURE:
<223> OTHER INFORMATION: Z73642LV2-18*01

<400> SEQUENCE: 144

Gln Ser Ala Leu Thr Gln Pro Pro Ser Val Ser Gly Ser Pro Gly Gln
1 5 10 15

Ser Val Thr Ile Ser Cys Thr Gly Thr Ser Ser Asp Val Gly Ser Tyr
20 25 30

Asn Arg Val Ser Trp Tyr Gln Gln Pro Pro Gly Thr Ala Pro Lys Leu
35 40 45

Met Ile Tyr Glu Val Ser Asn Arg Pro Ser Gly Val Pro Asp Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Leu Tyr Thr Ser Ser
85 90 95

Ser Thr Phe

<210> SEQ ID NO 145
<211> LENGTH: 99
<212> TYPE: PRT
<213> ORGANISM: Artificial Sequence
<220> FEATURE:
<223> OTHER INFORMATION: X14616LV2-23*01

<400> SEQUENCE: 145

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ser Tyr
20 25 30

Asn Leu Val Ser Trp Tyr Gln Gln His Pro Gly Lys Ala Pro Lys Leu
35 40 45

Met Ile Tyr Glu Gly Ser Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Cys Ser Tyr Ala Gly Ser
85 90 95

Ser Thr Leu

<210> SEQ ID NO 146
<211> LENGTH: 99
<212> TYPE: PRT
<213> ORGANISM: Artificial Sequence
<220> FEATURE:
<223> OTHER INFORMATION: X97462LV2-8*01

<400> SEQUENCE: 146

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ser Ser Tyr Ala Gly Ser
85 90 95

Asn Asn Phe

<210> SEQ ID NO 147
<211> LENGTH: 95
<212> TYPE: PRT
<213> ORGANISM: Artificial Sequence
<220> FEATURE:
<223> OTHER INFORMATION: X57826LV3-1*01

<400> SEQUENCE: 147

Ser Tyr Glu Leu Thr Gln Pro Pro Ser Val Ser Val Ser Pro Gly Gln
1 5 10 15

Thr Ala Ser Ile Thr Cys Ser Gly Asp Lys Leu Gly Asp Lys Tyr Ala
20 25 30

Cys Trp Tyr Gln Gln Lys Pro Gly Gln Ser Pro Val Leu Val Ile Tyr
35 40 45

Gln Asp Ser Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Gln Ala Trp Asp Ser Ser Thr Ala
85 90 95

<210> SEQ ID NO 148
<211> LENGTH: 95
<212> TYPE: PRT
<213> ORGANISM: Artificial Sequence
<220> FEATURE:
<223> OTHER INFORMATION: X97473LV3-9*01

<400> SEQUENCE: 148

Ser Tyr Glu Leu Thr Gln Pro Leu Ser Val Ser Val Ala Leu Gly Gln
1 5 10 15

Thr Ala Arg Ile Thr Cys Gly Gly Asn Asn Ile Gly Ser Lys Asn Val
20 25 30

His Trp Tyr Gln Gln Lys Pro Gly Gln Ala Pro Val Leu Val Ile Tyr
35 40 45

Arg Asp Ser Asn Arg Pro Ser Gly Ile Pro Glu Arg Phe Ser Gly Ser
50 55 60

Asn Ser Gly Asn Thr Ala Thr Leu Thr Ile Ser Arg Ala Gln Ala Gly
65 70 75 80

Asp Glu Ala Asp Tyr Tyr Cys Gln Val Trp Asp Ser Ser Thr Ala
85 90 95

<210> SEQ ID NO 149
<211> LENGTH: 96
<212> TYPE: PRT
<213> ORGANISM: Artificial Sequence
<220> FEATURE:
<223> OTHER INFORMATION: X97464LV3-10*01

<400> SEQUENCE: 149

Ser Tyr Glu Leu Thr Gln Pro Pro Ser Val Ser Val Ser Pro Gly Gln
1 5 10 15

Thr Ala Arg Ile Thr Cys Ser Gly Asp Ala Leu Pro Lys Lys Tyr Ala
20 25 30

Tyr Trp Tyr Gln Gln Lys Ser Gly Gln Ala Pro Val Leu Val Ile Tyr
35 40 45

Glu Asp Ser Lys Arg Pro Ser Gly Ile Pro Glu Arg Phe Ser Gly Ser
50 55 60

Ser Ser Gly Thr Met Ala Thr Leu Thr Ile Ser Gly Ala Gln Val Glu
65 70 75 80

Asp Glu Ala Asp Tyr Tyr Cys Tyr Ser Thr Asp Ser Ser Gly Asn His
85 90 95

<210> SEQ ID NO 150
<211> LENGTH: 96
<212> TYPE: PRT
<213> ORGANISM: Artificial Sequence
<220> FEATURE:
<223> OTHER INFORMATION: Z73658LV3-12*01

<400> SEQUENCE: 150

Ser Tyr Glu Leu Thr Gln Pro His Ser Val Ser Val Ala Thr Ala Gln
1 5 10 15

Met Ala Arg Ile Thr Cys Gly Gly Asn Asn Ile Gly Ser Lys Ala Val
20 25 30

His Trp Tyr Gln Gln Lys Pro Gly Gln Asp Pro Val Leu Val Ile Tyr
35 40 45

Ser Asp Ser Asn Arg Pro Ser Gly Ile Pro Glu Arg Phe Ser Gly Ser
50 55 60

Asn Pro Gly Asn Thr Thr Thr Leu Thr Ile Ser Arg Ile Glu Ala Gly
65 70 75 80

Asp Glu Ala Asp Tyr Tyr Cys Gln Val Trp Asp Ser Ser Ser Asp His
85 90 95

<210> SEQ ID NO 151
<211> LENGTH: 96
<212> TYPE: PRT
<213> ORGANISM: Artificial Sequence
<220> FEATURE:
<223> OTHER INFORMATION: X97471LV3-16*01

<400> SEQUENCE: 151

Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
            20                  25                  30

Tyr Trp Tyr Gln Gln Lys Pro Gly Gln Phe Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Ile Val Thr Leu Thr Ile Ser Gly Val Gln Ala Glu
65                  70                  75                  80

Asp Glu Ala Asp Tyr Tyr Cys Leu Ser Ala Asp Ser Ser Gly Thr Tyr
                85                  90                  95

<210> SEQ ID NO 152
<211> LENGTH: 96
<212> TYPE: PRT
<213> ORGANISM: Artificial Sequence
<220> FEATURE:
<223> OTHER INFORMATION: X56178LV3-19*01

<400> SEQUENCE: 152

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 153
<211> LENGTH: 96
<212> TYPE: PRT
<213> ORGANISM: Artificial Sequence
<220> FEATURE:
<223> OTHER INFORMATION: X71966LV3-21*01

<400> SEQUENCE: 153

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

<210> SEQ ID NO 154
<211> LENGTH: 94

<212> TYPE: PRT
<213> ORGANISM: Artificial Sequence
<220> FEATURE:
<223> OTHER INFORMATION: Z73666LV3-22*01

<400> SEQUENCE: 154

Ser Tyr Glu Leu Thr Gln Leu Pro Ser Val Ser Val Ser Pro Gly Gln
1 5 10 15

Thr Ala Arg Ile Thr Cys Ser Gly Asp Val Leu Gly Glu Asn Tyr Ala
20 25 30

Asp Trp Tyr Gln Gln Lys Pro Gly Gln Ala Pro Glu Leu Val Ile Tyr
35 40 45

Glu Asp Ser Glu Arg Tyr Pro Gly Ile Pro Glu Arg Phe Ser Gly Ser
50 55 60

Thr Ser Gly Asn Thr Thr Thr Leu Thr Ile Ser Arg Val Leu Thr Glu
65 70 75 80

Asp Glu Ala Asp Tyr Tyr Cys Leu Ser Gly Asp Glu Asp Asn
85 90

<210> SEQ ID NO 155
<211> LENGTH: 96
<212> TYPE: PRT
<213> ORGANISM: Artificial Sequence
<220> FEATURE:
<223> OTHER INFORMATION: X97474LV3-25*01

<400> SEQUENCE: 155

Ser Tyr Glu Leu Met Gln Pro Pro Ser Val Ser Val Ser Pro Gly Gln
1 5 10 15

Thr Ala Arg Ile Thr Cys Ser Gly Asp Ala Leu Pro Lys Gln Tyr Ala
20 25 30

Tyr Trp Tyr Gln Gln Lys Pro Gly Gln Ala Pro Val Leu Val Ile Tyr
35 40 45

Lys Asp Ser Glu Arg Pro Ser Gly Ile Pro Glu Arg Phe Ser Gly Ser
50 55 60

Ser Ser Gly Thr Thr Val Thr Leu Thr Ile Ser Gly Val Gln Ala Glu
65 70 75 80

Asp Glu Ala Asp Tyr Tyr Cys Gln Ser Ala Asp Ser Ser Gly Thr Tyr
85 90 95

<210> SEQ ID NO 156
<211> LENGTH: 94
<212> TYPE: PRT
<213> ORGANISM: Artificial Sequence
<220> FEATURE:
<223> OTHER INFORMATION: D86994LV3-27*01

<400> SEQUENCE: 156

Ser Tyr Glu Leu Thr Gln Pro Ser Ser Val Ser Val Ser Pro Gly Gln
1 5 10 15

Thr Ala Arg Ile Thr Cys Ser Gly Asp Val Leu Ala Lys Lys Tyr Ala
20 25 30

Arg Trp Phe Gln Gln Lys Pro Gly Gln Ala Pro Val Leu Val Ile Tyr
35 40 45

Lys Asp Ser Glu Arg Pro Ser Gly Ile Pro Glu Arg Phe Ser Gly Ser
50 55 60

Ser Ser Gly Thr Thr Val Thr Leu Thr Ile Ser Gly Ala Gln Val Glu
65 70 75 80

Asp Glu Ala Asp Tyr Tyr Cys Tyr Ser Ala Ala Asp Asn Asn

```
                85                  90


<210> SEQ ID NO 157
<211> LENGTH: 103
<212> TYPE: PRT
<213> ORGANISM: Artificial Sequence
<220> FEATURE:
<223> OTHER INFORMATION: X57828LV4-3*01

<400> SEQUENCE: 157

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
        35                  40                  45

Lys Val Lys Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100


<210> SEQ ID NO 158
<211> LENGTH: 99
<212> TYPE: PRT
<213> ORGANISM: Artificial Sequence
<220> FEATURE:
<223> OTHER INFORMATION: Z73667LV4-60*01

<400> SEQUENCE: 158

Gln Pro Val Leu Thr Gln Ser Ser Ser Ala Ser Ala Ser Leu Gly Ser
1               5                   10                  15

Ser Val Lys Leu Thr Cys Thr Leu Ser Ser Gly His Ser Ser Tyr Ile
            20                  25                  30

Ile Ala Trp His Gln Gln Gln Pro Gly Lys Ala Pro Arg Tyr Leu Met
        35                  40                  45

Lys Leu Glu Gly Ser Gly Ser Tyr Asn Lys Gly Ser Gly Val Pro Asp
    50                  55                  60

Arg Phe Ser Gly Ser Ser Ser Gly Ala Asp Arg Tyr Leu Thr Ile Ser
65                  70                  75                  80

Asn Leu Gln Leu Glu Asp Glu Ala Asp Tyr Tyr Cys Glu Thr Trp Asp
                85                  90                  95

Ser Asn Thr


<210> SEQ ID NO 159
<211> LENGTH: 99
<212> TYPE: PRT
<213> ORGANISM: Artificial Sequence
<220> FEATURE:
<223> OTHER INFORMATION: Z73648LV4-69*01

<400> SEQUENCE: 159

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
            20                  25                  30
```

Ile Ala Trp His Gln Gln Gln Pro Glu Lys Gly Pro Arg Tyr Leu Met
35 40 45

Lys Leu Asn Ser Asp Gly Ser His Ser Lys Gly Asp Gly Ile Pro Asp
50 55 60

Arg Phe Ser Gly Ser Ser Ser Gly Ala Glu Arg Tyr Leu Thr Ile Ser
65 70 75 80

Ser Leu Gln Ser Glu Asp Glu Ala Asp Tyr Tyr Cys Gln Thr Trp Gly
85 90 95

Thr Gly Ile

<210> SEQ ID NO 160
<211> LENGTH: 104
<212> TYPE: PRT
<213> ORGANISM: Artificial Sequence
<220> FEATURE:
<223> OTHER INFORMATION: Z73672LV5-37*01

<400> SEQUENCE: 160

Gln Pro Val Leu Thr Gln Pro Pro Ser Ser Ser Ala Ser Pro Gly Glu
1 5 10 15

Ser Ala Arg Leu Thr Cys Thr Leu Pro Ser Asp Ile Asn Val Gly Ser
20 25 30

Tyr Asn Ile Tyr Trp Tyr Gln Gln Lys Pro Gly Ser Pro Pro Arg Tyr
35 40 45

Leu Leu Tyr Tyr Tyr Ser Asp Ser Asp Lys Gly Gln Gly Ser Gly Val
50 55 60

Pro Ser Arg Phe Ser Gly Ser Lys Asp Ala Ser Ala Asn Thr Gly Ile
65 70 75 80

Leu Leu Ile Ser Gly Leu Gln Ser Glu Asp Glu Ala Asp Tyr Tyr Cys
85 90 95

Met Ile Trp Pro Ser Asn Ala Ser
100

<210> SEQ ID NO 161
<211> LENGTH: 104
<212> TYPE: PRT
<213> ORGANISM: Artificial Sequence
<220> FEATURE:
<223> OTHER INFORMATION: Z73668LV5-39*01

<400> SEQUENCE: 161

Gln Pro Val Leu Thr Gln Pro Thr Ser Leu Ser Ala Ser Pro Gly Ala
1 5 10 15

Ser Ala Arg Phe Thr Cys Thr Leu Arg Ser Gly Ile Asn Val Gly Thr
20 25 30

Tyr Arg Ile Tyr Trp Tyr Gln Gln Lys Pro Gly Ser Leu Pro Arg Tyr
35 40 45

Leu Leu Arg Tyr Lys Ser Asp Ser Asp Lys Gln Gln Gly Ser Gly Val
50 55 60

Pro Ser Arg Phe Ser Gly Ser Lys Asp Ala Ser Thr Asn Ala Gly Leu
65 70 75 80

Leu Leu Ile Ser Gly Leu Gln Ser Glu Asp Glu Ala Asp Tyr Tyr Cys
85 90 95

Ala Ile Trp Tyr Ser Ser Thr Ser
100

<210> SEQ ID NO 162
<211> LENGTH: 104

<212> TYPE: PRT
<213> ORGANISM: Artificial Sequence
<220> FEATURE:
<223> OTHER INFORMATION: Z73670LV5-45*01

<400> SEQUENCE: 162

Gln Ala Val Leu Thr Gln Pro Ala Ser Leu Ser Ala Ser Pro Gly Ala
1 5 10 15

Ser Ala Ser Leu Thr Cys Thr Leu Arg Ser Gly Ile Asn Val Gly Thr
20 25 30

Tyr Arg Ile Tyr Trp Tyr Gln Gln Lys Pro Gly Ser Pro Pro Gln Tyr
35 40 45

Leu Leu Arg Tyr Lys Ser Asp Ser Asp Lys Gln Gln Gly Ser Gly Val
50 55 60

Pro Ser Arg Phe Ser Gly Ser Lys Asp Ala Ser Ala Asn Ala Gly Ile
65 70 75 80

Leu Leu Ile Ser Gly Leu Gln Ser Glu Asp Glu Ala Asp Tyr Tyr Cys
85 90 95

Met Ile Trp His Ser Ser Ala Ser
100

<210> SEQ ID NO 163
<211> LENGTH: 105
<212> TYPE: PRT
<213> ORGANISM: Artificial Sequence
<220> FEATURE:
<223> OTHER INFORMATION: Z73669LV5-52*01

<400> SEQUENCE: 163

Gln Pro Val Leu Thr Gln Pro Ser Ser His Ser Ala Ser Ser Gly Ala
1 5 10 15

Ser Val Arg Leu Thr Cys Met Leu Ser Ser Gly Phe Ser Val Gly Asp
20 25 30

Phe Trp Ile Arg Trp Tyr Gln Gln Lys Pro Gly Asn Pro Pro Arg Tyr
35 40 45

Leu Leu Tyr Tyr His Ser Asp Ser Asn Lys Gly Gln Gly Ser Gly Val
50 55 60

Pro Ser Arg Phe Ser Gly Ser Asn Asp Ala Ser Ala Asn Ala Gly Ile
65 70 75 80

Leu Arg Ile Ser Gly Leu Gln Pro Glu Asp Glu Ala Asp Tyr Tyr Cys
85 90 95

Gly Thr Trp His Ser Asn Ser Lys Thr
100 105

<210> SEQ ID NO 164
<211> LENGTH: 98
<212> TYPE: PRT
<213> ORGANISM: Artificial Sequence
<220> FEATURE:
<223> OTHER INFORMATION: X14614LV7-43*01

<400> SEQUENCE: 164

Gln Thr Val Val Thr Gln Glu Pro Ser Leu Thr Val Ser Pro Gly Gly
1 5 10 15

Thr Val Thr Leu Thr Cys Ala Ser Ser Thr Gly Ala Val Thr Ser Gly
20 25 30

Tyr Tyr Pro Asn Trp Phe Gln Gln Lys Pro Gly Gln Ala Pro Arg Ala
35 40 45

Leu Ile Tyr Ser Thr Ser Asn Lys His Ser Trp Thr Pro Ala Arg Phe

```
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln


<210> SEQ ID NO 165
<211> LENGTH: 98
<212> TYPE: PRT
<213> ORGANISM: Artificial Sequence
<220> FEATURE:
<223> OTHER INFORMATION: Z73674LV7-46*01

<400> SEQUENCE: 165

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg


<210> SEQ ID NO 166
<211> LENGTH: 98
<212> TYPE: PRT
<213> ORGANISM: Artificial Sequence
<220> FEATURE:
<223> OTHER INFORMATION: Z73650LV8-61*01

<400> SEQUENCE: 166

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile


<210> SEQ ID NO 167
<211> LENGTH: 104
<212> TYPE: PRT
<213> ORGANISM: Artificial Sequence
<220> FEATURE:
<223> OTHER INFORMATION: Z73675LV9-49*01

<400> SEQUENCE: 167
```

```
Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
            100


<210> SEQ ID NO 168
<211> LENGTH: 98
<212> TYPE: PRT
<213> ORGANISM: Artificial Sequence
<220> FEATURE:
<223> OTHER INFORMATION: Z73676LV10-54*01

<400> SEQUENCE: 168

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala


<210> SEQ ID NO 169
<211> LENGTH: 12
<212> TYPE: PRT
<213> ORGANISM: Artificial Sequence
<220> FEATURE:
<223> OTHER INFORMATION: X04457LJ1*01

<400> SEQUENCE: 169

Tyr Val Phe Gly Thr Gly Thr Lys Val Thr Val Leu
1               5                   10


<210> SEQ ID NO 170
<211> LENGTH: 12
<212> TYPE: PRT
<213> ORGANISM: Artificial Sequence
<220> FEATURE:
<223> OTHER INFORMATION: M15641LJ2*01, M15642LJ3*01

<400> SEQUENCE: 170

Val Val Phe Gly Gly Gly Thr Lys Leu Thr Val Leu
1               5                   10
```

<210> SEQ ID NO 171
<211> LENGTH: 12
<212> TYPE: PRT
<213> ORGANISM: Artificial Sequence
<220> FEATURE:
<223> OTHER INFORMATION: M18338LJ6*01

<400> SEQUENCE: 171

Asn Val Phe Gly Ser Gly Thr Lys Val Thr Val Leu
1 5 10

<210> SEQ ID NO 172
<211> LENGTH: 12
<212> TYPE: PRT
<213> ORGANISM: Artificial Sequence
<220> FEATURE:
<223> OTHER INFORMATION: X51755LJ7*01

<400> SEQUENCE: 172

Ala Val Phe Gly Gly Gly Thr Gln Leu Thr Val Leu
1 5 10

<210> SEQ ID NO 173
<211> LENGTH: 98
<212> TYPE: PRT
<213> ORGANISM: Artificial Sequence
<220> FEATURE:
<223> OTHER INFORMATION: CAT-2200

<400> SEQUENCE: 173

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Gln Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 174
<211> LENGTH: 106
<212> TYPE: PRT
<213> ORGANISM: Artificial Sequence
<220> FEATURE:
<223> OTHER INFORMATION: D87017LC3*04, CAT-2200, X06875LC2*02,
J00253LC2*01

<400> SEQUENCE: 174

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys

```
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 175
<211> LENGTH: 104
<212> TYPE: PRT
<213> ORGANISM: Artificial Sequence
<220> FEATURE:
<223> OTHER INFORMATION: J00252LC1*01

<400> SEQUENCE: 175

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100


<210> SEQ ID NO 176
<211> LENGTH: 106
<212> TYPE: PRT
<213> ORGANISM: Artificial Sequence
<220> FEATURE:
<223> OTHER INFORMATION: X51755LC1*02

<400> SEQUENCE: 176

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 177
<211> LENGTH: 104
<212> TYPE: PRT
<213> ORGANISM: Artificial Sequence
<220> FEATURE:
<223> OTHER INFORMATION: J00254LC3*01

<400> SEQUENCE: 177
```

Pro Lys Ala Ala Pro Ser Val Thr Leu Phe Pro Pro Ser Ser Glu Glu
1 5 10 15

Leu Gln Ala Asn Lys Ala Thr Leu Val Cys Leu Ile Ser Asp Phe Tyr
20 25 30

Pro Gly Ala Val Thr Val Ala Trp Lys Ala Asp Ser Ser Pro Val Lys
35 40 45

Ala Gly Val Glu Thr Thr Thr Pro Ser Lys Gln Ser Asn Asn Lys Tyr
50 55 60

Ala Ala Ser Ser Tyr Leu Ser Leu Thr Pro Glu Gln Trp Lys Ser His
65 70 75 80

Lys Ser Tyr Ser Cys Gln Val Thr His Glu Gly Ser Thr Val Glu Lys
85 90 95

Thr Val Ala Pro Thr Glu Cys Ser
100

<210> SEQ ID NO 178
<211> LENGTH: 106
<212> TYPE: PRT
<213> ORGANISM: Artificial Sequence
<220> FEATURE:
<223> OTHER INFORMATION: K01326LC3*02

<400> SEQUENCE: 178

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Pro Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Lys Ser Tyr Ser Cys Gln Val Thr His Glu Gly Ser Thr Val
85 90 95

Glu Lys Thr Val Ala Pro Thr Glu Cys Ser
100 105

<210> SEQ ID NO 179
<211> LENGTH: 106
<212> TYPE: PRT
<213> ORGANISM: Artificial Sequence
<220> FEATURE:
<223> OTHER INFORMATION: X06876LC3*03

<400> SEQUENCE: 179

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Lys Ser Tyr Ser Cys Gln Val Thr His Glu Gly Ser Thr Val

```
                85                  90                  95

Glu Lys Thr Val Ala Pro Thr Glu Cys Ser
            100                 105


<210> SEQ ID NO 180
<211> LENGTH: 106
<212> TYPE: PRT
<213> ORGANISM: Artificial Sequence
<220> FEATURE:
<223> OTHER INFORMATION: J03011LC6*01

<400> SEQUENCE: 180

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105


<210> SEQ ID NO 181
<211> LENGTH: 106
<212> TYPE: PRT
<213> ORGANISM: Artificial Sequence
<220> FEATURE:
<223> OTHER INFORMATION: M61771LC7*02, X51755LC7*01

<400> SEQUENCE: 181

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105


<210> SEQ ID NO 182
<211> LENGTH: 106
<212> TYPE: PRT
<213> ORGANISM: Artificial Sequence
<220> FEATURE:
<223> OTHER INFORMATION: KM455557LC7*03

<400> SEQUENCE: 182

Gly Gln Pro Lys Ala Ala Pro Ser Val Thr Leu Phe Pro Pro Ser Ser
1               5                   10                  15
```

```
Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

UNITED STATES PATENT AND TRADEMARK OFFICE
CERTIFICATE OF CORRECTION

PATENT NO. : 11,161,915 B2
APPLICATION NO. : 15/765574
DATED : November 2, 2021
INVENTOR(S) : Urosev et al.

It is certified that error appears in the above-identified patent and that said Letters Patent is hereby corrected as shown below:

In the Claims

Column 408 Claim 16, Lines 61-64, delete:
"The construct of claim 15, wherein the PC is a human PC, a human IgG1 PC, a human IgA PC, a human IgG PC, a human IgD PC, a human IgE PC, a human IgM PC, a human IgG2 PC, a human IgG3 PC, or a human IgG4 Fc."

And replace with:
-- The construct of claim 15, wherein the Fc is a human Fc, a human IgG1 Fc, a human IgA Fc, a human IgG Fc, a human IgD Fc, a human IgE Fc, a human IgM Fc, a human IgG2 Fc, a human IgG3 Fc, or a human IgG4 Fc. --

Column 409 Claim 18, Lines 4-26, delete:
"i) a heterodimeric IgG1 Fc having the substitutions L351Y_F405A_Y407V in the first PC polypeptide, and the substitutions T366L_K3 92M_T394W in the second Fc polypeptide;
ii) a heterodimeric IgG1 Fc having the substitutions L351Y_F405A_Y407V in the first PC polypeptide, and the substitutions T366L_K392L_T394W in the second Fc polypeptide;
iii) a heterodimeric IgG1 Fc having the substitutions T350V_L35 1Y_F405A_Y407V in the first PC polypeptide, and the substitutions T350V_T3 66L_K392L_T394W in the second Fc polypeptide;
iv) a heterodimeric IgG1 Fc having the substitutions T350V_L35 1Y_F405A_Y407V in the first PC polypeptide, and the substitutions T350V_T366L_K392M_T394W in the second Fc polypeptide; or
v) a heterodimeric IgG1 Fc having the substitutions T350V_L351Y_S400E_F405A_Y407V in the first PC polypeptide, and the substitutions T350V_T366L_N390R_K3 92M_T394W in the second Fc polypeptide, wherein the numbering of amino acid residues in the PC is according to EU numbering."

And replace with:
-- i) a heterodimeric IgG1 Fc having the substitutions L351Y_F405A_Y407V in the first Fc polypeptide, and the substitutions T366L_K3 92M_T394W in the second Fc polypeptide;
ii) a heterodimeric IgG1 Fc having the substitutions L351Y_F405A_Y407V in the first Fc polypeptide, and the substitutions T366L_K392L_T394W in the second Fc polypeptide;

Signed and Sealed this
Thirty-first Day of May, 2022

Katherine Kelly Vidal
*Director of the United States Patent and Trademark Office* iii) a heterodimeric IgG1 Fc having the substitutions T350V_L351Y_F405A_Y407V in the first Fc polypeptide, and the substitutions T350V_T366L_K392L_T394W in the second Fc polypeptide;
iv) a heterodimeric IgG1 Fc having the substitutions T350V_L351Y_F405A_Y407V in the first Fc polypeptide, and the substitutions T350V_T366L_K392M_T394W in the second Fc polypeptide; or
v) a heterodimeric IgG1 Fc having the substitutions T350V_L351Y_S400E_F405A_Y407V in the first Fc polypeptide, and the substitutions T350V_T366L_N390R_K392M_T394W in the second Fc polypeptide, wherein the numbering of amino acid residues in the Fc is according to EU numbering. --